United States Patent
Dyckman et al.

(10) Patent No.: US 11,672,780 B2
(45) Date of Patent: Jun. 13, 2023

(54) [1,2,4]TRIAZOLO[1,5-A]PYRIDINYL SUBSTITUTED INDOLE COMPOUNDS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Tasir Shamsul Haque, Yardley, PA (US); Louis J. Lombardo, Belle Mead, NJ (US); John E. Macor, Washington Crossing, PA (US); Christopher P. Mussari, Princeton, NJ (US); Laxman Pasunoori, Warangal (IN); Sreekantha Ratna Kumar, Bangalore (IN); Trevor C. Sherwood, West Windsor, NJ (US); Shoshana L. Posy, Highland Park, NJ (US); Ramesh Kumar Sistla, Bangalore (IN); Subramanya Hegde, Bangalore (IN); Anupama Kandhi Ramachandra Reddy, Chitradurga (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 284 days.

(21) Appl. No.: 17/113,495

(22) Filed: Dec. 7, 2020

(65) Prior Publication Data
US 2021/0085651 A1    Mar. 25, 2021

Related U.S. Application Data

(63) Continuation of application No. 16/653,297, filed on Oct. 15, 2019, now Pat. No. 10,912,766, which is a continuation of application No. 16/042,116, filed on Jul. 23, 2018, now Pat. No. 10,478,424, which is a continuation of application No. 15/635,055, filed on Jun. 27, 2017, now Pat. No. 10,071,079.

(51) Int. Cl.
| | |
|---|---|
| A61K 31/4196 | (2006.01) |
| A61K 31/437 | (2006.01) |
| A61K 31/4427 | (2006.01) |
| A61K 45/06 | (2006.01) |
| C07D 471/04 | (2006.01) |
| C07D 249/00 | (2006.01) |

(52) U.S. Cl.
CPC ........ *A61K 31/4196* (2013.01); *A61K 31/437* (2013.01); *A61K 31/4427* (2013.01); *A61K 45/06* (2013.01); *C07D 249/00* (2013.01); *C07D 471/04* (2013.01)

(58) Field of Classification Search
CPC .............. A61K 31/4196; A61K 31/437; A61K 31/4427; A61K 45/06; C07D 249/00
See application file for complete search history.

(56) References Cited

U.S. PATENT DOCUMENTS

| | | | |
|---|---|---|---|
| 6,867,200 | B1 | 3/2005 | Allen et al. |
| 7,410,975 | B2 | 8/2008 | Lipford et al. |
| 8,138,187 | B2 | 3/2012 | Zemolka et al. |
| 8,354,400 | B2 | 1/2013 | Zheng et al. |
| 9,126,996 | B2 | 9/2015 | Lipford et al. |
| 9,126,999 | B2 | 9/2015 | Boivin et al. |
| 9,241,991 | B2 | 1/2016 | Ji et al. |
| 9,353,115 | B2 | 5/2016 | Lipford et al. |
| 9,376,398 | B2 | 6/2016 | Hori et al. |
| 9,428,495 | B2 | 8/2016 | Carlson et al. |
| 9,643,967 | B2 | 5/2017 | Koul et al. |
| 2006/0235037 | A1 | 10/2006 | Purandare et al. |
| 2010/0160314 | A1 | 6/2010 | Lipford et al. |
| 2011/0009444 | A1 | 1/2011 | Dubois et al. |
| 2011/0015219 | A1 | 1/2011 | Trawick et al. |

(Continued)

FOREIGN PATENT DOCUMENTS

| | | | | |
|---|---|---|---|---|
| WO | WO 2006/113458 | * | 10/2006 | ........... C07D 401/14 |
| WO | WO 2006/113458 A1 | | 10/2006 | |

(Continued)

OTHER PUBLICATIONS

Form PCT/ISA/220 (Jul. 2017), International Search Report Application No. PCT/US2017/039633, International filing date: Jun. 28, 2017, dated Sep. 7, 2017, 14 pgs.
Kawai, Taro, et al., "The role of pattern-recognition receptors in innate immunity: update on Toll-like receptors", Nature Immunol., May 2010, vol. 11, No. 5, pp. 373-384.
Lamphier, Marc, et al., "Novel Small Molecule Inhibitors of TLR7 and TLR9: Mechanism of Action and Efficacy In Vivo", Mol Pharmacol, Mar. 2014, vol. 85, pp. 429-440.
Patra, Mahesh Chandra, et al., "Recent progress in the development of Toll-like receptor (TLR) antagonists", Exp. Opin. on Therapeutic Patents, 2016, 26:6, pp. 719-730.
Sims, John E., et al., "The IL-1 family: regulators of immunity", Nature Reviews Immunology, Feb. 2010, vol. 10, pp. 89-102.

*Primary Examiner* — Erich A Leeser
(74) *Attorney, Agent, or Firm* — Gary Greenblatt

(57) ABSTRACT

Disclosed are compounds of Formula (I)

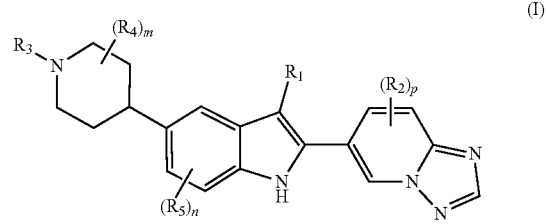

or a salt thereof, wherein $R_1$, $R_2$, $R_3$, $R_4$, $R_5$, m, n, and p are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

13 Claims, No Drawings

(56) References Cited

U.S. PATENT DOCUMENTS

| | | |
|---|---|---|
| 2011/0275631 A1 | 11/2011 | Abeywardane et al. |
| 2013/0045986 A1 | 2/2013 | Nagarathnam et al. |
| 2014/0066432 A1 | 3/2014 | Howbert et al. |
| 2014/0088085 A1 | 3/2014 | Burgess et al. |
| 2014/0242121 A1 | 8/2014 | Lipford et al. |
| 2016/0096833 A1 | 4/2016 | Emmitte et al. |

FOREIGN PATENT DOCUMENTS

| | | |
|---|---|---|
| WO | WO 2007/115306 A2 | 10/2007 |
| WO | WO 2008/065198 A1 | 6/2008 |
| WO | WO 2008/152471 A1 | 12/2008 |
| WO | WO 2009/030996 A1 | 3/2009 |
| WO | 2010093425 A1 | 8/2010 |
| WO | 2010144571 A1 | 12/2010 |
| WO | WO 2010/149769 A1 | 12/2010 |
| WO | 2013009140 A2 | 1/2013 |
| WO | WO 2015/088045 A1 | 6/2015 |
| WO | WO 2016/029077 A1 | 2/2016 |

\* cited by examiner

[1,2,4]TRIAZOLO[1,5-A]PYRIDINYL SUBSTITUTED INDOLE COMPOUNDS

CROSS-REFERENCE TO RELATED APPLICATIONS

This application is a continuation application of U.S. patent application 16,653,297 filed Oct. 15, 2019, which is a continuation application of U.S. patent application Ser. No. 16/042,116 filed Jul. 23, 2018, which is a continuation application of U.S. patent application Ser. No. 15/635,055 filed Jun. 27, 2017, which claims the benefit of Indian Provisional Application Serial No. 201611022328, filed Jun. 29, 2016.

DESCRIPTION

The present invention generally relates to [1,2,4]triazolo[1,5-a]pyridinyl substituted indole compounds useful as inhibitors of signaling through Toll-like receptor 7, 8, or 9 (TLR7, TLR8, TLR9) or combinations thereof. Provided herein are [1,2,4]triazolo[1,5-a]pyridinyl substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of [1,2,4]triazolo[1,5-a]pyridinyl substituted indole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

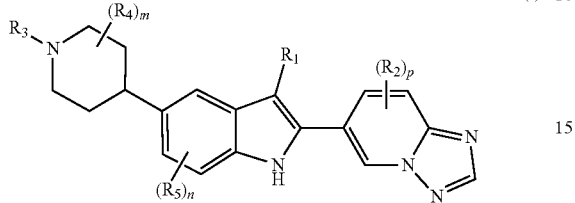

or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

each $R_2$ is independently halo, —CN, —OH, —$NO_2$, $C_{1-3}$ alkyl, —$CD_3$, $C_{1-2}$ fluoroalkyl, $C_{1-2}$ cyanoalkyl, $C_{1-3}$ hydroxyalkyl, $C_{1-3}$ aminoalkyl, —O($CH_2$)$_{1-2}$OH, —($CH_2$)$_{0-4}$O($C_{1-4}$ alkyl), $C_{1-3}$ fluoroalkoxy, —($CH_2$)$_{1-4}$O($C_{1-3}$ alkyl), —O($CH_2$)$_{1-2}$OC(O)($C_{1-3}$ alkyl), —O($CH_2$)$_{1-2}$$NR_xR_x$, —C(O)O($C_{1-3}$ alkyl), —C(O)$NR_yR_y$, —$NR_yR_y$, —$NR_y$($C_{1-3}$ fluoroalkyl), —$NR_y$($C_{1-4}$ hydroxyalkyl), —$NR_xCH_2$(phenyl), —$NR_xS(O)_2$($C_{3-6}$ cycloalkyl), —$NR_xC(O)$($C_{1-3}$ alkyl), —$NR_x(CH_2$-cyclopropyl), $C_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl);

$R_3$ is:
(a) -$L_1$-A; or
(b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_x$-$CR_x(OH)CR_xCR_xR_x$, —C=N($NR_xR_x$), —($CR_xR_x$)$_{1-4}$O($C_{1-3}$ alkyl), —($CR_xR_x$)$_{1-4}$O($CR_xR_x$)$_{1-3}$O($C_{1-3}$ alkyl), —$CH_2CH(OH)CH_2O$($C_{1-3}$ alkyl), —($CR_xR_x$)$_{1-3}$S($C_{1-3}$ alkyl), —($CH_2$)$_{1-3}$C(O)OC($CH_3$)$_3$, —($CR_xR_x$)$_{0-3}$$NR_xR_y$, —($CR_xR_x$)$_{0-3}$$NR_x$($C_{1-4}$ hydroxyalkyl), —$CH_2CH(OH)CH_2NR_xR_y$, —C(O)H, —C(O)($C_{1-6}$ alkyl), —C(O)($C_{1-4}$ hydroxyalkyl), —C(O)($C_{1-3}$ fluoroalkyl), —C(O)($C_{1-3}$ chloroalkyl), —C(O)($C_{1-3}$ cyanoalkyl), —($CR_xR_x$)$_{0-3}$C(O)OH, —C(O)($CH_2$)$_{0-2}$O($C_{1-4}$ alkyl), —C(O)($CR_xR_x$)$_{1-2}$O($CR_xR_x$)$_{1-2}$O($C_{1-3}$ alkyl), —C(O)($CR_xR_x$)$_{0-2}$O($CR_xR_x$)$_{1-2}$$NR_yR_y$, —C(O)$CR_xR_xS(O)_2$($C_{1-3}$ alkyl), —C(O)$CR_xR_xNR_xS(O)_2$($C_{1-3}$ alkyl), —C(O)$CR_xR_xOC(O)$($C_{1-3}$ alkyl), —C(O)($CR_xR_x$)$_{0-3}$$NR_yR_y$, —C(O)($CR_xR_x$)$_{0-1}$$NR_x$($C_{1-3}$ cyanoalkyl), —C(O)($CR_xR_x$)$_{0-2}$$NR_y$($C_{1-6}$ hydroxyalkyl), —C(O)($CR_xR_x$)$_{0-2}$$NR_x$($C_{1-3}$ fluoroalkyl), —C(O)($CR_xR_x$)$_{0-1}$$NR_x$($C_{1-5}$ hydroxy-fluoroalkyl), —C(O)($CR_xR_x$)$_{0-1}$$NR_x(CH_2)_{1-2}$O($C_{1-3}$ hydroxyalkyl), —C(O)($CR_xR_x$)$_{0-2}$$NR_x(CH_2)_{1-2}$$NR_xC(O)$($C_{1-2}$ alkyl), —C(O)($CR_xR_x$)$_{0-2}$$NR_x$(($CR_xR_x$)$_{1-2}$O($C_{1-2}$ alkyl)), —C(O)($CR_xR_x$)$_{0-2}$N(($CR_xR_x$)$_{1-2}$O($C_{1-2}$ alkyl))$_2$, —C(O)($CR_xR_x$)$_{0-2}$$NR_x$($CR_xR_x$)$_{1-3}$$NR_xR_x$, —C(O)$CR_x(NH_2)$($CR_xR_x$)$_{1-4}$$NR_xR_x$, —C(O)$CR_x(NH_2)$($CR_xR_x$)$_{1-4}$$NR_xC(O)NR_xR_x$, —C(O)($CR_xR_x$)$_{0-3}$$NR_x(CH_2)_{0-1}$C(O)($C_{1-3}$ alkyl), —C(O)($CR_xR_x$)$_{0-3}$N(($CH_2$)$_{0-1}$C(O)($C_{1-3}$ alkyl))$_2$, —C(O)($CR_xR_x$)$_{0-1}$$NR_x(CH_2)_{0-1}$C(O)($C_{1-3}$ cyanoalkyl), —C(O)($CR_xR_x$)$_{0-2}$$NR_x(CH_2)_{1-2}$C(O)$NR_yR_y$, —C(O)($CR_xR_x$)$_{1-3}$C(O)$NR_yR_y$, —C(O)($CR_xR_x$)$_{1-3}$S(O)$_2$$NR_yR_y$, —C(O)($CR_xR_x$)$_{0-2}$$NR_x$(CHR$_y$($CH_2OH$)), —($CR_xR_x$)$_{1-2}$C(O)$NR_yR_y$, —CH(CN)C(O)$NR_yR_y$, —($CR_xR_x$)$_{1-2}$C(O)$NR_y$($C_{1-3}$ fluoroalkyl), —($CR_xR_x$)$_{1-2}$C(O)$NR_y$($C_{1-4}$ hydroxyalkyl), —($CR_xR_x$)$_{1-2}$C(O)$NR_y$($C_{1-3}$ cyanoalkyl), —($CR_xR_x$)$_{1-2}$C(O)$NR_x(CH_2)_{1-2}$O($C_{1-3}$ alkyl), —($CR_xR_x$)$_{1-2}$C(O)$NR_xCH(C_{1-4}$ alkyl)($C_{1-3}$ hydroxyalkyl), —($CR_xR_x$)$_{1-2}$C(O)$NR_xCH(C_{1-3}$ hydroxyalkyl)($C_{3-6}$ cycloalkyl), —($CH_2$)$_{1-2}$C(O)$NR_x(CH_2)_{1-2}$C(O)$NR_xR_x$, —($CH_2$)$_{1-2}$C(O)$NR_x(CH_2)_{1-2}$S($C_{1-3}$ alkyl), —($CH_2$)$_{1-2}$C(O)$NR_x(CH_2)_{1-2}$S(O)$_2$OH, —($CH_2$)$_{1-2}$C(O)$NR_x(CH_2)_{1-2}$$NR_xC(O)$($C_{1-3}$ alkyl), —($CH_2$)$_{1-2}$C(O)$NR_x(CH_2)_{1-3}$$NR_xR_x$, —($CH_2$)$_{1-2}$C(O)N($CH_2CH_3$)($CH_2$)$_{1-3}$$NR_xR_x$, —($CR_xR_x$)$_{0-3}$S(O)$_2$($C_{1-4}$ alkyl), —($CH_2$)$_{0-2}$S(O)$_2$($C_{1-3}$ fluoroalkyl), —($CR_xR_x$)$_{0-2}$S(O)$_2$$NR_yR_y$, —($CR_xR_x$)$_{0-2}$$NR_xS(O)_2$($C_{1-3}$ alkyl), —C(O)C(O)OH, —C(O)C(O)$NR_yR_y$, or —C(O)C(O)$NR_x$($CR_xR_x$)$_{1-2}$$NR_yR_y$;

$L_1$ is a bond, —($CR_xR_x$)$_{1-2}$—, —($CR_xR_x$)$_{1-2}$$CR_x(OH)$—, —($CR_xR_x$)$_{1-2}$O—, —$CR_xR_xC(O)$—, —($CR_xR_x$)$_2$$NR_x$($CR_xR_x$)$_{0-1}$—, —$CR_xR_xC(O)NR_x$($CR_xR_x$)$_{0-4}$—, —C(O)($CR_xR_x$)$_{0-3}$—, —C(O)($CR_xR_x$)$_{0-2}$$NR_x$($CR_xR_x$)$_{0-2}$—, —C(O)($CR_xR_x$)$_{0-2}$N($C_{1-2}$ hydroxyalkyl)($CR_xR_x$)$_{0-2}$—, —C(O)($CR_xR_x$)$_{0-2}$$NR_x$($CR_xR_x$)$_{1-2}$$CR_x(OH)$—, —C(O)($CR_xR_x$)$_{1-2}$C(O)$NR_x$—, —($CR_xR_x$)$_{0-2}$C(O)$NR_x$($CR_xR_x$)$_{1-2}$$CR_x(OH)$—, —($CR_xR_x$)$_{0-2}$C(O)N($C_{1-2}$ hydroxyalkyl)($CR_xR_x$)$_{1-2}$—, —C(O)($CR_xR_x$)$_{0-1}$O—, —C(O)($CR_xR_x$)$_{1-2}$NHS(O)$_2$—, —C(O)$CR_x(NH_2)CR_xR_x$, —C(O)C(O)($CR_xR_x$)$_{0-2}$—, —C(O)$NR_x$($CR_xR_x$)$_{1-2}$—, or —S(O)$_2$—; A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, diazepanyl, dihydroinonyl, dihydropyrimidinonyl, dioxanyl, dioxidothiadiazinanyl, dioxidothiazolidinyl, dioxidothiomorpholinyl, dioxoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, octahydropyrrolo[3,4-b]pyridinyl, oxazolidinonyl, oxadiazolyl, oxazolyl, oxetanyl, phenyl, piperidinyl, piperidinonyl, piperazinyl, piperazinonyl, pyrazinyl, pyrazolyl, pyridazinyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrahydrothiopyranyl, tetrazolyl, thiadiazolyl, thiazolyl, triazolonyl, or triazolyl, each substituted with -$L_2$-$R_a$ and zero to 4 $R_b$;

$L_2$ is a bond or —$CR_xR_x$—;

$R_a$ is:
(a) H, F, Cl, —CN, —OH, $C_{1-6}$ alkyl, $C_{1-3}$ fluoroalkyl, $C_{1-5}$ hydroxyalkyl, —($CH_2$)$_{0-4}$O($C_{1-3}$ alkyl), —($CR_xR_x$)$_{1-3}$S($C_{1-3}$ alkyl), —($CR_xR_x$)$_{1-3}$NHC(O)O($C_{1-4}$ alkyl), —($CR_xR_x$)$_{1-3}$$NR_yR_y$, —($CR_xR_x$)$_{1-3}$C(O)$NR_yR_y$, —O($C_{1-3}$ fluoroalkyl), —S(O)$_2$$NR_xR_x$, —O($CR_xR_x$)$_{1-3}$$NR_xR_x$, —NHS(O)$_2$($C_{1-3}$ alkyl), —$NR_xR_x$, —$NR_x$($C_{1-4}$ alkyl), —$NR_xC(O)$($C_{1-4}$ alkyl), —($CR_xR_x$)$_{0-3}$C(O)OH, —C(O)($C_{1-5}$ alkyl), —C(O)($C_{1-3}$ fluoroalkyl), —C(O)O($C_{1-4}$ alkyl), —C(O)NH ($C_{1-3}$ cyanoalkyl), —C(O)NR$_y$R$_y$, —C(O)NR$_x$CH$_2$C(O)NR$_x$R$_x$, or —C(O)NR$_x$CH$_2$CH$_2$NHC(O)(C$_{1-3}$ alkyl);

(b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or (c) A$_1$, —CH$_2$A$_1$, —C(O)A$_1$, —NR$_x$A$_1$, or —C(O)NR$_x$A$_1$, wherein A$_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl);

each R$_b$ is independently F, —OH, —CH$_3$, —CF$_3$, or —OCH$_3$;

each R$_x$ is independently H or —CH$_3$;

each R$_y$ is independently H or C$_{1-6}$ alkyl;

R$_z$ is H, C$_{1-2}$ alkyl, or C$_{1-2}$ fluoroalkyl;

each R$_4$ is independently F, —OH, C$_{1-2}$ alkyl, or —OCH$_3$; or two R$_4$ attached to the same carbon atom form =O; or wherein when m is at least 2, two R$_4$, each attached to a different carbon atom adjacent to the nitrogen atom in the piperidinyl ring, can form a —CH$_2$CH$_2$— bridge;

each R$_5$ is independently F, Cl, —CN, C$_{1-2}$ alkyl, C$_{1-2}$ fluoroalkyl, or —OCH$_3$;

m is zero, 1, 2, 3, or 4;

n is zero, 1, or 2; and p is zero, 1, 2, 3, or 4.

The second aspect of the present invention provides at least one compound of Formula (I) or a salt thereof, wherein:

R$_1$ is H, Cl, —CN, C$_{1-4}$ alkyl, C$_{1-3}$ fluoroalkyl, C$_{1-3}$ hydroxy-fluoroalkyl, —CR$_z$=CH$_2$, C$_{3-6}$ cycloalkyl, —CH$_2$(C$_{3-6}$ cycloalkyl), —C(O)O(C$_{1-3}$ alkyl), or tetrahydropyranyl; each R$_2$ is independently halo, —CN, —OH, —NO$_2$+, C$_{1-3}$ alkyl, C$_{1-2}$ fluoroalkyl, C$_{1-3}$ hydroxyalkyl, C$_{1-3}$ aminoalkyl, —(CH$_2$)$_{0-4}$O(C$_{1-3}$ alkyl), C$_{1-3}$ fluoroalkoxy, C$_{2-4}$ alkoxyalkoxy, —O(CH$_2$)$_{1-2}$NR$_x$R$_x$, —C(O)O(C$_{1-3}$ alkyl), —C(O)NR$_y$R$_y$, —NR$_y$R$_y$, —NR$_x$C(O)(C$_{1-3}$ alkyl), —NR$_x$(CH$_2$-cyclopropyl), C$_{3-6}$ cycloalkyl, methylpiperidinyl, methylpiperazinyl, amino-oxadiazolyl, imidazolyl, triazolyl, or —C(O)(thiazolyl);

R$_3$ is:

(a) -L$_1$-A; or (b) H, C$_{1-6}$ alkyl, C$_{1-3}$ fluoroalkyl, C$_{1-3}$ cyanoalkyl, C$_{1-6}$ hydroxyalkyl, C$_{1-3}$ hydroxy-fluoroalkyl, —CR$_x$R$_x$CR$_x$(OH)CR$_x$R$_x$R$_x$, —(CR$_x$R$_x$)$_{1-4}$O(C$_{1-3}$ alkyl), —(CR$_x$R$_x$)$_{1-4}$O(CR$_x$R$_x$)$_{1-3}$O(C$_{1-3}$ alkyl), —CH$_2$CH(OH)CH$_2$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CR$_x$R$_x$)$_{0-3}$NR$_y$R$_y$, —(CR$_x$R$_x$)$_{0-3}$NR$_x$(C$_{1-4}$ hydroxyalkyl), —CH$_2$CH(OH)CH$_2$NR$_x$R$_y$, —C(O)H, —C(O)(C$_{1-6}$ alkyl), —C(O)(C$_{1-3}$ hydroxyalkyl), —C(O)(C$_{1-3}$ fluoroalkyl), —C(O)(C$_{1-3}$ chloroalkyl), —C(O)(C$_{1-3}$ cyanoalkyl), —C(CR$_x$)$_{0-3}$C(O)OH, —C(O)(CH$_2$)$_{0-2}$O(C$_{1-4}$ alkyl), —C(O)(CR$_x$R$_x$)$_{0-2}$(CR$_x$R$_x$)$_{1-2}$O(C$_{1-3}$ alkyl), —C(O)CR$_x$R$_x$S(O)$_2$(C$_{1-3}$ alkyl), —C(O)CR$_x$R$_x$NR$_x$S(O)$_2$(C$_{1-3}$ alkyl), —C(O)CR$_x$R$_x$OC(O)(C$_{1-3}$ alkyl), —C(O)(CR$_x$R$_x$)$_{0-3}$NR$_y$R$_y$, —C(O)(CR$_x$R$_x$)$_{0-1}$NR$_x$(C$_{1-3}$ cyanoalkyl), —C(O)(CR$_x$R$_x$)$_{0-2}$NR$_y$(C$_{1-6}$ hydroxyalkyl), —C(O)(CR$_x$R$_x$)$_{0-1}$NR$_x$(C$_{1-3}$ fluoroalkyl), —C(O)(CR$_x$R$_x$)$_{0-1}$NR$_x$(C$_{1-5}$ hydroxy-fluoroalkyl), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-1}$NR$_x$((CR$_x$R$_x$)$_{1-2}$O(C$_{1-2}$ alkyl)), —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{1-3}$NR$_x$(CH$_2$)$_{0-1}$C(O)(C$_{1-3}$ alkyl), —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-1}$NR$_x$(CH$_2$)$_{1-2}$C(O)NR$_y$R$_y$, —C(O)(CR$_x$R$_x$)$_{1-3}$C(O)NR$_y$R$_y$, —C(O)(CR$_x$R$_x$)$_{0-1}$NR$_x$(CHR$_y$(CH$_2$OH)), —(CR$_x$R$_x$)$_{1-2}$C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_y$(C$_{1-3}$ cyanoalkyl), —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)(C$_{1-3}$ hydroxyalkyl), —(CH$_2$)$_{1-2}$C(O)NR$_x$(CH$_2$)$_{1-2}$C(O)NR$_x$R$_x$, —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CH$_2$)$_{0-2}$S(O)$_2$(C$_{1-4}$ alkyl), —(CH$_2$)$_{0-2}$S(O)$_2$(C$_{1-3}$ fluoroalkyl), —(CH$_2$)$_{1-2}$S(O)$_2$NR$_x$R$_x$, —C(O)C(O)OH, —C(O)C(O)NR$_y$R$_y$, or —C(O)C(O)NR$_y$(CR$_x$R$_x$)$_{1-2}$NR$_y$R$_y$; L$_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N(C$_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)NR$_x$(CR$_x$R$_x$)$_{1-2}$—, or —S(O)$_2$-A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, C$_{3-6}$ cycloalkyl, diazepanyl, dihydroinonyl, dihydropyrimidinonyl, dioxidothiadiazinanyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -L$_2$-R$_a$ and zero to 4 R$_b$;

L$_2$ is a bond or —CR$_x$R$_x$—;

R$_a$ is:

(a) H, F, Cl, —CN, —OH, C$_{1-6}$ alkyl, C$_{1-3}$ fluoroalkyl, C$_{1-5}$ hydroxyalkyl, —(CH$_2$)$_{0-4}$O(C$_{1-3}$ alkyl), —(CR$_x$R$_x$)$_{1-3}$S(C$_{1-3}$ alkyl), —(CR$_x$R$_x$)$_{1-3}$NHC(O)O(C$_{1-4}$ alkyl), —(CR$_x$R$_x$)$_{1-3}$NR$_y$R$_y$, —(CR$_x$R$_x$)$_{1-3}$C(O)NR$_y$R$_y$, —O(C$_{1-3}$ fluoroalkyl), —S(O)$_2$NR$_x$R$_x$, —O(CR$_x$R$_x$)$_{1-3}$NR$_x$R$_x$, —NHS(O)$_2$(C$_{1-3}$ alkyl), —NR$_x$R$_x$, —NR$_x$(C$_{1-4}$ alkyl), —NR$_x$C(O)(C$_{1-4}$ alkyl), —(CR$_x$R$_x$)$_{0-3}$C(O)OH, —C(O)(C$_{1-5}$ alkyl), —C(O)(C$_{1-3}$ fluoroalkyl), —C(O)O(C$_{1-4}$ alkyl), —C(O)NH ($C_{1-3}$ cyanoalkyl), —C(O)NR$_y$R$_y$, —C(O)NR$_x$CH$_2$C(O)NR$_x$R$_x$, or —C(O)NR$_x$CH$_2$CH$_2$NHC(O)(C$_{1-3}$ alkyl);
(b) $C_{3-6}$ cycloalkyl or —C(O)NH(C$_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O(C$_{1-3}$ alkyl); or
(c) A$_1$, —CH$_2$A$_1$, —C(O)A$_1$, —NR$_x$A$_1$, or —C(O)NR$_x$A$_1$, wherein A$_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl);

each R$_b$ is independently F, —CH$_3$, —CF$_3$, or —OCH$_3$;
each R$_x$ is independently H or —CH$_3$;
each R$_y$ is independently H or $C_{1-6}$ alkyl;
R$_z$ is H, $C_{1-2}$ alkyl, or $C_{1-2}$ fluoroalkyl;
each R$_4$ is independently F, —OH, $C_{1-2}$ alkyl, or —OCH$_3$; or two R$_4$ attached to the same carbon atom form =O;
each R$_5$ is independently F, Cl, —CN, $C_{1-2}$ alkyl, $C_{1-2}$ fluoroalkyl, or —OCH$_3$;
m is zero, 1, 2, 3, or 4;
n is zero, 1, or 2; and
p is zero, 1, 2, 3, or 4.

One embodiment provides a compound of Formula (I) or a salt thereof, wherein R$_1$ is H, Cl, —CN, $C_{1-4}$ alkyl, $C_{1-3}$ fluoroalkyl, $C_{1-3}$ hydroxy-fluoroalkyl, $C_{3-6}$ cycloalkyl, —CH$_2$(C$_{3-6}$ cycloalkyl), or tetrahydropyranyl; and R$_2$, R$_3$, R$_4$, R$_5$, m, n, and p are defined in the first aspect or the second aspect. Included in this embodiment are compounds in which R$_1$ is H, Cl, —CN, $C_{1-4}$ alkyl, or $C_{1-2}$ fluoroalkyl. Also included are compounds in which R$_1$ is —CH$_2$CH$_3$, —CH(CH$_3$)$_2$, or —CH$_2$CHF$_2$; and compounds in which R$_1$ is —CH(CH$_3$)$_2$. Also included are compounds in which m is zero and n is zero.

One embodiment provides a compound of Formula (I) or a salt thereof, wherein each R$_2$ is independently F, Cl, —CN, —OH, $C_{1-3}$ alkyl, —CD$_3$, $C_{1-2}$ fluoroalkyl, $C_{1-3}$ hydroxyalkyl, $C_{1-2}$ cyanoalkyl, $C_{1-3}$ aminoalkyl, $C_{1-4}$ alkoxy, $C_{1-2}$ fluoroalkoxy, —O(CH$_2$)$_{1-2}$OH, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —C(O)NR$_y$R$_y$, —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), $C_{3-6}$ cycloalkyl, —NR$_x$C(O)(C$_{1-3}$ alkyl), —NR$_x$(CH$_2$-cyclopropyl), $C_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl); and R$_1$, R$_3$, R$_4$, R$_5$, R$_x$, R$_y$, m, n, and p are defined in the first aspect or the second aspect. Included in this embodiment are compounds in which each R$_2$ is independently F, Cl, —CN, $C_{1-3}$ alkyl, —CD$_3$, $C_{1-2}$ fluoroalkyl, $C_{1-3}$ hydroxyalkyl, $C_{1-2}$ cyanoalkyl, $C_{1-4}$ alkoxy, $C_{1-2}$ fluoroalkoxy, —O(CH$_2$)$_{1-2}$OH, —(CH$_2$)$_{1-4}$O(C$_{1-3}$ alkyl), —O(CH$_2$)$_{1-2}$OC(O)(C$_{1-3}$ alkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), $C_{3-6}$ cycloalkyl, morpholinyl, dioxothiomorpholinyl, or methylpiperazinyl. Also included in this embodiment are compounds in which each R$_2$ is independently F, Cl, —CN, —CH$_3$, —CH$_2$CH$_3$, —CH(CH$_3$)$_2$, —CD$_3$, —CF$_3$, —CH$_2$CN, —CH$_2$OH, —CH$_2$CH$_2$OH, —CH(CH$_3$)OH, —C(CH$_3$)$_2$OH, —OCH$_2$CH$_2$OH, —OCH$_3$, —OCH$_2$CH$_3$, —OCH$_2$CH(CH$_3$)$_2$, —OCHF$_2$, —CH$_2$OCH$_3$, —CH$_2$OCH$_2$CH$_3$, —OCH$_2$CH$_2$OC(O)CH$_3$, —N$_2$, —NH(CH$_2$CH$_3$), —NH(CH$_2$CF$_3$), —NH(CH$_2$C(CH$_3$)$_2$OH), —NHCH$_2$(phenyl), —NHS(O)$_2$(cyclopropyl), cyclopropyl, morpholinyl, dioxothiomorpholinyl, or methylpiperazinyl.

One embodiment provides a compound of Formula (I) or a salt thereof, wherein each R$_2$ is independently halo, —CN, $C_{1-3}$ alkyl, —CD$_3$, $C_{1-2}$ fluoroalkyl, $C_{1-2}$ cyanoalkyl, $C_{1-3}$ hydroxyalkyl, —O(CH$_2$)$_{1-2}$OH, —(CH$_2$)$_{0-4}$ O(C$_{1-4}$ alkyl), $C_{1-3}$ fluoroalkoxy, —O(CH$_2$)$_1$ and R$_1$, R$_3$, R$_4$, R$_5$, R$_x$, R$_y$, m, n, and p are defined in the first aspect or the second aspect. Included in this embodiment are compounds in which $_2$OC(O)(C$_{1-3}$ alkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), $C_{3-6}$ cycloalkyl, morpholinyl, dioxothiomorpholinyl, or methylpiperazinyl; and R$_1$, R$_3$, R$_4$, R$_5$, R$_x$, R$_y$, m, n, and p are defined in the first aspect or the second aspect. Included in this embodiment are compounds in which each R$_2$ is independently F, Cl, —CN, —OH, $C_{1-3}$ alkyl, —CD$_3$, $C_{1-2}$ fluoroalkyl, $C_{1-2}$ cyanoalkyl, $C_{1-3}$ hydroxyalkyl, —O(CH$_2$)$_{1-2}$OH, —O(C$_{1-4}$ alkyl), $C_{1-2}$ fluoroalkoxy, —(CH$_2$)$_{1-4}$O(C$_{1-3}$ alkyl), —O(CH$_2$)$_{1-2}$ OC(O)(C$_{1-3}$ alkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), $C_{3-6}$ cycloalkyl, morpholinyl, dioxothiomorpholinyl, or methylpiperazinyl. Also included are compounds in which m is zero and n is zero.

One embodiment provides a compound of Formula (I) or a salt thereof, wherein R$_2$ is F, Cl, —CN, $C_{1-2}$ alkyl, —CD$_3$, —CF$_3$, —CH$_2$OH, —C(CH$_3$)$_2$OH, —OCH$_3$, —CH$_2$OCH$_3$, —OCH$_2$CH$_3$, cyclopropyl, or morpholinyl; and R$_1$, R$_3$, R$_4$, R$_5$, m, n, and p are defined in the first aspect or the second aspect. Included in this embodiment are compounds in which each R$_2$ is independently —CH$_3$ or —OCH$_3$. Also included are compounds in which m is zero and n is zero.

One embodiment provides a compound of Formula (I) or a salt thereof, wherein R$_3$ is -L$_1$-A; and R$_1$, R$_2$, R$_4$, R$_5$, L$_1$, and A are defined in the first aspect or the second aspect. Included in this embodiment are compounds in which L$_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_2$N(C$_{1-2}$ hydroxyalkyl)(CR$_x$R$_x$)$_{0-2}$—, —C(O)(CR$_x$R$_x$)$_{1-2}$C(O)NR$_x$—, —C(O)(CR$_x$R$_x$)$_{0-2}$NR$_x$(CR$_x$R$_x$)$_{1-2}$CR$_x$(OH)—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)NR$_x$(CR$_x$R$_x$)$_{1-2}$—, or —S(O)$_2$—. Also included are compounds in which L$_1$ is a bond, —CR$_x$R$_x$—, —CR$_x$R$_x$C(O)—, —CR$_x$R$_x$C(O)NR$_x$—, or —C(O)(CR$_x$R$_x$)$_{0-2}$—. Also included are compounds in which m is zero and n is zero.

One embodiment provides a compound of Formula (I) or a salt thereof, wherein R$_3$ is -L$_1$-A; L$_1$ is a bond, —CR$_x$R$_x$—, —CR$_x$R$_x$C(O)—, —CR$_x$R$_x$C(O)NR$_x$—, or —C(O)(CR$_x$R$_x$)$_{0-2}$—; A is a ring selected from azetidinyl, $C_{3-6}$ cycloalkyl, dioxotetrahydrothiopyranyl, dioxidothiadiazinanyl, dioxidothiomorpholinyl, furanyl, imidazolyl, isoquinolinyl, morpholinyl, oxazolyl, 2-oxa-6-azaspiro[3.3]heptanyl, oxetanyl, phenyl, piperazinyl, piperidinyl, pyrazinyl, pyrazolyl, pyridinyl, pyrrolidinyl, pyrrolyl, quinolinyl, tetrahydrofuranyl, tetrahydropyranyl, tetrazolyl, thiadiazolyl, thiazolyl, and triazolyl, each substituted with -L$_2$-R$_a$ and zero to 4 $R_b$; and $R_1$, $R_2$, $R_4$, $R_5$, $R_x$, $L_2$, $R_a$ m, n, and p are defined in the first aspect or the second aspect. Included in this embodiment are compounds in which $L_2$ is a bond or —$CR_xR$—; and $R_a$ is (a) H, —CN, —OH, $C_{1-3}$ alkyl, $C_{1-2}$ fluoroalkyl, $C_{1-3}$ hydroxyalkyl, —$(CH_2)_{1-2}O(C_{1-3}$ alkyl), —$(CR_xR_x)_{1-3}NHC(O)O(C_{1-4}$ alkyl), —$(CR_xR_x)_{1-3}NH_2$, —$(CR_xR_x)_{1-3}NR_x(C_{1-4}$ alkyl), —$O(C_{1-2}$ fluoroalkyl), —$S(O)_2NR_xR_x$, —$NHS(O)_2(C_{1-3}$ alkyl), —$NR_xR_x$, —$NR_x(C_{1-4}$ alkyl), —$(CR_xR_x)_{1-2}C(O)OH$, —$C(O)OH$, —$C(O)(C_{1-3}$ alkyl), —$C(O)O(C_{1-3}$ alkyl), —$C(O)NR_x(C_{1-2}$ alkyl), —$C(O)N(C_{1-3}$ alkyl)$_2$, —$C(O)NR_xCH_2C(O)NR_xR_x$, or —$C(O)NR_xCH_2CH_2NHC(O)(C_{1-3}$ alkyl); (b) $C_{3-6}$ cycloalkyl or —$C(O)NH(C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —$C(O)O(C_{1-3}$ alkyl); or (c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —$C(O)(C_{1-2}$ alkyl), —$C(O)O(C_{1-3}$ alkyl), —$NR_xR_x$, phenyl, trifluoromethyl-phenyl, —$CH_2$(bromophenyl), and —$CH_2CH_2$(pyrrolidinyl). Also included are compounds in which m is zero and n is zero.

One embodiment provides a compound of Formula (I) or a salt thereof, wherein $R_3$ is H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_xCR_x(OH)CR_xCR_xR_x$, —$C=N(NR_xR_x)$, —$(CR_xR_x)_{1-4}O(C_{1-3}$ alkyl), —$(CR_xR_x)_{1-4}O(CR_xR_x)_{1-3}O(C_{1-3}$ alkyl), —$CH_2CH(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_yR_y$, —$(CR_xR_x)_{0-3}NR_x(C_{1-4}$ hydroxyalkyl), —$CH_2CH(OH)CH_2NR_xR_y$, —$C(O)H$, —$C(O)(C_{1-6}$ alkyl), —$C(O)(C_{1-4}$ hydroxyalkyl), —$C(O)(C_{1-3}$ fluoroalkyl), —$C(O)(C_{1-3}$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)(CR_xR_x)_{0-2}O(CR_xR_x)_{1-2}NR_yR_y$, —$C(O)CR_xR_xS(O)_2(C_{1-3}$ alkyl), —$C(O)CR_xR_xNR_xS(O)_2(C_{1-3}$ alkyl), —$C(O)CR_xR_xOC(O)(C_{1-3}$ alkyl), —$C(O)(CR_xR_x)_{0-3}NR_yR_y$, —$C(O)(CR_xR_x)_{0-1}NR_x(C_{1-3}$ cyanoalkyl), —$C(O)(CR_xR_x)_{0-2}NR_y(C_{1-6}$ hydroxyalkyl), —$C(O)(CR_xR_x)_{1-2}NR_x(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x(CH_2)_{1-2}O(C_{1-3}$ hydroxyalkyl), —$C(O)(CR_xR_x)_{0-2}NR_x(CH_2)_{1-2}NR_xC(O)(C_{1-2}$ alkyl), —$C(O)(CR_xR_x)_{0-2}NR_x((CR_xR_x)_{1-2}O(C_{1-2}$ alkyl)), —$C(O)(CR_xR_x)_{0-2}N((CR_xR_x)_{1-2}O(C_{1-2}$ alkyl))$_2$, —$C(O)(CR_xR_x)_{0-2}NR_x(CR_xR_x)_{1-3}NR_xR_x$, —$C(O)CR_x(NH_2)(CR_xR_x)_{1-4}NR_xR_x$, —$C(O)CR_x(NH_2)(CR_xR_x)_{1-4}NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-3}N((CH_2)_{0-1}C(O)(C_{1-3}$ alkyl))$_2$, —$C(O)(CR_xR_x)_{0-1}NR_x(CH_2)_{0-1}C(O)(C_{1-3}$ cyanoalkyl), —$C(O)(CR_xR_x)_{0-2}NR_x(CH_2)_{1-2}C(O)NR_yR_y$, —$C(O)(CR_xR_x)_{1-3}C(O)NR_yR_y$, —$C(O)(CR_xR_x)_{1-3}S(O)_2NR_yR_y$, —$C(O)(CR_xR_x)_{0-2}NR_x(CHR_y(CH_2OH))$, —$(CR_xR_x)_{1-2}C(O)NR_yR_y$, —$CH(CN)C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)$(C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(C_{1-3}$ alkyl), —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CR_xR_x)_{0-3}S(O)_2(C_{1-4}$ alkyl), —$(CH_2)_{0-2}S(O)_2(C_{1-3}$ fluoroalkyl), —$(CR_xR_x)_{0-2}S(O)_2NR_yR_y$, —$(CR_xR_x)_{0-2}NR_xS(O)_2(C_{1-3}$ alkyl), —$C(O)C(O)OH$, —$C(O)C(O)NR_yR_y$, or —$(O)C(O)NR_y(CR_xR_x)_{1-2}NR_yR_y$; and $R_1$, $R_2$, $R_4$, $R_5$, $R_x$, $R_y$, m, n, and p are defined in the first aspect or the second aspect. Also included are compounds in which m is zero and n is zero.

One embodiment provides a compound of Formula (I) or a salt thereof, wherein $R_3$ is H, $C_{1-6}$ alkyl, $C_{1-3}$ fluoroalkyl, $C_{1-3}$ cyanoalkyl, $C_{1-5}$ hydroxyalkyl, —$C=N(NR_xR_x)$, —$(CR_xR_x)_{1-2}O(C_{1-2}$ alkyl), —$(CR_xR_x)_{1-4}O(CR_xR_x)_{1-3}O(C_{1-3}$ alkyl), —$CH_2CH(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_xR_y$, —$(CR_xR_x)_{1-3}NR_x(C_{1-4}$ hydroxyalkyl), —$CH_2CH(OH)CH_2NR_xR_y$, —$C(O)(C_{1-6}$ alkyl), —$C(O)(C_{1-4}$ hydroxyalkyl), —$C(O)(C_{1-3}$ fluoroalkyl), —$C(O)(C_3$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)(CH_2)_{0-2}O(CH_2)_{1-2}HR_yR_y$, —$C(O)CR_xR_xS(O)_2(C_{1-2}$ alkyl), —$C(O)CR_xR_xNR_xS(O)_2(C_{1-2}$ alkyl), —$C(O)CR_xR_xOC(O)(C_{1-3}$ alkyl), —$C(O)(CR_xR_x)_{0-2}NR_yR_y$, —$C(O)(CR_xR_x)_{1-2}NR_x(C_{1-2}$ cyanoalkyl), —$C(O)(CR_xR_x)_{0-2}NR_y(C_{1-6}$ hydroxyalkyl), —$C(O)(CR_xR_x)_{0-2}NR_x(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x((CR_xR_x)_{1-2}O(C_{1-2}$ alkyl))$, —$C(O)(CR_xR_x)_{0-1}NR_x(CH_2)_{1-2}O(C_{1-3}$ hydroxyalkyl), —$C(O)(CR_xR_x)_{0-1}NR_x(CH_2)_{1-2}NR_xC(O)(C_{1-2}$ alkyl), —$C(O)(CR_xR_x)_{0-2}NR_x((CR_xR_x)_{1-2}O(C_{1-2}$ alkyl))$, —$C(O)(CR_xR_x)_{0-1}NR_x(CR_xR_x)_{1-3}NR_xR_x$, —$C(O)CR_x(NH_2)(CR_xR_x)_{1-4}NR_xR_x$, —$C(O)CR_x(NH_2)(CR_xR_x)_{1-4}NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-1}NR_x(CH_2)_{0-1}C(O)(C_{1-3}$ cyanoalkyl), —$C(O)(CR_xR_x)_{0-2}NR_x(CH_2)_{1-2}C(O)NR_yR_y$, —$C(O)(CR_xR_x)_{0-2}NR_x(CHR_y(OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_x(C_{1-3}$ cyanoalkyl), —$CH(CN)C(O)NR_yR_y$, —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)$(C_{1-3}$ hydroxyalkyl), —$(CH_2)_{1-2}C(O)NR_x(CH_2)_{1-2}C(O)NR_xR_x$, —$(CH_2)_{1-2}S(O)_2NR_x(CH_2)_{1-2}S(C_{1-2}$ alkyl), —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CR_xR_x)_{1-3}S(O)_2(C_{1-4}$ alkyl), —$(CH_2)_{0-2}S(O)_2(C_{1-3}$ fluoroalkyl), —$(CH_2)_{1-2}S(O)_2NR_yR_y$, —$C(O)C(O)OH$, —$C(O)C(O)NR_yR_y$, or —$C(O)C(O)NR_y(CR_xR_x)_{1-2}NR_yR_y$; and $R_1$, $R_2$, $R_4$, $R_5$, m, n, and p are defined in the first aspect or the second aspect. Also included are compounds in which m is zero and n is zero.

One embodiment provides a compound of Formula (I) or a salt thereof, wherein $R_3$ is —$C(O)CH_2$(2-oxa-6-azaspiro[3.3]heptanyl), —$C(O)CH_2$(piperazinonyl), —$C(O)CH_2$(piperazinyl), —$C(O)CH_2$(piperidinyl), —$C(O)CH_2$(pyrimidinyl), —$C(O)CH_2$(pyrrolidinyl), —$C(O)CH_2$(tetrahydropyranyl), —$C(O)CH_2$(tetrazolyl), —$C(O)CH_2$(thiazolyl), —$C(O)CH_2CH_2$(azepanyl), —$C(O)CH_2CH_2$(azetidinyl), —$C(O)CH_2CH_2$(dioxothiomorpholinyl), —$C(O)CH_2CH_2$(morpholinyl), —$C(O)CH_2CH_2$(piperidinonyl), —$C(O)CH_2CH_2$(piperidinyl), —$C(O)CH_2CH_2$(pyrrolidinonyl), —$C(O)CH_2CH_2$(pyrrolidinyl), —$C(O)CH_2CH(CH_3)$(oxetanyl), —$C(O)NH$(piperidinyl), —$C(O)NH$(pyrrolidinyl, —$C(O)CH_2NH$(cyclopropyl), —$C(O)CH_2NH$(cyclobutyl), —$C(O)CH_2NH$(cyclohexyl), —$C(O)CH_2NH$(oxetanyl), —$C(O)CH_2N(CH_3)$(cyclopropyl), —$C(O)CH_2N(CH_3)$(cyclohexyl), —$C(O)CH_2CH_2NH$(cyclopentyl), —$C(O)CH_2CH_2NH$(cyclohexyl), —$C(O)CH_2CH_2N(CH_3)$(cyclohexyl), —$C(O)CH_2N(CH_2CH_2OH)$(cyclopropyl), —$C(O)CH_2CH_2N(CH_2CH_2OH)$ (cyclopropyl), —C(O)CH$_2$CH$_2$NH(CH$_2$(cyclopropyl)), —C(O)CH$_2$CH$_2$NH(CH$_2$(tetrahydrofuranyl)), —C(O)CH$_2$NH(CH$_2$(cyclopropyl)), —C(O)CH$_2$NH(CH$_2$(cyclohexyl)), —C(O)CH$_2$NH(CH$_2$(tetrahydrofuranyl)), —C(O)NH(CH$_2$(piperidinyl)), —C(O)NH(CH$_2$(pyrrolidinyl)), —C(O)NH(CH$_2$CH$_2$(morpholinyl)), —C(O)NH(CH$_2$CH$_2$(piperazinyl)), —C(O)NH(CH$_2$CH$_2$(piperidinyl)), —C(O)NH(CH$_2$CH$_2$(pyrrolidinyl)), —C(O)O(azetidinyl), —C(O)O(piperidinyl), —C(O)O(pyrrolidinyl), —C(O)OCH$_2$(azetidinyl), —C(O)OCH$_2$(piperidinyl), —C(O)OCH$_2$(pyrrolidinyl), —C(O)OCH$_2$CH$_2$(dioxothiomorpholinyl), —C(O)OCH$_2$CH$_2$(imidazolyl), —C(O)OCH$_2$CH$_2$(morpholinyl), —C(O)OCH$_2$CH$_2$(piperazinyl), —C(O)OCH$_2$CH$_2$(piperidinyl), —C(O)OCH$_2$CH$_2$(pyrrolidinyl), —CH$_2$(cyclopropyl), —CH$_2$(dioxotetrahydrothiopyranyl), —CH$_2$(imidazolyl), —CH$_2$(isoxazolyl), —CH$_2$(morpholinyl), —CH$_2$(oxadiazolyl), —CH$_2$(oxazolyl), —CH$_2$(oxetanyl), —CH$_2$(phenyl), —CH$_2$(pyrazinyl), —CH$_2$(pyrazolyl), —CH$_2$(pyridazinyl), —CH$_2$(pyrimidinyl), —CH$_2$(tetrazolyl), —CH$_2$(thiadiazolyl), —CH$_2$(thiazolyl), —CH$_2$(triazolonyl), —CH$_2$(triazolyl), —CH(CH$_3$)(pyrazolyl), —CH(CH$_3$)(pyridazinyl), —CH(CH$_3$)(pyrimidinyl), —CH$_2$CH$_2$(dioxoisothiazolidinyl), —CH(CN)(oxetanyl), —CH(CH$_3$)CH$_2$S(O)$_2$(morpholinyl), —CH(CH$_3$)CH$_2$S(O)$_2$(piperidinyl), —CH$_2$C(O)(morpholinyl), —CH$_2$C(O)(2-oxa-6-azaspiro[3.3]heptanyl), —CH$_2$C(O)(azetidinyl), —CH$_2$C(O)(dioxidothiadiazinanyl), —CH$_2$C(O)(dioxidothiazolidinyl), —CH$_2$C(O)(dioxidothiomorpholinyl), —CH$_2$C(O)(dioxothiomorpholinyl), —CH$_2$C(O)(2-oxa-6-azaspiro[3.3]heptanyl), —CH$_2$C(O)(piperazinonyl), —CH$_2$C(O)(piperazinyl), —CH$_2$C(O)(piperidinyl), —CH$_2$C(O)(pyrrolidinyl), —CH$_2$C(O)NHCH(CH$_2$CH$_2$OH)(cyclopropyl), —CH$_2$C(O)N(CH$_2$CH$_2$OH)(cyclopropyl), —CH$_2$C(O)N(CH$_3$)(cyclopropyl), —CH$_2$C(O)N(CH$_3$)(tetrahydrofuranyl), —CH$_2$C(O)N(CH$_3$)(tetrahydropyranyl), —CH$_2$C(O)N(CH$_3$)CH$_2$CH$_2$(cyclopentyl), —CH$_2$C(O)N(CH$_3$)CH$_2$CH$_2$(pyrazolyl), —CH$_2$C(O)NH(azetidinyl), —CH$_2$C(O)NH(CH$_2$(oxetanyl)), —CH$_2$C(O)NH(cyclobutyl), —CH$_2$C(O)NH(cyclopropyl), —CH$_2$C(O)NH(oxetanyl), —CH$_2$C(O)NH(tetrahydropyranyl), —CH$_2$CH$_2$S(O)$_2$(morpholinyl), or —CH$_2$CH$_2$S(O)$_2$(phenyl); and R$_1$, R$_2$, R$_4$, R$_5$, m, n, and p are defined in the first aspect or the second aspect. Also included are compounds in which m is zero and n is zero.

One embodiment provides a compound of Formula (I) or a salt thereof, wherein R$_3$ is H, C$_{1-5}$ alkyl, C$_{2-3}$ fluoroalkyl, C$_{1-3}$ cyanoalkyl, C$_{2-5}$ hydroxyalkyl, —CH$_2$CH$_2$OCH$_3$, —CH$_2$N(CH$_3$)$_2$, —CH$_2$CH$_2$NH(CH$_3$), —C=N(NH$_2$), —C(O)CH$_3$, —C(O)CH(CH$_2$CH$_3$)$_2$, —C(O)CH$_2$CF$_3$, —C(O)CH$_2$CH$_2$OH, —C(O)CH(CH$_3$)OH, —C(O)CH$_2$CH(CH$_3$)OH, —C(O)CH$_2$C(CH$_3$)$_2$OH, —C(O)CH$_2$CN, —C(O)CH$_2$CH$_2$CN, —C(O)OC(CH$_3$)$_3$, —C(O)CH$_2$OCH$_3$, —C(O)CH$_2$CH$_2$OCH$_3$, —C(O)OCH$_2$CH$_2$NH$_2$, —C(O)OCH$_2$CH$_2$N(CH$_3$)$_2$, —C(O)OCH$_2$CH$_2$N(CH$_2$CH$_3$)$_2$, —C(O)CH$_2$S(O)$_2$CH$_3$, —C(O)CH$_2$CH$_2$S(O)$_2$CH$_3$, —C(O)CH$_2$NHS(O)$_2$CH$_3$, —C(O)NH(CH$_2$C(CH$_3$)$_3$), —C(O)CH$_2$NH(CH$_3$), —C(O)CH$_2$NH(CH$_2$CH$_3$), —C(O)CH$_2$NH(CH$_2$CH$_2$CH$_3$), —C(O)CH$_2$NH(CH$_2$CH$_2$CH$_3$), —C(O)CH$_2$NH(CH(CH$_3$)$_2$), —C(O)CH$_2$NH(CH$_2$CH(CH$_3$)$_2$), —C(O)CH$_2$NH(C(CH$_3$)$_3$), —C(O)CH$_2$N(CH$_3$)$_2$, —C(O)CH$_2$N(CH$_3$)(CH$_2$CH$_3$), —C(O)CH$_2$N(CH$_3$)(CH$_2$CH$_2$CH$_3$), —C(O)CH$_2$N(CH$_3$)(CH(CH$_3$)$_2$), —C(O)CH$_2$N(CH$_3$)(CH$_2$CH(CH$_3$)$_2$), —C(O)CH$_2$N(CH$_2$CH$_3$)$_2$, —C(O)CH$_2$NH(CH$_3$), —C(O)CH$_2$CH$_2$NH(CH$_3$), —C(O)CH$_2$NH(CH$_2$CH$_2$CH$_3$), —C(O)CH$_2$CH$_2$NH(CH$_2$CH$_2$CH$_3$), —C(O)CH$_2$CH$_2$NH(CH(CH$_3$)$_2$), —C(O)CH$_2$CH$_2$NH(CH$_2$C(CH$_3$)$_3$), —C(O)CH$_2$CH$_2$N(CH$_3$)$_2$, —C(O)CH$_2$CH$_2$N(CH$_3$)(CH$_2$CH$_3$), —C(O)CH$_2$CH$_2$N(CH$_3$)(CH$_2$CH$_2$CH$_3$), —C(O)CH$_2$CH$_2$N(CH$_3$)(CH(CH$_3$)$_2$), —C(O)CH(CH$_3$)NH(CH$_3$), —C(O)CH$_2$NH(CH$_2$CN), —C(O)CH$_2$N(CH$_3$)(CH$_2$CH$_2$CN), —C(O)CH$_2$NH(CH$_2$C(O)NH$_2$), —C(O)CH$_2$N(CH$_3$)(CH$_2$C(O)N(CH$_3$)$_2$), —C(O)CH$_2$CH$_2$NH(CH$_2$C(O)NH$_2$), —C(O)CH$_2$CH$_2$N(CH$_3$)CH$_2$C(O)N(CH$_3$)$_2$, —C(O)CH$_2$NH(CH$_2$CH$_2$OH), —C(O)CH$_2$N(CH$_3$)(CH$_2$CH$_2$OH), —C(O)CH$_2$NH(CH$_2$CH$_2$OH), —C(O)CH$_2$CH$_2$N(CH$_3$)(CH$_2$CH$_2$OH), —C(O)CH$_2$NH(CH$_2$CH$_2$F), —C(O)CH$_2$NH(CH$_2$CF$_3$), —C(O)CH$_2$CH$_2$NH(CH$_2$CH$_2$F), —C(O)CH$_2$NH(CH$_2$CH$_2$OCH$_3$), —C(O)CH$_2$N(CH$_3$)(CH$_2$CH$_2$OCH$_3$), —C(O)CH$_2$CH$_2$NH(CH$_2$CH$_2$OCH$_3$), —C(O)CH$_2$CH$_2$N(CH$_3$)(CH$_2$CH$_2$OCH$_3$), —C(O)CH$_2$N(CH$_2$CH$_2$OCH$_3$)$_2$, —C(O)CH$_2$CH$_2$CH$_2$S(O)$_2$NH$_2$, —CH$_2$C(O)NH$_2$, —CH$_2$C(O)NH(CH$_3$), —CH$_2$C(O)N(CH$_3$)$_2$, —CH$_2$C(O)NH(CH$_2$CH$_3$), —CH$_2$C(O)N(CH$_3$)(CH$_2$CH$_3$), —CH$_2$C(O)N(CH$_2$CH$_3$)$_2$, —CH$_2$C(O)NH(CH$_2$CH$_2$CH$_3$), —CH$_2$C(O)NH(CH(CH$_3$)$_2$), —CH(CN)C(O)N(CH$_3$)$_2$, —CH$_2$C(O)NH(CH$_2$CH$_2$CF$_3$), —CH$_2$C(O)N(CH$_3$)(CH$_2$CH$_2$OH), —CH$_2$C(O)N(CH$_3$)(CH$_2$CH$_2$OH), —CH$_2$C(O)N(CH$_2$CH$_3$)(CH$_2$CH$_2$OH), —CH$_2$C(O)N(CH$_2$CH$_2$CH$_3$)(CH$_2$CH$_2$OH), —CH$_2$C(O)N(CH$_3$)(CH$_2$CH$_2$OH), —CH$_2$C(O)NH(CH$_2$C(CH$_3$)$_2$OH), —CH$_2$C(O)N(CH$_2$CH(CH$_3$)CH$_2$CH$_3$)(CH$_2$CH$_2$OH), —CH$_2$C(O)NH(CH$_2$CH$_2$CN), —CH$_2$C(O)N(CH$_3$)(CH$_2$CH$_2$CN), —CH$_2$C(O)N(CH$_3$)(CH$_2$CH$_2$OCH$_3$), —CH(CH$_3$)CH$_2$S(O)$_2$(CH$_2$CH$_2$CH$_2$CH$_3$), —CH$_2$CH$_2$S(O)$_2$NH$_2$, —CH$_2$CH$_2$S(O)$_2$NH(CH$_3$), —CH$_2$CH$_2$S(O)$_2$N(CH$_3$)$_2$, —CH(CH$_3$)CH$_2$S(O)$_2$N(CH$_2$CH$_3$)$_2$, —CH$_2$CH$_2$NHS(O)$_2$CH$_3$, —CH$_2$CH$_2$N(CH$_3$)S(O)$_2$CH$_3$, —CH$_2$C(O)NH(CH$_2$CH$_2$SCH$_3$), —C(O)NH(CH$_2$CH$_2$NH$_2$), —C(O)N(CH$_3$)CH$_2$CH$_2$NH$_2$, —C(O)NH(CH$_2$CH$_2$N(CH$_3$)$_2$), —C(O)NH(CH$_2$CH$_2$CH$_2$NH$_2$), —CH$_2$CH$_2$S(O)$_2$CH$_3$, —CH$_2$CH$_2$CH$_2$S(O)$_2$CH$_3$, or —CH(CH$_3$)CH$_2$S(O)$_2$CH$_3$; and R$_1$, R$_2$, R$_4$, R$_5$, m, n, and p are defined in the first aspect or the second aspect. Also included are compounds in which m is zero and n is zero.

One embodiment provides a compound of Formula (I) or a salt thereof, wherein each R$_4$ is independently F, —OH, C$_{1-2}$ alkyl, or —OCH$_3$; or two R$_4$ attached to the same carbon atom form =O; and R$_1$, R$_2$, R$_3$, R$_5$, m, n and p are defined in the first aspect. Included in this embodiment are compounds in which each R$_4$ is independently F, —CH$_3$, or —OCH$_3$. Also included are compounds in which n is zero.

One embodiment provides a compound of Formula (I) or a salt thereof, wherein each R$_5$ is independently F, Cl, —CN, —CH$_3$, —CF$_3$, or —OCH$_3$; and R$_1$, R$_2$, R$_3$, R$_4$, m, n and p are defined in the first aspect. Included in this embodiment are compounds in which each R$_5$ is independently F, —CN, —CH$_3$, or —CF$_3$. Also included are compounds in which m is zero. Further, included are compounds in which m is zero and n is 1.

One embodiment provides a compound of Formula (I) or a salt thereof, wherein m is 2, 3, or 4; two R$_4$, each attached to a different carbon atom adjacent to the nitrogen atom in the piperidinyl ring, can form a —CH$_2$CH$_2$— bridge; and R$_1$, R$_2$, R$_3$, R$_5$, m, n, and p are defined in the first aspect. The compounds of this embodiment have the structure of Formula (Ia):

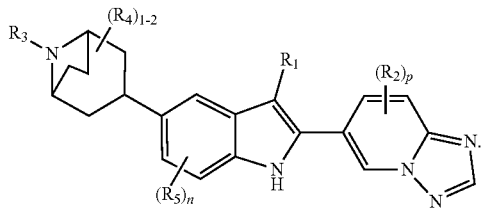

(Ia)

Included in this embodiment are compounds in which $R_1$ is —CH(CH$_3$)$_2$; each $R_2$ is —CH$_3$; $R_3$ is —CH$_2$CN, —CH$_2$C(O)N(CH$_3$)$_2$, or —CH$_2$CH$_2$S(O)$_2$CH$_3$; m is 2; n is zero, and p is zero, 1, or 2. Also included in this embodiment are compounds selected from 2-(3-(2-(7,8-dimethyl-[1,2,4]triazolo[1,5-a]pyridin-6-yl)-3-isopropyl-1H-indol-5-yl)-8-azabicyclo[3.2.1]octan-8-yl)acetonitrile (981); 2-(3-(2-(7,8-dimethyl-[1,2,4]triazolo[1,5-a]pyridin-6-yl)-3-isopropyl-1H-indol-5-yl)-8-azabicyclo[3.2.1]octan-8-yl)-N,N-dimethylacetamide (982-983); and 6-(3-isopropyl-5-(8-(2-(methylsulfonyl)ethyl)-8-azabicyclo[3.2.1]octan-3-yl)-1H-indol-2-yl)-7,8-dimethyl-[1,2,4]triazolo[1,5-a]pyridine (984-985).

One embodiment provides a compound of Formula (I) or a salt thereof, wherein: $R_1$ is H, Cl, —CN, $C_{1-4}$ alkyl, or $C_{1-2}$ fluoroalkyl; each $R_2$ is independently F, Cl, —CN, —OH, $C_{1-3}$ alkyl, —CD$_3$, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —O(C$_{1-4}$ alkyl), $C_{1-2}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —C(O)NR$_y$R$_y$, —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$(CH$_2$-cyclopropyl), $C_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl); $R_3$ is: (a) -L$_1$-A; or (b) H, $C_{1-6}$ alkyl, $C_{1-3}$ fluoroalkyl, $C_{1-3}$ cyanoalkyl, $C_{1-5}$ hydroxyalkyl, —C≡N (NR$_x$R$_x$), —(CR$_x$R$_x$)$_{1-2}$O(C$_{1-2}$ alkyl), —(CR$_x$R$_x$)$_{1-4}$O(CR$_x$R$_x$)$_{1-3}$O(C$_{1-3}$ alkyl), —CH$_2$CH(OH)CH$_2$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CR$_x$R$_x$)$_{0-3}$NR$_x$R$_y$, —(CR$_x$R$_x$)$_{1-3}$NR$_x$(C$_{1-4}$ hydroxyalkyl), —CH$_2$CH(OH)CH$_2$NR$_x$R$_y$, —C(O)(C$_{1-6}$ alkyl), —C(O)(C$_{1-4}$ hydroxyalkyl), —C(O)(C$_{1-3}$ fluoroalkyl), —C(O)(C$_{1-3}$ chloroalkyl), —C(O)(C$_{1-3}$ cyanoalkyl), —(CR$_x$R$_x$)$_{0-3}$C(O)OH, —C(O)(CH$_2$)$_{0-2}$O(C$_{1-4}$ alkyl), —C(O)(CR$_x$R$_x$)$_{0-2}$O(CR$_x$R$_x$)$_{1-2}$O(C$_{1-3}$ alkyl), —C(O)(CH$_2$)$_{0-2}$O(CH$_2$)$_{1-2}$HR$_y$R$_y$, —C(O)CR$_x$R$_x$S(O)$_2$(C$_{1-2}$ alkyl), —C(O)CR$_x$R$_x$NR$_x$S(O)$_2$(C$_{1-2}$ alkyl), —C(O)CR$_x$R$_x$OC(O)(C$_{1-3}$ alkyl), —C(O)(CR$_x$R$_x$)$_{0-2}$NR$_y$R$_y$, —C(O)(CR$_x$R$_x$)$_{0-2}$NR$_x$(C$_{1-2}$ cyanoalkyl), —C(O)(CR$_x$R$_x$)$_{0-2}$NR$_y$(C$_{1-6}$ hydroxyalkyl), —C(O)(CR$_x$R$_x$)$_{0-2}$NR$_y$(C$_{1-3}$ fluoroalkyl), —C(O)(CR$_x$R$_x$)$_{0-1}$NR$_x$(C$_{1-5}$ hydroxy-fluoroalkyl), —C(O)(CR$_x$R$_x$)$_{0-1}$NR$_x$((CR$_x$R$_x$)$_{1-2}$(C$_{1-2}$ alkyl)), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-2}$NR$_x$((CR$_x$R$_x$)$_{1-2}$O(C$_{1-2}$ alkyl)), —C(O)(CR$_x$R$_x$)$_{0-1}$NR$_x$(CR$_x$R$_x$)$_{1-3}$NR$_x$R$_x$, —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)(C$_{1-3}$ alkyl), —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-2}$NR$_x$(CH$_2$)$_{1-2}$C(O)NR$_y$R$_y$, —C(O)(CR$_x$R$_x$)$_{0-2}$NR$_x$(CHR$_y$(CH$_2$OH)), —(CR$_x$R$_x$)$_{1-2}$C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_x$(C$_{1-3}$ cyanoalkyl), —CH(CN)C(O)NR$_y$R$_y$, —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)(C$_{1-3}$ hydroxyalkyl), —(CH$_2$)$_{1-2}$C(O)NR$_x$(CH$_2$)$_{1-2}$C(O)NR$_x$R$_x$, —(CH$_2$)$_{1-2}$S(O)$_2$NR$_x$(CH$_2$)$_{1-2}$S(C$_{1-2}$ alkyl), —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CR$_x$R$_x$)$_{1-3}$S(O)$_2$(C$_{1-4}$ alkyl), —(CH$_2$)$_{0-2}$S(O)$_2$(C$_{1-3}$ fluoroalkyl), —(CH$_2$)$_{1-2}$S(O)$_2$NR$_y$R$_y$, —C(O)C(O)OH, —C(O)C(O)NR$_y$R$_y$, or —C(O)C(O)NR$_y$(CR$_x$R$_x$)$_{1-2}$NR$_y$R$_y$; L$_1$ is a bond, —CR$_x$R$_x$—, —CR$_x$R$_x$C(O)—, —CR$_x$R$_x$C(O)NR$_x$—, or —C(O)(CR$_x$R$_x$)$_{0-2}$—; A is a ring selected from azetidinyl, C$_{3-6}$ cycloalkyl, dioxotetrahydrothiopyranyl, dioxidothiadiazinanyl, dioxidothiomorpholinyl, furanyl, imidazolyl, isoquinolinyl, morpholinyl, oxazolyl, 2-oxa-6-azaspiro[3.3]heptanyl, oxetanyl, phenyl, piperazinyl, piperidinyl, pyrazinyl, pyrazolyl, pyridinyl, pyrrolidinyl, pyrrolyl, quinolinyl, tetrahydrofuranyl, tetrahydropyranyl, tetrazolyl, thiadiazolyl, thiazolyl, and triazolyl, each substituted with -L$_2$-R$_a$ and zero to 4 R$_b$; L$_2$ is a bond or —CR$_x$R$_x$—; R$_a$ is: (a) H, —CN, —OH, C$_{1-3}$ alkyl, C$_{1-2}$ fluoroalkyl, C$_{1-3}$ hydroxyalkyl, —(CH$_2$)$_{1-2}$O(C$_{1-3}$ alkyl), —(CR$_x$R$_x$)$_{1-3}$NHC(O)O(C$_{1-4}$ alkyl), —(CR$_x$R$_x$)$_{1-3}$NH$_2$, —(CR$_x$R$_x$)$_{13}$NR$_x$(C$_{1-4}$ alkyl), —O(C$_{1-2}$ fluoroalkyl), —S(O)$_2$NR$_x$R$_x$, —NHS(O)$_2$(C$_{1-3}$ alkyl), —NR$_x$R$_x$, —NR$_x$(C$_{1-4}$ alkyl), —(CR$_x$R$_x$)$_{1-2}$C(O)OH, —C(O)OH, —C(O)(C$_{1-3}$ alkyl), —C(O)O(C$_{1-3}$ alkyl), —C(O)NR$_x$(C$_{1-2}$ alkyl), —C(O)N(C$_{1-3}$ alkyl)$_2$, —C(O)NR$_x$CH$_2$C(O)NR$_x$R$_x$, or —C(O)NR$_x$CH$_2$CH$_2$NHC(O)(C$_{1-3}$ alkyl); (b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or (c) A$_1$, —CH$_2$A$_1$, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl); each R$_4$ is independently F, —OH, C$_{1-2}$ alkyl, or —OCH$_3$; or two R$_4$ attached to the same carbon atom form =O; R$_5$ is F, Cl, —CN, C$_2$ alkyl, or —OCH$_3$; each R$_b$ is independently —CH$_3$ or —CF$_3$; each R$_x$ is independently H or —CH$_3$; each R$_y$ is independently H or C$_{1-5}$ alkyl; m is zero, 1, or 2; n is zero or 1; and p is zero, 1, or 2.

One embodiment provides a compound of Formula (I) or a salt thereof, wherein: $R_1$ is —CH(CH$_3$)$_2$; each $R_2$ is independently —CH$_3$, —OCH$_3$, or —CH$_2$OCH$_3$; $R_3$ is H, —CH(CH$_3$)$_2$, —CH(CH$_3$)$_2$, —CH$_2$CH(CH$_3$)$_2$, —CH$_2$CN, —CH$_2$CH$_2$CN, —CH$_2$CH$_2$CH$_2$CN, —CH$_2$C(CH$_3$)$_2$OH, —C(O)CH$_3$, —C(O)CH(CH$_2$CH$_3$)$_2$, —C(O)CH$_2$OCH$_3$, —C(O)CH$_2$CH$_2$OCH$_3$, —C(O)CH$_2$CH(CH$_3$)OH, —C(O)CH$_2$CN, —C(O)CH$_2$CH$_2$CN, —C(O)CH(CH$_3$)NH(CH$_3$), —C(O)CH$_2$NH(CH$_3$), —C(O)CH$_2$N(CH$_3$)$_2$, —C(O)CH$_2$NHCH$_2$CH$_2$CH$_3$, —C(O)CH$_2$NHCH(CH$_3$)$_2$, —C(O)CH$_2$NHC(CH$_3$)$_3$, —C(O)CH$_2$N(CH$_3$)CH(CH$_3$)$_2$, —C(O)CH$_2$NHCH$_2$CH$_2$OCH$_3$, —CH$_2$C(O)NH$_2$, —CH$_2$C(O)NH(CH$_3$), —CH$_2$C(O)N(CH$_3$)CH$_2$CH$_3$, —CH$_2$C(O)NHCH$_2$CH$_2$CH$_3$, —CH$_2$C(O)NH(CH(CH$_3$)$_2$), —CH$_2$C(O)N(CH$_3$)$_2$, —CH$_2$C(O)N(CH$_2$CH$_3$)$_2$, —CH$_2$CH$_2$S(O)$_2$CH$_3$, —CH$_2$CH$_2$S(O)$_2$NH$_2$, —CH$_2$C(O)NH(cyclobutyl), —CH$_2$C(O)NH(cyclopropyl), —CH$_2$C(O)NH(methyloxetanyl), —CH$_2$C(O)N(CH$_3$)(cyclopropyl), oxetanyl, tetrahydropyranyl, dioxotetrahydrothiopyranyl, —CH$_2$(oxazolyl), —CH₂(pyrazolyl), —CH₂(tetrazolyl), —CH₂(triazolyl), —CH₂(methyltriazolyl), —CH₂C(O)(2-oxa-6-azaspiro[3.3]heptanyl), —CH₂C(O)(azetidinyl), —CH₂C(O)(dioxidothiadiazinanyl), —CH₂C(O)(dioxidothiomorpholinyl), —CH₂C(O)(morpholinyl), —CH₂C(O)(methoxyethylpiperazinyl), —CH₂C(O)(piperidinyl), —CH₂C(O)(hydroxypiperidinyl), —CH₂C(O)(pyrrolidinyl), —CH₂C(O)(hydroxypyrrolidinyl), —C(O)(azetidinyl), —C(O)(methylcyclopropyl), —C(O)(methyloxetanyl), or —C(O)CH₂(morpholinyl); m is zero; n is zero; and p is zero, 1 or 2.

One embodiment provides a compound of Formula (I) or a salt thereof, wherein R₁ is H, Cl, —CN, C₁₋₄ alkyl, C₁₋₂ fluoroalkyl, C₁₋₂ hydroxy-fluoroalkyl, C₃₋₆ cycloalkyl, —CH₂(C₃₋₆ cycloalkyl), —C(O)O(C₁₋₂ alkyl), or tetrahydropyranyl; and R₂, R₃, R₄, R₅, m, n, and p are defined in the first aspect. Included in this embodiment are compounds in which R₁ is H, Cl, —CN, C₁₋₄ alkyl, or C₁₋₂ fluoroalkyl. Also included in this embodiment are compounds in which R₁ is —CH(CH₃)₂. Also included are compounds in which m is zero and n is zero.

One embodiment provides a compound of Formula (I) or a salt thereof, wherein each R₂ is independently F, Cl, —CN, —OH, C₁₋₃ alkyl, C₁₋₂ fluoroalkyl, C₁₋₃ hydroxyalkyl, C₁₋₃ aminoalkyl, —(CH₂)₀₋₂O(C₁₋₂ alkyl), C₁₋₃ fluoroalkoxy, or C₃₋₆ cycloalkyl; and R₁, R₃, R₄, R₅, m, n, and p are defined in the first aspect. Included in this embodiment are compounds in which each R₂ is independently F, —CN, —OH, C₁₋₂ alkyl, or —(CH₂)₀₋₁O(C₁₋₂ alkyl). Also included in this embodiment are compounds in which each R₂ is independently —CH₃, —OCH₃, or —CH₂OCH₃. Also included are compounds in which m is zero and n is zero.

One embodiment provides a compound of Formula (I) or a salt thereof, wherein each R₂ is independently F, —CN, —OH, C₁₋₂ alkyl, or —(CH₂)₀₋₁₀(C₁₋₂ alkyl); p is zero, 1 or 2; and R₁, R₃, R₄, R₅, m, and n are defined in the first aspect. Included in this embodiment are compounds in which each R₂ is independently —CH₃, —OCH₃, or —CH₂OCH₃. Also included are compounds in which m is zero and n is zero.

One embodiment provides a compound of Formula (I) or a salt thereof, wherein the compound has one of the following structures:

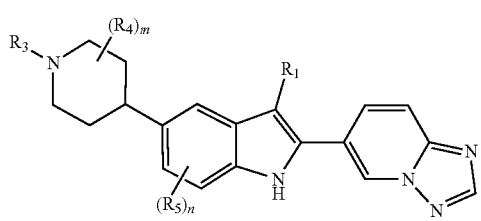
(I-1)

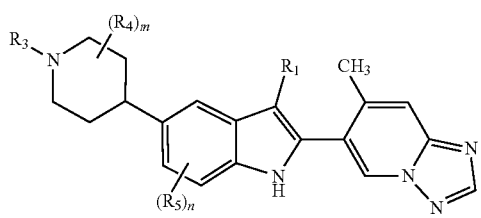
(I-2)

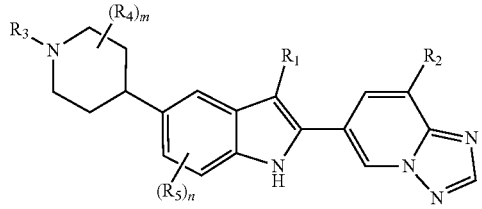
(I-3)

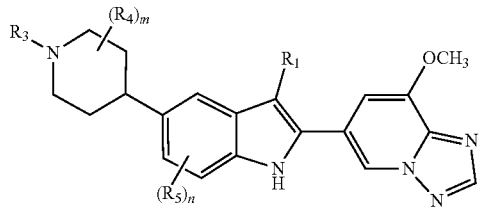
(I-4)

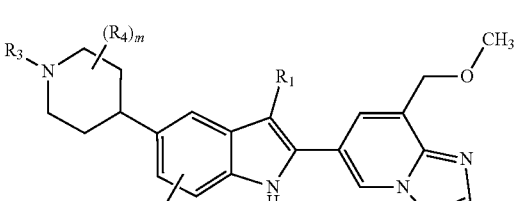
(I-5)

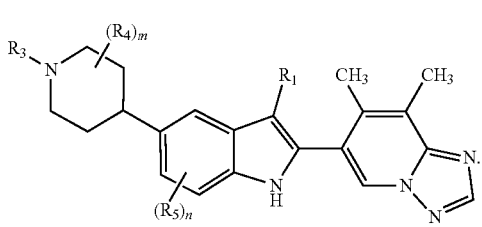
(I-6)

Included in this embodiment are compounds in which R₁ is H, Cl, —CN, C₁₋₄ alkyl, or C₁₋₂ fluoroalkyl. Also included in this embodiment are compounds in which R₁ is —CH(CH₃)₂. Also included are compounds in which m is zero and n is zero.

One embodiment provides a compound of Formula (I) or a salt thereof, wherein R₃ is -L₁-A; and R₁, R₂, R₄, R₅, L₁, A, m, n, and p are defined in the first aspect. Included in this embodiment are compounds in which L₁ is a bond, —CRₓRₓ—, —CRₓRₓC(O)—, —CRₓRₓC(O)NRₓ—, or —C(O)(CRₓRₓ)₀₋₂—; A is a ring selected from azetidinyl, C₃₋₆ cycloalkyl, dioxotetrahydrothiopyranyl, dioxidothiazinanyl, dioxidothiomorpholinyl, furanyl, imidazolyl, isoquinolinyl, morpholinyl, oxazolyl, 2-oxa-6-azaspiro[3.3]heptanyl, oxetanyl, phenyl, piperazinyl, piperidinyl, pyrazinyl, pyrazolyl, pyridinyl, pyrrolidinyl, pyrrolyl, quinolinyl, tetrahydrofuranyl, tetrahydropyranyl, tetrazolyl, thiadiazolyl, thiazolyl, and triazolyl, each substituted with -L₂-Rₐ and zero to 4 Rᵦ; L₂ is a bond or —CRₓRₓ—; Rₐ is (a) H, —CN, —OH, C₁₋₃ alkyl, C₁₋₂ fluoroalkyl, C₁₋₃ hydroxyalkyl, —(CH₂)₁₋₂O(C₁₋₃ alkyl), —(CRₓRₓ)₁₋₃NHC(O)O(C₁₋₄ alkyl), —(CRₓRₓ)₁₋₃NH₂, —(CRₓRₓ)₁₋₃NRₓ(C₁₋₄ alkyl), —O(C₁₋₂ fluoroalkyl), —S(O)₂NRₓRₓ, —NHS(O)₂(C₁₋₃ alkyl), —NRₓRₓ, —NRₓ(C₁₋₄ alkyl), —(CRₓRₓ)₁₋₂C(O)OH, —C(O)OH, —C(O)(C₁₋₃ alkyl), —C(O)O(C₁₋₃ alkyl), —C(O)NRₓ(C₁₋₂ alkyl), —C(O)N(C₁₋₃ alkyl)₂, —C(O)NRₓCH₂C(O)NRₓRₓ, or —C(O)NRₓCH₂CH₂NHC(O)(C₁₋₃ alkyl); (b) C₃₋₆ cycloalkyl or —C(O)NH(C₃₋₆ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or (c) $A_1$, —$CH_2A_1$, —C(O)$A_1$, or —C(O)NH$A_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —NR$_y$R$_x$, phenyl, trifluoromethyl-phenyl, —CH$_2$(bromophenyl), and —CH$_2$CH$_2$(pyrrolidinyl); each R$_b$ is independently —CH$_3$ or —CF$_3$; and each R$_x$ is independently H or —CH$_3$. Included in this embodiment are compounds in which $R_3$ is —CH$_2$C(O)NH(cyclobutyl), —CH$_2$C(O)NH(cyclopropyl), —CH$_2$C(O)NH(methyloxetanyl), —CH$_2$C(O)N(CH$_3$)(cyclopropyl), oxetanyl, tetrahydropyranyl, dioxotetrahydrothiopyranyl, —CH$_2$(oxazolyl), —CH$_2$(pyrazolyl), —CH$_2$(tetrazolyl), —CH$_2$(triazolyl), —CH$_2$(methyltriazolyl), —CH$_2$C(O)(2-oxa-6-azaspiro[3.3]heptanyl), —CH$_2$C(O)(azetidinyl), —CH$_2$C(O)(dioxidothiadiazinanyl), —CH$_2$C(O)(dioxidothiomorpholinyl), —CH$_2$C(O)(morpholinyl), —CH$_2$C(O)(methoxyethylpiperazinyl), —CH$_2$C(O)(piperidinyl), —CH$_2$C(O)(hydroxypiperidinyl), —CH$_2$C(O)(pyrrolidinyl), —CH$_2$C(O)(hydroxypyrrolidinyl), —C(O)(azetidinyl), —C(O)(methylcyclopropyl), —C(O)(methyloxetanyl), or —C(O)CH$_2$(morpholinyl). Also included are compounds in which m is zero and n is zero.

One embodiment provides a compound of Formula (I) or a salt thereof, wherein $R_3$ is H, $C_{1-6}$ alkyl, $C_{1-3}$ cyanoalkyl, $C_{1-4}$ hydroxyalkyl, —(CR$_x$R$_x$)$_{1-4}$O(C$_{1-3}$ alkyl), —(CR$_x$R$_x$)$_{1-4}$O(CR$_x$R$_x$)$_{1-3}$O(C$_{1-3}$ alkyl), —CH$_2$CH(OH)CH$_2$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CR$_x$R$_x$)$_{0-3}$NR$_y$R$_y$, —(CR$_x$R$_x$)$_{0-3}$NR$_x$(C$_{1-4}$ hydroxyalkyl), —CH$_2$CH(OH)CH$_2$NR$_y$R$_y$, —C(O)(C$_{1-6}$ alkyl), —C(O)(C$_{1-3}$ hydroxyalkyl), —C(O)(C$_{1-3}$ fluoroalkyl), —C(O)(C$_{1-3}$ chloroalkyl), —C(O)(C$_{1-3}$ cyanoalkyl), —(CR$_x$R$_x$)$_{0-3}$C(O)OH, —C(O)(CH$_2$)$_{1-2}$O(C$_{1-2}$ alkyl), —C(O)(CR$_x$R$_x$)$_{0-2}$O(CR$_x$R$_x$)$_{1-2}$O(C$_{1-3}$ alkyl), —C(O)CR$_x$R$_x$S(O)$_2$(C$_{1-3}$ alkyl), —C(O)CR$_x$R$_x$NR$_x$S(O)$_2$(C$_{1-3}$ alkyl), —C(O)CR$_x$R$_x$OC(O)(C$_{1-3}$ alkyl), —C(O)(CR$_x$R$_x$)$_{0-3}$NR$_y$R$_y$, —C(O)(CR$_x$R$_x$)$_{0-1}$NR$_x$(C$_{1-3}$ cyanoalkyl), —C(O)(CR$_x$R$_x$)$_{0-2}$NR$_y$(C$_{1-6}$ hydroxyalkyl), —C(O)(CR$_x$R$_x$)$_{0-1}$NR$_x$(C$_{1-3}$ fluoroalkyl), —C(O)(CR$_x$R$_x$)$_{0-1}$NR$_x$(C$_{1-5}$ hydroxy-fluoroalkyl), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-1}$NR$_x$((CR$_x$R$_x$)$_{1-2}$O(C$_{1-2}$ alkyl)), —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)(C$_{1-3}$ alkyl), —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-1}$NR$_x$(CH$_2$)$_{1-2}$C(O)NR$_y$R$_y$, —C(O)(CR$_x$R$_x$)$_{0-1}$NR$_x$(CHR$_x$(CH$_2$OH)), —(CR$_x$R$_x$)$_{1-2}$C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_y$(C$_{1-3}$ cyanoalkyl), —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)(C$_{1-3}$ hydroxyalkyl), —(CH$_2$)$_{1-2}$C(O)NR$_x$(CH$_2$)$_{1-2}$C(O)NR$_x$R$_x$, —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CH$_2$)$_{1-2}$S(O)$_2$(C$_{1-4}$ alkyl), —(CH$_2$)$_{0-2}$S(O)$_2$(C$_{1-3}$ fluoroalkyl), —(CH$_2$)$_{1-2}$S(O)$_2$NR$_x$R$_x$, —C(O)C(O)OH, —C(O)C(O)NR$_y$R$_y$, or —C(O)C(O)NR$_y$(CR$_x$R$_x$)$_{1-2}$NR$_y$R$_y$; and $R_1$, $R_2$, $R_4$, $R_5$, $R_x$, $R_y$, m, n, and p are defined in the first aspect. Included in this embodiment are compounds in which $R_3$ is H, —CH(CH$_3$)$_2$, —CH(CH$_3$)$_2$, —CH$_2$CH(CH$_3$)$_2$, —CH$_2$CN, —CH$_2$CH$_2$CN, —CH$_2$CH$_2$CH$_2$CN, —CH$_2$C(CH$_3$)$_2$OH, —C(O)CH$_3$, —C(O)CH(CH$_2$CH$_3$)$_2$, —C(O)CH$_2$OCH$_3$, —C(O)CH$_2$CH$_2$OCH$_3$, —C(O)CH$_2$CH(CH$_3$)OH, —C(O)CH$_2$CN, —C(O)CH$_2$CH$_2$CN, —C(O)CH(CH$_3$)NH(CH$_3$), —C(O)CH$_2$NH(CH$_3$), —C(O)CH$_2$N(CH$_3$)$_2$, —C(O)CH$_2$NHCH$_2$CH$_2$CH$_3$, —C(O)CH$_2$NHCH(CH$_3$)$_2$, —C(O)CH$_2$NHC(CH$_3$)$_3$, —C(O)CH$_2$N(CH$_3$)CH(CH$_3$)$_2$, —C(O)CH$_2$NHCH$_2$CH$_2$OCH$_3$, —CH$_2$C(O)NH$_2$, —CH$_2$C(O)NH(CH$_3$), —CH$_2$C(O)N(CH$_3$)CH$_2$CH$_3$, —CH$_2$C(O)NHCH$_2$CH$_2$CH$_3$, —CH$_2$C(O)NH(CH(CH$_3$)$_2$), —CH$_2$C(O)N(CH$_3$)$_2$, —CH$_2$C(O)N(CH$_2$CH$_3$)$_2$, —CH$_2$CH$_2$S(O)$_2$CH$_3$, or —CH$_2$CH$_2$S(O)$_2$NH$_2$. Also included are compounds in which m is zero and n is zero.

One embodiment provides a compound of Formula (I) or a salt thereof, wherein $R_3$ is H, —CH(CH$_3$)$_2$, —CH(CH$_3$)$_2$, —CH$_2$CH(CH$_3$)$_2$, —CH$_2$CN, —CH$_2$CH$_2$CN, —CH$_2$CH$_2$CH$_2$CN, —CH$_2$C(CH$_3$)$_2$OH, —C(O)CH$_3$, —C(O)CH(CH$_2$CH$_3$)$_2$, —C(O)CH$_2$OCH$_3$, —C(O)CH$_2$CH$_2$OCH$_3$, —C(O)CH$_2$CH(CH$_3$)OH, —C(O)CH$_2$CN, —C(O)CH$_2$CH$_2$CN, —C(O)CH(CH$_3$)NH(CH$_3$), —C(O)CH$_2$NH(CH$_3$), —C(O)CH$_2$N(CH$_3$)$_2$, —C(O)CH$_2$NHCH$_2$CH$_2$CH$_3$, —C(O)CH$_2$NHCH(CH$_3$)$_2$, —C(O)CH$_2$NHC(CH$_3$)$_3$, —C(O)CH$_2$N(CH$_3$)CH(CH$_3$)$_2$, —C(O)CH$_2$NHCH$_2$CH$_2$OCH$_3$, —CH$_2$C(O)NH$_2$, —CH$_2$C(O)NH(CH$_3$), —CH$_2$C(O)N(CH$_3$)CH$_2$CH$_3$, —CH$_2$C(O)NHCH$_2$CH$_2$CH$_3$, —CH$_2$C(O)NH(CH(CH$_3$)$_2$), —CH$_2$C(O)N(CH$_3$)$_2$, —CH$_2$C(O)N(CH$_2$CH$_3$)$_2$, —CH$_2$CH$_2$S(O)$_2$CH$_3$, —CH$_2$CH$_2$S(O)$_2$NH$_2$, —CH$_2$C(O)NH(cyclobutyl), —CH$_2$C(O)NH(cyclopropyl), —CH$_2$C(O)NH(methyloxetanyl), —CH$_2$C(O)N(CH$_3$)(cyclopropyl), oxetanyl, tetrahydropyranyl, dioxotetrahydrothiopyranyl, —CH$_2$(oxazolyl), —CH$_2$(pyrazolyl), —CH$_2$(tetrazolyl), —CH$_2$(triazolyl), —CH$_2$(methyltriazolyl), —CH$_2$C(O)(2-oxa-6-azaspiro[3.3]heptanyl), —CH$_2$C(O)(azetidinyl), —CH$_2$C(O)(dioxidothiadiazinanyl), —CH$_2$C(O)(dioxidothiomorpholinyl), —CH$_2$C(O)(morpholinyl), —CH$_2$C(O)(methoxyethylpiperazinyl), —CH$_2$C(O)(piperidinyl), —CH$_2$C(O)(hydroxypiperidinyl), —CH$_2$C(O)(pyrrolidinyl), —CH$_2$C(O)(hydroxypyrrolidinyl), —C(O)(azetidinyl), —C(O)(methylcyclopropyl), —C(O)(methyloxetanyl), or —C(O)CH$_2$(morpholinyl); and $R_1$, $R_2$, $R_4$, $R_5$, m, n, and p are defined in the first aspect. Included in this embodiment are compounds in which each $R_2$ is independently F, —CN, —OH, $C_{1-2}$ alkyl, or —(CH$_2$)$_{0-10}$($C_{1-2}$ alkyl); p is zero, 1 or 2. Included in this embodiment are compounds in which each $R_2$ is independently —CH$_3$, —OCH$_3$, or —CH$_2$OCH$_3$. Also included are compounds in which m is zero and n is zero.

One embodiment provides a compound of Formula (I) or a salt thereof, wherein m is zero, 1, or 2; and $R_1$, $R_2$, $R_3$, $R_4$, $R_5$, n, and p are defined in the first aspect. Included in this embodiment are compounds in which m is zero or 1. Also included in this embodiment are compounds in which m is zero. Also included are compounds in which m is zero and n is zero.

One embodiment provides a compound of Formula (I) or a salt thereof, wherein n is zero or 1; and $R_1$, $R_2$, $R_3$, $R_4$, $R_5$, m, and p are defined in the first aspect. Included in this embodiment are compounds in which n is zero. Also included are compounds in which m is zero. Also included are compounds in which m is zero and n is zero.

One embodiment provides a compound of Formula (I) or a salt thereof, wherein m is zero, 1, or 2; n is zero or 1; and p is zero, 1, or 2; and $R_1$, $R_2$, $R_3$, $R_4$, and $R_5$ are defined in the first aspect. Included in this embodiment are compounds in which m is zero or 1; n is zero; and p is zero, 1, or 2. Also included are compounds in which m is zero; n is zero; and p is zero, 1, or 2.

One embodiment provides a compound of Formula (I) or a salt thereof, wherein said compound has the structure of Formula (I-1):

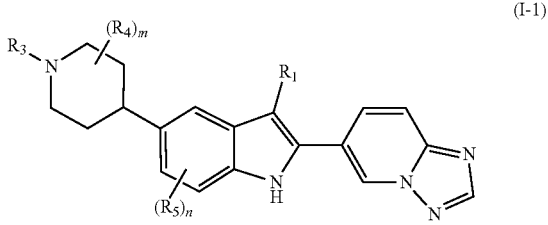

(I-1)

and $R_1$, $R_3$, $R_4$, $R_5$, m, and n are defined in the first aspect or the second aspect. Included in this embodiment are compounds in which $R_1$ is —CHCH$_3$ or —CH(CH$_3$)$_2$. Included in this embodiment are compounds in which $R_3$ is H, —CH$_3$, —CH(CH$_3$)$_2$, —CH$_2$CHF$_2$, —CH$_2$CH$_2$OH, —CH$_2$C(O)NH$_2$, —CH$_2$C(O)NH(CH$_3$), —CH$_2$C(O)NH (CH$_3$), —CH$_2$C(O)N(CH$_3$)$_2$, —CH$_2$C(CH$_3$)$_2$OH, —C(O) CH$_2$S(O)$_2$CH$_3$, —C(O)CH$_2$NH(CH$_3$), —C(O)CH$_2$ N(CH$_3$)$_2$, —C(O)CH$_2$CH(CH$_3$)OH, or -L$_1$-A; L$_1$ is —CH$_2$—, —C(O)—, or —C(O)CH$_2$CH(CH$_3$)—; and A is isoxazolyl, oxazolyl, oxetanyl, pyrazolyl, pyrimidinyl, pyrrolidinonyl, tetrahydrofuranyl, tetrahydropyranyl, thiazolyl, or triazolyl, each substituted with -L$_2$-R$_a$ and zero to 2 R$_b$; L$_2$ is a bond; R$_a$ is H, C$_{1-3}$ alkyl, —OCH$_3$, or —CH$_2$ (cyclopropyl); and each R$_b$ is —CH$_3$. Also included in this embodiment are compounds in which $R_1$ is —CH(CH$_3$)$_2$; m is zero, and n is zero.

One embodiment provides a compound of Formula (I) or a salt thereof, wherein said compound is
6-(3-isopropyl-5-(piperidin-4-yl)-1H-indol-2-yl)-[1,2,4]triazolo[1,5-a]pyridine (1); 1-(4-(2-([1,2,4]triazolo[1,5-a]pyridin-6-yl)-3-isopropyl-1H-indol-5-yl)piperidin-1-yl)-2-(methylamino)ethan-1-one (47);
1-(4-(2-([1,2,4]triazolo[1,5-a]pyridin-6-yl)-3-isopropyl-1H-indol-5-yl)piperidin-1-yl)-2-(dimethylamino)ethan-1-one (51); (S)-1-(4-(2-([1,2,4]triazolo [1,5-a]pyridin-6-yl)-3-isopropyl-1H-indol-5-yl)piperidin-1-yl)-3-hydroxybutan-1-one (53); 6-(3-ethyl-5-(piperidin-4-yl)-1H-indol-2-yl)-[1,2,4]triazolo[1,5-a]pyridine (121);
2-(4-(2-([1,2,4]triazolo[1,5-a]pyridin-6-yl)-3-isopropyl-1H-indol-5-yl)piperidin-1-yl)-N, N-dimethylacetamide (164);
2-(4-(2-([1,2,4]triazolo[1,5-a]pyridin-6-yl)-3-isopropyl-1H-indol-5-yl)piperidin-1-yl)-N-methylacetamide (240);
1-(4-(2-([1,2,4]triazolo[1,5-a]pyridin-6-yl)-3-isopropyl-1H-indol-5-yl)piperidin-1-yl)-2-methylpropan-2-ol (241);
2-(4-(2-([1,2,4]triazolo [1,5-a]pyridin-6-yl)-3-isopropyl-1H-indol-5-yl)piperidin-1-yl)-N-methylacetamide (242);
6-(3-isopropyl-5-(1-methylpiperidin-4-yl)-1H-indol-2-yl)-[1,2,4]triazolo[1,5-a]pyridine (350);
6-(3-isopropyl-5-(1-(tetrahydro-2H-pyran-4-yl)piperidin-4-yl)-1H-indol-2-yl)-[1,2,4]triazolo [1,5-a]pyridine (351);
6-(3-isopropyl-5-(1-(oxetan-3-yl)piperidin-4-yl)-1H-indol-2-yl)-[1,2,4]triazolo[1,5-a]pyridine (352);
6-(3-isopropyl-5-(1-((1-methyl-1H-1,2,4-triazol-3-yl) methyl) piperidin-4-yl)-1H-indol-2-yl)-[1,2,4]triazolo[1,5-a]pyridine (353);
6-(3-isopropyl-5-(1-(tetrahydro-2H-pyran-3-yl)piperidin-4-yl)-1H-indol-2-yl)-[1,2,4]triazolo[1,5-a]pyridine (354);
6-(3-isopropyl-5-(1-(tetrahydrofuran-3-yl)piperidin-4-yl)-1H-indol-2-yl)-[1,2,4]triazolo[1,5-a]pyridine (355);
2-(4-(2-([1,2,4]triazolo[1,5-a]pyridin-6-yl)-3-isopropyl-1H-indol-5-yl)piperidin-1-yl)ethan-1-ol (356);
6-(3-isopropyl-5-(1-(oxetan-3-ylmethyl)piperidin-4-yl)-1H-indol-2-yl)-[1,2,4]triazolo[1,5-a]pyridine (358);
6-(3-isopropyl-5-(1-((2-methoxypyrimidin-5-yl)methyl)piperidin-4-yl)-1H-indol-2-yl)-[1,2,4]triazolo[1,5-a]pyridine (359);
2-(4-(2-([1,2,4]triazolo[1,5-a]pyridin-6-yl)-3-isopropyl-1H-indol-5-yl) piperidin-1-yl)acetamide (360);
3-((4-(2-([1,2,4]triazolo[1,5-a]pyridin-6-yl)-3-isopropyl-1H-indol-5-yl)piperidin-1-yl)methyl)-5-methylisoxazole (361); 4-((4-(2-([1,2,4]triazolo[1,5-a]pyridin-6-yl)-3-isopropyl-1H-indol-5-yl)piperidin-1-yl)methyl)-2-isopropylthiazole (362);
6-(3-isopropyl-5-(1-((1-propyl-1H-pyrazol-4-yl)methyl)piperidin-4-yl)-1H-indol-2-yl)-[1,2,4]triazolo[1,5-a]pyridine (363);
6-(5-(1-((3,5-dimethyl-1H-pyrazol-4-yl)methyl)piperidin-4-yl)-3-isopropyl-1H-indol-2-yl)-[1,2,4]triazolo[1,5-a]pyridine (364);
6-(5-(1-((1H-1,2,3-triazol-4-yl)methyl)piperidin-4-yl)-3-isopropyl-1H-indol-2-yl)-[1,2,4]triazolo[1,5-a]pyridine (365);
6-(5-(1-((1-(cyclopropylmethyl)-1H-pyrazol-3-yl)methyl) piperidin-4-yl)-3-isopropyl-1H-indol-2-yl)-[1,2,4]triazolo[1,5-a]pyridine (366);
6-(3-isopropyl-5-(1-((1-methyl-1H-1,2,3-triazol-4-yl) methyl)piperidin-4-yl)-1H-indol-2-yl)-[1,2,4]triazolo[1, 5-a]pyridine (367);
6-(3-isopropyl-5-(1-((5-methoxy-1,3-dimethyl-1H-pyrazol-4-yl)methyl)piperidin-4-yl)-1H-indol-2-yl)-[1,2,4]triazolo[1,5-a]pyridine (368);
5-((4-(2-([1,2,4]triazolo[1,5-a]pyridin-6-yl)-3-isopropyl-1H-indol-5-yl)piperidin-1-yl)methyl)-2,4-dimethylthiazole (369); 4-((4-(2-([1,2,4]triazolo [1,5-a]pyridin-6-yl)-3-isopropyl-1H-indol-5-yl)piperidin-1-yl)methyl)-3,5-dimethylisoxazole (370);
6-(5-(1-((1,3-dimethyl-1H-pyrazol-4-yl)methyl)piperidin-4-yl)-3-isopropyl-1H-indol-2-yl)-[1,2,4]triazolo[1,5-a] pyridine (371);
4-((4-(2-([1,2,4]triazolo[1,5-a]pyridin-6-yl)-3-isopropyl-1H-indol-5-yl)piperidin-1-yl)methyl)-2,5-dimethyloxazole (372);
6-(5-(1-((1,3-dimethyl-1H-pyrazol-5-yl)methyl)piperidin-4-yl)-3-isopropyl-1H-indol-2-yl)-[1,2,4]triazolo[1,5-a] pyridine (373);
2-((4-(2-([1,2,4]triazolo[1,5-a]pyridin-6-yl)-3-isopropyl-1H-indol-5-yl)piperidin-1-yl)methyl)thiazole (374); 6-(3-isopropyl-5-(1-((1-isopropyl-1H-pyrazol-4-yl) methyl)piperidin-4-yl)-1H-indol-2-yl)-[1,2,4]triazolo[1,5-a] pyridine (375);
6-(3-isopropyl-5-(1-((1-methyl-1H-pyrazol-4-yl)methyl)piperidin-4-yl)-1H-indol-2-yl)-[1,2,4]triazolo[1,5-a]pyridine (376);
5-((4-(2-([1,2,4]triazolo[1,5-a]pyridin-6-yl)-3-isopropyl-1H-indol-5-yl) piperidin-1-yl)methyl)thiazole (377);
4-((4-(2-([1,2,4]triazolo[1,5-a]pyridin-6-yl)-3-isopropyl-1H-indol-5-yl)piperidin-1-yl)methyl)-2-methyloxazole (378);
6-(5-(1-((1H-pyrazol-5-yl)methyl)piperidin-4-yl)-3-isopropyl-1H-indol-2-yl)-[1,2,4]triazolo[1,5-a]pyridine (379);
6-(3-isopropyl-5-(1-((3-methyl-1H-pyrazol-4-yl)methyl)piperidin-4-yl)-1H-indol-2-yl)-[1,2,4]triazolo[1,5-a]pyridine (380);

6-(3-isopropyl-5-(1-((1-methyl-1H-pyrazol-3-yl)methyl)piperidin-4-yl)-1H-indol-2-yl)-[1,2,4]triazolo[1,5-a]pyridine (381);
6-(5-(1-((1-ethyl-1H-pyrazol-3-yl)methyl)piperidin-4-yl)-3-isopropyl-1H-indol-2-yl)-[1,2,4]triazolo[1,5-a]pyridine (382);
2-((4-(2-([1,2,4]triazolo[1,5-a]pyridin-6-yl)-3-isopropyl-1H-indol-5-yl) piperidin-1-yl)methyl)-5-methylthiazole (383);
4-((4-(2-([1,2,4]triazolo[1,5-a]pyridin-6-yl)-3-isopropyl-1H-indol-5-yl)piperidin-1-yl)methyl)oxazole (384);
6-(3-isopropyl-5-(1-isopropylpiperidin-4-yl)-1H-indol-2-yl)-[1,2,4]triazolo[1,5-a]pyridine (536); 4-(4-(2-([1,2,4]triazolo[1,5-a]pyridin-6-yl)-3-isopropyl-1H-indol-5-yl)piperidine-1-carbonyl)-1-methylpyrrolidin-2-one (601);
1-(4-(2-([1,2,4]triazolo[1,5-a]pyridin-6-yl)-3-isopropyl-1H-indol-5-yl)piperidin-1-yl)-2-(methylsulfonyl)ethan-1-one (619); or 1-(4-(2-([1,2,4]triazolo [1,5-a]pyridin-6-yl)-3-isopropyl-1H-indol-5-yl)piperidin-1-yl)-3-(oxetan-3-yl)butan-1-one (713).

One embodiment provides a compound of Formula (I) or a salt thereof, wherein said compound has the structure of Formula (I-2):

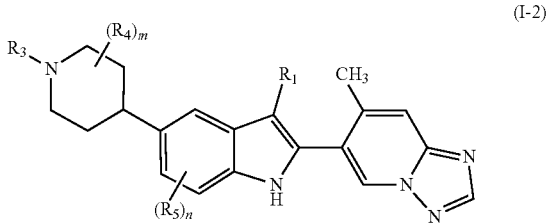

(I-2)

and $R_1$, $R_3$, $R_4$, $R_5$, m, and n are defined in the first aspect or the second aspect. Included in this embodiment are compounds in which $R_1$ is —CH(CH$_3$)$_2$. Included in this embodiment are compounds in which $R_3$ is H, $C_{1-3}$ cyanoalkyl, —CH$_2$C(CH$_3$)$_2$OH, —CH$_2$C(O)NH(CH$_3$), —CH$_2$C(O)N(CH$_3$)$_2$, —CH$_2$C(O)NH(CH$_2$CH$_3$), —CH$_2$C(O)NH(CH(CH$_3$)$_2$), —CH$_2$C(O)N(CH$_3$)(CH$_2$CH$_3$), —CH$_2$C(O)N(CH$_2$CH$_3$)$_2$, —CH$_2$C(O)N(CH$_3$)(CH$_2$CH$_2$OH), —CH$_2$CH$_2$S(O)$_2$CH$_3$, —CH(CH$_3$)CH$_2$S(O)$_2$CH$_3$, —CH$_2$CH$_2$S(O)$_2$NH$_2$, —CH$_2$CH$_2$S(O)$_2$NH(CH$_3$), —CH$_2$CH$_2$S(O)$_2$N(CH$_3$)$_2$, —CH$_2$CH$_2$NHS(O)$_2$CH$_3$, —C(O)CH$_2$CN, or -L$_1$-A; L$_1$ is —CH$_2$—, —CH$_2$C(O)—, —CH$_2$C(O)NH—, or —C(O)CH$_2$CH$_2$—; and A is cyclopropyl, dioxotetrahydrothiophenyl, dioxotetrahydrothiopyranyl, isoxazolyl, morpholinyl, oxadiazolyl, oxazolyl, oxetanyl, piperidinyl, pyrazinyl, pyrazolyl, pyridazinyl, pyrimidinyl, pyrrolidinyl, tetrahydropyranyl, thiazolyl, or triazolyl, each substituted with -L$_2$-R$_a$ and zero to 1 R$_b$; L$_2$ is a bond; R$_a$ is H, —CH$_3$, —CN, or —OCH$_3$; and R$_b$ is —OCH$_3$. Also included in this embodiment are compounds in which $R_1$ is —CH(CH$_3$)$_2$; m is zero, and n is zero.

One embodiment provides a compound of Formula (I) or a salt thereof, wherein said compound is
6-(3-isopropyl-5-(piperidin-4-yl)-1H-indol-2-yl)-7-methyl-[1,2,4]triazolo[1,5-a]pyridine (3); 3-(4-(3-isopropyl-2-(7-methyl-[1,2,4]triazolo[1,5-a]pyridin-6-yl)-1H-indol-5-yl)piperidin-1-yl)-3-oxopropanenitrile (49);
2-(4-(3-isopropyl-2-(7-methyl-[1,2,4]triazolo[1,5-a]pyridin-6-yl)-1H-indol-5-yl)piperidin-1-yl)ethane-1-sulfonamide (180);
2-(4-(3-isopropyl-2-(7-methyl-[1,2,4]triazolo[1,5-a]pyridin-6-yl)-1H-indol-5-yl)piperidin-1-yl)acetonitrile (181);
1-(4-(3-isopropyl-2-(7-methyl-[1,2,4]triazolo[1,5-a]pyridin-6-yl)-1H-indol-5-yl)piperidin-1-yl)-2-methylpropan-2-ol (182);
2-(4-(3-isopropyl-2-(7-methyl-[1,2,4]triazolo[1,5-a]pyridin-6-yl)-1H-indol-5-yl)piperidin-1-yl)ethane-1-sulfonamide (183);
2-(4-(3-isopropyl-2-(7-methyl-[1,2,4]triazolo[1,5-a]pyridin-6-yl)-1H-indol-5-yl)piperidin-1-yl)-N-methylethane-1-sulfonamide (184);
2-(4-(3-isopropyl-2-(7-methyl-[1,2,4]triazolo[1,5-a]pyridin-6-yl)-1H-indol-5-yl)piperidin-1-yl)-N,N-dimethylethane-1-sulfonamide (185);
1-((4-(3-isopropyl-2-(7-methyl-[1,2,4]triazolo[1,5-a]pyridin-6-yl)-1H-indol-5-yl)piperidin-1-yl)methyl)cyclopropane-1-carbonitrile (186);
1-((4-(3-isopropyl-2-(7-methyl-[1,2,4]triazolo[1,5-a]pyridin-6-yl)-1H-indol-5-yl)piperidin-1-yl)methyl)cyclopropane-1-carbonitrile (187);
3-(4-(3-isopropyl-2-(7-methyl-[1,2,4]triazolo[1,5-a]pyridin-6-yl)-1H-indol-5-yl)piperidin-1-yl) propanenitrile (188);
N-(2-(4-(3-isopropyl-2-(7-methyl-[1,2,4]triazolo[1,5-a]pyridin-6-yl)-1H-indol-5-yl)piperidin-1-yl)ethyl)methanesulfonamide (189);
2-(4-(3-isopropyl-2-(7-methyl-[1,2,4]triazolo[1,5-a]pyridin-6-yl)-1H-indol-5-yl)piperidin-1-yl)-N-methylacetamide (190);
2-(4-(3-isopropyl-2-(7-methyl-[1,2,4]triazolo[1,5-a]pyridin-6-yl)-1H-indol-5-yl) piperidin-1-yl)-N,N-dimethylacetamide (191);
6-(3-isopropyl-5-(1-(oxetan-3-yl)piperidin-4-yl)-1H-indol-2-yl)-7-methyl-[1,2,4]triazolo [1,5-a]pyridine (441);
6-(3-isopropyl-5-(1-((2-methoxypyrimidin-5-yl)methyl)piperidin-4-yl)-1H-indol-2-yl)-7-methyl-[1,2,4]triazolo[1,5-a]pyridine (442);
6-(3-isopropyl-5-(1-(tetrahydro-2H-pyran-4-yl)piperidin-4-yl)-1H-indol-2-yl)-7-methyl-[1,2,4]triazolo[1,5-a]pyridine (443);
6-(3-isopropyl-5-(1-((1-methyl-1H-pyrazol-5-yl)methyl)piperidin-4-yl)-1H-indol-2-yl)-7-methyl-[1,2,4]triazolo[1,5-a]pyridine (444);
6-(3-isopropyl-5-(1-((1-methyl-1H-pyrazol-3-yl)methyl)piperidin-4-yl)-1H-indol-2-yl)-7-methyl-[1,2,4]triazolo[1,5-a]pyridine (445); 2-((4-(3-isopropyl-2-(7-methyl-[1,2,4]triazolo[1,5-a]pyridin-6-yl)-1H-indol-5-yl)piperidin-1-yl)methyl)oxazole (446);
6-(3-isopropyl-5-(1-((4-methyl-4H-1,2,4-triazol-3-yl)methyl)piperidin-4-yl)-1H-indol-2-yl)-7-methyl-[1,2,4]triazolo[1,5-a]pyridine (447);
6-(5-(1-((1H-pyrazol-5-yl)methyl)piperidin-4-yl)-3-isopropyl-1H-indol-2-yl)-7-methyl-[1,2,4]triazolo[1,5-a]pyridine (448);
6-(3-isopropyl-5-(1-((1-methyl-1H-1,2,3-triazol-4-yl)methyl)piperidin-4-yl)-1H-indol-2-yl)-7-methyl-[1,2,4]triazolo[1,5-a]pyridine (449);
5-((4-(3-isopropyl-2-(7-methyl-[1,2,4]triazolo[1,5-a]pyridin-6-yl)-1H-indol-5-yl)piperidin-1-yl)methyl)thiazole (450); 6-(5-(1-((1H-1,2,3-triazol-5-yl) methyl)piperidin-4-yl)-3-isopropyl-1H-indol-2-yl)-7-methyl-[1,2,4]triazolo[1,5-a]pyridine (451);
6-(3-isopropyl-5-(1-(pyrimidin-5-ylmethyl)piperidin-4-yl)-1H-indol-2-yl)-7-methyl-[1,2, 4]triazolo[1,5-a]pyridine (452); 3-((4-(3-isopropyl-2-(7-methyl-[1,2,4]triazolo[1,5-a]pyridin-6-yl)-1H-indol-5-yl)piperidin-1-yl)methyl)-5-methylisoxazole (453);

6-(3-isopropyl-5-(1-(pyrimidin-2-ylmethyl)piperidin-4-yl)-1H-indol-2-yl)-7-methyl-[1,2,4]triazolo[1,5-a]pyridine (454);

4-(4-(3-isopropyl-2-(7-methyl-[1,2,4]triazolo[1,5-a]pyridin-6-yl)-1H-indol-5-yl)piperidin-1-yl)tetrahydro-2H-thiopyran 1,1-dioxide (455);

6-(5-(1-((4,6-dimethoxypyrimidin-2-yl)methyl)piperidin-4-yl)-3-isopropyl-1H-indol-2-yl)-7-methyl-[1,2,4]triazolo[1,5-a]pyridine (456);

6-(3-isopropyl-5-(1-((1-methyl-1H-1,2,4-triazol-3-yl)methyl)piperidin-4-yl)-1H-indol-2-yl)-7-methyl-[1,2,4]triazolo[1,5-a]pyridine (457);

2-((4-(3-isopropyl-2-(7-methyl-[1,2,4]triazolo[1,5-a]pyridin-6-yl)-1H-indol-5-yl)piperidin-yl-yl) methyl)-1,3,4-oxadiazole (458);

6-(5-(1-((1H-1,2,4-triazol-5-yl)methyl)piperidin-4-yl)-3-isopropyl-1H-indol-2-yl)-7-methyl-[1,2,4]triazolo[1,5-a]pyridine (459);

3-(4-(3-isopropyl-2-(7-methyl-[1,2,4]triazolo[1,5-a]pyridin-6-yl)-1H-indol-5-yl)piperidin-1-yl)tetrahydrothiophene 1,1-dioxide (460);

6-(3-isopropyl-5-(1-(pyridazin-3-ylmethyl)piperidin-4-yl)-1H-indol-2-yl)-7-methyl-[1,2,4]triazolo[1,5-a]pyridine ((461);

3-(4-(3-isopropyl-2-(7-methyl-[1,2,4]triazolo[1,5-a]pyridin-6-yl)-1H-indol-5-yl)piperidin-1-yl)butanenitrile (462);

6-(3-isopropyl-5-(1-((2-methylpyrimidin-5-yl)methyl)piperidin-4-yl)-1H-indol-2-yl)-7-methyl-[1,2,4]triazolo[1,5-a]pyridine (463);

6-(3-isopropyl-5-(1-(1-(methylsulfonyl)propan-2-yl)piperidin-4-yl)-1H-indol-2-yl)-7-methyl-[1,2,4]triazolo[1,5-a]pyridine (464);

6-(3-isopropyl-5-(1-((2-methylpyrimidin-4-yl)methyl)piperidin-4-yl)-1H-indol-2-yl)-7-methyl-[1,2,4]triazolo[1,5-a]pyridine (465);

6-(3-isopropyl-5-(1-((5-methylpyrazin-2-yl)methyl) piperidin-4-yl)-1H-indol-2-yl)-7-methyl-[1,2,4]triazolo[1,5-a]pyridine (466);

6-(3-isopropyl-5-(1-(pyrazin-2-ylmethyl)piperidin-4-yl)-1H-indol-2-yl)-7-methyl-[1,2,4]triazolo[1,5-a]pyridine (467);

2-(4-(3-isopropyl-2-(7-methyl-[1,2,4]triazolo[1,5-a]pyridin-6-yl)-1H-indol-5-yl)piperidin-1-yl)-1-(pyrrolidin-1-yl)ethan-1-one (802);

N-isopropyl-2-(4-(3-isopropyl-2-(7-methyl-[1,2,4]triazolo[1,5-a]pyridin-6-yl)-1H-indol-5-yl)piperidin-1-yl)acetamide (803);

N-ethyl-2-(4-(3-isopropyl-2-(7-methyl-[1,2,4]triazolo[1,5-a]pyridin-6-yl)-1H-indol-5-yl) piperidin-1-yl)-N-methylacetamide (804);

2-(4-(3-isopropyl-2-(7-methyl-[1,2,4]triazolo[1,5-a]pyridin-6-yl)-1H-indol-5-yl)piperidin-1-yl)-1-(piperidin-1-yl)ethan-1-one (805);

N-cyclopropyl-2-(4-(3-isopropyl-2-(7-methyl-[1,2,4]triazolo[1,5-a]pyridin-6-yl)-1H-indol-5-yl) piperidin-1-yl) acetamide (806);

N-ethyl-2-(4-(3-isopropyl-2-(7-methyl-[1,2,4]triazolo[1,5-a]pyridin-6-yl)-1H-indol-5-yl)piperidin-1-yl)acetamide (807);

N,N-diethyl-2-(4-(3-isopropyl-2-(7-methyl-[1,2,4]triazolo[1,5-a]pyridin-6-yl)-1H-indol-5-yl)piperidin-1-yl)acetamide (808);

2-(4-(3-isopropyl-2-(7-methyl-[1,2,4]triazolo[1,5-a]pyridin-6-yl)-1H-indol-5-yl) piperidin-1-yl)-1-morpholinoethan-1-one (809);

N-(2-hydroxyethyl)-2-(4-(3-isopropyl-2-(7-methyl-[1,2,4]triazolo[1,5-a]pyridin-6-yl)-1H-indol-5-yl)piperidin-1-yl)-N-methylacetamide (810); or 1-(4-(3-isopropyl-2-(7-methyl-[1,2,4]triazolo[1,5-a]pyridin-6-yl)-1H-indol-5-yl) piperidin-1-yl)-3-morpholinopropan-1-one (885).

One embodiment provides a compound of Formula (I) or a salt thereof, wherein said compound has the structure of Formula (I-3):

(I-3)

$R_2$ is —$CH_3$ or -$CD_3$; and $R_1$, $R_3$, $R_4$, $R_5$, m, and n are defined in the first aspect or the second aspect. Included in this embodiment are compounds in which $R_1$ is —$CHCH_3$, —$CH(CH_3)_2$, or —$CH_2CHF_2$. Included in this embodiment are compounds in which $R_3$ is H, $C_{3-5}$ alkyl, $C_{2-3}$ fluoroalkyl, $C_{2-5}$ hydroxyalkyl, $C_{1-3}$ cyanoalkyl, —$CH_2C(CH_3)_2OH$, —$CH_2CH_2OCH_3$, —$CH_2C(O)NH_2$, —$CH_2C(O)NH(CH_3)$, —$CH_2C(O)NH(CH_2CH_2CH_3)$, —$CH_2C(O)NH(CH(CH_3)_2)$, —$CH_2C(O)N(CH_3)_2$, —$CH_2C(O)N(CH_3)CH_2CH_3$, —$CH_2C(O)N(CH_2CH_3)_2$, —$CH(CN)C(O)N(CH_3)_2$, —$CH_2C(O)N(CH_3)(CH_2CH_2OH)$, —$CH_2C(O)N(CH_2CH_3)(CH_2CH_2OH)$, —$CH_2C(O)N(CH_2CH_3)(CH_2CH_2OH)$, —$CH_2C(O)N(CH_3)(CH_2CH_2CH_2OH)$, —$CH_2C(O)N(CH_3)(CH_2C(CH_3)_2OH)$, —$CH_2C(O)N(CH_2CH_2OH)(CH_2CH(CH_3)CH_2CH_3)$, —$CH_2C(O)NH(CH_2CH_2SCH_3)$, —$CH_2CH_2S(O)_2CH_3$, —$CH_2CH_2CH_2S(O)_2CH_3$, —$CH(CH_3)CH_2S(O)_2CH_3$, —$CH(CH_3)CH_2S(O)_2(CH_2CH_2CH_3)$, —$CH_2CH_2S(O)_2NH_2$, —$CH_2CH_2S(O)_2NH(CH_3)$, —$CH_2CH_2S(O)_2N(CH_3)_2$, —$CH(CH_3)CH_2S(O)_2N(CH_2CH_3)_2$, —$CH_2CH_2NHS(O)_2CH_3$, —$C(=N(NH_2)$, —$C(O)CH_3$, —$C(O)CH(CH_2CH_3)_2$, —$C(O)CH_2CH_2CN$, —$C(O)CH_2CH(CH_3)OH$, —$C(O)CH_2OCH_3$, —$C(O)CH_2CH_2OCH_3$, —$C(O)CH_2NH(CH_3)$, —$C(O)CH_2NH(CH_2CH_2CH_3)$, —$C(O)CH_2NHCH(CH_3)_2$, —$C(O)CH_2NHC(CH_3)_3$, —$C(O)CH_2N(CH_3)_2$, —$C(O)CH(CH_3)NH(CH_3)$, —$C(O)CH_2N(CH_3)CH(CH_3)_2$, —$C(O)CH_2N(CH_3)(CH_2CH_2OH)$, —$C(O)CH_2NH(CH_2CH_2OCH_3)$, —$C(O)CH_2S(O)_2CH_3$, —$C(O)CH_2CH_2S(O)_2CH_3$, —$C(O)CH_2NHS(O)_2CH_3$, or -$L_1$-A; $L_1$ is —$CH_2$—, —$CH_2C(O)$—, —$CH_2C(O)N(CH_2CH_2OH)$—, —$CH_2C(O)N(CH_3)$—, —$CH_2C(O)N(CH_3)$—, —$CH_2C(O)N(CH_3)CH_2CH_2$—, —$CH_2C(O)NH$—, —$CH_2CH_2S(O)_2$—, —$C(O)$—, —$C(O)CH_2$—, —$C(O)CH_2CH_2$—, —$C(O)CH_2CH_2N(CH_2CH_2OH)$—, —$C(O)CH_2N(CH_2CH_2OH)$—, —$C(O)CH_2NH$—, —$CH(CH_3)$—, or —$CH(CH_3)CH_2S(O)_2$—; and A is 2-oxa-6-azaspiro[3.3]heptanyl, azetidinyl, $C_{3-6}$ cycloalkyl, dioxidothiadiazinanyl, dioxidothiazolidinyl, dioxidothiomorpholinyl, dioxotetrahydrothiophenyl, dioxotetrahydrothiopyranyl, dioxothiomorpholinyl, imidazolyl, isoxazolyl, morpholinyl, oxa-azaspiro[3.3]heptanyl, oxadiazolyl, oxazolyl, oxetanyl, phenyl, piperazinyl, piperidinyl, pyrazinyl, pyrazolyl, pyridazinyl, pyrimidinyl, pyrrolidinonyl, pyrrolidinyl, tetrahydrofuranyl, tetrahydropyranyl, tetrahydrothiopyranyl, tetrazolyl, thiadiazolyl, thiazolyl, or triazolyl, each substituted with -$L_2$-$R_a$ and zero to 2 $R_b$; $L_2$ is a bond; $R_a$ is H, F, —$CH_3$, —$CN$, —OH, —OCH₃, —CH₂OH, —CH₂CH₂OH, —CH₂CH₂OCH₃, —C(O)CH₃, —C(O)OCH₂CH₃, —C(O)OC(CH₃)₃, —NHC(O)OC(CH₃)₃, —S(O)₂CH₃, cyclopropyl, or pyrazinyl; and each $R_b$ is independently F, —OH, —CH₃, or —OCH₃. Also included in this embodiment are compounds in which $R_1$ is —CH(CH₃)₂; m is zero, and n is zero. Additionally, included in this embodiment are compounds in which $R_2$ is —CH₃.

One embodiment provides a compound of Formula (I) or a salt thereof, wherein said compound is 6-(3-isopropyl-5-(piperidin-4-yl)-1H-indol-2-yl)-8-methyl-[1,2,4]triazolo[1,5-a]pyridine hydrochloride (2);
2-(4-(3-isopropyl-2-(8-methyl-[1,2,4]triazolo[1,5-a]pyridin-6-yl)-1H-indol-5-yl)piperidin-1-yl)-N-methylacetamide (7); 2-(4-(3-isopropyl-2-(8-methyl-[1,2,4]triazolo[1,5-a]pyridin-6-yl)-1H-indol-5-yl)piperidin-1-yl)acetonitrile (8);
3-(4-(3-isopropyl-2-(8-methyl-[1,2,4]triazolo[1,5-a]pyridin-6-yl)-1H-indol-5-yl)piperidin-1-yl)propanenitrile (9);
6-(5-(1-butylpiperidin-4-yl)-3-isopropyl-1H-indol-2-yl)-8-methyl-[1,2,4]triazolo[1,5-a]pyridine (10);
2-(4-(3-isopropyl-2-(8-methyl-[1,2,4]triazolo[1,5-a]pyridin-6-yl)-1H-indol-5-yl)piperidin-1-yl)acetamide (11);
1-(4-(3-isopropyl-2-(8-methyl-[1,2,4]triazolo[1,5-a]pyridin-6-yl)-1H-indol-5-yl)piperidin-1-yl)-2-methylpropan-2-ol (12);
6-(3-isopropyl-5-(1-(oxetan-3-yl)piperidin-4-yl)-1H-indol-2-yl)-8-methyl-[1,2,4]triazolo [1,5-a]pyridine (26);
6-(3-isopropyl-5-(1-isopropylpiperidin-4-yl)-1H-indol-2-yl)-8-methyl-[1,2,4]triazolo[1,5-a]pyridine (27);
6-(3-isopropyl-5-(1-propylpiperidin-4-yl)-1H-indol-2-yl)-8-methyl-[1,2,4]triazolo[1,5-a]pyridine (28);
6-(5-(1-isobutylpiperidin-4-yl)-3-isopropyl-1H-indol-2-yl)-8-methyl-[1,2,4]triazolo[1,5-a]pyridine (29);
6-(5-(1-((1H-pyrazol-5-yl)methyl)piperidin-4-yl)-3-isopropyl-1H-indol-2-yl)-8-methyl-[1,2,4]triazolo[1,5-a]pyridine (30);
4-((4-(3-isopropyl-2-(8-methyl-[1,2,4]triazolo[1,5-a]pyridin-6-yl)-1H-indol-5-yl)piperidin-1-yl)methyl)oxazole (31);
6-(5-(1-((1H-1,2,3-triazol-4-yl)methyl)piperidin-4-yl)-3-isopropyl-1H-indol-2-yl)-8-methyl-[1,2,4]triazolo[1,5-a]pyridine (32);
6-(5-(1-((4H-1,2,4-triazol-3-yl)methyl)piperidin-4-yl)-3-isopropyl-1H-indol-2-yl)-8-methyl-[1,2,4]triazolo[1,5-a]pyridine (33);
6-(5-(1-((1H-tetrazol-5-yl)methyl)piperidin-4-yl)-3-isopropyl-1H-indol-2-yl)-8-methyl-[1,2,4]triazolo[1,5-a]pyridine (34);
6-(3-isopropyl-5-(1-(tetrahydro-2H-pyran-4-yl)piperidin-4-yl)-1H-indol-2-yl)-8-methyl-[1,2,4]triazolo[1,5-a]pyridine (35); 2-(4-(3-isopropyl-2-(8-methyl-[1,2,4]triazolo[1,5-a]pyridin-6-yl)-1H-indol-5-yl)piperidin-1-yl)-N,N-dimethylacetamide (36);
4-(4-(3-isopropyl-2-(8-methyl-[1,2,4]triazolo[1,5-a]pyridin-6-yl)-1H-indol-5-yl)piperidin-1-yl)tetrahydro-2H-thiopyran 1,1-dioxide (37);
2-(dimethylamino)-1-(4-(3-isopropyl-2-(8-methyl-[1,2,4]triazolo[1,5-a]pyridin-6-yl)-1H-indol-5-yl)piperidin-1-yl)ethan-1-one (46);
1-(4-(3-isopropyl-2-(8-methyl-[1,2,4]triazolo[1,5-a]pyridin-6-yl)-1H-indol-5-yl)piperidin-1-yl)ethan-1-one (48);
1-(4-(3-isopropyl-2-(8-methyl-[1,2,4]triazolo[1,5-a]pyridin-6-yl)-1H-indol-5-yl) piperidin-1-yl)-2-(methylamino) ethan-1-one (50); 1-(4-(3-isopropyl-2-(8-methyl-[1,2,4]triazolo[1,5-a]pyridin-6-yl)-1H-indol-5-yl)piperidin-1-yl)-2-methoxyethan-1-one (52);
4-(4-(3-isopropyl-2-(8-methyl-[1,2,4]triazolo[1,5-a]pyridin-6-yl)-1H-indol-5-yl)piperidin-1-yl)-4-oxobutanenitrile (54);
(4-(3-isopropyl-2-(8-methyl-[1,2,4]triazolo[1,5-a]pyridin-6-yl)-1H-indol-5-yl)piperidin-1-yl)(1-methylcyclopropyl)methanone (55);
(S)-azetidin-2-yl(4-(3-isopropyl-2-(8-methyl-[1,2,4]triazolo [1,5-a]pyridin-6-yl)-1H-indol-5-yl)piperidin-1-yl) methanone (56);
2-(dimethylamino)-1-(4-(3-isopropyl-2-(8-methyl-[1,2,4]triazolo[1,5-a]pyridin-6-yl)-1H-indol-5-yl)piperidin-1-yl)ethan-1-one (57);
(S)-1-(4-(3-isopropyl-2-(8-methyl-[1,2,4]triazolo[1,5-a]pyridin-6-yl)-1H-indol-5-yl)piperidin-1-yl)-2-(methylamino) propan-1-one (58);
(R)-1-(4-(3-isopropyl-2-(8-methyl-[1,2,4]triazolo[1,5-a]pyridin-6-yl)-1H-indol-5-yl)piperidin-1-yl)-2-(methylamino)propan-1-one (59);
(S)-3-hydroxy-1-(4-(3-isopropyl-2-(8-methyl-[1,2,4]triazolo[1,5-a]pyridin-6-yl)-1H-indo 1-5-yl)piperidin-1-yl) butan-1-one (60);
1-(4-(3-isopropyl-2-(8-methyl-[1,2,4]triazolo[1,5-a]pyridin-6-yl)-1H-indol-5-yl) piperidin-1-yl)-3-methoxypropan-1-one (61); (4-(3-isopropyl-2-(8-methyl-[1,2,4]triazolo [1,5-a]pyridin-6-yl)-1H-indol-5-yl)piperidin-1-yl) (3-methyloxetan-3-yl)methanone (64);
2-ethyl-1-(4-(3-isopropyl-2-(8-methyl-[1,2,4]triazolo[1,5-a]pyridin-6-yl)-1H-indol-5-yl) piperidin-1-yl)butan-1-one (65);
1-(4-(3-isopropyl-2-(8-methyl-[1,2,4]triazolo[1,5-a]pyridin-6-yl)-1H-indol-5-yl)piperidin-1-yl)-2-morpholinoethan-1-one (68);
2-(tert-butylamino)-1-(4-(3-isopropyl-2-(8-methyl-[1,2,4]triazolo[1,5-a]pyridin-6-yl)-1H-indol-5-yl)piperidin-1-yl) ethan-1-one (69);
1-(4-(3-isopropyl-2-(8-methyl-[1,2,4]triazolo[1,5-a]pyridin-6-yl)-1H-indol-5-yl)piperidin-1-yl)-2-(isopropylamino)ethan-1-one (70);
1-(4-(3-isopropyl-2-(8-methyl-[1,2,4]triazolo[1,5-a]pyridin-6-yl)-1H-indol-5-yl)piperidin-1-yl)-2-((2-methoxyethyl)amino) ethan-1-one (71);
1-(4-(3-isopropyl-2-(8-methyl-[1,2,4]triazolo[1,5-a]pyridin-6-yl)-1H-indol-5-yl)piperidin-1-yl)-2-(propylamino) ethan-1-one (72);
2-(isopropyl(methyl)amino)-1-(4-(3-isopropyl-2-(8-methyl-[1,2,4]triazolo[1,5-a]pyridin-6-yl)-1H-indol-5-yl)piperidin-1-yl)ethan-1-one (73);
1-(1,1-dioxidothiomorpholino)-2-(4-(3-isopropyl-2-(8-methyl-[1,2,4]triazolo[1,5-a]pyridin-6-yl)-1H-indol-5-yl) piperidin-1-yl)ethan-1-one (74);
N-cyclopropyl-2-(4-(3-isopropyl-2-(8-methyl-[1,2,4]triazolo[1,5-a]pyridin-6-yl)-1H-indol-5-yl)piperidin-1-yl) acetamide (75);
N-ethyl-2-(4-(3-isopropyl-2-(8-methyl-[1,2,4]triazolo[1,5-a]pyridin-6-yl)-1H-indol-5-yl) piperidin-1-yl)-N-methylacetamide (76);
(S)-1-(3-hydroxypiperidin-1-yl)-2-(4-(3-isopropyl-2-(8-methyl-[1,2,4]triazolo[1,5-a]pyridin-6-yl)-1H-indol-5-yl) piperidin-1-yl) ethan-1-one (77);
N-cyclobutyl-2-(4-(3-isopropyl-2-(8-methyl-[1,2,4]triazolo[1,5-a]pyridin-6-yl)-1H-indol-5-yl)piperidin-1-yl)acetamide (78); 2-(4-(3-isopropyl-2-(8-methyl-[1,2,4]triazolo[1,5-a]pyridin-6-yl)-1H-indol-5-yl)piperidin-1-yl)-1-(2-oxa-6-azaspiro[3.3]heptan-6-yl)ethan-1-one (79);
N,N-diethyl-2-(4-(3-isopropyl-2-(8-methyl-[1,2,4]triazolo[1,5-a]pyridin-6-yl)-1H-indol-5-yl)piperidin-1-yl)acetamide (80); 2-(4-(3-isopropyl-2-(8-methyl-[1,2,4]triazolo[1,5-a]pyridin-6-yl)-1H-indol-5-yl)piperidin-1-yl)-N-propylacetamide (81);
(R)-1-(3-hydroxypiperidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (82);
(S)-1-(3-hydroxypyrrolidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (83);
(R)-1-(3-hydroxypyrrolidin-1-yl)-2-(4-(3-isopropyl-2-(8-methyl-[1,2,4]triazolo [1,5-a]pyridin-6-yl)-1H-indol-5-yl)piperidin-1-yl)ethan-1-one (84);
2-(4-(3-isopropyl-2-(8-methyl-[1,2,4]triazolo[1,5-a]pyridin-6-yl)-1H-indol-5-yl)piperidin-1-yl)-1-(4-(2-methoxyethyl)piperazin-1-yl)ethan-1-one (85);
1-(azetidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (86);
N-isopropyl-2-(4-(3-isopropyl-2-(8-methyl-[1,2,4]triazolo[1,5-a]pyridin-6-yl)-1H-indol-5-yl) piperidin-1-yl)acetamide (87);
2-(4-(3-isopropyl-2-(8-methyl-[1,2,4]triazolo[1,5-a]pyridin-6-yl)-1H-indol-5-yl)piperidin-1-yl)-1-morpholinoethan-1-one (88);
2-(4-(3-isopropyl-2-(8-methyl-[1,2,4]triazolo[1,5-a]pyridin-6-yl)-1H-indol-5-yl)piperidin-1-yl)-1-(piperidin-1-yl) ethan-1-one (89);
2-(4-(3-isopropyl-2-(8-methyl-[1,2,4]triazolo[1,5-a]pyridin-6-yl)-1H-indol-5-yl)piperidin-1-yl)-1-(pyrrolidin-1-yl)ethan-1-one (90);
1-(1,1-dioxidothiomorpholino)-2-(4-(3-isopropyl-2-(8-methyl-[1,2,4]triazolo[1,5-a]pyridin-6-yl)-1H-indol-5-yl)piperidin-1-yl) ethan-1-one (91);
2-(4-(3-isopropyl-2-(8-methyl-[1,2,4]triazolo[1,5-a]pyridin-6-yl)-1H-indol-5-yl)piperidin-1-yl)-N-(3-methyloxetan-3-yl)acetamide (92);
N-cyclopropyl-2-(4-(3-isopropyl-2-(8-methyl-[1,2,4]triazolo[1,5-a]pyridin-6-yl)-1H-indol-5-yl)piperidin-1-yl)-N-methylacetamide (93);
6-(3-isopropyl-5-(piperidin-4-yl)-1H-indol-2-yl)-8-(trideuteromethyl)-[1,2,4]triazolo[1,5-a]pyridine (117); 6-(3-ethyl-5-(piperidin-4-yl)-1H-indol-2-yl)-8-methyl-[1,2,4]triazolo [1,5-a]pyridine (158);
6-(3-(2,2-difluoroethyl)-5-(piperidin-4-yl)-1H-indol-2-yl)-8-methyl-[1,2,4]triazolo[1,5-a]pyridine (161);
6-(5-(1-isopentylpiperidin-4-yl)-3-isopropyl-1H-indol-2-yl)-8-methyl-[1,2,4]triazolo[1,5-a]pyridine (165); 6-(3-isopropyl-5-(1-(2-methoxyethyl) piperidin-4-yl)-1H-indol-2-yl)-8-methyl-[1,2,4]triazolo[1,5-a]pyridine (166);
4-((2-(4-(3-isopropyl-2-(8-methyl-[1,2,4]triazolo[1,5-a]pyridin-6-yl)-1H-indol-5-yl) piperidin-1-yl)ethyl)sulfonyl)morpholine (167); 2-(4-(3-isopropyl-2-(8-methyl-[1,2,4]triazolo[1,5-a]pyridin-6-yl)-1H-indol-5-yl)piperidin-1-yl)ethane-1-sulfonamide (168);
2-cyano-2-(4-(3-isopropyl-2-(8-methyl-[1,2,4]triazolo[1,5-a]pyridin-6-yl)-1H-indol-5-yl) piperidin-1-yl)-N,N-dimethylacetamide (169);
2-(4-(3-isopropyl-2-(8-methyl-[1,2,4]triazolo [1,5-a]pyridin-6-yl)-1H-indol-5-yl)piperidin-1-yl)propanenitrile (170);
1-((4-(3-isopropyl-2-(8-methyl-[1,2,4]triazolo[1,5-a]pyridin-6-yl)-1H-indol-5-yl)piperidin-1-yl)methyl)cyclopropane-1-carbonitrile (171-172);
6-(3-isopropyl-5-(1-(2-(phenylsulfonyl)ethyl) piperidin-4-yl)-1H-indol-2-yl)-8-methyl-[1,2,4]triazolo[1,5-a]pyridine (173);
2-(4-(3-isopropyl-2-(8-methyl-[1,2,4]triazolo[1,5-a]pyridin-6-yl)-1H-indol-5-yl)piperidin-1-yl)-N-methylethane-1-sulfonamide (174);
2-(4-(3-isopropyl-2-(8-methyl-[1,2,4]triazolo[1,5-a]pyridin-6-yl)-1H-indol-5-yl)piperidin-1-yl)-N,N-dimethylethane-1-sulfonamide (175);
N-(2-(4-(3-isopropyl-2-(8-methyl-[1,2,4]triazolo[1,5-a] pyridin-6-yl)-1H-indol-5-yl)piperidin-1-yl) ethyl)methanesulfonamide (176);
6-(3-isopropyl-5-(1-(2-(methylsulfonyl)ethyl)piperidin-4-yl)-1H-indol-2-yl)-8-methyl-[1,2,4]triazolo[1,5-a]pyridine (177);
6-(3-isopropyl-5-(1-(3-(methylsulfonyl)propyl)piperidin-4-yl)-1H-indol-2-yl)-8-methyl-[1,2,4]triazolo[1,5-a]pyridine (178);
1-(4-(3-isopropyl-2-(8-methyl-[1,2,4]triazolo[1,5-a]pyridin-6-yl)-1H-indol-5-yl)-[1,4'-bi piperidin]-1'-yl)ethan-1-one (179); 4-(4-(3-isopropyl-2-(8-methyl-[1,2,4]triazolo [1,5-a]pyridin-6-yl)-1H-indol-5-yl)piperidine-1-carbonyl)-1-methylpyrrolidin-2-one (243);
2-(4-(3-ethyl-2-(8-methyl-[1,2,4]triazolo[1,5-a]pyridin-6-yl)-1H-indol-5-yl)piperidin-1-yl)-N,N-dimethylacetamide (337);
2-(4-(3-ethyl-2-(8-methyl-[1,2,4]triazolo[1,5-a]pyridin-6-yl)-1H-indol-5-yl)piperidin-1-yl)-N-methylacetamide (338); 6-(3-ethyl-5-(1-(2-(methylsulfonyl) ethyl)piperidin-4-yl)-1H-indol-2-yl)-8-methyl-[1,2,4]triazolo[1,5-a] pyridine (339);
2-(4-(3-ethyl-2-(8-methyl-[1,2,4]triazolo[1,5-a]pyridin-6-yl)-1H-indol-5-yl)piperidin-1-yl)acetamide (340);
6-(3-ethyl-5-(1-(2-methoxyethyl)piperidin-4-yl)-1H-indol-2-yl)-8-methyl-[1,2,4]triazolo[1,5-a]pyridine (341);
1-(4-(3-ethyl-2-(8-methyl-[1,2,4]triazolo[1,5-a]pyridin-6-yl)-1H-indol-5-yl)piperidin-1-yl)-2-methylpropan-2-ol (342);
2-(4-(3-(2,2-difluoroethyl)-2-(8-methyl-[1,2,4]triazolo[1,5-a]pyridin-6-yl)-1H-indol-5-yl)piperidin-1-yl)-N,N-dimethylacetamide (343);
2-(4-(3-(2,2-difluoroethyl)-2-(8-methyl-[1,2,4]triazolo[1,5-a]pyridin-6-yl)-1H-indol-5-yl)piperidin-1-yl)-N-methylacetamide (344);
6-(3-isopropyl-5-(1-(oxetan-3-yl)piperidin-4-yl)-1H-indol-2-yl)-8-(trideuteromethyl)-[1,2,4]triazolo[1,5-a]pyridine (357);
6-(5-(1-(2,2-difluoroethyl)piperidin-4-yl)-3-isopropyl-1H-indol-2-yl)-8-methyl-[1,2,4]triazolo[1,5-a]pyridine (385);
6-(3-isopropyl-5-(1-(((1-methyl-1H-1,2,4-triazol-3-yl)methyl)piperidin-4-yl)-1H-indol-2-yl)-8-methyl-[1,2,4]triazolo[1,5-a]pyridine (386);
6-(3-isopropyl-5-(1-((2-methoxypyrimidin-5-yl)methyl)piperidin-4-yl)-1H-indol-2-yl)-8-methyl-[1,2,4]triazolo[1,5-a]pyridine (387);
2-(4-(3-isopropyl-2-(8-methyl-[1,2,4]triazolo [1,5-a]pyridin-6-yl)-1H-indol-5-yl)piperidin-1-yl)ethan-1-ol (388);
6-(3-isopropyl-5-(1-((1-methyl-1H-pyrazol-5-yl) methyl)piperidin-4-yl)-1H-indol-2-yl)-8-methyl-[1,2,4]triazolo[1,5-a]pyridine (389);
3-((4-(3-isopropyl-2-(8-methyl-[1,2,4]triazolo[1,5-a]pyridin-6-yl)-1H-indol-5-yl)piperidin-1-yl)methyl)-1,2,4-oxadiazole (390);
3-(4-(3-isopropyl-2-(8-methyl-[1,2,4]triazolo[1,5-a]pyridin-6-yl)-1H-indol-5-yl)piperidin-1-yl)propan-1-ol (391);
6-(3-isopropyl-5-(1-((4-methyl-4H-1,2,4-triazol-3-yl)methyl)piperidin-4-yl)-1H-indol-2-yl)-8-methyl-[1,2,4]triazolo[1,5-a]pyridine (392);

6-(3-isopropyl-5-(1-(tetrahydrofuran-3-yl) piperidin-4-yl)-1H-indol-2-yl)-8-methyl-[1,2,4]triazolo[1,5-a]pyridine (393);

6-(3-isopropyl-5-(1-(tetrahydro-2H-pyran-3-yl)piperidin-4-yl)-1H-indol-2-yl)-8-methyl-[1,2,4]triazolo[1,5-a]pyridine (394);

3-(4-(3-isopropyl-2-(8-methyl-[1,2,4]triazolo[1,5-a]pyridin-6-yl)-1H-indol-5-yl)piperidin-1-yl)tetrahydrothiophene 1,1-dioxide (395);

6-(3-isopropyl-5-(1-(pyrimidin-2-ylmethyl)piperidin-4-yl)-1H-indol-2-yl)-8-methyl-[1,2,4]triazolo[1,5-a]pyridine (396);

4-(4-(3-isopropyl-2-(8-methyl-[1,2,4]triazolo[1,5-a]pyridin-6-yl)-1H-indol-5-yl)piperidin-1-yl) butan-1-ol (397);

6-(5-(1-(2,6-difluorobenzyl)piperidin-4-yl)-3-isopropyl-1H-indol-2-yl)-8-methyl-[1,2,4]triazolo[1,5-a]pyridine (398); 6-(5-(1-((3,5-dimethyl-1l2-pyrazol-4-yl)methyl)piperidin-4-yl)-3-isopropyl-1H-indol-2-yl)-8-methyl-[1,2,4]triazolo[1,5-a]pyridine (399);

(3,5-difluoro-4-((4-(3-isopropyl-2-(8-methyl-[1,2,4]triazolo[1,5-a]pyridin-6-yl)-1H-indol-5-yl)piperidin-1-yl)methyl)phenyl)methanol (400);

3,5-difluoro-4-((4-(3-isopropyl-2-(8-methyl-[1,2,4]triazolo[1,5-a]pyridin-6-yl)-1H-indol-5-yl)piperidin-1-yl)methyl)benzonitrile (401);

6-(3-isopropyl-5-(1-(pyrimidin-5-ylmethyl)piperidin-4-yl)-1H-indol-2-yl)-8-methyl-[1,2,4]triazolo[1,5-a]pyridine (402);

4-(4-(3-isopropyl-2-(8-methyl-[1,2,4]triazolo[1,5-a]pyridin-6-yl)-1H-indol-5-yl)piperidin-1-yl)cyclohexan-1-ol (403);

6-(3-isopropyl-5-(1-((1-methyl-1H-1,2,4-triazol-5-yl)methyl)piperidin-4-yl)-1H-indol-2-yl)-8-methyl-[1,2,4]triazolo[1,5-a]pyridine (404);

6-(5-(1-((1,3-dimethyl-1H-pyrazol-5-yl)methyl)piperidin-4-yl)-3-isopropyl-1H-indol-2-yl)-8-methyl-[1,2,4]triazolo[1,5-a]pyridine (405);

4-((4-(3-isopropyl-2-(8-methyl-[1,2,4]triazolo[1,5-a]pyridin-6-yl)-1H-indol-5-yl)piperidin-1-yl)methyl)thiazole (406);

4-(4-(3-isopropyl-2-(8-methyl-[1,2,4]triazolo[1,5-a]pyridin-6-yl)-1H-indol-5-yl) piperidin-1-yl)methyl)-5-methylthiazole (407);

2-((4-(3-isopropyl-2-(8-methyl-[1,2,4]triazolo [1,5-a]pyridin-6-yl)-1H-indol-5-yl)piperidin-1-yl)methyl)thiazole (408);

6-(3-isopropyl-5-(1-((3-methyl-1H-pyrazol-5-yl)methyl)piperidin-4-yl)-1H-indol-2-yl)-8-methyl-[1,2,4]triazolo[1,5-a]pyridine (409);

6-(5-(1-((1,5-dimethyl-1H-pyrazol-3-yl)methyl)piperidin-4-yl)-3-isopropyl-1H-indol-2-yl)-8-methyl-[1,2,4]triazolo[1,5-a]pyridine (410);

4-((4-(3-isopropyl-2-(8-methyl-[1,2,4]triazolo[1,5-a]pyridin-6-yl)-1H-indol-5-yl)piperidin-1-yl)methyl)-1,2,3-thiadiazole (411);

6-(3-isopropyl-5-(1-(pyridazin-3-ylmethyl)piperidin-4-yl)-1H-indol-2-yl)-8-methyl-[1,2,4]triazolo[1,5-a]pyridine (412); (2-((4-(3-isopropyl-2-(8-methyl-[1,2,4]triazolo[1,5-a]pyridin-6-yl)-1H-indol-5-yl)piperidin-1-yl)methyl)pyrimidin-5-yl)methanol (413);

6-(3-isopropyl-5-(1-((2-methylpyrimidin-5-yl)methyl)piperidin-4-yl)-1H-indol-2-yl)-8-methyl-[1,2,4]triazolo[1,5-a]pyridine (414);

6-(3-isopropyl-5-(1-((2-methylpyrimidin-4-yl)methyl) piperidin-4-yl)-1H-indol-2-yl)-8-methyl-[1,2,4]triazolo[1,5-a]pyridine (415);

2-(4-(3-isopropyl-2-(8-methyl-[1,2,4]triazolo[1,5-a]pyridin-6-yl)-1H-indol-5-yl)piperidin-1-yl)-1-methylcyclopentane-1-carbonitrile (416-417);

6-(3-isopropyl-5-(1-(1-(6-methylpyridazin-3-yl)ethyl)piperidin-4-yl)-1H-indol-2-yl)-8-m ethyl-[1,2,4]triazolo[1,5-a]pyridine (418);

6-(3-isopropyl-5-(1-(1-methyl-1H-pyrazol-4-yl)ethyl)piperidin-4-yl)-1H-indol-2-yl)-8-methyl-[1,2,4]triazolo[1,5-a]pyridine (419);

6-(5-(1-(1-(1H-pyrazol-5-yl)ethyl)piperidin-4-yl)-3-isopropyl-1H-indol-2-yl)-8-methyl-[1,2,4]triazolo[1,5-a]pyridine (420);

6-(3-isopropyl-5-(1-(1-(pyrimidin-2-yl)ethyl)piperidin-4-yl)-1H-indol-2-yl)-8-methyl-[1,2,4]triazolo[1,5-a]pyridine (421);

6-(3-isopropyl-5-(1-(1-(methylsulfonyl)propan-2-yl)piperidin-4-yl)-1H-indol-2-yl)-8-methyl-[1,2,4]triazolo[1,5-a]pyridine (422); 3-(4-(3-isopropyl-2-(8-methyl-[1,2,4]triazolo[1,5-a]pyridin-6-yl)-1H-indol-5-yl)piperidin-1-yl)butanenitrile (423);

6-(3-isopropyl-5-(1-((5-methylpyrazin-2-yl)methyl)piperidin-4-yl)-1H-indol-2-yl)-8-methyl-[1,2,4]triazolo[1,5-a]pyridine (424);

6-(3-isopropyl-5-(1-(tetrahydro-2H-thiopyran-4-yl)piperidin-4-yl)-1H-indol-2-yl)-8-methyl-[1,2,4]triazolo[1,5-a]pyridine (425);

1-(4-(3-isopropyl-2-(8-methyl-[1,2,4]triazolo[1,5-a]pyridin-6-yl)-1H-indol-5-yl)piperidin-1-yl)-2-(1H-tetrazol-5-yl)ethan-1-one (426);

N,N-diethyl-2-(4-(3-isopropyl-2-(8-methyl-[1,2,4]triazolo[1,5-a]pyridin-6-yl)-1H-indol-5-yl)piperidin-1-yl)propane-1-sulfonamide (427);

6-(5-(1-(1-(butylsulfonyl)propan-2-yl)piperidin-4-yl)-3-isopropyl-1H-indol-2-yl)-8-meth yl-[1,2,4]triazolo[1,5-a]pyridine (428);

6-(3-isopropyl-5-(1-(pyrazin-2-ylmethyl)piperidin-4-yl)-1H-indol-2-yl)-8-methyl-[1,2,4]triazolo[1,5-a]pyridine (429); 4-((2-(4-(3-isopropyl-2-(8-methyl-[1,2,4]triazolo[1,5-a]pyridin-6-yl)-1H-indol-5-yl)piperidin-1-yl)propyl)sulfonyl)morpholine (430);

6-(3-isopropyl-5-(1-(1-(piperidin-1-ylsulfonyl)propan-2-yl)piperidin-4-yl)-1H-indol-2-yl)-8-methyl-[1,2,4]triazolo[1,5-a]pyridine (431);

3-(4-(3-isopropyl-2-(8-methyl-[1,2,4]triazolo[1,5-a]pyridin-6-yl)-1H-indol-5-yl)piperidin-1-yl)pentane-1,5-diol (432);

6-(3-isopropyl-5-(1-((2-methyl-2H-tetrazol-5-yl)methyl)piperidin-4-yl)-1H-indol-2-yl)-8-methyl-[1,2,4]triazolo[1,5-a]pyridine (433);

6-(3-isopropyl-5-(1-((1-methyl-1H-1,2,3-triazol-4-yl)methyl)piperidin-4-yl)-1H-indol-2-yl)-8-methyl-[1,2,4]triazolo[1,5-a]pyridine (434); 3-((4-(3-isopropyl-2-(8-methyl-[1,2,4]triazolo[1,5-a]pyridin-6-yl)-1H-indol-5-yl)piperidin-1-yl)methyl)-5-methylisoxazole (435);

5-((4-(3-isopropyl-2-(8-methyl-[1,2,4]triazolo[1,5-a]pyridin-6-yl)-1H-indol-5-yl)piperidin-1-yl)methyl)thiazole (436);

6-(3-isopropyl-5-(1-((1-methyl-1H-pyrazol-3-yl)methyl)piperidin-4-yl)-1H-indol-2-yl)-8-methyl-[1,2,4]triazolo[1,5-a]pyridine (437);

6-(5-(1-((4,6-dimethoxypyrimidin-2-yl)methyl)piperidin-4-yl)-3-isopropyl-1H-indol-2-yl)-8-methyl-[1,2,4]triazolo[1,5-a]pyridine (438);

5-cyclopropyl-2-((4-(3-isopropyl-2-(8-methyl-[1,2,4]triazolo[1,5-a]pyridin-6-yl)-1H-indol-5-yl)piperidin-1-yl)methyl)oxazole (439);

2-((4-(3-isopropyl-2-(8-methyl-[1,2,4]triazolo[1,5-a]pyridin-6-yl)-1H-indol-5-yl)piperidin-1-yl)methyl)oxazole (440);

6-(3-isopropyl-5-(1-(3,3,3-trifluoropropyl)piperidin-4-yl)-1H-indol-2-yl)-8-methyl-[1,2,4]triazolo[1,5-a]pyridine (537); tert-butyl (3-(4-(3-isopropyl-2-(8-methyl-[1,2,4]triazolo[1,5-a]pyridin-6-yl)-1H-indol-5-yl)piperidin-1-yl)cyclobutyl)carbamate (538); ethyl 3-(4-(3-isopropyl-2-(8-methyl-[1,2,4]triazolo[1,5-a]pyridin-6-yl)-1H-indol-5-yl) piperidin-1-yl)cyclobutane-1-carboxylate (539);

6-(3-isopropyl-5-(1-(tetrahydrofuran-3-yl) piperidin-4-yl)-1H-indol-2-yl)-8-methyl-[1,2,4]triazolo[1,5-a]pyridine (540-541);

6-(3-ethyl-5-(1-(oxetan-3-yl)piperidin-4-yl)-1H-indol-2-yl)-8-methyl-[1,2,4]triazolo[1,5-a]pyridine (596);

6-(3-(2,2-difluoroethyl)-5-(1-(oxetan-3-yl)piperidin-4-yl)-1H-indol-2-yl)-8-methyl-[1,2,4]triazolo[1,5-a]pyridine (597);

2-(4,4-difluoropiperidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (602);

1-(4-(3-isopropyl-2-(8-methyl-[1,2,4]triazolo[1,5-a]pyridin-6-yl)-1H-indol-5-yl)piperidin-1-yl)-2-(pyrazin-2-yl)ethan-1-one (603);

(4-(3-isopropyl-2-(8-methyl-[1,2,4]triazolo[1,5-a]pyridin-6-yl)-1H-indol-5-yl)piperidin-1-yl)(1-(pyrazin-2-yl)cyclopropyl)methanone (604);

1-(4-(3-isopropyl-2-(8-methyl-[1,2,4]triazolo[1,5-a]pyridin-6-yl)-1H-indol-5-yl)piperidin-1-yl)-2-(2-methyl-2H-tetrazol-5-yl)ethan-1-one (605);

1-(4-(3-isopropyl-2-(8-methyl-[1,2,4]triazolo[1,5-a]pyridin-6-yl)-1H-indol-5-yl)piperidin-1-yl)-2-(methylsulfonyl)ethan-1-one (606);

N-(2-(4-(3-isopropyl-2-(8-methyl-[1,2,4]triazolo[1,5-a]pyridin-6-yl)-1H-indol-5-yl) piperidin-1-yl)-2-oxoethyl)methanesulfonamide (607);

1-(4-(3-isopropyl-2-(8-methyl-[1,2,4]triazolo[1,5-a]pyridin-6-yl)-1H-indol-5-yl)piperidin-1-yl)-3-(methylsulfonyl)propan-1-one (608);

6-(3-isopropyl-5-(1-((2-methyl-1H-imidazol-4-yl)methyl)piperidin-4-yl)-1H-indol-2-yl)-8-methyl-[1,2,4]triazolo[1,5-a]pyridine (620);

(4-(3-isopropyl-2-(8-methyl-[1,2,4]triazolo [1,5-a]pyridin-6-yl)-1H-indol-5-yl)piperidin-1-yl)(2,2,3,3-tetramethylcyclopropyl)methanone (621);

((2S,4R)-4-hydroxypyrrolidin-2-yl)(4-(3-isopropyl-2-(8-methyl-[1,2,4]triazolo[1,5-a]pyridin-6-yl)-1H-indol-5-yl)piperidin-1-yl)methanone (622);

((2S,3R)-3-hydroxypyrrolidin-2-yl)(4-(3-isopropyl-2-(8-methyl-[1,2,4]triazolo[1,5-a]pyridin-6-yl)-1H-indol-5-yl)piperidin-1-yl)methanone (623);

((2S,4S)-4-hydroxypyrrolidin-2-yl)(4-(3-isopropyl-2-(8-methyl-[1,2,4]triazolo[1,5-a]pyridin-6-yl)-1H-indol-5-yl)piperidin-1-yl)methanone (624);

((2R,4R)-4-hydroxypyrrolidin-2-yl)(4-(3-isopropyl-2-(8-methyl-[1,2,4]triazolo[1,5-a]pyridin-6-yl)-1H-indol-5-yl)piperidin-1-yl)methanone (625);

(4-(3-isopropyl-2-(8-methyl-[1,2,4]triazolo[1,5-a]pyridin-6-yl)-1H-indol-5-yl)piperidin-1-yl)((2S,4R)-4-methoxypyrrolidin-2-yl)methanone (626);

((2S,4R)-4-fluoropyrrolidin-2-yl)(4-(3-isopropyl-2-(8-methyl-[1,2,4]triazolo[1,5-a]pyridin-6-yl)-1H-indol-5-yl)piperidin-1-yl)methanone (627);

1-((2S,4R)-4-hydroxy-2-(4-(3-isopropyl-2-(8-methyl-[1,2,4]triazolo[1,5-a]pyridin-6-yl)-1H-indol-5-yl)piperidine-1-carbonyl)pyrrolidin-1-yl)ethan-1-one (628);

2-(dimethylamino)-1-(4-(3-ethyl-2-(8-methyl-[1,2,4]triazolo[1,5-a]pyridin-6-yl)-1H-indo 1-5-yl)piperidin-1-yl)ethan-1-one (703);

1-(4-(3-ethyl-2-(8-methyl-[1,2,4]triazolo[1,5-a]pyridin-6-yl)-1H-indol-5-yl)piperidin-1-yl)-2-(methylamino)ethan-1-one (704);

(R)-1-(4-(3-(2,2-difluoroethyl)-2-(8-methyl-[1,2,4]triazolo[1,5-a]pyridin-6-yl)-1H-indol-5-yl)piperidin-1-yl)-3-hydroxybutan-1-one (705);

1-(4-(3-(2,2-difluoroethyl)-2-(8-methyl-[1,2,4]triazolo[1,5-a]pyridin-6-yl)-1H-indol-5-yl)piperidin-1-yl)-2-(methylamino)ethan-1-one (706);

(S)-1-(4-(3-(2,2-difluoroethyl)-2-(8-methyl-[1,2,4]triazolo[1,5-a]pyridin-6-yl)-1H-indol-5-yl)piperidin-1-yl)-3-hydroxybutan-1-one (707);

1-(4-(3-(2,2-difluoroethyl)-2-(8-methyl-[1,2,4]triazolo[1,5-a]pyridin-6-yl)-1H-indol-5-yl) piperidin-1-yl)-2-(dimethylamino)ethan-1-one (712);

2-((2-hydroxyethyl)(methyl)amino)-1-(4-(3-isopropyl-2-(8-methyl-[1,2,4]triazolo[1,5-a]pyridin-6-yl)-1H-indol-5-yl)piperidin-1-yl) ethan-1-one (714);

2-(cyclopropyl(2-hydroxyethyl)amino)-1-(4-(3-isopropyl-2-(8-methyl-[1,2,4]triazolo[1,5-a]pyridin-6-yl)-1H-indol-5-yl)piperidin-1-yl)ethan-1-one (715);

2-(3,3-difluoropyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (716);

2-(1,1-dioxidothiomorpholino)-1-(4-(3-isopropyl-2-(8-methyl-[1,2,4]triazolo[1,5-a]pyridin-6-yl)-1H-indol-5-yl)piperidin-1-yl)ethan-1-one (717);

1-(4-(3-isopropyl-2-(8-methyl-[1,2,4]triazolo[1,5-a]pyridin-6-yl)-1H-indol-5-yl) piperidin-1-yl)-2-((1-methylcyclopropyl)amino)ethan-1-one (768);

1-(4-(3-isopropyl-2-(8-methyl-[1,2,4]triazolo[1,5-a]pyridin-6-yl)-1H-indol-5-yl)piperidin-1-yl)-2-(piperidin-1-yl) ethan-1-one (769);

1-(4-(3-isopropyl-2-(8-methyl-[1,2,4]triazolo[1,5-a]pyridin-6-yl)-1H-indol-5-yl)piperidin-1-yl)-2-(pyrrolidin-1-yl)ethan-1-one (770);

1-(4-(3-isopropyl-2-(8-methyl-[1,2,4]triazolo[1,5-a]pyridin-6-yl)-1H-indol-5-yl)piperidin-1-yl)-2-(2-oxa-6-azaspiro[3.3]heptan-6-yl)ethan-1-one (771);

1-(4-(3-isopropyl-2-(8-methyl-[1,2,4]triazolo[1,5-a]pyridin-6-yl)-1H-indol-5-yl)piperidin-1-yl)-2-(4-(2-methoxyethyl)piperazin-1-yl)ethan-1-one (772);

1-(4-(3-isopropyl-2-(8-methyl-[1,2,4]triazolo[1,5-a]pyridin-6-yl)-1H-indol-5-yl) piperidin-1-yl)-2-(4-methoxypiperidin-1-yl)ethan-1-one (773);

(S)-2-(3-hydroxypyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (774);

(S)-2-(3-hydroxypiperidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (775);

(R)-2-(3-hydroxypyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (776);

2-(4-(3-isopropyl-2-(8-methyl-[1,2,4]triazolo[1,5-a]pyridin-6-yl)-1H-indol-5-yl)piperidin-1-yl)-1-(3-(methylsulfonyl) azetidin-1-yl)ethan-1-one (782);

1-(1,1-dioxidothiazolidin-3-yl)-2-(4-(3-isopropyl-2-(8-methyl-[1,2,4]triazolo[1,5-a]pyridin-6-yl)-1H-indol-5-yl)piperidin-1-yl)ethan-1-one (783-784);

2-(4-(3-isopropyl-2-(8-methyl-[1,2,4]triazolo[1,5-a]pyridin-6-yl)-1H-indol-5-yl) piperidin-1-yl)-N-(2-(methylthio)ethyl)acetamide (785);

1-((2R,4R)-2-(hydroxymethyl)-4-methoxypyrrolidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (786);

N-(2-hydroxyethyl)-2-(4-(3-isopropyl-2-(8-methyl-[1,2,4]triazolo[1,5-a]pyridin-6-yl)-1H-indol-5-yl)piperidin-1-yl)-N-methylacetamide (787);

N-ethyl-N-(2-hydroxyethyl)-2-(4-(3-isopropyl-2-(8-methyl-[1,2,4]triazolo[1,5-a]pyridin-6-yl)-1H-indol-5-yl)piperidin-1-yl)acetamide (788);

N-(2-hydroxyethyl)-2-(4-(3-isopropyl-2-(8-methyl-[1,2,4]triazolo[1,5-a]pyridin-6-yl)-1H-indol-5-yl)piperidin-1-yl)-N-propylacetamide (789);

(R)-1-(2-(hydroxymethyl)pyrrolidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (790);

2-(4-(3-isopropyl-2-(8-methyl-[1,2,4]triazolo[1,5-a]pyridin-6-yl)-1H-indol-5-yl)piperidin-1-yl)-N-methyl-N-(tetrahydro-2H-pyran-4-yl)acetamide (791);

N-(3-hydroxypropyl)-2-(4-(3-isopropyl-2-(8-methyl-[1,2,4]triazolo[1,5-a]pyridin-6-yl)-1H-indol-5-yl)piperidin-1-yl)-N-methylacetamide (792);

2-(4-(3-isopropyl-2-(8-methyl-[1,2,4]triazolo[1,5-a]pyridin-6-yl)-1H-indol-5-yl)piperidin-1-yl)-N-methyl-N-(tetrahydrofuran-3-yl)acetamide (793);

N-(2-(1-hydroxycyclopentyl)ethyl)-2-(4-(3-isopropyl-2-(8-methyl-[1,2,4]triazolo[1,5-a]pyridin-6-yl)-1H-indol-5-yl)piperidin-1-yl)-N-methylacetamide (794);

(R)-1-(3-(hydroxymethyl) morpholino)-2-(4-(3-isopropyl-2-(8-methyl-[1,2,4]triazolo[1,5-a]pyridin-6-yl)-1H-indol-5-yl)piperidin-1-yl)ethan-1-one (795);

N-(2-hydroxy-2-methylpropyl)-2-(4-(3-isopropyl-2-(8-methyl-[1,2,4]triazolo[1,5-a]pyridin-6-yl)-1H-indol-5-yl)piperidin-1-yl)-N-methylacetamide (796);

(S)-1-(3-(hydroxymethyl)morpholino)-2-(4-(3-isopropyl-2-(8-methyl-[1,2,4]triazolo [1,5-a]pyridin-6-yl)-1H-indol-5-yl)piperidin-1-yl)ethan-1-one (797);

(S)-2-(4-(3-isopropyl-2-(8-methyl-[1,2,4]triazolo[1,5-a]pyridin-6-yl)-1H-indol-5-yl)piperidin-1-yl)-N-methyl-N-(tetrahydrofuran-3-yl)acetamide (798);

1-((2R,4R)-2-(hydroxymethyl)-4-methylpyrrolidin-1-yl)-2-(4-(3-isopropyl-2-(8-methyl-[1,2,4]triazolo[1,5-a]pyridin-6-yl)-1H-indol-5-yl) piperidin-1-yl)ethan-1-one (799);

N-(2-hydroxyethyl)-2-(4-(3-isopropyl-2-(8-methyl-[1,2,4]triazolo[1,5-a]pyridin-6-yl)-1H-indol-5-yl)piperidin-1-yl)-N-(2-methylbutyl)acetamide (800);

N-cyclopropyl-N-(2-hydroxyethyl)-2-(4-(3-isopropyl-2-(8-methyl-[1,2,4]triazolo[1,5-a]pyridin-6-yl)-1H-indol-5-yl) piperidin-1-yl)acetamide (801);

1-(4-(3-isopropyl-2-(8-methyl-[1,2,4]triazolo[1,5-a]pyridin-6-yl)-1H-indol-5-yl)piperidin-1-yl)-3-morpholinopropan-1-one (882);

3-(cyclopropyl(2-hydroxyethyl)(methyl)-l4-azaneyl)-1-(4-(3-isopropyl-2-(8-methyl-[1,2,4]triazolo[1,5-a]pyridin-6-yl)-1H-indol-5-yl)piperidin-1-yl)propan-1-one (883);

3-(1,1-dioxidothiomorpholino)-1-(4-(3-isopropyl-2-(8-methyl-[1,2,4]triazolo[1,5-a]pyridin-6-yl)-1H-indol-5-yl) piperidin-1-yl)propan-1-one (884); or 4-(3-isopropyl-2-(8-methyl-[1,2,4]triazolo[1,5-a]pyridin-6-yl)-1H-indol-5-yl)piperidine-1-carboximidamide (994).

One embodiment provides a compound of Formula (I) or a salt thereof, wherein said compound has the structure of Formula (I-4):

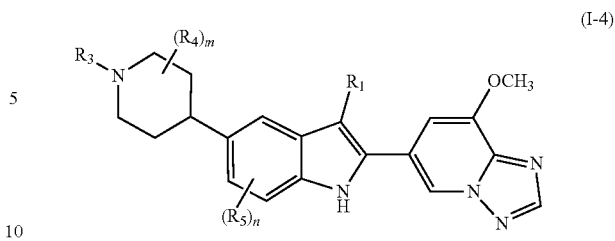

(I-4)

and $R_1$, $R_3$, $R_4$, $R_5$, m, and n are defined in the first aspect or the second aspect. Included in this embodiment are compounds in which $R_1$ is —CHCH$_3$, —CH(CH$_3$)$_2$, or —CH$_2$CHF$_2$. Included in this embodiment are compounds in which $R_3$ is H, —CH$_2$CH(CH$_3$)$_2$, —CH$_2$CN, —CH$_2$C(CH$_3$)$_2$OH, —CH$_2$CH$_2$OCH$_3$, —CH$_2$CH$_2$NH(CH$_3$), —CH$_2$CH$_2$S(O)$_2$CH$_3$, —CH(CH$_3$)CH$_2$S(O)$_2$CH$_3$, —CH$_2$C(O)NH$_2$, —CH$_2$C(O)NH(CH$_3$), —CH$_2$C(O)N(CH$_3$)$_2$, —CH$_2$C(O)NH(CH$_2$C(CH$_3$)$_2$OH), —CH$_2$C(O)N(CH$_3$)(CH$_2$CH$_3$), —C(O)CH$_2$S(O)$_2$CH$_3$, —C(O)CH$_2$OCH$_3$, —C(O)CH$_2$NH(CH$_3$), —C(O)CH$_2$NH(CH$_2$CH$_2$OCH$_3$), —C(O)CH$_2$N(CH$_3$)$_2$, —C(O)CH$_2$CH$_2$OCH$_3$, —C(O)CH$_2$CH$_2$N(CH$_3$)$_2$, —C(O)CH$_2$CH$_2$CH$_2$S(O)$_2$NH$_2$, —C(O)CH$_2$C(CH$_3$)$_2$OH, or -L$_1$-A; L$_1$ is —CH$_2$—, —C(O)—, —C(O)CH$_2$—, —C(O)CH$_2$CH$_2$—, —C(O)CH$_2$NH—, —CH$_2$C(O)—, or —CH$_2$C(O)NH—; and A is azetidinyl, cyclobutyl, dioxanyl, dioxotetrahydrothiopyranyl, dioxothiomorpholinyl, morpholinyl, oxetanyl, piperazinonyl, pyrrolidinonyl, pyrrolidinyl, tetrahydrofuranyl, or tetrahydropyranyl, each substituted with -L$_2$-R$_a$ and zero to 1 R$_b$; L$_2$ is a bond; R$_a$ is H, F, C$_{1-2}$ alkyl, —CN, —OH, —OCH$_3$, —C(O)CH$_3$, or —C(O)OC(CH$_3$)$_3$; and R$_b$ is F or —CH$_3$. Also included in this embodiment are compounds in which $R_1$ is —CH(CH$_3$)$_2$; m is zero, and n is zero.

One embodiment provides a compound of Formula (I) or a salt thereof, wherein said compound is 6-(3-isopropyl-5-(piperidin-4-yl)-1H-indol-2-yl)-8-methoxy-[1,2,4]triazolo[1,5-a]pyridine (5);

2-(4-(3-isopropyl-2-(8-methoxy-[1,2,4]triazolo[1,5-a]pyridin-6-yl)-1H-indol-5-yl)piperid in-1-yl)acetonitrile (21);

2-(4-(3-isopropyl-2-(8-methoxy-[1,2,4]triazolo[1,5-a]pyridin-6-yl)-1H-indol-5-yl)piperid in-1-yl)acetamide (22);

2-(4-(3-isopropyl-2-(8-methoxy-[1,2,4]triazolo[1,5-a]pyridin-6-yl)-1H-indol-5-yl)piperid in-1-yl)-N-methylacetamide (23);

1-(4-(3-isopropyl-2-(8-methoxy-[1,2,4]triazolo[1,5-a]pyridin-6-yl)-1H-indol-5-yl)piperid in-1-yl)-2-methylpropan-2-ol (24);

2-(4-(3-isopropyl-2-(8-methoxy-[1,2,4]triazolo[1,5-a]pyridin-6-yl)-1H-indol-5-yl)piperid in-1-yl)-N,N-dimethylacetamide (25);

6-(3-isopropyl-5-(1-(oxetan-3-yl)piperidin-4-yl)-1H-indol-2-yl)-8-methoxy-[1,2,4]triazolo[1,5-a]pyridine (44);

6-(3-isopropyl-5-(1-(tetrahydro-2H-pyran-4-yl)piperidin-4-yl)-1H-indol-2-yl)-8-methoxy-[1,2,4]triazolo[1,5-a]pyridine (45); 1-(4-(3-isopropyl-2-(8-methoxy-[1,2,4]triazolo [1,5-a]pyridin-6-yl)-1H-indol-5-yl)piperidin-1-yl)-2-(methylamino) ethan-1-one (62);

1-(4-(3-isopropyl-2-(8-methoxy-[1,2,4]triazolo[1,5-a]pyridin-6-yl)-1H-indol-5-yl)piperid in-1-yl)-2-methoxyethan-1-one (63);

2-(dimethylamino)-1-(4-(3-isopropyl-2-(8-methoxy-[1,2,4]triazolo[1,5-a]pyridin-6-yl)-1H-indol-5-yl)piperidin-1-yl)ethan-1-one (67);

6-(3-(2,2-difluoroethyl)-5-(piperidin-4-yl)-1H-indol-2-yl)-8-methoxy-[1,2,4]triazolo [1,5-a]pyridine (156);
6-(3-ethyl-5-(piperidin-4-yl)-1H-indol-2-yl)-8-methoxy-[1,2,4]triazolo[1,5-a]pyridine (157);
6-(3-isopropyl-5-(1-(2-(methylsulfonyl)ethyl)piperidin-4-yl)-1H-indol-2-yl)-8-methoxy-[1,2,4]triazolo[1,5-a]pyridine (263);
6-(3-isopropyl-5-(1-(1-(methylsulfonyl)propan-2-yl)piperidin-4-yl)-1H-indol-2-yl)-8-methoxy-[1,2,4]triazolo[1,5-a]pyridine (264);
6-(3-isopropyl-5-(1-(1-(methylsulfonyl)propan-2-yl)piperidin-4-yl)-1H-indol-2-yl)-8-methoxy-[1,2,4]triazolo[1,5-a]pyridine (265); 6-(3-isopropyl-5-(1-(2-methoxyethyl)piperidin-4-yl)-1H-indol-2-yl)-8-methoxy-[1,2,4]triazolo[1,5-a]pyridine (266);
2-(4-(3-(2,2-difluoroethyl)-2-(8-methoxy-[1,2,4]triazolo[1,5-a]pyridin-6-yl)-1H-indol-5-yl)piperidin-1-yl)-N,N-dimethylacetamide (329);
2-(4-(3-(2,2-difluoroethyl)-2-(8-methoxy-[1,2,4]triazolo [1,5-a]pyridin-6-yl)-1H-indol-5-yl)piperidin-1-yl)-N-methylacetamide (330);
2-(4-(3-ethyl-2-(8-methoxy-[1,2,4]triazolo [1,5-a]pyridin-6-yl)-1H-indol-5-yl)piperidin-1-yl)-N-methylacetamide (331);
6-(3-ethyl-5-(1-(2-(methylsulfonyl)ethyl)piperidin-4-yl)-1H-indol-2-yl)-8-methoxy-[1,2,4]triazolo[1,5-a]pyridine (332); 2-(4-(3-ethyl-2-(8-methoxy-[1,2,4]triazolo[1,5-a]pyridin-6-yl)-1H-indol-5-yl) piperidin-1-yl)acetamide (333);
1-(4-(3-ethyl-2-(8-methoxy-[1,2,4]triazolo[1,5-a]pyridin-6-yl)-1H-indol-5-yl)piperidin-1-yl)-2-methylpropan-2-ol (334);
2-(4-(3-ethyl-2-(8-methoxy-[1,2,4]triazolo[1,5-a]pyridin-6-yl)-1H-indol-5-yl)piperidin-1-yl)-N,N-dimethylacetamide (335); 6-(3-ethyl-5-(1-(2-methoxyethyl) piperidin-4-yl)-1H-indol-2-yl)-8-methoxy-[1,2,4]triazolo[1,5-a]pyridine (336);
1-(4-(3-(2,2-difluoroethyl)-2-(8-methoxy-[1,2,4]triazolo[1,5-a]pyridin-6-yl)-1H-indol-5-yl)piperidin-1-yl)-2-methylpropan-2-ol (349);
4-(4-(3-isopropyl-2-(8-methoxy-[1,2,4]triazolo[1,5-a]pyridin-6-yl)-1H-indol-5-yl)piperid in-1-yl)tetrahydro-2H-thiopyran 1,1-dioxide (561);
6-(5-(1-(2,2-dimethyltetrahydro-2H-pyran-4-yl)piperidin-4-yl)-3-isopropyl-1H-indol-2-yl)-8-methoxy-[1,2,4]triazolo [1,5-a]pyridine (562-564);
(R)-3-((4-(3-isopropyl-2-(8-methoxy-[1,2,4]triazolo [1,5-a]pyridin-6-yl)-1H-indol-5-yl)piperidin-1-yl)methyl)morpholine (565);
6-(3-isopropyl-5-(1-((3-methyloxetan-3-yl)methyl)piperidin-4-yl)-1H-indol-2-yl)-8-meth oxy-[1,2,4]triazolo[1,5-a]pyridine (566);
3-(4-(3-isopropyl-2-(8-methoxy-[1,2,4]triazolo[1,5-a]pyridin-6-yl)-1H-indol-5-yl)piperid in-1-yl)cyclobutane-1-carbonitrile (567);
6-(3-isopropyl-5-(1-(tetrahydrofuran-3-yl)piperidin-4-yl)-1H-indol-2-yl)-8-methoxy-[1,2,4]triazolo[1,5-a]pyridine (568-569); 2-(4-(3-isopropyl-2-(8-methoxy-[1,2,4]triazolo[1,5-a]pyridin-6-yl)-1H-indol-5-yl)piperidin-1-yl)-N-methylethan-1-amine (570);
6-(3-(2,2-difluoroethyl)-5-(1-(oxetan-3-yl)piperidin-4-yl)-1H-indol-2-yl)-8-methoxy-[1,2,4]triazolo[1,5-a]pyridine (598);
6-(3-ethyl-5-(1-(oxetan-3-yl)piperidin-4-yl)-1H-indol-2-yl)-8-methoxy-[1,2,4]triazolo[1,5-a]pyridine (600); (4-(3-isopropyl-2-(8-methoxy-[1,2,4]triazolo [1,5-a]pyridin-6-yl)-1H-indol-5-yl)piperidin-1-yl)(tetrahydrofuran-2-yl) methanone (663);
1-(4-(3-isopropyl-2-(8-methoxy-[1,2,4]triazolo[1,5-a]pyridin-6-yl)-1H-indol-5-yl)piperid in-1-yl)-3-methoxypropan-1-one (664);
4-(4-(3-isopropyl-2-(8-methoxy-[1,2,4]triazolo[1,5-a]pyridin-6-yl)-1H-indol-5-yl) piperidin-1-yl)-4-oxobutane-1-sulfonamide (665);
1-(4-(3-isopropyl-2-(8-methoxy-[1,2,4]triazolo[1,5-a]pyridin-6-yl)-1H-indol-5-yl)piperidin-1-yl)-2-(tetrahydro-2H-pyran-4-yl) ethan-1-one (666);
3-(dimethylamino)-1-(4-(3-isopropyl-2-(8-methoxy-[1,2,4]triazolo[1,5-a]pyridin-6-yl)-1H-indol-5-yl)piperidin-1-yl)propan-1-one (667);
1-(4-(3-isopropyl-2-(8-methoxy-[1,2,4]triazolo[1,5-a]pyridin-6-yl)-1H-indol-5-yl) piperidin-1-yl)-2-(methylsulfonyl)ethan-1-one (668);
3-hydroxy-1-(4-(3-isopropyl-2-(8-methoxy-[1,2,4]triazolo [1,5-a]pyridin-6-yl)-1H-indol-5-yl)piperidin-1-yl)-3-methylbutan-1-one (669);
(S)-1-(2-(4-(3-isopropyl-2-(8-methoxy-[1,2,4]triazolo[1,5-a]pyridin-6-yl)-1H-indol-5-yl) piperidine-1-carbonyl) pyrrolidin-1-yl)ethan-1-one (670);
1-(3-(4-(3-isopropyl-2-(8-methoxy-[1,2,4]triazolo[1,5-a]pyridin-6-yl)-1H-indol-5-yl)piperidin-1-yl)-3-oxopropyl) pyrrolidin-2-one (671);
(4-(3-isopropyl-2-(8-methoxy-[1,2,4]triazolo[1,5-a]pyridin-6-yl)-1H-indol-5-yl) piperidin-1-yl)(1-methylpyrrolidin-3-yl)methanone (672);
1-(4-(3-isopropyl-2-(8-methoxy-[1,2,4]triazolo[1,5-a]pyridin-6-yl)-1H-indol-5-yl)piperid in-1-yl)-2-morpholinoethan-1-one (673);
((2S,4R)-4-hydroxypyrrolidin-2-yl)(4-(3-isopropyl-2-(8-methoxy-[1,2,4]triazolo[1,5-a]pyridin-6-yl)-1H-indol-5-yl)piperidin-1-yl)methanone (674);
(4-(3-isopropyl-2-(8-methoxy-[1,2,4]triazolo[1,5-a]pyridin-6-yl)-1H-indol-5-yl)piperidin-1-yl)((2S,4R)-4-methoxypyrrolidin-2-yl)methanone (675);
(4-(3-isopropyl-2-(8-methoxy-[1,2,4]triazolo[1,5-a]pyridin-6-yl)-1H-indol-5-yl)piperidin-1-yl)(1-methylpyrrolidin-3-yl) methanone (676);
4-(4-(3-isopropyl-2-(8-methoxy-[1,2,4]triazolo[1,5-a]pyridin-6-yl)-1H-indol-5-yl)piperidine-1-carbonyl)-1-methylpyrrolidin-2-one (677);
4-(4-(3-isopropyl-2-(8-methoxy-[1,2,4]triazolo [1,5-a]pyridin-6-yl)-1H-indol-5-yl)piperidine-1-carbonyl)-1-methylpyrrolidin-2-one (678);
(4-(3-isopropyl-2-(8-methoxy-[1,2,4]triazolo[1,5-a]pyridin-6-yl)-1H-indol-5-yl)piperidin-1-yl)(1-methylpyrrolidin-3-yl)methanone (679);
2-(dimethylamino)-1-(4-(3-ethyl-2-(8-methoxy-[1,2,4]triazolo[1,5-a]pyridin-6-yl)-1H-indol-5-yl)piperidin-1-yl) ethan-1-one (701);
1-(4-(3-ethyl-2-(8-methoxy-[1,2,4]triazolo[1,5-a]pyridin-6-yl)-1H-indol-5-yl)piperidin-1-yl)-2-(methylamino)ethan-1-one (702);
1-(4-(3-isopropyl-2-(8-methoxy-[1,2,4]triazolo[1,5-a]pyridin-6-yl)-1H-indol-5-yl)piperidin-1-yl)-2-((2-methoxyethyl)amino)ethan-1-one (780); 1-(4-(3-isopropyl-2-(8-methoxy-[1,2,4]triazolo [1,5-a]pyridin-6-yl)-1H-indol-5-yl)piperidin-1-yl)-2-((3-methyloxetan-3-yl)amino)ethan-1-one (781);
2-(4-(3-isopropyl-2-(8-methoxy-[1,2,4]triazolo[1,5-a]pyridin-6-yl)-1H-indol-5-yl) piperidin-1-yl)-N-(3-methyloxetan-3-yl) acetamide (854); tert-butyl 3-(2-(4-(3-isopropyl-2-(8-methoxy-[1,2,4]triazolo[1,5-a]pyridin-6-yl)-1H-indol-5-yl)piperidin-1-yl)acetamido) azetidine-1-carboxylate (855);
2-(4-(3-isopropyl-2-(8-methoxy-[1,2,4]triazolo[1,5-a]pyridin-6-yl)-1H-indol-5-yl)piperid in-1-yl)-N-(4-methyltetrahydro-2H-pyran-4-yl)acetamide (856);
N-(2-hydroxy-2-methylpropyl)-2-(4-(3-isopropyl-2-(8-methoxy-[1,2,4]triazolo[1,5-a]pyridin-6-yl)-1H-indol-5-yl)piperidin-1-yl) acetamide (857);
1-(1,1-dioxidothiomorpholino)-2-(4-(3-isopropyl-2-(8-methoxy-[1,2,4]triazolo[1,5-a]pyridin-6-yl)-1H-indol-5-yl)piperidin-1-yl)ethan-1-one (858);
N-ethyl-2-(4-(3-isopropyl-2-(8-methoxy-[1,2,4]triazolo[1,5-a]pyridin-6-yl)-1H-indol-5-yl)piperidin-1-yl)-N-methylacetamide (859);
2-(4-(3-isopropyl-2-(8-methoxy-[1,2,4]triazolo[1,5-a]pyridin-6-yl)-1H-indol-5-yl)piperid in-1-yl)-N-(1-methylcyclobutyl)acetamide (860);
N-((3-ethyloxetan-3-yl)methyl)-2-(4-(3-isopropyl-2-(8-methoxy-[1,2,4]triazolo[1,5-a]pyridin-6-yl)-1H-indol-5-yl) piperidin-1-yl)acetamide (861);
2-(4-(3-isopropyl-2-(8-methoxy-[1,2,4]triazolo[1,5-a]pyridin-6-yl)-1H-indol-5-yl)piperidin-1-yl)-N-((3-methyloxetan-3-yl)methyl)acetamide (862);
(R)-1-(3-hydroxypyrrolidin-1-yl)-2-(4-(3-isopropyl-2-(8-methoxy-[1,2,4]triazolo[1,5-a]pyridin-6-yl)-1H-indol-5-yl)piperidin-1-yl) ethan-1-one (863);
1-(3-fluoroazetidin-1-yl)-2-(4-(3-isopropyl-2-(8-methoxy-[1,2,4]triazolo [1,5-a]pyridin-6-yl)-1H-indol-5-yl)piperidin-1-yl)ethan-1-one (864);
1-(3,3-difluoroazetidin-1-yl)-2-(4-(3-isopropyl-2-(8-methoxy-[1,2,4]triazolo[1,5-a]pyridin-6-yl)-1H-indol-5-yl) piperidin-1-yl)ethan-1-one (865);
4-(2-(4-(3-isopropyl-2-(8-methoxy-[1,2,4]triazolo[1,5-a]pyridin-6-yl)-1H-indol-5-yl)piperidin-1-yl) acetyl)piperazin-2-one (866);
1-(3-hydroxyazetidin-1-yl)-2-(4-(3-isopropyl-2-(8-methoxy-[1,2,4]triazolo[1,5-a]pyridin-6-yl)-1H-indol-5-yl)piperidin-1-yl)ethan-1-one (867);
(R)-1-(3-fluoropyrrolidin-1-yl)-2-(4-(3-isopropyl-2-(8-methoxy-[1,2,4]triazolo[1,5-a]pyridin-6-yl)-1H-indol-5-yl)piperidin-1-yl) ethan-1-one (868);
1-((2S,6R)-2,6-dimethylmorpholino)-2-(4-(3-isopropyl-2-(8-methoxy-[1,2,4]triazolo[1,5-a]pyridin-6-yl)-1H-indol-5-yl)piperidin-1-yl) ethan-1-one (869);
1-(azetidin-1-yl)-2-(4-(3-isopropyl-2-(8-methoxy-[1,2,4]triazolo[1,5-a]pyridin-6-yl)-1H-indol-5-yl) piperidin-1-yl) ethan-1-one (870);
(R)-2-(4-(3-isopropyl-2-(8-methoxy-[1,2,4]triazolo [1,5-a]pyridin-6-yl)-1H-indol-5-yl)piperidin-1-yl)-1-(3-methylmorpholino)ethan-1-one (871);
1-(3,3-difluoropyrrolidin-1-yl)-2-(4-(3-isopropyl-2-(8-methoxy-[1,2,4]triazolo[1,5-a]pyridin-6-yl)-1H-indol-5-yl)piperidin-1-yl)ethan-1-one (872);
1-(2,5-dimethylpyrrolidin-1-yl)-2-(4-(3-isopropyl-2-(8-methoxy-[1,2,4]triazolo[1,5-a]pyridin-6-yl)-1H-indol-5-yl) piperidin-1-yl)ethan-1-one (873);
(S)-1-(3-hydroxypyrrolidin-1-yl)-2-(4-(3-isopropyl-2-(8-methoxy-[1,2,4]triazolo[1,5-a]pyridin-6-yl)-1H-indol-5-yl) piperidin-1-yl)ethan-1-one (874);
(S)-1-(3-fluoropyrrolidin-1-yl)-2-(4-(3-isopropyl-2-(8-methoxy-[1,2,4]triazolo[1,5-a]pyridin-6-yl)-1H-indol-5-yl) piperidin-1-yl)ethan-1-one (875);
2-(4-(4-fluoro-3-isopropyl-2-(8-methoxy-[1,2,4]triazolo[1,5-a]pyridin-6-yl)-1H-indol-5-yl) piperidin-1-yl)-N,N-dimethylacetamide (991);
6-(4-fluoro-5-(1-isobutylpiperidin-4-yl)-3-isopropyl-1H-indol-2-yl)-8-methoxy-[1,2,4]triazolo[1,5-a]pyridine (992);
or 6-(5-(1-(2,2-dimethyl-1,3-dioxan-5-yl) piperidin-4-yl)-4-fluoro-3-isopropyl-1H-indol-2-yl)-8-methoxy-[1,2,4]triazolo[1,5-a]pyri dine (993).

One embodiment provides a compound of Formula (I-4) or a salt thereof, wherein $R_1$ is —$CH(CH_3)_2$; m is zero; n is zero, and $R_3$ is defined in the first aspect or the second aspect. Compounds of this embodiment have the structure of Formula (I-4a)

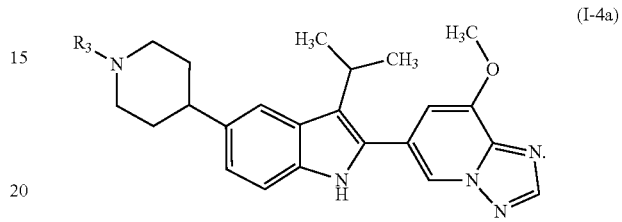

(I-4a)

Included in this embodiment are compounds in which $R_3$ is —$(CR_xR_x)_{1-2}C(O)NR_yR_y$ wherein each $R_x$ is independently H or —$CH_3$; and each $R_x$ is independently H or —$CH_3$. Also included in this embodiment are compounds in which $R_3$ is —$CH_2C(O)NH_2$, —$CH_2C(O)NH(CH_3)$, or —$CH_2C(O)N(CH_3)_2$.

One embodiment provides a compound of Formula (I) or a salt thereof, wherein said compound is:

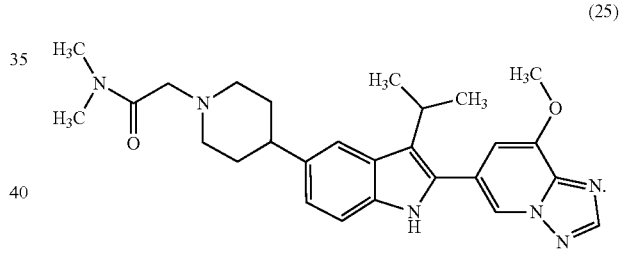

(25)

Included in this embodiment is 2-(4-(3-isopropyl-2-(8-methoxy-[1,2,4]triazolo[1,5-a]pyridin-6-yl)-1H-indol-5-yl) piperid in-1-yl)-N,N-dimethylacetamide (25). Also included in this embodiment is one or more salts of 2-(4-(3-isopropyl-2-(8-methoxy-[1,2,4]triazolo[1,5-a]pyridin-6-yl)-1H-indol-5-yl)piperidin-1-yl)-N,N-dimethylacetamide.

One embodiment provides a compound of Formula (I) or a salt thereof, wherein said compound has the structure of Formula (I-5):

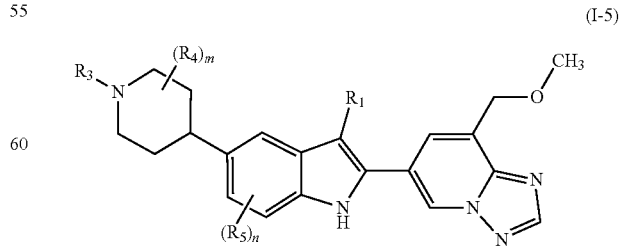

(I-5)

and $R_1$, $R_3$, $R_4$, $R_5$, m, and n are defined in the first aspect or the second aspect. Included in this embodiment are compounds in which $R_1$ is —CH(CH$_3$)$_2$. Included in this embodiment are compounds in which $R_3$ is H, —CH$_2$CN, —CH$_2$C(O)NH$_2$, —CH$_2$C(O)NH(CH$_3$), —CH$_2$C(O)NH (CH$_2$CH$_3$), —CH$_2$C(O)NH(CH$_2$CH$_2$CN), —CH$_2$C(O)NH (CH$_2$CH$_2$CF$_3$), —CH$_2$C(O)NH(CH(CH$_3$)$_2$), —CH$_2$C(O)N (CH$_3$)CH$_2$CH$_2$OCH$_3$, —CH$_2$C(O)N(CH$_3$)CH$_2$CH$_2$CN, —CH$_2$C(O)N(CH$_3$)CH$_2$CH$_2$CH$_2$OH, —CH$_2$CH$_2$S(O)$_2$NH$_2$, —CH$_2$CH$_2$S(O)$_2$CH$_3$, —CH$_2$C(O)NHCH (CH$_2$CH$_2$H)(cyclopropyl), or -L$_1$-A; L$_1$ is —CH$_2$—, —CH$_2$CH$_2$—, —CH$_2$C(O)—, —CH$_2$C(O)N(CH$_3$)—, or —CH$_2$C(O)N(CH$_3$)CH$_2$CH$_2$—; A is azetidinyl, dioxidothiadiazinanyl, dioxoisothiazolidinyl, dioxothiomorpholinyl, morpholinyl, oxetanyl, piperidinyl, pyrazolyl, pyrimidinyl, pyrrolidinyl, tetrahydrofuranyl, tetrahydropyranyl, or triazolyl, each substituted with -L$_2$-R$_a$ and zero to 1 R$_b$; L$_2$ is a bond; R$_a$ is H, F, —CH$_3$, —CN, —CH$_2$OH, or —S(O)$_2$CH$_3$; and R$_b$ is F, —CH$_3$, —CF$_3$, or —OCH$_3$. Also included in this embodiment are compounds in which $R_1$ is —CH(CH$_3$)$_2$; m is zero, and n is zero.

One embodiment provides a compound of Formula (I) or a salt thereof, wherein said compound is 6-(3-isopropyl-5-(piperidin-4-yl)-1H-indol-2-yl)-8-(methoxymethyl)-[1,2,4]triazolo[1,5-a]pyridine (6);
2-(4-(3-isopropyl-2-(8-(methoxymethyl)-[1,2,4]triazolo[1,5-a]pyridin-6-yl)-1H-indol-5-yl)piperidin-1-yl)-N,N-dimethylacetamide (198);
2-(4-(3-isopropyl-2-(8-(methoxymethyl)-[1,2,4]triazolo[1,5-a]pyridin-6-yl)-1H-indol-5-yl)piperidin-1-yl) acetamide (199);
6-(3-isopropyl-5-(1-(2-(methylsulfonyl)ethyl)piperidin-4-yl)-1H-indol-2-yl)-8-(methoxy methyl)-[1,2,4]triazolo[1,5-a]pyridine (200);
2-(4-(3-isopropyl-2-(8-(methoxymethyl)-[1,2,4]triazolo[1,5-a]pyridin-6-yl)-1H-indol-5-yl)piperidin-1-yl)acetonitrile (201);
2-(4-(3-isopropyl-2-(8-(methoxymethyl)-[1,2,4]triazolo[1,5-a]pyridin-6-yl)-1H-indol-5-yl)piperidin-1-yl)-N-methylacetamide (202);
2-(4-(3-isopropyl-2-(8-(methoxymethyl)-[1,2,4]triazolo[1,5-a]pyridin-6-yl)-1H-indol-5-yl)piperidin-1-yl)ethane-1-sulfonamide (203);
6-(3-isopropyl-5-(1-((1-methyl-1H-1,2,3-triazol-4-yl)methyl)piperidin-4-yl)-1H-indol-2-yl)-8-(methoxymethyl)-[1,2,4]triazolo[1,5-a]pyridine (470);
6-(3-isopropyl-5-(1-((2-methylpyrimidin-5-yl)methyl)piperidin-4-yl)-1H-indol-2-yl)-8-(methoxymethyl)-[1,2,4]triazolo[1,5-a]pyridine (471);
6-(3-isopropyl-5-(1-((3-methyloxetan-3-yl)methyl)piperidin-4-yl)-1H-indol-2-yl)-8-(methoxymethyl)-[1,2,4]triazolo[1,5-a]pyridine (472);
6-(3-isopropyl-5-(1-(oxetan-3-yl)piperidin-4-yl)-1H-indol-2-yl)-8-(methoxymethyl)-[1,2,4]triazolo[1,5-a]pyridine (473);
2-(2-(4-(3-isopropyl-2-(8-(methoxymethyl)-[1,2,4]triazolo[1,5-a]pyridin-6-yl)-1H-indol-5-yl)piperidin-1-yl)ethyl)isothiazolidine 1,1-dioxide (474);
N-(2-cyanoethyl)-2-(4-(3-isopropyl-2-(8-(methoxymethyl)-[1,2,4]triazolo[1,5-a]pyridin-6-yl)-1H-indol-5-yl) piperidin-1-yl)-N-methylacetamide (811);
(S)-1-(2-(hydroxymethyl)pyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (812);
1-(1,1-dioxido-1,2,4-thiadiazinan-4-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (813);
N-(3-hydroxypropyl)-2-(4-(3-isopropyl-2-(8-(methoxymethyl)-[1,2,4]triazolo[1,5-a]pyridin-6-yl)-1H-indol-5-yl)piperidin-1-yl)-N-methylacetamide (814);
2-(4-(3-isopropyl-2-(8-(methoxymethyl)-[1,5-a]pyridin-6-yl)-1H-indol-5-yl)piperidin-1-yl)-N-methyl-N-(tetrahydro-2H-pyran-4-yl)acetamide (815);
N-ethyl-2-(4-(3-isopropyl-2-(8-(methoxymethyl)-[1,2,4]triazolo[1,5-a]pyridin-6-yl)-1H-indol-5-yl)piperidin-1-yl) acetamide (816);
N,N-diethyl-2-(4-(3-isopropyl-2-(8-(methoxymethyl)-[1,2,4]triazolo[1,5-a]pyridin-6-yl)-1H-indol-5-yl)piperidin-1-yl)acetamide (817);
N-(2-hydroxyethyl)-2-(4-(3-isopropyl-2-(8-(methoxymethyl)-[1,2,4]triazolo[1,5-a]pyridin-6-yl)-1H-indol-5-yl)piperidin-1-yl)-N-methylacetamide (818);
N-ethyl-2-(4-(3-isopropyl-2-(8-(methoxymethyl)-[1,2,4]triazolo[1,5-a]pyridin-6-yl)-1H-indol-5-yl)piperidin-1-yl)-N-methylacetamide (819);
2-(4-(3-isopropyl-2-(8-(methoxymethyl)-[1,2,4]triazolo[1,5-a]pyridin-6-yl)-1H-indol-5-yl)piperidin-1-yl)-N-(2-methoxyethyl)-N-methylacetamide (820);
N-isopropyl-2-(4-(3-isopropyl-2-(8-(methoxymethyl)-[1,2,4]triazolo[1,5-a]pyridin-6-yl)-1H-indol-5-yl)piperidin-1-yl)acetamide (821);
1-((2R,4R)-2-(hydroxymethyl)-4-methoxypyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (822);
(S)-2-(4-(3-isopropyl-2-(8-(methoxymethyl)-[1,2,4]triazolo[1,5-a]pyridin-6-yl)-1H-indol-5-yl)piperidin-1-yl)-N-methyl-N-(tetrahydrofuran-3-yl)acetamide (823);
1-((2R,4R)-2-(hydroxymethyl)-4-(trifluoromethyl)pyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (824);
N-ethyl-N-(2-hydroxyethyl)-2-(4-(3-isopropyl-2-(8-(methoxymethyl)-[1,2,4]triazolo[1,5-a]pyridin-6-yl)-1H-indol-5-yl)piperidin-1-yl)acetamide (825);
2-(4-(3-isopropyl-2-(8-(methoxymethyl)-[1,2,4]triazolo[1,5-a]pyridin-6-yl)-1H-indol-5-yl)piperidin-1-yl)-1-(3-(methylsulfonyl)azetidin-1-yl)ethan-1-one (826);
1-(1,1-dioxidothiomorpholino)-2-(4-(3-isopropyl-2-(8-(methoxymethyl)-[1,2,4]triazolo[1,5-a]pyridin-6-yl)-1H-indol-5-yl)piperidin-1-yl)ethan-1-one (827);
N-(2-hydroxy-2-methylpropyl)-2-(4-(3-isopropyl-2-(8-(methoxymethyl)-[1,2,4]triazolo[1,5-a]pyridin-6-yl)-1H-indol-5-yl)piperidin-1-yl)-N-methylacetamide (828);
(R)-1-(3-(hydroxymethyl)morpholino)-2-(4-(3-isopropyl-2-(8-(methoxymethyl)-[1,2,4]triazolo[1,5-a]pyridin-6-yl)-1H-indol-5-yl)piperidin-1-yl)ethan-1-one (829);
1-(4,4-difluoropiperidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (830);
1-(3,3-dimethylazetidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (831);
2-(4-(3-isopropyl-2-(8-(methoxymethyl)-[1,2,4]triazolo[1,5-a]pyridin-6-yl)-1H-indol-5-yl)piperidin-1-yl)-N-(3,3,3-trifluoropropyl)acetamide (832);
1-(3,3-difluoropyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (833);
N-(1-cyclopropyl-3-hydroxypropyl)-2-(4-(3-isopropyl-2-(8-(methoxymethyl)-[1,2,4]triazolo[1,5-a]pyridin-6-yl)-1H-indol-5-yl)piperidin-1-yl)acetamide (834);

(R)-1-(2-(hydroxymethyl)pyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (835);

N-(2-(1H-pyrazol-4-yl) ethyl)-2-(4-(3-isopropyl-2-(8-(methoxymethyl)-[1,2,4]triazolo[1,5-a]pyridin-6-yl)-1H-indol-5-yl)piperidin-1-yl)-N-methylacetamide (836);

1-((2R,4R)-2-(hydroxymethyl)-4-methylpyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (837);

1-(2-(4-(3-isopropyl-2-(8-(methoxymethyl)-[1,2,4]triazolo[1,5-a]pyridin-6-yl)-1H-indol-5-yl)piperidin-1-yl)acetyl)azetidine-3-carbonitrile (838);

2-(4-(3-isopropyl-2-(8-(methoxymethyl)-[1,2,4]triazolo[1,5-a]pyridin-6-yl)-1H-indol-5-yl)piperidin-1-yl)-N-methyl-N-(tetrahydrofuran-3-yl)acetamide (839);

1-(3,3-difluoroazetidin-1-yl)-2-(4-(3-isopropyl-2-(8-(methoxymethyl)-[1,2,4]triazolo [1,5-a]pyridin-6-yl)-1H-indol-5-yl)piperidin-1-yl)ethan-1-one (840);

1-((2S,4S)-2-(hydroxymethyl)-4-(trifluoromethyl)pyrrolidin-1-yl)-2-(4-(3-isopropyl-2-(8-(methoxymethyl)-[1,2,4]triazolo[1,5-a]pyridin-6-yl)-1H-indol-5-yl)piperidin-1-yl)ethan-1-one (841); or N-(2-cyanoethyl)-2-(4-(3-isopropyl-2-(8-(methoxymethyl)-[1,2,4]triazolo[1,5-a]pyridin-6-yl)-1H-indol-5-yl)piperidin-1-yl)acetamide (842).

One embodiment provides a compound of Formula (I) or a salt thereof, wherein said compound has the structure of Formula (I-6):

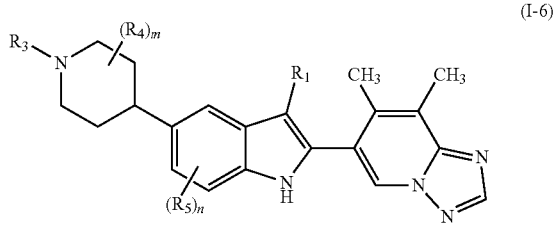

(I-6)

and $R_1$, $R_3$, $R_4$, $R_5$, m, and n are defined in the first aspect or the second aspect. Included in this embodiment are compounds in which $R_1$ is —CH(CH$_3$)$_2$ or —CH$_2$CHF$_2$. Included in this embodiment are compounds in which $R_3$ is H, $C_{1-5}$ alkyl, $C_{1-2}$ cyanoalkyl, —CH$_2$CH$_2$CF$_3$, —CH$_2$C(CH$_3$)$_2$OH, —CH$_2$CH$_3$, —CH$_2$CH$_2$OCH$_3$, —CH$_2$N(CH$_3$)$_2$, —CH$_2$C(O)NH$_2$, —CH$_2$C(O)NH(CH$_3$), —CH$_2$C(O)N(CH$_3$)$_2$, —CH$_2$C(O)N(CH$_3$)(CH$_2$CH$_2$OH), —CH$_2$CH$_2$S(O)$_2$CH$_3$, —CH$_2$CH$_2$S(O)$_2$NH$_2$, —CH$_2$CH$_2$S(O)$_2$N(CH$_3$)$_2$, —CH$_2$CH$_2$NHS(O)$_2$CH$_3$, —CH$_2$CH$_2$N(CH$_3$)S(O)$_2$CH$_3$, —C(O)OCH$_2$CH$_2$NH$_2$, —C(O)OCH$_2$CH$_2$N(CH$_3$)$_2$, —C(O)OCH$_2$CH$_2$N(CH$_2$CH$_3$)$_2$, —C(O)OC(CH$_3$)$_3$, —C(O)NHCH$_2$C(CH$_3$)$_3$, —C(O)NH(CH$_2$CH$_2$NH$_2$), —C(O)NH(CH$_2$CH$_2$N(CH$_3$)$_2$), —C(O)NH(CH$_2$CH$_2$CH$_2$NH$_2$), —C(O)N(CH$_3$)CH$_2$CH$_2$NH$_2$, —C(O)CH$_2$NHCH(CH$_3$)$_2$, —C(O)CH$_2$NHC(CH$_3$)$_3$, —C(O)CH$_2$NH(CH$_3$), —C(O)CH$_2$NH(CH$_2$CN), —C(O)CH$_2$NH(CH$_2$CH$_3$), —C(O)CH$_2$NH(CH$_2$CH$_2$OH), —C(O)CH$_2$NH(CH$_2$CH$_2$OCH$_3$), —C(O)CH$_2$NH(CH$_2$CH$_2$F), —C(O)CH$_2$NH(CH$_2$CH$_2$CH$_3$), —C(O)CH$_2$NH(CH$_2$CH(CH$_3$)$_2$), —C(O)CH$_2$NH(CH$_2$CF$_3$), —C(O)CH$_2$NH(CH$_2$C(O)NH$_2$), —C(O)CH$_2$N(CH$_3$)CH$_2$CH$_3$, —C(O)CH$_2$N(CH$_3$)CH$_2$CN, —C(O)CH$_2$N(CH$_3$)CH$_2$CH$_2$CH$_3$, —C(O)CH$_2$N(CH$_3$)CH(CH$_3$)$_2$, —C(O)CH$_2$N(CH$_3$)C(CH$_3$)$_3$, —C(O)CH$_2$N(CH$_3$)CH$_2$C(O)N(CH$_3$)$_2$, —C(O)CH$_2$N(CH$_3$)CH(CH$_3$)$_2$, —C(O)CH$_2$N(CH$_3$)$_2$, —C(O)CH$_2$N(CH$_3$)(CH$_2$CH$_2$OH), —C(O)CH$_2$N(CH$_3$)(CH$_2$CH$_2$OCH$_3$), —C(O)CH$_2$N(CH$_2$CH$_3$)$_2$, —C(O)CH$_2$N(CH$_2$CH$_2$OCH$_3$)$_2$, —C(O)CH$_2$CH$_2$NH(CH$_3$), —C(O)CH$_2$CH$_2$NH(CH$_2$CH$_3$), —C(O)CH$_2$CH$_2$NH(CH$_2$CH$_2$OH), —C(O)CH$_2$CH$_2$NH(CH$_2$CH$_2$OCH$_3$), —C(O)CH$_2$CH$_2$NH(CH$_2$CH$_2$F), —C(O)CH$_2$CH$_2$NH(CH$_2$CH$_2$CH$_3$), —C(O)CH$_2$CH$_2$NH(CH$_2$C(O)NH$_2$), —C(O)CH$_2$CH$_2$NH(CH$_2$C(CH$_3$)$_3$), —C(O)CH$_2$CH$_2$NH(CH(CH$_3$)$_2$), —C(O)CH$_2$CH$_2$N(CH$_3$)CH$_2$CH$_2$OH, —C(O)CH$_2$CH$_2$N(CH$_3$)CH$_2$CH$_2$OCH$_3$, —C(O)CH$_2$CH$_2$N(CH$_3$)CH$_2$C(O)N(CH$_3$)$_2$, —C(O)CH$_2$CH$_2$N(CH$_3$)(CH$_2$CH$_3$), —C(O)CH$_2$CH$_2$N(CH$_3$)(CH$_2$CH$_2$CH$_3$), —C(O)CH$_2$CH$_2$N(CH$_3$)(CH$_2$CH$_2$CH$_3$), —C(O)CH$_2$CH$_2$N(CH$_3$)(CH(CH$_3$)$_2$), or -L$_1$-A; L$_1$ is —CH$_2$—, —CH$_2$CH$_2$—, —CH(CN)—, —C(O)—, —C(O)CH$_2$—, —C(O)CH$_2$CH$_2$—, —C(O)CH$_2$NH—, —C(O)CH$_2$N(CH$_3$)—, —C(O)CH$_2$CH$_2$NH—, —C(O)CH$_2$CH$_2$N(CH$_3$)—, —C(O)CH$_2$NHCH$_2$—, —C(O)CH$_2$CH$_2$NHCH$_2$—, —CH$_2$C(O)—, —CH$_2$C(O)NH—, —C(O)NH—, —C(O)NHCH$_2$—, —C(O)NHCH$_2$CH$_2$—, —C(O)O—, —C(O)OCH$_2$—, or —C(O)OCH$_2$CH$_2$—; and A is azepanyl, azetidinyl, cyclobutyl, cyclohexyl, cyclopentyl, cyclopropyl, dioxoisothiazolidinyl, dioxotetrahydrothiopyranyl, dioxothiomorpholinyl, imidazolyl, morpholinyl, octahydropyrrolo[3,4-b]pyridinyl, oxa-azaspiro[3.3]heptan-6-yl, oxetanyl, piperazinonyl, piperazinyl, piperidinonyl, piperidinyl, pyridinyl, pyrimidinyl, pyrrolidinyl, tetrahydrofuranyl, tetrahydropyranyl, triazolonyl, or triazolyl; azetidinyl, cyclobutyl, dioxanyl, dioxotetrahydrothiopyranyl, dioxothiomorpholinyl, morpholinyl, oxetanyl, piperazinonyl, pyrrolidinonyl, pyrrolidinyl, tetrahydrofuranyl, or tetrahydropyranyl, each substituted with -L$_2$-R$_a$ and zero to 1 R$_b$; L$_2$ is a bond; R$_a$ is H, F, $C_{1-3}$ alkyl, $C_{1-2}$ hydroxyalkyl, —CH$_2$OCH$_3$, —CH$_2$CH$_2$OCH$_3$, —OH, —OCH$_3$, —NH$_2$, —C(O)CH$_3$, —C(O)CH(CH$_2$CH$_3$)$_2$, —C(O)NH$_2$, —C(O)N(CH$_2$CH$_3$)$_2$, —C(O)OC(CH$_3$)$_3$, —S(O)$_2$CH$_3$, or pyridinyl; and R$_b$ is F or —CH$_3$. Also included in this embodiment are compounds in which $R_1$ is —CH(CH$_3$)$_2$; m is zero, and n is zero.

One embodiment provides a compound of Formula (I) or a salt thereof, wherein said compound is 6-(3-isopropyl-5-(piperidin-4-yl)-1H-indol-2-yl)-7,8-dimethyl-[1,2,4]triazolo [1,5-a]pyridine (4);

2-(4-(2-(7,8-dimethyl-[1,2,4]triazolo[1,5-a]pyridin-6-yl)-3-isopropyl-1H-indol-5-yl)piperidin-1-yl)acetonitrile (13);

3-(4-(2-(7,8-dimethyl-[1,2,4]triazolo[1,5-a]pyridin-6-yl)-3-isopropyl-1H-indol-5-yl)piperidin-1-yl)propanenitrile (14);

2-(4-(2-(7,8-dimethyl-[1,2,4]triazolo[1,5-a]pyridin-6-yl)-3-isopropyl-1H-indol-5-yl)piperidin-1-yl) acetamide (15);

2-(4-(2-(7,8-dimethyl-[1,2,4]triazolo[1,5-a]pyridin-6-yl)-3-isopropyl-1H-indol-5-yl)piperidin-1-yl)-N-methylacetamide (16); 1-(4-(2-(7,8-dimethyl-[1,2,4]triazolo [1,5-a]pyridin-6-yl)-3-isopropyl-1H-indol-5-yl)piperidin-1-yl)-2-methylpropan-2-ol (17);

6-(3-isopropyl-5-(1-(2-(methylsulfonyl)ethyl)piperidin-4-yl)-1H-indol-2-yl)-7,8-dimethyl-[1,2,4]triazolo[1,5-a]pyridine (18);

2-(4-(2-(7,8-dimethyl-[1,2,4]triazolo[1,5-a]pyridin-6-yl)-3-isopropyl-1H-indol-5-yl)piperidin-1-yl)ethane-1-sulfonamide (19);

4-(4-(2-(7,8-dimethyl-[1,2,4]triazolo[1,5-a]pyridin-6-yl)-3-isopropyl-1H-indol-5-yl)piperidin-1-yl)tetrahydro-2H-thiopyran 1,1-dioxide (20);

6-(3-isopropyl-5-(1-(oxetan-3-yl)piperidin-4-yl)-1H-indol-2-yl)-7,8-dimethyl-[1,2,4]triazolo[1,5-a]pyridine (38);

6-(5-(1-((1H-1,2,3-triazol-5-yl)methyl) piperidin-4-yl)-3-isopropyl-1H-indol-2-yl)-7,8-dimethyl-[1,2,4]triazolo[1,5-a]pyridine (39);

6-(3-isopropyl-5-(1-(tetrahydro-2H-pyran-4-yl)piperidin-4-yl)-1H-indol-2-yl)-7,8-dimethyl-[1,2,4]triazolo[1,5-a]pyridine (40);
2-(4-(2-(7,8-dimethyl-[1,2,4]triazolo[1,5-a]pyridin-6-yl)-3-isopropyl-1H-indol-5-yl)piperidin-1-yl)-N,N-dimethylacetamide (41);
6-(3-isopropyl-5-(1-((1-methyl-1H-1,2,3-triazol-4-yl)methyl)piperidin-4-yl)-1H-indol-2-yl)-7,8-dimethyl-[1,2,4]triazolo[1,5-a]pyridine (42);
6-(3-isopropyl-5-(1-((1-methyl-1H-1,2,4-triazol-3-yl)methyl) piperidin-4-yl)-1H-indol-2-yl)-7,8-dimethyl-[1,2,4]triazolo[1,5-a]pyridine (43);
1-(4-(2-(7,8-dimethyl-[1,2,4]triazolo[1,5-a]pyridin-6-yl)-3-isopropyl-1H-indol-5-yl)piperidin-1-yl)-2-(dimethylamino)ethan-1-one (66);
6-(3-isopropyl-5-(piperidin-4-yl)-1H-indol-2-yl)-5,8-dimethyl-[1,2,4]triazolo[1,5-a]pyridine (110);
6-(3-isopropyl-5-(piperidin-4-yl)-1H-indol-2-yl)-2,8-dimethyl-[1,2,4]triazolo[1,5-a]pyridine (124);
6-(3-isopropyl-5-(piperidin-4-yl)-1H-indol-2-yl)-2,7-dimethyl-[1,2,4]triazolo[1,5-a]pyridine (125);
N-(2-(4-(2-(7,8-dimethyl-[1,2,4]triazolo[1,5-a]pyridin-6-yl)-3-isopropyl-1H-indol-5-yl)piperidin-1-yl)ethyl)methanesulfonamide (204); N-(2-(4-(2-(7,8-dimethyl-[1,2,4]triazolo [1,5-a]pyridin-6-yl)-3-isopropyl-1H-indol-5-yl)piperidin-1-yl)ethyl)-N-methylmethanesulfonamide (205);
2-(4-(2-(7,8-dimethyl-[1,2,4]triazolo[1,5-a]pyridin-6-yl)-3-isopropyl-1H-indol-5-yl)piperidin-1-yl)-N,N-dimethylethane-1-sulfonamide (206);
2-(2-(4-(2-(7,8-dimethyl-[1,2,4]triazolo[1,5-a]pyridin-6-yl)-3-isopropyl-1H-indol-5-yl)piperidin-1-yl)ethyl)isothiazolidine 1,1-dioxide (475); 2-(4-(2-(7,8-dimethyl-[1,2,4]triazolo[1,5-a]pyridin-6-yl)-3-isopropyl-1H-indol-5-yl) piperidin-1-yl)-2-(3-methyloxetan-3-yl)acetonitrile (476); 1-(4-(2-(7,8-dimethyl-[1,2,4]triazolo[1,5-a]pyridin-6-yl)-3-isopropyl-1H-indol-5-yl) piperidin-1-yl)-2-morpholinoethan-1-one (477);
6-(5-(1-isobutylpiperidin-4-yl)-3-isopropyl-1H-indol-2-yl)-7,8-dimethyl-[1,2,4]triazolo[1,5-a]pyridine (478);
6-(5-(1-isopentylpiperidin-4-yl)-3-isopropyl-1H-indol-2-yl)-7,8-dimethyl-[1,2,4]triazolo[1,5-a]pyridine (479);
6-(5-(1-ethylpiperidin-4-yl)-3-isopropyl-1H-indol-2-yl)-7,8-dimethyl-[1,2,4]triazolo[1,5-a]pyridine (480);
6-(5-(1-propylpiperidin-4-yl)-1H-indol-2-yl)-7,8-dimethyl-[1,2,4]triazolo [1,5-a]pyridine (481);
6-(5-(1-ethylpiperidin-4-yl)-3-isopropyl-1H-indol-2-yl)-7,8-dimethyl-[1,2,4]triazolo[1,5-a]pyridine (482);
5-((4-(2-(7,8-dimethyl-[1,2,4]triazolo[1,5-a]pyridin-6-yl)-3-isopropyl-1H-indol-5-yl)piperidin-1-yl)methyl)-2,4-dihydro-3H-1,2,4-triazol-3-one (483);
6-(3-isopropyl-5-(1-(3,3,3-trifluoropropyl)piperidin-4-yl)-1H-indol-2-yl)-7,8-dimethyl-[1,2,4]triazolo[1,5-a]pyridine (484);
6-(3-isopropyl-5-(1-methylpiperidin-4-yl)-1H-indol-2-yl)-7,8-dimethyl-[1,2,4]triazolo[1,5-a]pyridine (485);
6-(3-isopropyl-5-(1-(2-methoxyethyl)piperidin-4-yl)-1H-indol-2-yl)-7,8-dimethyl-[1,2,4]triazolo[1,5-a]pyridine (486); tert-butyl 4-(2-(7,8-dimethyl-[1,2,4]triazolo[1,5-a]pyridin-6-yl)-3-isopropyl-1H-indol-5-yl)piperidine-1-carboxylate (609);
1-(4-(2-(7,8-dimethyl-[1,2,4]triazolo[1,5-a]pyridin-6-yl)-3-isopropyl-1H-indol-5-yl)piperidin-1-yl)-3-morpholinopropan-1-one (610);
2-(bis(2-methoxyethyl)amino)-1-(4-(2-(7,8-dimethyl-[1,2,4]triazolo[1,5-a]pyridin-6-yl)-3-isopropyl-1H-indol-5-yl)piperidin-1-yl)ethan-1-one (718);
1-(4-(2-(7,8-dimethyl-[1,2,4]triazolo[1,5-a]pyridin-6-yl)-3-isopropyl-1H-indol-5-yl) piperidin-1-yl)-2-(3-hydroxypyrrolidin-1-yl)ethan-1-one (719);
1-(4-(2-(7,8-dimethyl-[1,2,4]triazolo[1,5-a]pyridin-6-yl)-3-isopropyl-1H-indol-5-yl)piperidin-1-yl)-2-(2,6-dimethylmorpholino)ethan-1-one (720); 1-(1-(2-(4-(2-(7,8-dimethyl-[1,2,4]triazolo[1,5-a]pyridin-6-yl)-3-isopropyl-1H-indol-5-yl)piperidin-1-yl)-2-oxoethyl)piperidin-3-yl)-2-ethylbutan-1-one (721); (S)-1-(4-(2-(7,8-dimethyl-[1,2,4]triazolo [1,5-a]pyridin-6-yl)-3-isopropyl-1H-indol-5-yl)piperidin-1-yl)-2-(2-(methoxymethyl) pyrrolidin-1-yl)ethan-1-one (722);
1-(4-(2-(7,8-dimethyl-[1,2,4]triazolo[1,5-a]pyridin-6-yl)-3-isopropyl-1H-indol-5-yl) piperidin-1-yl)-2-(isobutyl(methyl)amino)ethan-1-one (723);
1-(2-(4-(2-(7,8-dimethyl-[1,2,4]triazolo[1,5-a]pyridin-6-yl)-3-isopropyl-1H-indol-5-yl)piperidin-1-yl)-2-oxoethyl)piperidine-4-carboxamide (724); 4-(2-(4-(2-(7,8-dimethyl-[1,2,4]triazolo [1,5-a]pyridin-6-yl)-3-isopropyl-1H-indol-5-yl)piperidin-1-yl)-2-oxoethyl)piperazin-2-one (725);
3-((2-(4-(2-(7,8-dimethyl-[1,2,4]triazolo[1,5-a]pyridin-6-yl)-3-isopropyl-1H-indol-5-yl)piperidin-1-yl)-2-oxoethyl)(methyl)amino)propanenitrile (726);
2-(cyclopentylamino)-1-(4-(2-(7,8-dimethyl-[1,2,4]triazolo [1,5-a]pyridin-6-yl)-3-isopropyl-1H-indol-5-yl)piperidin-1-yl)ethan-1-one (727);
2-(cyclohexylamino)-1-(4-(2-(7,8-dimethyl-[1,2,4]triazolo [1,5-a]pyridin-6-yl)-3-isopropyl-1H-indol-5-yl)piperidin-1-yl)ethan-1-one (728);
1-(4-(2-(7,8-dimethyl-[1,2,4]triazolo[1,5-a]pyridin-6-yl)-3-isopropyl-1H-indol-5-yl)piperidin-1-yl)-2-((4-hydroxycyclohexyl)amino)ethan-1-one (729);
2-((cyclohexylmethyl)amino)-1-(4-(2-(7,8-dimethyl-[1,2,4]triazolo[1,5-a]pyridin-6-yl)-3-isopropyl-1H-indol-5-yl)piperidin-1-yl)ethan-1-one (730);
1-(4-(2-(7,8-dimethyl-[1,2,4]triazolo[1,5-a]pyridin-6-yl)-3-isopropyl-1H-indol-5-yl)piperidin-1-yl)-2-(((tetrahydrofuran-2-yl)methyl)amino)ethan-1-one (731);
2-(tert-butylamino)-1-(4-(2-(7,8-dimethyl-[1,2,4]triazolo[1,5-a]pyridin-6-yl)-3-isopropyl-1H-indol-5-yl)piperidin-1-yl)ethan-1-one (732);
1-(4-(2-(7,8-dimethyl-[1,2,4]triazolo[1,5-a]pyridin-6-yl)-3-isopropyl-1H-indol-5-yl)piperidin-1-yl)-2-(neopentylamino)ethan-1-one (733);
1-(4-(2-(7,8-dimethyl-[1,2,4]triazolo[1,5-a]pyridin-6-yl)-3-isopropyl-1H-indol-5-yl)piperidin-1-yl)-2-(propylamino)ethan-1-one (734);
(R)-1-(4-(2-(7,8-dimethyl-[1,2,4]triazolo[1,5-a]pyridin-6-yl)-3-isopropyl-1H-indol-5-yl) piperidin-1-yl)-2-(3-hydroxypyrrolidin-1-yl)ethan-1-one (735);
(S)-1-(4-(2-(7,8-dimethyl-[1,2,4]triazolo[1,5-a]pyridin-6-yl)-3-isopropyl-1H-indol-5-yl) piperidin-1-yl)-2-(3-hydroxypyrrolidin-1-yl)ethan-1-one (736);
1-(4-(2-(7,8-dimethyl-[1,2,4]triazolo[1,5-a]pyridin-6-yl)-3-isopropyl-1H-indol-5-yl)piperidin-1-yl)-2-(isopropylamino)ethan-1-one (737);
(S)-1-(4-(2-(7,8-dimethyl-[1,2,4]triazolo[1,5-a]pyridin-6-yl)-3-isopropyl-1H-indol-5-yl) piperidin-1-yl)-2-(3-fluoropyrrolidin-1-yl)ethan-1-one (738);
1-(4-(2-(7,8-dimethyl-[1,2,4]triazolo[1,5-a]pyridin-6-yl)-3-isopropyl-1H-indol-5-yl) piperidin-1-yl)-2-((2-fluoroethyl)amino)ethan-1-one (739); 1-(4-(2-(7,8-dimethyl-[1,2,4]triazolo[1,5-a]pyridin-6-yl)-3-isopropyl-1H-indol-5-yl)piperidin-1-yl)-2-(ethylamino)ethan-1-one (740);

2-(4,4-difluoropiperidin-1-yl)-1-(4-(2-(7,8-dimethyl-[1,2,4]triazolo[1,5-a]pyridin-6-yl)-3-isopropyl-1H-indol-5-yl)piperidin-1-yl)ethan-1-one (741);

2-(cyclopropylamino)-1-(4-(2-(7,8-dimethyl-[1,2,4]triazolo[1,5-a]pyridin-6-yl)-3-isopropyl-1H-indol-5-yl)piperidin-1-yl)ethan-1-one (742);

1-(4-(2-(7,8-dimethyl-[1,2,4]triazolo[1,5-a]pyridin-6-yl)-3-isopropyl-1H-indol-5-yl)piperidin-1-yl)-2-((2-methoxyethyl)amino)ethan-1-one (743);

1-(4-(2-(7,8-dimethyl-[1,2,4]triazolo[1,5-a]pyridin-6-yl)-3-isopropyl-1H-indol-5-yl)piperidin-1-yl)-2-(piperidin-1-yl)ethan-1-one (744); 1-(4-(2-(7,8-dimethyl-[1,2,4]triazolo [1,5-a]pyridin-6-yl)-3-isopropyl-1H-indol-5-yl)piperidin-1-yl)-2-(pyrrolidin-1-yl) ethan-1-one (745);

1-(4-(2-(7,8-dimethyl-[1,2,4]triazolo[1,5-a]pyridin-6-yl)-3-isopropyl-1H-indol-5-yl)piperidin-1-yl)-2-(isobutylamino)ethan-1-one (746); 1-(4-(2-(7,8-dimethyl-[1,2,4]triazolo [1,5-a]pyridin-6-yl)-3-isopropyl-1H-indol-5-yl)piperidin-1-yl)-2-(3,3-dimethylpiperidin-1-yl)ethan-1-one (747); 2-((2-(4-(2-(7,8-dimethyl-[1,2,4]triazolo[1,5-a]pyridin-6-yl)-3-isopropyl-1H-indol-5-yl)piperidin-1-yl)-2-oxoethyl)amino)acetamide (748);

(S)-1-(4-(2-(7,8-dimethyl-[1,2,4]triazolo[1,5-a]pyridin-6-yl)-3-isopropyl-1H-indol-5-yl) piperidin-1-yl)-2-(2-(hydroxymethyl)pyrrolidin-1-yl)ethan-1-one (749);

1-(4-(2-(7,8-dimethyl-[1,2,4]triazolo[1,5-a]pyridin-6-yl)-3-isopropyl-1H-indol-5-yl)piperidin-1-yl)-2-(4-methoxypiperidin-1-yl)ethan-1-one (750);

2-(cyclohexyl(methyl)amino)-1-(4-(2-(7,8-dimethyl-[1,2,4]triazolo[1,5-a]pyridin-6-yl)-3-isopropyl-1H-indol-5-yl)piperidin-1-yl)ethan-1-one (751);

2-((2-(4-(2-(7,8-dimethyl-[1,2,4]triazolo[1,5-a]pyridin-6-yl)-3-isopropyl-1H-indol-5-yl)piperidin-1-yl)-2-oxoethyl)amino)acetonitrile (752); 1-(4-(2-(7,8-dimethyl-[1,2,4]triazolo[1,5-a]pyridin-6-yl)-3-isopropyl-1H-indol-5-yl)piperidin-1-yl)-2-(methylamino) ethan-1-one (753);

2-(azepan-1-yl)-1-(4-(2-(7,8-dimethyl-[1,2,4]triazolo[1,5-a]pyridin-6-yl)-3-isopropyl-1H-indol-5-yl) piperidin-1-yl) ethan-1-one (754); 1-(4-(2-(7,8-dimethyl-[1,2,4]triazolo[1,5-a]pyridin-6-yl)-3-isopropyl-1H-indol-5-yl)piperidin-1-yl)-2-(4-hydroxypiperidin-1-yl)ethan-1-one (755); 1-(4-(2-(7,8-dimethyl-[1,2,4]triazolo[1,5-a]pyridin-6-yl)-3-isopropyl-1H-indol-5-yl)piperidin-1-yl)-2-((2-hydroxyethyl)(methyl)amino) ethan-1-one (756); 1-(4-(2-(7,8-dimethyl-[1,2,4]triazolo[1,5-a]pyridin-6-yl)-3-isopropyl-1H-indol-5-yl)piperidin-1-yl)-2-((2-hydroxyethyl) amino)ethan-1-one (757); 2-((cyclopropylmethyl)amino)-1-(4-(2-(7,8-dimethyl-[1,2,4]triazolo[1,5-a]pyridin-6-yl)-3-isopropyl-1H-indol-5-yl)piperidin-1-yl)ethan-1-one (758);

2-((2-(4-(2-(7,8-dimethyl-[1,2,4]triazolo[1,5-a]pyridin-6-yl)-3-isopropyl-1H-indol-5-yl) piperidin-1-yl)-2-oxoethyl)(methyl)amino)-N,N-dimethylacetamide (759);

1-(4-(2-(7,8-dimethyl-[1,2,4]triazolo[1,5-a]pyridin-6-yl)-3-isopropyl-1H-indol-5-yl)piperidin-1-yl)-2-((2-methoxyethyl)(methyl)amino)ethan-1-one (760);

1-(4-(2-(7,8-dimethyl-[1,2,4]triazolo[1,5-a]pyridin-6-yl)-3-isopropyl-1H-indol-5-yl)piperidin-1-yl)-2-((2,2,2-trifluoroethyl)amino)ethan-1-one (761);

1-(4-(2-(7,8-dimethyl-[1,2,4]triazolo[1,5-a]pyridin-6-yl)-3-isopropyl-1H-indol-5-yl)piperidin-1-yl)-2-(methyl(propyl)amino)ethan-1-one (762);

2-(diethylamino)-1-(4-(2-(7,8-dimethyl-[1,2,4]triazolo [1,5-a]pyridin-6-yl)-3-isopropyl-1H-indol-5-yl)piperidin-1-yl)ethan-1-one (763);

2-(cyclobutylamino)-1-(4-(2-(7,8-dimethyl-[1,2,4]triazolo[1,5-a]pyridin-6-yl)-3-isopropyl-1H-indol-5-yl)piperidin-1-yl)ethan-1-one (764);

2-(azetidin-1-yl)-1-(4-(2-(7,8-dimethyl-[1,2,4]triazolo[1,5-a]pyridin-6-yl)-3-isopropyl-1H-indol-5-yl)piperidin-1-yl) ethan-1-one (765);

1-(4-(2-(7,8-dimethyl-[1,2,4]triazolo[1,5-a]pyridin-6-yl)-3-isopropyl-1H-indol-5-yl)piperidin-1-yl)-2-(ethyl(methyl)amino)ethan-1-one (766);

1-(4-(2-(7,8-dimethyl-[1,2,4]triazolo[1,5-a]pyridin-6-yl)-3-isopropyl-1H-indol-5-yl)piperidin-1-yl)-2-(isopropyl(methyl)amino)ethan-1-one (767); 2-(4-(2-(7,8-dimethyl-[1,2,4]triazolo[1,5-a]pyridin-6-yl)-3-isopropyl-1H-indol-5-yl)piperidin-1-yl)-1-morpholinoethan-1-one (843);

1-(azetidin-1-yl)-2-(4-(2-(7,8-dimethyl-[1,2,4]triazolo[1,5-a]pyridin-6-yl)-3-isopropyl-1H-indol-5-yl)piperidin-1-yl) ethan-1-one (844);

2-(4-(2-(7,8-dimethyl-[1,2,4]triazolo[1,5-a]pyridin-6-yl)-3-isopropyl-1H-indol-5-yl) piperidin-1-yl)-1-(3-(methylsulfonyl)azetidin-1-yl)ethan-1-one (845);

2-(4-(2-(7,8-dimethyl-[1,2,4]triazolo[1,5-a]pyridin-6-yl)-3-isopropyl-1H-indol-5-yl)piperidin-1-yl)-N-(3-methyloxetan-3-yl)acetamide (846);

2-(4-(2-(7,8-dimethyl-[1,2,4]triazolo[1,5-a]pyridin-6-yl)-3-isopropyl-1H-indol-5-yl)piperidin-1-yl)-1-(1,1-dioxidothiomorpholino)ethan-1-one (847);

2-(4-(2-(7,8-dimethyl-[1,2,4]triazolo[1,5-a]pyridin-6-yl)-3-isopropyl-1H-indol-5-yl) piperidin-1-yl)-N-(2-hydroxyethyl)-N-methylacetamide (848);

2-(4-(2-(7,8-dimethyl-[1,2,4]triazolo[1,5-a]pyridin-6-yl)-3-isopropyl-1H-indol-5-yl)piperidin-1-yl)-1-(2-oxa-6-azaspiro [3.3]heptan-6-yl)ethan-1-one (849);

1-(4-(2-(7,8-dimethyl-[1,2,4]triazolo[1,5-a]pyridin-6-yl)-3-isopropyl-1H-indol-5-yl) piperidin-1-yl)-3-((4-hydroxycyclohexyl)amino)propan-1-one (886);

1-(4-(2-(7,8-dimethyl-[1,2,4]triazolo[1,5-a]pyridin-6-yl)-3-isopropyl-1H-indol-5-yl) piperidin-1-yl)-3-(((tetrahydrofuran-2-yl)methyl)amino)propan-1-one (887);

(R)-1-(4-(2-(7,8-dimethyl-[1,2,4]triazolo[1,5-a]pyridin-6-yl)-3-isopropyl-1H-indol-5-yl)piperidin-1-yl)-3-(3-fluoropyrrolidin-1-yl)propan-1-one (888); 1-(4-(2-(7,8-dimethyl-[1,2,4]triazolo[1,5-a]pyridin-6-yl)-3-isopropyl-1H-indol-5-yl)piperidin-1-yl)-3-((2-hydroxyethyl)amino) propan-1-one (889);

1-(4-(2-(7,8-dimethyl-[1,2,4]triazolo[1,5-a]pyridin-6-yl)-3-isopropyl-1H-indol-5-yl)piperidin-1-yl)-3-(propylamino) propan-1-one (890); 2-((3-(4-(2-(7,8-dimethyl-[1,2,4]triazolo[1,5-a]pyridin-6-yl)-3-isopropyl-1H-indol-5-yl) piperidin-1-yl)-3-oxopropyl)amino)acetamide (891); 3-((cyclopropylmethyl)amino)-1-(4-(2-(7,8-dimethyl-[1,2,4]triazolo[1,5-a]pyridin-6-yl)-3-isopropyl-1H-indol-5-yl)piperidin-1-yl)propan-1-one (892);

3-(azetidin-1-yl)-1-(4-(2-(7,8-dimethyl-[1,2,4]triazolo[1,5-a]pyridin-6-yl)-3-isopropyl-1H-indol-5-yl) piperidin-1-yl) propan-1-one (893);

1-(4-(2-(7,8-dimethyl-[1,2,4]triazolo[1,5-a]pyridin-6-yl)-3-isopropyl-1H-indol-5-yl)piperidin-1-yl)-3-(ethyl(methyl)amino)propan-1-one (894);

1-(4-(2-(7,8-dimethyl-[1,2,4]triazolo[1,5-a]pyridin-6-yl)-3-isopropyl-1H-indol-5-yl)piperidin-1-yl)-3-(methyl(propyl)amino)propan-1-one (895);

1-(4-(2-(7,8-dimethyl-[1,2,4]triazolo[1,5-a]pyridin-6-yl)-3-isopropyl-1H-indol-5-yl)piperidin-1-yl)-3-(isopropyl(methyl)amino)propan-1-one (896);

2-((3-(4-(2-(7,8-dimethyl-[1,2,4]triazolo[1,5-a]pyridin-6-yl)-3-isopropyl-1H-indol-5-yl)piperidin-1-yl)-3-oxopropyl)(methyl)amino)-N,N-dimethylacetamide (897);

1-(4-(2-(7,8-dimethyl-[1,2,4]triazolo[1,5-a]pyridin-6-yl)-3-isopropyl-1H-indol-5-yl)piperidin-1-yl)-3-((2-methoxyethyl)(methyl)amino)propan-1-one (898);

(R)-1-(4-(2-(7,8-dimethyl-[1,2,4]triazolo[1,5-a]pyridin-6-yl)-3-isopropyl-1H-indol-5-yl) piperidin-1-yl)-3-(3-hydroxypyrrolidin-1-yl)propan-1-one (899);

3-(4,4-difluoropiperidin-1-yl)-1-(4-(2-(7,8-dimethyl-[1,2,4]triazolo[1,5-a]pyridin-6-yl)-3-isopropyl-1H-indol-5-yl)piperidin-1-yl) propan-1-one (900);

1-(4-(2-(7,8-dimethyl-[1,2,4]triazolo[1,5-a]pyridin-6-yl)-3-isopropyl-1H-indol-5-yl)piperidin-1-yl)-3-((2-methoxyethyl)amino)propan-1-one (901);

1-(4-(2-(7,8-dimethyl-[1,2,4]triazolo[1,5-a]pyridin-6-yl)-3-isopropyl-1H-indol-5-yl)piperidin-1-yl)-3-(isopropylamino)propan-1-one (902);

1-(4-(2-(7,8-dimethyl-[1,2,4]triazolo[1,5-a]pyridin-6-yl)-3-isopropyl-1H-indol-5-yl)piperidin-1-yl)-3-(ethylamino)propan-1-one (903);

1-(4-(2-(7,8-dimethyl-[1,2,4]triazolo[1,5-a]pyridin-6-yl)-3-isopropyl-1H-indol-5-yl)piperidin-1-yl)-3-(piperidin-1-yl)propan-1-one (904);

1-(4-(2-(7,8-dimethyl-[1,2,4]triazolo[1,5-a]pyridin-6-yl)-3-isopropyl-1H-indol-5-yl)piperidin-1-yl)-3-(methylamino)propan-1-one (905);

1-(4-(2-(7,8-dimethyl-[1,2,4]triazolo[1,5-a]pyridin-6-yl)-3-isopropyl-1H-indol-5-yl)piperidin-1-yl)-3-(2,6-dimethylmorpholino)propan-1-one (906);

1-(3-(4-(2-(7,8-dimethyl-[1,2,4]triazolo[1,5-a]pyridin-6-yl)-3-isopropyl-1H-indol-5-yl)piperidin-1-yl)-3-oxopropyl)-N,N-diethylpiperidine-3-carboxamide (907);

1-(4-(2-(7,8-dimethyl-[1,2,4]triazolo[1,5-a]pyridin-6-yl)-3-isopropyl-1H-indol-5-yl)piperidin-1-yl)-3-(3,3-dimethylpiperidin-1-yl)propan-1-one (908);

1-(4-(2-(7,8-dimethyl-[1,2,4]triazolo[1,5-a]pyridin-6-yl)-3-isopropyl-1H-indol-5-yl) piperidin-1-yl)-3-(4-hydroxypiperidin-1-yl)propan-1-one (909);

3-(azepan-1-yl)-1-(4-(2-(7,8-dimethyl-[1,2,4]triazolo[1,5-a]pyridin-6-yl)-3-isopropyl-1H-indol-5-yl)piperidin-1-yl)propan-1-one (910);

(S)-1-(4-(2-(7,8-dimethyl-[1,2,4]triazolo[1,5-a]pyridin-6-yl)-3-isopropyl-1H-indol-5-yl) piperidin-1-yl)-3-(2-(methoxymethyl)pyrrolidin-1-yl)propan-1-one (911);

1-(3-(4-(2-(7,8-dimethyl-[1,2,4]triazolo[1,5-a]pyridin-6-yl)-3-isopropyl-1H-indol-5-yl)piperidin-1-yl)-3-oxopropyl)piperidine-4-carboxamide (912);

4-(3-(4-(2-(7,8-dimethyl-[1,2,4]triazolo[1,5-a]pyridin-6-yl)-3-isopropyl-1H-indol-5-yl)piperidin-1-yl)-3-oxopropyl) piperazin-2-one (913);

1-(4-(2-(7,8-dimethyl-[1,2,4]triazolo[1,5-a]pyridin-6-yl)-3-isopropyl-1H-indol-5-yl)piperidin-1-yl)-3-((2-hydroxyethyl)(methyl)amino)propan-1-one (914);

1-(4-(2-(7,8-dimethyl-[1,2,4]triazolo[1,5-a]pyridin-6-yl)-3-isopropyl-1H-indol-5-yl)piperidin-1-yl)-3-(4-methoxypiperidin-1-yl)propan-1-one (915);

1-(4-(2-(7,8-dimethyl-[1,2,4]triazolo [1,5-a]pyridin-6-yl)-3-isopropyl-1H-indol-5-yl)piperidin-1-yl)-3-(pyrrolidin-1-yl)propan-1-one (916);

(S)-1-(4-(2-(7,8-dimethyl-[1,2,4]triazolo[1,5-a]pyridin-6-yl)-3-isopropyl-1H-indol-5-yl) piperidin-1-yl)-3-(2-(hydroxymethyl)pyrrolidin-1-yl)propan-1-one (917);

3-(cyclobutylamino)-1-(4-(2-(7,8-dimethyl-[1,2,4]triazolo[1,5-a]pyridin-6-yl)-3-isopropyl-1H-indol-5-yl)piperidin-1-yl)propan-1-one (918);

3-(cyclopentylamino)-1-(4-(2-(7,8-dimethyl-[1,2,4]triazolo[1,5-a]pyridin-6-yl)-3-isopropyl-1H-indol-5-yl)piperidin-1-yl)propan-1-one (919);

3-(cyclohexylamino)-1-(4-(2-(7,8-dimethyl-[1,2,4]triazolo[1,5-a]pyridin-6-yl)-3-isopropyl-1H-indol-5-yl)piperidin-1-yl)propan-1-one (920); (S)-1-(4-(2-(7,8-dimethyl-[1,2,4]triazolo[1,5-a]pyridin-6-yl)-3-isopropyl-1H-indol-5-yl) piperidin-1-yl)-3-(3-fluoropyrrolidin-1-yl)propan-1-one (921);

(S)-1-(4-(2-(7,8-dimethyl-[1,2,4]triazolo[1,5-a]pyridin-6-yl)-3-isopropyl-1H-indol-5-yl) piperidin-1-yl)-3-(3-hydroxypyrrolidin-1-yl)propan-1-one (922);

1-(4-(2-(7,8-dimethyl-[1,2,4]triazolo[1,5-a]pyridin-6-yl)-3-isopropyl-1H-indol-5-yl)piperidin-1-yl)-3-(3-hydroxypyrrolidin-1-yl)propan-1-one (923);

3-(cyclohexyl(methyl)amino)-1-(4-(2-(7,8-dimethyl-[1,2,4]triazolo[1,5-a]pyridin-6-yl)-3-isopropyl-1H-indol-5-yl)piperidin-1-yl)propan-1-one (924);

1-(4-(2-(7,8-dimethyl-[1,2,4]triazolo[1,5-a]pyridin-6-yl)-3-isopropyl-1H-indol-5-yl)piperidin-1-yl)-3-((2-fluoroethyl)amino)propan-1-one (925);

1-(4-(2-(7,8-dimethyl-[1,2,4]triazolo[1,5-a]pyridin-6-yl)-3-isopropyl-1H-indol-5-yl)piperidin-1-yl)-3-(neopentylamino)propan-1-one (926); azetidin-3-yl 4-(2-(7,8-dimethyl-[1,2,4]triazolo[1,5-a]pyridin-6-yl)-3-isopropyl-1H-indol-5-yl)piperidine-1-carboxylate (927); 2-aminoethyl 4-(2-(7,8-dimethyl-[1,2,4]triazolo[1,5-a]pyridin-6-yl)-3-isopropyl-1H-indol-5-yl)piperidine-1-carboxylate (928); (R)-pyrrolidin-3-yl 4-(2-(7,8-dimethyl-[1,2,4]triazolo[1,5-a]pyridin-6-yl)-3-isopropyl-1H-indol-5-yl)piperidine-1-carboxylate (929); piperidin-3-yl 4-(2-(7,8-dimethyl-[1,2,4]triazolo[1,5-a]pyridin-6-yl)-3-isopropyl-1H-indol-5-yl)piperidine-1-carboxylate (930); (S)-pyrrolidin-3-yl 4-(2-(7,8-dimethyl-[1,2,4]triazolo[1,5-a]pyridin-6-yl)-3-isopropyl-1H-indol-5-yl)piperidine-1-carboxylate (931); piperidin-3-ylmethyl 4-(2-(7,8-dimethyl-[1,2,4]triazolo[1,5-a]pyridin-6-yl)-3-isopropyl-1H-indol-5-yl)piperidine-1-carboxylate (932);

(S)-pyrrolidin-2-ylmethyl 4-(2-(7,8-dimethyl-[1,2,4]triazolo[1,5-a]pyridin-6-yl)-3-isopropyl-1H-indol-5-yl)piperidine-1-carboxylate (933); 3-aminopropyl 4-(2-(7,8-dimethyl-[1,2,4]triazolo [1,5-a]pyridin-6-yl)-3-isopropyl-1H-indol-5-yl)piperidine-1-carboxylate (934); piperidin-4-yl 4-(2-(7,8-dimethyl-[1,2,4]triazolo[1,5-a]pyridin-6-yl)-3-isopropyl-1H-indol-5-yl)piperidine-1-carboxylate (935); piperidin-4-ylmethyl 4-(2-(7,8-dimethyl-[1,2,4]triazolo[1,5-a]pyridin-6-yl)-3-isopropyl-1H-indol-5-yl)piperidine-1-carboxylate (936); pyrrolidin-2-ylmethyl 4-(2-(7,8-dimethyl-[1,2,4]triazolo[1,5-a]pyridin-6-yl)-3-isopropyl-1H-indol-5-yl)piperidine-1-carboxylate (937-938); (R)-pyrrolidin-3-ylmethyl 4-(2-(7,8-dimethyl-[1,2,4]triazolo[1,5-a]pyridin-6-yl)-3-isopropyl-1H-indol-5-yl)piperidine-1-carboxylate (939); pyrrolidin-3-yl-4-(2-(7,8-dimethyl-[1,2,4]triazolo[1,5-a]pyridin-6-yl)-3-isopropyl-1H-indol-5-yl)piperidine-1-carboxylate (940); azetidin-3-ylmethyl 4-(2-(7,8-dimethyl-[1,2,4]triazolo[1,5-a]pyridin-6-yl)-3-isopropyl-1H-indol-5-yl)piperidine-1-carboxylate (941); (S)-(1-methylpyrrolidin-2-yl)methyl 4-(2-(7,8-dimethyl-[1,2,4]triazolo[1,5-a]pyridin-6-yl)-3-isopropyl-1H-indol-5-yl) piperidine-1-carboxylate (942); 2-(dimethylamino)ethyl 4-(2-(7,8-dimethyl-[1,2,4]triazolo [1,5-a]pyridin-6-yl)-3-isopropyl-1H-indol-5-yl)piperidine-1-carboxylate (943);

2-(1H-imidazol-1-yl)ethyl 4-(2-(7,8-dimethyl-[1,2,4]triazolo[1,5-a]pyridin-6-yl)-3-isopropyl-1H-indol-5-yl)piperidine-1-carboxylate (944); 1-isopropylpyrrolidin-3-yl 4-(2-(7,8-dimethyl-[1,2,4]triazolo[1,5-a]pyridin-6-yl)-3-isopropyl-1H-indol-5-yl)piperidine-1-carboxylate (945); 2-(1,1-dioxidothiomorpholino)ethyl 4-(2-(7,8-dimethyl-[1,2,4]triazolo[1,5-a]pyridin-6-yl)-3-isopropyl-1H-indol-5-yl)piperidine-1-carboxylate (946); 2-(piperidin-1-yl)ethyl 4-(2-(7,8-dimethyl-[1,2,4]triazolo[1,5-a]pyridin-6-yl)-3-isopropyl-1H-indol-5-yl)piperidine-1-carboxylate (947); 2-(pyrrolidin-1-yl)ethyl 4-(2-(7,8-dimethyl-[1,2,4]triazolo[1,5-a]pyridin-6-yl)-3-isopropyl-1H-indol-5-yl)piperidine-1-carboxylate (948); 2-(diethylamino)ethyl 4-(2-(7,8-dimethyl-[1,2,4]triazolo[1,5-a]pyridin-6-yl)-3-isopropyl-1H-indol-5-yl)piperidine-1-carboxylate (949); (1-(2-methoxyethyl)pyrrolidin-3-yl)methyl 4-(2-(7,8-dimethyl-[1,2,4]triazolo[1,5-a]pyridin-6-yl)-3-isopropyl-1H-indol-5-yl)piperidine-1-carboxylate (950); 2-(4-methylpiperazin-1-yl)ethyl 4-(2-(7,8-dimethyl-[1,2,4]triazolo[1,5-a]pyridin-6-yl)-3-isopropyl-1H-indol-5-yl)piperidine-1-carboxylate (951); 2-morpholinoethyl 4-(2-(7,8-dimethyl-[1,2,4]triazolo[1,5-a]pyridin-6-yl)-3-isopropyl-1H-indol-5-yl)piperidine-1-carboxylate (952); (R)-(1-methylpyrrolidin-2-yl)methyl 4-(2-(7,8-dimethyl-[1,2,4]triazolo[1,5-a]pyridin-6-yl)-3-isopropyl-1H-indol-5-yl)piperidine-1-carboxylate (953); 1-methylpyrrolidin-3-yl 4-(2-(7,8-dimethyl-[1,2,4]triazolo[1,5-a]pyridin-6-yl)-3-isopropyl-1H-indol-5-yl)piperidine-1-carboxylate (954); 1-(2-methoxyethyl)azetidin-3-yl 4-(2-(7,8-dimethyl-[1,2,4]triazolo[1,5-a]pyridin-6-yl)-3-isopropyl-1H-indol-5-yl)piperidine-1-carboxylate (955); 1-propylazetidin-3-yl 4-(2-(7,8-dimethyl-[1,2,4]triazolo[1,5-a]pyridin-6-yl)-3-isopropyl-1H-indol-5-yl)piperidine-1-carboxylate (956); (4-(2-(7,8-dimethyl-[1,2,4]triazolo[1,5-a]pyridin-6-yl)-3-isopropyl-1H-indol-5-yl)piperidin-1-yl)(4-methylpiperazin-1-yl)methanone (957); (4-(2-(7,8-dimethyl-[1,2,4]triazolo[1,5-a]pyridin-6-yl)-3-isopropyl-1H-indol-5-yl)piperid in-1-yl)(4-(2-hydroxyethyl)piperazin-1-yl)methanone (958); N-(3-aminopropyl)-4-(2-(7,8-dimethyl-[1,2,4]triazolo[1,5-a]pyridin-6-yl)-3-isopropyl-1H-indol-5-yl)piperidine-1-carboxamide (959); (4-(2-(7,8-dimethyl-[1,2,4]triazolo[1,5-a]pyridin-6-yl)-3-isopropyl-1H-indol-5-yl)piperid in-1-yl)(octahydro-6H-pyrrolo[3,4-b]pyridin-6-yl)methanone ((960); (R)-4-(2-(7,8-dimethyl-[1,2,4]triazolo[1,5-a]pyridin-6-yl)-3-isopropyl-1H-indol-5-yl)-N-(pyrrolidin-3-yl)piperidine-1-carboxamide (961); N-(2-aminoethyl)-4-(2-(7,8-dimethyl-[1,2,4]triazolo[1,5-a]pyridin-6-yl)-3-isopropyl-1H-indol-5-yl)piperidine-1-carboxamide (962); 4-(4-(2-(7,8-dimethyl-[1,2,4]triazolo[1,5-a]pyridin-6-yl)-3-isopropyl-1H-indol-5-yl)piperidine-1-carbonyl)-1-methylpiperazin-2-one (963); 4-(2-(7,8-dimethyl-[1,2,4]triazolo[1,5-a]pyridin-6-yl)-3-isopropyl-1H-indol-5-yl)-N-(piperidin-3-yl)piperidine-1-carboxamide (964); (4-(2-(7,8-dimethyl-[1,2,4]triazolo[1,5-a]pyridin-6-yl)-3-isopropyl-1H-indol-5-yl)piperid in-1-yl)(4-propylpiperazin-1-yl)methanone (965); 4-(2-(7,8-dimethyl-[1,2,4]triazolo[1,5-a]pyridin-6-yl)-3-isopropyl-1H-indol-5-yl)-N-(piperidin-2-ylmethyl) piperidine-1-carboxamide (966); (3-aminoazetidin-1-yl)(4-(2-(7,8-dimethyl-[1,2,4]triazolo[1,5-a]pyridin-6-yl)-3-isopropyl-1H-indol-5-yl)piperidin-1-yl)methanone (967); 4-(2-(7,8-dimethyl-[1,2,4]triazolo[1,5-a]pyridin-6-yl)-3-isopropyl-1H-indol-5-yl)-N-(pyrrolidin-3-yl) piperidine-1-carboxamide (968); (4-(2-(7,8-dimethyl-[1,2,4]triazolo[1,5-a]pyridin-6-yl)-3-isopropyl-1H-indol-5-yl)piperid in-1-yl)(4-(pyridin-4-yl)piperazin-1-yl)methanone (969); 4-(2-(7,8-dimethyl-[1,2,4]triazolo[1,5-a]pyridin-6-yl)-3-isopropyl-1H-indol-5-yl)-N-(piperidin-4-ylmethyl)piperidine-1-carboxamide (970); (S)-4-(2-(7,8-dimethyl-[1,2,4]triazolo[1,5-a]pyridin-6-yl)-3-isopropyl-1H-indol-5-yl)-N-(pyrrolidin-3-yl)piperidine-1-carboxamide (971); N-(2-aminoethyl)-4-(2-(7,8-dimethyl-[1,2,4]triazolo[1,5-a]pyridin-6-yl)-3-isopropyl-1H-indol-5-yl)-N-methylpiperidine-1-carboxamide (972); (4-(2-(7,8-dimethyl-[1,2,4]triazolo [1,5-a]pyridin-6-yl)-3-isopropyl-1H-indol-5-yl)piperidin-1-yl)(4-isopropylpiperazin-1-yl)methanone (973); 4-(2-(7,8-dimethyl-[1,2,4]triazolo[1,5-a]pyridin-6-yl)-3-isopropyl-1H-indol-5-yl)-N-(2-(pyrrolidin-1-yl)ethyl)piperidine-1-carboxamide (974); 4-(2-(7,8-dimethyl-[1,2,4]triazolo[1,5-a]pyridin-6-yl)-3-isopropyl-1H-indol-5-yl)-N-((1-(2-methoxyethyl) pyrrolidin-2-yl)methyl)piperidine-1-carboxamide (975); 4-(2-(7,8-dimethyl-[1,2,4]triazolo [1,5-a]pyridin-6-yl)-3-isopropyl-1H-indol-5-yl)-N-(2-(4-methylpiperazin-1-yl)ethyl) piperidine-1-carboxamide (976); 4-(2-(7,8-dimethyl-[1,2,4]triazolo[1,5-a]pyridin-6-yl)-3-isopropyl-1H-indol-5-yl)-N-((1-methylpyrrolidin-2-yl)methyl)piperidine-1-carboxamide (977); 4-(2-(7,8-dimethyl-[1,2,4]triazolo[1,5-a]pyridin-6-yl)-3-isopropyl-1H-indol-5-yl)-N-(2-(dimethylamino)ethyl)piperidine-1-carboxamide (978); 4-(2-(7,8-dimethyl-[1,2,4]triazolo [1,5-a]pyridin-6-yl)-3-isopropyl-1H-indol-5-yl)-N-(2-morpholinoethyl)piperidine-1-carb oxamide (979); 4-(2-(7,8-dimethyl-[1,2,4]triazolo[1,5-a]pyridin-6-yl)-3-isopropyl-1H-indol-5-yl)-N-(2-(piperidin-1-yl)ethyl)piperidine-1-carboxamide (980); 6-(3-isopropyl-5-(1-(pyridin-2-yl)piperidin-4-yl)-1H-indol-2-yl)-7,8-dimethyl-[1,2,4]triazolo[1,5-a]pyridine (986); 1-(6-(4-(2-(7,8-dimethyl-[1,2,4]triazolo[1,5-a]pyridin-6-yl)-3-isopropyl-1H-indol-5-yl)piperidin-1-yl)pyridin-3-yl)-N,N-dimethylmethanamine (987); 1-(2-(4-(2-(7,8-dimethyl-[1,2,4]triazolo[1,5-a]pyridin-6-yl)-3-isopropyl-1H-indol-5-yl)piperidin-1-yl)pyridin-4-yl)-N,N-dimethylmethanamine (988); or 6-(3-isopropyl-5-(1-(pyrimidin-2-yl)piperidin-4-yl)-1H-indol-2-yl)-7,8-dimethyl-[1,2,4]triazolo[1,5-a]pyridine (989).

One embodiment provides a compound of Formula (I-6) or a salt thereof, wherein $R_1$ is —CH(CH$_3$)$_2$; m is zero; n is zero, and $R_3$ is defined in the first aspect or the second aspect. Compounds of this embodiment have the structure of Formula (I-6a)

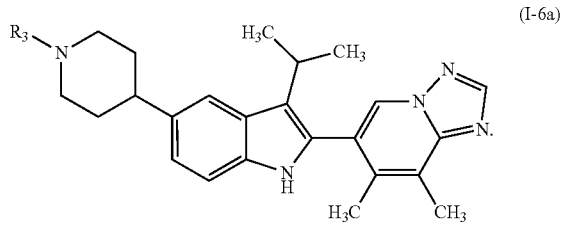

(I-6a)

Included in this embodiment are compounds in which $R_3$ is —$(CR_xR_x)_{1-2}C(O)NR_yR_y$, wherein each $R_x$ is independently H or —$CH_3$; and each $R_y$ is independently H or —$CH_3$. Also included in this embodiment are compounds in which $R_3$ is —$CH_2C(O)NH_2$, —$CH_2C(O)NH(CH_3)$, or —$CH_2C(O)N(CH_3)_2$.

One embodiment provides a compound of Formula (I) or a salt thereof, wherein said compound is selected from:

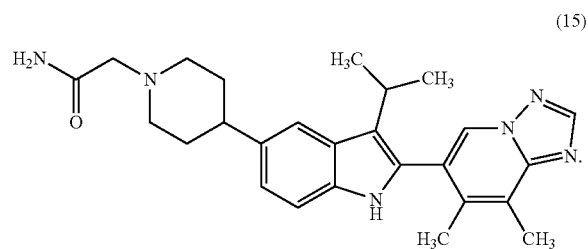 [SMILES: Cc1c(-c2[nH]c3ccc(C4CCN(CC(N)=O)CC4)cc3c2C(C)C)cn2ncnc2c1C]

(15)

Included in this embodiment is 2-(4-(2-(7,8-dimethyl-[1,2,4]triazolo[1,5-a]pyridin-6-yl)-3-isopropyl-1H-indol-5-yl)piperidin-1-yl) acetamide (15). Also included in this embodiment is one or more salts of 2-(4-(2-(7,8-dimethyl-[1,2,4]triazolo[1,5-a]pyridin-6-yl)-3-isopropyl-1H-indol-5-yl)piperidin-1-yl) acetamide (15).

One embodiment provides a compound of Formula (I) or a salt thereof, wherein said compound has the structure of Formula (I-7):

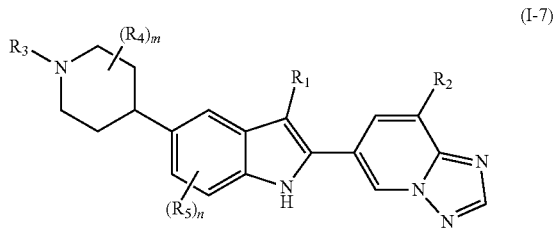

(I-7)

wherein $R_2$ is F, Cl, —CN, —$NH_2$, —$CH_2CH_3$, —$CH(CH_3)_2$, —$CF_3$, $C_{1-3}$ hydroxyalkyl, —$CH_2CN$, —$CH_2OCH_2CH_3$, —$OCH_2F$, —$OCH_2CH_3$, —$OCH_2CH(CH_3)_2$, —$OCH_2CH_2OH$, —$OCH_2CH_2OC(O)CH_3$, —$NH(CH_2CH_3)$, —$NH(CH_2CF_3)$, —$NH(CH_2C(CH_3)_2OH)$, —$NHCH_2$(phenyl), —$NHS(O)_2$(cyclopropyl), cyclopropyl, morpholinyl, methyl-piperazinyl, or dioxothiomorpholinyl; and $R_1$, $R_3$, $R_4$, $R_5$, m, and n are defined in the first aspect or the second aspect. Included in this embodiment are compounds in which $R_1$ is —$CH(CH_3)_2$. Included in this embodiment are compounds in which $R_3$ is H, $C_{3-4}$ alkyl, $C_{1-2}$ cyanoalkyl, —$CH_2C(CH_3)_2OH$, —$CH_2C(O)N(CH_3)_2$, —$CH_2C(O)NH(CH_3)$, —$CH_2C(O)NH_2$, —$CH_2CH_2NHS(O)_2CH_3$, —$CH_2CH_2S(O)_2CH_3$, —$CH_2CH_2S(O)_2NH_2$, —$C(O)CH_2CF_3$, —$C(O)CH_2CH_2OH$, —$C(O)CH(CH_3)OH$, —$C(O)CH_2CH(CH_3)OH$, —$C(O)CH_2C(CH_3)_2OH$, —$C(O)CH_2OCH_3$, —$C(O)CH_2CH_2OCH_3$, —$C(O)CH_2NH(CH_3)$, —$C(O)CH_2N(CH_3)_2$, —$C(O)CH_2N(CH_3)(CH_2CH_3)$, —$C(O)CH_2N(CH_3)CH(CH_3)_2$, —$C(O)CH_2CH_2N(CH_3)_2$, or -$L_1$-A; $L_1$ is —$CH_2$—, —$CH_2CH_2$—, —C(O)—, —C(O)CH_2$—, —C(O)CH_2CH_2$—, —C(O)CH_2N(CH_3)$—, —$CH_2C(O)$—; and A is cyclopropyl, dioxoisothiazolidinyl, dioxotetrahydrothiopyranyl, morpholinyl, oxetanyl, piperidinyl, pyrazinyl, pyrazolyl, pyrimidinyl, tetrahydrofuranyl, tetrahydropyranyl, tetrazolyl, thiadiazolyl, thiazolyl, or triazolyl, each substituted with -$L_2$-$R_a$; $L_2$ is a bond; and $R_a$ is H, —CN, —$CH_3$, —$CF_3$, or —$OCH_3$. Also included in this embodiment are compounds in which $R_1$ is —$CH(CH_3)_2$; m is zero, and n is zero.

One embodiment provides a compound of Formula (I) or a salt thereof, wherein said compound is selected from 8-ethyl-6-(3-isopropyl-5-(piperidin-4-yl)-1H-indol-2-yl)-[1,2,4]triazolo[1,5-a]pyridine (94);
8-isopropyl-6-(3-isopropyl-5-(piperidin-4-yl)-1H-indol-2-yl)-[1,2,4]triazolo[1,5-a]pyridine (95);
8-(ethoxymethyl)-6-(3-isopropyl-5-(piperidin-4-yl)-1H-indol-2-yl)-[1,2,4]triazolo[1,5-a]pyridine (99);
2-(6-(3-isopropyl-5-(piperidin-4-yl)-1H-indol-2-yl)-[1,2,4]triazolo[1,5-a]pyridin-8-yl)propan-2-ol (100);
1-(6-(3-isopropyl-5-(piperidin-4-yl)-1H-indol-2-yl)-[1,2,4]triazolo[1,5-a]pyridin-8-yl)ethan-1-ol (103);
6-(3-isopropyl-5-(piperidin-4-yl)-1H-indol-2-yl)-[1,2,4]triazolo[1,5-a]pyridine-8-carbonitrile (111);
8-fluoro-6-(3-isopropyl-5-(piperidin-4-yl)-1H-indol-2-yl)-[1,2,4]triazolo[1,5-a]pyridine(112);
(6-(3-isopropyl-5-(piperidin-4-yl)-1H-indol-2-yl)-[1,2,4]triazolo[1,5-a]pyridin-8-yl)methanol (113);
2-((6-(3-isopropyl-5-(piperidin-4-yl)-1H-indol-2-yl)-[1,2,4]triazolo[1,5-a]pyridin-8-yl)oxy)ethan-1-ol (114); 2-(6-(3-isopropyl-5-(piperidin-4-yl)-1H-indol-2-yl)-[1,2,4]triazolo [1,5-a]pyridin-8-yl)ethan-1-ol (115);
2-((6-(3-isopropyl-5-(piperidin-4-yl)-1H-indol-2-yl)-[1,2,4]triazolo[1,5-a]pyridin-8-yl)oxy)ethyl acetate (116);
8-chloro-6-(3-isopropyl-5-(piperidin-4-yl)-1H-indol-2-yl)-[1,2,4]triazolo[1,5-a]pyridine (118);
6-(3-isopropyl-5-(piperidin-4-yl)-1H-indol-2-yl)-8-(trifluoromethyl)-[1,2,4]triazolo[1,5-a]pyridine (128);
8-ethoxy-6-(3-isopropyl-5-(piperidin-4-yl)-1H-indol-2-yl)-[1,2,4]triazolo[1,5-a]pyridine (132);
8-isobutoxy-6-(3-isopropyl-5-(piperidin-4-yl)-1H-indol-2-yl)-[1,2,4]triazolo[1,5-a]pyridine (136);
4-(6-(3-isopropyl-5-(piperidin-4-yl)-1H-indol-2-yl)-[1,2,4]triazolo[1,5-a]pyridin-8-yl) morpholine (143);
N-ethyl-6-(3-isopropyl-5-(piperidin-4-yl)-1H-indol-2-yl)-[1,2,4]triazolo [1,5-a]pyridin-8-amine (144);
6-(3-isopropyl-5-(piperidin-4-yl)-1H-indol-2-yl)-N-(2,2,2-trifluoroethyl)-[1,2,4]triazolo[1,5-a]pyridin-8-amine (145);
1-((6-(3-isopropyl-5-(piperidin-4-yl)-1H-indol-2-yl)-[1,2,4]triazolo[1,5-a]pyridin-8-yl)amino)-2-methylpropan-2-ol (146);
N-(6-(3-isopropyl-5-(piperidin-4-yl)-1H-indol-2-yl)-[1,2,4]triazolo[1,5-a]pyridin-8-yl) cyclopropanesulfonamide (147);
4-(6-(3-isopropyl-5-(piperidin-4-yl)-1H-indol-2-yl)-[1,2,4]triazolo[1,5-a]pyridin-8-yl)thiomorpholine 1,1-dioxide (148);
6-(3-isopropyl-5-(piperidin-4-yl)-1H-indol-2-yl)-8-(4-methylpiperazin-1-yl)-[1,2,4]triazolo[1,5-a]pyridine (149);

8-cyclopropyl-6-(3-isopropyl-5-(piperidin-4-yl)-1H-indol-2-yl)-[1,2,4]triazolo[1,5-a]pyridine (151);

N-benzyl-6-(3-isopropyl-5-(piperidin-4-yl)-1H-indol-2-yl)-[1,2,4]triazolo[1,5-a]pyridin-8-amine (159);

8-(difluoromethoxy)-6-(3-isopropyl-5-(piperidin-4-yl)-1H-indol-2-yl)-[1,2,4]triazolo[1,5-a]pyridine (160); 2-(4-(2-(8-(ethoxymethyl)-[1,2,4]triazolo[1,5-a]pyridin-6-yl)-3-isopropyl-1H-indol-5-yl)piperidin-1-yl)-N,N-dimethylacetamide (163);

2-(4-(2-(8-fluoro-[1,2,4]triazolo[1,5-a]pyridin-6-yl)-3-isopropyl-1H-indol-5-yl)piperidin-1-yl)-N,N-dimethylacetamide (193);

8-fluoro-6-(3-isopropyl-5-(1-(2-(methylsulfonyl)ethyl) piperidin-4-yl)-1H-indol-2-yl)-[1,2,4]triazolo[1,5-a]pyridine (194);

2-(4-(2-(8-fluoro-[1,2,4]triazolo[1,5-a]pyridin-6-yl)-3-isopropyl-1H-indol-5-yl)piperidin-1-yl)acetonitrile (195);

2-(4-(2-(8-fluoro-[1,2,4]triazolo[1,5-a]pyridin-6-yl)-3-isopropyl-1H-indol-5-yl) piperidin-1-yl)acetamide (196);

2-(4-(2-(8-fluoro-[1,2,4]triazolo[1,5-a]pyridin-6-yl)-3-isopropyl-1H-indol-5-yl)piperidin-1-yl)-N-methylacetamide (197);

3-(4-(2-(8-(2-hydroxypropan-2-yl)-[1,2,4]triazolo[1,5-a]pyridin-6-yl)-3-isopropyl-1H-indol-5-yl) piperidin-1-yl) propanenitrile (211);

2-(4-(2-(8-(2-hydroxypropan-2-yl)-[1,2,4]triazolo[1,5-a]pyridin-6-yl)-3-isopropyl-1H-indol-5-yl)piperidin-1-yl) acetonitrile (212);

2-(4-(2-(8-(2-hydroxypropan-2-yl)-[1,2,4]triazolo[1,5-a]pyridin-6-yl)-3-isopropyl-1H-indol-5-yl) piperidin-1-yl) acetamide (213);

2-(6-(3-isopropyl-5-(1-(2-(methylsulfonyl)ethyl)piperidin-4-yl)-1H-indol-2-yl)-[1,2,4]triazolo[1,5-a]pyridin-8-yl)propan-2-ol (214);

N-(2-(4-(2-(8-(2-hydroxypropan-2-yl)-[1,2,4]triazolo[1,5-a]pyridin-6-yl)-3-isopropyl-1H-indol-5-yl)piperidin-1-yl)ethyl)methanesulfonamide (215);

2-(4-(2-(8-(2-hydroxypropan-2-yl)-[1,2,4]triazolo[1,5-a]pyridin-6-yl)-3-isopropyl-1H-indol-5-yl)piperidin-1-yl)-N-methylacetamide (216);

2-(4-(2-(8-(2-hydroxypropan-2-yl)-[1,2,4]triazolo[1,5-a]pyridin-6-yl)-3-isopropyl-1H-indol-5-yl) piperidin-1-yl)-N,N-dimethylacetamide (217);

2-(4-(2-(8-(2-hydroxypropan-2-yl)-[1,2,4]triazolo[1,5-a]pyridin-6-yl)-3-isopropyl-1H-indol-5-yl)piperidin-1-yl)ethane-1-sulfonamide (218);

N-(2-(4-(2-(8-cyano-[1,2,4]triazolo[1,5-a]pyridin-6-yl)-3-isopropyl-1H-indol-5-yl) piperidin-1-yl)ethyl)methanesulfonamide (220); 6-(5-(1-(2-hydroxy-2-methylpropyl) piperidin-4-yl)-3-isopropyl-1H-indol-2-yl)-[1,2,4]triazolo[1,5-a]pyridine-8-carbonitrile (221);

6-(3-isopropyl-5-(1-(2-(methylsulfonyl)ethyl)piperidin-4-yl)-1H-indol-2-yl)-[1,2,4]triazolo[1,5-a]pyridine-8-carbonitrile (222);

6-(5-(1-(cyanomethyl)piperidin-4-yl)-3-isopropyl-1H-indol-2-yl)-[1,2,4]triazolo[1,5-a]pyridine-8-carbonitrile (223);

2-(4-(2-(8-cyano-[1,2,4]triazolo[1,5-a]pyridin-6-yl)-3-isopropyl-1H-indol-5-yl)piperidin-1-yl)-N,N-dimethylacetamide (224);

2-(4-(2-(8-(1-hydroxyethyl)-[1,2,4]triazolo[1,5-a]pyridin-6-yl)-3-isopropyl-1H-indol-5-yl)piperidin-1-yl)-N,N-dimethylacetamide (225);

2-(4-(2-(8-(cyanomethyl)-[1,2,4]triazolo[1,5-a]pyridin-6-yl)-3-isopropyl-1H-indol-5-yl)piperidin-1-yl)-N,N-dimethylacetamide (228);

2-(4-(2-(8-(1-hydroxyethyl)-[1,2,4]triazolo[1,5-a]pyridin-6-yl)-3-isopropyl-1H-indol-5-yl)piperidin-1-yl)acetonitrile (229);

2-(4-(2-(8-(hydroxymethyl)-[1,2,4]triazolo[1,5-a]pyridin-6-yl)-3-isopropyl-1H-indol-5-yl)piperidin-1-yl)-N,N-dimethylacetamide (231);

2-(4-(2-(8-(hydroxymethyl)-[1,2,4]triazolo[1,5-a]pyridin-6-yl)-3-isopropyl-1H-indol-5-yl)piperidin-1-yl)acetonitrile (232);

(6-(3-isopropyl-5-(1-(2-(methylsulfonyl)ethyl)piperidin-4-yl)-1H-indol-2-yl)-[1,2,4]triazolo[1,5-a]pyridin-8-yl) methanol (233);

2-(4-(2-(8-(hydroxymethyl)-[1,2,4]triazolo[1,5-a]pyridin-6-yl)-3-isopropyl-1H-indol-5-yl)piperidin-1-yl)-N-methylacetamide (234); 3-(4-(2-(8-(hydroxymethyl)-[1,2,4]triazolo[1,5-a]pyridin-6-yl)-3-isopropyl-1H-indol-5-yl)piperidin-1-yl)oxetane-3-carbonitrile (235);

2-(4-(2-(8-(2-hydroxyethoxy)-[1,2,4]triazolo[1,5-a]pyridin-6-yl)-3-isopropyl-1H-indol-5-yl)piperidin-1-yl)-N,N-dimethylacetamide (236);

2-(4-(3-isopropyl-2-(8-(trifluoromethyl)-[1,2,4]triazolo[1,5-a]pyridin-6-yl)-1H-indol-5-yl)piperidin-1-yl)-N-methylacetamide (250);

2-(4-(3-isopropyl-2-(8-(trifluoromethyl)-[1,2,4]triazolo[1,5-a]pyridin-6-yl)-1H-indol-5-yl)piperidin-1-yl)-N,N-dimethylacetamide (251);

1-(4-(3-isopropyl-2-(8-(trifluoromethyl)-[1,2,4]triazolo[1,5-a]pyridin-6-yl)-1H-indol-5-yl)piperidin-1-yl)-2-methylpropan-2-ol (252);

2-(4-(3-isopropyl-2-(8-(trifluoromethyl)-[1,2,4]triazolo[1,5-a]pyridin-6-yl)-1H-indol-5-yl)piperidin-1-yl) acetonitrile (253);

6-(3-isopropyl-5-(1-(2-(methylsulfonyl)ethyl)piperidin-4-yl)-1H-indol-2-yl)-8-(trifluoro methyl)-[1,2,4]triazolo[1,5-a]pyridine (254);

2-(4-(2-(8-ethoxy-[1,2,4]triazolo[1,5-a]pyridin-6-yl)-3-isopropyl-1H-indol-5-yl)piperidin-1-yl)-N,N-dimethylacetamide (268); 2-(4-(2-(8-ethoxy-[1,2,4]triazolo[1,5-a]pyridin-6-yl)-3-isopropyl-1H-indol-5-yl)piperidin-1-yl)-N-methylacetamide (269);

1-(4-(2-(8-ethoxy-[1,2,4]triazolo[1,5-a]pyridin-6-yl)-3-isopropyl-1H-indol-5-yl)piperidin-1-yl)-2-methylpropan-2-ol (270);

2-(4-(2-(8-isobutoxy-[1,2,4]triazolo[1,5-a]pyridin-6-yl)-3-isopropyl-1H-indol-5-yl)piperidin-1-yl)-N,N-dimethylacetamide (278);

2-(4-(2-(8-isobutoxy-[1,2,4]triazolo[1,5-a]pyridin-6-yl)-3-isopropyl-1H-indol-5-yl)piperidin-1-yl)-N-methylacetamide (279);

2-(4-(2-(8-chloro-[1,2,4]triazolo[1,5-a]pyridin-6-yl)-3-isopropyl-1H-indol-5-yl)piperidin-1-yl)-N,N-dimethylacetamide (280); 2-(4-(2-(8-chloro-[1,2,4]triazolo [1,5-a]pyridin-6-yl)-3-isopropyl-1H-indol-5-yl)piperidin-1-yl)-N-methylacetamide (281);

1-(4-(2-(8-chloro-[1,2,4]triazolo[1,5-a]pyridin-6-yl)-3-isopropyl-1H-indol-5-yl)piperidin-1-yl)-2-methylpropan-2-ol (282);

2-(4-(3-isopropyl-2-(8-morpholino-[1,2,4]triazolo[1,5-a]pyridin-6-yl)-1H-indol-5-yl)piperidin-1-yl)-N-methylacetamide (291);

2-(4-(3-isopropyl-2-(8-morpholino-[1,2,4]triazolo[1,5-a]pyridin-6-yl)-1H-indol-5-yl)piperidin-1-yl)-N,N-dimethylacetamide (292);

2-(4-(2-(8-ethyl-[1,2,4]triazolo[1,5-a]pyridin-6-yl)-3-isopropyl-1H-indol-5-yl)piperidin-1-yl)-N,N-dimethylacetamide (293); 2-(4-(2-(8-ethyl-[1,2,4]triazolo [1,5-a]pyridin-6-yl)-3-isopropyl-1H-indol-5-yl)piperidin-1-yl)-N-methylacetamide (294);
2-(4-(3-isopropyl-2-(8-isopropyl-[1,2,4]triazolo[1,5-a]pyridin-6-yl)-1H-indol-5-yl)piperidin-1-yl)-N,N-dimethylacetamide (295);
2-(4-(3-isopropyl-2-(8-isopropyl-[1,2,4]triazolo[1,5-a]pyridin-6-yl)-1H-indol-5-yl)piperidin-1-yl)-N-methylacetamide (296);
2-(4-(2-(8-(ethylamino)-[1,2,4]triazolo[1,5-a]pyridin-6-yl)-3-isopropyl-1H-indol-5-yl)piperidin-1-yl)-N-methylacetamide (297);
2-(4-(3-isopropyl-2-(8-((2,2,2-trifluoroethyl)amino)-[1,2,4]triazolo[1,5-a]pyridin-6-yl)-1H-indol-5-yl)piperidin-1-yl)-N,N-dimethylacetamide (298);
2-(4-(3-isopropyl-2-(8-((2,2,2-trifluoroethyl)amino)-[1,2,4]triazolo[1,5-a]pyridin-6-yl)-1H-indol-5-yl)piperidin-1-yl)-N-methylacetamide (299);
2-(4-(2-(8-((2-hydroxy-2-methylpropyl) amino)-[1,2,4]triazolo[1,5-a]pyridin-6-yl)-3-isopropyl-1H-indol-5-yl)piperidin-1-yl)-N, N-dimethylacetamide (300);
2-(4-(2-(8-((2-hydroxy-2-methylpropyl)amino)-[1,2,4]triazolo[1,5-a]pyridin-6-yl)-3-isopropyl-1H-indol-5-yl)piperidin-1-yl)-N-methylacetamide (301);
2-(4-(2-(8-(cyclopropanesulfonamido)-[1,2,4]triazolo[1,5-a]pyridin-6-yl)-3-isopropyl-1H-indol-5-yl) piperidin-1-yl)-N-methylacetamide (307);
2-(4-(2-(8-(1,1-dioxidothiomorpholino)-[1,2,4]triazolo[1,5-a]pyridin-6-yl)-3-isopropyl-1H-indol-5-yl)piperidin-1-yl)-N-methylacetamide (308);
2-(4-(2-(8-(1,1-dioxidothiomorpholino)-[1,2,4]triazolo[1,5-a]pyridin-6-yl)-3-isopropyl-1H-indol-5-yl)piperidin-1-yl)-N,N-dimethylacetamide (309);
6-(3-isopropyl-5-(1-(2-(methylsulfonyl)ethyl)piperidin-4-yl)-1H-indol-2-yl)-8-(4-methyl piperazin-1-yl)-[1,2,4]triazolo[1,5-a]pyridine (310);
6-(3-isopropyl-5-(1-(2-(methylsulfonyl)ethyl)piperidin-4-yl)-1H-indol-2-yl)-8-(4-methyl piperazin-1-yl)-[1,2,4]triazolo[1,5-a]pyridine (311);
2-(4-(2-(8-cyclopropyl-[1,2,4]triazolo[1,5-a]pyridin-6-yl)-3-isopropyl-1H-indol-5-yl)piperidin-1-yl)-N-methylacetamide (319);
2-(4-(2-(8-cyclopropyl-[1,2,4]triazolo[1,5-a]pyridin-6-yl)-3-isopropyl-1H-indol-5-yl)piperidin-1-yl)-N,N-dimethylacetamide (320);
8-cyclopropyl-6-(3-isopropyl-5-(1-(2-(methylsulfonyl)ethyl)piperidin-4-yl)-1H-indol-2-yl)-[1,2,4]triazolo[1,5-a]pyridine (321);
1-(4-(2-(8-cyclopropyl-[1,2,4]triazolo[1,5-a]pyridin-6-yl)-3-isopropyl-1H-indol-5-yl)piperidin-1-yl)-2-methylpropan-2-ol (322); 2-(4-(2-(8-(difluoromethoxy)-[1,2,4]triazolo[1,5-a]pyridin-6-yl)-3-isopropyl-1H-indol-5-yl) piperidin-1-yl)-N,N-dimethylacetamide (347);
2-(4-(2-(8-(benzylamino)-[1,2,4]triazolo[1,5-a]pyridin-6-yl)-3-isopropyl-1H-indol-5-yl)piperidin-1-yl)-N,N-dimethylacetamide (348);
8-fluoro-6-(3-isopropyl-5-(1-((1-methyl-1H-1,2,3-triazol-4-yl)methyl)piperidin-4-yl)-1H-indol-2-yl)-[1,2,4]triazolo[1,5-a]pyridine (468);
8-fluoro-6-(3-isopropyl-5-(1-(oxetan-3-yl)piperidin-4-yl)-1H-indol-2-yl)-[1,2,4]triazolo[1,5-a]pyridine (469);
2-(6-(3-isopropyl-5-(1-((2-methylpyrimidin-5-yl)methyl)piperidin-4-yl)-1H-indol-2-yl)-[1,2,4]triazolo[1,5-a]pyridin-8-yl)propan-2-ol (490);
2-(6-(3-isopropyl-5-(1-((1-methyl-1H-pyrazol-3-yl)methyl)piperidin-4-yl)-1H-indol-2-yl)-[1,2,4]triazolo[1,5-a]pyridin-8-yl)propan-2-ol (491);

2-(6-(3-isopropyl-5-(1-(oxetan-3-yl)piperidin-4-yl)-1H-indol-2-yl)-[1,2,4]triazolo[1,5-a]pyridin-8-yl)propan-2-ol (492);
2-(6-(3-isopropyl-5-(1-(tetrahydro-2H-pyran-4-yl)piperidin-4-yl)-1H-indol-2-yl)-[1,2,4]triazolo[1,5-a]pyridin-8-yl)propan-2-ol (493);
2-(6-(3-isopropyl-5-(1-(pyrimidin-2-ylmethyl)piperidin-4-yl)-1H-indol-2-yl)-[1,2,4]triazolo[1,5-a]pyridin-8-yl)propan-2-ol (494);
2-(6-(3-isopropyl-5-(1-((1-methyl-1H-1,2,4-triazol-3-yl)methyl)piperidin-4-yl)-1H-indol-2-yl)-[1,2,4]triazolo[1,5-a]pyridin-8-yl)propan-2-ol (495);
4-(4-(2-(8-(2-hydroxypropan-2-yl)-[1,2,4]triazolo[1,5-a]pyridin-6-yl)-3-isopropyl-1H-indol-5-yl)piperidin-1-yl) tetrahydro-2H-thiopyran 1,1-dioxide (496);
2-(6-(5-(1-((1H-1,2,3-triazol-4-yl)methyl)piperidin-4-yl)-3-isopropyl-1H-indol-2-yl)-[1,2,4]triazolo[1,5-a]pyridin-8-yl)propan-2-ol (497);
2-(2-(4-(2-(8-(2-hydroxypropan-2-yl)-[1,2,4]triazolo[1,5-a]pyridin-6-yl)-3-isopropyl-1H-indol-5-yl) piperidin-1-yl) ethyl)isothiazolidine 1,1-dioxide (498);
6-(3-isopropyl-5-(1-(tetrahydro-2H-pyran-4-yl)piperidin-4-yl)-1H-indol-2-yl)-[1,2,4]triazolo[1,5-a]pyridine-8-carbonitrile (500);
6-(3-isopropyl-5-(1-(oxetan-3-yl)piperidin-4-yl)-1H-indol-2-yl)-[1,2,4]triazolo[1,5-a]pyridine-8-carbonitrile (501);
1-(6-(3-isopropyl-5-(1-((1-methyl-H-1,2,3-triazol-4-yl)methyl)piperidin-4-yl)-1H-indol-2-yl)-[1,2,4]triazolo[1,5-a]pyridin-8-yl)ethan-1-ol (502);
1-(6-(3-isopropyl-5-(1-(oxetan-3-yl)piperidin-4-yl)-1H-indol-2-yl)-[1,2,4]triazolo[1,5-a]pyridin-8-yl)ethan-1-ol (503);
2-(6-(3-isopropyl-5-(1-(tetrahydro-2H-pyran-4-yl)piperidin-4-yl)-1H-indol-2-yl)-[1,2,4]triazolo[1,5-a]pyridin-8-yl)acetonitrile (506);
(6-(3-isopropyl-5-(1-(oxetan-3-yl)piperidin-4-yl)-1H-indol-2-yl)-[1,2,4]triazolo[1,5-a]pyridin-8-yl)methanol (510);
(6-(3-isopropyl-5-(1-((1-methyl-1H-1,2,4-triazol-3-yl)methyl)piperidin-4-yl)-1H-indol-2-yl)-[1,2,4]triazolo[1,5-a]pyridin-8-yl)methanol (511);
(6-(3-isopropyl-5-(1-((2-methylpyrimidin-5-yl)methyl)piperidin-4-yl)-1H-indol-2-yl)-[1,2,4]triazolo[1,5-a]pyridin-8-yl)methanol (512);
(6-(5-(1-((1H-1,2,3-triazol-5-yl)methyl)piperidin-4-yl)-3-isopropyl-1H-indol-2-yl)-[1,2,4]triazolo[1,5-a]pyridin-8-yl)methanol (513);
4-(4-(2-(8-(hydroxymethyl)-[1,2,4]triazolo[1,5-a]pyridin-6-yl)-3-isopropyl-1H-indol-5-yl)piperidin-1-yl)tetrahydro-2H-thiopyran 1,1-dioxide (514);
(6-(3-isopropyl-5-(1-((2-methoxypyrimidin-5-yl)methyl) piperidin-4-yl)-1H-indol-2-yl)-[1,2,4]triazolo[1,5-a]pyridin-8-yl)methanol (515);
(6-(3-isopropyl-5-(1-((1-methyl-1H-pyrazol-3-yl)methyl) piperidin-4-yl)-1H-indol-2-yl)-[1,2,4]triazolo[1,5-a]pyridin-8-yl)methanol (516);
(6-(3-isopropyl-5-(1-(pyrimidin-5-ylmethyl) piperidin-4-yl)-1H-indol-2-yl)-[1,2,4]triazolo[1,5-a]pyridin-8-yl) methanol (517);
(6-(5-(1-(((1,2,3-thiadiazol-4-yl)methyl)piperidin-4-yl)-3-isopropyl-1H-indol-2-yl)-[1,2,4]triazolo[1,5-a]pyridin-8-yl)methanol (518);
(6-(3-isopropyl-5-(1-((2-methylpyrimidin-4-yl)methyl) piperidin-4-yl)-1H-indol-2-yl)-[1,2,4]triazolo[1,5-a]pyridin-8-yl)methanol (519);
(6-(3-isopropyl-5-(1-(pyrimidin-2-ylmethyl)piperidin-4-yl)-1H-indol-2-yl)-[1,2,4]triazolo[1,5-a]pyridin-8-yl)methanol (520);

(6-(3-isopropyl-5-(1-(tetrahydro-2H-pyran-4-yl)piperidin-4-yl)-1H-indol-2-yl)-[1,2,4]triazolo[1,5-a]pyridin-8-yl)methanol (521);

(6-(3-isopropyl-5-(1-((2-methyl-2H-tetrazol-5-yl)methyl)piperidin-4-yl)-1H-indol-2-yl)-[1,2,4]triazolo[1,5-a]pyridin-8-yl)methanol (522);

(6-(3-isopropyl-5-(1-((1-methyl-1H-1,2,3-triazol-4-yl)methyl)piperidin-4-yl)-1H-indol-2-yl)-[1,2,4]triazolo[1,5-a]pyridin-8-yl)methanol (523);

(6-(3-isopropyl-5-(1-((5-methylpyrazin-2-yl)methyl)piperidin-4-yl)-1H-indol-2-yl)-[1,2, 4]triazolo[1,5-a]pyridin-8-yl)methanol (524);

2-(6-(3-isopropyl-5-(1-(oxetan-3-yl)piperidin-4-yl)-1H-indol-2-yl)-[1,2,4]triazolo[1,5-a]pyridin-8-yl)ethan-1-ol (525);

2-(6-(3-isopropyl-5-(1-((2-methylpyrimidin-5-yl)methyl)piperidin-4-yl)-1H-indol-2-yl)-[1,2,4]triazolo[1,5-a]pyridin-8-yl)ethan-1-ol (526);

2-(6-(3-isopropyl-5-(1-((1-methyl-1H-1,2,3-triazol-4-yl)methyl) piperidin-4-yl)-1H-indol-2-yl)-[1,2,4]triazolo[1,5-a]pyridin-8-yl)ethan-1-ol (527);

2-((6-(3-isopropyl-5-(1-(oxetan-3-yl)piperidin-4-yl)-1H-indol-2-yl)-[1,2,4]triazolo[1,5-a]pyridin-8-yl)oxy)ethyl acetate (528);

2-((6-(3-isopropyl-5-(1-(oxetan-3-yl)piperidin-4-yl)-1H-indol-2-yl)-[1,2,4]triazolo[1,5-a]pyridin-8-yl)oxy)ethan-1-ol (529-530);

6-(3-isopropyl-5-(1-(oxetan-3-yl)piperidin-4-yl)-1H-indol-2-yl)-8-(trifluoromethyl)-[1,2,4]triazolo[1,5-a]pyridine (549);

4-(4-(3-isopropyl-2-(8-(trifluoromethyl)-[1,2,4]triazolo[1,5-a]pyridin-6-yl)-1H-indol-5-yl)piperidin-1-yl)tetrahydro-2H-thiopyran 1,1-dioxide (550);

6-(3-isopropyl-5-(1-isopropylpiperidin-4-yl)-1H-indol-2-yl)-8-(trifluoromethyl)-[1,2,4]triazolo[1,5-a]pyridine (551);

6-(3-isopropyl-5-(1-(tetrahydro-2H-pyran-4-yl)piperidin-4-yl)-1H-indol-2-yl)-8-(trifluoromethyl)-[1,2,4]triazolo[1,5-a]pyridine (552);

6-(5-(1-isobutylpiperidin-4-yl)-3-isopropyl-1H-indol-2-yl)-8-(trifluoromethyl)-[1,2,4]triazolo[1,5-a]pyridine (553);

6-(3-isopropyl-5-(1-(tetrahydro-2H-pyran-3-yl)piperidin-4-yl)-1H-indol-2-yl)-8-(trifluoromethyl)-[1,2,4]triazolo[1,5-a]pyridine (554);

6-(3-isopropyl-5-(1-((3-methyloxetan-3-yl)methyl)piperidin-4-yl)-1H-indol-2-yl)-8-(trifluoromethyl)-[1,2,4]triazolo[1,5-a]pyridine (555);

6-(3-isopropyl-5-(1-(tetrahydrofuran-3-yl)piperidin-4-yl)-1H-indol-2-yl)-8-(trifluoromethyl)-[1,2,4]triazolo[1,5-a]pyridine (556-557);

8-ethoxy-6-(3-isopropyl-5-(1-(tetrahydro-2H-pyran-4-yl)piperidin-4-yl)-1H-indol-2-yl)-[1,2,4]triazolo[1,5-a]pyridine (571);

8-ethoxy-6-(3-isopropyl-5-(1-(oxetan-3-yl)piperidin-4-yl)-1H-indol-2-yl)-[1,2,4]triazolo[1,5-a]pyridine (572);

4-(4-(2-(8-ethoxy-[1,2,4]triazolo[1,5-a]pyridin-6-yl)-3-isopropyl-1H-indol-5-yl)piperidin-1-yl)tetrahydro-2H-thiopyran 1,1-dioxide (573);

4-(6-(3-isopropyl-5-(1-(oxetan-3-yl)piperidin-4-yl)-1H-indol-2-yl)-[1,2,4]triazolo[1,5-a]pyridin-8-yl) morpholine (581);

8-ethyl-6-(5-(1-isobutylpiperidin-4-yl)-3-isopropyl-1H-indol-2-yl)-[1,2,4]triazolo[1,5-a]pyridine (582);

8-ethyl-6-(3-isopropyl-5-(1-(oxetan-3-yl)piperidin-4-yl)-1H-indol-2-yl)-[1,2,4]triazolo[1,5-a]pyridine (583);

6-(5-(1-isobutylpiperidin-4-yl)-3-isopropyl-1H-indol-2-yl)-8-isopropyl-[1,2,4]triazolo[1,5-a]pyridine (584);

8-isopropyl-6-(3-isopropyl-5-(1-(oxetan-3-yl)piperidin-4-yl)-1H-indol-2-yl)-[1,2,4]triazolo[1,5-a]pyridine (585);

6-(3-isopropyl-5-(1-(oxetan-3-yl)piperidin-4-yl)-1H-indol-2-yl)-N-(2,2,2-trifluoroethyl)-[1,2,4]triazolo[1,5-a]pyridin-8-amine (586);

N-(6-(3-isopropyl-5-(1-(oxetan-3-yl)piperidin-4-yl)-1H-indol-2-yl)-[1,2,4]triazolo[1,5-a]pyridin-8-yl)cyclopropanesulfonamide (590);

4-(6-(3-isopropyl-5-(1-(oxetan-3-yl)piperidin-4-yl)-1H-indol-2-yl)-[1,2,4]triazolo[1,5-a]pyridin-8-yl)thiomorpholine 1,1-dioxide (591);

6-(3-isopropyl-5-(1-(oxetan-3-yl)piperidin-4-yl)-1H-indol-2-yl)-8-(4-methylpiperazin-1-yl)-[1,2,4]triazolo[1,5-a]pyridine (592);

8-cyclopropyl-6-(3-isopropyl-5-(1-(oxetan-3-yl)piperidin-4-yl)-1H-indol-2-yl)-[1,2,4]triazolo[1,5-a]pyridine (593);

2-(dimethylamino)-1-(4-(2-(8-fluoro-[1,2,4]triazolo[1,5-a]pyridin-6-yl)-3-isopropyl-1H-indol-5-yl)piperidin-1-yl)ethan-1-one (640);

1-(4-(3-isopropyl-2-(8-(trifluoromethyl)-[1,2,4]triazolo[1,5-a]pyridin-6-yl)-1H-indol-5-yl)piperidin-1-yl)-2-(methylamino)ethan-1-one (641);

2-(dimethylamino)-1-(4-(3-isopropyl-2-(8-(trifluoromethyl)-[1,2,4]triazolo[1,5-a]pyridin-6-yl)-1H-indol-5-yl)piperidin-1-yl)ethan-1-one (642);

1-(4-(3-isopropyl-2-(8-(trifluoromethyl)-[1,2,4]triazolo[1,5-a]pyridin-6-yl)-1H-indol-5-yl)piperidin-1-yl)-2-methoxyethan-1-one (643);

1-(4-(3-isopropyl-2-(8-(trifluoromethyl)-[1,2,4]triazolo[1,5-a]pyridin-6-yl)-1H-indol-5-yl)piperidin-1-yl)-3-(piperidin-1-yl)propan-1-one (644);

(4-(3-isopropyl-2-(8-(trifluoromethyl)-[1,2,4]triazolo[1,5-a]pyridin-6-yl)-1H-indol-5-yl) piperidin-1-yl)(tetrahydrofuran-2-yl)methanone (645);

1-(4-(3-isopropyl-2-(8-(trifluoromethyl)-[1,2,4]triazolo[1,5-a]pyridin-6-yl)-1H-indol-5-yl)piperidin-1-yl)-3-methoxypropan-1-one (646);

3-hydroxy-1-(4-(3-isopropyl-2-(8-(trifluoromethyl)-[1,2,4]triazolo[1,5-a]pyridin-6-yl)-1H-indol-5-yl)piperidin-1-yl)propan-1-one (647);

3,3,3-trifluoro-1-(4-(3-isopropyl-2-(8-(trifluoromethyl)-[1,2,4]triazolo[1,5-a]pyridin-6-yl)-1H-indol-5-yl)piperidin-1-yl)propan-1-one (648);

3-(dimethylamino)-1-(4-(3-isopropyl-2-(8-(trifluoromethyl)-[1,2,4]triazolo[1,5-a]pyridin-6-yl)-1H-indol-5-yl) piperidin-1-yl)propan-1-one (649);

1-(4-(3-isopropyl-2-(8-(trifluoromethyl)-[1,2,4]triazolo[1,5-a]pyridin-6-yl)-1H-indol-5-yl)piperidin-1-yl)-2-(2-methylthiazol-4-yl)ethan-1-one (650);

3-hydroxy-1-(4-(3-isopropyl-2-(8-(trifluoromethyl)-[1,2,4]triazolo[1,5-a]pyridin-6-yl)-1H-indol-5-yl)piperidin-1-yl)-3-methylbutan-1-one (651);

2-hydroxy-1-(4-(3-isopropyl-2-(8-(trifluoromethyl)-[1,2,4]triazolo[1,5-a]pyridin-6-yl)-1H-indol-5-yl)piperidin-1-yl)propan-1-one (652);

(4-(3-isopropyl-2-(8-(trifluoromethyl)-[1,2,4]triazolo[1,5-a]pyridin-6-yl)-1H-indol-5-yl)piperidin-1-yl)(1-(trifluoromethyl)cyclopropyl) methanone (653);

(4-(3-isopropyl-2-(8-(trifluoromethyl)-[1,2,4]triazolo[1,5-a]pyridin-6-yl)-1H-indol-5-yl) piperidin-1-yl)(oxetan-3-yl)methanone (654);

1-(4-(3-isopropyl-2-(8-(trifluoromethyl)-[1,2,4]triazolo[1,5-a]pyridin-6-yl)-1H-indol-5-yl)piperidin-1-yl)-2-morpholinoethan-1-one (655);

2-(dimethylamino)-1-(4-(2-(8-ethoxy-[1,2,4]triazolo[1,5-a]pyridin-6-yl)-3-isopropyl-1H-indol-5-yl)piperidin-1-yl)ethan-1-one (680);

1-(4-(2-(8-ethoxy-[1,2,4]triazolo[1,5-a]pyridin-6-yl)-3-isopropyl-1H-indol-5-yl)piperidin-1-yl)-2-(methylamino)ethan-1-one (681);

2-(dimethylamino)-1-(4-(2-(8-isobutoxy-[1,2,4]triazolo[1,5-a]pyridin-6-yl)-3-isopropyl-1H-indol-5-yl)piperidin-1-yl)ethan-1-one (684);

(S)-1-(4-(2-(8-chloro-[1,2,4]triazolo[1,5-a]pyridin-6-yl)-3-isopropyl-1H-indol-5-yl)piperidin-1-yl)-3-hydroxybutan-1-one (685);

1-(4-(2-(8-chloro-[1,2,4]triazolo[1,5-a]pyridin-6-yl)-3-isopropyl-1H-indol-5-yl)piperidin-1-yl)-2-(dimethylamino)ethan-1-one (686);

2-(dimethylamino)-1-(4-(3-isopropyl-2-(8-morpholino-[1,2,4]triazolo[1,5-a]pyridin-6-yl)-1H-indol-5-yl)piperidin-1-yl)ethan-1-one (690);

2-(dimethylamino)-1-(4-(2-(8-(1,1-dioxidothiomorpholino)-[1,2,4]triazolo[1,5-a]pyridin-6-yl)-3-isopropyl-1H-indol-5-yl)piperidin-1-yl)ethan-1-one (691);

1-(4-(2-(8-cyclopropyl-[1,2,4]triazolo[1,5-a]pyridin-6-yl)-3-isopropyl-1H-indol-5-yl)piperidin-1-yl)-2-(dimethylamino)ethan-1-one (696);

1-(4-(2-(8-cyclopropyl-[1,2,4]triazolo[1,5-a]pyridin-6-yl)-3-isopropyl-1H-indol-5-yl)piperidin-1-yl)-2-(methylamino)ethan-1-one (697);

2-isopropyl(methyl)amino)-1-(4-(3-isopropyl-2-(8-(trifluoromethyl)-[1,2,4]triazolo[1,5-a]pyridin-6-yl)-1H-indol-5-yl)piperidin-1-yl)ethan-1-one (777);

2-(ethyl(methyl)amino)-1-(4-(3-isopropyl-2-(8-(trifluoromethyl)-[1,2,4]triazolo[1,5-a]pyridin-6-yl)-1H-indol-5-yl)piperidin-1-yl)ethan-1-one (778);

2-(cyclopropyl(methyl)amino)-1-(4-(3-isopropyl-2-(8-(trifluoromethyl)-[1,2,4]triazolo[1,5-a]pyridin-6-yl)-1H-indol-5-yl)piperidin-1-yl)ethan-1-one (779);

2-(4-(2-(8-(2-hydroxypropan-2-yl)-[1,2,4]triazolo[1,5-a]pyridin-6-yl)-3-isopropyl-1H-indol-5-yl)piperidin-1-yl)-1-morpholinoethan-1-one (850); and 2-(4-(2-(8-amino-[1,2,4]triazolo[1,5-a]pyridin-6-yl)-3-isopropyl-1H-indol-5-yl)piperidin-1-yl)-N,N-dimethylacetamide (990).

One embodiment provides a compound of Formula (I) or a salt thereof, wherein said compound has the structure of Formula (I-8):

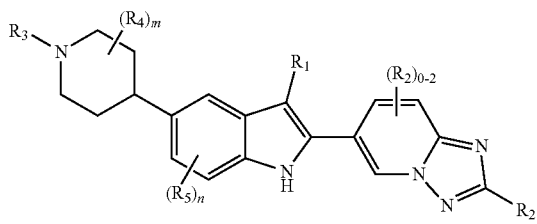

(I-8)

wherein each $R_2$ is independently F, Cl, —$NH_2$, $C_{1-2}$ alkyl, —$CF_3$, —$OCH_3$, —$OCH_2CH_3$, —$OCHF_2$, cyclopropyl, or morpholinyl; and $R_1$, $R_3$, $R_4$, $R_5$, m, and n are defined in the first aspect or the second aspect. Included in this embodiment are compounds in which $R_1$ is —$CH_2CH_3$, —$CH(CH_3)_2$, or —$CH_2CHF_2$. Included in this embodiment are compounds in which $R_3$ is H, —$CH(CH_3)_2$, —$CH_2CH(CH_3)_2$, —$CH_2C(CH_3)_2OH$, —$CH_2C(O)NH(CH_3)$, —$CH_2C(O)N(CH_3)_2$, —$C(O)CH_2CH(CH_3)OH$, —$C(O)CH_2C(CH_3)_2OH$, —$C(O)CH_2NH(CH_3)$, —$C(O)CH_2N(CH_3)_2$, or -$L_1$-A; $L_1$ is —$CH_2$—, —$C(O)$—, or —$CH_2C(O)$—; and A is dioxotetrahydrothiopyranyl, dioxothiomorpholinyl, imidazolyl, morpholinyl, oxetanyl, pyrazolyl, pyrrolidinyl, tetrahydrofuranyl, or tetrahydropyranyl, each substituted with -$L_2$-$R_a$ and zero to 1 $R_b$; $L_2$ is a bond; $R_a$ is H, —OH, —$CH_3$, or —$C(O)OC(CH_3)_3$; and $R_b$ is —OH. Also included in this embodiment are compounds in which $R_1$ is —$CH(CH_3)_2$; m is zero, and n is zero.

One embodiment provides a compound of Formula (I) or a salt thereof, wherein said compound is selected from 8-chloro-6-(3-isopropyl-5-(piperidin-4-yl)-1H-indol-2-yl)-2-methyl-[1,2,4]triazolo[1,5-a]pyridine (96);

8-ethyl-6-(3-isopropyl-5-(piperidin-4-yl)-1H-indol-2-yl)-2-methyl-[1,2,4]triazolo[1,5-a]pyridine (97);

6-(3-ethyl-5-(piperidin-4-yl)-1H-indol-2-yl)-[1,2,4]triazolo[1,5-a]pyridin-2-amine (109);

6-(3-isopropyl-5-(piperidin-4-yl)-1H-indol-2-yl)-8-methyl-2-(trifluoromethyl)-[1,2,4]triazolo[1,5-a]pyridine (120);

6-(3-isopropyl-5-(piperidin-4-yl)-1H-indol-2-yl)-2-methyl-[1,2,4]triazolo[1,5-a]pyridine (122);

6-(3-isopropyl-5-(piperidin-4-yl)-1H-indol-2-yl)-2,8-dimethyl-[1,2,4]triazolo[1,5-a]pyridine (124);

6-(3-isopropyl-5-(piperidin-4-yl)-1H-indol-2-yl)-2,7-dimethyl-[1,2,4]triazolo[1,5-a]pyridine (125);

8-fluoro-6-(3-isopropyl-5-(piperidin-4-yl)-1H-indol-2-yl)-2-methyl-[1,2,4]triazolo[1,5-a]pyridine (126);

7-fluoro-6-(3-isopropyl-5-(piperidin-4-yl)-1H-indol-2-yl)-2-methyl-[1,2,4]triazolo[1,5-a]pyridine (127);

6-(3-isopropyl-5-(piperidin-4-yl)-1H-indol-2-yl)-8-methoxy-2-methyl-[1,2,4]triazolo[1,5-a]pyridine (133);

8-(difluoromethoxy)-6-(3-isopropyl-5-(piperidin-4-yl)-1H-indol-2-yl)-2-methyl-[1,2,4]triazolo[1,5-a]pyridine (134);

8-ethoxy-6-(3-isopropyl-5-(piperidin-4-yl)-1H-indol-2-yl)-2-methyl-[1,2,4]triazolo[1,5-a]pyridine (135);

8-chloro-6-(3-isopropyl-5-(piperidin-4-yl)-1H-indol-2-yl)-2,7-dimethyl-[1,2,4]triazolo[1,5-a]pyridine (138);

8-cyclopropyl-6-(3-isopropyl-5-(piperidin-4-yl)-1H-indol-2-yl)-2-methyl-[1,2,4]triazolo[1,5-a]pyridine (141);

6-(3-(2,2-difluoroethyl)-5-(piperidin-4-yl)-1H-indol-2-yl)-2-methyl-[1,2,4]triazolo[1,5-a]pyridine (142);

4-(6-(3-isopropyl-5-(piperidin-4-yl)-1H-indol-2-yl)-2-methyl-[1,2,4]triazolo[1,5-a]pyridin-8-yl) morpholine (150);

6-(3-isopropyl-5-(piperidin-4-yl)-1H-indol-2-yl)-2-methyl-8-(trifluoromethyl)-[1,2,4]triazolo[1,5-a]pyridine (153);

6-(3-isopropyl-5-(piperidin-4-yl)-1H-indol-2-yl)-8-methoxy-2-(trifluoromethyl)-[1,2,4]triazolo[1,5-a]pyridine (154);

6-(3-isopropyl-5-(piperidin-4-yl)-1H-indol-2-yl)-2,5-dimethyl-[1,2,4]triazolo[1,5-a]pyridine (155);

6-(3-(2,2-difluoroethyl)-5-(piperidin-4-yl)-1H-indol-2-yl)-2,8-dimethyl-[1,2,4]triazolo [1,5-a]pyridine (162);

2-(4-(3-isopropyl-2-(2-methyl-[1,2,4]triazolo[1,5-a]pyridin-6-yl)-1H-indol-5-yl)piperidin-1-yl)-N-methylacetamide (237); 2-(4-(3-isopropyl-2-(2-methyl-[1,2,4]triazolo[1,5-a]pyridin-6-yl)-1H-indol-5-yl)piperidin-1-yl)-N,N-dimethylacetamide (238);

1-(4-(3-isopropyl-2-(2-methyl-[1,2,4]triazolo[1,5-a]pyridin-6-yl)-1H-indol-5-yl)piperidin-1-yl)-2-methylpropan-2-ol (239);

2-(4-(2-(2,8-dimethyl-[1,2,4]triazolo[1,5-a]pyridin-6-yl)-3-isopropyl-1H-indol-5-yl)piperidin-1-yl)-N-methylacetamide (244);

2-(4-(2-(2,8-dimethyl-[1,2,4]triazolo[1,5-a]pyridin-6-yl)-3-isopropyl-1H-indol-5-yl)piperidin-1-yl)-N,N-dimethylacetamide (245);

1-(4-(2-(2,8-dimethyl-[1,2,4]triazolo[1,5-a]pyridin-6-yl)-3-isopropyl-1H-indol-5-yl)piperidin-1-yl)-2-methylpropan-2-ol (246);

2-(4-(2-(2,7-dimethyl-[1,2,4]triazolo[1,5-a]pyridin-6-yl)-3-isopropyl-1H-indol-5-yl)piperidin-1-yl)-N,N-dimethylacetamide (247);

2-(4-(2-(2,7-dimethyl-[1,2,4]triazolo[1,5-a]pyridin-6-yl)-3-isopropyl-1H-indol-5-yl)piperidin-1-yl)-N-methylacetamide (248);

1-(4-(2-(2,7-dimethyl-[1,2,4]triazolo[1,5-a]pyridin-6-yl)-3-isopropyl-1H-indol-5-yl)piperidin-1-yl)-2-methylpropan-2-ol (249);

2-(4-(3-(2,2-difluoroethyl)-2-(2-methyl-[1,2,4]triazolo[1,5-a]pyridin-6-yl)-1H-indol-5-yl)piperidin-1-yl)-N-methylacetamide (255);

2-(4-(3-(2,2-difluoroethyl)-2-(2-methyl-[1,2,4]triazolo[1,5-a]pyridin-6-yl)-1H-indol-5-yl)piperidin-1-yl)-N,N-dimethylacetamide (256);

2-(4-(2-(2,5-dimethyl-[1,2,4]triazolo[1,5-a]pyridin-6-yl)-3-isopropyl-1H-indol-5-yl)piperidin-1-yl)-N,N-dimethylacetamide (257);

2-(4-(2-(2,5-dimethyl-[1,2,4]triazolo[1,5-a]pyridin-6-yl)-3-isopropyl-1H-indol-5-yl)piperidin-1-yl)-N-methylacetamide (258);

2-(4-(3-isopropyl-2-(2-methyl-8-(trifluoromethyl)-[1,2,4]triazolo [1,5-a]pyridin-6-yl)-1H-indol-5-yl)piperidin-1-yl)-N,N-dimethylacetamide (259);

2-(4-(2-(8-chloro-2-methyl-[1,2,4]triazolo[1,5-a]pyridin-6-yl)-3-isopropyl-1H-indol-5-yl)piperidin-1-yl)-N,N-dimethylacetamide (260);

2-(4-(2-(8-chloro-2-methyl-[1,2,4]triazolo[1,5-a]pyridin-6-yl)-3-isopropyl-1H-indol-5-yl)piperidin-1-yl)-N-methylacetamide (261);

1-(4-(2-(8-chloro-2-methyl-[1,2,4]triazolo[1,5-a]pyridin-6-yl)-3-isopropyl-1H-indol-5-yl)piperidin-1-yl)-2-methylpropan-2-ol (262);

2-(4-(3-isopropyl-2-(8-methoxy-2-methyl-[1,2,4]triazolo[1,5-a]pyridin-6-yl)-1H-indol-5-yl)piperidin-1-yl)-N,N-dimethylacetamide (271);

2-(4-(3-isopropyl-2-(8-methoxy-2-methyl-[1,2,4]triazolo[1,5-a]pyridin-6-yl)-1H-indol-5-yl)piperidin-1-yl)-N-methylacetamide (272);

1-(4-(3-isopropyl-2-(8-methoxy-2-methyl-[1,2,4]triazolo[1,5-a]pyridin-6-yl)-1H-indol-5-yl)piperidin-1-yl)-2-methylpropan-2-ol (273);

2-(4-(2-(8-(difluoromethoxy)-2-methyl-[1,2,4]triazolo[1,5-a]pyridin-6-yl)-3-isopropyl-1H-indol-5-yl) piperidin-1-yl)-N,N-dimethylacetamide (274);

2-(4-(2-(8-(difluoromethoxy)-2-methyl-[1,2,4]triazolo[1,5-a]pyridin-6-yl)-3-isopropyl-1H-indol-5-yl)piperidin-1-yl)-N-methylacetamide (275);

2-(4-(2-(8-ethoxy-2-methyl-[1,2,4]triazolo[1,5-a]pyridin-6-yl)-3-isopropyl-1H-indol-5-yl)piperidin-1-yl)-N,N-dimethylacetamide (276); 2-(4-(2-(8-ethoxy-2-methyl-[1,2,4]triazolo[1,5-a]pyridin-6-yl)-3-isopropyl-1H-indol-5-yl)piperidin-1-yl)-N-methylacetamide (277);

2-(4-(2-(8-ethyl-2-methyl-[1,2,4]triazolo[1,5-a]pyridin-6-yl)-3-isopropyl-1H-indol-5-yl) piperidin-1-yl)-N,N-dimethylacetamide (283); 1-(4-(2-(8-ethyl-2-methyl-[1,2,4]triazolo [1,5-a]pyridin-6-yl)-3-isopropyl-1H-indol-5-yl)piperidin-1-yl)-2-methylpropan-2-ol (284);

2-(4-(2-(8-ethyl-2-methyl-[1,2,4]triazolo[1,5-a]pyridin-6-yl)-3-isopropyl-1H-indol-5-yl) piperidin-1-yl)-N-methylacetamide (285);

2-(4-(3-isopropyl-2-(8-methyl-2-(trifluoromethyl)-[1,2,4]triazolo[1,5-a]pyridin-6-yl)-1H-indol-5-yl)piperidin-1-yl)-N,N-dimethylacetamide (312);

2-(4-(3-isopropyl-2-(8-methyl-2-(trifluoromethyl)-[1,2,4]triazolo[1,5-a]pyridin-6-yl)-1H-indol-5-yl)piperidin-1-yl)-N-methylacetamide (313);

1-(4-(3-isopropyl-2-(8-methyl-2-(trifluoromethyl)-[1,2,4]triazolo[1,5-a]pyridin-6-yl)-1H-indol-5-yl)piperidin-1-yl)-2-methylpropan-2-ol (314);

2-(4-(3-isopropyl-2-(2-methyl-8-morpholino-[1,2,4]triazolo [1,5-a]pyridin-6-yl)-1H-indol-5-yl)piperidin-1-yl)-N,N-dimethylacetamide (315);

2-(4-(3-isopropyl-2-(2-methyl-8-morpholino-[1,2,4]triazolo [1,5-a]pyridin-6-yl)-1H-indol-5-yl)piperidin-1-yl)-N-methylacetamide (316);

2-(4-(3-isopropyl-2-(8-methoxy-2-(trifluoromethyl)-[1,2,4]triazolo[1,5-a]pyridin-6-yl)-1H-indol-5-yl)piperidin-1-yl)-N-methylacetamide (317);

2-(4-(3-isopropyl-2-(8-methoxy-2-(trifluoromethyl)-[1,2,4]triazolo[1,5-a]pyridin-6-yl)-1H-indol-5-yl)piperidin-1-yl)-N,N-dimethylacetamide (318);

2-(4-(2-(8-cyclopropyl-2-methyl-[1,2,4]triazolo[1,5-a]pyridin-6-yl)-3-isopropyl-1H-indol-5-yl)piperidin-1-yl)-N-methylacetamide (323);

1-(4-(2-(8-cyclopropyl-2-methyl-[1,2,4]triazolo[1,5-a]pyridin-6-yl)-3-isopropyl-1H-indo 1-5-yl)piperidin-1-yl)-2-methylpropan-2-ol (324);

2-(4-(2-(8-cyclopropyl-2-methyl-[1,2,4]triazolo[1,5-a]pyridin-6-yl)-3-isopropyl-1H-indo 1-5-yl)piperidin-1-yl)-N,N-dimethylacetamide (325);

2-(4-(3-(2,2-difluoroethyl)-2-(2,8-dimethyl-[1,2,4]triazolo [1,5-a]pyridin-6-yl)-1H-indol-5-yl)piperidin-1-yl)-N,N-dimethylacetamide (345);

2-(4-(3-(2,2-difluoroethyl)-2-(2,8-dimethyl-[1,2,4]triazolo [1,5-a]pyridin-6-yl)-1H-indol-5-yl)piperidin-1-yl)-N-methylacetamide (346);

2-(4-(3-isopropyl-2-(2-methyl-[1,2,4]triazolo[1,5-a]pyridin-6-yl)-1H-indol-5-yl)piperidin-1-yl)-N-methylethan-1-amine (531);

6-(3-isopropyl-5-(1-((2-methyl-1H-imidazol-4-yl)methyl)piperidin-4-yl)-1H-indol-2-yl)-2-methyl-[1,2,4]triazolo [1,5-a]pyridine (532);

6-(3-isopropyl-5-(1-isopropylpiperidin-4-yl)-1H-indol-2-yl)-2-methyl-[1,2,4]triazolo[1,5-a]pyridine (533);

6-(3-isopropyl-5-(1-(oxetan-3-yl)piperidin-4-yl)-1H-indol-2-yl)-2-methyl-[1,2,4]triazolo [1,5-a]pyridine (534);

6-(3-isopropyl-5-(1-(tetrahydro-2H-pyran-4-yl)piperidin-4-yl)-1H-indol-2-yl)-2-methyl-[1,2,4]triazolo[1,5-a]pyridine (535);

6-(3-isopropyl-5-(1-(oxetan-3-yl)piperidin-4-yl)-1H-indol-2-yl)-2,8-dimethyl-[1,2,4]triazolo [1,5-a]pyridine (542);

6-(3-isopropyl-5-(1-(tetrahydro-2H-pyran-4-yl)piperidin-4-yl)-1H-indol-2-yl)-2,8-dimethyl-[1,2,4]triazolo[1,5-a]pyridine (543);

6-(5-(1-isobutylpiperidin-4-yl)-3-isopropyl-1H-indol-2-yl)-2,8-dimethyl-[1,2,4]triazolo[1,5-a]pyridine (544);

4-(4-(2-(2,8-dimethyl-[1,2,4]triazolo[1,5-a]pyridin-6-yl)-3-isopropyl-1H-indol-5-yl)piperidin-1-yl)tetrahydro-2H-thiopyran 1,1-dioxide (545);

6-(3-isopropyl-5-(1-(tetrahydro-2H-pyran-4-yl) piperidin-4-yl)-1H-indol-2-yl)-2,7-dimethyl-[1,2,4]triazolo[1,5-a]pyridine (546);

6-(3-isopropyl-5-(1-(oxetan-3-yl)piperidin-4-yl)-1H-indol-2-yl)-2,7-dimethyl-[1,2,4]triazolo[1,5-a]pyridine (547);

4-(4-(2-(2,7-dimethyl-[1,2,4]triazolo[1,5-a]pyridin-6-yl)-3-isopropyl-1H-indol-5-yl)piperidin-1-yl)tetrahydro-2H-thiopyran 1,1-dioxide (548);

6-(3-isopropyl-5-(1-(oxetan-3-yl)piperidin-4-yl)-1H-indol-2-yl)-2,5-dimethyl-[1,2,4]triazolo[1,5-a]pyridine (558);

6-(3-isopropyl-5-(1-isopropylpiperidin-4-yl)-1H-indol-2-yl)-2,5-dimethyl-[1,2,4]triazolo[1,5-a]pyridine (559);

6-(3-isopropyl-5-(1-((1-methyl-H-pyrazol-4-yl)methyl) piperidin-4-yl)-1H-indol-2-yl)-2,5-dimethyl-[1,2,4]triazolo[1,5-a]pyridine (560);

6-(3-isopropyl-5-(1-(oxetan-3-yl)piperidin-4-yl)-1H-indol-2-yl)-8-methoxy-2-methyl-[1,2,4]triazolo[1,5-a]pyridine (574);

6-(3-isopropyl-5-(1-(tetrahydrofuran-3-yl)piperidin-4-yl)-1H-indol-2-yl)-8-methoxy-2-m ethyl-[1,2,4]triazolo[1,5-a]pyridine (575-576);

8-ethyl-6-(3-isopropyl-5-(1-(tetrahydro-2H-pyran-4-yl)piperidin-4-yl)-1H-indol-2-yl)-2-methyl-[1,2,4]triazolo[1,5-a]pyridine (577);

8-ethyl-6-(3-isopropyl-5-(1-(oxetan-3-yl)piperidin-4-yl)-1H-indol-2-yl)-2-methyl-[1,2,4]triazolo[1,5-a]pyridine (578);

8-cyclopropyl-6-(3-isopropyl-5-(1-(oxetan-3-yl)piperidin-4-yl)-1H-indol-2-yl)-2-methyl-[1,2,4]triazolo[1,5-a]pyridine (594);

6-(3-isopropyl-5-(1-isopropylpiperidin-4-yl)-1H-indol-2-yl)-2,8-dimethyl-[1,2,4]triazolo [1,5-a]pyridine (599);

2-(dimethylamino)-1-(4-(3-isopropyl-2-(2-methyl-[1,2,4]triazolo[1,5-a]pyridin-6-yl)-1H-indol-5-yl)piperidin-1-yl)ethan-1-one (612);

(R)-3-hydroxy-1-(4-(3-isopropyl-2-(2-methyl-[1,2,4]triazolo[1,5-a]pyridin-6-yl)-1H-indol-5-yl)piperidin-1-yl) butan-1-one (613);

3-hydroxy-1-(4-(3-isopropyl-2-(2-methyl-[1,2,4]triazolo[1,5-a]pyridin-6-yl)-1H-indol-5-yl)piperidin-1-yl)-3-methylbutan-1-one (614);

((2S,3R)-3-hydroxypyrrolidin-2-yl)(4-(3-isopropyl-2-(2-methyl-[1,2,4]triazolo[1,5-a]pyridin-6-yl)-1H-indol-5-yl) piperidin-1-yl)methanone (615);

((2S,4R)-4-hydroxypyrrolidin-2-yl)(4-(3-isopropyl-2-(2-methyl-[1,2,4]triazolo[1,5-a]pyridin-6-yl)-1H-indol-5-yl) piperidin-1-yl)methanone (616);

(S)-3-hydroxy-1-(4-(3-isopropyl-2-(2-methyl-[1,2,4]triazolo[1,5-a]pyridin-6-yl)-1H-indo 1-5-yl) piperidin-1-yl) butan-1-one (617);

1-(4-(3-isopropyl-2-(2-methyl-[1,2,4]triazolo[1,5-a]pyridin-6-yl)-1H-indol-5-yl)piperidin-1-yl)-2-(methylamino) ethan-1-one (618);

1-(4-(2-(2,8-dimethyl-[1,2,4]triazolo[1,5-a]pyridin-6-yl)-3-isopropyl-1H-indol-5-yl)piperidin-1-yl)-2-(methylamino) ethan-1-one (629);

1-(4-(2-(2,8-dimethyl-[1,2,4]triazolo[1,5-a]pyridin-6-yl)-3-isopropyl-1H-indol-5-yl)piperidin-1-yl)-2-(dimethylamino)ethan-1-one (630);

(S)-1-(4-(2-(2,8-dimethyl-[1,2,4]triazolo[1,5-a]pyridin-6-yl)-3-isopropyl-1H-indol-5-yl) piperidin-1-yl)-3-hydroxybutan-1-one (631);

1-(4-(2-(2,8-dimethyl-[1,2,4]triazolo[1,5-a]pyridin-6-yl)-3-isopropyl-1H-indol-5-yl)piperidin-1-yl)-3-hydroxy-3-methylbutan-1-one (632);

(R)-1-(4-(2-(2,8-dimethyl-[1,2,4]triazolo[1,5-a]pyridin-6-yl)-3-isopropyl-1H-indol-5-yl) piperidin-1-yl)-3-hydroxybutan-1-one (633); tert-butyl (2S,3R)-2-(4-(2-(2,8-dimethyl-[1,2,4]triazolo[1,5-a]pyridin-6-yl)-3-isopropyl-1H-indol-5-yl)piperidine-1-carbonyl)-3-hydroxypyrrolidine-1-carboxylate (634);

(4-(2-(2,8-dimethyl-[1,2,4]triazolo[1,5-a]pyridin-6-yl)-3-isopropyl-1H-indol-5-yl)piperid in-1-yl)((2S,3R)-3-hydroxypyrrolidin-2-yl)methanone (635);

(4-(2-(2,8-dimethyl-[1,2,4]triazolo[1,5-a]pyridin-6-yl)-3-isopropyl-1H-indol-5-yl)piperid in-1-yl) ((2S,4R)-4-hydroxypyrrolidin-2-yl)methanone (636);

(S)-1-(4-(2-(2,7-dimethyl-[1,2,4]triazolo[1,5-a]pyridin-6-yl)-3-isopropyl-1H-indol-5-yl)piperidin-1-yl)-3-hydroxybutan-1-one (637);

1-(4-(2-(2,7-dimethyl-[1,2,4]triazolo[1,5-a]pyridin-6-yl)-3-isopropyl-1H-indol-5-yl) piperidin-1-yl)-2-(dimethylamino)ethan-1-one (638);

1-(4-(2-(2,7-dimethyl-[1,2,4]triazolo [1,5-a]pyridin-6-yl)-3-isopropyl-1H-indol-5-yl)piperidin-1-yl)-2-(methylamino) ethan-1-one (639);

1-(4-(3-(2,2-difluoroethyl)-2-(2-methyl-[1,2,4]triazolo[1,5-a]pyridin-6-yl)-1H-indol-5-yl)piperidin-1-yl)-2-(dimethylamino)ethan-1-one (656);

(R)-1-(4-(3-(2,2-difluoroethyl)-2-(2-methyl-[1,2,4]triazolo [1,5-a]pyridin-6-yl)-1H-indol-5-yl)piperidin-1-yl)-3-hydroxybutan-1-one (657);

1-(4-(3-(2,2-difluoroethyl)-2-(2-methyl-[1,2,4]triazolo[1,5-a]pyridin-6-yl)-1H-indol-5-yl)piperidin-1-yl)-3-hydroxy-3-methylbutan-1-one (658);

1-(4-(3-(2,2-difluoroethyl)-2-(2-methyl-[1,2,4]triazolo[1,5-a]pyridin-6-yl)-1H-indol-5-yl)piperidin-1-yl)-2-(methylamino)ethan-1-one (659);

1-(4-(2-(2,5-dimethyl-[1,2,4]triazolo[1,5-a]pyridin-6-yl)-3-isopropyl-1H-indol-5-yl)piperidin-1-yl)-2-(dimethylamino)ethan-1-one (660);

1-(4-(2-(2,5-dimethyl-[1,2,4]triazolo[1,5-a]pyridin-6-yl)-3-isopropyl-1H-indol-5-yl)piperidin-1-yl)-2-(methylamino) ethan-1-one (661);

1-(4-(2-(8-chloro-2-methyl-[1,2,4]triazolo[1,5-a]pyridin-6-yl)-3-isopropyl-1H-indol-5-yl)piperidin-1-yl)-2-(dimethylamino)ethan-1-one (662);

2-(dimethylamino)-1-(4-(3-isopropyl-2-(8-methoxy-2-methyl-[1,2,4]triazolo[1,5-a]pyridin-6-yl)-1H-indol-5-yl) piperidin-1-yl)ethan-1-one (682);

1-(4-(3-isopropyl-2-(8-methoxy-2-methyl-[1,2,4]triazolo[1,5-a]pyridin-6-yl)-1H-indol-5-yl)piperidin-1-yl)-2-(methylamino) ethan-1-one (683);

2-(dimethylamino)-1-(4-(2-(8-ethyl-2-methyl-[1,2,4]triazolo[1,5-a]pyridin-6-yl)-3-isopropyl-1H-indol-5-yl)piperidin-1-yl)ethan-1-one (687);

1-(4-(2-(8-ethyl-2-methyl-[1,2,4]triazolo[1,5-a]pyridin-6-yl)-3-isopropyl-1H-indol-5-yl) piperidin-1-yl)-2-(methylamino)ethan-1-one (688);

2-(dimethylamino)-1-(4-(3-isopropyl-2-(8-methyl-2-(trifluoromethyl)-[1,2,4]triazolo[1,5-a]pyridin-6-yl)-1H-indol-5-yl)piperidin-1-yl)ethan-1-one (692);

1-(4-(3-isopropyl-2-(8-methyl-2-(trifluoromethyl)-[1,2,4]triazolo[1,5-a]pyridin-6-yl)-1H-indol-5-yl)piperidin-1-yl)-2-(methylamino)ethan-1-one (693);

(4-(3-isopropyl-2-(8-methyl-2-(trifluoromethyl)-[1,2,4]triazolo[1,5-a]pyridin-6-yl)-1H-indol-5-yl)piperidin-1-yl)(1-methylpiperidin-4-yl)methanone (694);

2-(dimethylamino)-1-(4-(3-isopropyl-2-(8-methoxy-2-(trifluoromethyl)-[1,2,4]triazolo[1,5-a]pyridin-6-yl)-1H-indol-5-yl)piperidin-1-yl) ethan-1-one (695);

1-(4-(2-(8-cyclopropyl-2-methyl-[1,2,4]triazolo[1,5-a]pyridin-6-yl)-3-isopropyl-1H-indo 1-5-yl)piperidin-1-yl)-2-(dimethylamino)ethan-1-one (698);

1-(4-(3-(2,2-difluoroethyl)-2-(2,8-dimethyl-[1,2,4]triazolo [1,5-a]pyridin-6-yl)-1H-indol-5-yl)piperidin-1-yl)-2-(dimethylamino)ethan-1-one (708);

(S)-1-(4-(3-(2,2-difluoroethyl)-2-(2,8-dimethyl-[1,2,4]triazolo[1,5-a]pyridin-6-yl)-1H-indol-5-yl)piperidin-1-yl)-3-hydroxybutan-1-one (709);

1-(4-(3-(2,2-difluoroethyl)-2-(2,8-dimethyl-[1,2,4]triazolo [1,5-a]pyridin-6-yl)-1H-indol-5-yl)piperidin-1-yl)-3-hydroxy-3-methylbutan-1-one (710);

1-(4-(3-(2,2-difluoroethyl)-2-(2,8-dimethyl-[1,2,4]triazolo [1,5-a]pyridin-6-yl)-1H-indol-5-yl)piperidin-1-yl)-2-(methylamino)ethan-1-one (711);

2-(4-(2-(2,8-dimethyl-[1,2,4]triazolo[1,5-a]pyridin-6-yl)-3-isopropyl-1H-indol-5-yl)piperidin-1-yl)-1-(pyrrolidin-1-yl)ethan-1-one (851);

2-(4-(2-(2,8-dimethyl-[1,2,4]triazolo[1,5-a]pyridin-6-yl)-3-isopropyl-1H-indol-5-yl)piperidin-1-yl)-1-morpholino-ethan-1-one (852); and 2-(4-(2-(2,8-dimethyl-[1,2,4]triazolo[1,5-a]pyridin-6-yl)-3-isopropyl-1H-indol-5-yl)piperidin-1-yl)-1-(1,1-dioxido-thiomorpholino)ethan-1-one (853).

One embodiment provides a compound of Formula (I) or a salt thereof, wherein said compound has the structure of Formula (I-9):

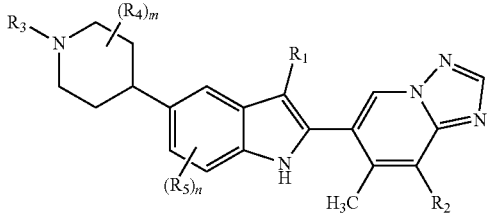

(I-9)

wherein $R_2$ is F, Cl, —$CH_2CH_3$, —$CF_3$, —$OCH_3$, —$CH_2OH$, —$CH_2OCH_3$, or cyclopropyl; and $R_1$, $R_3$, $R_4$, $R_5$, m, and n are defined in the first aspect or the second aspect. Included in this embodiment are compounds in which $R_1$ is —$CH(CH_3)_2$. Included in this embodiment are compounds in which $R_3$ is H, —$CH(CH_3)_2$, —$CH_2CH(CH_3)_2$, —$CH_2C(CH_3)_2OH$, —$CH_2C(O)NH(CH_3)$, —$CH_2C(O)N(CH_3)_2$, —$C(O)CH_2CH(CH_3)OH$, —$C(O)CH_2C(CH_3)_2OH$, —$C(O)CH_2NH(CH_3)$, —$C(O)CH_2N(CH_3)_2$, or -$L_1$-A; $L_1$ is —$CH_2$—, —$CH_2C(O)NHCH_2$—, or —$CH_2C(O)$—; and A is azetidinyl, dioxothiomorpholinyl, morpholinyl, oxetanyl, tetrahydropyranyl, or triazolyl, each substituted with -$L_2$-$R_a$; $L_2$ is a bond; $R_a$ is H or —$CH_3$. Also included in this embodiment are compounds in which $R_1$ is —$CH(CH_3)_2$; m is zero, and n is zero.

One embodiment provides a compound of Formula (I) or a salt thereof, wherein said compound is selected from tert-butyl 4-(2-(8-ethyl-7-methyl-[1,2,4]triazolo[1,5-a]pyridin-6-yl)-3-isopropyl-1H-indol-5-yl)piperidine-1-carboxylate (98);

6-(3-isopropyl-5-(piperidin-4-yl)-1H-indol-2-yl)-8-(methoxymethyl)-7-methyl-[1,2,4]triazolo[1,5-a]pyridine (101);

8-fluoro-6-(3-isopropyl-5-(piperidin-4-yl)-1H-indol-2-yl)-7-methyl-[1,2,4]triazolo[1,5-a]pyridine (102);

(6-(3-isopropyl-5-(piperidin-4-yl)-1H-indol-2-yl)-7-methyl-[1,2,4]triazolo [1,5-a]pyridin-8-yl)methanol (104);

8-fluoro-6-(3-isopropyl-5-(piperidin-4-yl)-1H-indol-2-yl)-7-methyl-[1,2,4]triazolo[1,5-a]pyridine (106);

8-fluoro-6-(3-isopropyl-5-(piperidin-4-yl)-1H-indol-2-yl)-7-methyl-[1,2,4]triazolo[1,5-a]pyridine (107);

8-chloro-6-(3-isopropyl-5-(piperidin-4-yl)-1H-indol-2-yl)-7-methyl-[1,2,4]triazolo[1,5-a]pyridine (119);

6-(3-isopropyl-5-(piperidin-4-yl)-1H-indol-2-yl)-8-methoxy-7-methyl-[1,2,4]triazolo[1,5-a] pyridine (140);

8-cyclopropyl-6-(3-isopropyl-5-(piperidin-4-yl)-1H-indol-2-yl)-7-methyl-[1,2,4]triazolo[1,5-a]pyridine (152);

2-(4-(3-isopropyl-2-(8-(methoxymethyl)-7-methyl-[1,2,4]triazolo[1,5-a]pyridin-6-yl)-1H-indol-5-yl)piperidin-1-yl)-N,N-dimethylacetamide (219);

2-(4-(2-(8-(hydroxymethyl)-7-methyl-[1,2,4]triazolo[1,5-a]pyridin-6-yl)-3-isopropyl-1H-indol-5-yl)piperidin-1-yl)-N,N-dimethylacetamide (226);

2-(4-(2-(8-(hydroxymethyl)-7-methyl-[1,2,4]triazolo[1,5-a]pyridin-6-yl)-3-isopropyl-1H-indol-5-yl)piperidin-1-yl) acetonitrile (227);

2-(4-(2-(8-chloro-7-methyl-[1,2,4]triazolo[1,5-a]pyridin-6-yl)-3-isopropyl-1H-indol-5-yl)piperidin-1-yl)-N,N-dimethylacetamide (286);

1-(4-(2-(8-chloro-7-methyl-[1,2,4]triazolo[1,5-a]pyridin-6-yl)-3-isopropyl-1H-indol-5-yl)piperidin-1-yl)-2-methyl-propan-2-ol (287);

2-(4-(2-(8-chloro-7-methyl-[1,2,4]triazolo[1,5-a]pyridin-6-yl)-3-isopropyl-1H-indol-5-yl)piperidin-1-yl)-N-methyl-acetamide (288);

2-(4-(2-(8-chloro-7-methyl-[1,2,4]triazolo[1,5-a]pyridin-6-yl)-3-isopropyl-1H-indol-5-yl)piperidin-1-yl)-N-methyl-acetamide (289);

8-chloro-6-(3-isopropyl-5-(1-(2-(methylsulfonyl)ethyl)piperidin-4-yl)-1H-indol-2-yl)-7-methyl-[1,2,4]triazolo[1,5-a]pyridine (290);

2-(4-(2-(8-ethyl-7-methyl-[1,2,4]triazolo[1,5-a]pyridin-6-yl)-3-isopropyl-1H-indol-5-yl) piperidin-1-yl)-N,N-dimethylacetamide (302);

2-(4-(3-isopropyl-2-(8-methoxy-7-methyl-[1,2,4]triazolo[1,5-a]pyridin-6-yl)-1H-indol-5-yl)piperidin-1-yl)-N-methylacetamide (303);

2-(4-(3-isopropyl-2-(8-methoxy-7-methyl-[1,2,4]triazolo[1,5-a]pyridin-6-yl)-1H-indol-5-yl)piperidin-1-yl)-N,N-dimethylacetamide (304);

1-(4-(3-isopropyl-2-(8-methoxy-7-methyl-[1,2,4]triazolo[1,5-a]pyridin-6-yl)-1H-indol-5-yl)piperidin-1-yl)-2-methylpropan-2-ol (305);

6-(3-isopropyl-5-(1-(2-(methylsulfonyl)ethyl)piperidin-4-yl)-1H-indol-2-yl)-8-methoxy-7-methyl-[1,2,4]triazolo[1,5-a]pyridine (306);

2-(4-(2-(8-cyclopropyl-7-methyl-[1,2,4]triazolo[1,5-a]pyridin-6-yl)-3-isopropyl-1H-indo 1-5-yl)piperidin-1-yl)-N-methylacetamide (326);

2-(4-(2-(8-cyclopropyl-7-methyl-[1,2,4]triazolo[1,5-a]pyridin-6-yl)-3-isopropyl-1H-indo 1-5-yl)piperidin-1-yl)-N,N-dimethylacetamide (327);

1-(4-(2-(8-cyclopropyl-7-methyl-[1,2,4]triazolo[1,5-a]pyridin-6-yl)-3-isopropyl-1H-indo 1-5-yl)piperidin-1-yl)-2-methylpropan-2-ol (328);

6-(3-isopropyl-5-(1-(oxetan-3-yl)piperidin-4-yl)-1H-indol-2-yl)-8-(methoxymethyl)-7-m ethyl-[1,2,4]triazolo[1,5-a]pyridine (499);

(6-(3-isopropyl-5-(1-(oxetan-3-yl)piperidin-4-yl)-1H-indol-2-yl)-7-methyl-[1,2,4]triazolo[1,5-a]pyridin-8-yl)methanol (504); (6-(5-(1-((1H-1,2,3-triazol-4-yl) methyl)piperidin-4-yl)-3-isopropyl-1H-indol-2-yl)-7-methyl-[1,2,4] triazolo[1,5-a]pyridin-8-yl)methanol (505);

8-fluoro-6-(3-isopropyl-5-(1-(oxetan-3-yl)piperidin-4-yl)-1H-indol-2-yl)-7-methyl-[1,2,4]triazolo[1,5-a]pyridine (507);

8-chloro-6-(3-isopropyl-5-(1-(tetrahydro-2H-pyran-4-yl)piperidin-4-yl)-1H-indol-2-yl)-7-methyl-[1,2,4]triazolo[1,5-a]pyridine (579);

8-chloro-6-(3-isopropyl-5-(1-(oxetan-3-yl)piperidin-4-yl)-1H-indol-2-yl)-7-methyl-[1,2,4]triazolo[1,5-a]pyridine (580);

8-ethyl-6-(3-isopropyl-5-(1-(oxetan-3-yl)piperidin-4-yl)-1H-indol-2-yl)-7-methyl-[1,2,4]triazolo[1,5-a]pyridine (587); 6-(3-isopropyl-5-(1-(oxetan-3-yl) piperidin-4-yl)-1H-indol-2-yl)-8-methoxy-7-methyl-[1,2,4]triazolo[1,5-a]pyridine (588);

6-(3-isopropyl-5-(1-((3-methyloxetan-3-yl)methyl)piperidin-4-yl)-1H-indol-2-yl)-8-methoxy-7-methyl-[1,2,4]triazolo[1,5-a]pyridine (589);

8-cyclopropyl-6-(3-isopropyl-5-(1-(oxetan-3-yl)piperidin-4-yl)-1H-indol-2-yl)-7-methyl-[1,2,4]triazolo[1,5-a]pyridine (595);

1-(4-(2-(8-chloro-7-methyl-[1,2,4]triazolo[1,5-a]pyridin-6-yl)-3-isopropyl-1H-indol-5-yl)piperidin-1-yl)-2-(dimethylamino)ethan-1-one (689);

1-(4-(2-(8-cyclopropyl-7-methyl-[1,2,4]triazolo [1,5-a]pyridin-6-yl)-3-isopropyl-1H-indol-5-yl)piperidin-1-yl)-2-(dimethylamino)ethan-1-one (699);

1-(4-(2-(8-cyclopropyl-7-methyl-[1,2,4]triazolo[1,5-a]pyridin-6-yl)-3-isopropyl-1H-indol-5-yl)piperidin-1-yl)-2-(methylamino)ethan-1-one (700);

2-(4-(3-isopropyl-2-(8-methoxy-7-methyl-[1,2,4]triazolo[1,5-a]pyridin-6-yl)-1H-indol-5-yl)piperidin-1-yl)-N-((3-methyloxetan-3-yl)methyl)acetamide (876);

2-(4-(3-isopropyl-2-(8-methoxy-7-methyl-[1,2,4]triazolo[1,5-a]pyridin-6-yl)-1H-indol-5-yl)piperidin-1-yl)-N-(3-methyloxetan-3-yl) acetamide (877);

1-(azetidin-1-yl)-2-(4-(3-isopropyl-2-(8-methoxy-7-methyl-[1,2,4]triazolo [1,5-a]pyridin-6-yl)-1H-indol-5-yl)piperidin-1-yl)ethan-1-one (878);

N-ethyl-2-(4-(3-isopropyl-2-(8-methoxy-7-methyl-[1,2,4]triazolo[1,5-a]pyridin-6-yl)-1H-indol-5-yl) piperidin-1-yl)-N-methylacetamide (879);

1-(1,1-dioxidothiomorpholino)-2-(4-(3-isopropyl-2-(8-methoxy-7-methyl-[1,2,4]triazolo [1,5-a]pyridin-6-yl)-1H-indol-5-yl)piperidin-1-yl) ethan-1-one (880); and 2-(4-(3-isopropyl-2-(8-methoxy-7-methyl-[1,2,4]triazolo[1,5-a]pyridin-6-yl)-1H-indol-5-yl)piperidin-1-yl)-1-morpholinoethan-1-one (881).

One embodiment provides a compound of Formula (I) or a salt thereof, wherein said compound has the structure of Formula (I-10):

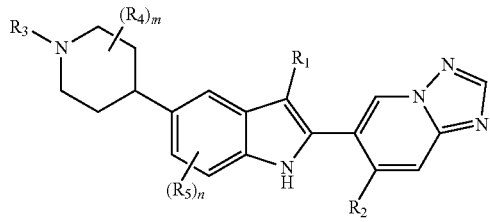

(I-10)

wherein $R_2$ is —$CH_3$, —$OCH_3$, or —$CH_2OH$; and $R_1$, $R_3$, $R_4$, $R_5$, m, and n are defined in the first aspect or the second aspect. Included in this embodiment are compounds in which $R_1$ is —$CH(CH_3)_2$. Included in this embodiment are compounds in which $R_3$ is H, —$CH_2CN$, —$CH_2C(O)NH_2$, —$CH_2C(O)N(CH_3)_2$, —$CH_2$(triazolyl), or oxetanyl. Also included in this embodiment are compounds in which $R_1$ is —$CH(CH_3)_2$; m is zero; and n is zero.

One embodiment provides a compound of Formula (I) or a salt thereof, wherein said compound is selected from (6-(3-isopropyl-5-(piperidin-4-yl)-1H-indol-2-yl)-[1,2,4]triazolo [1,5-a]pyridin-7-yl)methanol (108); 6-(3-isopropyl-5-(piperidin-4-yl)-1H-indol-2-yl)-7-methoxy-[1,2,4]triazolo[1,5-a]pyridine (131); 2-(4-(3-isopropyl-2-(7-methyl-[1,2,4]triazolo [1,5-a]pyridin-6-yl)-1H-indol-5-yl)piperidin-1-yl)acetamide (192); 2-(4-(2-(7-(hydroxymethyl)-[1,2,4]triazolo[1,5-a]pyridin-6-yl)-3-isopropyl-1H-indol-5-yl)piperidin-1-yl)acetonitrile (230); 2-(4-(3-isopropyl-2-(7-methoxy-[1,2,4]triazolo[1,5-a]pyridin-6-yl)-1H-indol-5-yl)piperid in-1-yl)-N,N-dimethylacetamide (267); (6-(3-isopropyl-5-(1-(oxetan-3-yl) piperidin-4-yl)-1H-indol-2-yl)-[1,2,4]triazolo[1,5-a]pyridin-7-yl)methanol (508); and (6-(3-isopropyl-5-(1-((1-methyl-1H-1,2,3-triazol-4-yl)methyl)piperidin-4-yl)-1H-indol-2-yl)-[1,2,4]triazolo[1,5-a]pyridin-7-yl) methanol (509).

One embodiment provides a compound of Formula (I) or a salt thereof, wherein said compound has the structure of Formula (I-11):

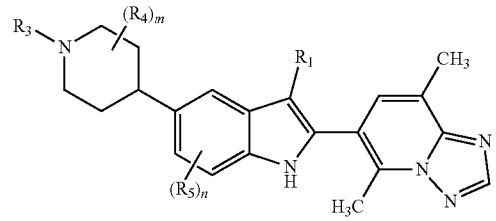

(I-11)

wherein $R_1$, $R_3$, $R_4$, $R_5$, m, and n are defined in the first aspect or the second aspect. Included in this embodiment are compounds in which $R_1$ is —$CH(CH_3)_2$. Included in this embodiment are compounds in which $R_3$ is —$CH_2CN$, —$CH_2C(O)N(CH_3)_2$, —$CH_2CH_2S(O)_2CH_3$, —$CH_2$(methyltriazolyl), —$C(O)CH_2N(CH_3)_2$, dioxotetrahydrothiopyranyl, oxetanyl, or tetrahydropyranyl. Also included in this embodiment are compounds in which $R_1$ is —$CH(CH_3)_2$; m is zero, and n is zero.

One embodiment provides a compound of Formula (I) or a salt thereof, wherein said compound is selected from 2-(4-(2-(5,8-dimethyl-[1,2,4]triazolo[1,5-a]pyridin-6-yl)-3-isopropyl-1H-indol-5-yl)piperidin-1-yl)-N,N-dimethylacetamide (207);

6-(3-isopropyl-5-(1-((1-methyl-1H-1,2,4-triazol-3-yl)methyl)piperidin-4-yl)-1H-indol-2-yl)-5,8-dimethyl-[1,2,4]triazolo[1,5-a]pyridine (208);

6-(3-isopropyl-5-(1-(2-(methylsulfonyl)ethyl)piperidin-4-yl)-1H-indol-2-yl)-5,8-dimethyl-[1,2,4]triazolo[1,5-a]pyridine (209);

2-(4-(2-(5,8-dimethyl-[1,2,4]triazolo[1,5-a]pyridin-6-yl)-3-isopropyl-1H-indol-5-yl)piperidin-1-yl)acetonitrile (210);

6-(3-isopropyl-5-(1-(oxetan-3-yl)piperidin-4-yl)-1H-indol-2-yl)-5,8-dimethyl-[1,2,4]triazolo[1,5-a]pyridine (487);

6-(3-isopropyl-5-(1-(tetrahydro-2H-pyran-4-yl)piperidin-4-yl)-1H-indol-2-yl)-5,8-dimethyl-[1,2,4]triazolo[1,5-a]pyridine (488);

4-(4-(2-(5,8-dimethyl-[1,2,4]triazolo[1,5-a]pyridin-6-yl)-3-isopropyl-1H-indol-5-yl)piperidin-1-yl)tetrahydro-2H-thiopyran 1,1-dioxide (489); and 1-(4-(2-(5,8-dimethyl-[1,2,4]triazolo[1,5-a]pyridin-6-yl)-3-isopropyl-1H-indol-5-yl)piperidin-1-yl)-2-(dimethylamino)ethan-1-one (611).

One embodiment provides a compound of Formula (I) or a salt thereof, wherein said compound is selected from 2-(6-(3-isopropyl-5-(piperidin-4-yl)-1H-indol-2-yl)-[1,2,4]triazolo[1,5-a]pyridin-8-yl)acetonitrile (105); and 6-(3-isopropyl-5-(piperidin-4-yl)-1H-indol-2-yl)-5-methyl-[1,2,4]triazolo[1,5-a]pyridine (123);

One embodiment provides a compound of Formula (I) or a salt thereof, wherein said compound is selected from 6-(3-isopropyl-5-(piperidin-4-yl)-1H-indol-2-yl)-[1,2,4]triazolo[1,5-a]pyridine (1);

6-(3-isopropyl-5-(piperidin-4-yl)-1H-indol-2-yl)-8-methyl-[1,2,4]triazolo[1,5-a]pyridine hydrochloride (2);
6-(3-isopropyl-5-(piperidin-4-yl)-1H-indol-2-yl)-7-methyl-[1,2,4]triazolo[1,5-a]pyridine (3);
6-(3-isopropyl-5-(piperidin-4-yl)-1H-indol-2-yl)-7,8-dimethyl-[1,2,4]triazolo[1,5-a]pyridine (4);
6-(3-isopropyl-5-(piperidin-4-yl)-1H-indol-2-yl)-8-methoxy-[1,2,4]triazolo[1,5-a]pyridine (5);
6-(3-isopropyl-5-(piperidin-4-yl)-1H-indol-2-yl)-8-(methoxymethyl)-[1,2,4]triazolo[1,5-a]pyridine (6);
2-(4-(3-isopropyl-2-(8-methyl-[1,2,4]triazolo[1,5-a]pyridin-6-yl)-1H-indol-5-yl)piperidin-1-yl)-N-methylacetamide (7); 2-(4-(3-isopropyl-2-(8-methyl-[1,2,4]triazolo[1,5-a]pyridin-6-yl)-1H-indol-5-yl)piperidin-1-yl) acetonitrile (8);
3-(4-(3-isopropyl-2-(8-methyl-[1,2,4]triazolo[1,5-a]pyridin-6-yl)-1H-indol-5-yl)piperidin-1-yl) propanenitrile (9); 6-(5-(1-butylpiperidin-4-yl)-3-isopropyl-1H-indol-2-yl)-8-methyl-[1,2,4]triazolo[1,5-a]pyridine (10); 2-(4-(3-isopropyl-2-(8-methyl-[1,2,4]triazolo[1,5-a]pyridin-6-yl)-1H-indol-5-yl)piperidin-1-yl)acetamide (11);
1-(4-(3-isopropyl-2-(8-methyl-[1,2,4]triazolo[1,5-a]pyridin-6-yl)-1H-indol-5-yl)piperidin-1-yl)-2-methylpropan-2-ol (12);
2-(4-(2-(7,8-dimethyl-[1,2,4]triazolo[1,5-a]pyridin-6-yl)-3-isopropyl-1H-indol-5-yl)piperidin-1-yl)acetonitrile (13); 3-(4-(2-(7,8-dimethyl-[1,2,4]triazolo[1,5-a]pyridin-6-yl)-3-isopropyl-1H-indol-5-yl)piperidin-1-yl)propanenitrile (14);
2-(4-(2-(7,8-dimethyl-[1,2,4]triazolo[1,5-a]pyridin-6-yl)-3-isopropyl-1H-indol-5-yl)piperidin-1-yl) acetamide (15);
2-(4-(2-(7,8-dimethyl-[1,2,4]triazolo[1,5-a]pyridin-6-yl)-3-isopropyl-1H-indol-5-yl)piperidin-1-yl)-N-methylacetamide (16); 1-(4-(2-(7,8-dimethyl-[1,2,4]triazolo [1,5-a]pyridin-6-yl)-3-isopropyl-1H-indol-5-yl)piperidin-1-yl)-2-methylpropan-2-ol (17);
6-(3-isopropyl-5-(1-(2-(methylsulfonyl)ethyl)piperidin-4-yl)-1H-indol-2-yl)-7,8-dimethyl-[1,2,4]triazolo[1,5-a]pyridine (18);
2-(4-(2-(7,8-dimethyl-[1,2,4]triazolo[1,5-a]pyridin-6-yl)-3-isopropyl-1H-indol-5-yl)piperidin-1-yl)ethane-1-sulfonamide (19);
4-(4-(2-(7,8-dimethyl-[1,2,4]triazolo[1,5-a]pyridin-6-yl)-3-isopropyl-1H-indol-5-yl) piperidin-1-yl)tetrahydro-2H-thiopyran 1,1-dioxide (20);
2-(4-(3-isopropyl-2-(8-methoxy-[1,2,4]triazolo[1,5-a]pyridin-6-yl)-1H-indol-5-yl)piperidin-1-yl) acetonitrile (21); 2-(4-(3-isopropyl-2-(8-methoxy-[1,2,4]triazolo[1,5-a]pyridin-6-yl)-1H-indol-5-yl) piperidin-1-yl)acetamide (22);
2-(4-(3-isopropyl-2-(8-methoxy-[1,2,4]triazolo[1,5-a]pyridin-6-yl)-1H-indol-5-yl)piperidin-1-yl)-N-methylacetamide (23); 1-(4-(3-isopropyl-2-(8-methoxy-[1,2,4]triazolo[1,5-a]pyridin-6-yl)-1H-indol-5-yl)piperidin-1-yl)-2-methylpropan-2-ol (24);
2-(4-(3-isopropyl-2-(8-methoxy-[1,2,4]triazolo[1,5-a]pyridin-6-yl)-1H-indol-5-yl)piperidin-1-yl)-N,N-dimethylacetamide (25);
6-(3-isopropyl-5-(1-(oxetan-3-yl)piperidin-4-yl)-1H-indol-2-yl)-8-methyl-[1,2,4]triazolo[1,5-a]pyridine (26);
6-(3-isopropyl-5-(1-isopropylpiperidin-4-yl)-1H-indol-2-yl)-8-methyl-[1,2,4]triazolo[1,5-a]pyridine (27);
6-(3-isopropyl-5-(1-propylpiperidin-4-yl)-1H-indol-2-yl)-8-methyl-[1,2,4]triazolo[1,5-a]pyridine (28);
6-(5-(1-isobutylpiperidin-4-yl)-3-isopropyl-1H-indol-2-yl)-8-methyl-[1,2,4]triazolo[1,5-a]pyridine (29); 6-(5-(1-((1H-pyrazol-5-yl)methyl) piperidin-4-yl)-3-isopropyl-1H-indol-2-yl)-8-methyl-[1,2,4]triazolo[1,5-a]pyridine (30);
4-((4-(3-isopropyl-2-(8-methyl-[1,2,4]triazolo[1,5-a]pyridin-6-yl)-1H-indol-5-yl) piperidin-1-yl)methyl)oxazole (31);
6-(5-(1-((1H-1,2,3-triazol-4-yl)methyl)piperidin-4-yl)-3-isopropyl-1H-indol-2-yl)-8-methyl-[1,2,4]triazolo[1,5-a]pyridine (32);
6-(5-(1-((4H-1,2,4-triazol-3-yl)methyl)piperidin-4-yl)-3-isopropyl-1H-indol-2-yl)-8-methyl-[1,2,4]triazolo[1,5-a]pyridine (33);
6-(5-(1-((1H-tetrazol-5-yl)methyl)piperidin-4-yl)-3-isopropyl-1H-indol-2-yl)-8-methyl-[1,2,4]triazolo[1,5-a]pyridine (34);
6-(3-isopropyl-5-(1-(tetrahydro-2H-pyran-4-yl)piperidin-4-yl)-1H-indol-2-yl)-8-methyl-[1,2,4]triazolo[1,5-a]pyridine (35);
2-(4-(3-isopropyl-2-(8-methyl-[1,2,4]triazolo[1,5-a]pyridin-6-yl)-1H-indol-5-yl)piperidin-1-yl)-N,N-dimethylacetamide (36);
4-(4-(3-isopropyl-2-(8-methyl-[1,2,4]triazolo[1,5-a]pyridin-6-yl)-1H-indol-5-yl)piperidin-1-yl)tetrahydro-2H-thiopyran 1,1-dioxide (37);
6-(3-isopropyl-5-(1-(oxetan-3-yl)piperidin-4-yl)-1H-indol-2-yl)-7,8-dimethyl-[1,2,4]triazolo[1,5-a]pyridine (38);
6-(5-(1-((1H-1,2,3-triazol-5-yl)methyl)piperidin-4-yl)-3-isopropyl-1H-indol-2-yl)-7,8-di methyl-[1,2,4]triazolo[1,5-a]pyridine (39);
6-(3-isopropyl-5-(1-(tetrahydro-2H-pyran-4-yl) piperidin-4-yl)-1H-indol-2-yl)-7,8-dimethyl-[1,2,4]triazolo[1,5-a]pyridine (40);
2-(4-(2-(7,8-dimethyl-[1,2,4]triazolo[1,5-a]pyridin-6-yl)-3-isopropyl-1H-indol-5-yl)piperidin-1-yl)-N,N-dimethylacetamide (41); 6-(3-isopropyl-5-(1-((1-methyl-H-1,2,3-triazol-4-yl)methyl) piperidin-4-yl)-1H-indol-2-yl)-7,8-dimethyl-[1,2,4]triazolo[1,5-a]pyridine (42);
6-(3-isopropyl-5-(1-((1-methyl-1H-1,2,4-triazol-3-yl) methyl)piperidin-4-yl)-1H-indol-2-yl)-7,8-dimethyl-[1,2,4]triazolo[1,5-a]pyridine (43); 6-(3-isopropyl-5-(1-(oxetan-3-yl) piperidin-4-yl)-1H-indol-2-yl)-8-methoxy-[1,2,4]triazolo[1,5-a]pyridine (44);
6-(3-isopropyl-5-(1-(tetrahydro-2H-pyran-4-yl)piperidin-4-yl)-1H-indol-2-yl)-8-methoxy-[1,2,4]triazolo[1,5-a]pyridine (45);
2-(dimethylamino)-1-(4-(3-isopropyl-2-(8-methyl-[1,2,4]triazolo[1,5-a]pyridin-6-yl)-1H-indol-5-yl)piperidin-1-yl) ethan-1-one (46);
1-(4-(2-([1,2,4]triazolo[1,5-a]pyridin-6-yl)-3-isopropyl-1H-indol-5-yl) piperidin-1-yl)-2-(methylamino)ethan-1-one (47); 1-(4-(3-isopropyl-2-(8-methyl-[1,2,4]triazolo[1,5-a]pyridin-6-yl)-1H-indol-5-yl)piperidin-1-yl)ethan-1-one (48);
3-(4-(3-isopropyl-2-(7-methyl-[1,2,4]triazolo[1,5-a]pyridin-6-yl)-1H-indol-5-yl)piperidin-1-yl)-3-oxopropanenitrile (49); 1-(4-(3-isopropyl-2-(8-methyl-[1,2,4]triazolo[1,5-a]pyridin-6-yl)-1H-indol-5-yl)piperidin-1-yl)-2-(methylamino)ethan-1-one (50); 1-(4-(2-([1,2,4]triazolo[1,5-a]pyridin-6-yl)-3-isopropyl-1H-indol-5-yl)piperidin-1-yl)-2-(dimethylamino)ethan-1-one (51); 1-(4-(3-isopropyl-2-(8-methyl-[1,2,4]triazolo[1,5-a]pyridin-6-yl)-1H-indol-5-yl)piperidin-1-yl)-2-methoxyethan-1-one (52);
(S)-1-(4-(2-([1,2,4]triazolo[1,5-a]pyridin-6-yl)-3-isopropyl-1H-indol-5-yl)piperidin-1-yl)-3-hydroxybutan-1-one (53);

4-(4-(3-isopropyl-2-(8-methyl-[1,2,4]triazolo[1,5-a]pyridin-6-yl)-1H-indol-5-yl) piperidin-1-yl)-4-oxobutanenitrile (54);

(4-(3-isopropyl-2-(8-methyl-[1,2,4]triazolo[1,5-a]pyridin-6-yl)-1H-indol-5-yl)piperidin-1-yl)(1-methylcyclopropyl)methanone (55);

(S)-azetidin-2-yl(4-(3-isopropyl-2-(8-methyl-[1,2,4]triazolo[1,5-a]pyridin-6-yl)-1H-indol-5-yl) piperidin-1-yl)methanone (56);

2-(dimethylamino)-1-(4-(3-isopropyl-2-(8-methyl-[1,2,4]triazolo[1,5-a]pyridin-6-yl)-1H-indol-5-yl)piperidin-1-yl)ethan-1-one (57);

(S)-1-(4-(3-isopropyl-2-(8-methyl-[1,2,4]triazolo[1,5-a]pyridin-6-yl)-1H-indol-5-yl)piperidin-1-yl)-2-(methylamino)propan-1-one (58);

(R)-1-(4-(3-isopropyl-2-(8-methyl-[1,2,4]triazolo[1,5-a]pyridin-6-yl)-1H-indol-5-yl)piperidin-1-yl)-2-(methylamino)propan-1-one (59);

(S)-3-hydroxy-1-(4-(3-isopropyl-2-(8-methyl-[1,2,4]triazolo[1,5-a]pyridin-6-yl)-1H-indo 1-5-yl) piperidin-1-yl) butan-1-one (60);

1-(4-(3-isopropyl-2-(8-methyl-[1,2,4]triazolo[1,5-a]pyridin-6-yl)-1H-indol-5-yl)piperidin-1-yl)-3-methoxypropan-1-one (61);

1-(4-(3-isopropyl-2-(8-methoxy-[1,2,4]triazolo[1,5-a]pyridin-6-yl)-1H-indol-5-yl)piperid in-1-yl)-2-(methylamino)ethan-1-one (62);

1-(4-(3-isopropyl-2-(8-methoxy-[1,2,4]triazolo[1,5-a]pyridin-6-yl)-1H-indol-5-yl)piperidin-1-yl)-2-methoxyethan-1-one (63);

(4-(3-isopropyl-2-(8-methyl-[1,2,4]triazolo[1,5-a]pyridin-6-yl)-1H-indol-5-yl)piperidin-1-yl)(3-methyloxetan-3-yl)methano ne (64);

2-ethyl-1-(4-(3-isopropyl-2-(8-methyl-[1,2,4]triazolo[1,5-a]pyridin-6-yl)-1H-indol-5-yl) piperidin-1-yl)butan-1-one (65);

1-(4-(2-(7,8-dimethyl-[1,2,4]triazolo[1,5-a]pyridin-6-yl)-3-isopropyl-1H-indol-5-yl)piperidin-1-yl)-2-(dimethylamino)ethan-1-one (66);

2-(dimethylamino)-1-(4-(3-isopropyl-2-(8-methoxy-[1,2,4]triazolo[1,5-a]pyridin-6-yl)-1H-indol-5-yl)piperidin-1-yl)ethan-1-one (67);

1-(4-(3-isopropyl-2-(8-methyl-[1,2,4]triazolo[1,5-a]pyridin-6-yl)-1H-indol-5-yl)piperidin-1-yl)-2-morpholinoethan-1-one (68);

2-(tert-butylamino)-1-(4-(3-isopropyl-2-(8-methyl-[1,2,4]triazolo[1,5-a]pyridin-6-yl)-1H-indol-5-yl)piperidin-1-yl)ethan-1-one (69);

1-(4-(3-isopropyl-2-(8-methyl-[1,2,4]triazolo[1,5-a]pyridin-6-yl)-1H-indol-5-yl)piperidin-1-yl)-2-(isopropylamino)ethan-1-one (70); 1-(4-(3-isopropyl-2-(8-methyl-[1,2,4]triazolo[1,5-a]pyridin-6-yl)-1H-indol-5-yl)piperidin-1-yl)-2-((2-methoxyethyl)amino)ethan-1-one (71);

1-(4-(3-isopropyl-2-(8-methyl-[1,2,4]triazolo[1,5-a]pyridin-6-yl)-1H-indol-5-yl)piperidin-1-yl)-2-(propylamino)ethan-1-one (72); 2-(isopropyl(methyl)amino)-1-(4-(3-isopropyl-2-(8-methyl-[1,2,4]triazolo[1,5-a]pyridin-6-yl)-1H-indol-5-yl)piperidin-1-yl) ethan-1-one (73);

1-(1,1-dioxido-1,2,4-thiadiazinan-4-yl)-2-(4-(3-isopropyl-2-(8-methyl-[1,2,4]triazolo[1,5-a]pyridin-6-yl)-1H-indol-5-yl)piperidin-1-yl)ethan-1-one (74); N-cyclopropyl-2-(4-(3-isopropyl-2-(8-methyl-[1,2,4]triazolo[1,5-a]pyridin-6-yl)-1H-indol-5-yl)piperidin-1-yl)acetamide (75); N-ethyl-2-(4-(3-isopropyl-2-(8-methyl-[1,2,4]triazolo[1,5-a]pyridin-6-yl)-1H-indol-5-yl)piperidin-1-yl)-N-methylacetamide (76);

(S)-1-(3-hydroxypiperidin-1-yl)-2-(4-(3-isopropyl-2-(8-methyl-[1,2,4]triazolo[1,5-a]pyridin-6-yl)-1H-indol-5-yl)piperidin-1-yl)ethan-1-one (77);

N-cyclobutyl-2-(4-(3-isopropyl-2-(8-methyl-[1,2,4]triazolo[1,5-a]pyridin-6-yl)-1H-indol-5-yl)piperidin-1-yl)acetamide (78);

2-(4-(3-isopropyl-2-(8-methyl-[1,2,4]triazolo[1,5-a]pyridin-6-yl)-1H-indol-5-yl) piperidin-1-yl)-1-(2-oxa-6-azaspiro[3.3]heptan-6-yl)ethan-1-one (79);

N,N-diethyl-2-(4-(3-isopropyl-2-(8-methyl-[1,2,4]triazolo[1,5-a]pyridin-6-yl)-1H-indol-5-yl)piperidin-1-yl)acetamide (80);

2-(4-(3-isopropyl-2-(8-methyl-[1,2,4]triazolo[1,5-a]pyridin-6-yl)-1H-indol-5-yl)piperidin-1-yl)-N-propylacetamide (81);

(R)-1-(3-hydroxypiperidin-1-yl)-2-(4-(3-isopropyl-2-(8-methyl-[1,2,4]triazolo[1,5-a]pyridin-6-yl)-1H-indol-5-yl) piperidin-1-yl)ethan-1-one (82);

(S)-1-(3-hydroxypyrrolidin-1-yl)-2-(4-(3-isopropyl-2-(8-methyl-[1,2,4]triazolo[1,5-a]pyridin-6-yl)-1H-indol-5-yl) piperidin-1-yl)ethan-1-one (83);

(R)-1-(3-hydroxypyrrolidin-1-yl)-2-(4-(3-isopropyl-2-(8-methyl-[1,2,4]triazolo[1,5-a]pyridin-6-yl)-1H-indol-5-yl) piperidin-1-yl)ethan-1-one (84);

2-(4-(3-isopropyl-2-(8-methyl-[1,2,4]triazolo[1,5-a]pyridin-6-yl)-1H-indol-5-yl) piperidin-1-yl)-1-(4-(2-methoxyethyl) piperazin-1-yl)ethan-1-one (85);

1-(azetidin-1-yl)-2-(4-(3-isopropyl-2-(8-methyl-[1,2,4]triazolo[1,5-a]pyridin-6-yl)-1H-indol-5-yl)piperidin-1-yl) ethan-1-one (86);

N-isopropyl-2-(4-(3-isopropyl-2-(8-methyl-[1,2,4]triazolo[1,5-a]pyridin-6-yl)-1H-indol-5-yl) piperidin-1-yl)acetamide (87);

2-(4-(3-isopropyl-2-(8-methyl-[1,2,4]triazolo[1,5-a]pyridin-6-yl)-1H-indol-5-yl)piperidin-1-yl)-1-morpholinoethan-1-one (88);

2-(4-(3-isopropyl-2-(8-methyl-[1,2,4]triazolo[1,5-a]pyridin-6-yl)-1H-indol-5-yl) piperidin-1-yl)-1-(piperidin-1-yl)ethan-1-one (89); 2-(4-(3-isopropyl-2-(8-methyl-[1,2,4]triazolo[1,5-a]pyridin-6-yl)-1H-indol-5-yl)piperidin-1-yl)-1-(pyrrolidin-1-yl)ethan-1-one (90);

1-(1,1-dioxidothiomorpholino)-2-(4-(3-isopropyl-2-(8-methyl-[1,2,4]triazolo[1,5-a]pyridin-6-yl)-1H-indol-5-yl) piperidin-1-yl)ethan-1-one (91); 2-(4-(3-isopropyl-2-(8-methyl-[1,2,4]triazolo[1,5-a]pyridin-6-yl)-1H-indol-5-yl) piperidin-1-yl)-N-(3-methyloxetan-3-yl) acetamide (92); and N-cyclopropyl-2-(4-(3-isopropyl-2-(8-methyl-[1,2,4]triazolo[1,5-a]pyridin-6-yl)-1H-indol-5-yl)piperidin-1-yl)-N-methylacetamide (93).

One embodiment provides a compound of Formula (I) or a salt thereof, wherein $R_1$ is —CH(CH$_3$)$_2$; each $R_2$ is independently —CH$_3$ or —OCH$_3$; $R_3$ is —(CR$_x$R$_x$)$_{1-2}$C(O)NR$_y$R$_y$; m is zero, n is zero, p is 1 or 2; each $R_x$ is independently H or —CH$_3$; and each $R_y$ is independently H or —CH$_3$. Included in this embodiment are compounds in which $R_3$ is —CH$_2$C(O)NR$_y$R$_y$. Also included in this embodiment are compounds having the structure of Formula (I-4b) or Formula (I-6b) in which each $R_y$ is H or —CH$_3$:

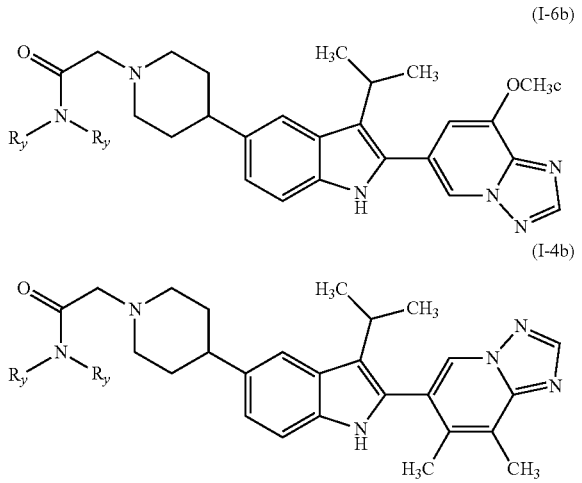

(I-6b)

(I-4b)

Additionally, included in this embodiment are compounds in which R₃ is —CH₂C(O)NH₂ or —CH₂C(O)N(CH₃)₂.

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH₂.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF₃ and —CH₂CF₃.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of fluoroalkyl groups include, but are not limited to, —CCl₃ and —CH₂CCl₃.

The term "cyanoalkyl" includes both branched and straight-chain saturated alkyl groups substituted with one or more cyano groups. For example, "cyanoalkyl" includes —CH₂CN, —CH₂CH₂CN, and $C_{1-4}$ cyanoalkyl.

The term "aminoalkyl" includes both branched and straight-chain saturated alkyl groups substituted with one or more amine groups. For example, "aminoalkyl" includes —CH₂NH₂, —CH₂CH₂NH₂, and $C_{1-4}$ aminoalkyl.

The term "hydroxyalkyl" includes both branched and straight-chain saturated alkyl groups substituted with one or more hydroxyl groups. For example, "hydroxyalkyl" includes —CH₂OH, —CH₂CH₂OH, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and C$_{1-4}$ hydroxyfluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_3$-C$_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "C$_{1-4}$ fluoroalkoxy" is intended to include C$_1$, C$_2$, C$_3$, and C$_4$ fluoroalkoxy groups.

The term "alkoxyalkoxy," as used herein, refers to an alkoxy group attached through its oxygen atom to a carbon atom in a second alkoxy group, which is attached to the parent molecular moiety through an oxygen atom, for example, methoxymethoxy group (—OCH$_2$OCH$_3$). For example, "C$_{2-4}$ alkoxyalkoxy" denotes alkoxyalkoxy groups with two to four carbon atoms, such as —OCH$_2$OCH$_3$, —OCH$_2$CH$_2$OCH$_3$, —OCH$_2$OCH$_2$CH$_3$, and —OCH$_2$CH$_2$OCH$_2$CH$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic 3-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PRO-GRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPA-MUNE®) or derivatives thereof.

The above other therapeutic agents, when employed in combination with the compounds of the present invention, may be used, for example, in those amounts indicated in the *Physicians'Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one nontoxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof, and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, compounds of Formula (I) can be produced, starting with the substituted 5-bromoindoles (2). 2 can be prepared from the 3-formyl indoles (via reduction) or from the 3-H indoles, via alkylation. Transition metal catalyzed cross coupling of 2 and boronate 3 followed by olefin reduction and Boc deprotection affords 4, which can then be coupled with pyridyl boronic acids and deprotected to give 6. Alkylation of 6 leads to the production of the compounds of Formula I.

SCHEME 1

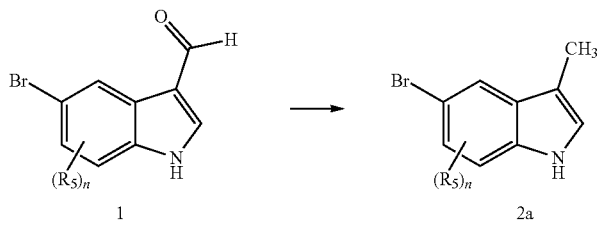

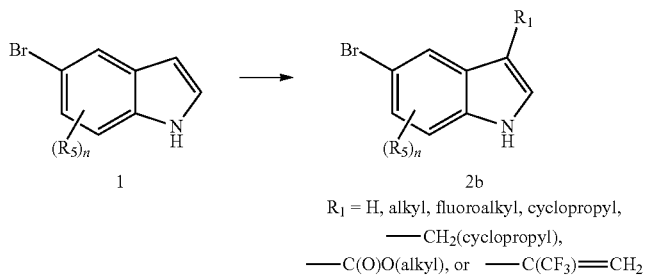

$R_1$ = H, alkyl, fluoroalkyl, cyclopropyl,
—$CH_2$(cyclopropyl),
—C(O)O(alkyl), or —C($CF_3$)=$CH_2$

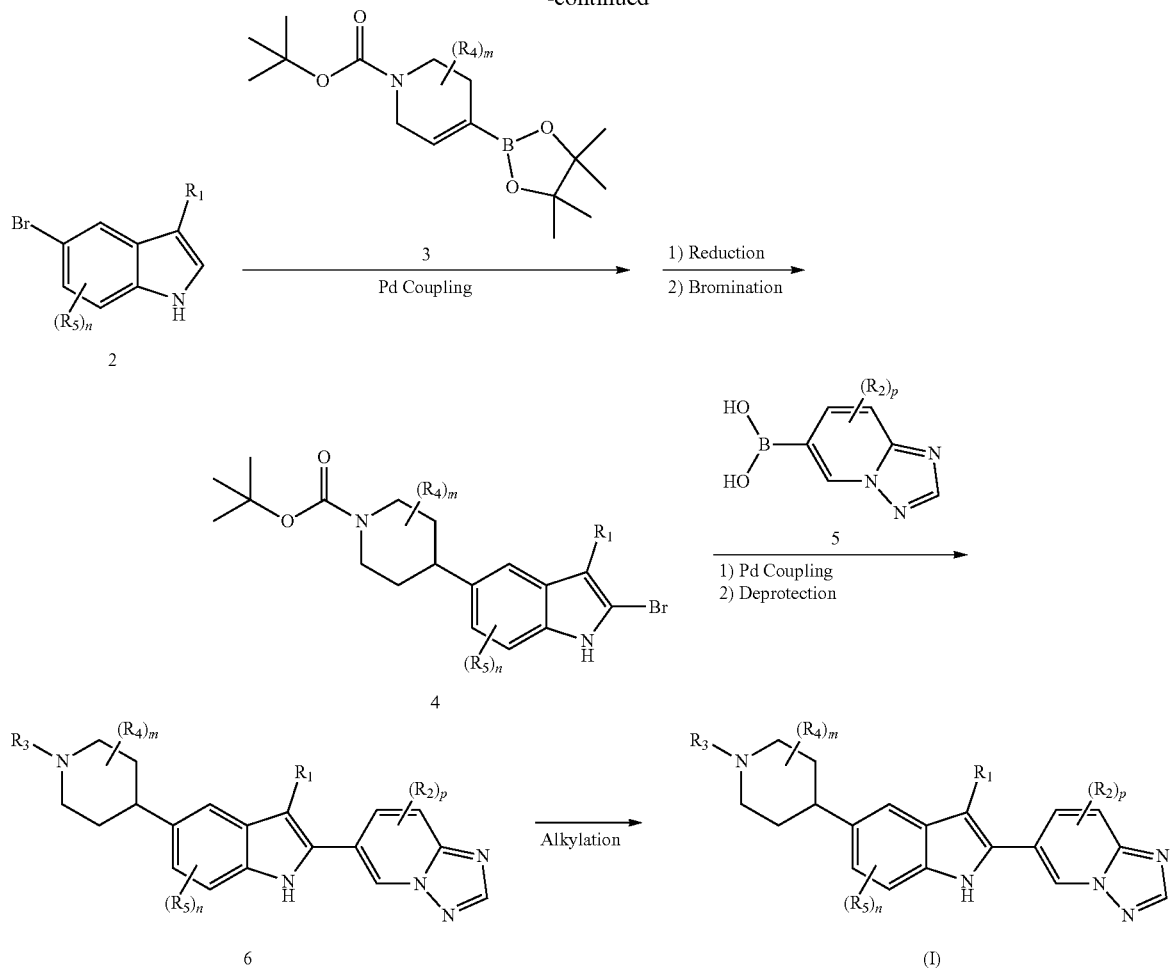
In an alternative preparation, bromoindole 2b can first be coupled with boronate 3 and reduced. Chlorination proceeds selectively on the 3-position, with bromination then providing the di-halogenated compound 7.
Scheme 2
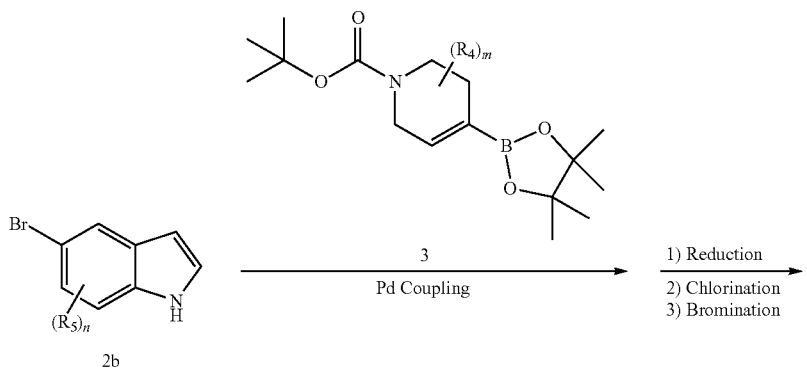

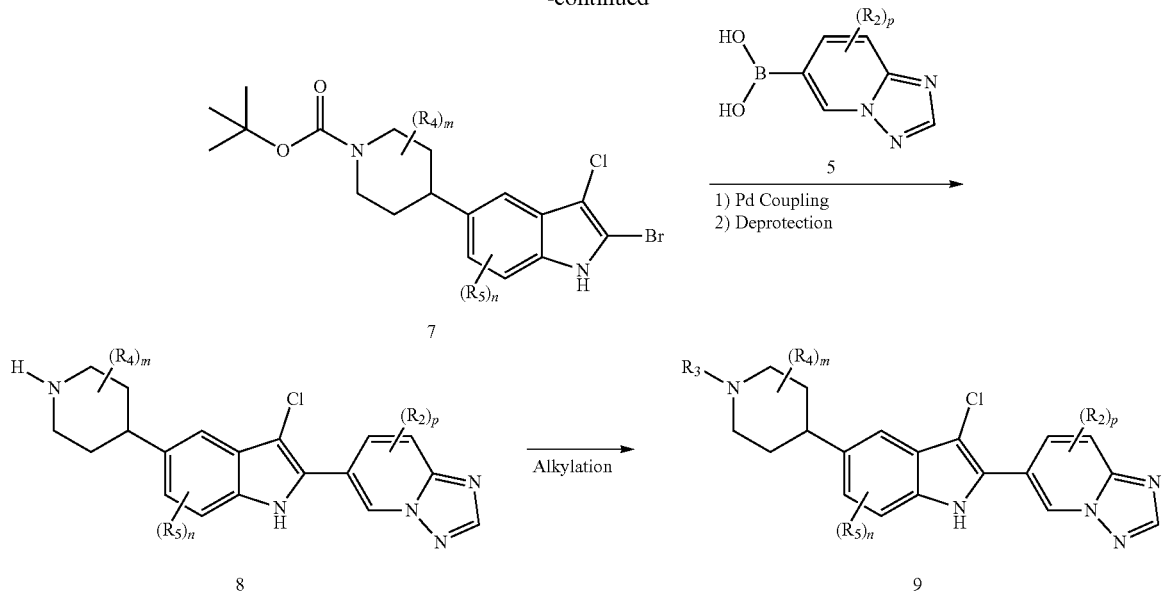

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
AcOH acetic acid
ACN acetonitrile
AIBN 2,2-azobisisobutyronitrile
anhyd. anhydrous
aq. aqueous
$BH_3DMS$ boron dimethylsulfide
Bn benzyl
Bu butyl
Boc tert-butoxycarbonyl
CV Column Volumes
DBU 1,8-diazabicyclo[5.4.0]undec-7-ene
DCE dichloroethane
DCM dichloromethane
DEA diethylamine
DIPEA diisopropylethylamine
DMF dimethylformamide
DMAP dimethylaminopyridine
DMF-DMA N,N-dimethylformamide dimethyl acetal
DMSO dimethylsulfoxide
$Et_3N$ triethylamine
EtOAc ethyl acetate
Et ethyl
EtOH ethanol
$Et_2O$ diethyl ether
H or $H_2$ hydrogen
h, hr or hrs hour(s)
HATU O-(7-azabenzotriazol-1-yl)-N,N,N',N'-tetramethyluronium hexafluorophosphate
hex hexane
i iso
IPA isopropyl alcohol
HOAc acetic acid
HCl hydrochloric acid
HPLC high pressure liquid chromatography
LAH lithium aluminum hydride
LC liquid chromatography
LCMS Liquid Chromatograph-Mass Spectroscopy
M molar
mM millimolar
Me methyl
MeOH methanol
MHz megahertz
min. minute(s)
mins minute(s)
$M^{+1}$ $(M+H)^+$
MOM-Cl chloromethyl methyl ether
MS mass spectrometry
n or N normal
NBS n-bromosuccinimide
NIS N-iodosuccinimide
nm nanometer
nM nanomolar
NMP N-methylpyrrolidine
Pd/C palladium on carbon
$PdCl_2(dppf)$ [1,1'-bis(diphenylphosphino)ferrocene]dichloropalladium(II)
$Pd_2(dba)_3$ tris-(dibenzylideneacetone)dipalladium
$Pd(OAc)_2$ palladium acetate
Pet ether petroleum ether
Ph phenyl
Ret Time retention time
sat. saturated
TEA triethylamine
TFA trifluoroacetic acid THF tetrahydrofuran
TsCl 4-toluenesulfonyl chloride
2nd Generation Xphos Precatalyst: (Chloro(2-dicyclohexylphosphino-2',4',6'-triisopropyl-1,1'-biphenyl)[2-(2'-amino-1,1'-bi phenyl)]palladium(II)

Analytical and Preparative HPLC Conditions:

Method QC-ACN-AA-XB: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC Method:

Method QC-ACN-TFA-XB: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) BEH C18, 2.1×50 mm, 1.7 µm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 254 nm; Detector 2: MS (ESI+).

Method B1: L2 Aquity(4); Column: (LCMS) BEH C18, 2.1×50 mm, 1.7 µm particles; Mobile Phase: (A) water; (B) acetonitrile; Buffer: 0.05% TFA; Gradient Range: 2%-98% B (0 to 1 min) 98% B (to 1.5 min) 98%-2% B (to 1.5 min); Gradient Time: 1.8 min; Flow Rate: 0.8 mL/min; Analysis Time: 2.2 min; Detection: Detector 1: UV at 254 nm; Detector 2: MS (ESI+).

Method C1 SCP: Column: Waters Acquity UPLC BEH C18, 2.1×50 mm, 1.7 m particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75-minute hold at 100% B; Flow: 1.11 mL/min; Detection: UV at 220 nm.

Method D1 SCP: Column: Waters Acquity UPLC BEH C18, 2.1×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method E1 iPAC: Column: Waters Xbridge C18 4.6×50 mm 5 µm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm. Method F1 iPAC: Column: Waters Acquity BEH C18 2.1×50 mm 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.

(A): Column-Ascentis Express C18 (50×2.1 mm 2.7 µm) Mphase A: 10 mM NH$_4$COOH in water:ACN (98:02); Mphase B: 10 mM NH$_4$COOH in water:ACN (02:98), Gradient: 0-100% B over 3 minutes, Flow=1 mL/min.

(B): Waters Acquity BEH C18 (2.1×50 mm) 1.7 µm; Buffer: 5 mM ammonium acetate pH 5 adjusted with HCOOH, Solvent A:Buffer:ACN (95:5), Solvent B:Buffer:ACN (5:95), Method:% B: 0 min-5%: 1.1 min-95%: 1.7 min-95%, Flow: 0.8 mL/min.

(C): Column-Ascentis Express C18 (50×2.1 mm 2.7 µm) Mobile phase A: 0.1% HCOOH in water; Mobile phase B: ACN. Temperature: 50° C.; Gradient: 0-100% B over 3 minutes; Flow rate: 1.0 mL/min.

(D): Kinetex XB-C18 (75×3 mm) 2.6 µm; Solvent A: 10 mM ammonium formate in water:acetonitrile (98:02); Mobile Phase B: 10 mM ammonium formate in water:acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 µm; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 minutes; Flow: 1.1 mL/min.

(F): Column: Ascentis Express C18(50×2.1) mm, 2.7 µm; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min.

(G): Column: Waters Acquity UPLC BEH C18 (2.1×50 mm), 1.7 µm; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.

(H): Column: Acentis Express C18 (50×2.1 mm) 1.7 µm, Acentis C8 NH$_4$COOH 5 min. M, Mobile Phase A: −10 mM ammonium formate:ACN (98:2), Mobile Phase B: −10 mM ammonium formate:ACN (2:98), Flow: 1 mL/min.

(I) Column: Sunfire C18 (4.6×150) mm, 3.5 µm; Mobile Phase A: 5:95 acetonitrile:water with 0.05% TFA; Mobile Phase B: 95:5 acetonitrile:water with 0.05% TFA; Temperature: 50° C.; Gradient: 10-100% B over 12 minutes; Flow: 1 mL/min.

(J) Column: Sunfire C18 (4.6×150) mm, 3.5 µm; Mobile Phase A: 5:95 acetonitrile:water with 0.05% TFA; Mobile Phase B: 95:5 acetonitrile:water with 0.05% TFA; Temperature: 50° C.; Gradient: 10-100% B over 25 minutes; Flow: 1 mL/min.

(K): Column: Acquity UPLC BEH C18, 3.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Method: % B: 0 min-20%: 1.1 min-90%: 1.7 min-90%; Flow: 0.7 mL/min.

(L): Column: Kinetex XB-C18 (75×3 mm-2.6 µm), Mobile Phase A: 10 mM ammonium formate:ACN (98:2), Mobile Phase B: 10 mM ammonium formate:ACN (2:98), Flow: 1 mL/min.

(M): Column: Acquity BEH C18 (3.0×50 mm) 1.7 µm, Mobile phase A: 0.1% TFA in water: Mobile phase B: 0.1% TFA in ACN,% B: 0 min-20%: 1.0 min-90%: 1.6 min 90%, Flow: 0.7 mL/min.

(N) Column: XBridge BEH XP C18 (50×2.1) mm, 2.5 µm; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, Flow: 1.1 mL/min; Detection: UV at 220 nm.

INTERMEDIATES

Intermediate T-1: Tert-butyl 4-(2-bromo-3-isopropyl-1H-indol-5-yl)piperidine-1-carboxylate

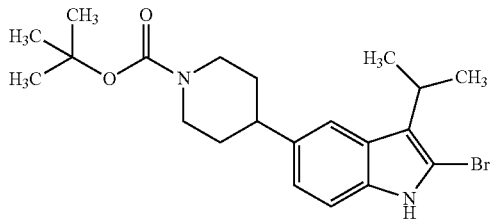
(T-1)

Intermediate T-1A: 5-bromo-3-isopropyl-1H-indole

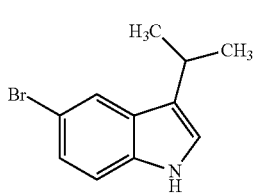
(T-1A)

A 250 mL round bottom flask was charged with triethylsilane (8.90 g, 77 mmol), trichloroacetic acid (6.25 g, 38.3 mmol) and toluene (50 mL). The solution was heated to 70° C., then a solution of 5-bromo-1H-indole (5.0 g, 25.5 mmol) and acetone (2.247 mL, 30.6 mmol) in toluene (30 mL) was added drop wise via an addition funnel. The resulting brown solution was heated at 70° C. for 1.5 h. The solution was cooled to 10° C., quenched with 10% sodium bicarbonate and diluted with diethyl ether. The organic layer was separated, dried and concentrated under vacuum to afford crude compound. The crude compound was purified using silica gel chromatography eluting with 5% ethyl acetate in hexanes to afford 5-bromo-3-isopropyl-1H-indole (5.5 g, 23.10 mmol 95% yield) as an oil. LC retention time 1.42 min [D]. MS (E−) m/z: 238.2 (M+H).

Intermediate T-1B: Tert-butyl 4-(3-isopropyl-1H-indol-5-yl)-5,6-dihydropyridine-1(2H)-carboxylate

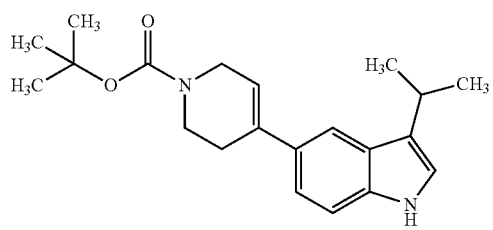
(T-1B)

To a mixture of 5-bromo-3-isopropyl-1H-indole (5.5 g, 23.10 mmol) and tert-butyl 4-(4,4,5,5-tetramethyl-1,3,2-dioxaborolan-2-yl)-5,6-dihydropyridine-1(2H)-carboxylate (7.50 g, 24.25 mmol) in a 250 mL round bottom flask were added THF (50 mL) followed by an aqueous solution of potassium phosphate, dibasic (12.07 g, 69.3 mmol, 20 mL). The resulting reaction mixture was degassed for 10 minutes with nitrogen gas, then PdCl$_2$(dppf)-CH$_2$Cl$_2$ adduct, (0.472 g, 0.577 mmol) was added. The mixture was degassed again for 5 min. The resulting reaction mixture was heated at 75° C. for 18 hours. The reaction mixture was diluted with ethyl acetate (100 mL), poured into a separate funnel and was washed with water (2×50 mL), brine (50 mL), dried over sodium sulfate, and concentrated to give crude product. The crude material was purified using silica gel chromatography, eluting with 15% ethyl acetate in hexane. The fractions were collected and concentrated to afford tert-butyl 4-(3-isopropyl-1H-indol-5-yl)-5,6-dihydropyridine-1(2H)-carboxylate (6.5 g, 83% yield) as an oil. LCMS retention time 1.21 min [B]. MS (E−) m/z: 339 (M−H).

Intermediate T-1C: tert-butyl 4-(3-isopropyl-1H-indol-5-yl)piperidine-1-carboxylate

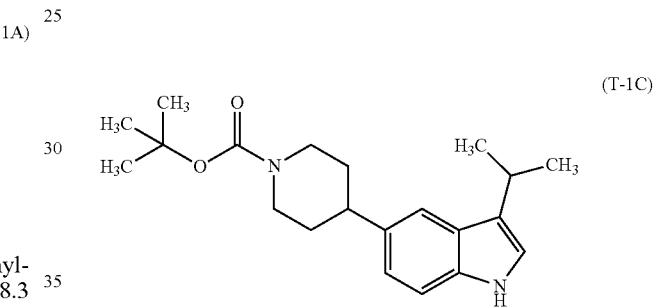
(T-1C)

To a solution of tert-butyl 4-(3-isopropyl-1H-indol-5-yl)-5,6-dihydropyridine-1(2H)-carboxylate (7.9 g, 23.20 mmol) in ethyl acetate (150 mL) under a nitrogen atmosphere, was added palladium on carbon (0.617 g, 0.580 mmol). The vessel was pumped/purged three times with nitrogen gas and then evacuated. Hydrogen gas was introduced via a balloon and the mixture was stirred at room temperature for 5 hours. The suspension was filtered through celite and the filtrate was concentrated to give crude compound. The crude residue was purified by silica gel chromatography, eluting with 15% ethyl acetate in hexane. The combined fractions were collected and concentrated to afford tert-butyl 4-(3-isopropyl-1H-indol-5-yl)piperidine-1-carboxylate (6.5 g, 82% yield) as a white solid. LCMS retention time 2.48 min [C]. MS (E−) m/z: 341 (M−H).

Intermediate T-1

To a solution of tert-butyl 4-(3-isopropyl-1H-indol-5-yl)piperidine-1-carboxylate (6.3 g, 18.40 mmol) in DCE (60 mL) was added NBS (3.27 g, 18.40 mmol) dissolved in DCE (50 mL) drop wise via an addition funnel over 10 min at 0° C. The resulting brown solution was stirred at room temperature for 20 min. The reaction was quenched with sodium sulfite solution (15 mL). The volatiles were removed. The residue was taken up in DCM (50 mL) and the aqueous layer was separated. The organic layer was dried over Na$_2$SO$_4$ and concentrated to afford crude compound. The crude compound was purified by silica gel chromatography, the compound was eluted in 15% ethyl acetate in Pet ether, the fractions was collected, and concentrated to afford tert-butyl 4-(2-bromo-3-isopropyl-1H-indol-5-yl) piperidine-1-carboxylate (6.4 g, 83% yield) as a white solid. LCMS retention time 2.58 min [H]. MS (E−) m/z: 367.2 (M−H). ¹H NMR (500 MHz, CHLOROFORM-d) δ 7.84 (br. s., 1H), 7.49 (d, J=0.9 Hz, 1H), 7.22 (d, J=8.4 Hz, 1H), 7.02 (dd, J=8.4, 1.5 Hz, 1H), 4.27 (br. s., 2H), 3.23 (quin, J=7.1 Hz, 1H), 2.84 (br. s., 3H), 1.88 (d, J=13.1 Hz, 2H), 1.50 (s, 9H), 1.43 (d, J=7.2 Hz, 6H), 1.24 (s, 2H).

Alternative Preparation of Intermediate T-1

Intermediate T-1A

A 5-liter 4-neck round bottom flask was charged with triethylsilane (489 mL, 3061 mmol), trichloroacetic acid (250 g, 1530 mmol) and toluene (500 mL). The solution was heated to 70° C. Next, 5-bromo-1H-indole (200 g, 1020 mmol) dissolved in acetone (150 mL, 2040 mmol) and toluene (700 mL) was added dropwise over 30 minutes. After the addition was complete, the resulting solution was heated at 90° C. for 3 h. The reaction was then quenched by adding 10% NaHCO₃ solution (~2.5 liter) dropwise at 0-10° C. until the pH was basic. The organic layer and the aqueous layer were separated and the aqueous layer was extracted with MTBE (2×1000 mL). The combined organic layers were washed with water and brine solution, dried over Na₂SO₄ and concentrated under vacuum to get a brown color oil. The crude residue was purified by 750 g silica gel chromatography eluting with PE:EtOAc (9:1). The product was eluted at 8% EtOAc in petroleum ether, collected, and concentrated under vacuum at 50° C. A light brown gummy liquid was obtained and hexane (100 mL) was added. The mixture was stirred and cooled to −40° C. to −50° C. After 10 min, a solid was formed which was filtered and washed with a minimal amount cold hexane. The compound was dried under vacuum to afford 5-bromo-3-isopropyl-1H-indole (215 g, 890 mmol, 87% yield) as an off-white solid. LCMS MH⁺: 237.5; HPLC Ret. Time 3.75 min. Method D.

Intermediate T-1B 5-bromo-3-isopropyl-1H-indole (90 g, 378 mmol) and tert-butyl 4-(4,4,5,5-tetramethyl-1,3,2-dioxaborolan-2-yl)-5,6-dihydropyridine-1(2H)-carboxylate (140 g, 454 mmol) was dissolved in THF (1200 mL) in a 2 L round-bottomed flask. Tripotassium phosphate (241 g, 1134 mmol) was dissolved in water (300 mL). The aqueous solution was added to the reaction mixture. The reaction mixture was purged with N₂. Then PdCl₂(dppf)-CH₂Cl₂ adduct (7.72 g, 9.45 mmol) was added to the reaction mixture. The reaction mixture was again purged with N₂. The reaction mixture was stirred at 80° C. for 18 h. The reaction mixture was filtered through celite and extracted with EtOAc. The combined organic layers were washed with brine, dried (sodium sulfate), and concentrated to remove the solvent. The crude material was purified by silica gel chromatography. The product was collected by eluting with 30% EtOAc:PE to afford tert-butyl 4-(3-isopropyl-1H-indol-5-yl)-5,6-dihydropyridine-1(2H)-carboxylate (125 g, 367 mmol). LCMS MH⁺: 341.2; HPLC Ret. Time 2.90 min.; Method: Column: Zorbax SB-18 (50×4.6 mm-5.0 μm); M. phase A: 10 mM NH₄COOH in H₂O:ACN (98:2); M. phase B: 10 mM NH₄COOH in H₂O:ACN (2:98); Flow rate: 1.5/min; Gradient: 30% B-100% B over 4 min. UV 220 nm.

Intermediate T-1C

In a 2 L round-bottomed flask, tert-butyl 4-(3-isopropyl-1H-indol-5-yl)-5,6-dihydropyridine-1(2H)-carboxylate (125 g, 367 mmol) was dissolved in ethyl acetate (1200 mL). Pd/C (15.63 g, 14.69 mmol) was added and the reaction mixture was degassed under N₂. The reaction mixture was stirred at room temperature for 18 h under H₂. Approximately 80% starting material was converted to product. The reaction mass was filtered through celite and concentrated. The crude material was purified with silica gel chromatography. The product was collected by eluting with 20% EtOAc:PE to afford tert-butyl 4-(3-isopropyl-1H-indol-5-yl)piperidine-1-carboxylate (105 g, 307 mmol, 84% yield). LCMS MH⁺: 343.4; HPLC Ret. Time 2.61 min.; Method: Column: Zorbax SB-18 (50×4.6 mm-5.0 μm); M. phase A: 10 mM NH₄COOH in H₂O:ACN (98:2); M. phase B: 10 mM NH₄COOH in H₂O:ACN (2:98); Flow rate: 1.5/min; Gradient: 30% B-100% B over 4 min.; UV 220 nm.

Intermediate T-1

In a 2 L round-bottomed flask tert-butyl 4-(3-isopropyl-1H-indol-5-yl)piperidine-1-carboxylate (100 g, 292 mmol) was dissolved in 1,2-dichloroethane (1200 mL). NBS (52.0 g, 292 mmol) solution in 1,2-dichloroethane (400 mL) and THF (800 mL) was added dropwise at 0° C. After the addition of NBS solution, the reaction mixture was stirred for 30 min. The reaction mass was quenched with 10% sodium thiosulfate solution at 0° C. and diluted with DCM. The combined organic layers were washed with brine, dried (sodium sulfate), and concentrated. The crude material was purified with silica gel chromatography. The product was collected by eluting with 10% EtOAc:PE. The dibromo product was observed (approximately 5-10%). The material was washed with cooled hexane to remove the dibromo product and afford tert-butyl 4-(2-bromo-3-isopropyl-1H-indol-5-yl)piperidine-1-carboxylate (87 g, 206 mmol, 70.7% yield). LCMS MH⁺-56: 365.0; HPLC Ret. Time 4.21 min.; Method: Column: Kinetex XB-C18 (75×3 mm-2.6 μm); M. phase A: 10 mM NH₄COOH in H₂O:ACN (98:02); M. phase B: 10 mM NH₄COOH in H₂O:ACN (02:98); Flow rate: 1.0/min; Gradient: 20% B-100% B over 4 min. UV 220 nm.

Intermediate T-2: Tert-butyl 4-(3-isopropyl-2-(4,4,5,5-tetramethyl-1,3,2-dioxaborolan-2-yl)-1H-indol-5-yl)piperidine-1-carboxylate

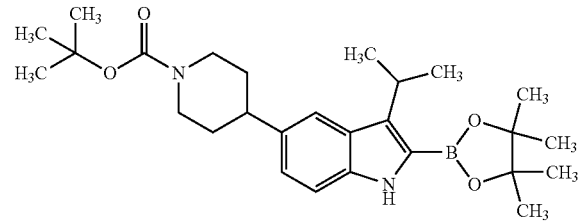

(T-2)

To a mixture of tert-butyl 4-(2-bromo-3-isopropyl-1H-indol-5-yl)piperidine-1-carboxylate (1.0 g, 2.373 mmol), 2-dicyclohexylphosphino-2',6'-dimethoxybiphenyl (0.117 g, 0.285 mmol), and bis(benzonitrile)palladium(II)chloride (0.027 g, 0.071 mmol) in a 50 mL reaction tube was added dioxane (10 mL). The resulting reaction mixture was degassed for 10 min and then pinacolborane (0.456 g, 3.56 mmol) was added followed by the dropwise addition of TEA (0.992 mL, 7.12 mmol). The solution was again degassed for 5 min. The resulting reaction mixture was heated at 85° C. for 3 h. The reaction mixture was concentrated and the crude residue was dissolved in ethyl acetate (100 mL), poured into a separatory funnel and washed thoroughly with water (2×250 mL). The organic layer was dried over $Na_2SO_4$ and filtered. The filtrate was concentrated under vacuum to afford the crude product. The residue was taken up in DCM (3 mL). The crude material was purified by combiflash system by eluting with 12% EtOAc/Pet ether. Following concentration of the fractions, the product was isolated as a white gummy product (0.75 g, 67.5% yield). LCMS retention time 4.27 min [H]. MS (E−) m/z: 467.3 (M−H). $^1$H NMR (400 MHz, CHLOROFORM-d) δ 8.35-8.12 (m, 1H), 7.66-7.59 (m, 1H), 7.11-7.04 (m, 1H), 4.40-4.23 (m, 2H), 3.80-3.63 (m, 1H), 2.99-2.67 (m, 3H), 1.98-1.84 (m, 2H), 1.79-1.64 (m, 2H), 1.54-1.51 (m, 9H), 1.49-1.45 (m, 6H), 1.39-1.35 (m, 12H).

Alternative Preparation of Intermediate T-2

In a 1 L round-bottomed flask, tert-butyl 4-(2-bromo-3-isopropyl-1H-indol-5-yl) piperidine-1-carboxylate (85 g, 202 mmol) was dissolved in dioxane (850 mL). Next, 2-dicyclohexylphosphino-2',6'-dimethoxybiphenyl (9.11 g, 22.19 mmol) and bis(benzonitrile) palladium chloride (3.87 g, 10.09 mmol) were added. Pinacolborane (387 g, 3026 mmol) was added followed by the addition of TEA (84 mL, 605 mmol). The reaction mixture was purged with nitrogen for 15-20 min. The reaction mixture was stirred at 90° C. for 20 h. The reaction mixture was filtered through celite and the reaction was quenched with brine solution. Effervescence was observed. The reaction mixture was extracted with EtOAc, dried (sodium sulfate), and concentrated. The crude material was purified with silica gel chromatography. The product was collected by eluting with 10% EtOAc:PE to afford tert-butyl 4-(3-isopropyl-2-(4,4,5,5-tetramethyl-1,3,2-dioxaborolan-2-yl)-1H-indol-5-yl) piperidine-1-carboxylate (62.5 g, 133 mmol, 66.1% yield). LCMS MH$^+$: 469.4. HPLC Ret. Time 3.04 min.; Method: Column: Zorbax SB-18 (50×4.6 mm-5.0 µm); M. phase A: 10 mM $NH_4COOH$ in $H_2O$:ACN (98:2); M. phase B: 10 mM $NH_4COOH$ in $H_2O$:ACN (2:98); Flow rate: 1.5/min; Gradient: 30% B-100% B over 4 min.; UV 220 nm.

Intermediate T-3: Tert-butyl 4-(2-(7,8-dimethyl-[1,2,4]triazolo[1,5-a]pyridin-6-yl)-3-isopropyl-1H-indol-5-yl)piperidine-1-carboxylate

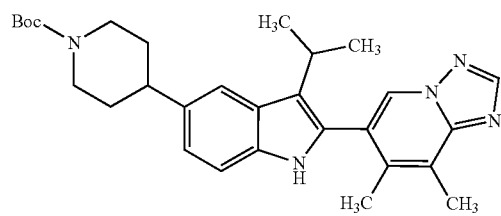

(T-3)

To a mixture of tert-butyl 4-(2-bromo-3-isopropyl-1H-indol-5-yl)piperidine-1-carboxylate (60 g, 142 mmol), bis (benzonitrile)palladium(ii) chloride (1.639 g, 4.27 mmol), 2-dicyclohexylphosphino-2',6'-dimethoxybiphenyl (3.51 g, 8.54 mmol) and anhydrous dioxane (407 ml) under $N_2$ at room temperature were added pinacolborane (62.0 mL, 427 mmol) and triethylamine (59.5 mL, 427 mmol). The mixture was heated at 85° C. for 5 min. The starting material was consumed. After the reaction mixture was cooled to room temperature (a water ice bath was used to fasten the cooling), 2 mL of 2 M $K_3PO_4$ solution was added. After the generation of bubbles diminished, the remainder of the 2 M potassium phosphate tribasic solution (214 mL, 427 mmol) was added, followed by 6-bromo-7,8-dimethyl-[1,2,4]triazolo[1,5-a]pyridine (29.9 g, 132 mmol) and $PdCl_2$(dppf)-$CH_2Cl_2$ adduct (4.07 g, 4.98 mmol). The reaction mixture was heated at 85° C. for 2 h. The reaction went to completion. After the mixture was cooled to room temperature, the organic layer (a suspension) and the aqueous layer was separated. The top organic layer was a suspension. It was concentrated and dissolved in DCM (1.5 L) to give a dark DCM solution and aqueous layer on the top. The water was removed and the DCM extraction was dried over $Na_2SO_4$, filtered through a Celite pad, washed with DCM and concentrated to give 150 g crude wet mud. The material was purified with silica gel chromatography using a Silica 40 g Gold column. The column was eluted with DCM and ethyl acetate. The product was collected when eluting with 50% ethyl acetate:DCM to afford tert-butyl 4-(2-(7,8-dimethyl-[1,2,4]triazolo[1,5-a]pyridin-6-yl)-3-isopropyl-1H-indol-5-yl)piperidine-1-carboxylate (56.9 g, 117.0 mmol, 82% yield) as an off-white solid. LCMS MH$^+$: 488.5. HPLC Ret. Time 1.13 min. Method G. $^1$H NMR (499 MHz, CHLOROFORM-d) δ 8.45-8.41 (m, 1H), 8.36-8.33 (m, 1H), 7.90-7.84 (m, 1H), 7.66-7.63 (m, 1H), 7.39-7.34 (m, 1H), 7.17-7.12 (m, 1H), 4.39-4.26 (m, 2H), 3.04-2.94 (m, 1H), 2.92-2.75 (m, 3H), 2.72-2.65 (m, 3H), 2.27-2.21 (m, 3H), 2.00-1.90 (m, 2H), 1.83-1.71 (m, 2H), 1.54-1.51 (m, 9H), 1.42-1.38 (m, 6H).

Intermediate T-4: Tert-butyl 4-(3-isopropyl-2-(8-methoxy-[1,2,4]triazolo[1,5-a]pyridin-6-yl)-1H-indol-5-yl)piperidine-1-carboxylate

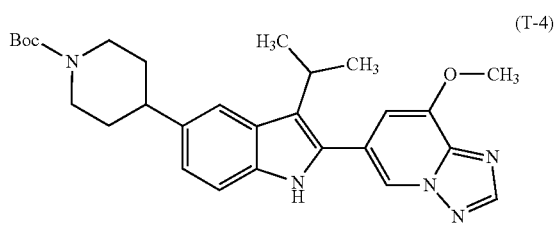 [SMILES: COc1cc(-c2[nH]c3ccc(C4CCN(C(=O)OC(C)(C)C)CC4)cc3c2C(C)C)cn2ncnc12]

(T-4)

To a mixture of tert-butyl 4-(2-bromo-3-isopropyl-1H-indol-5-yl)piperidine-1-carboxylate (40 g, 95 mmol), bis (benzonitrile)palladium(ii) chloride (1.092 g, 2.85 mmol), 2-dicyclohexylphosphino-2',6'-dimethoxybiphenyl (2.338 g, 5.70 mmol) and anhydrous dioxane (271 mL) under $N_2$ at room temperature, were added pinacolborane (41.3 mL, 285 mmol) and triethylamine (39.7 mL, 285 mmol). The mixture was heated at 85° C. for 10 min. The starting material was consumed. After the reaction mixture was cooled to room temperature, 2-5 mL of 2 M $K_3PO_4$ aqueous solution was added. After bubbling slowed down, the remainder of the 2 M potassium phosphate tribasic solution (142 mL, 285 mmol) was added, followed by 6-bromo-8-methoxy-[1,2,4]triazolo[1,5-a]pyridine (20 g, 88 mmol) and PdCl₂(dppf)-CH₂Cl₂ adduct (3.10 g, 3.80 mmol). The mixture was heated at 70° C. for 1.5 h. After completion of the reaction, 81 g of crude product after concentration was purified by silica gel chromatography (3 kg Gold column) eluting with DCM and ethyl acetate. The product was collected at 35% ethyl acetate:DCM to afford tert-butyl 4-(3-isopropyl-2-(8-methoxy-[1,2,4]triazolo[1,5-a]pyridin-6-yl)-1H-indol-5-yl)piperidine-1-carboxylate (52.6 g, 107 mmol, 113% yield). LCMS MH+: 490.1. HPLC Ret. Time 1.08 min. Method G.

Intermediate F-1: 6-bromo-[1,2,4]triazolo[1,5-a]pyridine

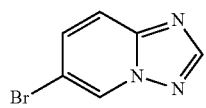

(F-1)

Commercially available reagent: CAS No 356560-80-0

Intermediate F-2: 6-bromo-8-methyl-[1,2,4]triazolo[1,5-a]pyridine

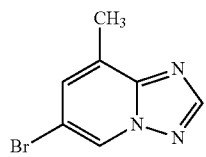

(F-2)

To a stirred solution of 5-bromo-3-methylpyridin-2-amine (1.75 g, 9.36 mmol) in N,N-dimethylformamide (13.04 mL, 168 mmol) was added DMF-DMA (12.53 mL, 94 mmol). The reaction mixture was heated to 130° C. overnight. After cooling to room temperature, the volatiles were removed under reduced pressure to afford a brown oil. To an ice-cooled, stirred solution of the crude product in methanol (100 mL) and pyridine (15 mL) was added hydroxylamine-O-sulfonic acid (1.587 g, 14.03 mmol). The reaction mixture was allowed to warm to room temperature and was stirred overnight. The volatiles were removed under reduced pressure, and the residue was partitioned between aqueous sodium bicarbonate solution and ethyl acetate. The aqueous layer was further extracted with ethyl acetate, and the combined organic layers were washed sequentially with water (10 mL) and saturated aqueous brine solution (10 mL), dried over magnesium sulfate, and concentrated in vacuo to afford 6-bromo-8-methyl-[1,2,4]triazolo[1,5-a]pyridine (1.98 g). LC-MS: M+1=212/214. Rt=0.80 min, [A1]; ¹H NMR (400 MHz, DMSO-d₆) δ 9.20 (s, 1H), 8.48 (s, 1H), 7.67 (s, 1H), 2.55 (s, 3H).

Intermediate F-3: 6-bromo-7-methyl-[1,2,4]triazolo[1,5-a]pyridine

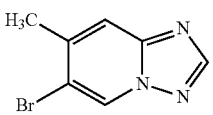

(F-3)

To a 40 mL vial with a pressure relief septum were added 5-bromo-4-methylpyridin-2-amine (5.00 g, 26.7 mmol), DMF (10 mL) and N,N-dimethylformamide dimethyl acetal (11.99 mL, 90 mmol). The vial was heated to 130° C. for 6 hours. The vial was cooled to room temperature, the volatiles were removed under vacuum. The resulting oil was dissolved in MeOH (5 mL) and pyridine (3.24 mL, 40.1 mmol) and cooled to ° C. Hydroxylamine-O-sulfonic acid (4.53 g, 40.1 mmol) was added over 15 minutes and the mixture was allowed to warm to room temperature overnight. The solution was concentrated under vacuum. The resulting white solid was partitioned between EtOAc and saturated sodium bicarbonate. The organic layer was separated and the bicarbonate layer was extracted with EtOAc (2×50 mL). The combined organics were washed with water (50 mL) and brine (50 mL), dried over magnesium sulfate, filtered and concentrated to afford 6-bromo-7-methyl-[1,2,4]triazolo[1,5-a]pyridine as a white solid. (4.5 g, 21.22 mmol, 79% yield). LC-MS: M+1=212/214, rt=0.70 min., [A1].

Intermediate F-4: 6-bromo-7,8-dimethyl-[1,2,4]triazolo[1,5-a]pyridine

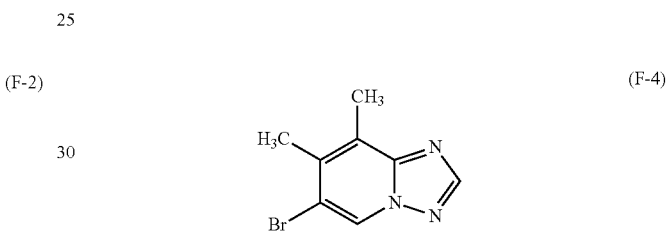

(F-4)

To a 40 mL vial with a pressure relief septum were added 5-bromo-3,4-dimethylpyridin-2-amine (5.00 g, 24.87 mmol), DMF (10 mL) and N,N-dimethylformamide dimethyl acetal (11.15 mL, 83 mmol). The vial was heated to 80° C. for 6 hours. The vial was cooled to room temperature. The volatiles were removed under vacuum and the resulting oil was dissolved in MeOH (5 mL) and pyridine (3.02 mL, 37.3 mmol) and cooled to 0° C. Hydroxylamine-O-sulfonic acid (4.22 g, 37.3 mmol) was added over 15 minutes and the mixture allowed to warm to room temperature overnight. The solution was concentrated under vacuum. The resulting white solid was partitioned between EtOAc and 1.5 M potassium phosphate solution. The organic layer was separated and the aqueous layer was extracted with EtOAc (2×50 mL). The combined organics were washed with water (50 mL) and brine (50 mL), dried over magnesium sulfate, filtered and concentrated to give a white solid. The solid was dissolved in DCM and MeOH and charged to an 80 G silica gel column which was eluted with 0-100% ethyl acetate/hexane. Following concentration of the fractions, 6-bromo-7,8-dimethyl-[1,2,4]triazolo[1,5-a]pyridine (5.2 g, 23.00 mmol, 92% yield) was collected as a whitish solid. LC-MS: M+1=226/228, rt=0.75 min, [A1]; ¹H NMR: ¹H NMR (400 MHz, CHLOROFORM-d) δ 8.68 (s, 1H), 8.26 (s, 1H), 2.68 (s, 3H), 2.50 (s, 3H).

Alternative Preparation of Intermediate F-4

To the suspension of 5-bromo-3,4-dimethylpyridin-2-amine (10 g, 49.7 mmol) in DMF (50 mL) was added 1,1-dimethoxy-N,N-dimethylmethanamine (15.32 mL, 114 mmol). The mixture was stirred at 110° C. for 12 h under N₂. All the starting material amine was converted to intermediate imine (M+1, 256) after 12 h. The reaction mixture was concentrated to remove volatiles under high vacuum rotavap. Solvent DMF still remained in the black reaction mixture. The resulting residue was diluted with MeOH (50 mL) and pyridine (6.03 mL, 74.6 mmol). The mixture was cooled to 0° C. and hydroxylamine-O-sulfonic acid (8.88 g, 74.6 mmol) was added over 15 min. The mixture was stirred at room temperature over 24 h. The reaction was completed and the desired product was found after 19 h. The crude reaction mixture was concentrated to remove volatiles. The resulting yellow solid was dissolved in 200 mL EtOAc and quenched with saturated NaHCO$_3$ solution slowly (200 mL) with gas generated during the addition of sodium bicarbonate. The organic layer was separated and the aqueous layer was back-extracted with EtOAc. The combined organic layer was washed with H$_2$O (30 mL), brine (2×30 mL) and dried over Na$_2$SO$_4$. The crude product was purified with silica gel chromatography eluting with EtOAc and hexane to afford 6-bromo-7,8-dimethyl-[1,2,4]triazolo[1,5-a]pyridine (8 g, 35.4 mmol, 71.1% yield). LCMS MH$^+$: 226.08. HPLC Ret. Time 0.71 min. Method G. $^1$H NMR (400 MHz, CHLOROFORM-d) δ 8.79-8.63 (m, 1H), 8.39-8.10 (m, 1H), 2.81-2.61 (m, 3H), 2.57-2.48 (m, 3H).

Intermediate F-5: 6-bromo-8-methoxy-[1,2,4]triazolo[1,5-a]pyridine

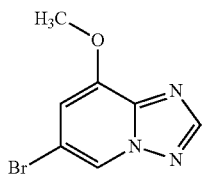

(F-5)

To a stirred solution of 5-bromo-3-methoxypyridin-2-amine (7.5 g, 36.9 mmol) in DMF (15 mL) was added DMF-DMA (15 mL, 112 mmol). The reaction mixture was heated to 130° C. overnight. After cooling to room temperature, the volatiles were removed under reduced pressure to provide a brown oil. To an ice-cooled, stirred solution of the brown oil in methanol (150 mL) and pyridine (20 mL) was added hydroxylamine-O-sulfonic acid (6.27 g, 55.4 mmol). The reaction mixture was allowed to warm to room temperature and was stirred overnight. The volatiles were removed under reduced pressure, and the residue was partitioned between aqueous sodium bicarbonate solution and ethyl acetate. The aqueous layer was further extracted with ethyl acetate, and the combined organic layers were washed sequentially with water (10 mL) and saturated aqueous brine solution (10 mL), dried over sodium sulfate, and concentrated in vacuo to afford crude product. The residue was taken up in DCM (3 mL). The crude was purified by combiflash 3% MeOH: 97% CHCl$_3$. Following concentration of fractions, 6-bromo-8-methoxy-[1,2,4]triazolo[1,5-a]pyridine (5.0 g, 21.93 mmol, 59.4% yield) was collected as a yellow solid. LCMS: M$^{+1}$=228.5, R$_t$=1.06 min., Column: ZORBAX SB C18 (50 X4.6 mm, 5.0 µM) Method: 10 mM NH$_4$COOH in water+ACN; $^1$H NMR (400 MHz, DMSO-d$_6$) δ=4.01 (s, 3H), 7.26 (s, 1H), 8.45 (s, 1H), 8.95 (s, 1H).

Intermediate F-6: 6-bromo-8-(methoxymethyl)-[1,2,4]triazolo[1,5-a]pyridine

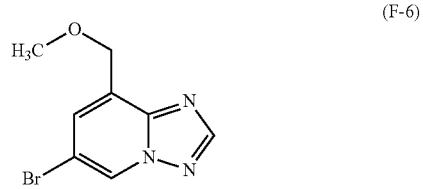

(F-6)

To a 40 mL reaction vial, were added 6-bromo-8-methyl-[1,2,4]triazolo[1,5-a]pyridine (2.000 g, 9.43 mmol), AIBN (0.155 g, 0.943 mmol), NBS (1.679 g, 9.43 mmol), and CCl$_4$ (15 mL). The vial was sealed and heated to 75° C. overnight. The reaction mixture was cooled to room temperature and concentrated to dryness. The residue was used without purification in the subsequent step.

To a 40 mL vial, were added the above residue, THE (15 mL), MeOH (10 mL), and aqueous NaOH (28.3 mL, 28.3 mmol). The reaction vial was capped and heated to 75° C. for 1 hour. LC-MS showed clean conversion to the product. Water and ethyl acetate was added and the layers were separated. The organics were washed with water, then brine, dried over Na$_2$SO$_4$, filtered, and concentrated to give an off-white solid. LC-MS: M+1=242, rt=1.31 min, [A1]. $^1$H NMR (400 MHz, DMSO-d$_6$) δ 9.41-9.28 (m, 1H), 8.52 (s, 1H), 7.78-7.65 (m, 1H), 4.84-4.70 (m, 2H), 3.42 (s, 3H).

Intermediate F-7: 6-2-(2-amino-5-bromo-1,2-dihydropyridin-3-yl)ethanol

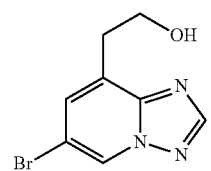

(F-7)

In a 100 mL 2-neck round bottom flask, and under a nitrogen atmosphere, was added 2-(2-aminopyridin-3-yl) acetic acid (0.250 g, 1.622 mmol) and THE (8 mL). At 5° C., LAH was added portion-wise to the solution. The ice bath was removed and the reaction mixture was heated at reflux overnight. After 16 hours, the solvent had evaporated. Diethyl ether was added. Following cooling, the reaction mixture was placed in an ice bath. The LAH was quenched with MeOH, then water. Sodium sulfate was added and the mixture was filtered, and washed with diethyl ether. The filtrate was concentrated and then dissolved in DCM (5 mL) and cooled to 5° C. Next, NBS (0.289 g, 1.622 mmol) in DCM (2 mL) was added. The reaction mixture was warmed to room temperature. The reaction was quenched with 2 mL of a 10% sodium sulfite solution. DCM (20 mL) and water (20 mL) were added and the contents was added to a separatory funnel. The layers were separated. The organics were washed with brine dried over Na$_2$SO$_4$, filtered and concentrated to give crude product. LC-MS: M$^{+1}$=219, R$_t$=0.49 min, [A1]. This material was carried on similarly as in general procedure for F-2 to afford (6-bromo-[1,2,4]

triazolo[1,5-a]pyridin-8-yl)ethanol (0.065 g, 73%). LC-MS: M$^{+1}$=242/244, R$_f$=0.65 min, [A1].

Intermediate F-8: (6-bromo-[1,2,4]triazolo[1,5-a]pyridin-8-yl)methanol

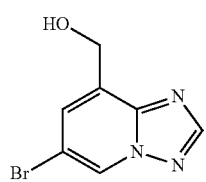
(F-8)

Intermediate F-8 was prepared according to general procedure for F-6 starting from 6-bromo-8-methyl-[1,2,4]triazolo[1,5-a]pyridine and without methanol in the second step. LC-MS: M$^{+1}$=228/230, R$_f$=0.60 min, [A1].

Intermediate F-9: rac-1-(6-bromo-[1,2,4]triazolo[1,5-a]pyridin-8-yl)ethan-1-ol

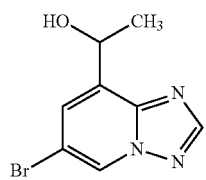
(F-9)

In a 40 mL reaction vial were added 2-amino-5-bromonicotinaldehyde (0.750 g, 3.73 mmol) and under nitrogen gas, THE (10 mL). The mixture was cooled to −20° C. and 3 M methylmagnesium chloride in Et$_2$O (4.97 mL, 14.92 mmol) was added via syringe over 20 minutes. The reaction mixture was warmed to room temperature and stirred for 3 hours. The reaction mixture was cooled to −20° C. and quenched slowly with saturated ammonium chloride. Water and ethyl acetate were added and the layers were separated. The collected organics were washed with saturated NaCl, dried over Na$_2$SO$_4$, filtered and concentrated to dryness to afford rac-1-(2-amino-5-bromopyridin-3-yl)ethanol. This material was carried on similarly as in general procedure for F-1 to afford rac-1-(6-bromo-[1,2,4]triazolo[1,5-a]pyridin-8-yl)ethan-1-ol (0.53 g, 58%). LC-MS: M$^{+1}$=242/244, R$_f$=0.58 min, [A1].

Intermediate F-10: 2-(6-bromo-[1,2,4]triazolo[1,5-a]pyridin-8-yl)propan-2-ol

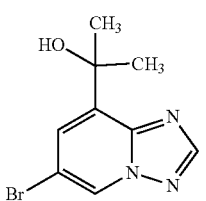
(F-10)

In a 40 mL reaction vial was added methyl 2-amino-5-bromonicotinate (1.240 g, 5.37 mmol) and under a nitrogen atmosphere, THF (10.73 mL). The mixture was cooled to −20° C. and 3 M methylmagnesium chloride in Et$_2$O (7.16 mL, 21.47 mmol) was added via syringe over 20 minutes. The reaction mixture was warmed to room temperature and stirred for 3 hours. The reaction mixture was cooled to −20° C. and the reaction was quenched slowly with the addition of saturated ammonium chloride. Water and ethyl acetate were added and the layers were separated. The collected organics were washed with saturated NaCl, dried over Na$_2$SO$_4$, filtered and concentrated to dryness to afford 2-(2-amino-5-bromopyridin-3-yl) propan-2-ol LC-MS: M$^{+1}$=231.3/233.0, R$_f$=0.49 min, [A1]. This material was carried on similarly as in general procedure for F-1 to afford 2-(6-bromo-[1,2,4]triazolo[1,5-a]pyridin-8-yl)propan-2-ol (0.65 g, 59%). LC-MS: M$^{+1}$=255.6/257.8, R$_f$=0.85 min, [D1].

Intermediate F-11: (6-bromo-7-methyl-[1,2,4]triazolo[1,5-a]pyridin-8-yl)methanol

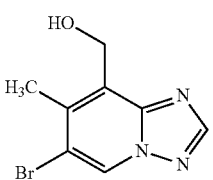
(F-11)

Intermediate F-11A: (2-amino-4-methylpyridin-3-yl)methanol

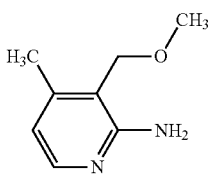
(F-11A)

In a 100 mL Schlenk flask (heat gun dried) was added N-(4-methylpyridin-2-yl) pivalamide (0.300 g, 1.560 mmol). Diethyl ether (5.20 mL) was added and the reaction mixture was cooled to −78° C. Next, 1.7 M tert-butyllithium in pentane (2.019 mL, 3.43 mmol) was added via syringe, drop-wise. The reaction mixture was stirred at −78° C. for 3 hours and then chloromethyl methyl ether (0.142 mL, 1.872 mmol) was introduced. The reaction mixture was warmed to room temperature and stirred overnight. The reaction was quenched with water. Ethyl acetate was added to the mixture. The mixture was poured into a separatory funnel and the layers were separated. The organics were washed with water, then brine, dried over Na$_2$SO$_4$, filtered and concentrated. The crude oil was purified on a silica gel using 0-50% ethyl acetate/hexane. Following concentration of the fractions, N-(3-(methoxymethyl)-4-methylpyridin-2-yl)pivalamide was collected as a tan oil. This material was suspended in 4 M aqueous HCl and heated to 110° C. for 48 hours. The reaction mixture was cooled to room temperature, diluted with diethyl ether and the contents poured into a separatory funnel. The layers were separated and the organic layer was discarded. The aqueous layer was basified with 1.5 M potassium phosphate dibasic solution and the suspension was extracted with ethyl acetate (three times extracted). The combined organics were washed with brine, dried over $Na_2SO_4$, filtered and concentrated to afford (2-amino-4-methylpyridin-3-yl)methanol (0.1 g, 46%). LC-MS: ($M^{+1}$) not observed on instrument, $R_t$=0.39 min by UV only, [A1].

Intermediate F-11B:
(2-amino-5-bromo-4-methylpyridin-3-yl)methanol

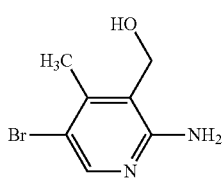

(F-11B)

In a 40 mL reaction vial was added (2-amino-4-methylpyridin-3-yl)methanol (0.200 g, 1.448 mmol), DCM, and NBS (0.258 g, 1.448 mmol) as a suspension in 5 mL of DCM. The reaction mixture was stirred for 15 minutes. The reaction was quenched with a 10% sodium sulfite solution (1 mL). The reaction mixture was diluted with water and DCM, and transferred to a separatory funnel. The layers were separated and the organics were washed with brine, dried over $Na_2SO_4$, filtered and concentrated to afford (2-amino-5-bromo-4-methylpyridin-3-yl)methanol (0.08 g, 26%). LC-MS: $M^{+1}$=217/219, $R_t$=0.45 min, [A1].

Intermediate F-11

Intermediate F-11 was prepared from Intermediate F-11B according to the general procedure for F-2 to afford (6-bromo-7-methyl-[1,2,4]triazolo[1,5-a]pyridin-8-yl)methanol LC-MS: $M^{+1}$=242/244, $R_t$=0.60 min, [A1].

Intermediate F-12: 6-bromo-8-(methoxymethyl)-7-methyl-[1,2,4]triazolo[1,5-a]pyridine

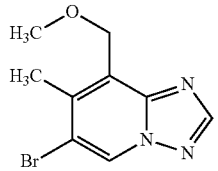

(F-12)

Intermediate F-12A 6-bromo-8-(methoxymethyl)-7-methyl-[1,2,4]triazolo[1,5-a]pyridine

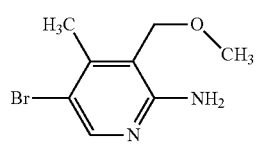

(F-12A)

In a 40 mL reaction vial were added N-(3-(methoxymethyl)-4-methylpyridin-2-yl) pivalamide (0.100 g, 0.423 mmol) and 6N aqueous HCl (2.116 mL, 2.116 mmol). The vial was capped and heated to 80° C. overnight. The mixture was basified with a 1.5 M dibasic potassium phosphate solution. The aqueous layer was extracted with ethyl acetate (2×50 mL). The combined organics were washed with a saturated NaCl solution, dried over $Na_2SO_4$, filtered and concentrated to afford 3-(methoxymethyl)-4-methylpyridin-2-amine ($R_t$=0.44 min.) [A1]. This material was suspended in DCM (4 mL). NBS (0.075 g, 0.423 mmol) was dissolved in 1 mL of DCM and added to the reaction mixture dropwise via a pipet over 5 minutes. The reaction was quenched with the addition of 1 mL of a 10% sodium sulfite solution. The organic layer was pipetted off and concentrated. The residue was purified on silica gel using 0-10% MeOH/DCM. Following concentration of the fractions, 5-bromo-3-(methoxymethyl)-4-methylpyridin-2-amine was collected as a tan oil. LC-MS: $M^{+1}$=231/233, $R_t$=0.53 min. 0.60 min, [D1].

Intermediate F-12

Intermediate F-12 was prepared from Intermediate F-12A according to the general procedure for F-1 to afford 6-bromo-8-(methoxymethyl)-7-methyl-[1,2,4]triazolo[1,5-a]pyridine (0.03 g, 30%). LC-MS: $M^{+1}$=256/258, $R_t$=1.07 min. 0.60 min, [A1].

Intermediate F-13: 2-(6-bromo-[1,2,4]triazolo[1,5-a]pyridin-8-yl)acetonitrile

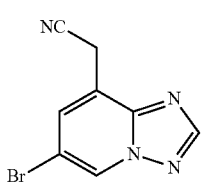

(F-13)

To a 40 mL reaction vial was added (6-bromo-[1,2,4]triazolo[1,5-a]pyridin-8-yl) methanol (0.500 g, 2.193 mmol) followed by the slow addition of $SOCl_2$ (1.600 mL, 21.93 mmol). The reaction mixture was stirred at 50° C. overnight. The reaction mixture was concentrated and placed under vacuum to remove the excess thionyl chloride. Next, acetonitrile, water and KCN (0.714 g, 10.96 mmol) in water (1 mL) were added. The reaction vessel was sealed and heated to 50° C. overnight. The reaction mixture was diluted with 1.5 M dibasic potassium phosphate solution and ethyl acetate was added. The reaction mixture was poured into a separatory funnel and the layers were separated. The organics were washed with brine, then dried over $Na_2SO_4$, filtered and concentrated to afford 2-(6-bromo-[1,2,4]triazolo[1,5-a]pyridin-8-yl)acetonitrile as a tan solid (0.21 g, 40%). LC-MS: $M^{+1}$=236/238, $R_t$=0.60 min, [A1].

Intermediate F-14: 6-bromo-8-fluoro-7-methyl-[1,2,4]triazolo[1,5-a]pyridine

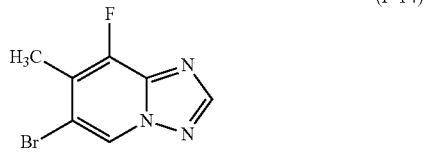
(F-14)

In a 40 mL reaction vial was added 3-fluoro-4-methylpyridin-2-amine (0.250 g, 1.982 mmol) in DCM (5 mL). To this was added a suspension of NBS (0.353 g, 1.982 mmol) in DCM (2 mL). The reaction mixture was stirred for 30 minutes. The reaction was quenched with the addition of 5 mL of a 10% sodium sulfite solution. DCM and water were added and the reaction mixture was poured into a separatory funnel. The layers were separated. The collected organics were washed with brine, dried over $Na_2SO_4$, filtered and concentrated to afford 5-bromo-3-fluoro-4-methylpyridin-2-amine. This material was carried on similarly as in general procedure for F-2 to afford 6-bromo-8-fluoro-7-methyl-[1,2,4]triazolo[1,5-a]pyridine (0.45 g, 49%). LC-MS: $M^{+1}$=230/232, $R_t$=0.71 min. 0.60 min, [A1].

Intermediate F-15: (6-bromo-[1,2,4]triazolo[1,5-a]pyridin-7-yl)methanol

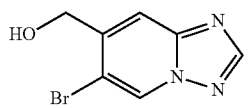
(F-15)

Intermediate F-15A: 6-bromo-7-(bromomethyl)-[1,2,4]triazolo[1,5-a]pyridine

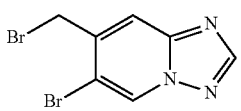
(F-15A)

In a 40 mL reaction vial were added 6-bromo-7-methyl-[1,2,4]triazolo[1,5-a]pyridine (0.670 g, 3.16 mmol), carbon tetrachloride (6.32 mL), NBS (0.562 g, 3.16 mmol) and AIBN (0.052 g, 0.316 mmol). The reaction vial was capped and heated at 75° C. for 5 hours. The reaction mixture was cooled to room temperature, filtered and the precipitate was washed with $CCl_4$. The filtrate was concentrated to afford 6-bromo-7-(bromomethyl)-[1,2,4]triazolo [1,5-a]pyridine as a light yellow residue (0.72 g, 78%). LC-MS: $M^{+1}$=290/292/294, $R_t$=0.75 min., [A1].

Intermediate F-15

To a 40 mL vial were added 6-bromo-7-(bromomethyl)-[1,2,4]triazolo[1,5-a]pyridine (1.000 g, 3.44 mmol), acetone (11 mL), sodium iodide (0.515 g, 3.44 mmol) and potassium acetate (0.675 g, 6.87 mmol). The reaction mixture was capped and heated to 55° C. for 17 hours. The volatiles were removed under a stream of nitrogen gas and to the residue were added THF (10 mL), 1 mL of water, and sodium hydroxide (2.58 mL, 10.31 mmol). The vial was capped and heated at 65° C. for 8 hours. The mixture was treated with 1N HCl to approximately pH 7. Ethyl acetate was added and the layers were separated. The organics were washed with brine, dried over $Na_2SO_4$, filtered and concentrated to afford (6-bromo-[1,2,4]triazolo[1,5-a]pyridin-7-yl)methanol as a whitish solid (0.35 g, 44%). LC-MS: $M^{+1}$=228/230, $R_t$=0.54 min., [A1].

Intermediate F-16: 2-((6-bromo-[1,2,4]triazolo[1,5-a]pyridin-8-yl)oxy)ethylacetate

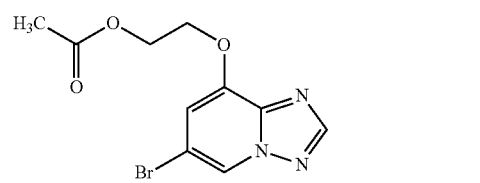
(F-16)

Intermediate F-16A: 2-((2-amino-5-bromopyridin-3-yl)oxy)ethyl acetate

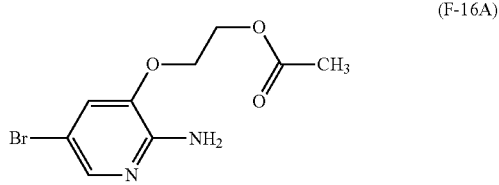
(F-16A)

In a 40 mL reaction vial under nitrogen gas, was added 2-amino-5-bromopyridin-3-ol (0.320 g, 1.693 mmol) and DMF (5 mL). The mixture was cooled to 5° C. and NaH (0.102 g, 2.54 mmol) was added. The reaction mixture was stirred at 5° C. for 1 hour. Next, 2-bromoethyl acetate (0.283 mL, 2.54 mmol) was introduced neat via a syringe. The reaction mixture was stirred at 5° C. and slowly warmed to room temperature overnight. The mixture was cooled to 5° C. and carefully diluted with water. Ethyl acetate was added and the mixture was transferred to a separatory funnel. The layers were separated and the organics were washed with brine, dried over sodium sulfate, filtered and concentrated to afford 2-((2-amino-5-bromopyridin-3-yl)oxy)ethyl acetate as a tan oil (0.45 g, 97%). LC-MS: $M^{+1}$=275/277, rt=0.52 min, [A1].

Intermediate F-16

Intermediate F-16A carried on similarly to general procedure for F-1 to afford 2-((6-bromo-[1,2,4]triazolo[1,5-a]pyridin-8-yl)oxy)ethyl acetate as a tan solid. LC-MS: $M^{+1}$=300/302, $R_t$=0.69 min, [A1].

Intermediate F-17: 6-bromo-8-(ethoxymethyl)-[1,2,4]triazolo[1,5-a]pyridine

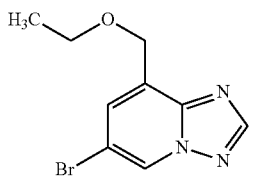
(F-17)

Intermediate F-17A: 6-bromo-8-(bromomethyl)-[1,2,4]triazolo[1,5-a]pyridine

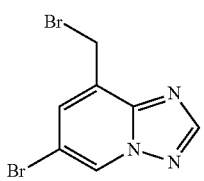
(F-17-1)

To a 40 mL reaction vial were added 6-bromo-8-methyl-[1,2,4]triazolo[1,5-a]pyridine (2.000 g, 9.43 mmol), AIBN (0.155 g, 0.943 mmol), NBS (1.679 g, 9.43 mmol), and CCl$_4$ (15 mL). The vial was sealed and heated to 75° C. overnight. The reaction mixture was cooled to room temperature, filtered and the precipitate was washed with CCl$_4$. The filtrate was concentrated to dryness to afford 6-bromo-8-(bromomethyl)-[1,2,4]triazolo[1,5-a]pyridine, as a light yellow residue (1.9 g, 69%). LC-MS: M*$^1$=290/292/294, R$_t$=0.73 min., [A1].

Intermediate F-17

To a 40 mL reaction vial were added 6-bromo-8-(bromomethyl)-[1,2,4]triazolo[1,5-a]pyridine (0.300 g, 1.031 mmol), ethanol (3.44 mL), sodium iodide (0.015 g, 0.103 mmol) and potassium acetate (0.051 g, 0.516 mmol). The reaction vial was capped and heated to 55° C. overnight. The reaction mixture was cooled to room temperature and concentrated to dryness. Water and ethyl acetate were added and the mixture was transferred to a separatory funnel. The layers were separated and the organics were washed with water, then brine, dried over Na$_2$SO$_4$, filtered, and concentrated to afford 6-bromo-8-(ethoxymethyl)-[1,2,4]triazolo[1,5-a]pyridine (0.2 g, 72%). LC-MS: M$^{+1}$=256/258, R$_t$=0.79 min, [A1].

The following Fragments were prepared in a fashion similar to the synthetic methods described above.

TABLE 1

| Interm. No. | Starting Material | Structure | LCMS MH$^+$ | Ret Time | HPLC Method |
|---|---|---|---|---|---|
| F-18 | 5-bromo-3,6-dimethylpyridin-2-amine | 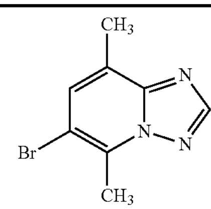 | 226/228 | 0.77 | [TS1] |
| F-19 | 2-amino-5-bromonicotinonitrile | 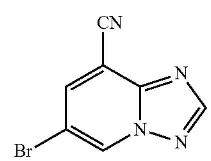 [SMILES: N#Cc1cc(Br)cn2ncnc12] | 222.9 | 0.60 | [TS1] |
| F-20 | 5-bromo-3-fluoropyridin-2-amine | 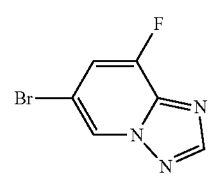 [SMILES: Fc1cc(Br)cn2ncnc12] | 216/218 | 0.62 | [A1] |
| F-21 | 5-bromo-4-methylpyridin-2-amine | 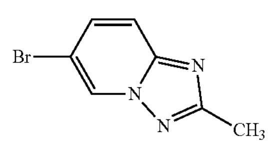 | 212/214 | 1.40 | D |
| F-22 | 5-bromo-6-methylpyridin-2-amine | 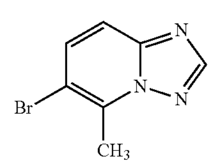 | 212/214 | 1.47 | D |

TABLE 1-continued

| Interm. No. | Starting Material | Structure | LCMS MH+ | Ret Time | HPLC Method |
|---|---|---|---|---|---|
| F-23 | 5-bromo-3-methylpyridin-2-amine | 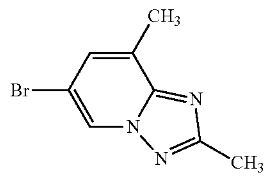 | 226/228 | 1.46 | D |
| F-24 | 5-bromo-4-methylpyridin-2-amine | 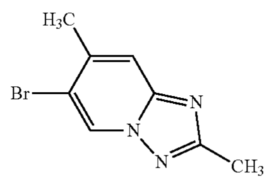 | 226/228 | 1.45 | D |
| F-25 | 5-bromo-3-fluoropyridin-2-amine | 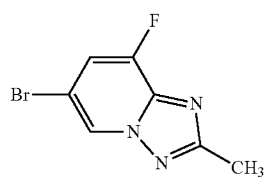 | 230/232 | 1.22 | D |
| F-26 | 5-bromo-4-fluoropyridin-2-amine | 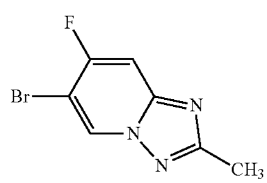 | 230/232 | 1.12 | D |
| F-27 | 5-bromo-3-(trifluoromethyl)pyridin-2-amine | 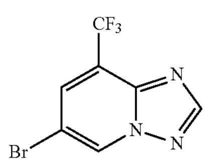 [SMILES: FC(F)(F)c1cc(Br)cn2ncnc12] | 266/268 | 1.73 | D |
| F-28 | 5-bromo-4-methoxypyridin-2-amine | 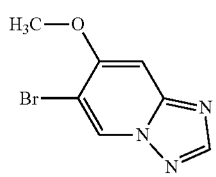 | 228/230 | 1.39 | D |
| F-29 | 5-bromo-3-ethoxypyridin-2-amine | 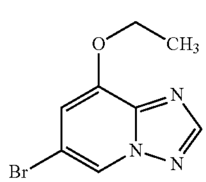 | 242/244 | 0.99 | D |
| F-30 | 5-bromo-3-ethoxypyridin-2-amine | 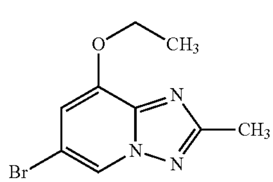 | 256/258 | 1.93 | D |

TABLE 1-continued

| Interm. No. | Starting Material | Structure | LCMS MH+ | Ret Time | HPLC Method |
|---|---|---|---|---|---|
| F-31 | 5-bromo-3-methoxypyridin-2-amine | 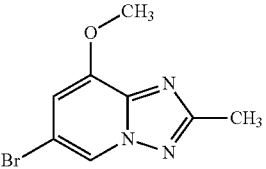 | 242/244 | 1.55 | D |
| F-32 | 5-bromo-3-(difluoromethoxy)pyridin-2-amine | 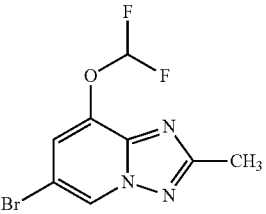 | 278/280 | 2.06 | D |
| F-33 | 5-bromo-4-isobutoxypyridin-2-amine | 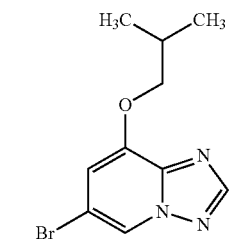 | 270/272 | 2.06 | D |
| F-34 | 5-bromo-3-chloro-4-methylpyridin-2-amine | 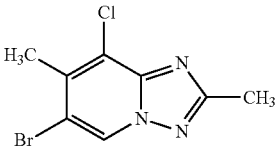 | 260/262 | 1.41 | B |
| F-35 | 3,5-dibromo-4-methylpyridin-2-amine | 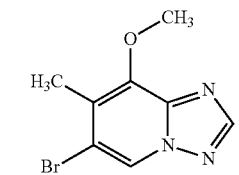 | 242/244 | 1.1 | B |
| F-36 | 5-bromo-3-chloro-4-methylpyridin-2-amine | 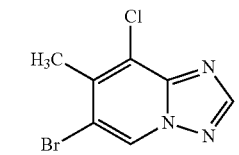 | 246/248 | 9.9 | A |
| F-37 | 5-bromo-6-methylpyridin-2-amine | 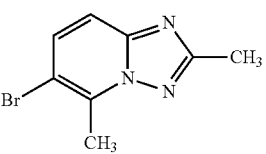 | 226/228 | 0.55 | A |
| F-38 | 5-bromo-3-chloropyridin-2-amine | 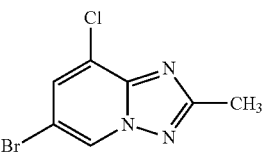 | 246/248 | 0.55 | A |

TABLE 1-continued

| Interm. No. | Starting Material | Structure | LCMS MH+ | Ret Time | HPLC Method |
|---|---|---|---|---|---|
| F-39 | 5-bromo-3-chloropyridin-2-amine | ![structure] | 232/234 | 0.48 | A |
| F-40 | 5-bromo-4-(trifluoromethyl)pyridin-2-amine | ![structure] | 280/282 | 0.67 | K |

Intermediate F-41: 4-(6-bromo-[1,2,4]triazolo[1,5-a]pyridin-8-yl)morpholine

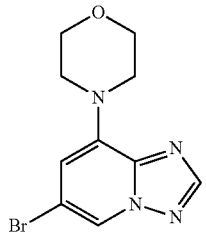

(F-41)

Intermediate F-41A: 5-bromo-3-iodopyridin-2-amine

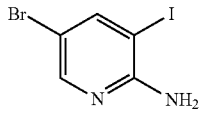

(F-41A)

To a stirred solution of 5-bromopyridin-2-amine (4.0 g, 23.12 mmol), TFA (2.316 mL, 30.1 mmol) in DMF (100 mL) at 0° C. were added portion wise NIS (6.76 g, 30.1 mmol). The reaction mixture was stirred at 50° C. for 16 h. The reaction mixture was quenched with ice cold water and sodium thiosulphate solution (3:1), the product was precipitated by adding the saturated NaHCO$_3$ solution (adjust pH-8), stirred for 10 min at 0° C. The resulting solid compound was collected by filtration to afford 5-bromo-3-iodopyridin-2-amine (5.1 g, 17.06 mmol, 73.8% yield) as a brown solid. MS (E$^+$) m/z: 298.9 (M). Retention time: 1.16 min. [K].

Intermediate F-42B: (E)-N'-(5-bromo-3-iodopyridin-2-yl)-N, N-dimethylformimidamide

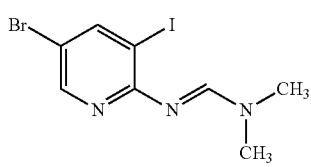

(F-42B)

A solution of DMF-DMA (11.42 mL, 85 mmol) and 5-bromo-3-iodopyridin-2-amine (5.1 g, 17.06 mmol) in DMF (20.0 mL) was stirred at 130° C. for 16 h. The reaction mixture was cooled to room temperature and the volatiles were evaporated. The mixture was dried in high vacuum to afford (E)-N'-(5-bromo-3-iodopyridin-2-yl)-N,N-dimethylformimidamide (6.2 g, 17.51 mmol, 103% yield) as a brown semi-solid. MS (E$^+$) m/z: 355.8 (M+2H). Retention time: 1.51 min. [K].

Intermediate F-43C: 6-bromo-8-iodo-[1,2,4]triazolo[1,5-a]pyridine

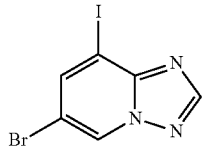 [SMILES: Clc1cc(Br)cn2ncnc12]

(F-43C)

To a stirred solution of (E)-N'-(5-bromo-3-iodopyridin-2-yl)-N,N-dimethylformimidamide (6.1 g, 17.23 mmol) and pyridine (6.97 mL, 86 mmol) in MeOH (80.0 mL) at 0° C. was added hydroxylamine-O-sulfonic acid (3.89 g, 34.5 mmol). The reaction mixture was stirred at room temperature for 16 h. The reaction mixture was quenched with ice cold water and volatiles were evaporated. The mixture was dried in high vacuum. The residue was dissolved in saturated NaHCO$_3$ solution and extracted with chloroform (2×200 mL) and washed with brine. The organic layer was dried over sodium sulphate and concentrated. The resulting material was purified by silica gel chromatography. The compound was eluted with 65% ethyl acetate and petroleum ether to afford 6-bromo-8-iodo-[1,2,4]triazolo[1,5-a]pyridine (1.8 g, 5.56 mmol, 32.2% yield) as a light yellow solid. MS (E$^+$) m/z: 325.8, Retention time: 1.577 min. [L].

Intermediate F-43

A stirred mixture of 6-bromo-8-iodo-[1,2,4]triazolo[1,5-a]pyridine (0.300 g, 0.926 mmol), morpholine (0.403 g, 4.63 mmol), and Cs$_2$CO$_3$ (0.905 g, 2.78 mmol) in DMF (10.0 mL) was degassed for 5 min. Next, Pd$_2$(dba)$_3$ (0.085 g, 0.093 mmol) and Xantphos (0.054 g, 0.093 mmol) were added. The reaction mixture was stirred at 120° C. for 2.5 h in a microwave system. The reaction mixture was diluted with ethyl acetate, filtered and washed with excess ethyl acetate. The combined organic layers were washed with water, brine, dried over sodium sulphate and evaporated to afford crude material. The crude material was purified using a 24 g silica gel column, compound was eluted with 35% ethyl acetate and petroleum ether to afford 4-(6-bromo-[1,2,4]triazolo[1,5-a]pyridin-8-yl)morpholine (0.180 g, 0.636 mmol, 68.6% yield) as a light yellow solid. MS (E$^+$) m/z: 285.0, R$_t$: 1.60 min. [L].

The following examples were prepared according to the general procedure described above for Intermediate F-43.

TABLE 2

| Intermediate No. | Structure | LCMS [M + 2H] | R$_t$ (min) | HPLC Method |
|---|---|---|---|---|
| F-44 | 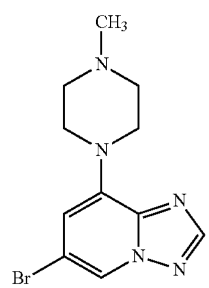 [SMILES: CN1CCN(c2cc(Br)cn3ncnc23)CC1] | 298.0 | 0.78 | K |
| F-45 | 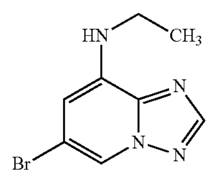 | 243.0 | 1.05 | K |
| F-46 | 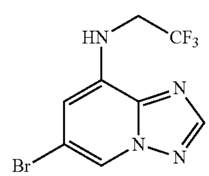 [SMILES: FC(F)(F)CNc1cc(Br)cn2ncnc12] | 297.0 | 1.06 | K |
| F-47 | 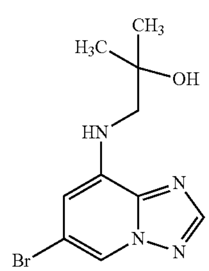 [SMILES: CC(C)(O)CNc1cc(Br)cn2ncnc12] | 287.0 | 0.90 | K |
| F-48 | 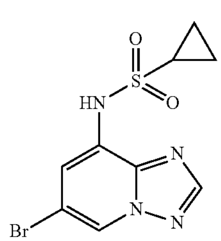 [SMILES: O=S(=O)(Nc1cc(Br)cn2ncnc12)C1CC1] | 319.0 | 0.76 | K |
| F-49 | | 333.0 | 0.75 | K |
| F-50 | | 271.0 | 0.79 | K |
| F-51 | | 305.8 | 1.350 | K |

Intermediate F-52: 6-bromo-8-cyclopropyl-[1,2,4]triazolo[1,5-a]pyridine

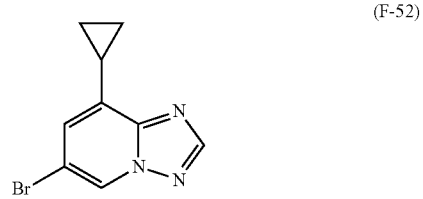 [SMILES: Brc1cc(C2CC2)c2ncnn2c1]

(F-52)

A solution of 6-bromo-8-iodo-[1,2,4]triazolo[1,5-a]pyridine (0.400 g, 1.235 mmol) and cyclopropylboronic acid (0.318 g, 3.70 mmol) in a mixture of toluene (10.0 mL) and water (2.0 mL) was degassed for 5 min. Next, tricyclohexylphosphine (0.069 g, 0.247 mmol), Pd(OAc)$_2$ (0.028 g, 0.123 mmol) and Na$_2$CO$_3$ (1.852 mL, 3.70 mmol) were added. The resultant reaction mixture was stirred at 100° C. for 14 h in a sealed tube. The reaction mixture was cooled to room temperature, diluted with ethyl acetate, filtered, and washed with excess ethyl acetate. The combined organic layers were washed with water, brine, dried over sodium sulphate, and evaporated to afford the crude compound. The crude compound was purified using a 40 g silica column. The compound was eluted with 35% ethyl acetate and pet ether to afford 6-bromo-8-cyclopropyl-[1,2,4]triazolo[1,5-a]pyridine (0.240 g, 1.008 mmol, 82% yield) as a light yellow solid. MS (E$^+$) m/z: 240.0, R$_t$: 1.05 min. [M].

Intermediate F-53: 4-(6-bromo-2-methyl-[1,2,4]triazolo[1,5-a]pyridin-8-yl)morpholine

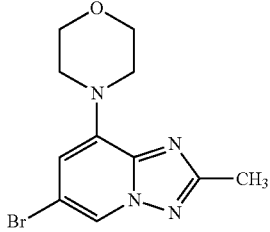
(F-53)

Intermediate F-53A: (E)-N'-(5-bromo-3-iodopyridin-2-yl)-N,N-dimethylacetimidamide

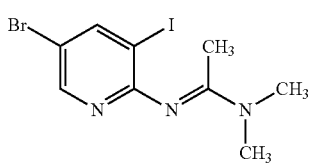
(F-53A)

A solution of 1,1-dimethoxy-N,N-dimethylpropan-2-amine (24.63 g, 167 mmol) and 5-bromo-3-iodopyridin-2-amine (5.0 g, 16.73 mmol) in DMF (20.0 mL) was stirred at 130° C. for 16 h. The reaction mixture was cooled to room temperature. The volatiles were evaporated and the material was dried in high vacuum to afford (E)-N'-(5-bromo-3-iodopyridin-2-yl)-N,N-dimethylacetimidamide (5.8 g, 15.76 mmol, 94% yield) as a brown semi-solid. MS (E⁺) m/z: 370.0, $R_t$: 0.68 min. [M].

Intermediate F-53B: 6-bromo-8-iodo-2-methyl-[1,2,4]triazolo[1,5-a]pyridine

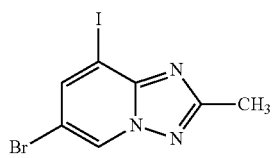
(F-53B)

To a stirred solution of (E)-N'-(5-bromo-3-iodopyridin-2-yl)-N,N-dimethylacetimidamide (4.5 g, 12.23 mmol) and pyridine (4.94 mL, 61.1 mmol) in methanol (80.0 mL) at 0° C. was added hydroxylamine-O-sulfonic acid (2.76 g, 24.46 mmol). The reaction mixture was stirred at room temperature for 16 h. The reaction was quenched with ice cold water. The volatiles were evaporated and the resulting material was dried in high vacuum. The residue was dissolved in saturated NaHCO₃ solution, extracted with chloroform (2×200 mL) and washed with brine. The organic layer was dried over sodium sulphate and concentrated to afford crude material. The crude material was purified using a 40 g silica column. The compound was eluted with 50% ethyl acetate and pet ether to afford 6-bromo-8-iodo-2-methyl-[1,2,4]triazolo[1,5-a]pyridine (2.2 g, 6.51 mmol, 53.2% yield) as a light yellow solid. MS (E⁺) m/z: 337.9 (M), $R_t$: 1.04 min. [L].

Intermediate F-53

A stirred mixture of 6-bromo-8-iodo-2-methyl-[1,2,4]triazolo[1,5-a]pyridine (0.300 g, 0.888 mmol), morpholine (0.232 g, 2.66 mmol), and Cs₂CO₃ (0.723 g, 2.219 mmol) in DMF (10.0 mL) was degassed for 5 min. Next, Xantphos (0.051 g, 0.089 mmol) and Pd₂(dba)₃ (0.081 g, 0.089 mmol) were added. The reaction mixture was stirred at 120° C. for 2.5 h in a microwave system. The reaction mixture was diluted with ethyl acetate, filtered and washed with excess ethyl acetate. The combined organic layers were washed with water, brine, dried over sodium sulphate, and evaporated to obtain crude material. The crude material was purified using a 24 g silica column. The compound was eluted with 80% ethyl acetate and pet ether to afford 4-(6-bromo-2-methyl-[1,2,4]triazolo[1,5-a]pyridin-8-yl)morpholine (0.180 g, 0.606 mmol, 68.2% yield) as a light yellow solid. MS (E⁺) m/z: 298.8, $R_t$: 1.08 min. [K].

Intermediate F-54: 6-bromo-8-cyclopropyl-2-methyl-[1,2,4]triazolo[1,5-a]pyridine

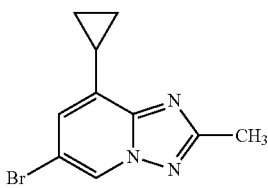
(F-54)

A solution of 6-bromo-8-iodo-2-methyl-[1,2,4]triazolo[1,5-a]pyridine (0.400 g, 1.184 mmol) and cyclopropylboronic acid (0.305 g, 3.55 mmol) in a mixture of toluene (10.0 mL) and water (2.0 mL) was degassed for 5 min. Next, tricyclohexylphosphine (0.066 g, 0.237 mmol), Pd(OAc)₂ (0.027 g, 0.118 mmol) and Na₂CO₃ (1.775 mL, 3.55 mmol) were added. The reaction mixture was stirred at 100° C. for 14 h in a sealed tube. The reaction mixture was cooled to room temperature. The mixture was diluted with ethyl acetate, filtered, and washed with excess ethyl acetate. The combined organic layers were washed with water, brine, dried over sodium sulphate, and evaporated to afford the crude compound. The crude compound was purified using a 24 g silica column. The compound was eluted with 35% ethyl acetate and pet ether to afford 6-bromo-8-cyclopropyl-2-methyl-[1,2,4]triazolo[1,5-a]pyridine (0.220 g, 0.873 mmol, 73.7% yield) as a light yellow solid. MS (E⁺) m/z: 254.0, $R_t$: 1.12 min. [K].

Intermediate F-55: 6-bromo-8-cyclopropyl-7-methyl-[1,2,4]triazolo[1,5-a]pyridine

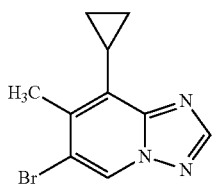
(F-55)

Intermediate F-55A:
5-bromo-3-iodo-4-methylpyridin-2-amine

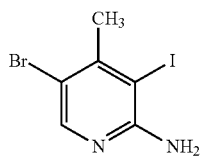

(F-55A)

To a stirred solution of 5-bromo-4-methylpyridin-2-amine (5.0 g, 26.7 mmol), TFA (2.471 mL, 32.1 mmol) in DMF (100 mL) at 0° C. was added portion-wise NIS (9.02 g, 40.1 mmol). The reaction mixture was stirred at 55° C. for 2 h. The reaction was quenched with ice cold water and sodium thiosulphate solution (3:1). The product was precipitated by adding saturated NaHCO$_3$ solution (adjust pH-8) and stirring for 10 min at 0° C. The solid compound was collected by filtration to afford 5-bromo-3-iodo-4-methylpyridin-2-amine (8 g, 25.6 mmol, 96% yield) as a brown solid. MS (E$^+$) m/z: 314.9, R$_t$: 0.92 min. [M].

Intermediate F-55B (E)-N'-(5-bromo-3-iodo-4-methylpyridin-2-yl)-N,N-dimethylformimidamide

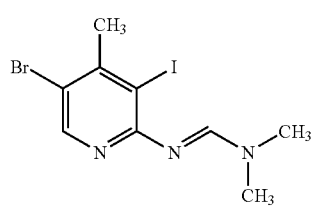

(F-55B)

A solution of DMF-DMA (10.70 mL, 80 mmol) and 5-bromo-3-iodo-4-methylpyridin-2-amine (2.5 g, 7.99 mmol) in DMF (15.0 mL) was stirred at 130° C. for 16 h. The reaction mixture was cooled to room temperature and the volatiles were evaporated. The material was dried in high vacuum to afford crude (E)-N'-(5-bromo-3-iodo-4-methylpyridin-2-yl)-N,N-dimethylformimidamide (2.8 g, 7.61 mmol, 95% yield) as a brown semi-solid. MS (E$^+$) m/z: 370.1, R$_t$: 1.59 min. [K].

Intermediate F-55C: 6-bromo-8-iodo-7-methyl-[1,2,4]triazolo[1,5-a]pyridine

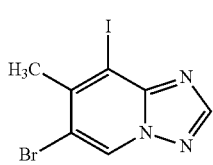

(F-55C)

To a stirred solution of (E)-N'-(5-bromo-3-iodo-4-methylpyridin-2-yl)-N,N-dimethyl formimidamide (2.8 g, 7.61 mmol) and pyridine (3.08 mL, 38.0 mmol) in methanol (60.0 mL) at 0° C. was added hydroxylamine-O-sulfonic acid (1.290 g, 11.41 mmol). The reaction mixture was stirred at room temperature for 16 h. The reaction was quenched with ice cold water. The volatiles were evaporated and the mixture was dried in high vacuum. The residue was dissolved in saturated NaHCO$_3$ solution, extracted with chloroform (2×150 mL), and washed with brine. The organic layer was dried over sodium sulphate and concentrated to afford crude product. The crude product was purified by silica gel chromatography. The compound eluted with 65% ethyl acetate and pet ether to afford 6-bromo-8-iodo-7-methyl-[1,2,4]triazolo[1,5-a]pyridine (1.5 g, 4.44 mmol, 58.3% yield) as a light yellow solid. MS (E$^+$) m/z: 338.2 (M), Retention time: 1.11 min. [K].

Intermediate F-55

A solution of 6-bromo-8-iodo-7-methyl-[1,2,4]triazolo[1,5-a]pyridine (0.400 g, 1.184 mmol) and cyclopropylboronic acid (0.305 g, 3.55 mmol) in mixture of toluene (15.0 mL) and water (3.0 mL) was degassed for 5 min. Next, tricyclohexylphosphine (0.066 g, 0.237 mmol), Pd(OAc)$_2$ (0.027 g, 0.118 mmol) and Na$_2$CO$_3$ (1.775 mL, 3.55 mmol) were added. The reaction mixture was stirred at 100° C. for 14 h in a sealed tube. The reaction mixture was cooled to room temperature, diluted with ethyl acetate, filtered, and washed with excess ethyl acetate. The combined organic layers were washed with water, brine, dried over sodium sulphate, and evaporated to afford crude compound. The crude compound was purified by silica gel chromatography. The compound eluted with 35% ethyl acetate and pet ether to afford 6-bromo-8-cyclopropyl-7-methyl-[1,2,4]triazolo[1,5-a]pyridine (0.280 g, 1.111 mmol, 94% yield) as a light yellow solid. MS (E$^+$) m/z: 254.0, R$_t$: 2.11 min. [L]

Intermediate F-56: 6-bromo-8-methyl-2-(trifluoromethyl)-[1,2,4]triazolo[1,5-a]pyridine

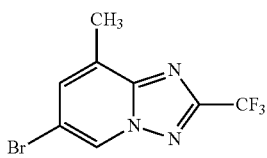

(F-56)

Intermediate F-56A: 5-bromo-3-methyl-1λ$^4$-pyridine-1,2-diamine 2,4,6-trimethylbenzenesulfonate

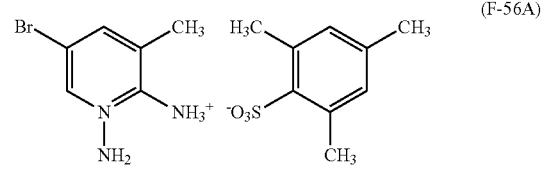

(F-56A)

To a stirred solution of ethyl o-mesitylsulfonylacetohydroxamate (3.05 g, 10.69 mmol) in dioxane (20 mL) cooled to 0° C. was added perchloric acid (1.074 g, 10.69 mmol). The mixture was stirred at ambient temperature for 30 min.

The reaction mass was quenched with ice cold water, extracted with dichloromethane (100 mL), dried over sodium sulphate, and concentrated to afford crude 1-amino-5-bromo-3-methyl-1λ4-pyridin-2-aminium 2,4,6-trimethylbenzenesulfonate. To a stirred solution of 5-bromo-3-methylpyridin-2-amine (2 g, 10.69 mmol) in DCM (10 mL) was added 1-amino-5-bromo-3-methyl-1λ⁴-pyridin-2-aminium 2,4,6-trimethylbenzenesulfonate at 0° C. The reaction mixture was stirred at ambient temperature for 1 h. The reaction mixture was diluted with water (25 mL), extracted with DCM (2×100 mL), dried over sodium sulphate, and concentrated to afford 1,2-diamino-5-bromo-3-methylpyridin-1-ium,2,4,6-trimethylbenzenesulfonate as a white solid (2.1 g, 93%). ¹H NMR (300 MHz, CHLOROFORM-d) δ=7.91 (br. s., 1H), 7.63 (d, J=15.9 Hz, 1H), 7.28 (s, 2H), 6.89 (s, 1H), 3.72 (s, 1H), 2.81-2.47 (m, 6H), 2.36-2.02 (m, 6H), 1.23 (t, J=7.0 Hz, 2H).

Intermediate F-56

To a stirred solution of 1,2-diamino-5-bromo-3-methylpyridin-1-ium,2,4,6-trimethylbenzenesulfonate (1 g, 2.141 mmol) in MeOH (25 mL) at 0° C. was added trifluoroacetic anhydride (0.351 mL, 2.486 mmol). The reaction mixture was stirred for 10 min at the same temperature. Next, Et₃N (0.346 mL, 2.486 mmol) was added and the reaction mixture was stirred at ambient temperature for 16 h. The reaction mixture was concentrated. The reaction was quenched with water (25 mL). The reaction mixture was extracted with EtOAc (2×100 mL), dried over sodium sulphate, and concentrated to afford 6-bromo-8-methyl-2-(trifluoromethyl)-[1,2,4]triazolo[1,5-a]pyridine. The crude mass was purified by silica gel chromatography and eluted in 40% EtOAc in hexane to afford 6-bromo-8-methyl-2-(trifluoromethyl)-[1,2,4]triazolo[1,5-a]pyridine (500 mg, 71.8%) as off white solid. LC retention time=1.28 min [K]. MS (E⁻) m/z: 280.0 (M+H).

Intermediate F-57

6-bromo-8-methoxy-2-(trifluoromethyl)-[1,2,4]triazolo[1,5-a]pyridine

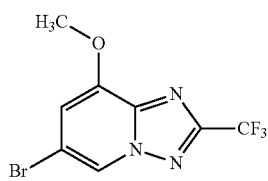
(F-57)

Intermediate F-57A: 3,5-dibromo-1λ⁴-pyridine-1,2-diamine 2,4,6-trimethylbenzenesulfonate

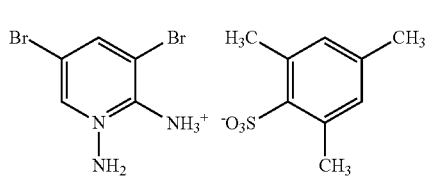
(F-57A)

To a stirred solution of ethyl o-mesitylsulfonylacetohydroxamate (2.266 g, 7.94 mmol) in dioxane (20 mL) cooled to 0° C. was added perchloric acid (1.074 g, 10.69 mmol). The reaction mixture was stirred at ambient temperature for 30 min. The reaction was quenched with ice cold water. The reaction mixture was extracted with dichloromethane (100 mL), dried over sodium sulphate, and concentrated to afford crude 1-amino-3,5-dibromo-1λ⁴-pyridin-2-aminium 2,4,6-trimethylbenzenesulfonate. To a stirred solution of 3,5-dibromopyridin-2-amine (2 g, 7.94 mmol) in DCM (10 mL) was added 1-amino-3,5-dibromo-1λ4-pyridin-2-aminium 2,4,6-trimethylbenzenesulfonate at 0° C. The reaction mixture was stirred at ambient temperature for 1 h. The reaction mixture was diluted with water (25 mL), extracted with DCM (2×100 mL), dried over sodium sulphate, and concentrated to afford 1,2-diamino-3,5-dibromopyridin-1-ium, 2,4,6-trimethylbenzenesulfonate as a white solid (2.1 g, 93.5%). ¹H NMR (400 MHz, DMSO-d₆) δ=7.88 (d, J=2.0 Hz, 1H), 7.70 (d, J=2.0 Hz, 1H), 7.12 (s, 1H), 6.70 (s, 4H), 3.56 (s, 1H), 2.10 (s, 6H).

Intermediate F-57B: 6,8-dibromo-2-(trifluoromethyl)-[1,2,4]triazolo[1,5-a]pyridine (F-57B)

To a stirred solution of 1,2-diamino-3,5-dibromopyridin-1-ium, 2,4,6-trimethylbenzenesulfonate (1 g, 2.141 mmol) in MeOH (25 mL) cooled to 0° C. was added trifluoroacetic anhydride (0.351 mL, 2.486 mmol). The reaction mixture was stirred for 10 mins. After Et₃N (0.346 mL, 2.486 mmol) was added, the reaction mixture was stirred at ambient temperature for 16 h. The reaction mixture was concentrated, quenched with water (25 mL), extracted with EtOAc (2×100 mL), dried over sodium sulphate, and concentrated to afford 6,8-dibromo-2-(trifluoromethyl)-[1,2,4]triazolo[1,5-a]pyridine. The crude mass was purified by silica gel chromatography, and eluted with 40% EtOAc in hexane to afford 6,8-dibromo-2-(trifluoromethyl)-[1,2,4]triazolo[1,5-a]pyridine (650 mg, 73.8%) as off white solid. LC retention time=1.37 min [K]. MS (E⁻) m/z: 344.0 (M+H).

Intermediate F-57

To a solution of 6,8-dibromo-2-(trifluoromethyl)-[1,2,4]triazolo[1,5-a]pyridine (350 mg, 1.015 mmol) in acetonitrile (15 mL) was added sodium methoxide (54.8 mg, 1.015 mmol). The resulting mixture was stirred at 85° C. for 1 h. The reaction mixture was quenched with water (20 mL), extracted with EtOAc (2×50 mL), dried over sodium sulphate, and concentrated to afford 6-bromo-8-methoxy-2-(trifluoromethyl)-[1,2,4]triazolo[1,5-a]pyridine. The crude mass was purified by silica gel chromatography, and was eluted with 50% EtOAc in hexane to afford 6-bromo-8-methoxy-2-(trifluoromethyl)-[1,2,4]triazolo[1,5-a]pyridine (160 mg, 53.5%) as white solid. LC retention time=1.26 min [K]. MS (E⁻) m/z: 294.0 (M–H).

125

Intermediate F-58: 6-bromo-[1,2,4]triazolo[1,5-a]pyridin-2-amine

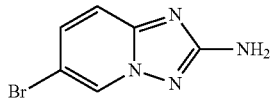

(F-58)

Commercially available reagent: CAS No 356560-80-0.

Intermediate F-59: 6-chloro-8-trideuteromethyl-[1,2,4]triazolo[1,5-a]pyridine

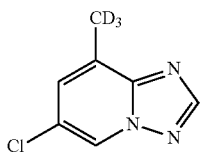

(F-59)

8-bromo-6-chloro-[1,2,4]triazolo[1,5-a]pyridine was prepared following the general procedure for F-2 starting from 3-bromo-5-chloropyridin-2-amine. LC retention time 0.67 min [TS1]. MS (ES$^+$) m/z: 233.9 (M+H).

A solution of 8-bromo-6-chloro-[1,2,4]triazolo[1,5-a]pyridine (150 mg, 0.645 mmol) in THF (5.0 mL) was degassed with nitrogen gas for 5 minutes. Iron(III) acetylacetonate (22.79 mg, 0.065 mmol) was added. The light yellow solution became red and was degassed again, and then evacuated and backfilled with nitrogen gas three times. Trideuteromethylmagnesium iodide (0.97 mL, 0.97 mmol) was added and the reaction mixture was stirred for 30 minutes at room temperature. Upon completion, the reaction mixture was diluted with dichloromethane (20 mL), ammonium chloride (10 mL) and water (10 mL). The layers were separated, and the aqueous layer was extracted with dichloromethane (2×15 mL). The combined organic layers were dried over sodium sulfate, filtered, and concentrated to afford a crude residue, which was purified using silica gel chromatography eluting with hexanes/ethyl acetate 0-70% to afford 6-chloro-8-trideuteromethyl-[1,2,4]triazolo[1,5-a]pyridine (41 mg, 0.240 mmol, 37.2% yield). LC retention time 0.64 min [TS1]. MS (ES$^+$) m/z: 171.08 (M+H). $^1$H NMR (400 MHz, CHLOROFORM-d) δ 8.50 (d, J=2.0 Hz, 1H), 8.30 (s, 1H), 7.29 (d, J=2.0 Hz, 1H).

Example 1

6-(3-isopropyl-5-(piperidin-4-yl)-1H-indol-2-yl)-[1,2,4]triazolo[1,5-a]pyridine

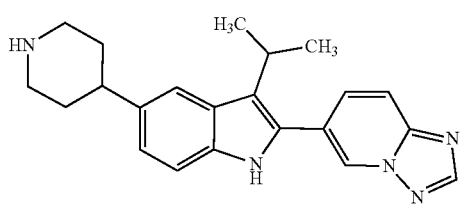

(1)

126

Intermediate 1A: tert-butyl 4-(2-([1,2,4]triazolo[1,5-a]pyridin-6-yl)-3-isopropyl-1H-indol-5-yl)piperidine-1-carboxylate

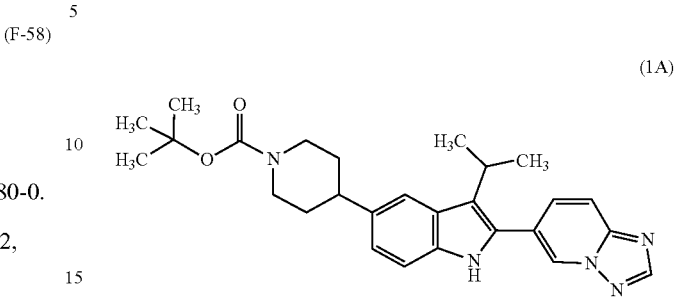

(1A)

To a stirred solution of tert-butyl 4-(3-isopropyl-2-(4,4,5,5-tetramethyl-1,3,2-dioxaborolan-2-yl)-1H-indol-5-yl)piperidine-1-carboxylate (50 mg, 0.107 mmol), 6-bromo-[1,2,4]triazolo[1,5-a]pyridine (31.7 mg, 0.160 mmol) in tetrahydrofuran (5 mL), and water (0.5 mL) was added potassium phosphate tribasic (68.0 mg, 0.320 mmol). The solution was degassed with nitrogen for 10 mins. Next, PdCl$_2$(dppf) (7.81 mg, 10.67 μmol) was added and the solution was degassed again for 10 mins. The reaction mixture was heated to 75° C. for 16 h. The reaction progress was monitored by LCMS. The reaction mass was filtered through a celite bed, washed with EtOAc, and concentrated to afford tert-butyl 4-(2-([1,2,4]triazolo[1,5-a]pyridin-6-yl)-3-isopropyl-1H-indol-5-yl) piperidine-1-carboxylate (50 mg, 0.109 mmol). The material was carried on directly into the subsequent step without further purification.

Example 1

To a stirred solution of tert-butyl 4-(2-([1,2,4]triazolo[1,5-a]pyridin-6-yl)-3-isopropyl-1H-indol-5-yl)piperidine-1-carboxylate (50 mg, 0.109 mmol) in DCM (2 mL) was added 1,4-dioxane (4N HCl) (0.2 mL).

The reaction mixture was stirred at room temperature for 16 h. The progress of the reaction was monitored by LCMS. The reaction mixture was concentrated and the crude material was purified by preparative LC/MS with the following conditions: Waters Xbridge C18, 19×150 mm, 5 μm; Guard Column: Waters XBridge C18, 19×10 mm, 5 μm; Mobile Phase A: 5:95 acetonitrile:water with 0.1% TFA; Mobile Phase B: 95:5 acetonitrile:water with 0.1% TFA; Gradient: 2-20% B over 25 minutes, followed by a 10 minute hold at 20% B and 5 minute hold at 100% B; Flow: 15 mL/min. Fractions containing the product were combined and dried using a Genevac centrifugal evaporator. The yield of the product was 5.4 mg, and its estimated purity by LCMS analysis was 100%. Two analytical LC/MS injections were used to determine the final purity. Injection 1 conditions: Column: Ascentis Express C18(50×2.1) mm, 2.7 μm; Mobile Phase A: 5:95 Acetonitrile:water with 10 mM NH$_4$OAc; Mobile Phase B: 95:5 Acetonitrile:water with 10 mM NH$_4$OAc; Temperature: 50° C.; Gradient: 0-100% B over 3 minutes; Flow: 1.1 mL/min. Injection 2 conditions: Column: Ascentis Express C18(50×2.1) mm, 2.7 μm; Mobile Phase A: 5:95 acetonitrile:water with 0.1% TFA; Mobile Phase B: 95: 5 Acetonitrile:water with 0.1% TFA; Temperature: 50° C.; Gradient: 0-100% B over 3 minutes; Flow: 1.1 mL/min. LCMS MH$^+$=360 Ret. Time=0.66 min [A1]; Proton NMR was acquired in deuterated DMSO. $^1$H NMR (400 MHz, DMSO-d$_6$) δ=11.24 (s, 1H), 9.01 (d, J=1.0

Hz, 1H), 8.66-8.55 (m, 1H), 8.03-7.96 (m, 1H), 7.79 (dd, J=9.0, 1.5 Hz, 1H), 7.57 (s, 1H), 7.35 (d, J=8.5 Hz, 1H), 7.02 (dd, J=8.3, 1.3 Hz, 1H), 3.41 (d, J=12.0 Hz, 2H), 3.30-3.23 (m, 1H), 3.10-3.00 (m, 2H), 2.96-2.90 (m, 1H), 2.03-1.94 (m, 2H), 1.91-1.84 (m, 2H), 1.45 (d, J=7.0 Hz, 6H).

Example 2

6-(3-isopropyl-5-(piperidin-4-yl)-1H-indol-2-yl)-8-methyl-[1,2,4]triazolo[1,5-a]pyridine Hydrochloride

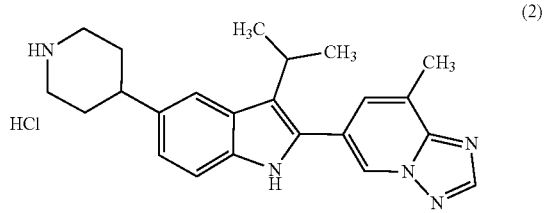 [SMILES: Cl ; Cc1cc(-c2[nH]c3ccc(C4CCNCC4)cc3c2C(C)C)cn2ncnc12]

(2)

Intermediate 2A: tert-butyl 4-(3-isopropyl-2-(8-methyl-[1,2,4]triazolo[1,5-a]pyridin-6-yl)-1H-indol-5-yl)piperidine-1-carboxylate

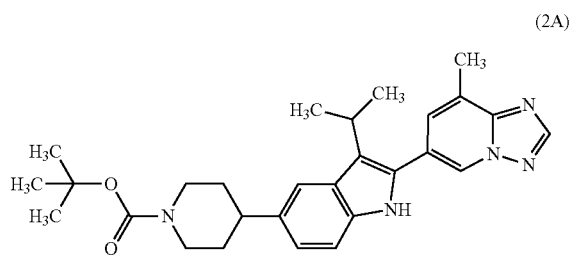 [SMILES: Cc1cc(-c2[nH]c3ccc(C4CCN(C(=O)OC(C)(C)C)CC4)cc3c2C(C)C)cn2ncnc12]

(2A)

The preparation was performed in two batches and combined for workup.
Batch #1: To a mixture of tert-butyl 4-(2-bromo-3-isopropyl-1H-indol-5-yl)piperidine-1-carboxylate (10 g, 23.73 mmol), bis(benzonitrile)palladium(II) chloride (0.182 g, 0.475 mmol), 2-dicyclohexylphosphino-2',6'-dimethoxybiphenyl (0.390 g, 0.949 mmol) in dioxane (80 mL) under nitrogen were added pinacolborane (8.61 mL, 59.3 mmol) and triethylamine (6.62 mL, 47.5 mmol). The mixture was heated at 85° C. for 5 min. After cooling down to room temperature, 2 M potassium phosphate tribasic solution (35.6 mL, 71.2 mmol) was added slowly. Next, 6-bromo-8-methyl-[1,2,4]triazolo[1,5-a]pyridine (4.53 g, 21.36 mmol) was added, followed by PdCl$_2$(dppf)-CH$_2$Cl$_2$ adduct (0.775 g, 0.949 mmol). The reaction mixture was stirred for 30 min at 65° C.

Batch #2: In a 1 L round bottom flask, pinacolborane (25.8 mL, 178 mmol) and triethylamine (19.85 mL, 142 mmol) were added to a mixture of tert-butyl 4-(2-bromo-3-isopropyl-1H-indol-5-yl)piperidine-1-carboxylate (30 g, 71.2 mmol), bis(benzonitrile) palladium(II) chloride (0.546 g, 1.424 mmol), and 2-dicyclohexylphosphino-2',6'-dimethoxybiphenyl (1.169 g, 2.85 mmol) in dioxane (240 mL) under nitrogen. The mixture was heated at 85° C. for 5 min. After cooling down to room temperature, 2 M potassium phosphate tribasic solution (107 mL, 214 mmol) was added very slowly first for the first 10 mL. When there were no more bubbles, the remainder of the K$_3$PO$_4$ solution was rapidly added, followed by the additions of 6-bromo-8-methyl-[1,2,4]triazolo[1,5-a]pyridine (13.59 g, 64.1 mmol) and PdCl$_2$(dppf)-CH$_2$Cl$_2$ adduct (2.326 g, 2.85 mmol). The reaction mixture was stirred for 1 h at 65° C.

The two batches were combined for workup. The aqueous layer was removed and the organic layer was washed with brine, dried over Na$_2$SO$_4$, filtered through a Celite pad, and concentrated to give a dark oil (87 g). The material was purified by silica gel chromatography (hexanes/ethyl acetate as eluent) affording 29 grams of the product. LCMS MH$^+$=430.1 Ret. Time=0.63 min [C1]; $^1$H NMR (400 MHz, DMSO-d$_6$) δ 11.11 (s, 1H), 8.80 (d, J=0.7 Hz, 1H), 8.53 (s, 1H), 7.65-7.52 (m, 2H), 7.30 (d, J=8.4 Hz, 1H), 7.02 (dd, J=8.4, 1.5 Hz, 1H), 4.19-4.04 (m, 2H), 3.28-3.19 (m, 1H), 2.96-2.70 (m, 3H), 2.63 (s, 6H), 2.38-2.26 (m, 1H), 1.80 (d, J=12.6 Hz, 2H), 1.56 (qd, J=12.4, 4.0 Hz, 2H), 1.47-1.38 (m, 12H).

Alternative Preparation of Intermediate 2A

To a 500 mL round bottle flask were added tert-butyl 4-(2-bromo-3-isopropyl-1H-indol-5-yl)piperidine-1-carboxylate (11 g, 26.1 mmol), bis(benzonitrile)palladium(II) chloride (0.200 g, 0.522 mmol), 2-dicyclohexylphosphino-2',6'-dimethoxybiphenyl (0.429 g, 1.044 mmol) and dioxane (87 mL). Nitrogen was bubbled through the reaction mixture for 5 min. Next, pinacolborane (9.47 ml, 65.3 mmol) and triethylamine (9.10 ml, 65.3 mmol) were added to the reaction mixture. The triethylamine was added in small portions slowly for the first ⅓ and then the rest ⅔ was added quickly. The reaction mixture was heated at 85° C. for 10 min under N$_2$. The reaction temperature reached 100° C. The reaction mixture was cooled to room temperature with an ice-water bath. Next, 2 M potassium phosphate tribasic solution (39.2 mL, 78 mmol) was added. The first ¹/₁₀ was added slowly. When there was no more bubbles, the remainder of the K$_3$PO$_4$ solution was added, followed by 6-bromo-8-methyl-[1,2,4]triazolo[1,5-a]pyridine (4.98 g, 23.49 mmol), PdCl$_2$(dppf)-CH$_2$Cl$_2$ adduct (0.853 g, 1.044 mmol) washed in with dioxane (10 mL). The mixture was heated at 65° C. for 1 h under N$_2$. After the mixture was cooled to room temperature, the organic layer and the aqueous layer was separated. EtOAc was used to wash the flask during the transfer. The organic layer was washed with brine, dried over Na$_2$SO$_4$, filtered through a Celite pad and concentrated to give 44.4 g crude oil. It was purified with silica gel chromatography using a 1.5 kg silica column. The column was eluted with hexane and ethyl acetate. The product was eluted at 60% ethyl acetate:hexane to afford tert-butyl 4-(3-isopropyl-2-(8-methyl-[1,2,4]triazolo[1,5-a]pyridin-6-yl)-1H-indol-5-yl)piperidine-1-carboxylate (9.27 g, 19.58 mmol, 75% yield) as a lighted tinted foam. LCMS MH$^+$: 474.3; HPLC Ret. Time 1.15 min. Method G. $^1$H NMR (400 MHz, CHLOROFORM-d) δ 8.61-8.54 (m, 1H), 8.43-8.38 (m, 1H), 7.96-7.88 (m, 1H), 7.70-7.64 (m, 1H), 7.48-7.44 (m, 1H), 7.40-7.35 (m, 1H), 7.17-7.09 (m, 1H), 4.40-4.23 (m, 2H), 3.40-3.26 (m, 1H), 2.75 (s, 6H), 1.98-1.89 (m, 2H), 1.85-1.67 (m, 2H), 1.53 (m, 12H), 1.52-1.49 (s, 3H).

Example 2

To a stirred solution of tert-butyl 4-(3-isopropyl-2-(8-methyl-[1,2,4]triazolo[1,5-a]pyridin-6-yl)-1H-indol-5-yl)piperidine-1-carboxylate (29 g, 61.2 mmol) in DCM (102 mL), was added 4 M HCl in dioxane (77 mL, 306 mmol)

through a syringe. The temperature was observed to increased several degrees. The solution turned into a suspension during the addition, then a clear solution, then a heavy suspension again. MeOH (306 mL) was added to give a clear solution. LCMS showed the reaction was close to completion after 2.5 hr at room temperature. The reaction mixture was concentrated under reduced pressure with a water bath (T=45° C.) and then diluted with diethyl ether (200 mL). The product was collected by filtration to afford 6-(3-isopropyl-5-(piperidin-4-yl)-1H-indol-2-yl)-8-methyl-[1,2,4]triazolo[1,5-a]pyridine dihydrochloride. LC-MS: M+1=374, rt=0.80 min., [A1]; $^1$H NMR (400 MHz, DMSO-$d_6$) δ 11.10 (s, 1H), 8.80 (d, J=0.7 Hz, 1H), 8.54 (s, 1H), 7.66-7.50 (m, 2H), 7.30 (d, J=8.3 Hz, 1H), 7.02 (dd, J=8.4, 1.5 Hz, 1H), 4.09 (q, J=5.3 Hz, 1H), 3.38-3.23 (m, 6H), 3.18 (d, J=5.3 Hz, 2H), 3.06 (d, J=11.5 Hz, 1H), 2.74-2.59 (m, 4H), 1.75 (d, J=10.0 Hz, 2H), 1.68-1.52 (m, 2H), 1.51-1.37 (m, 6H).

Alternative Preparation of Example 2

To a stirred solution of tert-butyl 4-(3-isopropyl-2-(8-methyl-[1,2,4]triazolo[1,5-a]pyridin-6-yl)-1H-indol-5-yl)piperidine-1-carboxylate (7.45 g, 15.73 mmol) in DCM (40 mL) was added 4 M HCl in dioxane (35.4 mL, 142 mmol) through a syringe at room temperature. The solution turned to a suspension during the addition, then a clear solution, then a heavy suspension again. MeOH (100 mL) was added to give a clear solution. The reaction was complete in 2 h. The reaction mixture was concentrated under reduced pressure and then diluted with diethyl ether (200 mL). The desired product HCl salt was collected by filtration to afford 6-(3-isopropyl-5-(piperidin-4-yl)-1H-indol-2-yl)-8-methyl-[1,2,4]triazolo[1,5-a]pyridine hydrochloride (6.4 g, 15.64 mmol, 99.4% yield) as a yellow. LCMS MH$^+$: 374.1; HPLC Ret. Time 0.64 min. Method G.

The following examples were prepared according to the general procedures disclosed in Examples 1 and 2.

TABLE 3

| Ex. No. | Structure | Interm. | LCMS [M + H] | Rt (min) | Method |
|---|---|---|---|---|---|
| 3 | 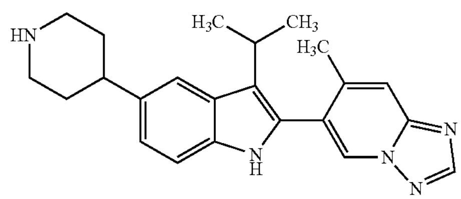 [SMILES: Cc1cc2ncnn2cc1-c1[nH]c2ccc(C3CCNCC3)cc2c1C(C)C] | F-3 | 374.3 | 1.07 | QC-ACN-TFA-XB |
| 4 | 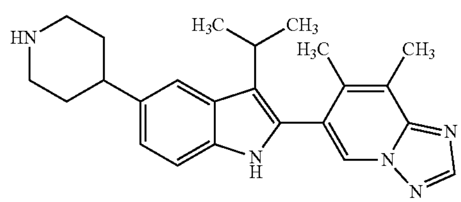 [SMILES: Cc1c(-c2[nH]c3ccc(C4CCNCC4)cc3c2C(C)C)cn2ncnc2c1C] | F-4 | 388.3 | 1.26 | QC-ACN-AA-XB |
| 5 | 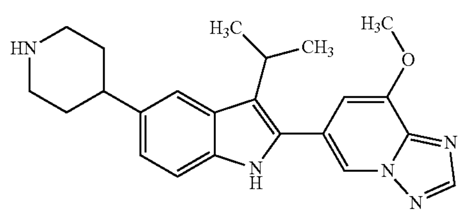 [SMILES: COc1cc(-c2[nH]c3ccc(C4CCNCC4)cc3c2C(C)C)cn2ncnc12] | F-5 | 390.3 | 1.02 | Method E |
| 6 | 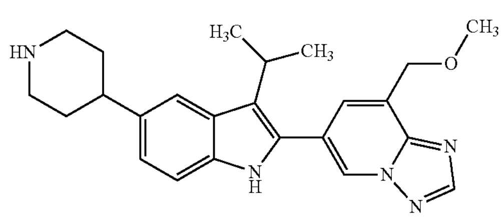 [SMILES: COCc1cc(-c2[nH]c3ccc(C4CCNCC4)cc3c2C(C)C)cn2ncnc12] | F-6 | 404.3 | 1.21 | QC-ACN-AA-XB |

Example 4

6-(3-isopropyl-5-(piperidin-4-yl)-1H-indol-2-yl)-7,8-dimethyl-[1,2,4]triazolo[1,5-a]pyridine Dihydrochloride

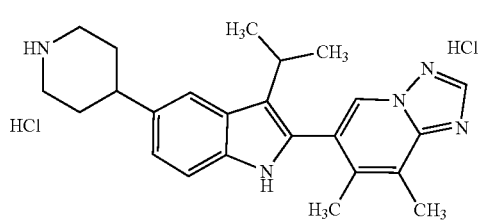

(4)

To a stirred suspension of tert-butyl 4-(2-(7,8-dimethyl-[1,2,4]triazolo[1,5-a]pyridin-6-yl)-3-isopropyl-1H-indol-5-yl)piperidine-1-carboxylate (37.8 g, 78 mmol) in DCM (97 ml) and MeOH (291 ml) was added 4 M HCl in dioxane (97 mL, 388 mmol) at room temperature to give a clear solution. After a few hours, the reaction mixture became a white suspension. The reaction was complete after 4 h. The reaction mixture was concentrated under reduced pressure and then diluted with diethyl ether (250 mL). The product bis-HCl salt was collected by filtration to afford 6-(3-isopropyl-5-(piperidin-4-yl)-1H-indol-2-yl)-7,8-dimethyl-[1,2,4]triazolo[1,5-a]pyridine, 2 HCl (34.66 g, 75 mmol, 97% yield) as an off-white solid. LCMS MH$^+$. 388.3; HPLC Ret. Time 1.26 min. Method QC-ACN-AA-XB. $^1$H NMR (500 MHz, DMSO-d$_6$) δ 11.08-10.95 (m, 1H), 8.77-8.67 (m, 1H), 8.55-8.41 (m, 1H), 7.64-7.48 (m, 1H), 7.39-7.27 (m, 1H), 7.05-6.94 (m, 1H), 3.47-3.34 (m, 1H), 3.11-2.99 (m, 2H), 2.98-2.82 (m, 2H), 2.61-2.57 (m, 3H), 2.56-2.54 (m, 1H), 2.18-2.13 (m, 3H), 2.03-1.83 (m, 4H), 1.39-1.26 (m, 6H).

Example 5

6-(3-isopropyl-5-(piperidin-4-yl)-1H-indol-2-yl)-8-methoxy-[1,2,4]triazolo[1,5-a]pyridine Dihydrochloride

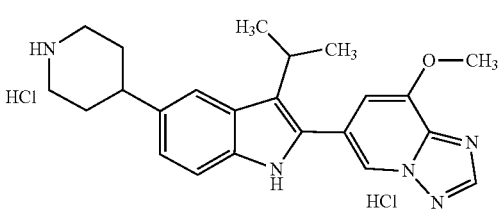

(5)

To a stirred suspension of tert-butyl 4-(3-isopropyl-2-(8-methoxy-[1,2,4]triazolo[1,5-a]pyridin-6-yl)-1H-indol-5-yl)piperidine-1-carboxylate (46.5 g, 95 mmol) in DCM (47.5 mL) and MeOH (190 mL), was added 4 M HCl in dioxane (119 mL, 475 mmol) at room temperature. After 1 h, the clear solution became a white suspension. MeOH (50 mL) was added and the suspension was stirred for another hour. The reaction mixture was concentrated under reduced pressure and then diluted with diethyl ether (300 mL). The desired product HCl salt was collected by filtration and dried for two days to afford 6-(3-isopropyl-5-(piperidin-4-yl)-1H-indol-2-yl)-8-methoxy-[1,2,4]triazolo[1,5-a]pyridine dihydrochloride (33.6 g, 72.7 mmol, 76% yield) as an off-white solid. LCMS MH+. 390.1. HPLC Ret. Time 0.64 min. Method G.

Example 7

2-(4-(3-isopropyl-2-(8-methyl-[1,2,4]triazolo[1,5-a]pyridin-6-yl)-1H-indol-5-yl)piperidin-1-yl)-N-methylacetamide

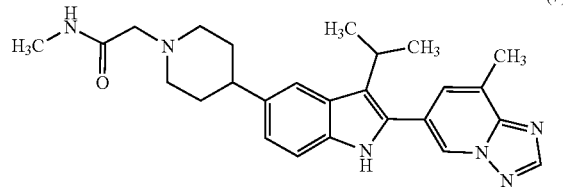

(7)

Triethylamine (9.70 mL, 69.6 mmol) and 2-chloro-N-methylacetamide (2.246 g, 20.88 mmol) were added to a solution of 6-(3-isopropyl-5-(piperidin-4-yl)-1H-indol-2-yl)-8-methyl-[1,2,4]triazolo[1,5-a]pyridine (2.6 g, 6.96 mmol) in THF (50 mL). The reaction mixture was stirred at room temperature for 12 h. The reaction mass was concentrated under vacuum and the residue obtained was quenched with 150 mL ice cold water resulting in the formation of a precipitate. The solids were collected by vacuum filtration and air dried. The collected solids were further dried under vacuum for 15 h to afford 2-(4-(3-isopropyl-2-(8-methyl-[1,2,4]triazolo[1,5-a]pyridin-6-yl)-1H-indol-5-yl) piperidin-1-yl)-N-methylacetamide (1.5 g) as an off-white solid. $^1$H NMR (400 MHz, DMSO-d$_6$) δ 1.42 (d, J=7.20 Hz, 6H), 1.69-1.72 (m, 4H), 1.75-1.81 (m, 1H), 2.78-2.82 (m, 6H), 2.85-2.88 (m, 4H), 3.25-3.31 (m, 2H), 7.05 (dd, J=1.60, 8.40 Hz, 1H), 7.31 (d, J=8.40 Hz, 1H), 7.59 (d, J=10.00 Hz, 2H), 7.72-7.73 (m, 1H), 8.54 (s, 1H), 8.81 (s, 1H), 11.12 (s, 1H). LCMS for molecular formula $C_{26}H_{32}N_6O$ was 444.264; found 445 (M$^+$). Waters Xbridge C18, 19×150 mm, 5 μm; Guard Column: Waters XBridge C18, 19×10 mm, 5 μm; Mobile Phase A: 5:95 Acetonitrile:water with 10 mM NH$_4$OAc; Mobile Phase B: 95:5 Acetonitrile:water with 10 mM NH$_4$OAc; Gradient: 10-50% B over 25 minutes, followed by a 10 minute hold at 50% B and 5 minute hold at 100% B; Flow: 15 mL/min. RT Min: 1.91, Wave length: 220 nm. HPLC: XBridge Phenyl (4.6×150) mm, 3.5 μm SC/749 Buffer: 0.05% TFA in water pH 2.5 Mobile Phase A: Buffer:ACN (95:5) Mobile Phase B: ACN:Buffer (95:5) FLOW: 1 mL\min TIME B % 0 10, 12 100, 15 100. Retention Time: 6.19 minutes.

The following examples were prepared according to the general procedures disclosed in Example 7.

TABLE 4

| Ex. No. | Structure | LCMS MH+ | R$_t$ (min) | Method |
|---|---|---|---|---|
| 8 | 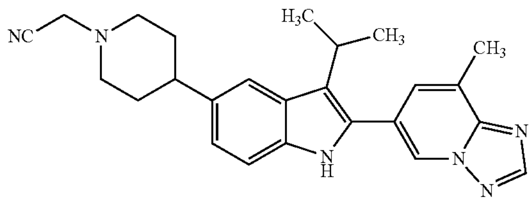 [SMILES: Cc1cc(-c2[nH]c3ccc(C4CCN(CC#N)CC4)cc3c2C(C)C)cn2ncnc12] | 413.3 | 1.28 | QC-ACN-TFA-XB |
| 9 | 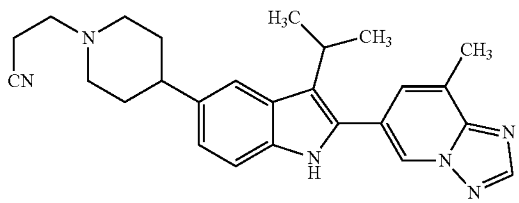 [SMILES: Cc1cc(-c2[nH]c3ccc(C4CCN(CCC#N)CC4)cc3c2C(C)C)cn2ncnc12] | 427.2 | 1.82 | QC-ACN-AA-XB |
| 10 | 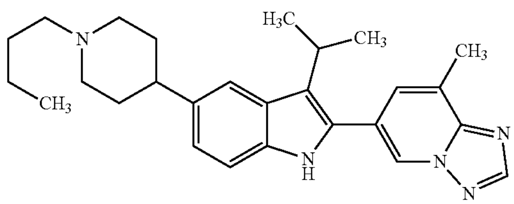 [SMILES: CCCCN1CCC(c2ccc3[nH]c(-c4cc(C)c5ncnn5c4)c(C(C)C)c3c2)CC1] | 430 | 1.57 | QC-ACN-AA-XB |
| 11 | 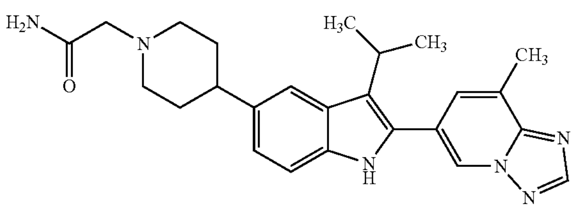 [SMILES: Cc1cc(-c2[nH]c3ccc(C4CCN(CC(N)=O)CC4)cc3c2C(C)C)cn2ncnc12] | 431.4 | 1.24 | QC-ACN-AA-XB |
| 12 | 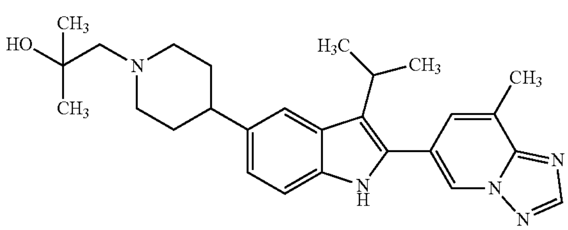 [SMILES: Cc1cc(-c2[nH]c3ccc(C4CCN(CC(C)(C)O)CC4)cc3c2C(C)C)cn2ncnc12] | 446.3 | 1.707 | Method E |
| 13 | 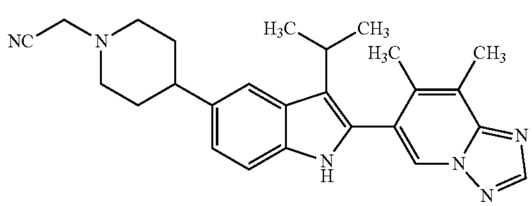 [SMILES: Cc1c(-c2[nH]c3ccc(C4CCN(CC#N)CC4)cc3c2C(C)C)cn2ncnc2c1C] | 427.3 | 1.46 | QC-ACN-TFA-XB |
| 14 | 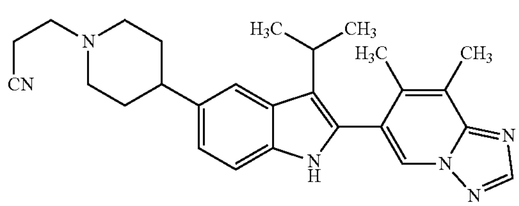 [SMILES: Cc1c(-c2[nH]c3ccc(C4CCN(CCC#N)CC4)cc3c2C(C)C)cn2ncnc2c1C] | 441.3 | 1.27 | QC-ACN-TFA-XB |

TABLE 4-continued

| Ex. No. | Structure | LCMS MH+ | R$_t$ (min) | Method |
|---|---|---|---|---|
| 15 | 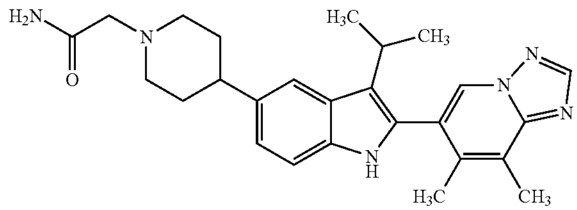 [SMILES: Cc1c(-c2[nH]c3ccc(C4CCN(CC(N)=O)CC4)cc3c2C(C)C)cn2ncnc2c1C] | 445 | 1.19 | QC-ACN-TFA-XB |
| 16 | 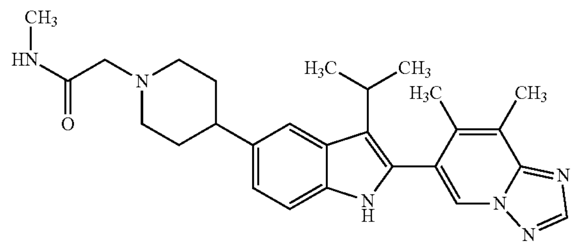 [SMILES: CNC(=O)CN1CCC(c2ccc3[nH]c(-c4cn5ncnc5c(C)c4C)c(C(C)C)c3c2)CC1] | 459.5 | 1.71 | QC-ACN-AA-XB |
| 17 | 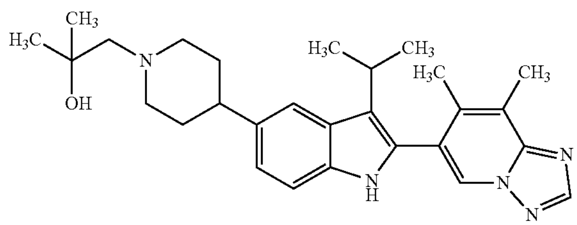 [SMILES: Cc1c(-c2[nH]c3ccc(C4CCN(CC(C)(C)O)CC4)cc3c2C(C)C)cn2ncnc2c1C] | 460 | 1.7 | QC-ACN-AA-XB |
| 18 | 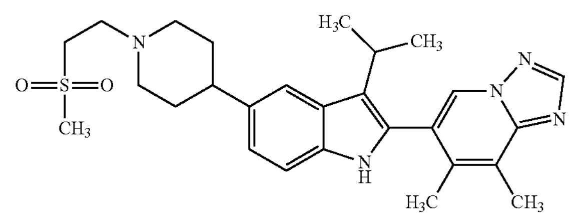 [SMILES: Cc1c(-c2[nH]c3ccc(C4CCN(CCS(C)(=O)=O)CC4)cc3c2C(C)C)cn2ncnc2c1C] | 494.3 | 1.71 | QC-ACN-AA-XB |
| 19 | 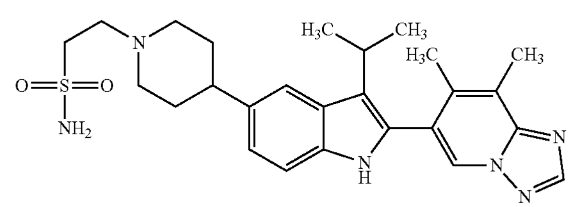 [SMILES: Cc1c(-c2[nH]c3ccc(C4CCN(CCS(N)(=O)=O)CC4)cc3c2C(C)C)cn2ncnc2c1C] | 495.2 | 1.62 | QC-ACN-AA-XB |
| 20 | 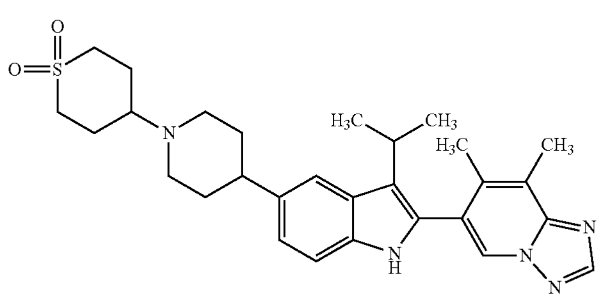 [SMILES: Cc1c(-c2[nH]c3ccc(C4CCN(C5CCS(=O)(=O)CC5)CC4)cc3c2C(C)C)cn2ncnc2c1C] | 520.5 | 1.31 | QC-ACN-TFA-XB |

TABLE 4-continued

| Ex. No. | Structure | LCMS MH+ | $R_t$ (min) | Method |
|---|---|---|---|---|
| 21 | 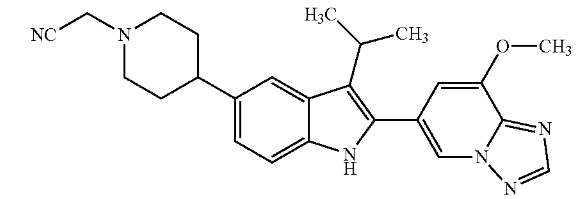 [SMILES: COc1cc(-c2[nH]c3ccc(C4CCN(CC#N)CC4)cc3c2C(C)C)cn2ncnc12] | 429.2 | 1.94 | Method E |
| 22 | 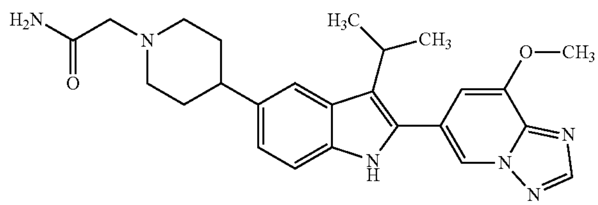 [SMILES: COc1cc(-c2[nH]c3ccc(C4CCN(CC(N)=O)CC4)cc3c2C(C)C)cn2ncnc12] | 447.2 | 1.64 | Method E |
| 23 | 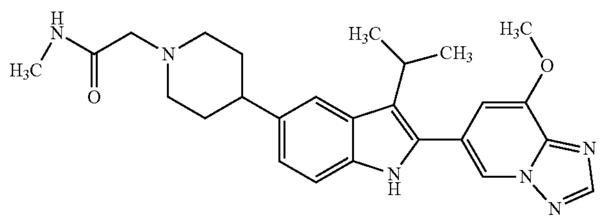 [SMILES: CNC(=O)CN1CCC(c2ccc3[nH]c(-c4cc(OC)c5ncnn5c4)c(C(C)C)c3c2)CC1] | 461.2 | 1.73 | Method E |
| 24 | 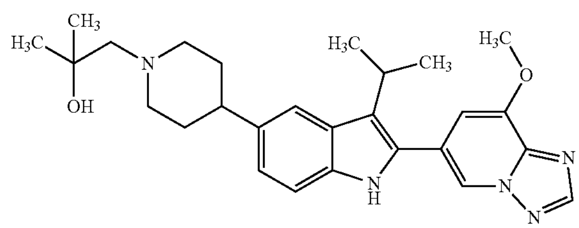 [SMILES: COc1cc(-c2[nH]c3ccc(C4CCN(CC(C)(C)O)CC4)cc3c2C(C)C)cn2ncnc12] | 462.4 | 1.40 | Method E |
| 25 | 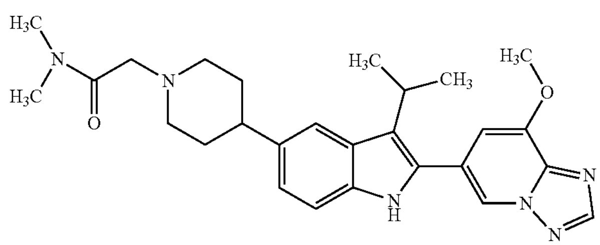 [SMILES: COc1cc(-c2[nH]c3ccc(C4CCN(CC(=O)N(C)C)CC4)cc3c2C(C)C)cn2ncnc12] | 475.4 | 1.37 | Method E |

Example 13

2-(4-(2-(7,8-dimethyl-[1,2,4]triazolo[1,5-a]pyridin-6-yl)-3-isopropyl-1H-indol-5-yl)piperidin-1-yl)acetonitrile (13)

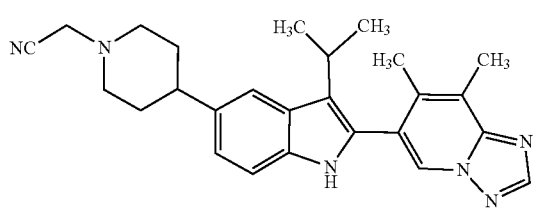

To a 1 dram vial were added 6-(3-isopropyl-5-(piperidin-4-yl)-1H-indol-2-yl)-7,8-dimethyl-[1,2,4]triazolo[1,5-a]pyridine hydrochloride (0.050 g, 0.118 mmol), NMP, and DBU (0.025 ml, 0.164 mmol). The material went into solution and 2-bromoacetonitrile (0.014 g, 0.118 mmol) was added. The reaction vial was capped. The reaction mixture was stirred overnight at room temperature. The sample was diluted with solvent (90:10:0.1 CH₃CN:water:TFA), filtered, and purified with preparative HLPC. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 30-70% B over 20 minutes, then a 5-minute hold at 100% B; Flow: 20 mL/min. Fractions containing the desired product were combined and dried via centrifugal evaporation to afford 2-(4-(2-(7,8-dimethyl-[1,2,4]triazolo[1,5-a]pyridin-6-yl)-3-isopropyl-1H-indol-5-yl) piperidin-1-yl)acetonitrile (16.8 mg, 0.039 mmol, 32.7% yield). LCMS MH+: 427.1. HPLC Ret. Time 1.30 min. Method QC-ACN-TFA-XB. $^1$H NMR (500 MHz, DMSO-$d_6$) δ 8.77-8.69 (m, 1H), 8.50-8.35 (m, 1H), 7.61-7.51 (m, 1H), 7.33-7.23 (m, 1H), 7.08-6.93 (m, 1H), 3.44-3.34 (m, 1H), 2.98-2.83 (m, 3H), 2.63-2.56 (m, 4H), 2.56-2.53 (m, 2H), 2.39-2.28 (m, 2H), 2.21-2.12 (m, 3H), 1.90-1.69 (m, 4H), 1.37-1.26 (m, 6H).

Example 15

2-(4-(2-(7,8-dimethyl-[1,2,4]triazolo[1,5-a]pyridin-6-yl)-3-isopropyl-1H-indol-5-yl) piperidin-1-yl)acetamide (15)

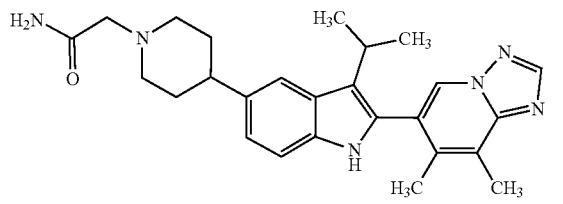

To a reaction flask were added 6-(3-isopropyl-5-(piperidin-4-yl)-1H-indol-2-yl)-7,8-dimethyl-[1,2,4]triazolo[1,5-a]pyridine, 2 HCl (47.66 g, 104 mmol), DCE (220 mL), DBU (62.4 mL, 414 mmol), and 2-bromoacetamide (17.14 g, 124 mmol). The reaction flask was capped. The reaction mixture was stirred overnight at room temperature. The reaction mixture was concentrated, diluted with water, and stirred for 30 minutes then filtered. The solid was recrystallized using ethanol to afford 2-(4-(2-(7,8-dimethyl-[1,2,4]triazolo[1,5-a]pyridin-6-yl)-3-isopropyl-1H-indol-5-yl)piperidin-1-yl) acetamide (42.3 g, 93 mmol, 90% yield) as a white solid. LCMS MH+: 445. HPLC Ret. Time 1.20 min. Method QC-ACN-TFA-XB. $^1$H NMR (400 MHz, DMSO-$d_6$) δ 10.97-10.86 (m, 1H), 8.78-8.69 (m, 1H), 8.54-8.40 (m, 1H), 7.64-7.49 (m, 1H), 7.30-7.21 (m, 2H), 7.17-7.09 (m, 1H), 7.06-6.93 (m, 1H), 2.99-2.82 (m, 5H), 2.62-2.54 (m, 4H), 2.24-2.12 (m, 5H), 1.92-1.72 (m, 4H), 1.37-1.29 (m, 6H).

Example 18

6-(3-isopropyl-5-(1-(2-(methylsulfonyl)ethyl)piperidin-4-yl)-1H-indol-2-yl)-7,8-dimethyl-[1,2,4]triazolo[1,5-a]pyridine (18)

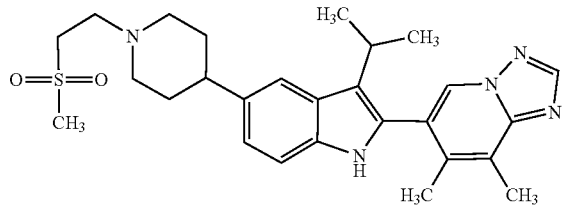

Preparation 1

To a 40 ml vial was added 6-(3-isopropyl-5-(piperidin-4-yl)-1H-indol-2-yl)-7,8-dimethyl-[1,2,4]triazolo[1,5-a]pyridine (0.800 g, 2.064 mmol), DCM (5 mL) and DBU (0.622 mL, 4.13 mmol). The material went into solution and 2-bromoacetamide (0.299 g, 2.168 mmol) was added. The reaction vial was capped. The reaction mixture was stirred overnight at room temperature. The reaction mixture was diluted with water and extracted with DCM. The organics were washed with brine, dried over Na$_2$SO$_4$, filtered and concentrated. The residue was dissolved in minimal DCM and purified by silica gel chromatography, eluting with 0-10% MeOH/DCM. Following concentration of the fractions, the product was collected as a white solid (0.6 g). To this was added 40 mL of a 10% MeOH/ethyl acetate solution and the suspension was taken to a boil. The solids were filtered off and rinsed with hot MeOH/ethyl acetate (1:10). The filtrate was reheated and capped to recrystallize. After 3 days, the white solid was filtered off and washed with ethyl acetate, then ether, and dried on the vacuum pump overnight to afford 2-(4-(2-(7,8-dimethyl-[1,2,4]triazolo[1,5-a]pyridin-6-yl)-3-isopropyl-1H-indol-5-yl)piperidin-1-yl)acetamide (480 mg, 1.07 mmol, 51.8% yield). MS (M*$^1$) m/z: 445.3 (MH+). LC retention time 0.69 min [G]. $^1$H NMR (400 MHz, DMSO-$d_6$) δ 11.00-10.85 (m, 1H), 8.79-8.69 (m, 1H), 8.53-8.43 (m, 1H), 7.60-7.49 (m, 1H), 7.32-7.21 (m, 2H), 7.18-7.11 (m, 1H), 7.06-6.99 (m, 1H), 3.00-2.83 (m, 5H), 2.63-2.55 (m, 4H), 2.24-2.12 (m, 5H), 1.92-1.72 (m, 4H), 1.40-1.24 (m, 6H).

Preparation 2

To a reaction vial were added 6-(3-isopropyl-5-(piperidin-4-yl)-1H-indol-2-yl)-7,8-dimethyl-[1,2,4]triazolo[1,5-a]pyridine, 2 HCl (40 g, 87 mmol), DCE (280 mL), and DBU (45.8 mL, 304 mmol). The material went into solution and 1-bromo-2-(methylsulfonyl) ethane (18.46 g, 99 mmol) was added. The reaction mixture was stirred overnight at room temperature under N$_2$. The sample was concentrated, diluted with water, stirred for 30 minutes, and then filtered. The solid was recrystallized using EtOH to afford 6-(3-isopropyl-5-(1-(2-(methylsulfonyl)ethyl)piperidin-4-yl)-1H-indol-2-yl)-7,8-dimethyl-[1,2,4]triazolo[1,5-a]pyridine (40 g, 81 mmol, 93% yield) as a white solid. LCMS MH+: 494.3; HPLC Ret. Time 1.70 min. Method QC-ACN-AA-XB. $^1$H NMR (400 MHz, CHLOROFORM-d) δ 8.45-8.38 (m, 1H), 8.37-8.30 (m, 1H), 8.18-8.12 (m, 1H), 7.69-7.62 (m, 1H), 7.43-7.35 (m, 1H), 7.19-7.12 (m, 1H), 3.29-3.20 (m, 2H), 3.16-3.07 (m, 5H), 3.02-2.92 (m, 3H), 2.74-2.67 (m, 1H), 2.66-2.60 (m, 3H), 2.31-2.22 (m, 2H), 2.21-2.17 (m, 3H), 2.07-1.79 (m, 4H), 1.42-1.35 (m, 6H).

Example 25

2-(4-(3-isopropyl-2-(8-methoxy-[1,2,4]triazolo[1,5-a]pyridin-6-yl)-1H-indol-5-yl)piperidin-1-yl)-N,N-dimethylacetamide (25)

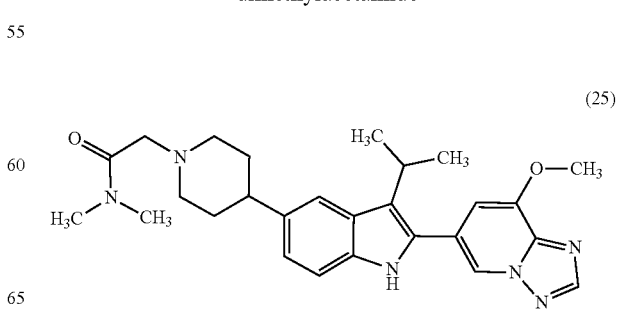

Preparation 1

To a solution of 6-(3-isopropyl-5-(piperidin-4-yl)-1H-indol-2-yl)-8-methoxy-[1,2,4]triazolo[1,5-a]pyridine (0.05 g, 0.128 mmol) in THF (2 mL) and DMF (1 mL) solvent mixture were added 2-chloro-N,N-dimethylacetamide (0.023 g, 0.193 mmol) and TEA (0.179 mL, 1.284 mmol) at room temperature. The reaction mixture was stirred at room temperature for 24 h. The reaction mixture was concentrated under vacuum. To the solid material was added water (5 mL) and extracted with ethyl acetate. The organic layer was dried over Na$_2$SO$_4$, filtered and concentrated under vacuum. The crude material was purified via preparative LC/MS with the following conditions: Column: Waters XBridge C18, 19×150 mm, 5 μm particles; Mobile Phase A: 10 mM ammonium acetate; Mobile Phase B: methanol; Gradient: 10-50% B over 30 minutes, then a 5-minute hold at 100% B; Flow: 15 mL/min. Fractions containing the product were combined and dried via centrifugal evaporation to afford 2-(4-(3-isopropyl-2-(8-methoxy-[1,2,4]triazolo[1,5-a]pyridin-6-yl)-1H-indol-5-yl)piperid in-1-yl)-N,N-dimethylacetamide (14.2 mg, 0.03 mmol, 23.31% yield). MS (M$^{+1}$) m/z: 475.4 (MH$^+$). LC retention time 1.38 min [A]. $^1$H NMR (400 MHz, DMSO-d$_6$) δ 11.38 (s, 1H), 8.83-8.75 (m, 2H), 7.83 (s, 1H), 7.57 (d, J=8.3 Hz, 1H), 7.41 (d, J=1.2 Hz, 1H), 7.30 (dd, J=8.4, 1.6 Hz, 1H), 4.34 (s, 3H), 3.43 (d, J=5.9 Hz, 3H), 3.34 (s, 4H), 3.22 (d, J=11.0 Hz, 4H), 3.09 (s, 3H), 2.79 (d, J=1.7 Hz, 3H), 2.48-2.38 (m, 2H), 2.15 (s, 5H), 2.08-1.95 (m, 4H), 1.72 (d, J=7.1 Hz, 6H).

Preparation 2

To a solution of 6-(3-isopropyl-5-(piperidin-4-yl)-1H-indol-2-yl)-8-methoxy-[1,2,4]triazolo[1,5-a]pyridin e, HCl (30.6 g, 71.8 mmol) in a DMF (700 mL) solvent mixture were added 2-chloro-N,N-dimethylacetamide (9.62 mL, 93 mmol) and TEA (50.1 mL, 359 mmol) at room temperature. The reaction mixture was stirred at room temperature for 12 h. The starting material was converted to product. Next, water (2 L) was added to the above solution, the upper layer and the lower layer were extracted with ethyl acetate. The combination of the organic layers was washed with brine, dried and concentrated to give a solid, which was purified by recrystallization from ethanol to afford 2-(4-(3-isopropyl-2-(8-methoxy-[1,2,4]triazolo[1,5-a]pyridin-6-yl)-1H-indol-5-yl)piperid in-1-yl)-N,N-dimethylacetamide (28.3 g, 59.3 mmol, 83% yield). LCMS MH$^+$: 475.2. HPLC Ret. Time 0.66 min. Method G. C: 68.28%, H: 7.19%, N: 17.63%.

Example 26

6-(3-isopropyl-5-(1-(oxetan-3-yl)piperidin-4-yl)-1H-indol-2-yl)-8-methyl-[1,2,4]triazolo [1,5-a]pyridine (26)

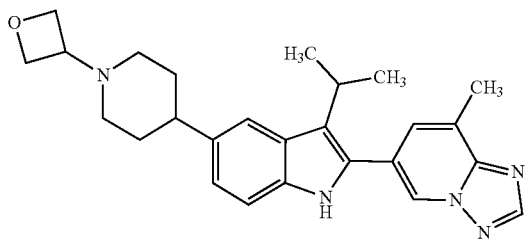

To a solution of 6-(3-isopropyl-5-(piperidin-4-yl)-1H-indol-2-yl)-8-methyl-[1,2,4]triazolo[1,5-a]pyridine hydrochloride (24.5 g, 59.8 mmol) in DCM (610 mL) were added triethylamine (24.19 g, 239 mmol), oxetan-3-one (17.23 g, 239 mmol), acetic acid (7.18 g, 120 mmol), and sodium triacetoxyborohydride (50.7 g, 239 mmol). The solution was stirred at room temperature. After 5 min, LCMS showed 20% conversion; and after overnight, HPLC showed no starting material. The solvent was removed under vacuum. The residue was dissolved in 500 mL ethyl acetate and washed with saturated NaHCO$_3$ solution (4×300 mL), dried over Na$_2$SO$_4$, and concentrated under reduced pressure. The residue was purified by recrystallization from a mixture of EtOH/water (20/80), dried to afford 6-(3-isopropyl-5-(1-(oxetan-3-yl)piperidin-4-yl)-1H-indol-2-yl)-8-methyl-[1,2,4]triazolo [1,5-a]pyridine (24.6 g, 57.0 mmol, 95% yield) as a white solid. LCMS MH$^+$=430.1 Ret. Time=0.63 min; Column: BEH C18 2.1×50 mm 1.7 μm Vial: 3:1; HPLC Ret. Time 7.86 min. Waters XSelect CSH C18 2.5 μM 4.6 μM×7.5 mm. Solvent A: H$_2$O w/0.1% TFA. Solvent B ACN w/0.1% TFA. Gradient Complex Start % B 10% 16 min 45% B 20 min 90% 24 min 90% 25 min 10% Stop time 25 min Flow Rate 1.5 mL/min. $^1$H NMR (500 MHz, DMSO-d$_6$) δ 11.11 (s, 1H), 8.75 (s, 1H), 8.51 (s, 1H), 7.56 (d, J=16.5 Hz, 2H), 7.30 (d, J=8.4 Hz, 1H), 7.03 (d, J=8.3 Hz, 1H), 4.64-4.33 (m, 4H), 4.72-4.27 (m, 4H), 3.65 (br. s., 2H), 3.47-3.12 (m, 2H), 2.79 (d, J=10.4 Hz, 2H), 2.61 (s, 3H), 1.99-1.59 (m, 7H), 1.41 (d, J=6.8 Hz, 6H).

Alternative Preparation of Example 26

To a solution of 6-(3-isopropyl-5-(piperidin-4-yl)-1H-indol-2-yl)-8-methyl-[1,2,4]triazolo[1,5-a]pyridine hydrochloride (24.5 g, 59.8 mmol) in DCM (610 ml) were added triethylamine (24.19 g, 239 mmol), oxetan-3-one (17.23 g, 239 mmol), acetic acid (7.18 g, 120 mmol) and sodium triacetoxyborohydride (50.7 g, 239 mmol). The solution was stirred at room temperature, after 5 min the reaction progressed 20%. The reaction went to completion overnight. The solvent was removed under reduced pressure. The residue was dissolved in 500 mL ethyl acetate and washed with saturated NaHCO$_3$ solution (300 mL×4), dried over Na$_2$SO$_4$, and concentrated under reduced pressure to afford the crude product. The crude material was purified to remove Pd in the treatment described below and recrystallized from a mixture of EtOH/water (20/80) and dried to afford 6-(3-isopropyl-5-(1-(oxetan-3-yl) piperidin-4-yl)-1H-indol-2-yl)-8-methyl-[1,2,4]triazolo[1,5-a]pyridine (24.6 g, 57.0 mmol, 95% yield) as a solid. LCMS MH$^+$: 430.1; HPLC Ret. Time 0.63 min. Method G; $^1$H NMR (400 MHz, DMSO-d$_6$) δ 11.18-11.05 (m, 1H), 8.88-8.76 (m, 1H), 8.58-8.47 (m, 1H), 7.64-7.54 (m, 2H), 7.34-7.26 (m, 1H), 7.09-6.96 (m, 1H), 4.61-4.53 (m, 2H), 4.51-4.42 (m, 2H), 3.48-3.37 (m, 1H), 3.31-3.20 (m, 1H), 2.86-2.78 (m, 2H), 2.68-2.63 (m, 3H), 2.63-2.55 (m, 1H), 1.96-1.68 (m, 6H), 1.49-1.38 (m, 6H).

Pd Removal Procedure: The sample was treated to remove Pd using the following steps: 1. The crude sample was dissolved in 500 mL THF and treated with SiliaMetS@DMT (40 g, from SiliCycle). The solution was stirred overnight at room temperature under N$_2$. 2. After filtration, the solvent was removed and the residue was dissolved in AcOEt and washed with brine and dried. 3. After concentration, the residue was recrystallized from EtOH-water (20/80) to afford the product.

The following examples were prepared according to the general procedure of Examples 26.

TABLE 5

| Ex. No. | Structure | LCMS MH+ | R$_t$ (min) | Method |
|---|---|---|---|---|
| 27 | 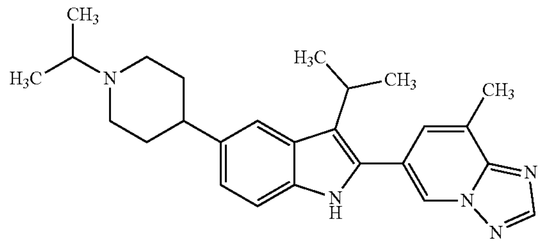 [SMILES: Cc1cc(-c2[nH]c3ccc(C4CCN(C(C)C)CC4)cc3c2C(C)C)cn2ncnc12] | 416.4 | 2.39 | Method F |
| 28 | 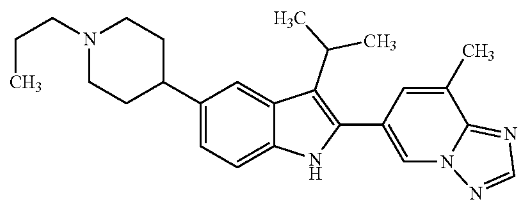 [SMILES: CCCN1CCC(c2ccc3[nH]c(-c4cc(C)c5ncnn5c4)c(C(C)C)c3c2)CC1] | 416 | 1.43 | QC-ACN-AA-XB |
| 29 | 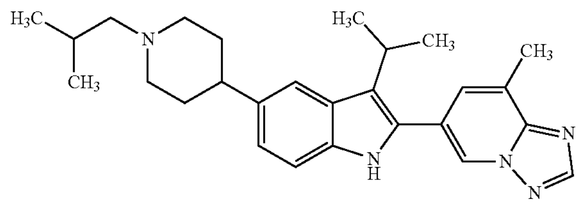 | 430.1 | 1.7 | QC-ACN-AA-XB |
| 30 | 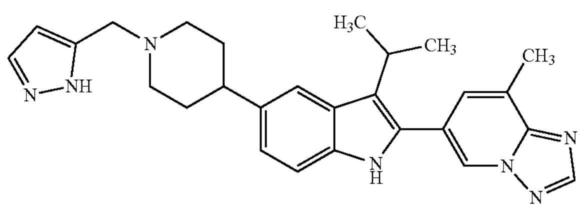 [SMILES: Cc1cc(-c2[nH]c3ccc(C4CCN(Cc5ccn[nH]5)CC4)cc3c2C(C)C)cn2ncnc12] | 454.2 | 1.29 | QC-ACN-TFA-XB |
| 31 | 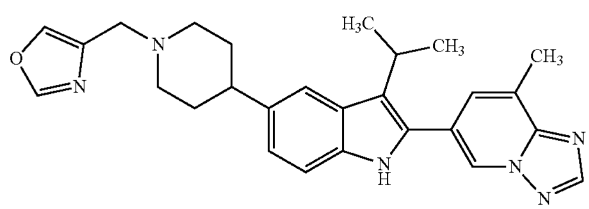 [SMILES: Cc1cc(-c2[nH]c3ccc(C4CCN(Cc5cocn5)CC4)cc3c2C(C)C)cn2ncnc12] | 455.3 | 1.54 | QC-ACN-AA-XB |
| 32 | 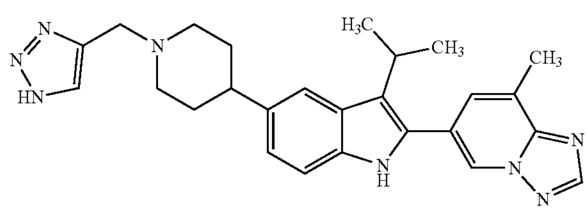 [SMILES: Cc1cc(-c2[nH]c3ccc(C4CCN(Cc5c[nH]nn5)CC4)cc3c2C(C)C)cn2ncnc12] | 455.2 | 1.22 | QC-ACN-TFA-XB |
| 33 | 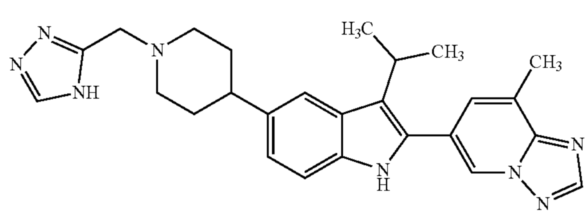 | 455.4 | 1.11 | QC-ACN-TFA-XB |

TABLE 5-continued

| Ex. No. | Structure | LCMS MH+ | R$_t$ (min) | Method |
|---|---|---|---|---|
| 34 | 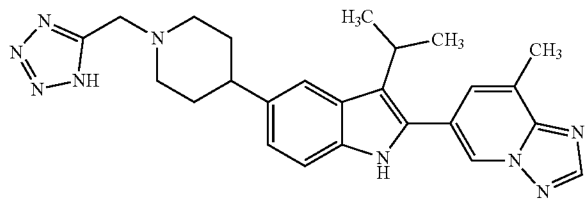 [SMILES: Cc1cc(-c2[nH]c3ccc(C4CCN(Cc5nnn[nH]5)CC4)cc3c2C(C)C)cn2ncnc12] | 455.9 | 1.13 | QC-ACN-AA-XB |
| 35 | 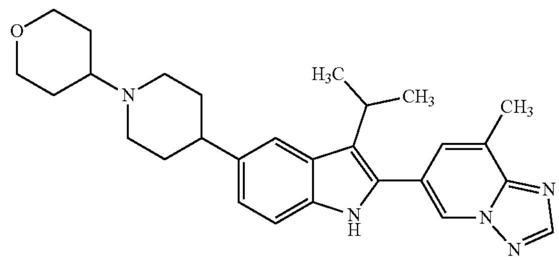 [SMILES: Cc1cc(-c2[nH]c3ccc(C4CCN(C5CCOCC5)CC4)cc3c2C(C)C)cn2ncnc12] | 458.4 | 1.33 | QC-ACN-AA-XB |
| 36 | 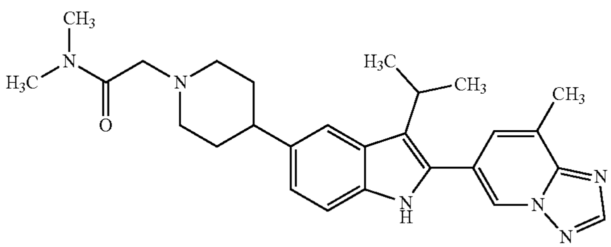 | 459.3 | 1.37 | Method A |
| 37 | 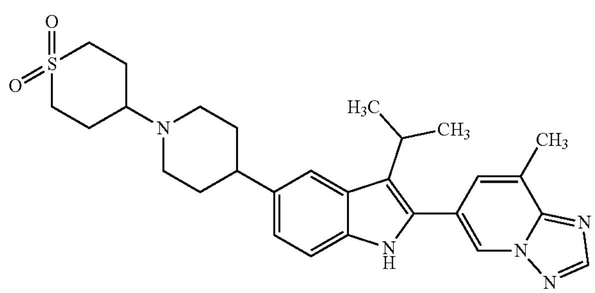 | 506.3 | 1.43 | QC-ACN-AA-XB |
| 38 | 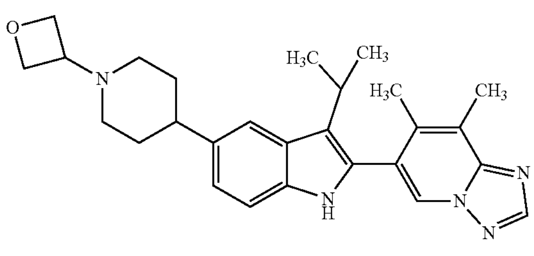 [SMILES: Cc1c(-c2[nH]c3ccc(C4CCN(C5COC5)CC4)cc3c2C(C)C)cn2ncnc2c1C] | 444.3 | 1.24 | QC-ACN-TFA-XB |
| 39 | 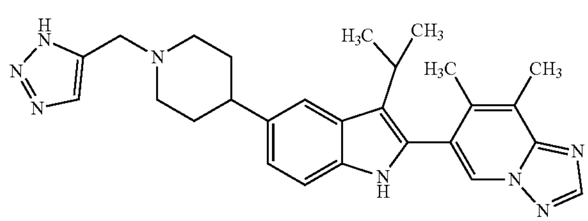 [SMILES: Cc1c(-c2[nH]c3ccc(C4CCN(Cc5cnn[nH]5)CC4)cc3c2C(C)C)cn2ncnc2c1C] | 469.2 | 1.46 | QC-ACN-AA-XB |

TABLE 5-continued

| Ex. No. | Structure | LCMS MH+ | R$_t$ (min) | Method |
|---|---|---|---|---|
| 40 | 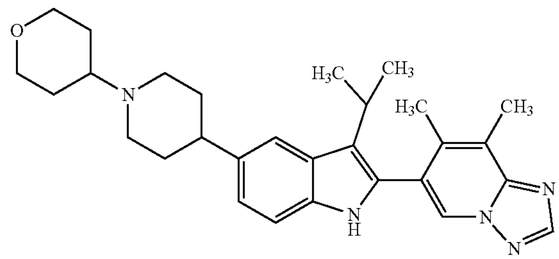 [SMILES: Cc1c(-c2[nH]c3ccc(C4CCN(C5CCOCC5)CC4)cc3c2C(C)C)cn2ncnc2c1C] | 471.9 | 1.47 | QC-ACN-AA-XB |
| 41 | 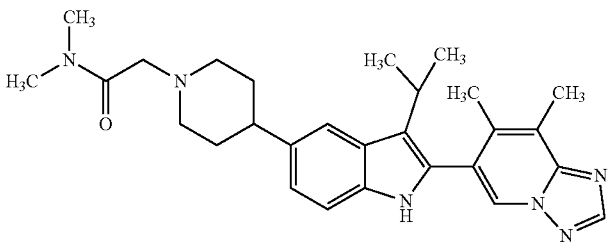 [SMILES: Cc1c(-c2[nH]c3ccc(C4CCN(CC(=O)N(C)C)CC4)cc3c2C(C)C)cn2ncnc2c1C] | 473.4 | 1.41 | QC-ACN-AA-XB |
| 42 | 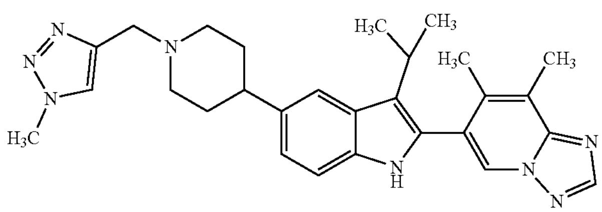 [SMILES: Cc1c(-c2[nH]c3ccc(C4CCN(Cc5cn(C)nn5)CC4)cc3c2C(C)C)cn2ncnc2c1C] | 483 | 1.52 | QC-ACN-AA-XB |
| 43 | 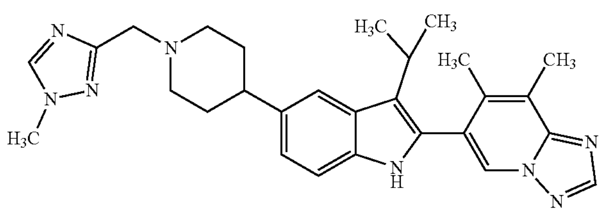 [SMILES: Cc1c(-c2[nH]c3ccc(C4CCN(Cc5ncn(C)n5)CC4)cc3c2C(C)C)cn2ncnc2c1C] | 483 | 1.68 | QC-ACN-AA-XB |
| 44 | 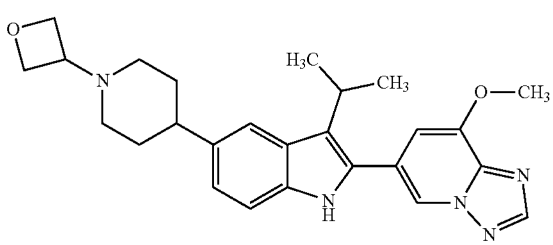 | 446.2 | 1.91 | Method E |
| 45 | 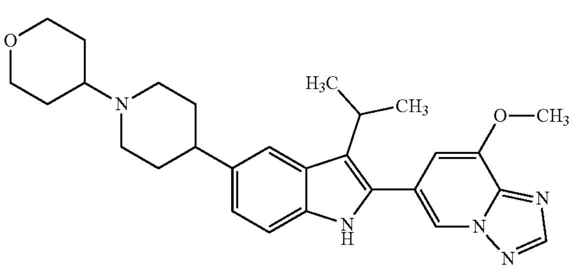 [SMILES: COc1cc(-c2[nH]c3ccc(C4CCN(C5CCOCC5)CC4)cc3c2C(C)C)cn2ncnc12] | 474.4 | 1.31 | Method E |

Example 44

6-(3-isopropyl-5-(1-(oxetan-3-yl)piperidin-4-yl)-1H-indol-2-yl)-8-methoxy-[1,2,4]triazolo[1,5-a]pyridine

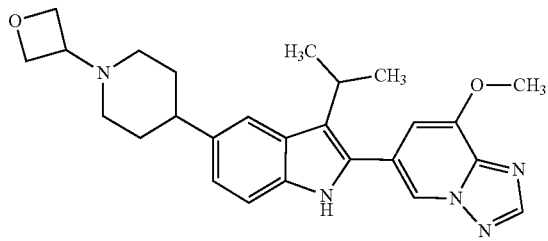

(44)

To a solution of 6-(3-isopropyl-5-(piperidin-4-yl)-1H-indol-2-yl)-8-methoxy-[1,2,4]triazolo[1,5-a]pyridine dihydrochloride (39.7 g, 86 mmol) in DCM (859 ml) was added triethylamine (34.8 g, 343 mmol), oxetan-3-one (24.75 g, 343 mmol), acetic acid (10.31 g, 172 mmol) and sodium triacetoxyborohydride (72.8 g, 343 mmol). The solution was stirred at room temperature. After 9 h, the starting material was no longer detected. The solvent was removed by rotavapor. The residue was dissolved in 1500 mL ethyl acetate and washed with saturated NaHCO$_3$ solution (500 mL×4), dried over Na$_2$SO$_4$, and concentrated under reduced pressure to give residue. The residue was purified by recrystallization from a mixture of EtOH/water (60/40) two times, dried to give 6-(3-isopropyl-5-(1-(oxetan-3-yl) piperidin-4-yl)-1H-indol-2-yl)-8-methoxy-[1,2,4]triazolo[1,5-a]pyridine (32.3 g, 72.2 mmol, 84% yield) as a white solid. LCMS MH$^+$. 446.1. HPLC Ret. Time 0.63 min. Method G. $^1$H NMR (400 MHz, CHLOROFORM-d) δ 8.42-8.31 (m, 2H), 8.20-8.10 (m, 1H), 7.77-7.67 (m, 1H), 7.44-7.36 (m, 1H), 7.31-7.26 (m, 1H), 7.21-7.12 (m, 1H), 6.95-6.85 (m, 1H), 4.80-4.63 (m, 4H), 4.12-4.03 (m, 3H), 3.62-3.51 (m, 1H), 3.42-3.25 (m, 1H), 3.02-2.87 (m, 2H), 2.73-2.58 (m, 1H), 2.10-1.85 (m, 6H), 1.55-1.44 (m, 6H).

Example 46

2-(dimethylamino)-1-(4-(3-isopropyl-2-(8-methyl-[1,2,4]triazolo[1,5-a]pyridin-6-yl)-1H-indol-5-yl)piperidin-1-yl)ethan-1-one

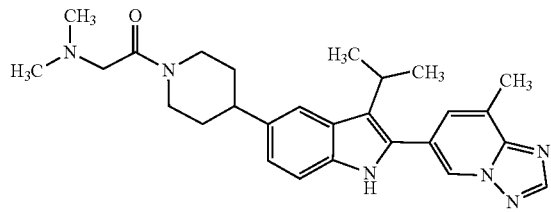

(46)

To a solution of 6-(3-isopropyl-5-(piperidin-4-yl)-1H-indol-2-yl)-8-methyl-[1,2,4]triazolo[1,5-a]pyridine (75 mg, 0.201 mmol) in DMF (1 mL) were added TEA (0.140 mL, 1.004 mmol), 2-(dimethylamino)acetic acid (20.71 mg, 0.201 mmol), and HATU (76 mg, 0.201 mmol). The reaction mixture was stirred at room temperature for 12 h. The reaction mass was diluted with methanol (2 mL) and passed through a syringe pad to filter away inorganics, and then purified by reverse phase preparative chromatography. The crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 20-60% B over 30 minutes, then a 5-minute hold at 100% B; Flow: 15 mL/min. Fractions containing the product were combined and dried via centrifugal evaporation. The yield of the product was 11.7 mg, and its estimated purity by LCMS analysis was 96%. Two analytical LC/MS injections were used to determine the final purity. Injection 1 conditions: Column: Ascentis Express C18(50×2.1) mm, 2.7 μm; Mobile Phase A: 5:95 Acetonitrile:water with 10 mM NH$_4$OAc; Mobile Phase B: 95:5 Acetonitrile:water with 10 mM NH$_4$OAc; Temperature: 50° C.; Gradient: 0-100% B over 3 minutes; Flow: 1.1 mL/min. Injection 2 conditions: Column: Ascentis Express C18 (50×2.1) mm, 2.7 μm; Mobile Phase A: 5:95 Acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min. $^1$H-NMR (400 MHz, DMSO-d$_6$): δ 1.12 (d, J=6.00 Hz, 3H), 1.44 (d, J=6.80 Hz, 6H), 1.69-1.72 (m, 2H), 1.75-1.81 (m, 2H), 2.32-2.34 (m, 1H), 2.50 (s, 3H), 2.62-2.71 (m, 4H), 2.80-2.94 (m, 1H), 3.25-3.32 (m, 2H), 3.54-3.58 (m, 2H), 4.00-4.07 (m, 1H), 4.60 (d, J=11.20 Hz, 1H), 7.04 (dd, J=1.20, 8.40 Hz, 1H), 7.30 (d, J=8.40 Hz, 1H), 7.58 (d, J=8.80 Hz, 1H), 8.53 (s, 1H), 8.80 (s, 1H), 11.11 (s, 1H). LCMS for molecular formula C$_{26}$H$_{32}$N$_6$O was 444.264, found 445 (M*). Waters Xbridge C18, 19×150 mm, 5 μm; Guard Column: Waters XBridge C18, 19×10 mm, 5 μm; Mobile Phase A: 5:95 Acetonitrile:water with 10 mM NH$_4$OAc; Mobile Phase B: 95:5 acetonitrile:water with 10 mM NH$_4$OAc; Gradient: 10-50% B over 25 minutes, followed by a 10 minute hold at 50% B and 5 minute hold at 100% B; Flow: 15 mL/min. R$_t$ Min: 1.91, Wave length: 220 nm.

Example 47

1-(4-(2-([1,2,4]triazolo[1,5-a]pyridin-6-yl)-3-isopropyl-1H-indol-5-yl)piperidin-1-yl)-2-(methylamino)ethan-1-one

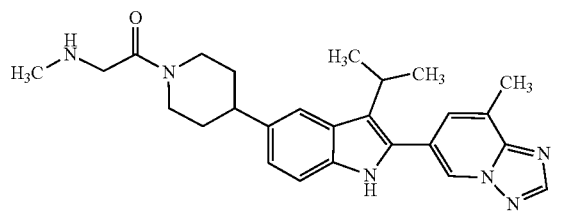

(47)

To a 1 dram vial were added 6-(3-isopropyl-5-(piperidin-4-yl)-1H-indol-2-yl)-[1,2,4]triazolo[1,5-a]pyridine (0.035 g, 0.091 mmol), CH$_3$CN, TEA (0.038 mL, 0.273 mmol), and HATU (0.036 g, 0.091 mmol). The material went into solution and 2-((tert-butoxycarbonyl)(methyl)amino)acetic acid (0.034 g, 0.182 mmol) was added. The reaction vial was capped and allowed to stir overnight at room temperature. After 18 hrs LC-MS showed product had formed. The samples were diluted with ethyl acetate and washed with water. The combined organics were washed with brine, dried over Na$_2$SO$_4$ filtered, and concentrated. To this was added 1 mL of DCM and 1 mL of 4 M HCl in dioxane. The reaction mixture was stirred for 30 minutes at room temperature, concentrated, diluted with Solvent B (90:10:0.1 CH$_3$CN:Water:TFA, filtered and purified by preparative reverse phase chromatography. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the product were combined and dried via centrifugal evaporation. The yield of the product was 7.4 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-10% B over 3 minutes, then a 0.75-minute hold at 100% B; Flow: 1.0 mL/min; Detection: UV at 220 nm. Proton NMR was acquired in deuterated DMSO. LC-MS: M+1=431, rt=1.127 min., [D1]. Proton NMR was acquired in deuterated DMSO. $^1$H NMR (500 MHz, DMSO-d$_6$) δ 11.19 (s, 1H), 8.97 (s, 1H), 8.58 (s, 1H), 7.98 (d, J=9.2 Hz, 1H), 7.79 (d, J=10.4 Hz, 1H), 7.56 (s, 1H), 7.33 (d, J=8.3 Hz, 1H), 7.03 (d, J=8.8 Hz, 1H), 4.55 (d, J=13.0 Hz, 1H), 3.88 (d, J=13.2 Hz, 1H), 3.58 (s, 1H), 3.33-3.21 (m, 1H), 3.16-3.06 (m, 1H), 2.88 (d, J=7.5 Hz, 2H), 2.77-2.63 (m, 2H), 2.38 (s, 5H), 1.73-1.59 (m, 2H), 1.43 (d, J=7.0 Hz, 6H).

The following examples were prepared according to the general methods disclosed in Examples 46 or 47.

TABLE 6

| Ex. No. | Structure | LCMS MH+ | R$_t$ (min) | Method |
|---|---|---|---|---|
| 48 | 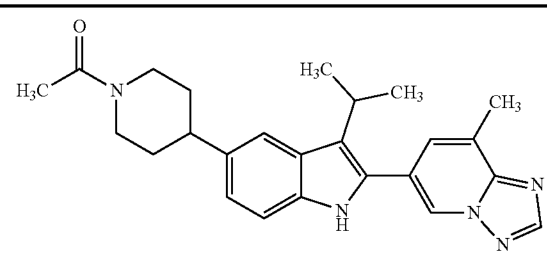 | 415.9 | 1.62 | QC-ACN-AA-XB |
| 49 | 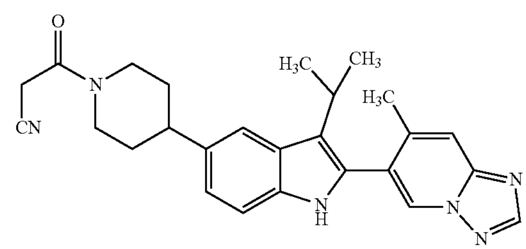 [SMILES: Cc1cc2ncnn2cc1-c1[nH]c2ccc(C3CCN(C(=O)CC#N)CC3)cc2c1C(C)C] | 441.3 | 1.46 | QC-ACN-TFA-XB |
| 50 | 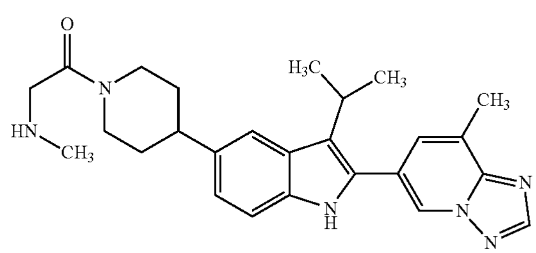 [SMILES: CNCC(=O)N1CCC(c2ccc3[nH]c(-c4cc(C)c5ncnn5c4)c(C(C)C)c3c2)CC1] | 445.3 | 1.47 | Method A |
| 51 | 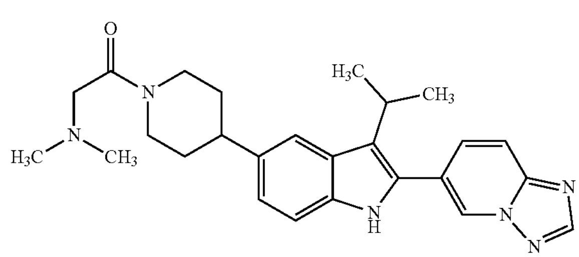 [SMILES: CC(C)c1c(-c2ccc3ncnn3c2)[nH]c2ccc(C3CCN(C(=O)CN(C)C)CC3)cc12] | 445.1 | 1.21 | QC-ACN-AA-XB |

TABLE 6-continued

| Ex. No. | Structure | LCMS MH+ | R_t (min) | Method |
|---|---|---|---|---|
| 52 | 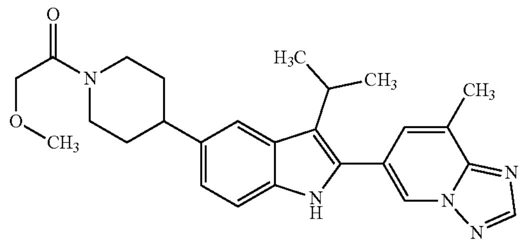 [SMILES: COCC(=O)N1CCC(c2ccc3[nH]c(-c4cc(C)c5ncnn5c4)c(C(C)C)c3c2)CC1] | 446.4 | 1.57 | Method E |
| 53 | 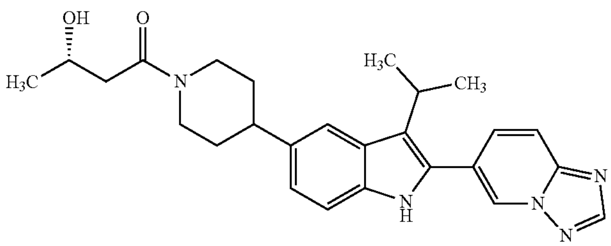 [SMILES: CC(C)c1c(-c2ccc3ncnn3c2)[nH]c2ccc(C3CCN(C(=O)C[C@H](C)O)CC3)cc12] | 446.2 | 1.70 | Method E |
| 54 | 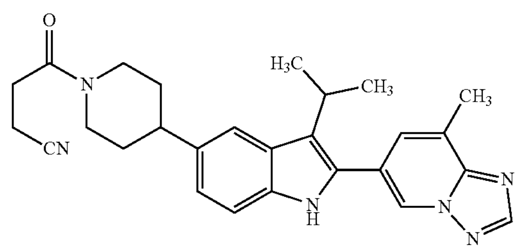 [SMILES: Cc1cc(-c2[nH]c3ccc(C4CCN(C(=O)CCC#N)CC4)cc3c2C(C)C)cn2ncnc12] | 455.3 | 1.74 | QC-ACN-AA-XB |
| 55 | 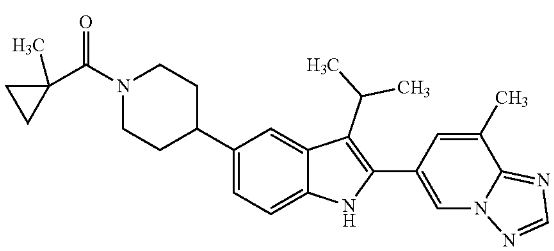 [SMILES: Cc1cc(-c2[nH]c3ccc(C4CCN(C(=O)C5(C)CC5)CC4)cc3c2C(C)C)cn2ncnc12] | 456.4 | 1.85 | Method E |
| 56 | 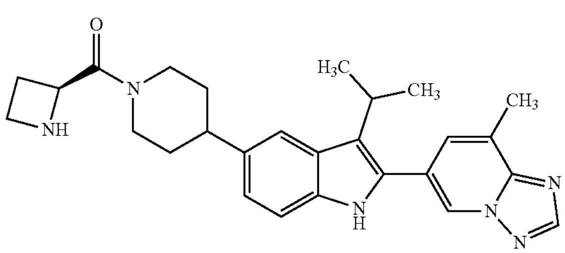 [SMILES: Cc1cc(-c2[nH]c3ccc(C4CCN(C(=O)[C@@H]5CCN5)CC4)cc3c2C(C)C)cn2ncnc12] | 457.4 | 1.27 | Method F |
| 57 | 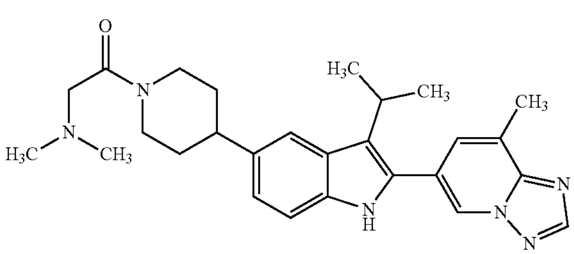 [SMILES: Cc1cc(-c2[nH]c3ccc(C4CCN(C(=O)CN(C)C)CC4)cc3c2C(C)C)cn2ncnc12] | 459.5 | 1.16 | QC-ACN-TFA-XB |

TABLE 6-continued

| Ex. No. | Structure | LCMS MH+ | R$_t$ (min) | Method |
|---|---|---|---|---|
| 58 | 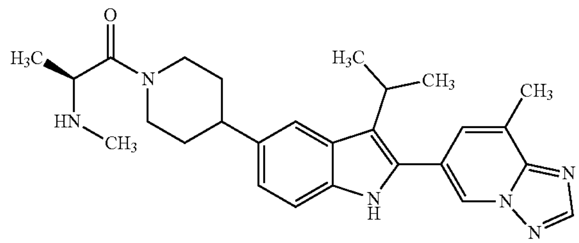 [SMILES: CN[C@@H](C)C(=O)N1CCC(c2ccc3[nH]c(-c4cc(C)c5ncnn5c4)c(C(C)C)c3c2)CC1] | 459.4 | 1.29 | Method F |
| 59 | 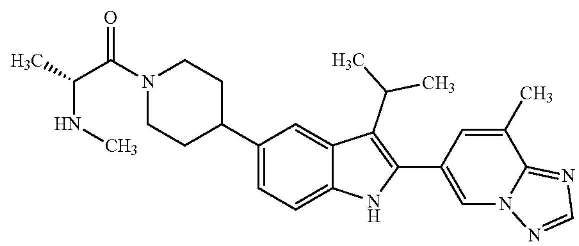 [SMILES: CN[C@H](C)C(=O)N1CCC(c2ccc3[nH]c(-c4cc(C)c5ncnn5c4)c(C(C)C)c3c2)CC1] | 459.4 | 1.29 | Method F |
| 60 | 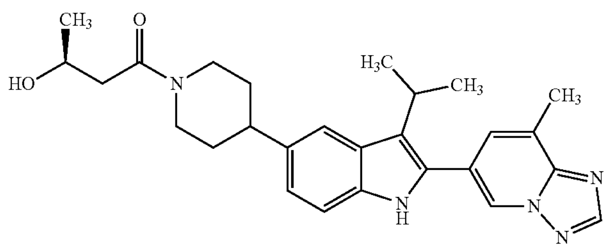 [SMILES: Cc1cc(-c2[nH]c3ccc(C4CCN(C(=O)C[C@H](C)O)CC4)cc3c2C(C)C)cn2ncnc12] | 460.3 | 1.79 | A |
| 61 | 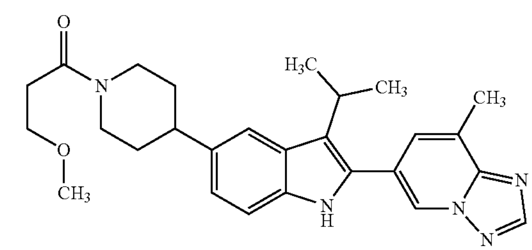 [SMILES: COCCC(=O)N1CCC(c2ccc3[nH]c(-c4cc(C)c5ncnn5c4)c(C(C)C)c3c2)CC1] | 460.4 | 1.66 | Method F |
| 62 | 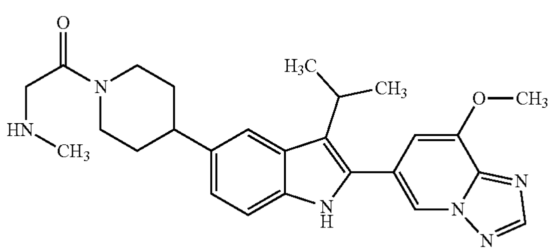 [SMILES: CNCC(=O)N1CCC(c2ccc3[nH]c(-c4cc(OC)c5ncnn5c4)c(C(C)C)c3c2)CC1] | 461.3 | 1.43 | Method E |
| 63 | 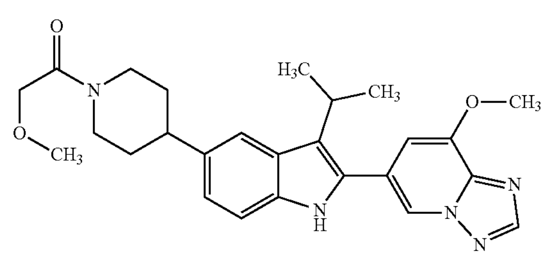 [SMILES: COCC(=O)N1CCC(c2ccc3[nH]c(-c4cc(OC)c5ncnn5c4)c(C(C)C)c3c2)CC1] | 462.3 | 1.52 | Method E |

TABLE 6-continued

| Ex. No. | Structure | LCMS MH+ | R_t (min) | Method |
|---|---|---|---|---|
| 64 | 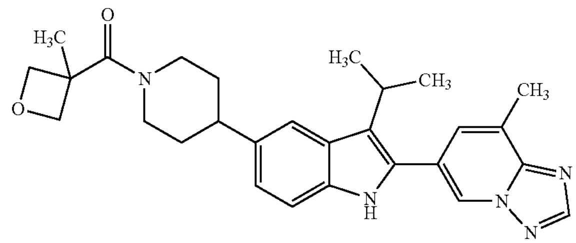 [SMILES: Cc1cc(-c2[nH]c3ccc(C4CCN(C(=O)C5(C)COC5)CC4)cc3c2C(C)C)cn2ncnc12] | 472.4 | 1.56 | Method E |
| 65 | 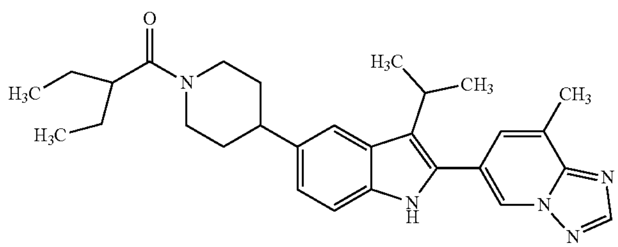 [SMILES: CCC(CC)C(=O)N1CCC(c2ccc3[nH]c(-c4cc(C)c5ncnn5c4)c(C(C)C)c3c2)CC1] | 472.4 | 2.12 | Method E |
| 66 | 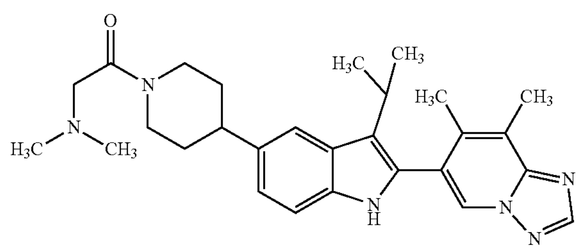 [SMILES: Cc1c(-c2[nH]c3ccc(C4CCN(C(=O)CN(C)C)CC4)cc3c2C(C)C)cn2ncnc2c1C] | 473 | 1.65 | QC-ACN-AA-XB |
| 67 | 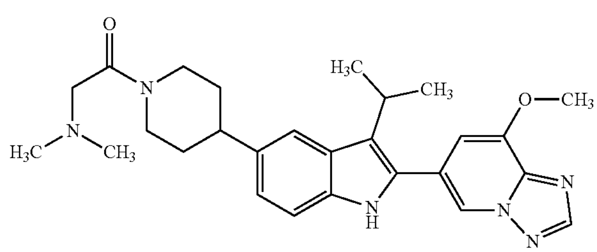 [SMILES: COc1cc(-c2[nH]c3ccc(C4CCN(C(=O)CN(C)C)CC4)cc3c2C(C)C)cn2ncnc12] | 475.3 | 1.50 | Method E |

Example 68

1-(4-(3-isopropyl-2-(8-methyl-[1,2,4]triazolo[1,5-a]pyridin-6-yl)-1H-indol-5-yl) piperidin-1l-yl)-2-morpholinoethan-1-one (68)

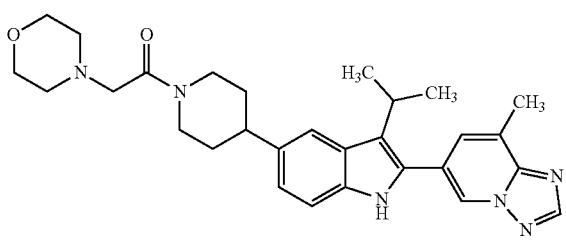

6-(3-Isopropyl-5-(piperidin-4-yl)-1H-indol-2-yl)-8-methyl-[1,2,4]triazolo[1,5-a]pyridine hydrochloride (0.250 g, 0.610 mmol) was dissolved in NMP (5 mL). Et$_3$N (0.255 mL, 1.829 mmol) and 2-chloroacetyl chloride (0.073 mL, 0.915 mmol) were added sequentially. The reaction was monitored by LCMS. After stirring for 1.5 hours, the reaction mixture was diluted with NMP and used as a solution in the next step.

2-Chloro-1-(4-(3-isopropyl-2-(8-methyl-[1,2,4]triazolo[1,5-a]pyridin-6-yl)-1H-indol-5-yl)piperidin-1-yl)ethanone (0.035 g, 0.078 mmol) was dissolved in NMP (1 mL). DBU (0.059 mL, 0.389 mmol) and morpholine (0.020 mL, 0.233 mmol) were added sequentially. The reaction was monitored by LCMS. The reaction mixture was stirred overnight. The reaction mixture was diluted with solvent (90:10 ACN:water, 0.1% TFA) and the crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the product were combined and dried via centrifugal evaporation.

The yield of the product was 37.9 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LC-MS: M+1=501, rt=1.157 min., [D1]. Proton NMR was acquired in deuterated DMSO. $^1$H NMR (400 MHz, DMSO-$d_6$) δ=11.12 (s, 1H), 8.79 (d, J=0.8 Hz, 1H), 8.53 (s, 1H), 7.59 (d, J=6.4 Hz, 2H), 7.29 (d, J=8.4 Hz, 1H), 7.02 (dd, J=8.4, 1.2 Hz, 1H), 4.88-4.82 (m, 2H), 4.52-4.48 (m, 1H), 4.28-4.22 (m, 2H), 4.09-4.04 (n, 1H), 3.28-3.21 (m, 1H), 3.19-3.02 (m, 6H), 2.85-2.76 (m, 1H), 2.68-2.59 (m, 2H), 2.58 (s, 3H), 1.88-1.80 (m, 2H), 1.69-1.50 (m, 2H), 1.43 (d, J=7.2 Hz, 6H).

The following examples were prepared according to the general process disclosed in Example 68.

TABLE 7

| Ex. No. | Structure | LCMS MH+ | R$_t$ (min) | Method |
|---|---|---|---|---|
| 69 | 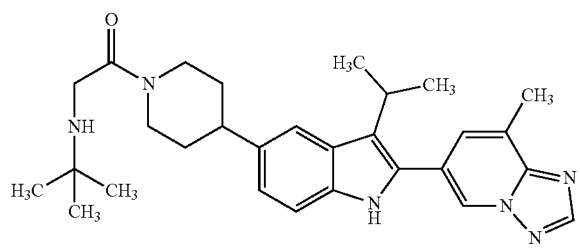 [SMILES: Cc1cc(-c2[nH]c3ccc(C4CCN(C(=O)CNC(C)(C)C)CC4)cc3c2C(C)C)cn2ncnc12] | 487.4 | 1.28 | Method F |
| 70 | 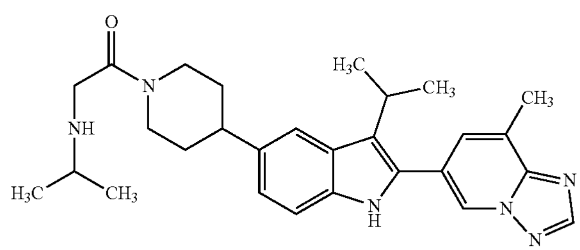 [SMILES: Cc1cc(-c2[nH]c3ccc(C4CCN(C(=O)CNC(C)C)CC4)cc3c2C(C)C)cn2ncnc12] | 473.4 | 1.35 | Method E |
| 71 | 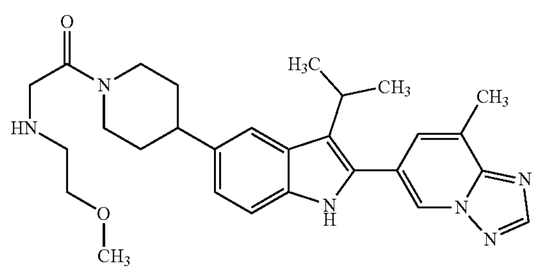 [SMILES: COCCNCC(=O)N1CCC(c2ccc3[nH]c(-c4cc(C)c5ncnn5c4)c(C(C)C)c3c2)CC1] | 489.4 | 1.40 | Method E |
| 72 | 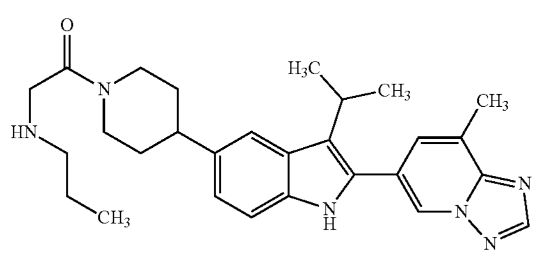 [SMILES: CCCNCC(=O)N1CCC(c2ccc3[nH]c(-c4cc(C)c5ncnn5c4)c(C(C)C)c3c2)CC1] | 473.4 | 1.39 | Method E |

TABLE 7-continued

| Ex. No. | Structure | LCMS MH+ | $R_t$ (min) | Method |
|---|---|---|---|---|
| 73 | 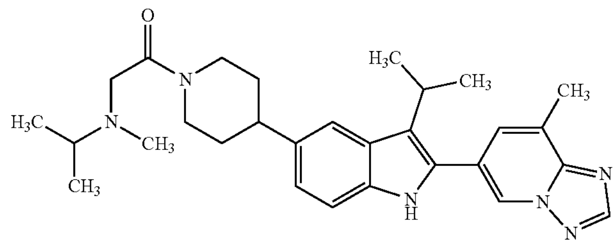 [SMILES: Cc1cc(-c2[nH]c3ccc(C4CCN(C(=O)CN(C)C(C)C)CC4)cc3c2C(C)C)cn2ncnc12] | 487.4 | 1.25 | Method F |

Example 74

1-(1,1-dioxido-1,2,4-thiadiazinan-4-yl)-2-(4-(3-isopropyl-2-(8-methyl-[1,2,4]triazolo[1,5-a]pyridin-6-yl)-1H-indol-5-yl)piperidin-1-yl)ethan-1-one (74)

Intermediate 74A 2-(4-(3-isopropyl-2-(8-methyl-[1,2,4]triazolo[1,5-a]pyridin-6-yl)-1H-indol-5-yl)piperidin-1-yl)acetic acid (74A)

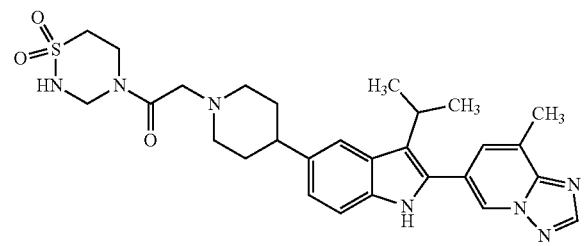

In a glass vial, 6-(3-isopropyl-5-(piperidin-4-yl)-1H-indol-2-yl)-8-methyl-[1,2,4]triazolo[1,5-a]pyridine (0.580 g, 1.233 mmol) was dissolved in $CH_2Cl_2$ (8.22 mL) and N,N-diisopropylethylamine (1.074 mL, 6.16 mmol). Methyl 2-bromoacetate (0.141 mL, 1.479 mmol) was added to the vial, resulting in a clear, bright yellow solution. The reaction mixture was stirred for 1.5 h at room temperature. Excess solvent was evaporated from the reaction mixture under a nitrogen stream. The material was purified by silica gel chromatography using hexane and ethyl acetate as eluents (0%-100% Ethyl acetate gradient). The product fractions were combined and evaporated to dryness. The material was dissolved in 2 mL THF and 2 mL MeOH and treated with 2 mL of 4 M NaOH. Next, 1 mL of water was added and the mixture was stirred at 45° C. overnight. The mixture was diluted with water and acidified to pH=5 with 1N HCl. Ethyl acetate was added and the layers were separated. The combined organics were washed with dried over $Na_2SO_4$, filtered and concentrated to afford 2-(4-(3-isopropyl-2-(8-methyl-[1,2,4]triazolo[1,5-a]pyridin-6-yl)-1H-indol-5-yl)piperidin-1-yl)acetic acid.

Example 74

In a 2 dram vial were added 2-(4-(3-isopropyl-2-(8-methyl-[1,2,4]triazolo[1,5-a]pyridin-6-yl)-1H-indol-5-yl)piperidin-1-yl)acetic acid (0.025 g, 0.058 mmol), $CH_3CN$ and TEA (0.024 mL, 0.174 mmol). The sample went into solution and HATU (0.033 g, 0.087 mmol) was added. The reaction vial was capped and allowed to stir overnight at room temperature. The sample was diluted with solvent (90:10:0.1 $CH_3CN$:water:TFA), filtered and then purified by preparative reverse phase HPLC.

The crude material was purified via preparative LC/MS with the following conditions: Column: XBridge Phenyl, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the product were combined and dried via centrifugal evaporation. The yield of the product was 0.8 mg and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Proton NMR was acquired in deuterated DMSO.

The following examples were prepared according to the general process described in Example 74.

TABLE 8

| Ex. No. | Structure | LCMS MH+ | R_t (min) | Method |
|---|---|---|---|---|
| 75 | 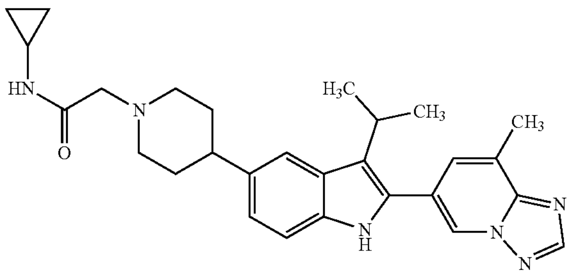 [SMILES: Cc1cc(-c2[nH]c3ccc(C4CCN(CC(=O)NC5CC5)CC4)cc3c2C(C)C)cn2ncnc12] | 471.4 | 1.72 | Method E |
| 76 | 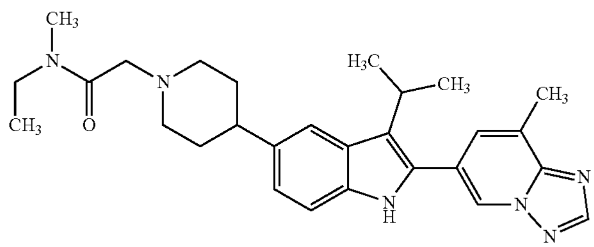 [SMILES: CCN(C)C(=O)CN1CCC(c2ccc3[nH]c(-c4cc(C)c5ncnn5c4)c(C(C)C)c3c2)CC1] | 473.4 | 1.56 | Method E |
| 77 | 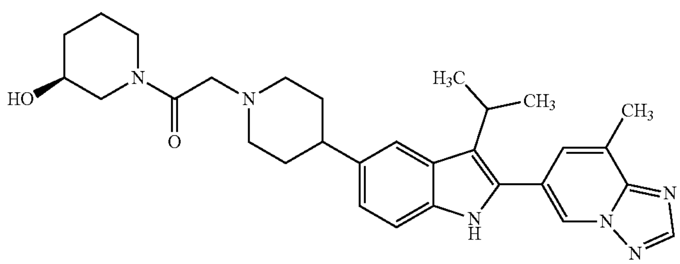 [SMILES: Cc1cc(-c2[nH]c3ccc(C4CCN(CC(=O)N5CCC[C@H](O)C5)CC4)cc3c2C(C)C)cn2ncnc12] | 515.4 | 1.40 | Method E |
| 78 | 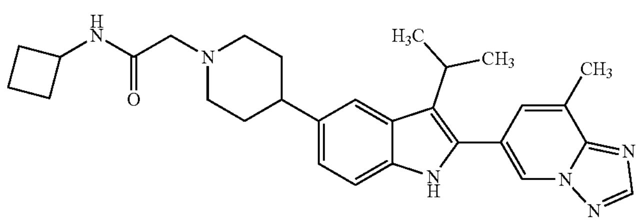 [SMILES: Cc1cc(-c2[nH]c3ccc(C4CCN(CC(=O)NC5CCC5)CC4)cc3c2C(C)C)cn2ncnc12] | 485.4 | 1.25 | Method F |
| 79 | 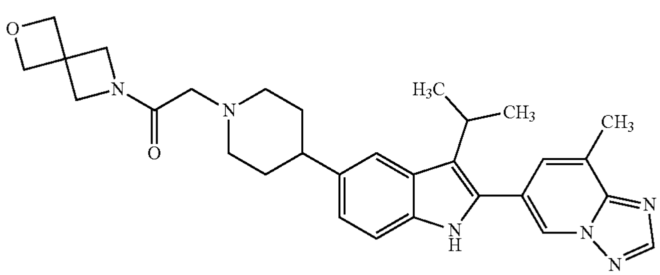 [SMILES: Cc1cc(-c2[nH]c3ccc(C4CCN(CC(=O)N5CC6(COC6)C5)CC4)cc3c2C(C)C)cn2ncnc12] | 513.4 | 1.08 | Method F |
| 80 | 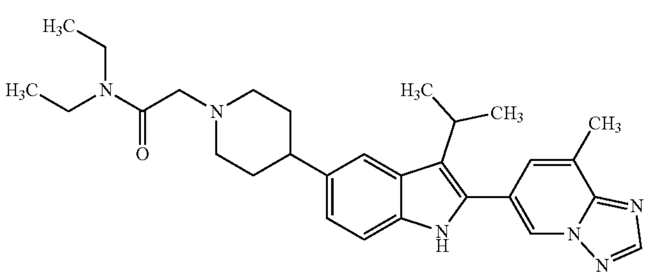 [SMILES: CCN(CC)C(=O)CN1CCC(c2ccc3[nH]c(-c4cc(C)c5ncnn5c4)c(C(C)C)c3c2)CC1] | 487.4 | 1.29 | Method F |

TABLE 8-continued

| Ex. No. | Structure | LCMS MH+ | R$_t$ (min) | Method |
|---|---|---|---|---|
| 81 | 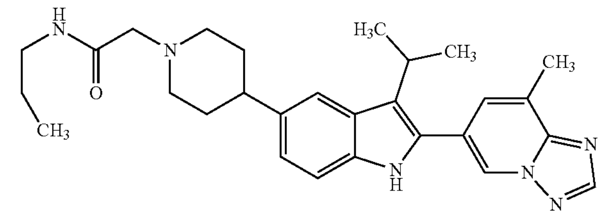 [SMILES: CCCNC(=O)CN1CCC(c2ccc3[nH]c(-c4cc(C)c5ncnn5c4)c(C(C)C)c3c2)CC1] | 473.4 | 1.83 | Method E |
| 82 | 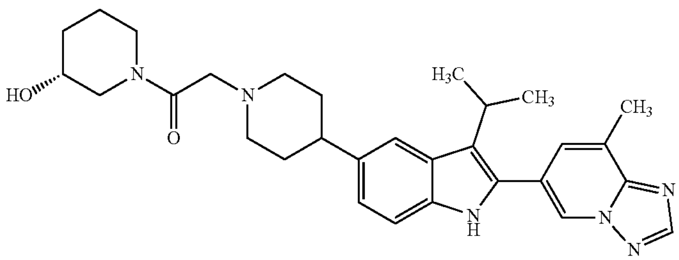 [SMILES: Cc1cc(-c2[nH]c3ccc(C4CCN(CC(=O)N5CCC[C@@H](O)C5)CC4)cc3c2C(C)C)cn2ncnc12] | 515.4 | 1.10 | Method F |
| 83 | 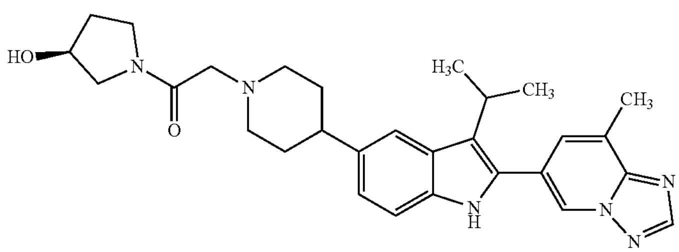 [SMILES: Cc1cc(-c2[nH]c3ccc(C4CCN(CC(=O)N5CC[C@H](O)C5)CC4)cc3c2C(C)C)cn2ncnc12] | 501.4 | 1.06 | Method F |
| 84 | 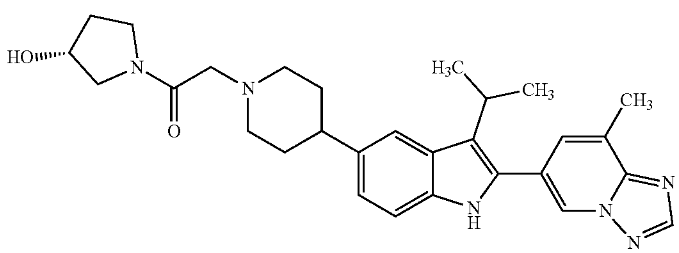 [SMILES: Cc1cc(-c2[nH]c3ccc(C4CCN(CC(=O)N5CC[C@@H](O)C5)CC4)cc3c2C(C)C)cn2ncnc12] | 501.4 | 1.05 | Method F |
| 85 | 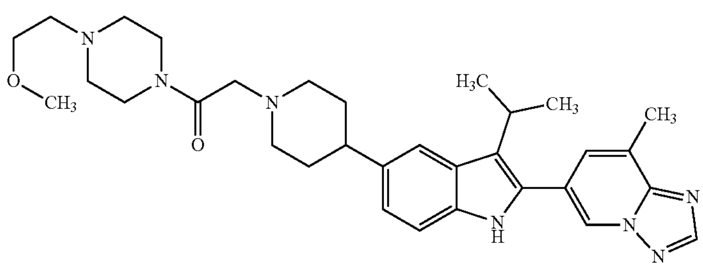 [SMILES: COCCN1CCN(C(=O)CN2CCC(c3ccc4[nH]c(-c5cc(C)c6ncnn6c5)c(C(C)C)c4c3)CC2)CC1] | 558.5 | 0.96 | Method F |
| 86 | 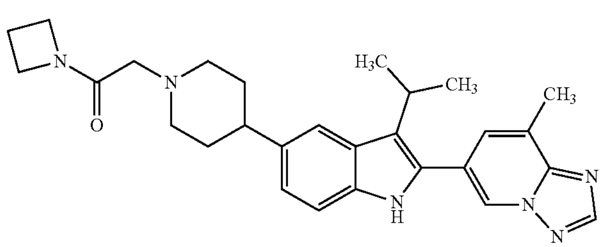 [SMILES: Cc1cc(-c2[nH]c3ccc(C4CCN(CC(=O)N5CCC5)CC4)cc3c2C(C)C)cn2ncnc12] | 471.4 | 1.13 | Method F |

TABLE 8-continued

| Ex. No. | Structure | LCMS MH+ | R$_t$ (min) | Method |
|---|---|---|---|---|
| 87 | 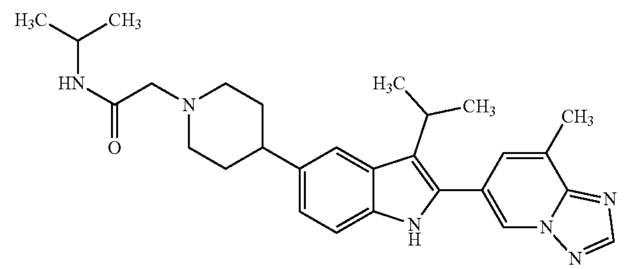 [SMILES: Cc1cc(-c2[nH]c3ccc(C4CCN(CC(=O)NC(C)C)CC4)cc3c2C(C)C)cn2ncnc12] | 473.4 | 1.23 | Method F |
| 88 | 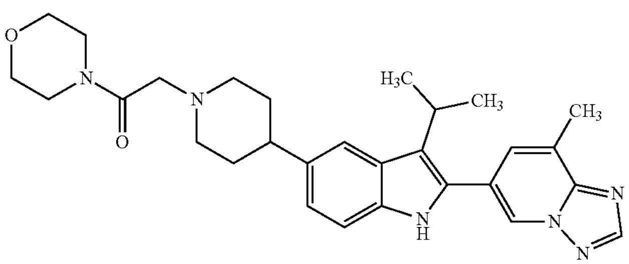 [SMILES: Cc1cc(-c2[nH]c3ccc(C4CCN(CC(=O)N5CCOCC5)CC4)cc3c2C(C)C)cn2ncnc12] | 501.4 | 1.11 | Method F |
| 89 | 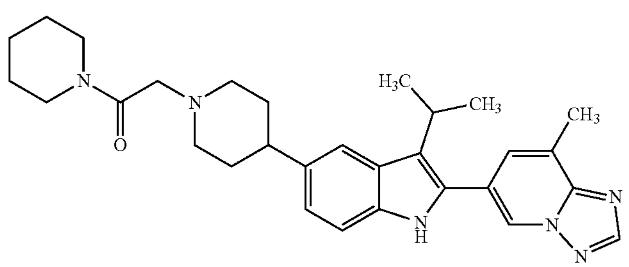 [SMILES: Cc1cc(-c2[nH]c3ccc(C4CCN(CC(=O)N5CCCCC5)CC4)cc3c2C(C)C)cn2ncnc12] | 499.4 | 1.3 | Method F |
| 90 | 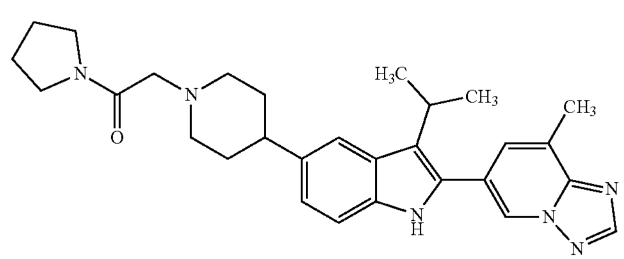 [SMILES: Cc1cc(-c2[nH]c3ccc(C4CCN(CC(=O)N5CCCC5)CC4)cc3c2C(C)C)cn2ncnc12] | 485.4 | 1.59 | Method E |
| 91 | 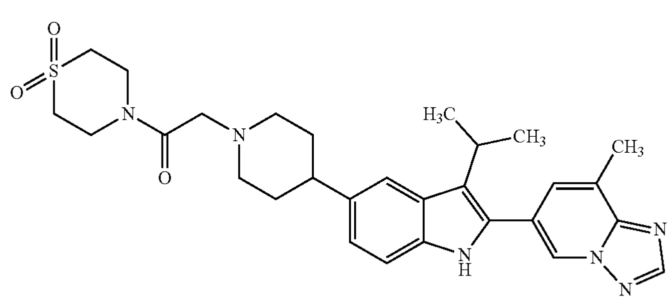 [SMILES: Cc1cc(-c2[nH]c3ccc(C4CCN(CC(=O)N5CCS(=O)(=O)CC5)CC4)cc3c2C(C)C)cn2ncnc12] | 549.4 | 1.52 | Method E |

TABLE 8-continued

| Ex. No. | Structure | LCMS MH+ | R<sub>t</sub> (min) | Method |
|---|---|---|---|---|
| 92 | 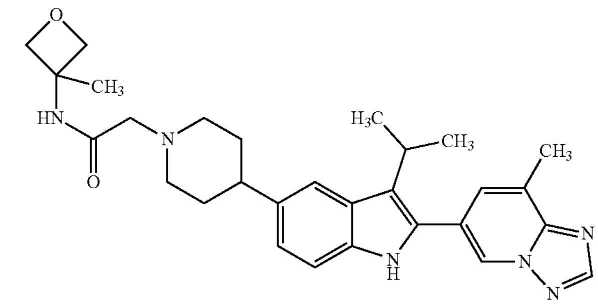 [SMILES: Cc1cc(-c2[nH]c3ccc(C4CCN(CC(=O)NC5(C)COC5)CC4)cc3c2C(C)C)cn2ncnc12] | 501.4 | 1.66 | Method E |
| 93 | 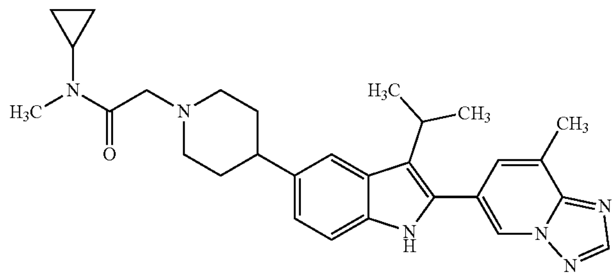 [SMILES: Cc1cc(-c2[nH]c3ccc(C4CCN(CC(=O)N(C)C5CC5)CC4)cc3c2C(C)C)cn2ncnc12] | 485.4 | 1.58 | Method E |

Example 94

8-ethyl-6-(3-isopropyl-5-(piperidin-4-yl)-1H-indol-2-yl)-[1,2,4]triazolo[1,5-a]pyridine (94)

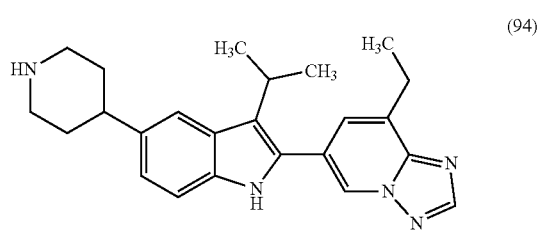 [SMILES: CCc1cc(-c2[nH]c3ccc(C4CCNCC4)cc3c2C(C)C)cn2ncnc12]

Intermediate 94A: 6-bromo-8-iodo-[1,2,4]triazolo[1,5-a]pyridine (94A)

To a stirred solution of 6-bromo-8-iodo-[1,2,4]triazolo[1,5-a]pyridine (100 mg, 0.309 mmol) in EtOH (20 mL) was added vinylboronic acid pinacol ester (62.0 mg, 0.463 mmol). The mixture was degassed for 10 min using N₂. Next, PdCl₂(dppf)-CH₂Cl₂ (12.61 mg, 0.015 mmol) and Et₃N (0.129 mL, 0.926 mmol) were added and the reaction mixture was heated to 80° C. for 16 h. The reaction mixture was filtered through pad of celite, washed with EtOAc, and concentrated organic layer to afford 6-bromo-8-vinyl-[1,2,4]triazolo[1,5-a]pyridine (70 mg, 95%). LC retention time 1.0.4 min [K]. MS (E−) m/z: 226 (M+H).

Intermediate 94B: Tert-butyl 4-(3-isopropyl-2-(8-vinyl-[1,2,4]triazolo[1,5-a]pyridin-6-yl)-1H-indol-5-yl)piperidine-1-carboxylate (94B)

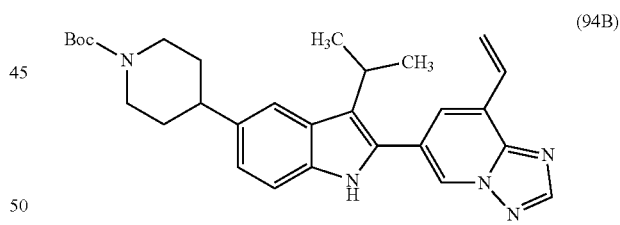

To a stirred solution of tert-butyl 4-(3-isopropyl-2-(4,4,5,5-tetramethyl-1,3,2-dioxaborolan-2-yl)-1H-indol-5-yl)piperidine-1-carboxylate (300 mg, 0.640 mmol), and 6-bromo-8-vinyl-[1,2,4]triazolo[1,5-a]pyridine (215 mg, 0.961 mmol) in dioxane (15 mL) and water (2 mL) was added potassium phosphate tribasic (408 mg, 1.921 mmol). The mixture was degassed with N₂ for 10 min. Next, PdCl₂(dppf) (46.9 mg, 0.064 mmol) was added the mixture was degassed for 10 min. The reaction mixture was heated 80° C. for 16 h. The reaction mass was filtered through pad of celite, washed with EtOAc, and concentrated to afford tert-butyl 4-(3-isopropyl-2-(8-vinyl-[1,2,4]triazolo[1,5-a]pyridin-6-yl)-1H-indol-5-yl) piperidine-1-carboxylate. The crude mass was purified by silica gel chromatography to afford tert-butyl 4-(3-isopropyl-2-(8-vinyl-[1,2,4]triazolo[1,5-a]

pyridin-6-yl)-1H-indol-5-yl)piperidine-1-carboxylate (230 mg, 74%) as white solid. LC retention time 1.74 min [K]. MS (E−) m/z: 486 (M+H).

Intermediate 94C: Tert-butyl 4-(2-(8-ethyl-[1,2,4]triazolo[1,5-a]pyridin-6-yl)-3-isopropyl-1H-indol-5-yl)piperidine-1-carboxylate

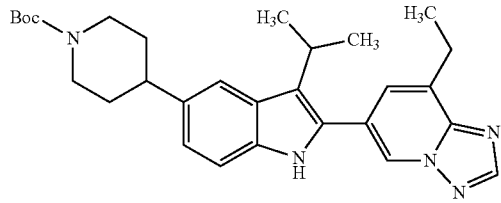

(94C)

A solution of tert-butyl 4-(3-isopropyl-2-(8-vinyl-[1,2,4]triazolo[1,5-a]pyridin-6-yl)-1H-indol-5-yl)piperidine-1-carboxylate (180 mg, 0.371 mmol) in ethyl acetate (15 mL) was purged with nitrogen ($N_2$). Palladium on carbon (39.4 mg, 0.371 mmol)) was added and the mixture was purged with $N_2$ three times. Hydrogen gas ($H_2$) was introduced via a balloon to the mixture. The reaction mixture was stirred at room temperature for 5 h. The suspension was filtered through celite, the filtrate was collected and concentrated to afford crude compound. The crude was purified by silica gel chromatography. The compound was eluted in 15% ethyl acetate in hexane, the fractions were collected and concentrated to afford to afford tert-butyl 4-(2-(8-ethyl-[1,2,4]triazolo[1,5-a]pyridin-6-yl)-3-isopropyl-1H-indol-5-yl)piperidine-1-carboxylate (150 mg, 83% yield) as a white solid. LCMS retention time 1.70 min [K]. MS (E−) m/z: 488 (M+H).

Example 94

To a solution of tert-butyl 4-(2-(8-ethyl-[1,2,4]triazolo[1,5-a]pyridin-6-yl)-3-isopropyl-1H-indol-5-yl)piperidine-1-carboxylate (140 mg, 0.287 mmol) in DCM (10 mL) was added 4 M HCl in dioxane (3.05 µl, 0.100 mmol at ambient temperature. The mixture was stirred at the same temperature for 1 h. The solution was concentrated to afford crude product. The crude material was purified by prep LCMS with the following conditions: Waters Xbridge C18, 19×150 mm, 5 µm; Guard Column: Waters XBridge C18, 19×10 mm, 5 µm; Mobile Phase A: 5:95 methanol:water with 10 mM $NH_4OAc$; Mobile Phase B: 95:5 methanol:water with 10 mM $NH_4OAc$; Gradient: 15-65% B over 25 minutes, followed by a 10 minute hold at 65% B and 5 minute hold at 100% B; Flow: 15 mL/min. Fractions containing the product were combined and dried using a Genevac centrifugal evaporator to provide 8-ethyl-6-(3-isopropyl-5-(piperidin-4-yl)-1H-indol-2-yl)-[1,2,4]triazolo[1,5-a]pyridine (5.4 mg, 8.5%) as a white solid. LC retention time=1.38 min [E]. MS (E−) m/z: 388 (M+H).

Example 95

8-isopropyl-6-(3-isopropyl-5-(piperidin-4-yl)-1H-indol-2-yl)-[1,2,4]triazolo[1,5-a]pyridine

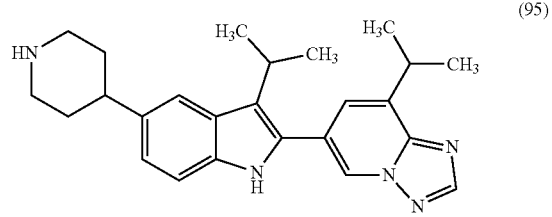 [SMILES: CC(C)c1c(-c2cc(C(C)C)c3ncnn3c2)[nH]c2ccc(C3CCNCC3)cc12]

(95)

Intermediate 95A: 6-bromo-8-(prop-1-en-2-yl)-[1,2,4]triazolo[1,5-a]pyridine

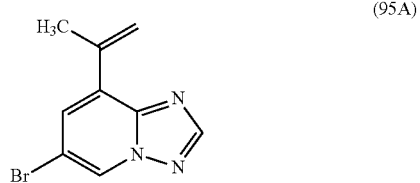

(95A)

To a stirred solution of 6-bromo-8-iodo-[1,2,4]triazolo[1,5-a]pyridine (300 mg, 0.926 mmol) and 4,4,5,5-tetramethyl-2-(prop-1-en-2-yl)-1,3,2-dioxaborolane (202 mg, 1.204 mmol) in dioxane (10 mL) and water (0.5 mL) was added potassium phosphate tribasic (590 mg, 2.78 mmol). The reaction mixture was degassed with $N_2$ for 10 min. Next, $PdCl_2$(dppf) (67.8 mg, 0.093 mmol) was added and the reaction mixture was degassed for 10 min. The reaction mixture was heated to 80° C. for 16 h. The reaction mass was filtered through a pad of celite, washed with EtOAc, and concentrated. The crude mass was purified by silica gel chromatography using 60% EtOAc-hexanes to afford (6-bromo-8-(prop-1-en-2-yl)-[1,2,4]triazolo[1,5-a]pyridine (200 mg, 0.840 mmol, 91% yield) as an off-white solid. LC retention time 1.19 min [K]. MS (E⁻) m/z: 240 (M+H).

Intermediate 95B: tert-butyl 4-(3-isopropyl-2-(8-(prop-1-en-2-yl)-[1,2,4]triazolo[1,5-a]pyridin-6-yl)-1H-indol-5-yl)piperidine-1-carboxylate

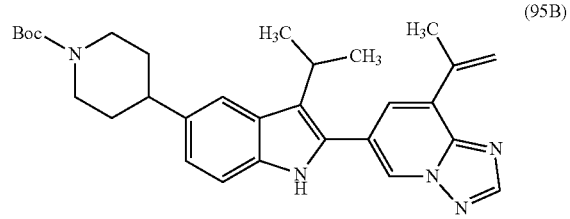 [SMILES: C=C(C)c1cc(-c2[nH]c3ccc(C4CCN(C(=O)OC(C)(C)C)CC4)cc3c2C(C)C)cn2ncnc12]

(95B)

To a stirred solution of tert-butyl 4-(3-isopropyl-2-(4,4,5,5-tetramethyl-1,3,2-dioxaborolan-2-yl)-1H-indol-5-yl)piperidine-1-carboxylate (300 mg, 0.640 mmol), 6-bromo-8-(prop-1-en-2-yl)-[1,2,4]triazolo[1,5-a]pyridine (229 mg, 0.961 mmol) in dioxane (15 mL), and water (2 mL) was added potassium phosphate tribasic (408 mg, 1.921 mmol) degassed with N$_2$ for 10 mins, then PdCl$_2$(dppf) (46.9 mg, 0.064 mmol) was added. The reaction mixture was heated 100° C. for 16 h. Reaction mass filtered through celite bed washed with EtOAc and concentrated to afford crude material. This material was purified by silica gel chromatography to afford tert-butyl 4-(3-isopropyl-2-(8-(prop-1-en-2-yl)-[1,2,4]triazolo[1,5-a]pyridin-6-yl)-1H-indol-5-yl)piperidine-1-carboxylate. The crude mass was purified by ISCO silica column to afford tert-butyl 4-(3-isopropyl-2-(8-(prop-1-en-2-yl)-[1,2,4]triazolo[1,5-a]pyridin-6-yl)-1H-indol-5-yl)piperidine-1-carboxylate (260 mg, 81% yield) as a brown liquid. LC retention time 1.87 min [K]. MS (E−) m/z: 500 (M+H).

Intermediate 95C: Tert-butyl 4-(3-isopropyl-2-(8-isopropyl-[1,2,4]triazolo[1,5-a]pyridin-6-yl)-1H-indol-5-yl)piperidine-1-carboxylate

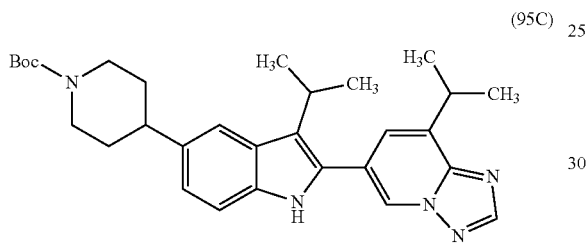

(95C)

A solution of tert-butyl 4-(3-isopropyl-2-(8-(prop-1-en-2-yl)-[1,2,4]triazolo[1,5-a]pyridin-6-yl)-1H-indol-5-yl)piperidine-1-carboxylate (180 mg, 0.360 mmol) in ethyl acetate (15 mL), was purged with nitrogen (N$_2$). Next, palladium on carbon (38.3 mg, 0.360 mmol) was added and the mixture was purged with N$_2$ three times. Hydrogen gas (H$_2$) was introduced via a balloon to the mixture. The reaction mixture was stirred at room temperature for 5 h. The suspension was filtered through celite and the filtrate was collected and concentrated to afford the crude compound. The crude material was purified by silica gel chromatography and the compound eluted in 15% ethyl acetate in hexane. The fractions were collected and concentrated to afford tert-butyl 4-(3-isopropyl-2-(8-isopropyl-[1,2,4]triazolo[1,5-a]pyridin-6-yl)-1H-indol-5-yl)piperidine-1-carboxylate (160 mg, 89% yield). LCMS retention time 1.81 min [K]. MS (E−) m/z: 502 (M+H).

Example 95

To a solution of tert-butyl 4-(3-isopropyl-2-(8-isopropyl-[1,2,4]triazolo[1,5-a]pyridin-6-yl)-1H-indol-5-yl)piperidine-1-carboxylate (140 mg, 0.279 mmol) in DCM (10 mL) was added 4 M HCl in dioxane (5 mL) at ambient temperature. The mixture was stirred at the same temperature for 1 h. The solution was concentrated to afford crude product. The crude sample was purified by preparative LCMS with the following conditions: Waters Xbridge C18, 19×150 mm, 5 m; Guard Column: Waters XBridge C18, 19×10 mm, 5 μm; Mobile Phase A: 5:95 Methanol:water with 10 mM NH$_4$OAc; Mobile Phase B: 95:5 Methanol:water with 10 mM NH$_4$OAc; Gradient: 15-65% B over 25 minutes, followed by a 10 minute hold at 65% B and 5 minute hold at 100% B; Flow: 15 mL/min. Fractions containing the product were combined and dried using a Genevac centrifugal evaporator to provide 8-isopropyl-6-(3-isopropyl-5-(piperidin-4-yl)-1H-indol-2-yl)-[1,2,4]triazolo[1,5-a]pyridine (1.5 mg, 1.3%) as a white solid. LC retention time=1.49 min [E]. MS (E−) m/z: 402 (M+H).

Example 96

8-chloro-6-(3-isopropyl-5-(piperidin-4-yl)-1H-indol-2-yl)-2-methyl-[1,2,4]triazolo[1,5-a]pyridine

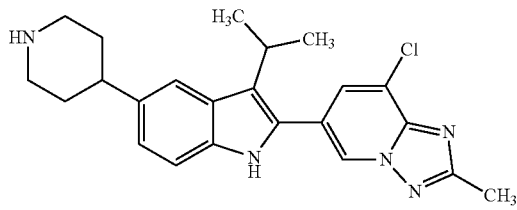

(96)

Intermediate 96A: Tert-butyl 4-(2-(8-chloro-2-methyl-[1,2,4]triazolo[1,5-a]pyridin-6-yl)-3-isopropyl-1H-indol-5-yl)piperidine-1-carboxylate

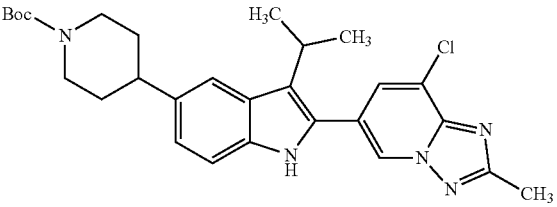

(96A)

A solution of tert-butyl 4-(3-isopropyl-2-(4,4,5,5-tetramethyl-1,3,2-dioxaborolan-2-yl)-1H-indol-5-yl)piperidine-1-carboxylate (2.0 g, 4.27 mmol), 6-bromo-8-chloro-2-methyl-[1,2,4]triazolo[1,5-a]pyridine (1.158 g, 4.70 mmol) and potassium phosphate, tribasic (2.231 g, 12.81 mmol) in dioxane (60 mL) and water (4 mL) was degassed with N$_2$ for 10 min. Next, PdCl$_2$(dppf)-CH$_2$Cl$_2$ adduct (0.174 g, 0.213 mmol) was added and the mixture was degassed for 5 min. The resulting reaction mixture was heated at 90° C. for 12 h. The reaction mixture was concentrated. The residue was dissolved in ethyl acetate and the solution was washed with water. The organic layer was collected, dried over Na$_2$SO$_4$ and concentrated to afford crude compound. The residue was taken up in DCM (1 mL) and recrystallized with pet ether (3×10 mL). The brown solid formed was filtered and dried to afford tert-butyl 4-(2-(8-chloro-2-methyl-[1,2,4]triazolo[1,5-a]pyridin-6-yl)-3-isopropyl-1H-indol-5-yl)piperidine-1-carboxylate (1.4 g, 2.76 mmol, 64.5%) as a pale yellow solid. LCMS retention time 3.74 min [D]. MS (E−) m/z: 508.3 (M+H).

Example 96

To a stirred solution of tert-butyl 4-(2-(8-chloro-2-methyl-[1,2,4]triazolo[1,5-a]pyridin-6-yl)-3-isopropyl-1H- indol-5-yl)piperidine-1-carboxylate (250 mg, 0.492 mmol) in CH$_2$Cl$_2$ (2 mL) was added TFA (0.2 mL) at room temperature. The reaction mixture was stirred at the same temperature 2 h. The reaction mass was concentrated to afford crude compound. The crude material was purified via preparative LC/MS with the following conditions: Column: Waters XBridge C18, 19×150 mm, 5-μm particles; Mobile Phase A: 0.1% trifluoroacetic acid; Mobile Phase B: acetonitrile; Gradient: 10-35% B over 25 minutes, then a 5-minute hold at 100% B; Flow: 15 mL/min. Fractions containing the product were combined and dried via centrifugal evaporation to afford 8-chloro-6-(3-isopropyl-5-(piperidin-4-yl)-1H-indol-2-yl)-2-methyl-[1,2,4]triazolo[1,5-a]pyridine (0.200 g, 99% yield) as a pale solid. LC retention time=2.31 min [E]. MS (E$^-$) m/z: 409.4 (M+H). $^1$H NMR (400 MHz, DMSO-d$_6$) δ ppm 1.32-1.52 (m, 7H) 1.80-1.96 (m, 3H) 2.07 (s, 1H) 2.28-2.40 (m, 1H) 2.61-2.72 (m, 1H) 2.88-3.04 (m, 2H) 3.17 (d, J=5.02 Hz, 2H) 3.21-3.28 (m, 2H) 4.10 (q, J=5.02 Hz, 1H) 7.02 (dd, J=8.53, 1.51 Hz, 1H) 7.35 (d, J=8.03 Hz, 1H) 7.57 (s, 1H), 8.02 (d, J=1.51 Hz, 1H) 8.77-8.94 (m, 1H) 11.24 (s, 1H).

Example 97

8-ethyl-6-(3-isopropyl-5-(piperidin-4-yl)-1H-indol-2-yl)-2-methyl-[1,2,4]triazolo[1,5-a]pyridine

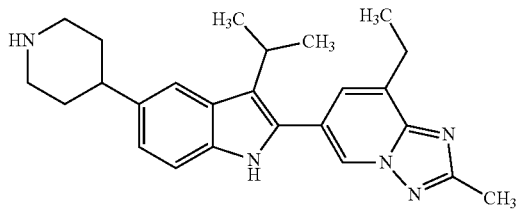

(97)

Intermediate 97A: tert-butyl 4-(2-(8-ethyl-2-methyl-[1,2,4]triazolo[1,5-a]pyridin-6-yl)-3-isopropyl-1H-indol-5-yl)piperidine-1-carboxylate

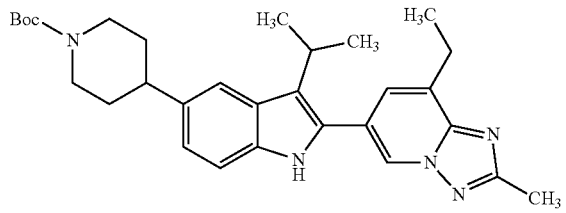

(97A)

A solution of tert-butyl 4-(2-(8-chloro-2-methyl-[1,2,4]triazolo[1,5-a]pyridin-6-yl)-3-isopropyl-1H-indol-5-yl)piperidine-1-carboxylate (0.1 mg, 0.197 μmol), ethylboronic acid (0.015 mg, 0.197 μmol), and potassium phosphate, dibasic (0.086 mg, 0.492 μmol) in toluene (2 mL) and water (0.5 mL) was degassed with N$_2$ for 10 min. Next, Pd(OAc)$_2$ (4.42 μg, 0.020 μmol) and tricyclohexylphosphine (2.76 μg, 0.0098 μmol) were added and the reaction mixture was degassed for 5 min. The reaction mixture was heated at 100° C. for 12 h. The reaction mixture was concentrated. The residue was dissolved in ethyl acetate and the solution was washed with water. The organic layer was collected, dried over Na$_2$SO$_4$, and concentrated to afford tert-butyl 4-(2-(8-ethyl-2-methyl-[1,2,4]triazolo[1,5-a]pyridin-6-yl)-3-isopropyl-1H-indol-5-yl) piperidine-1-carboxylate (80 mg, 1.59 mmol, 81%) as a pale yellow solid. LCMS retention time 3.93 min [D]. MS (E$^-$) m/z: 502.3 (M+H).

Example 97

To a solution of tert-butyl 4-(2-(8-ethyl-2-methyl-[1,2,4] triazolo[1,5-a]pyridin-6-yl)-3-isopropyl-1H-indol-5-yl)piperidine-1-carboxylate (0.08 g, 0.159 mmol) in DCM (2 mL) was added 4 M HCl in dioxane (0.399 mL, 1.595 mmol) drop wise. The reaction mixture was stirred at 25° C. for 1 h. The reaction mass was concentrated to afford crude compound. The crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 8-38% B over 25 minutes, then a 5-minute hold at 100% B; Flow: 15 mL/min. Fractions containing the product were combined and dried via centrifugal evaporation to afford 8-ethyl-6-(3-isopropyl-5-(piperidin-4-yl)-1H-indol-2-yl)-2-methyl-[1,2,4]triazolo[1,5-a]pyridine (0.0013 g, 2% yield) as a pale solid. LC retention time=1.369 min [D1]. MS (E$^-$) m/z: 402 (M+H). $^1$H NMR (400 MHz, DMSO-d$_6$) δ ppm 11.17 (s, 1H), 8.69 (s, 1H), 7.54 (d, J=18.6 Hz, 2H), 7.41-7.30 (m, 1H), 7.01 (d, J=9.0 Hz, 1H), 3.19-3.16 (m, 5H), (3.08-2.95 (m, 8H), 2.08 (s, 1H), 1.99 (d, J=13.2 Hz, 6H), 1.87 (d, J=12.2 Hz, 7H), 1.45 (d, J=7.1 Hz, 9H), 1.40-1.34 (m, 3H).

Example 98

Tert-butyl 4-(2-(8-ethyl-7-methyl-[1,2,4]triazolo[1,5-a]pyridin-6-yl)-3-isopropyl-1H-indol-5-yl)piperidine-1-carboxylate

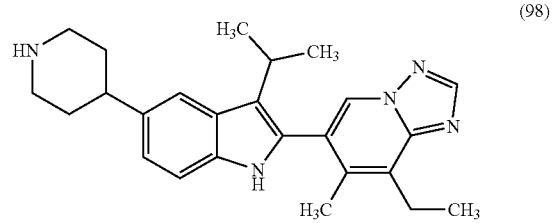 [SMILES: CCc1c(C)c(-c2[nH]c3ccc(C4CCNCC4)cc3c2C(C)C)cn2ncnc12]

(98)

Intermediate 98A: 6-bromo-7-methyl-8-vinyl-[1,2,4]triazolo[1,5-a]pyridine

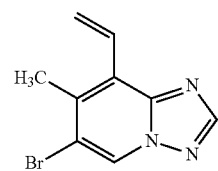

(98A)

A solution of 6-bromo-8-iodo-7-methyl-[1,2,4]triazolo[1,5-a]pyridine (0.25 g, 0.740 mmol) and potassium vinyltrifluoroborate (0.099 g, 0.740 mmol) in ethanol (5 mL) was degassed with N₂ for 10 min. Next, PdCl₂(dppf)-CH₂Cl₂ adduct (0.030 g, 0.037 mmol) was added and the reaction mixture was degassed for 5 min followed by the addition of TEA (0.412 mL, 2.96 mmol). The resulting reaction mixture was heated at 85° C. for 12 h. The reaction mixture was concentrated. The residue was dissolved in ethyl acetate and the solution was washed with water. The organic layer was collected, dried over Na₂SO₄, and concentrated to afford 6-bromo-7-methyl-8-vinyl-[1,2,4]triazolo[1,5-a]pyridine (0.25 g, 0.473 mmol, 63.9% yield) as a yellow solid. LCMS retention time 1.42 min [H]. MS (E⁻) m/z: 240.3 (M+2H).

Intermediate 98B: tert-butyl 4-(3-isopropyl-2-(7-methyl-8-vinyl-[1,2,4]triazolo[1,5-a]pyridin-6-yl)-1H-indol-5-yl)piperidine-1-carboxylate

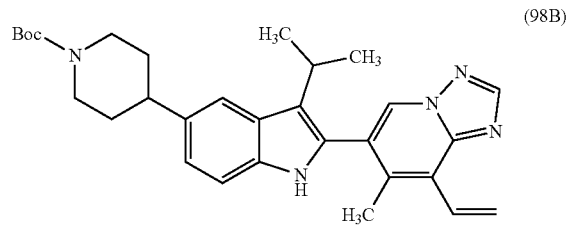 [SMILES: C=Cc1c(C)c(-c2[nH]c3ccc(C4CCN(C(=O)OC(C)(C)C)CC4)cc3c2C(C)C)cn2ncnc12]

(98B)

A solution of tert-butyl 4-(3-isopropyl-2-(4,4,5,5-tetramethyl-1,3,2-dioxaborolan-2-yl)-1H-indol-5-yl)piperidine-1-carboxylate (0.4 g, 0.854 mmol), 6-bromo-7-methyl-8-vinyl-[1,2,4]triazolo[1,5-a]pyridine (0.224 g, 0.939 mmol), and potassium phosphate tribasic (0.446 g, 2.56 mmol) in dioxane (5 mL) and water (1 mL) was degassed with N₂ for 10 min. Next, PdCl₂(dppf)-CH₂Cl₂ adduct (0.035 g, 0.043 mmol) was added and the mixture was again degassed for 5 min. The resulting reaction mixture was heated at 90° C. for 12 h. The reaction mixture was concentrated. The residue was dissolved in ethyl acetate and the solution was washed with water. The organic layer was collected, dried over Na₂SO₄, and concentrated to afford crude compound. The residue was taken up in DCM (1 mL) and recrystallized with pet ether (3×10 mL). The crude material was purified by combiflash 5% MeOH/CHCl₃.
Concentration of fractions provided tert-butyl 4-(3-isopropyl-2-(7-methyl-8-vinyl-[1,2,4]triazolo[1,5-a]pyridin-6-yl)-1H-indol-5-yl)piperidine-1-carboxylate (0.35 g, 0.700 mmol, 82%) as a yellow solid. LCMS retention time 3.11 min [D]. MS (E⁻) m/z: 500.3 (M+H).

Intermediate 98C: Tert-butyl 4-(2-(8-ethyl-7-methyl-[1,2,4]triazolo[1,5-a]pyridin-6-yl)-3-isopropyl-1H-indol-5-yl)piperidine-1-carboxylate

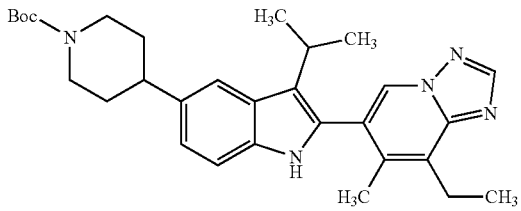

(98C)

A solution of tert-butyl 4-(3-isopropyl-2-(7-methyl-8-vinyl-[1,2,4]triazolo[1,5-a]pyridin-6-yl)-1H-indol-5-yl)piperidine-1-carboxylate (0.35 g, 0.700 mmol) in methanol (10 mL) was purged with nitrogen (N₂). Next, Pd/C (0.019 g, 0.018 mmol) was added and the mixture was purged with N₂ three times. Hydrogen gas (H₂) was introduced via a balloon to the mixture. The reaction mixture was stirred at room temperature for 5 h. The suspension was filtered through celite bed, the filtrate was collected, and concentrated to afford tert-butyl 4-(2-(8-ethyl-7-methyl-[1,2,4]triazolo[1,5-a]pyridin-6-yl)-3-isopropyl-1H-indol-5-yl) piperidine-1-carboxylate (250 mg, 0.498 mmol, 72%) as a white solid. LCMS retention time 4.45 min [H]. MS (E⁻) m/z: 502.3 (M+H).

Example 98

To a solution of tert-butyl 4-(2-(8-ethyl-7-methyl-[1,2,4]triazolo[1,5-a]pyridin-6-yl)-3-isopropyl-1H-indol-5-yl)piperidine-1-carboxylate (0.25 g, 0.498 mmol) in DCM (2 mL) was added 4 M HCl in dioxane (0.249 mL, 0.997 mmol) drop wise. The reaction mixture was stirred at 25° C. for 1 h. The crude material was purified via preparative LC/MS with the following conditions: Column: Waters XBridge C18, 19×150 mm, 5-µm particles; Mobile Phase A: 10-mM ammonium acetate; Mobile Phase B: methanol; Gradient: 20-60% B over 20 minutes, then a 5-minute hold at 100% B; Flow: 15 mL/min. Fractions containing the product were combined and dried via centrifugal evaporation to afford 8-ethyl-6-(3-isopropyl-5-(piperidin-4-yl)-1H-indol-2-yl)-7-methyl-[1,2,4]triazolo[1,5-a]pyridine (180 mg, 90%) as a pale solid. LCMS retention time 1.368 min [E]. MS (E⁻) m/z: 402.2 (M+H).

The following examples were prepared according to the general procedures disclosed in Examples 1 and 2.

TABLE 9

| Ex. No. | Fragment Starting Material | Structure | LCMS MH+ | R_t (min) | HPLC Method |
|---|---|---|---|---|---|
| 99 | F-17 | 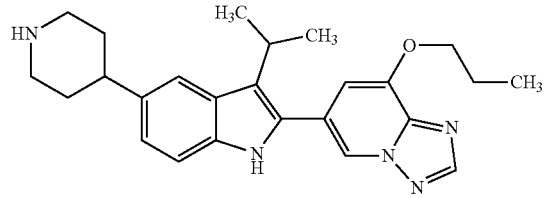 [SMILES: CCCOc1cc(-c2[nH]c3ccc(C4CCNCC4)cc3c2C(C)C)cn2ncnc12] | 418.2 | 1.33 | QC-ACN-AA-XB |

TABLE 9-continued
| Ex. No. | Fragment Starting Material | Structure | LCMS MH+ | $R_t$ (min) | HPLC Method |
|---|---|---|---|---|---|
| 100 | F-10 | 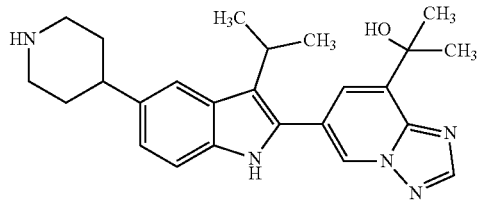 [SMILES: CC(C)c1c(-c2cc(C(C)(C)O)c3ncnn3c2)[nH]c2ccc(C3CCNCC3)cc12] | 417.9 | 1.18 | QC-ACN-AA-XB |
| 101 | F-12 | 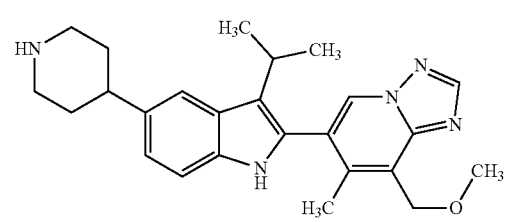 | 418.0 | 0.65 | A1 |
| 102 | F-14 | 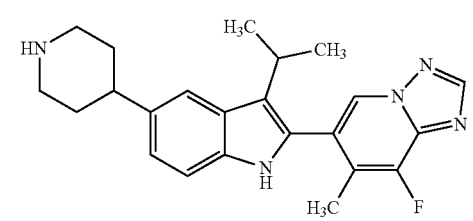 | 392.0 | 1.2 | QC-ACN-AA-XB |
| 103 | F-9 | 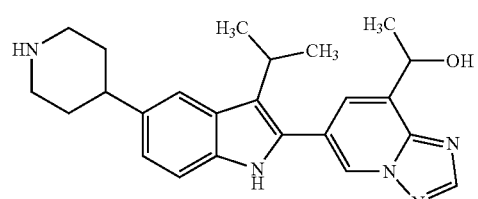 | 403.9 | 1.14 | QC-ACN-TFA-XB |
| 104 | F-11 | 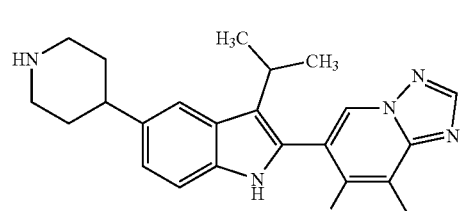 | 404.2 | 0.99 | QC-ACN-AA-XB |
| 105 | F-13 | 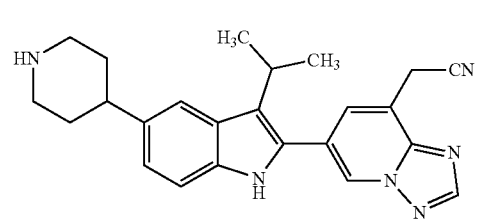 [SMILES: CC(C)c1c(-c2cc(CC#N)c3ncnn3c2)[nH]c2ccc(C3CCNCC3)cc12] | 399.1 | 1.21 | QC-ACN-AA-XB |
| 106 | F-14 | 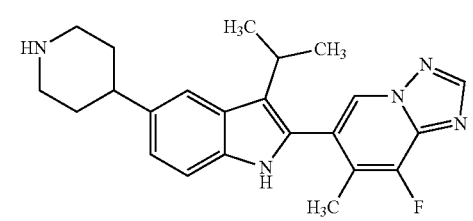 [SMILES: Cc1c(-c2[nH]c3ccc(C4CCNCC4)cc3c2C(C)C)cn2ncnc2c1F] | 392.0 | 1.2 | QC-ACN-TFA-XB |

TABLE 9-continued
| Ex. No. | Fragment Starting Material | Structure | LCMS MH+ | R$_t$ (min) | HPLC Method |
|---|---|---|---|---|---|
| 107 | F-14 | 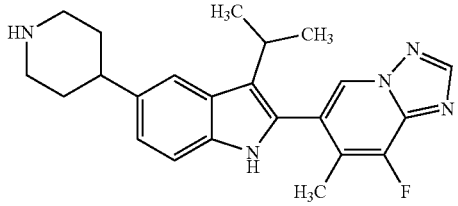 [SMILES: Cc1c(-c2[nH]c3ccc(C4CCNCC4)cc3c2C(C)C)cn2ncnc2c1F] | 392.0 | 1.42 | QC-ACN-AA-XB |
| 108 | F-8 | 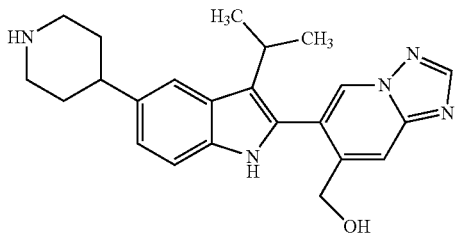 [SMILES: CC(C)c1c(-c2cn3ncnc3cc2CO)[nH]c2ccc(C3CCNCC3)cc12] | 389.9 | 0.88 | QC-ACN-AA-XB |
| 109 | F-58 | 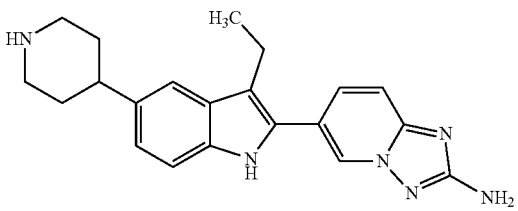 [SMILES: CCc1c(-c2ccc3nc(N)nn3c2)[nH]c2ccc(C3CCNCC3)cc12] | 361.3 | 0.71 | QC-ACN-AA-XB |
| 110 | F-18 | 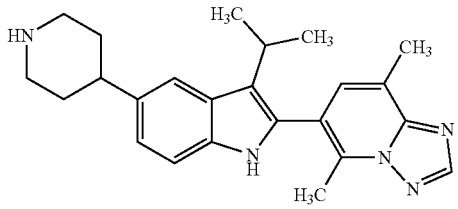 [SMILES: Cc1cc(-c2[nH]c3ccc(C4CCNCC4)cc3c2C(C)C)c(C)n2ncnc12] | 388.2 | 1.25 | QC-ACN-TFA-XB |
| 111 | F-19 | 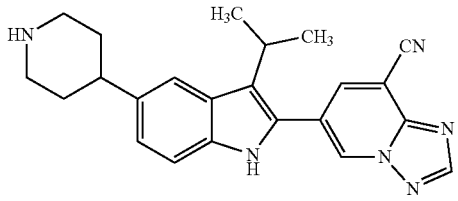 [SMILES: CC(C)c1c(-c2cc(C#N)c3ncnn3c2)[nH]c2ccc(C3CCNCC3)cc12] | 385.2 | 1.19 | QC-ACN-TFA-XB |
| 112 | F-20 | 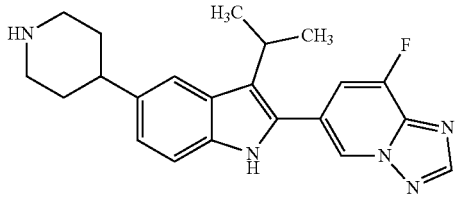 [SMILES: CC(C)c1c(-c2cc(F)c3ncnn3c2)[nH]c2ccc(C3CCNCC3)cc12] | 378.0 | 1.148 | QC-ACN-AA-XB |
| 113 | F-8 | 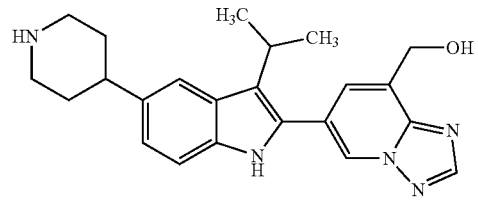 | 390.2 | 0.61 | A1 |

TABLE 9-continued

| Ex. No. | Fragment Starting Material | Structure | LCMS MH+ | R<sub>t</sub> (min) | HPLC Method |
|---|---|---|---|---|---|
| 114 | F16 | 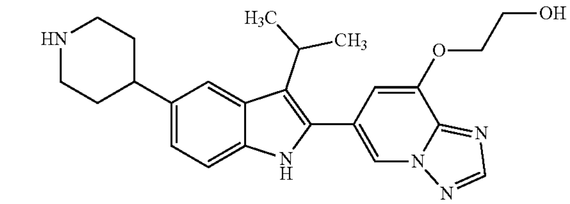 [SMILES: CC(C)c1c(-c2cc(OCCO)c3ncnn3c2)[nH]c2ccc(C3CCNCC3)cc12] | 420.2 | 0.61 | A1 |
| 115 | F-7 | 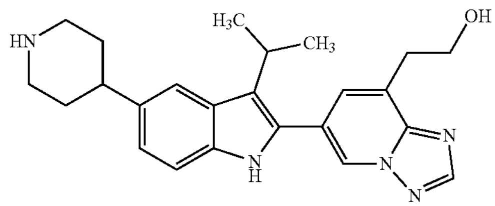 [SMILES: CC(C)c1c(-c2cc(CCO)c3ncnn3c2)[nH]c2ccc(C3CCNCC3)cc12] | — | 0.63 | A1 |
| 116 | F-16 | 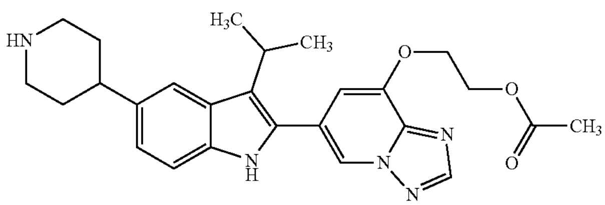 [SMILES: CC(=O)OCCOc1cc(-c2[nH]c3ccc(C4CCNCC4)cc3c2C(C)C)cn2ncnc12] | 462.2 | 0.67 | A1 |
| 117 | F-59 | 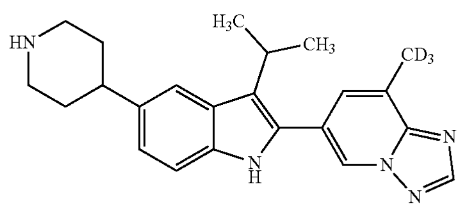 [SMILES: [2H]C([2H])([2H])c1cc(-c2[nH]c3ccc(C4CCNCC4)cc3c2C(C)C)cn2ncnc12] | 377.2 | 0.66 | TS1 |

TABLE 10

| Ex. No. | Fragment Starting Material | Structure | LCMS MH+ | R$_t$ (min) | HPLC Method |
|---|---|---|---|---|---|
| 118 | F-39 | 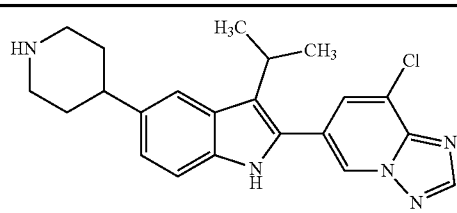 | 395.3 | 2.01 | E |
| 119 | F-36 | 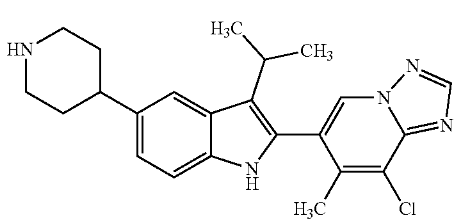 [SMILES: Cc1c(-c2[nH]c3ccc(C4CCNCC4)cc3c2C(C)C)cn2ncnc2c1Cl] | 409.1 | 1.37 | E |

TABLE 10-continued
| Ex. No. | Fragment Starting Material | Structure | LCMS MH+ | R$_t$ (min) | HPLC Method |
|---|---|---|---|---|---|
| 120 | F-40 | 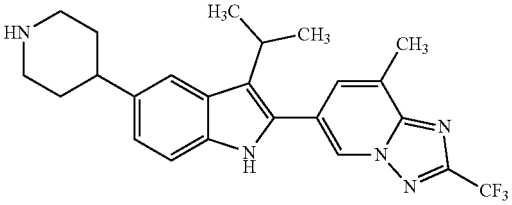 [SMILES: Cc1cc(-c2[nH]c3ccc(C4CCNCC4)cc3c2C(C)C)cn2nc(C(F)(F)F)nc12] | 443.2 | 1.78 | E |
| 121 | F-1 | 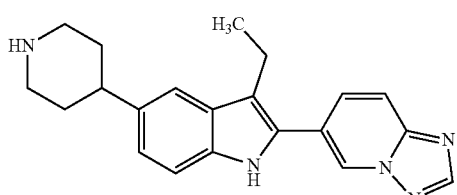 | 346.6 | 0.81 | E |
| 122 | F-21 | 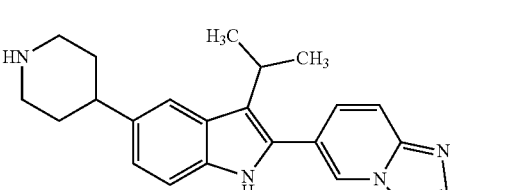 | 375.3 | 1.06 | E |
| 123 | F-22 | 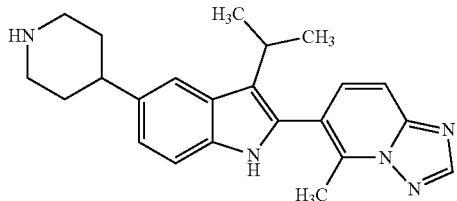 | 375.2 | 1.28 | E |
| 124 | F-23 | 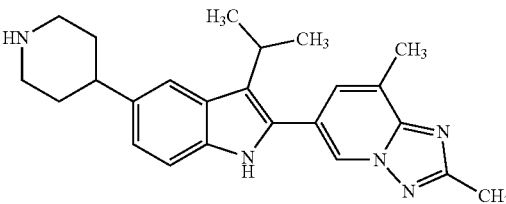 | 389.3 | 1.22 | F |
| 125 | F-24 | 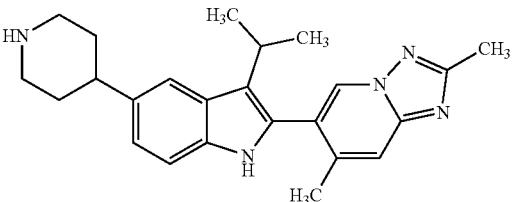 | 389.2 | 1.30 | F |
| 126 | F-25 | 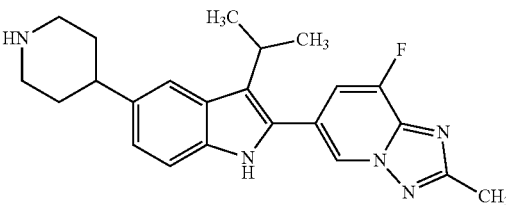 | 392.3 | 1.39 | F |

TABLE 10-continued
| Ex. No. | Fragment Starting Material | Structure | LCMS MH+ | R$_t$ (min) | HPLC Method |
|---|---|---|---|---|---|
| 127 | F-26 | 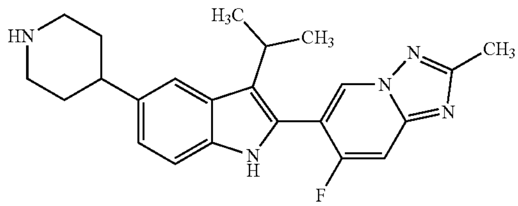 [SMILES: Cc1nc2cc(F)c(-c3[nH]c4ccc(C5CCNCC5)cc4c3C(C)C)cn2n1] | 391.3 | 1.13 | E |
| 128 | F-27 | 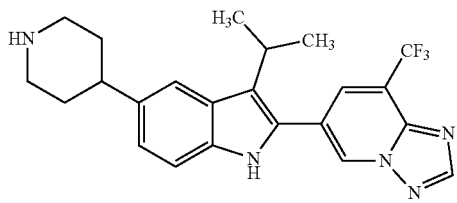 | 428.2 | 1.46 | F |
| 131 | F-28 | 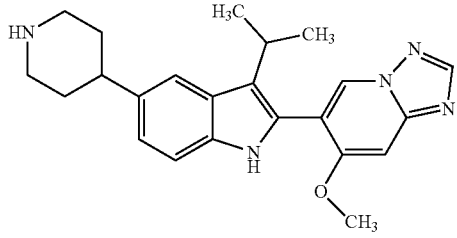 [SMILES: COc1cc2ncnn2cc1-c1[nH]c2ccc(C3CCNCC3)cc2c1C(C)C] | 391.3 | 0.95 | E |
| 132 | F-29 | 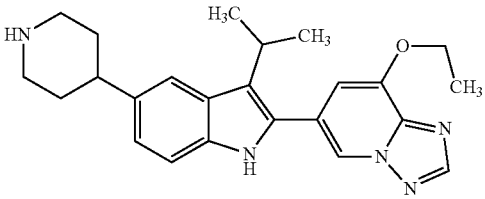 [SMILES: CCOc1cc(-c2[nH]c3ccc(C4CCNCC4)cc3c2C(C)C)cn2ncnc12] | 405.3 | 1.16 | E |
| 133 | F-31 | 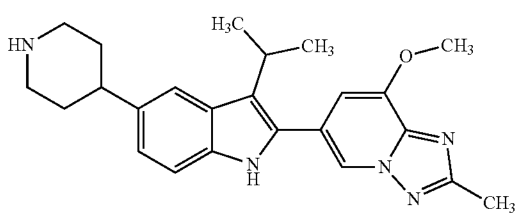 [SMILES: COc1cc(-c2[nH]c3ccc(C4CCNCC4)cc3c2C(C)C)cn2nc(C)nc12] | 405.2 | 1.37 | E |
| 134 | F-32 | 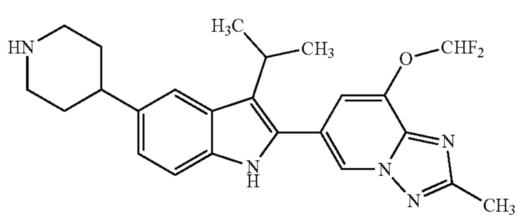 [SMILES: Cc1nc2c(OC(F)F)cc(-c3[nH]c4ccc(C5CCNCC5)cc4c3C(C)C)cn2n1] | 441.2 | 1.43 | E |
| 135 | F-30 | 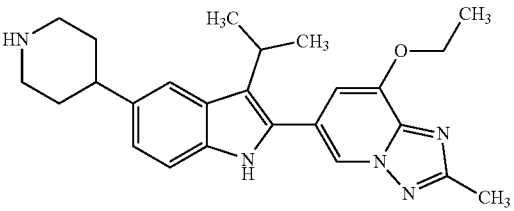 [SMILES: CCOc1cc(-c2[nH]c3ccc(C4CCNCC4)cc3c2C(C)C)cn2nc(C)nc12] | 419.3 | 1.39 | E |

TABLE 10-continued
| Ex. No. | Fragment Starting Material | Structure | LCMS MH+ | R_t (min) | HPLC Method |
|---|---|---|---|---|---|
| 136 | F-33 | 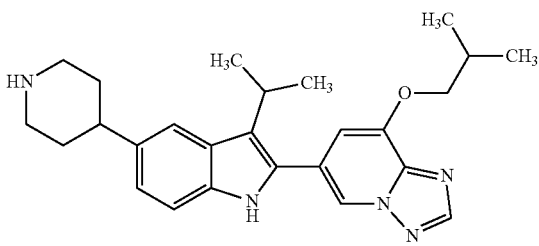 [SMILES: CC(C)COc1cc(-c2[nH]c3ccc(C4CCNCC4)cc3c2C(C)C)cn2ncnc12] | 433.4 | 1.41 | E |
| 138 | F-34 | 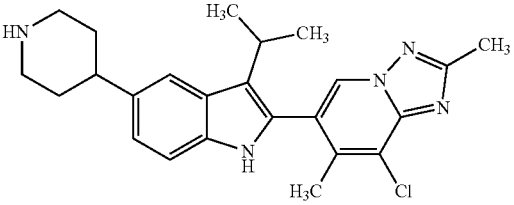 [SMILES: Cc1nc2c(Cl)c(C)c(-c3[nH]c4ccc(C5CCNCC5)cc4c3C(C)C)cn2n1] | 423.2 | 1.42 | E |
| 140 | F-35 | 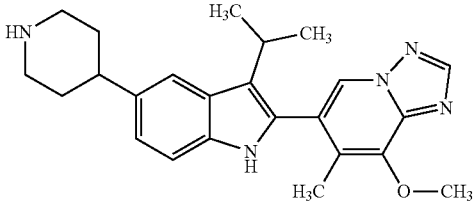 [SMILES: COc1c(C)c(-c2[nH]c3ccc(C4CCNCC4)cc3c2C(C)C)cn2ncnc12] | 405.2 | 1.36 | E |
| 141 | F-54 | 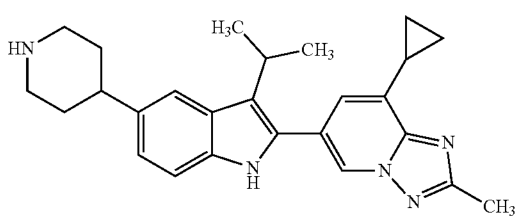 [SMILES: Cc1nc2c(C3CC3)cc(-c3[nH]c4ccc(C5CCNCC5)cc4c3C(C)C)cn2n1] | 415.1 | 1.40 | F |
| 142 | F-21 | 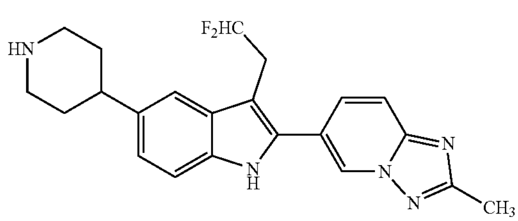 [SMILES: Cc1nc2ccc(-c3[nH]c4ccc(C5CCNCC5)cc4c3CC(F)F)cn2n1] | 396.3 | 0.88 | E |
| 143 | F-41 | 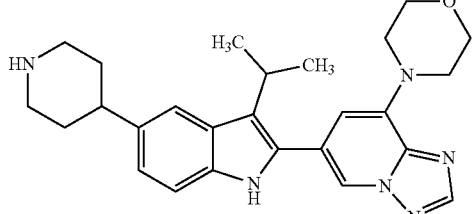 | 446.3 | 1.37 | E |

TABLE 10-continued

| Ex. No. | Fragment Starting Material | Structure | LCMS MH+ | R_t (min) | HPLC Method |
|---|---|---|---|---|---|
| 144 | F-45 | 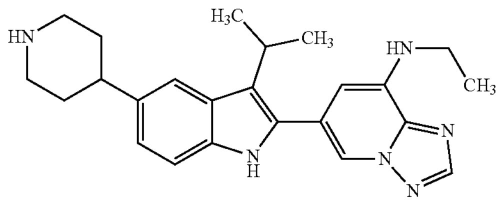 [SMILES: CCNc1cc(-c2[nH]c3ccc(C4CCNCC4)cc3c2C(C)C)cn2ncnc12] | 404.2 | 1.43 | F |
| 145 | F-46 | 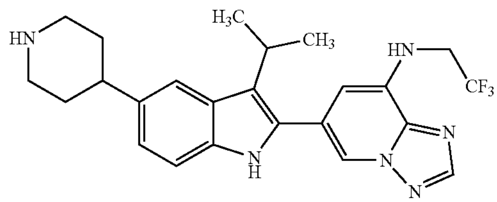 [SMILES: CC(C)c1c(-c2cc(NCC(F)(F)F)c3ncnn3c2)[nH]c2ccc(C3CCNCC3)cc12] | 458.2 | 1.49 | F |
| 146 | F-47 | 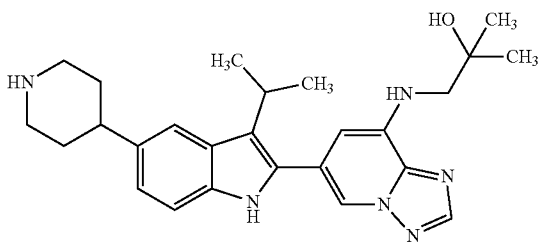 [SMILES: CC(C)c1c(-c2cc(NCC(C)(C)O)c3ncnn3c2)[nH]c2ccc(C3CCNCC3)cc12] | 448.3 | 1.32 | F |
| 147 | F-48 | 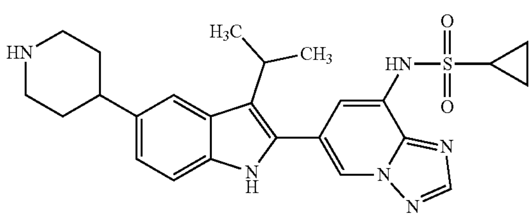 [SMILES: CC(C)c1c(-c2cc(NS(=O)(=O)C3CC3)c3ncnn3c2)[nH]c2ccc(C3CCNCC3)cc12] | 480.2 | 1.28 | F |
| 148 | F-49 | 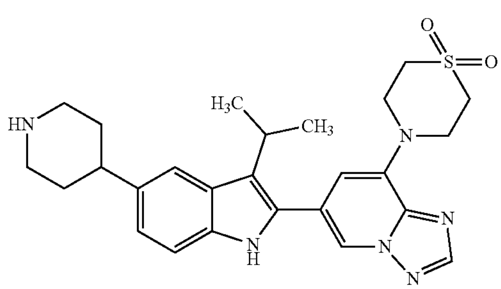 [SMILES: CC(C)c1c(-c2cc(N3CCS(=O)(=O)CC3)c3ncnn3c2)[nH]c2ccc(C3CCNCC3)cc12] | 493.2 | 1.28 | F |
| 149 | F-44 | 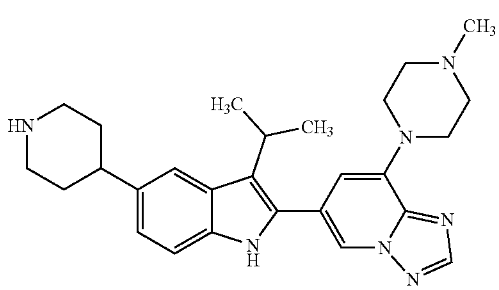 [SMILES: CC(C)c1c(-c2cc(N3CCN(C)CC3)c3ncnn3c2)[nH]c2ccc(C3CCNCC3)cc12] | 459.3 | 1.07 | F |

TABLE 10-continued

| Ex. No. | Fragment Starting Material | Structure | LCMS MH+ | R$_t$ (min) | HPLC Method |
|---|---|---|---|---|---|
| 150 | F-41 | 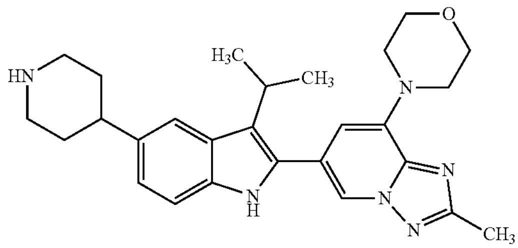 [SMILES: Cc1nc2c(N3CCOCC3)cc(-c3[nH]c4ccc(C5CCNCC5)cc4c3C(C)C)cn2n1] | 460.3 | 1.42 | F |
| 151 | F-52 | 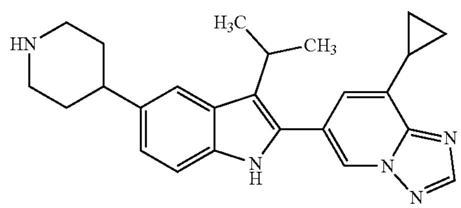 [SMILES: CC(C)c1c(-c2cc(C3CC3)c3ncnn3c2)[nH]c2ccc(C3CCNCC3)cc12] | 401.3 | 1.21 | F |
| 152 | F-55 | 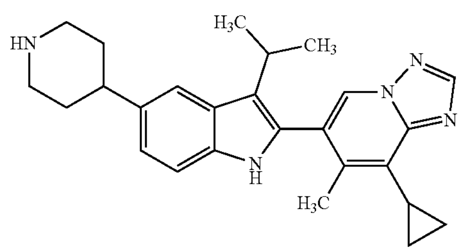 [SMILES: Cc1c(-c2[nH]c3ccc(C4CCNCC4)cc3c2C(C)C)cn2ncnc2c1C1CC1] | 414.2 | 1.36 | F |
| 153 | F-40 | 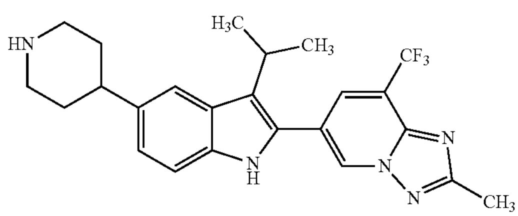 [SMILES: Cc1nc2c(C(F)(F)F)cc(-c3[nH]c4ccc(C5CCNCC5)cc4c3C(C)C)cn2n1] | 443.2 | 1.33 | E |
| 154 | F-57 | 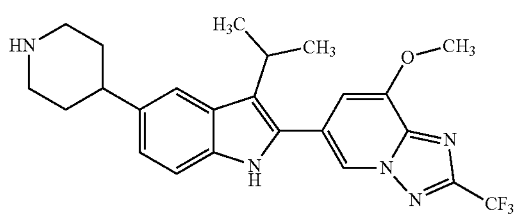 [SMILES: COc1cc(-c2[nH]c3ccc(C4CCNCC4)cc3c2C(C)C)cn2nc(C(F)(F)F)nc12] | 459.2 | 1.68 | E |
| 155 | F-37 | 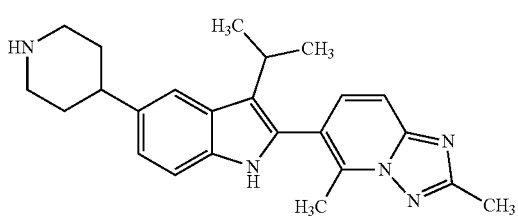 | 389.2 | 1.15 | F |
| 156 | F-5 | 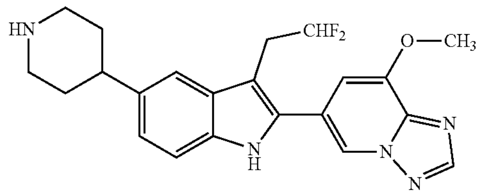 [SMILES: COc1cc(-c2[nH]c3ccc(C4CCNCC4)cc3c2CC(F)F)cn2ncnc12] | 412.2 | 0.92 | E |

TABLE 10-continued

| Ex. No. | Fragment Starting Material | Structure | LCMS MH+ | R$_t$ (min) | HPLC Method |
|---|---|---|---|---|---|
| 157 | F-5 | 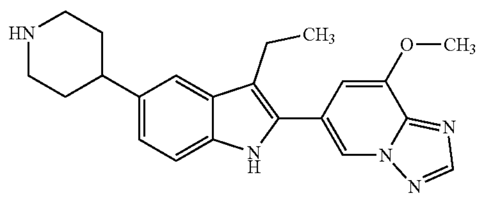 [SMILES: CCc1c(-c2cc(OC)c3ncnn3c2)[nH]c2ccc(C3CCNCC3)cc12] | 376.4 | 1.34 | D |
| 158 | F-2 | 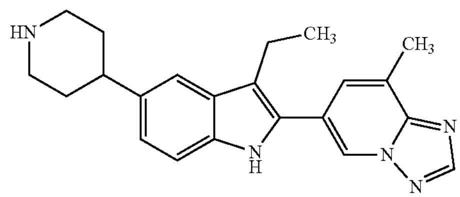 [SMILES: CCc1c(-c2cc(C)c3ncnn3c2)[nH]c2ccc(C3CCNCC3)cc12] | 360.2 | 1.40 | D |
| 159 | F-51 | 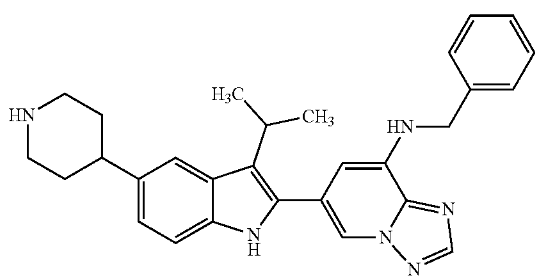 [SMILES: CC(C)c1c(-c2cc(NCc3ccccc3)c3ncnn3c2)[nH]c2ccc(C3CCNCC3)cc12] | 465.3 | 1.54 | N |
| 160 | | 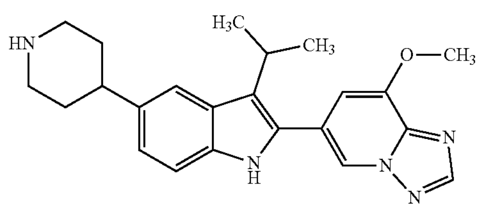 [SMILES: COc1cc(-c2[nH]c3ccc(C4CCNCC4)cc3c2C(C)C)cn2ncnc12] | 426.2 | 1.35 | N |

Example 161

6-(3-(2,2-difluoroethyl)-5-(piperidin-4-yl)-1H-indol-2-yl)-8-methyl-[1,2,4]triazolo[1,5-a]pyridine

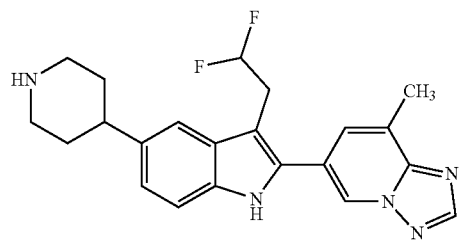

(161)

Intermediate 161A: 5-bromo-1-tosyl-1H-indole

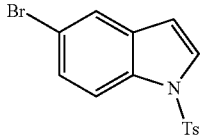

(161A)

To a stirred solution of 5-bromo-1H-indole (5.0 g, 25.5 mmol), TsCl (6.03 g, 31.6 mmol), and tetrabutylammonium hydrogen sulfate (0.63 g, 1.855 mmol) in toluene (100 mL) was added NaOH (50% solution in water, 10.20 g, 255 mmol) dropwise. The reaction mixture was stirred for 16 h at room temperature. The reaction was quenched with water (20 mL). The layers were separated, the aqueous layer was extracted with EtOAc (2×50 mL), the combined organic extracts were dried (Na$_2$SO$_4$) and concentrated to yield crude material. The crude material was purified by silica gel chromatography. The compound was eluted in 4% EA in hexanes, the fractions was collected and concentrated to afford 5-bromo-1-tosyl-1H-indole (7.1 g, 20.27 mmol) as a white solid. LC retention time=2.230 min [A]. MS (E⁻) m/z: 393.3 (M−H).

Intermediate 161B: 1-(5-bromo-1-tosyl-1H-indol-3-yl)-2,2-difluoroethan-1-one

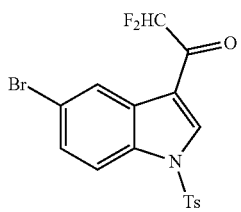

(161B)

To a suspension of AlCl₃ (6.85 g, 51.4 mmol) in DCM (50 mL) was added difluoroacetic anhydride (4.47 g, 25.7 mmol). The reaction mixture was stirred for 15 min, then a solution of 5-bromo-1-tosyl-1H-indole (3 g, 8.57 mmol)) in DCM (30 mL) was added. The reaction mixture was stirred for 1 h at ambient temperature. The reaction was quenched with ice-water. The mixture was extracted with DCM (2×50 mL), combined extracts was washed with aqueous NaHCO₃, brine, dried over MgSO₄, filtered and concentrated to yield crude material. The crude material was purified by silica gel chromatography, the compound was eluted in 10% EtOAc in hexane, the fraction was collected and concentrated to afford 1-(5-bromo-1-tosyl-1H-indol-3-yl)-2,2-difluoroethanone (2.21 g, 4.1 mmol) as a crystalline solid. LC retention time=2.732 min [A]. MS (E⁻) m/z: 428.0 (M+H).

Intermediate 161C: 1-(5-bromo-1H-indol-3-yl)-2,2-difluoroethan-1-one

(161C)

To a solution of 1-(5-bromo-1-tosyl-1H-indol-3-yl)-2,2-difluoroethanone (0.2 g, 0.467 mmol) in THF (4 mL) and MeOH (4.00 mL) solvent mixture was added Cs₂CO₃ (0.45 g, 1.381 mmol) at room temperature. The mixture was stirred at room temperature for 12 h. The reaction mixture was concentrated, the residue was diluted with minimum amount of water and undissolved solids were filtered and dried under vacuum to afford 1-(5-bromo-1H-indol-3-yl)-2,2-difluoroethanone (105 mg, 0.244 mmol) as a white solid. LC retention time=2.233 min [A]. MS (E⁻) m/z: 276 (M+2H).

Intermediate 161D: 5-bromo-3-(2,2-difluoroethyl)-1H-indole

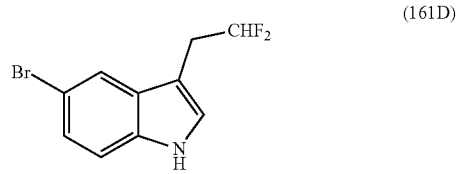 [SMILES: FC(F)Cc1c[nH]c2ccc(Br)cc12]

(161D)

To the stirred solution of 1-(5-bromo-1H-indol-3-yl)-2,2-difluoroethanone (0.25 g, 0.912 mmol) in THF (10 mL) was added BH₃DMS (1.368 mL, 2.74 mmol) at 0° C. under nitrogen. The reaction mixture was stirred at 80° C. for 20 h. The reaction was quenched with water (2 mL) at 0° C. The reaction mixture was diluted with ethyl acetate (100 mL), washed with sodium bicarbonate (2×25 mL) and water (2×25 mL), combined organic extracts was dried over anhydrous sodium sulphate, filtered and concentrated to yield crude compound. The crude material was purified on silica gel chromatography, the compound was eluted at 8% ethyl acetate/hexane, the fractions was collected and concentrated to afford 5-bromo-3-(2,2-difluoroethyl)-1H-indole (120 mg, 0.438 mmol) as an oil. LC retention time=2.802 min [D]. MS (E⁻) m/z: 260 (M+H).

Intermediate 161E: Tert-butyl 4-(3-(2,2-difluoroethyl)-1H-indol-5-yl)-3,6-dihydropyridine-1(2H)-carboxylate

(161E)

Tert-butyl 4-(3-(2,2-difluoroethyl)-1H-indol-5-yl)-5,6-dihydropyridine-1(2H)-carboxylate was prepared according to the general procedure described in Intermediate T-1B using 5-bromo-3-(2,2-difluoroethyl)-1H-indole as the starting intermediate (0.14 g, 80% yield). LC retention time 3.075 min [D]. MS (E⁻) m/z: 361.2 (M−H).

Intermediate 161F: Tert-butyl 4-(3-(2,2-difluoroethyl)-1H-indol-5-yl)piperidine-1-carboxylate

(161F)

Tert-butyl 4-(3-(2,2-difluoroethyl)-1H-indol-5-yl)piperidine-1-carboxylate was prepared according to the general procedure described in Intermediate T-1C using tert-butyl 4-(3-(2,2-difluoroethyl)-1H-indol-5-yl)-5,6-dihydropyridine-1(2H)-carboxylate as the starting intermediate (0.9 g, 88% yield). LC retention time 3.282 min [D]. MS (E⁻) m/z: 265.0 (M+H−Boc).

Intermediate 161G: Tert-butyl 4-(2-bromo-3-(2,2-difluoroethyl)-1H-indol-5-yl)piperidine-1-carboxylate

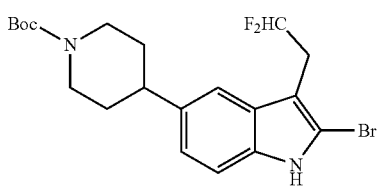

(161G)

Tert-butyl 4-(2-bromo-3-(2,2-difluoroethyl)-1H-indol-5-yl)piperidine-1-carboxylate was prepared according to the general procedure described in Intermediate 194D using tert-butyl 4-(3-(2,2-difluoroethyl)-1H-indol-5-yl)piperidine-1-carboxylate as the starting intermediate (0.3 g, 52% yield). LC retention time 1.10 min [G]. MS (E⁻) m/z: 389.0 (M+2H−tBu).

Intermediate 161H: Tert-butyl 4-(3-(2,2-difluoroethyl)-2-(4,4,5,5-tetramethyl-1,3,2-dioxaborolan-2-yl)-1H-indol-5-yl)piperidine-1-carboxylate

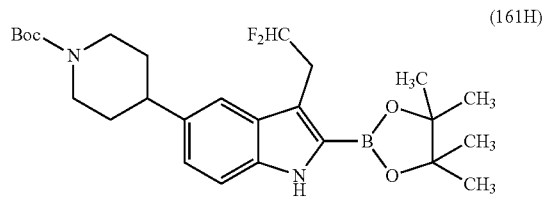 [SMILES: CC(C)(C)OC(=O)N1CCC(c2ccc3[nH]c(B4OC(C)(C)C(C)(C)O4)c(CC(F)F)c3c2)CC1]

(161H)

A mixture of pinacolborane (1.444 g, 11.28 mmol), tert-butyl 4-(2-bromo-3-(2,2-difluoroethyl)-1H-indol-5-yl)piperidine-1-carboxylate (1.0 g, 2.256 mmol), bis(benzonitrile)palladium(II) chloride (0.086 g, 0.226 mmol), TEA (0.683 g, 6.77 mmol), and 2-dicyclohexylphosphino-2',6'-dimethoxybiphenyl (0.092 g, 0.226 mmol) in dioxane (20 mL) was degassed with nitrogen for 10 min. The reaction mixture was stirred at 80° C. for 1 h in a sealed tube. The reaction was quenched with ice cold water. The reaction mixture was diluted with ethyl acetate, filtered and washed with excess ethyl acetate, combined organic layers was washed with water, brine, dried over sodium sulphate and evaporated to afford crude compound. The crude material was purified by silica gel chromatography, the compound was eluted with 25% ethyl acetate in hexane, the fractions were collected and concentrated to afford tert-butyl 4-(3-(2,2-difluoroethyl)-2-(4,4,5,5-tetramethyl-1,3,2-dioxaborolan-2-yl)-1H-indol-5-yl)piperidine-1-carboxylate (0.650 g, 1.325 mmol, 58.8% yield) as an off-white solid. LC retention time 3.282 min [D]. MS (E⁻) m/z: 435.4 (M+H−tBu).

Intermediate 161I: tert-butyl 4-(3-(2,2-difluoroethyl)-2-(8-methyl-[1,2,4]triazolo[1,5-a]pyridin-6-yl)-1H-indol-5-yl)piperidine-1-carboxylate

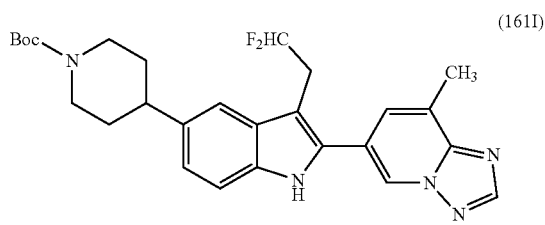 [SMILES: Cc1cc(-c2[nH]c3ccc(C4CCN(C(=O)OC(C)(C)C)CC4)cc3c2CC(F)F)cn2ncnc12]

(161I)

A Mixture of Tert-Butyl 4-(3-(2,2-difluoroethyl)-2-(4,4,5,5-tetramethyl-1,3,2-dioxaborolan-2-yl)-1H-indol-5-yl)piperidine-1-carboxylate (0.300, 0.612 mmol), 6-bromo-8-methyl-[1,2,4]triazolo[1,5-a]pyridine (0.156 g, 0.734 mmol), PdCl₂(dppf)-CH₂Cl₂ adduct (0.050 g, 0.061 mmol), and tripotassium phosphate (0.390 g, 1.835 mmol) in a solvent mixture of dioxane (20 mL) and water (2.5 mL) was degassed with nitrogen for 10 min. Next, the resulting slurry was stirred at 95° C. for 3 h in a sealed tube. The reaction mixture was diluted with ethyl acetate, filtered and washed with excess ethyl acetate, combined organic layers were washed with water, brine, dried over sodium sulphate and evaporated to afford crude compound. The crude material was purified by silica gel chromatography, the compound was eluted with 85% ethyl acetate and pet ether to afford tert-butyl 4-(3-(2,2-difluoroethyl)-2-(8-methyl-[1,2,4]triazolo[1,5-a]pyridin-6-yl)-1H-indol-5-yl)piperidine-1-carboxylate (0.210 g, 0.424 mmol, 69.3% yield) as a light yellow solid. LC retention time 1.42 min [G]. MS (E⁻) m/z: 496.4 (M+H).

Example 161

To a Solution of Tert-Butyl 4-(3-(2,2-difluoroethyl)-2-(8-methyl-[1,2,4]triazolo[1,5-a]pyridin-6-yl)-1H-indol-5-yl)piperidine-1-carboxylate (0.210 g, 0.424 mmol) in dioxane (5.0 mL) was added 4 M HCl in dioxane (1.059 mL, 4.24 mmol) at room temperature. The mixture was stirred at the same temperature for 2 h. The volatiles were evaporated and dried under vacuum to afford crude compound. The crude material was triturated with diethyl ether, dried under vacuum to afford 6-(3-(2,2-difluoroethyl)-5-(piperidin-4-yl)-1H-indol-2-yl)-8-methyl-[1,2,4]triazolo[1,5-a ]pyridine (0.165 g, 0.417 mmol, 98% yield) as a light yellow solid. LCMS retention time 1.021 min [E]. MS (E⁻) m/z: 396.2 (M+H).

Example 162

6-(3-(2,2-difluoroethyl)-5-(piperidin-4-yl)-1H-indol-2-yl)-2,8-dimethyl-[1,2,4]triazolo[1,5-a]pyridine

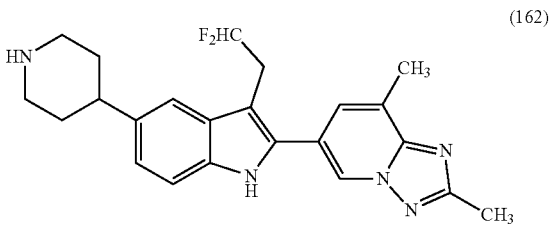 [SMILES: Cc1nc2c(C)cc(-c3[nH]c4ccc(C5CCNCC5)cc4c3CC(F)F)cn2n1]

(162)

Intermediate 162A: Tert-butyl 4-(3-(2,2-difluoroethyl)-2-(2,8-dimethyl-[1,2,4]triazolo[1,5-a]pyridin-6-yl)-1H-indol-5-yl)piperidine-1-carboxylate

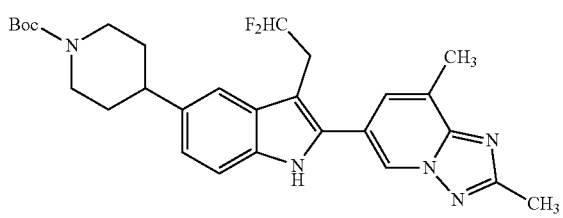

(162A)

Tert-butyl 4-(3-(2,2-difluoroethyl)-2-(2,8-dimethyl-[1,2,4]triazolo[1,5-a]pyridin-6-yl)-1H-indol-5-yl)piperidine-1-carboxylate was prepared according to the general procedure described for Intermediate 161I using tert-butyl 4-(3-(2,2-difluoroethyl)-2-(4,4,5,5-tetramethyl-1,3,2-dioxaborolan-2-yl)-1H-indol-5-yl)piperidine-1-carboxylate (0.250 g, 0.510 mmol). LC retention time 3.102 min [D]. MS (E⁻) m/z: 510.2 (M+H).

Example 162

6-(3-(2,2-difluoroethyl)-5-(piperidin-4-yl)-1H-indol-2-yl)-2,8-dimethyl-[1,2,4]triazolo[1,5-a]pyridine was prepared according to the general procedure described in Example 161 using tert-butyl 4-(3-(2,2-difluoroethyl)-2-(2,8-dimethyl-[1,2,4]triazolo[1,5-a]pyridin-6-yl)-1H-indol-5-yl)piperidine-1-carboxylate (0.200 g, 0.392 mmol). LC retention time 1.831 min [D]. MS (E⁻) m/z: 410.2 (M+H).

The following examples were prepared according to the general procedures disclosed in Example 7.

TABLE 11

| Ex. No. | Template Starting Material | Structure | LCMS MH⁺ | $R_t$ (min) | HPLC Method |
|---|---|---|---|---|---|
| 163 | EX-99 | 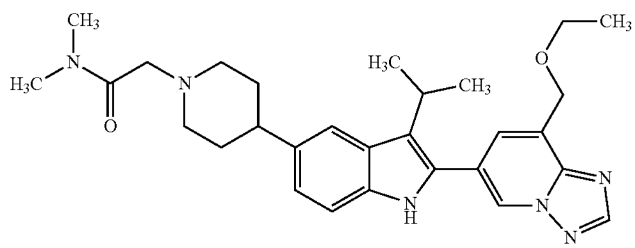 [SMILES: CCOCc1cc(-c2[nH]c3ccc(C4CCN(CC(=O)N(C)C)CC4)cc3c2C(C)C)cn2ncnc12] | 503.2 | 1.31 | QC-ACN-TFA-XB |
| 164 | EX-1 | 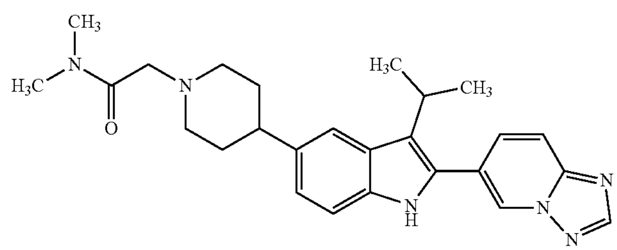 [SMILES: CC(C)c1c(-c2ccc3ncnn3c2)[nH]c2ccc(C3CCN(CC(=O)N(C)C)CC3)cc12] | 445.4 | 1.31 | QC-ACN-AA-XB |
| 165 | EX-2 | 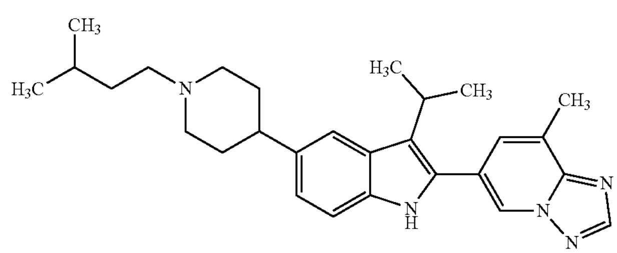 [SMILES: Cc1cc(-c2[nH]c3ccc(C4CCN(CCC(C)C)CC4)cc3c2C(C)C)cn2ncnc12] | 444.4 | 1.7 | QC-ACN-AA-XB |
| 166 | EX-2 | 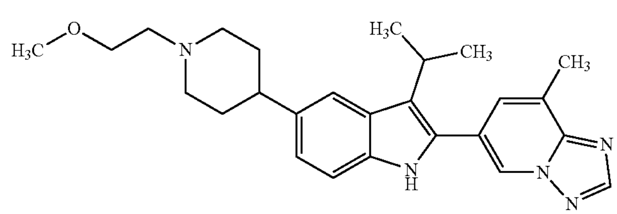 [SMILES: COCCN1CCC(c2ccc3[nH]c(-c4cc(C)c5ncnn5c4)c(C(C)C)c3c2)CC1] | 431.9 | 1.33 | QC-ACN-TFA-XB |

TABLE 11-continued

| Ex. No. | Template Starting Material | Structure | LCMS MH+ | R$_t$ (min) | HPLC Method |
|---|---|---|---|---|---|
| 167 | EX-2 | 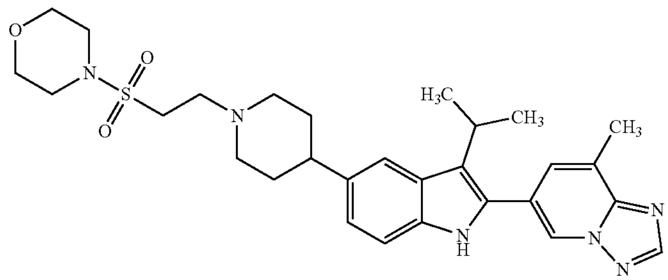 [SMILES: Cc1cc(-c2[nH]c3ccc(C4CCN(CCS(=O)(=O)N5CCOCC5)CC4)cc3c2C(C)C)cn2ncnc12] | 550.9 | 1.75 | QC-ACN-AA-XB |
| 168 | EX-2 | 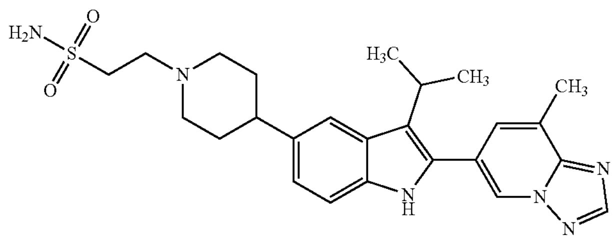 [SMILES: Cc1cc(-c2[nH]c3ccc(C4CCN(CCS(N)(=O)=O)CC4)cc3c2C(C)C)cn2ncnc12] | 481.2 | 1.48 | QC-ACN-AA-XB |
| 169 | EX-2 | 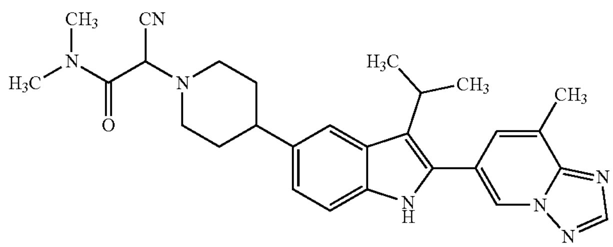 [SMILES: Cc1cc(-c2[nH]c3ccc(C4CCN(C(C#N)C(=O)N(C)C)CC4)cc3c2C(C)C)cn2ncnc12] | 484.0 | 1.85 | QC-ACN-AA-XB |
| 170 | EX-2 | 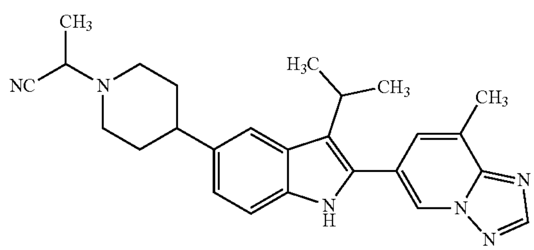 [SMILES: Cc1cc(-c2[nH]c3ccc(C4CCN(C(C)C#N)CC4)cc3c2C(C)C)cn2ncnc12] | 427.1 | 1.17 | QC-ACN-TFA-XB |
| 171 | EX-2 | 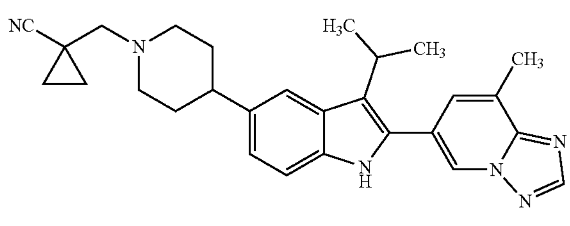 [SMILES: Cc1cc(-c2[nH]c3ccc(C4CCN(CC5(C#N)CC5)CC4)cc3c2C(C)C)cn2ncnc12] | 453.0 | 1.97 | QC-ACN-AA-XB |
| 172 | EX-2 | 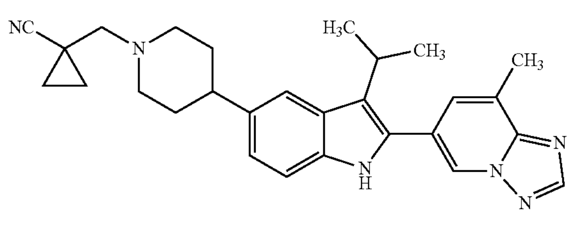 [SMILES: Cc1cc(-c2[nH]c3ccc(C4CCN(CC5(C#N)CC5)CC4)cc3c2C(C)C)cn2ncnc12] | 453.0 | 2.09 | QC-ACN-AA-XB |

TABLE 11-continued

| Ex. No. | Template Starting Material | Structure | LCMS MH+ | R$_t$ (min) | HPLC Method |
|---|---|---|---|---|---|
| 173 | EX-2 | 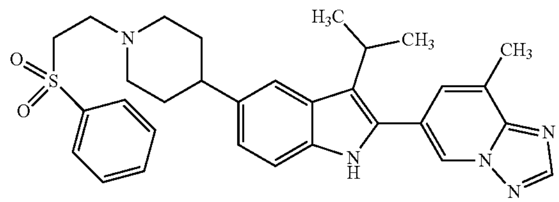 [SMILES: Cc1cc(-c2[nH]c3ccc(C4CCN(CCS(=O)(=O)c5ccccc5)CC4)cc3c2C(C)C)cn2ncnc12] | 542.0 | 2.16 | QC-ACN-AA-XB |
| 174 | EX-2 | 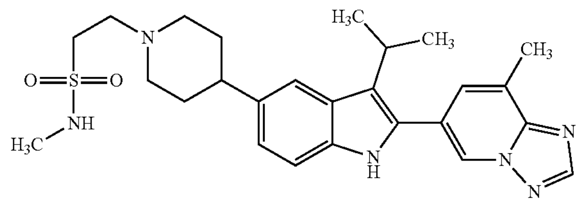 [SMILES: CNS(=O)(=O)CCN1CCC(c2ccc3[nH]c(-c4cc(C)c5ncnn5c4)c(C(C)C)c3c2)CC1] | 495.1 | 1.58 | QC-ACN-AA-XB |
| 175 | EX-2 | 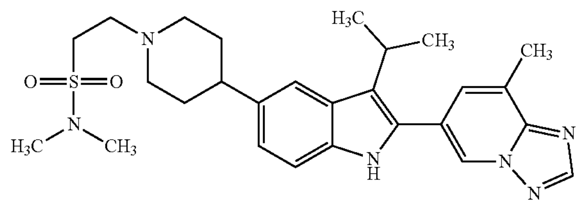 [SMILES: Cc1cc(-c2[nH]c3ccc(C4CCN(CCS(=O)(=O)N(C)C)CC4)cc3c2C(C)C)cn2ncnc12] | 509.0 | 1.76 | QC-ACN-AA-XB |
| 176 | EX-2 | 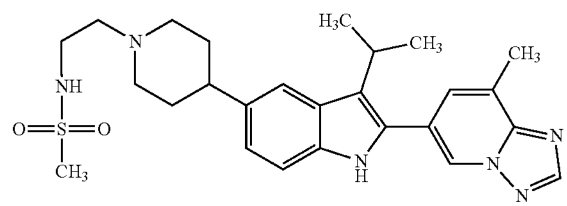 [SMILES: Cc1cc(-c2[nH]c3ccc(C4CCN(CCNS(C)(=O)=O)CC4)cc3c2C(C)C)cn2ncnc12] | 495.0 | 1.34 | QC-ACN-TFA-XB |
| 177 | EX-2 | 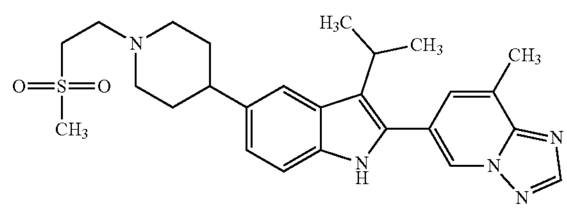 [SMILES: Cc1cc(-c2[nH]c3ccc(C4CCN(CCS(C)(=O)=O)CC4)cc3c2C(C)C)cn2ncnc12] | 480.1 | 1.08 | QC-ACN-TFA-XB |
| 178 | EX-2 | 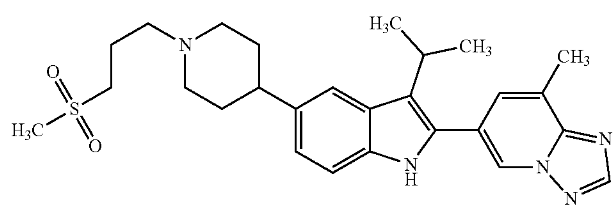 [SMILES: Cc1cc(-c2[nH]c3ccc(C4CCN(CCCS(C)(=O)=O)CC4)cc3c2C(C)C)cn2ncnc12] | 495.1 | 1.25 | QC-ACN-AA-XB |
| 179 | EX-2 | 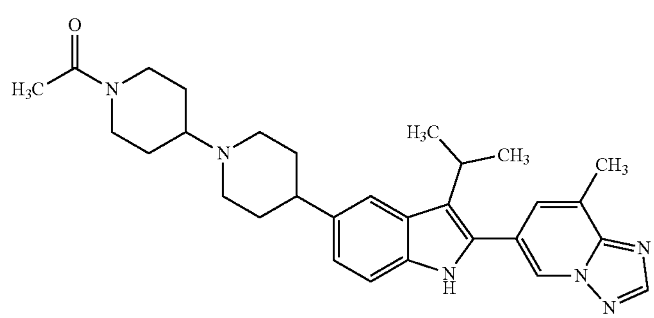 [SMILES: CC(=O)N1CCC(N2CCC(c3ccc4[nH]c(-c5cc(C)c6ncnn6c5)c(C(C)C)c4c3)CC2)CC1] | 499.4 | 1.23 | QC-ACN-AA-XB |

TABLE 11-continued

| Ex. No. | Template Starting Material | Structure | LCMS MH+ | R_t (min) | HPLC Method |
|---|---|---|---|---|---|
| 180 | EX-3 | 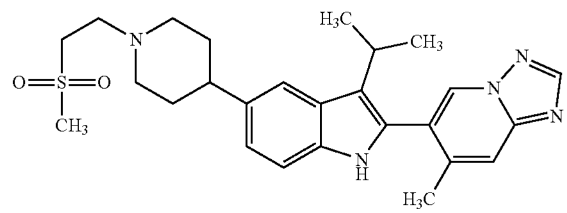 [SMILES: Cc1cc2ncnn2cc1-c1[nH]c2ccc(C3CCN(CCS(C)(=O)=O)CC3)cc2c1C(C)C] | 480.1 | 1.56 | QC-ACN-AA-XB |
| 181 | EX-3 | 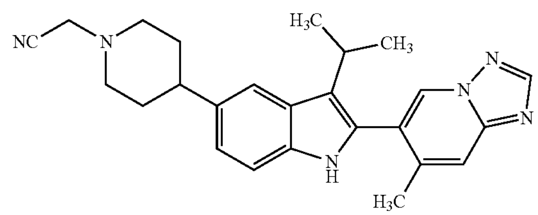 [SMILES: Cc1cc2ncnn2cc1-c1[nH]c2ccc(C3CCN(CC#N)CC3)cc2c1C(C)C] | 412.9 | 1.84 | QC-ACN-AA-XB |
| 182 | EX-3 | 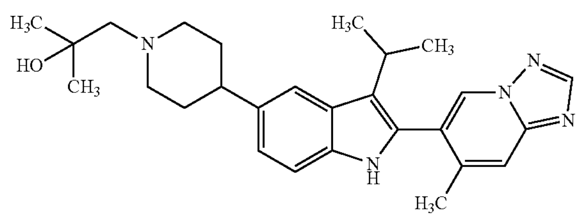 [SMILES: Cc1cc2ncnn2cc1-c1[nH]c2ccc(C3CCN(CC(C)(C)O)CC3)cc2c1C(C)C] | 446.0 | 1.41 | QC-ACN-AA-XB |
| 183 | EX-3 | 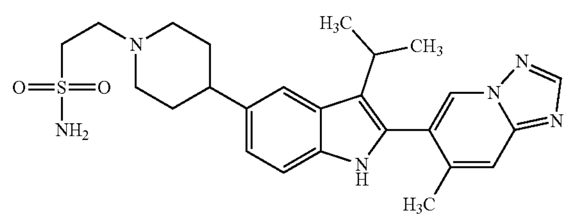 | 481.0 | 0.98 | QC-ACN-TFA-XB |
| 184 | EX-3 | 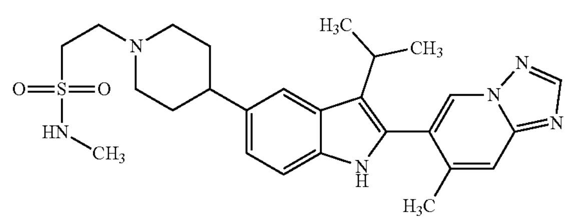 [SMILES: CNS(=O)(=O)CCN1CCC(c2ccc3[nH]c(-c4cn5ncnc5cc4C)c(C(C)C)c3c2)CC1] | 495.0 | 1.47 | QC-ACN-AA-XB |
| 185 | EX-3 | 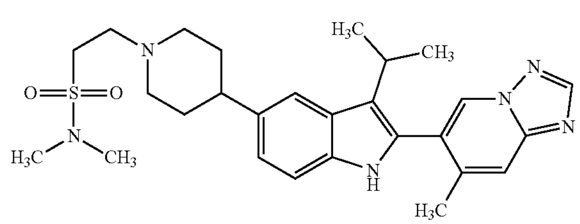 [SMILES: Cc1cc2ncnn2cc1-c1[nH]c2ccc(C3CCN(CCS(=O)(=O)N(C)C)CC3)cc2c1C(C)C] | 509.1 | 1.71 | QC-ACN-AA-XB |
| 186 | EX-3 | 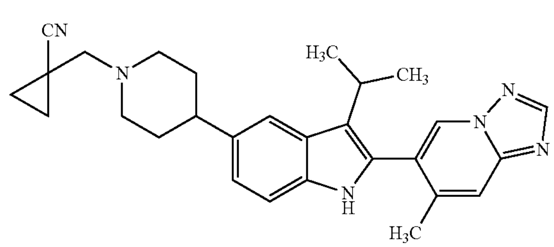 [SMILES: Cc1cc2ncnn2cc1-c1[nH]c2ccc(C3CCN(CC4(C#N)CC4)CC3)cc2c1C(C)C] | 453.0 | 2.19 | QC-ACN-AA-XB |

TABLE 11-continued

| Ex. No. | Template Starting Material | Structure | LCMS MH+ | R_t (min) | HPLC Method |
|---|---|---|---|---|---|
| 187 | EX-3 | 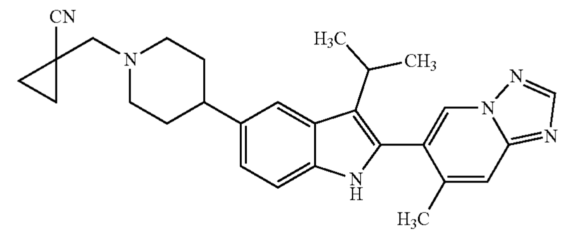 [SMILES: Cc1cc2ncnn2cc1-c1[nH]c2ccc(C3CCN(CC4(C#N)CC4)CC3)cc2c1C(C)C] | 453.3 | 1.32 | QC-ACN-TFA-XB |
| 188 | EX-3 | 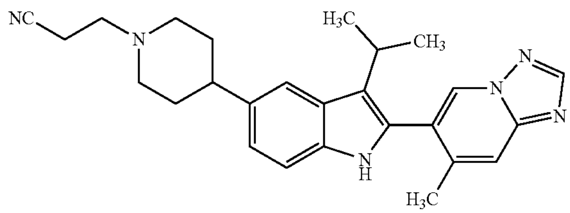 [SMILES: Cc1cc2ncnn2cc1-c1[nH]c2ccc(C3CCN(CCC#N)CC3)cc2c1C(C)C] | 427.0 | 1.73 | QC-ACN-AA-XB |
| 189 | EX-3 | 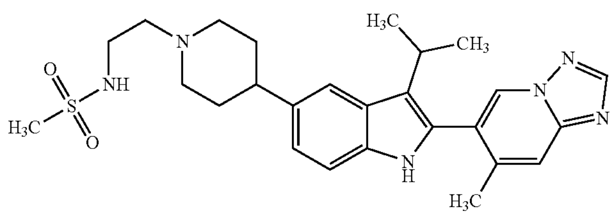 [SMILES: Cc1cc2ncnn2cc1-c1[nH]c2ccc(C3CCN(CCNS(C)(=O)=O)CC3)cc2c1C(C)C] | 494.9 | 1.42 | QC-ACN-AA-XB |
| 190 | EX-3 | 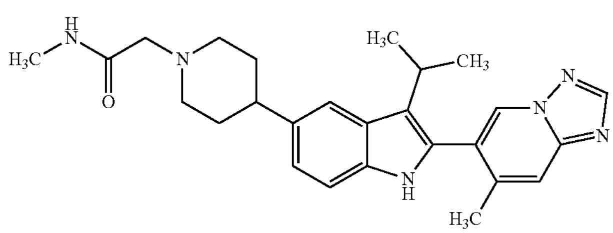 [SMILES: CNC(=O)CN1CCC(c2ccc3[nH]c(-c4cn5ncnc5cc4C)c(C(C)C)c3c2)CC1] | 445.4 | 1.05 | QC-ACN-TFA-XB |
| 191 | EX-3 | 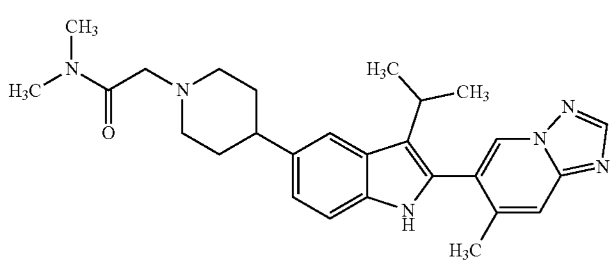 [SMILES: Cc1cc2ncnn2cc1-c1[nH]c2ccc(C3CCN(CC(=O)N(C)C)CC3)cc2c1C(C)C] | 459.4 | 1.33 | QC-ACN-AA-XB |
| 192 | EX-3 | 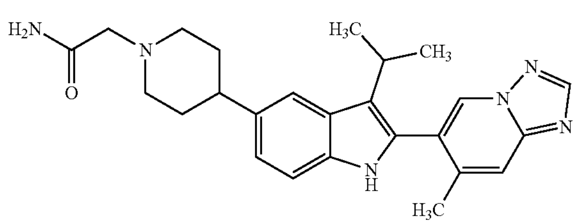 [SMILES: Cc1cc2ncnn2cc1-c1[nH]c2ccc(C3CCN(CC(N)=O)CC3)cc2c1C(C)C] | 431.1 | 1.35 | QC-ACN-AA-XB |

TABLE 11-continued

| Ex. No. | Template Starting Material | Structure | LCMS MH+ | R$_t$ (min) | HPLC Method |
|---|---|---|---|---|---|
| 193 | EX-112 | 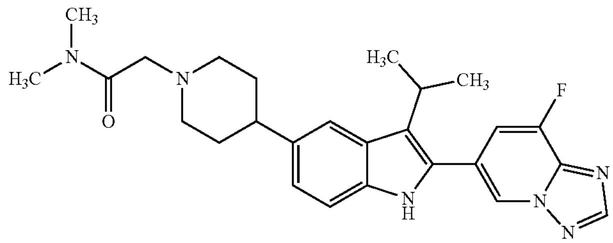 [SMILES: CC(C)c1c(-c2cc(F)c3ncnn3c2)[nH]c2ccc(C3CCN(CC(=O)N(C)C)CC3)cc12] | 463.3 | 1.27 | QC-ACN-TFA-XB |
| 194 | EX-112 | 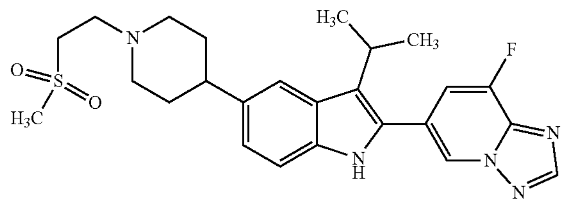 [SMILES: CC(C)c1c(-c2cc(F)c3ncnn3c2)[nH]c2ccc(C3CCN(CCS(C)(=O)=O)CC3)cc12] | 484.0 | 1.71 | QC-ACN-AA-XB |
| 195 | EX-112 | 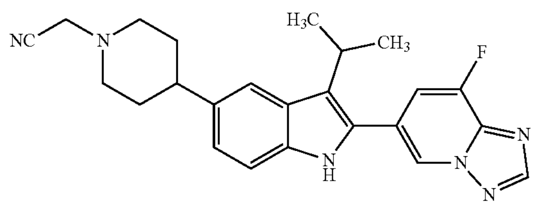 [SMILES: CC(C)c1c(-c2cc(F)c3ncnn3c2)[nH]c2ccc(C3CCN(CC#N)CC3)cc12] | 417.2 | 1.88 | QC-ACN-AA-XB |
| 196 | EX-112 | 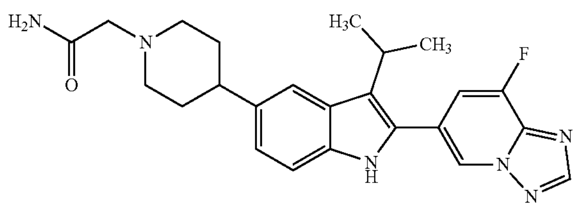 [SMILES: CC(C)c1c(-c2cc(F)c3ncnn3c2)[nH]c2ccc(C3CCN(CC(N)=O)CC3)cc12] | 435.1 | 1.42 | QC-ACN-AA-XB |
| 197 | EX-112 | 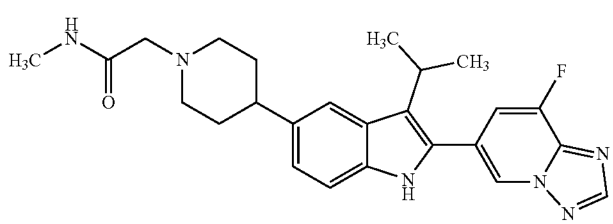 [SMILES: CNC(=O)CN1CCC(c2ccc3[nH]c(-c4cc(F)c5ncnn5c4)c(C(C)C)c3c2)CC1] | 449.2 | 1.40 | QC-ACN-AA-XB |
| 198 | EX-6 | 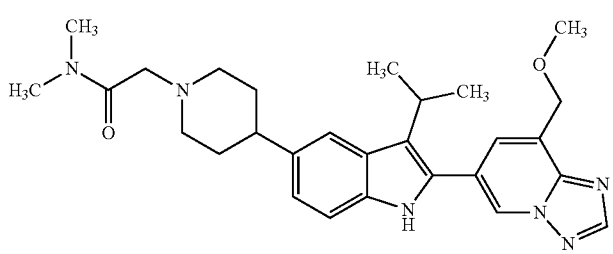 [SMILES: COCc1cc(-c2[nH]c3ccc(C4CCN(CC(=O)N(C)C)CC4)cc3c2C(C)C)cn2ncnc12] | 489.4 | 1.44 | QC-ACN-AA-XB |
| 199 | EX-6 | 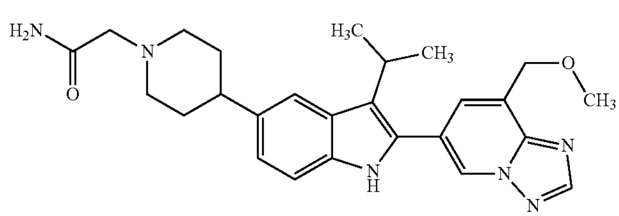 [SMILES: COCc1cc(-c2[nH]c3ccc(C4CCN(CC(N)=O)CC4)cc3c2C(C)C)cn2ncnc12] | 461.1 | 1.38 | QC-ACN-AA-XB |

TABLE 11-continued
| Ex. No. | Template Starting Material | Structure | LCMS MH+ | R_t (min) | HPLC Method |
|---|---|---|---|---|---|
| 200 | EX-6 | 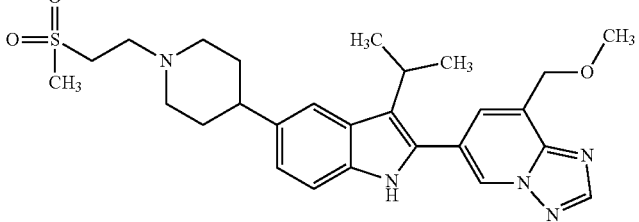 | 510.2 | 1.25 | QC-ACN-TFA-XB |
| 201 | EX-6 | 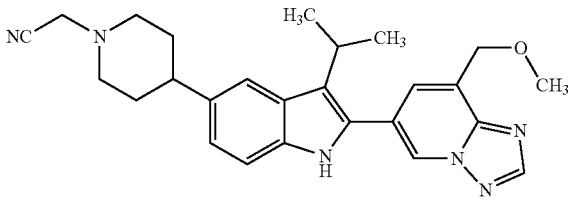 [SMILES: COCc1cc(-c2[nH]c3ccc(C4CCN(CC#N)CC4)cc3c2C(C)C)cn2ncnc12] | 443.0 | 1.84 | QC-ACN-AA-XB |
| 202 | EX-6 | 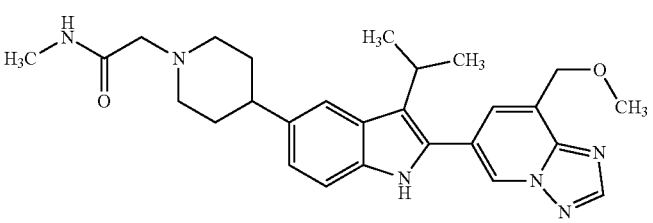 | 475.0 | 1.25 | QC-ACN-TFA-XB |
| 203 | EX-6 | 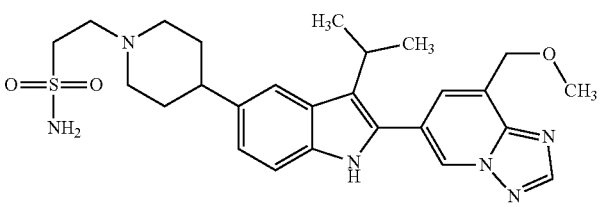 [SMILES: COCc1cc(-c2[nH]c3ccc(C4CCN(CCS(N)(=O)=O)CC4)cc3c2C(C)C)cn2ncnc12] | 511.3 | 1.54 | QC-ACN-AA-XB |
| 204 | EX-4 | 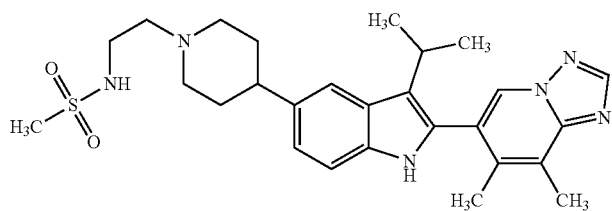 [SMILES: Cc1c(-c2[nH]c3ccc(C4CCN(CCNS(C)(=O)=O)CC4)cc3c2C(C)C)cn2ncnc2c1C] | 509.2 | 1.47 | QC-ACN-AA-XB |
| 205 | EX-4 | 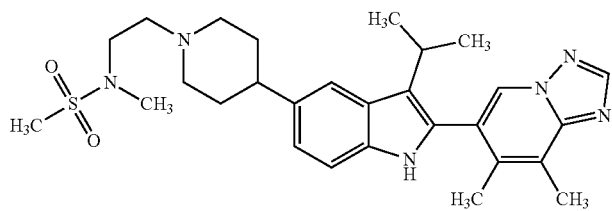 [SMILES: Cc1c(-c2[nH]c3ccc(C4CCN(CCN(C)S(C)(=O)=O)CC4)cc3c2C(C)C)cn2ncnc2c1C] | 523.0 | 1.73 | QC-ACN-AA-XB |
| 206 | EX-4 | 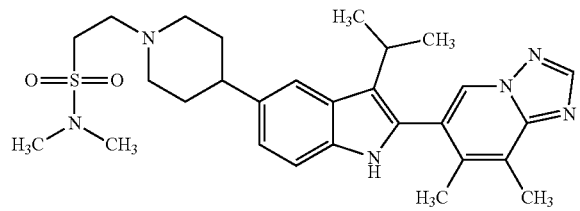 | 523.0 | 1.37 | QC-ACN-TFA-XB |

TABLE 11-continued

| Ex. No. | Template Starting Material | Structure | LCMS MH+ | R_t (min) | HPLC Method |
|---|---|---|---|---|---|
| 207 | EX-110 | (structure) | 473.0 | 1.35 | QC-ACN-TFA-XB |
| 208 | EX-110 | (structure) | 483.4 | 1.46 | QC-ACN-AA-XB |
| 209 | EX-110 | (structure) | 494.3 | 1.65 | QC-ACN-AA-XB |
| 210 | EX-110 | (structure) | 427.35, 427.35 | | QC-ACN-TFA-XB |
| 211 | EX-100 | (structure) | 470.9 | 1.32 | QC-ACN-TFA-XB |
| 212 | EX-100 | (structure) | 457.3 | 1.33 | QC-ACN-TFA-XB |
| 213 | EX-100 | (structure) | 475.1 | 1.47 | QC-ACN-AA-XB |

TABLE 11-continued

| Ex. No. | Template Starting Material | Structure | LCMS MH+ | R<sub>t</sub> (min) | HPLC Method |
|---|---|---|---|---|---|
| 214 | EX-100 | 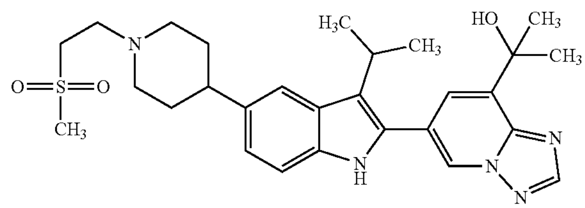 | 524.3 | 1.63 | QC-ACN-AA-XB |
| 215 | EX-100 | 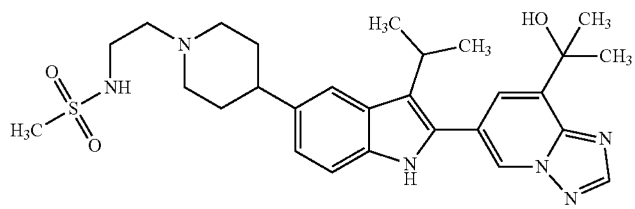 [SMILES: CC(C)c1c(-c2cc(C(C)(C)O)c3ncnn3c2)[nH]c2ccc(C3CCN(CCNS(C)(=O)=O)CC3)cc12] | 539.0 | 1.63 | QC-ACN-AA-XB |
| 216 | EX-100 | 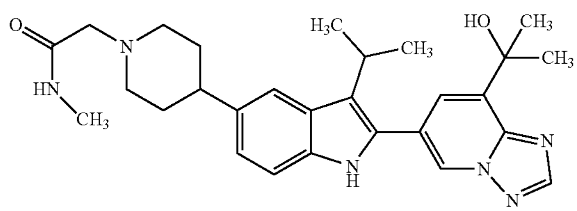 [SMILES: CNC(=O)CN1CCC(c2ccc3[nH]c(-c4cc(C(C)(C)O)c5ncnn5c4)c(C(C)C)c3c2)CC1] | 489.4 | 1.52 | QC-ACN-AA-XB |
| 217 | EX-100 | 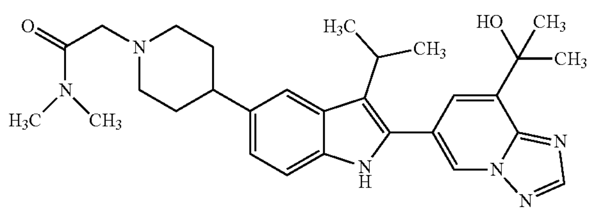 [SMILES: CC(C)c1c(-c2cc(C(C)(C)O)c3ncnn3c2)[nH]c2ccc(C3CCN(CC(=O)N(C)C)CC3)cc12] | 503.1 | 1.3 | QC-ACN-TFA-XB |
| 218 | EX-100 | 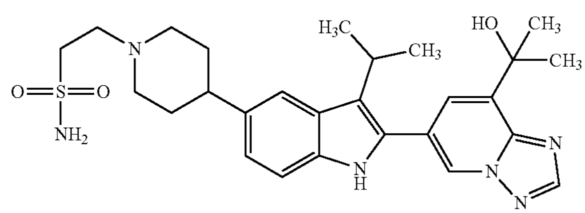 [SMILES: CC(C)c1c(-c2cc(C(C)(C)O)c3ncnn3c2)[nH]c2ccc(C3CCN(CCS(N)(=O)=O)CC3)cc12] | 525.1 | 1.15 | QC-ACN-TFA-XB |
| 219 | EX-101 | 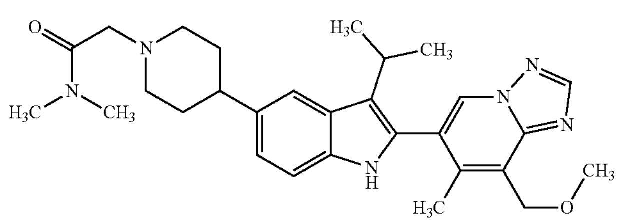 [SMILES: COCc1c(C)c(-c2[nH]c3ccc(C4CCN(CC(=O)N(C)C)CC4)cc3c2C(C)C)cn2ncnc12] | 503.2 | 1.22 | QC-ACN-TFA-XB |
| 220 | EX-111 | 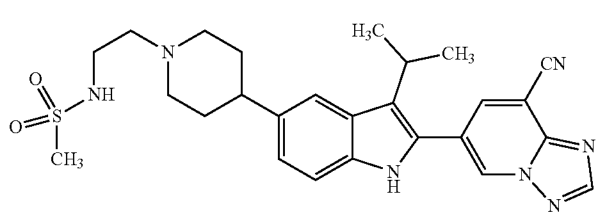 [SMILES: CC(C)c1c(-c2cc(C#N)c3ncnn3c2)[nH]c2ccc(C3CCN(CCNS(C)(=O)=O)CC3)cc12] | 506.2 | 1.24 | QC-ACN-AA-XB |

TABLE 11-continued

| Ex. No. | Template Starting Material | Structure | LCMS MH+ | R$_t$ (min) | HPLC Method |
|---|---|---|---|---|---|
| 221 | EX-111 | 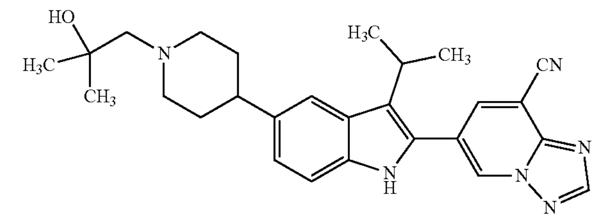 [SMILES: CC(C)c1c(-c2cc(C#N)c3ncnn3c2)[nH]c2ccc(C3CCN(CC(C)(C)O)CC3)cc12] | 457.0 | 1.31 | QC-ACN-TFA-XB |
| 222 | EX-111 | 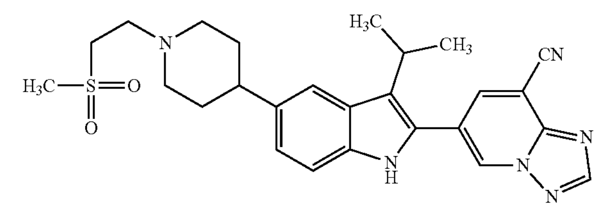 [SMILES: CC(C)c1c(-c2cc(C#N)c3ncnn3c2)[nH]c2ccc(C3CCN(CCS(C)(=O)=O)CC3)cc12] | 491.2 | 1.66 | QC-ACN-AA-XB |
| 223 | EX-111 | 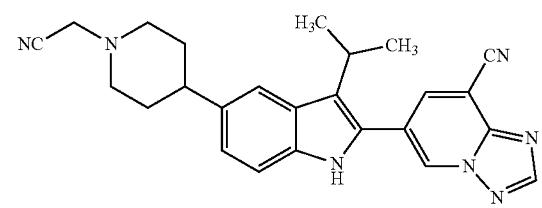 [SMILES: CC(C)c1c(-c2cc(C#N)c3ncnn3c2)[nH]c2ccc(C3CCN(CC#N)CC3)cc12] | 424.3 | 1.93 | QC-ACN-AA-XB |
| 224 | EX-111 | 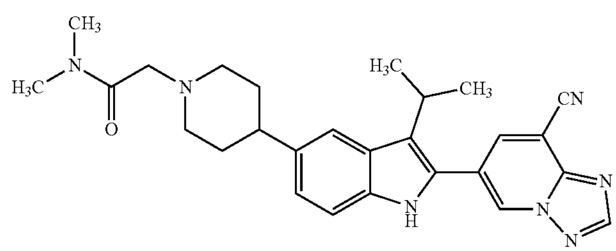 [SMILES: CC(C)c1c(-c2cc(C#N)c3ncnn3c2)[nH]c2ccc(C3CCN(CC(=O)N(C)C)CC3)cc12] | 470.0 | 1.27 | QC-ACN-TFA-XB |
| 225 | EX-102 | 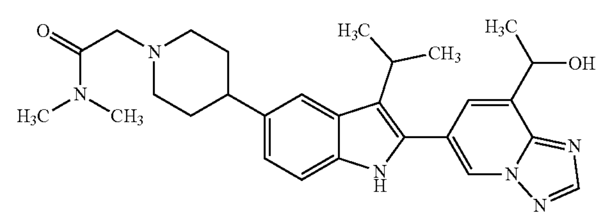 [SMILES: CC(C)c1c(-c2cc(C(C)O)c3ncnn3c2)[nH]c2ccc(C3CCN(CC(=O)N(C)C)CC3)cc12] | 489.4 | 1.1 | QC-ACN-TFA-XB |
| 226 | EX-104 | 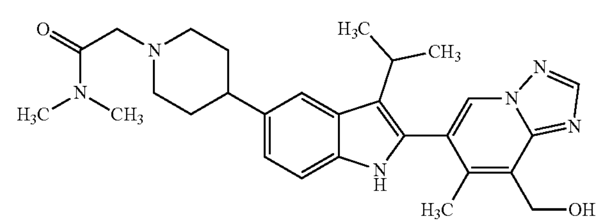 [SMILES: Cc1c(-c2[nH]c3ccc(C4CCN(CC(=O)N(C)C)CC4)cc3c2C(C)C)cn2ncnc2c1CO] | 489.0 | 1.18 | QC-ACN-AA-XB |
| 227 | EX-104 | 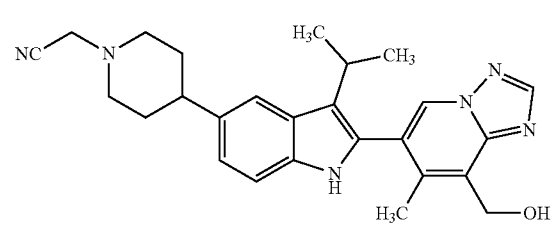 [SMILES: Cc1c(-c2[nH]c3ccc(C4CCN(CC#N)CC4)cc3c2C(C)C)cn2ncnc2c1CO] | 442.9 | 1.21 | QC-ACN-TFA-XB |

TABLE 11-continued

| Ex. No. | Template Starting Material | Structure | LCMS MH+ | R$_t$ (min) | HPLC Method |
|---|---|---|---|---|---|
| 228 | EX-105 | 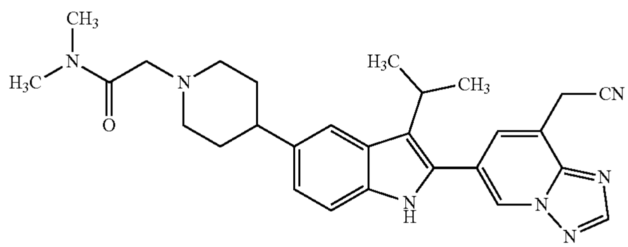 [SMILES: CC(C)c1c(-c2cc(CC#N)c3ncnn3c2)[nH]c2ccc(C3CCN(CC(=O)N(C)C)CC3)cc12] | 484.3 | 1.43 | QC-ACN-AA-XB |
| 229 | EX-103 | 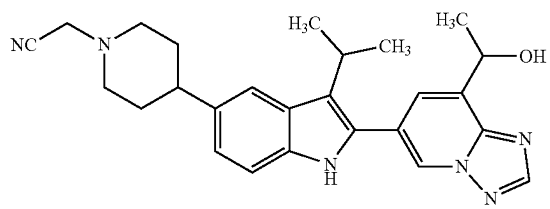 [SMILES: CC(C)c1c(-c2cc(C(C)O)c3ncnn3c2)[nH]c2ccc(C3CCN(CC#N)CC3)cc12] | 443.0 | 1.27 | QC-ACN-TFA-XB |
| 230 | EX-108 | 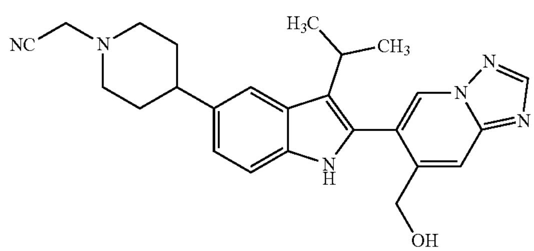 [SMILES: CC(C)c1c(-c2cn3ncnc3cc2CO)[nH]c2ccc(C3CCN(CC#N)CC3)cc12] | 429.1 | 1.16 | QC-ACN-TFA-XB |
| 231 | EX-113 | 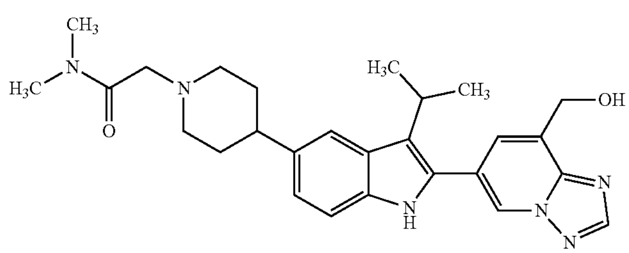 | 475.1 | 1.0 | QC-ACN-TFA-XB |
| 232 | EX-113 | 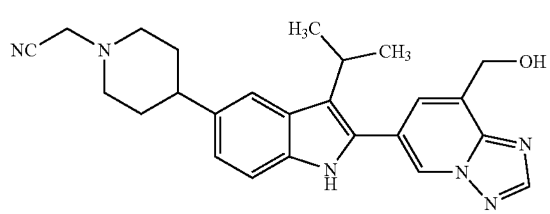 [SMILES: CC(C)c1c(-c2cc(CO)c3ncnn3c2)[nH]c2ccc(C3CCN(CC#N)CC3)cc12] | 429.2 | 1.53 | QC-ACN-AA-XB |
| 233 | EX-113 | 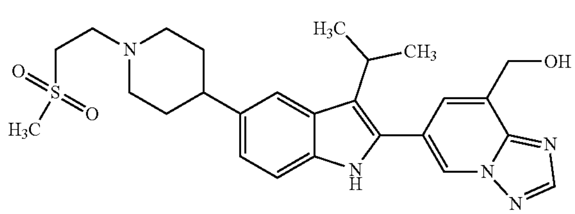 [SMILES: CC(C)c1c(-c2cc(CO)c3ncnn3c2)[nH]c2ccc(C3CCN(CCS(C)(=O)=O)CC3)cc12] | 496.0 | 1.12 | QC-ACN-TFA-XB |

TABLE 11-continued

| Ex. No. | Template Starting Material | Structure | LCMS MH+ | R$_t$ (min) | HPLC Method |
|---|---|---|---|---|---|
| 234 | EX-113 | 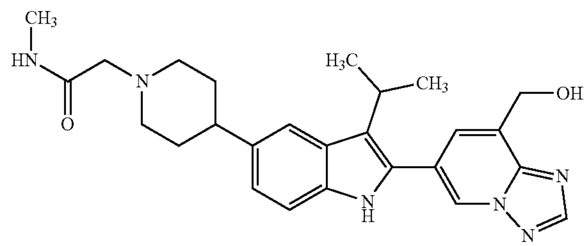 [SMILES: CNC(=O)CN1CCC(c2ccc3[nH]c(-c4cc(CO)c5ncnn5c4)c(C(C)C)c3c2)CC1] | 461.3 | 0.97 | QC-ACN-TFA-XB |
| 235 | EX-113 | 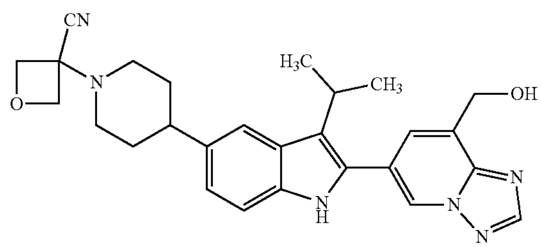 [SMILES: CC(C)c1c(-c2cc(CO)c3ncnn3c2)[nH]c2ccc(C3CCN(C4(C#N)COC4)CC3)cc12] | 471.1 | 1.63 | QC-ACN-TFA-XB |
| 236 | EX-114 | 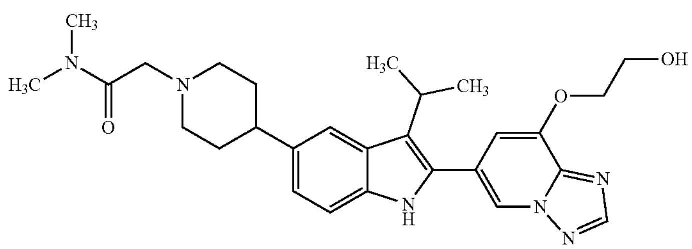 [SMILES: CC(C)c1c(-c2cc(OCCO)c3ncnn3c2)[nH]c2ccc(C3CCN(CC(=O)N(C)C)CC3)cc12] | 505.2 | 1.19 | QC-ACN-AA-XB |

TABLE 12

| Ex. No. | Template Starting Material | Structure | LCMS MH+ | R$_t$ (min) | HPLC Method |
|---|---|---|---|---|---|
| 237 | EX-122 | 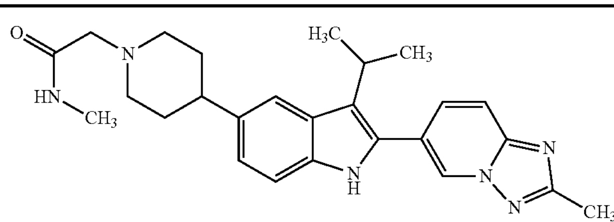 | 445.3 | 1.76 | E |
| 238 | EX-122 | 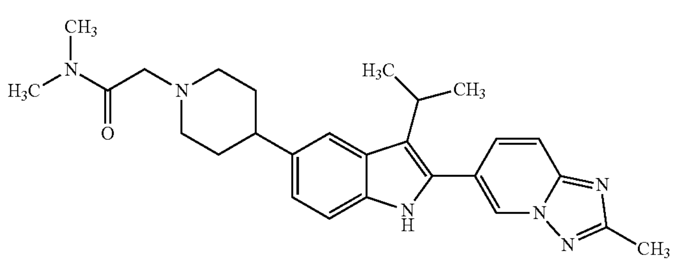 | 459.3 | 1.62 | E |

TABLE 12-continued

| Ex. No. | Template Starting Material | Structure | LCMS MH+ | R$_t$ (min) | HPLC Method |
|---|---|---|---|---|---|
| 239 | EX-122 | 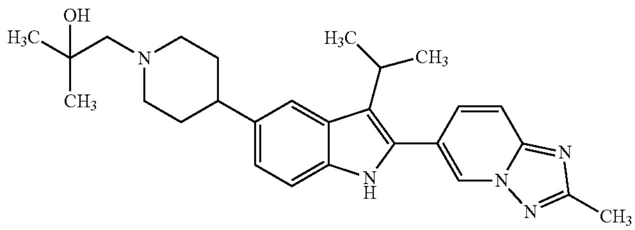 [SMILES: Cc1nc2ccc(-c3[nH]c4ccc(C5CCN(CC(C)(C)O)CC5)cc4c3C(C)C)cn2n1] | 446.3 | 1.59 | E |
| 240 | EX-1 | 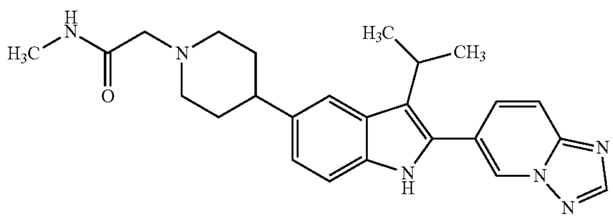 [SMILES: CNC(=O)CN1CCC(c2ccc3[nH]c(-c4ccc5ncnn5c4)c(C(C)C)c3c2)CC1] | 431.2 | 1.71 | E |
| 241 | EX-1 | 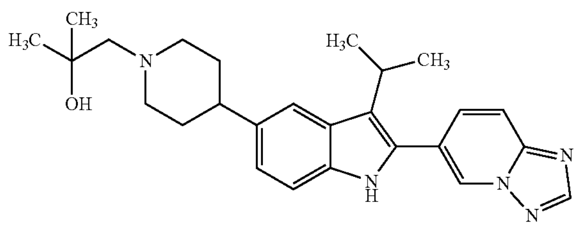 [SMILES: CC(C)c1c(-c2ccc3ncnn3c2)[nH]c2ccc(C3CCN(CC(C)(C)O)CC3)cc12] | 432.3 | 1.51 | E |
| 242 | EX-1 | 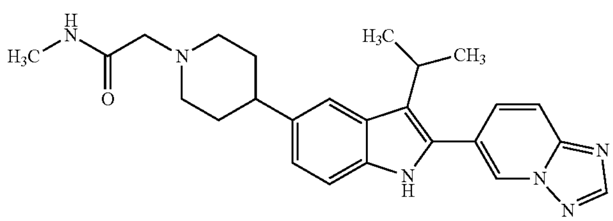 [SMILES: CNC(=O)CN1CCC(c2ccc3[nH]c(-c4ccc5ncnn5c4)c(C(C)C)c3c2)CC1] | 431.2 | 1.75 | E |
| 243 | EX-2 | 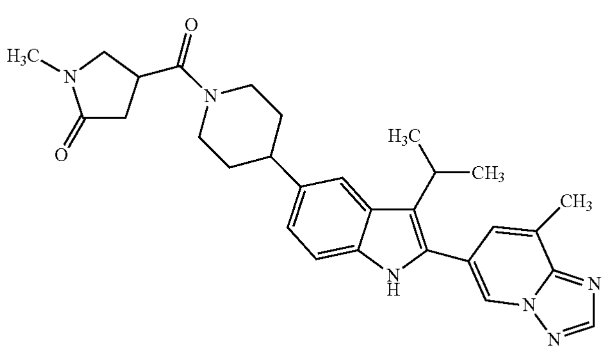 [SMILES: Cc1cc(-c2[nH]c3ccc(C4CCN(C(=O)C5CC(=O)N(C)C5)CC4)cc3c2C(C)C)cn2ncnc12] | 499.3 | 2.1 | D |
| 244 | EX-124 | 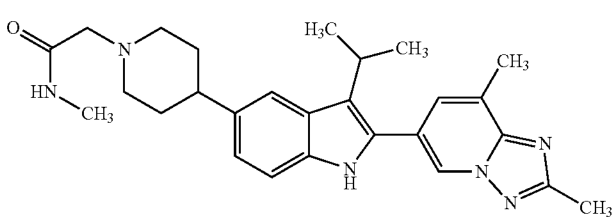 | 459.3 | 1.74 | E |

TABLE 12-continued

| Ex. No. | Template Starting Material | Structure | LCMS MH+ | R$_t$ (min) | HPLC Method |
|---|---|---|---|---|---|
| 245 | EX-124 | 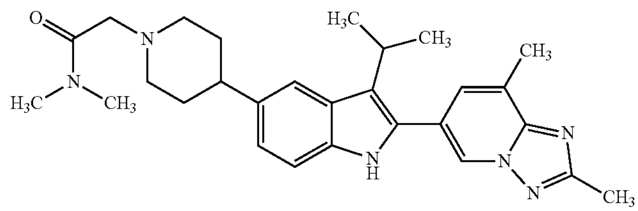 [SMILES: Cc1nc2c(C)cc(-c3[nH]c4ccc(C5CCN(CC(=O)N(C)C)CC5)cc4c3C(C)C)cn2n1] | 473.3 | 2.09 | D |
| 246 | EX-124 | 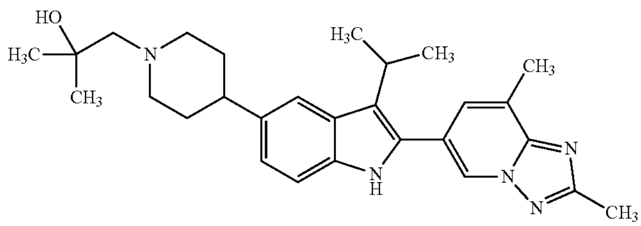 [SMILES: Cc1nc2c(C)cc(-c3[nH]c4ccc(C5CCN(CC(C)(C)O)CC5)cc4c3C(C)C)cn2n1] | 460 | 1.74 | E |
| 247 | EX-125 | 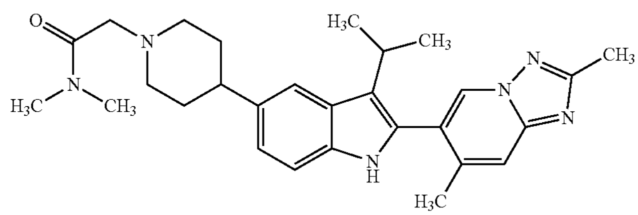 [SMILES: Cc1nc2cc(C)c(-c3[nH]c4ccc(C5CCN(CC(=O)N(C)C)CC5)cc4c3C(C)C)cn2n1] | 473.3 | 1.56 | E |
| 248 | EX-125 | 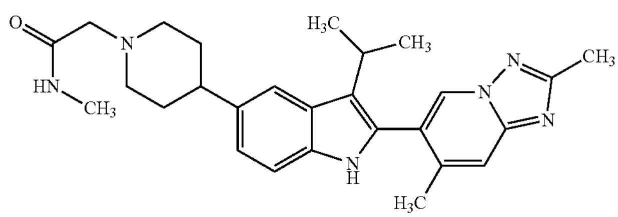 [SMILES: CNC(=O)CN1CCC(c2ccc3[nH]c(-c4cn5nc(C)nc5cc4C)c(C(C)C)c3c2)CC1] | 459.2 | 1.72 | E |
| 249 | EX-125 | 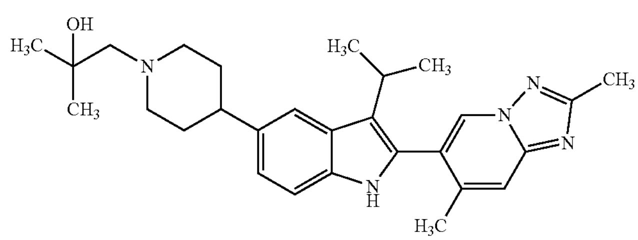 [SMILES: Cc1nc2cc(C)c(-c3[nH]c4ccc(C5CCN(CC(C)(C)O)CC5)cc4c3C(C)C)cn2n1] | 460 | 1.66 | E |
| 250 | EX-128 | 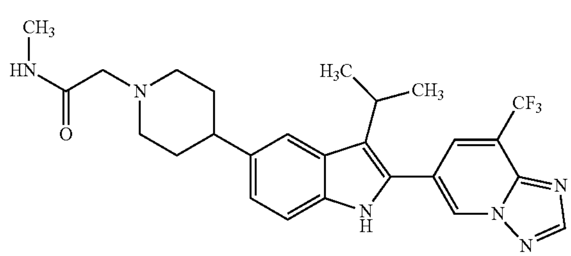 [SMILES: CNC(=O)CN1CCC(c2ccc3[nH]c(-c4cc(C(F)(F)F)c5ncnn5c4)c(C(C)C)c3c2)CC1] | 499.3 | 2.08 | E |

TABLE 12-continued

| Ex. No. | Template Starting Material | Structure | LCMS MH+ | R$_t$ (min) | HPLC Method |
|---|---|---|---|---|---|
| 251 | EX-128 | 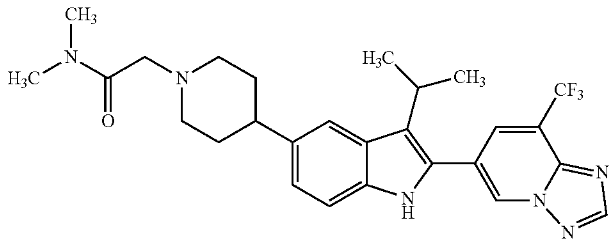 [SMILES: CC(C)c1c(-c2cc(C(F)(F)F)c3ncnn3c2)[nH]c2ccc(C3CCN(CC(=O)N(C)C)CC3)cc12] | 513 | 1.65 | E |
| 252 | EX-128 | 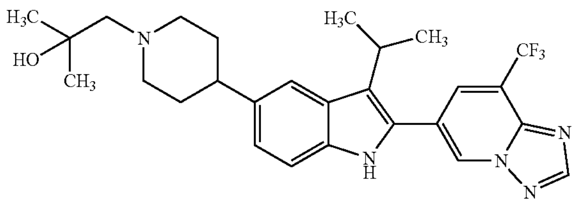 | 500 | 1.74 | E |
| 253 | EX-128 | 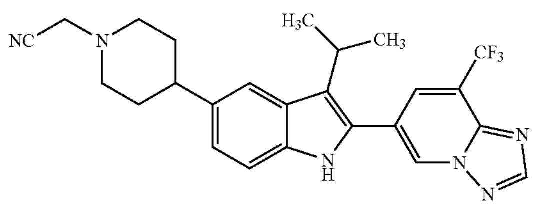 [SMILES: CC(C)c1c(-c2cc(C(F)(F)F)c3ncnn3c2)[nH]c2ccc(C3CCN(CC#N)CC3)cc12] | 467.2 | 2.26 | E |
| 254 | EX-128 | 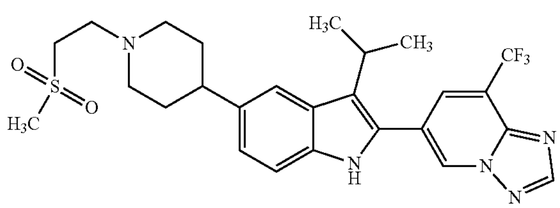 [SMILES: CC(C)c1c(-c2cc(C(F)(F)F)c3ncnn3c2)[nH]c2ccc(C3CCN(CCS(C)(=O)=O)CC3)cc12] | 534.1 | 2.07 | E |
| 255 | EX-142 | 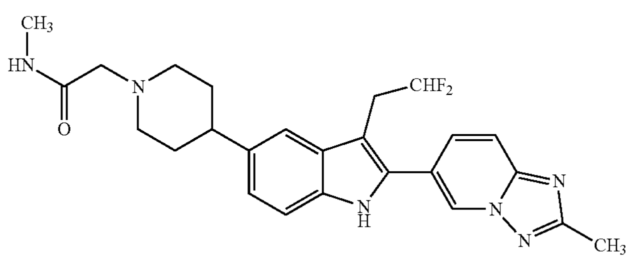 [SMILES: CNC(=O)CN1CCC(c2ccc3[nH]c(-c4ccc5nc(C)nn5c4)c(CC(F)F)c3c2)CC1] | 467.2 | 1.41 | E |
| 256 | EX-142 | 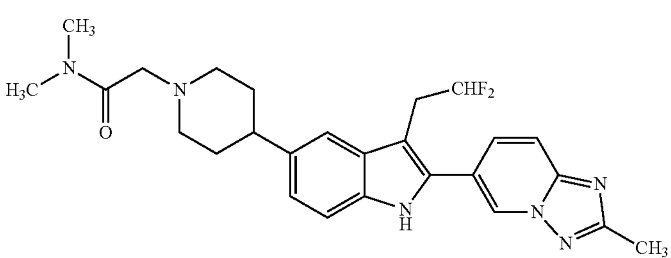 | 481.2 | 1.26 | E |

TABLE 12-continued
| Ex. No. | Template Starting Material | Structure | LCMS MH+ | $R_t$ (min) | HPLC Method |
|---|---|---|---|---|---|
| 257 | EX-155 | 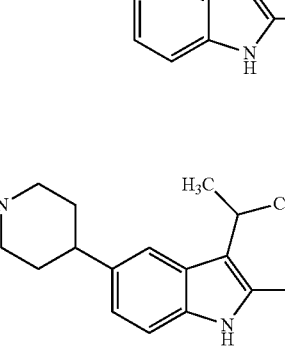 | 473 | 1.65 | E |
| 258 | EX-155 | 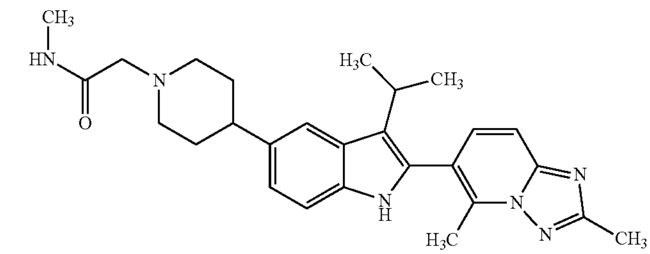 [SMILES: CNC(=O)CN1CCC(c2ccc3[nH]c(-c4ccc5nc(C)nn5c4C)c(C(C)C)c3c2)CC1] | 459 | 1.83 | E |
| 259 | EX-153 | 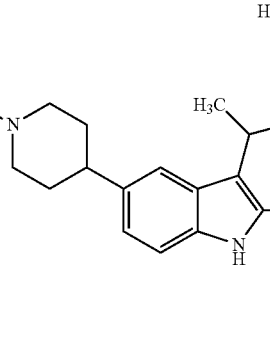 | 527.3 | 1.91 | E |
| 260 | EX-96 | 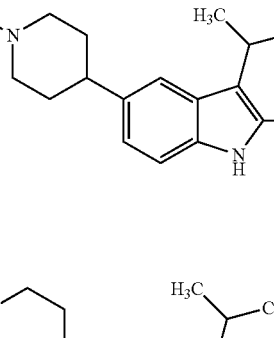 | 493 | 1.73 | E |
| 261 | EX-96 | 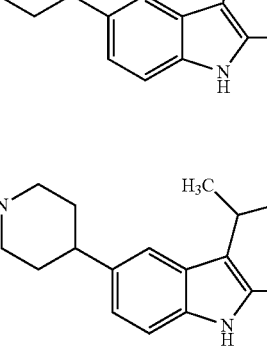 | 479 | 1.94 | E |
| 262 | EX-96 | 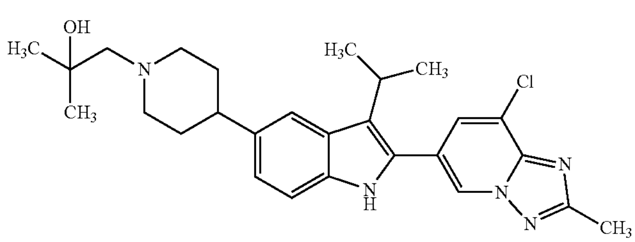 | 480.3 | 1.61 | E |

TABLE 12-continued

| Ex. No. | Template Starting Material | Structure | LCMS MH+ | R$_t$ (min) | HPLC Method |
|---|---|---|---|---|---|
| 263 | EX-5 | 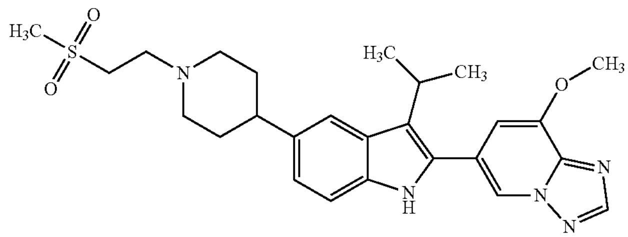 [SMILES: COc1cc(-c2[nH]c3ccc(C4CCN(CCS(C)(=O)=O)CC4)cc3c2C(C)C)cn2ncnc12] | 496.2 | 1.81 | E |
| 264 | EX-5 | 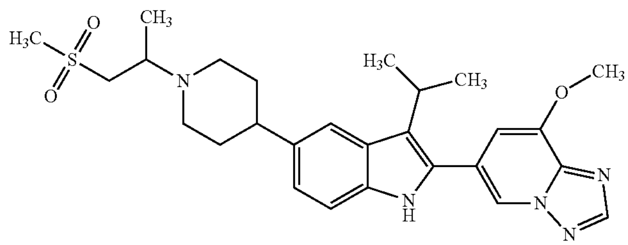 [SMILES: COc1cc(-c2[nH]c3ccc(C4CCN(C(C)CS(C)(=O)=O)CC4)cc3c2C(C)C)cn2ncnc12] | 510.2 | 5.65 | I |
| 265 | EX-5 | 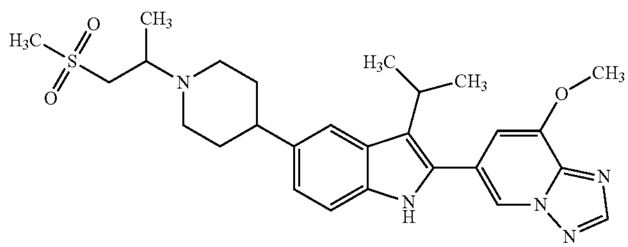 [SMILES: COc1cc(-c2[nH]c3ccc(C4CCN(C(C)CS(C)(=O)=O)CC4)cc3c2C(C)C)cn2ncnc12] | 510.1 | 5.63 | I |
| 266 | EX-5 | 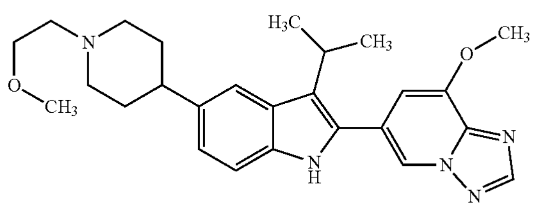 [SMILES: COCCN1CCC(c2ccc3[nH]c(-c4cc(OC)c5ncnn5c4)c(C(C)C)c3c2)CC1] | 448.2 | 1.87 | E |
| 267 | EX-131 | 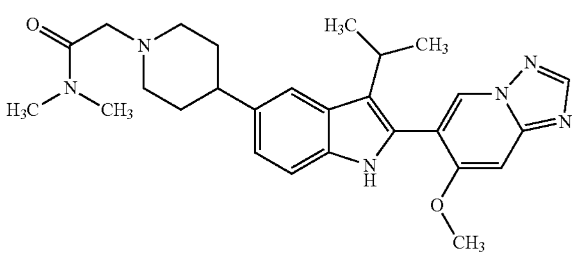 [SMILES: COc1cc2ncnn2cc1-c1[nH]c2ccc(C3CCN(CC(=O)N(C)C)CC3)cc2c1C(C)C] | 475.3 | 1.58 | E |
| 268 | EX-132 | 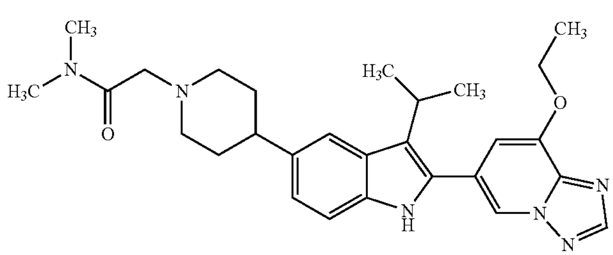 [SMILES: CCOc1cc(-c2[nH]c3ccc(C4CCN(CC(=O)N(C)C)CC4)cc3c2C(C)C)cn2ncnc12] | 489 | 1.55 | E |

TABLE 12-continued

| Ex. No. | Template Starting Material | Structure | LCMS MH+ | R$_t$ (min) | HPLC Method |
|---|---|---|---|---|---|
| 269 | EX-132 | 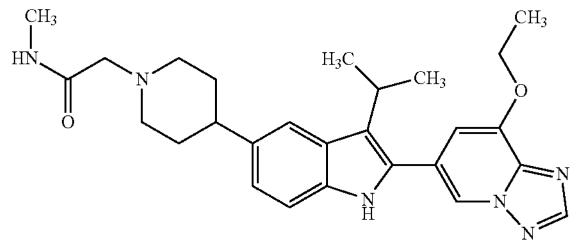 [SMILES: CCOc1cc(-c2[nH]c3ccc(C4CCN(CC(=O)NC)CC4)cc3c2C(C)C)cn2ncnc12] | 475.3 | 1.95 | E |
| 270 | EX-132 | 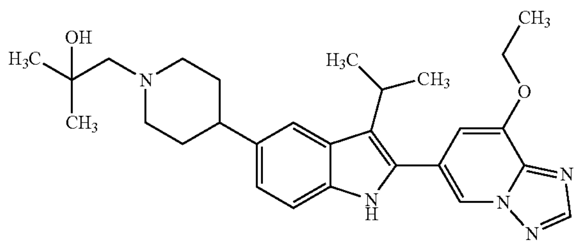 [SMILES: CCOc1cc(-c2[nH]c3ccc(C4CCN(CC(C)(C)O)CC4)cc3c2C(C)C)cn2ncnc12] | 476.2 | 1.76 | E |
| 271 | EX-133 | 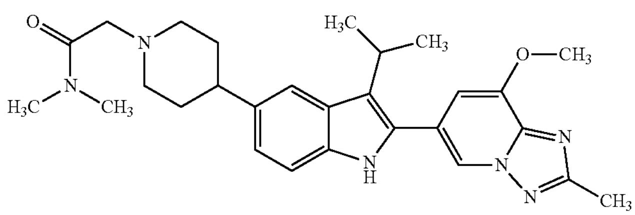 [SMILES: COc1cc(-c2[nH]c3ccc(C4CCN(CC(=O)N(C)C)CC4)cc3c2C(C)C)cn2nc(C)nc12] | 489.3 | 1.71 | E |
| 272 | EX-133 | 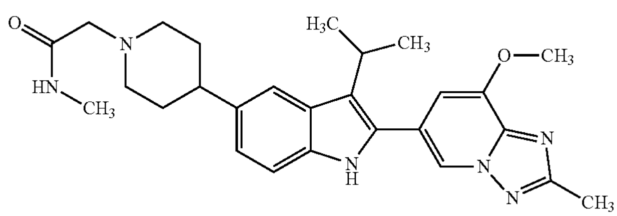 [SMILES: CNC(=O)CN1CCC(c2ccc3[nH]c(-c4cc(OC)c5nc(C)nn5c4)c(C(C)C)c3c2)CC1] | 475.3 | 1.84 | E |
| 273 | EX-133 | 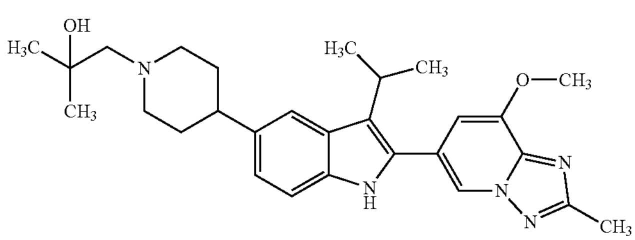 | 476.3 | 1.7 | E |
| 274 | EX-134 | 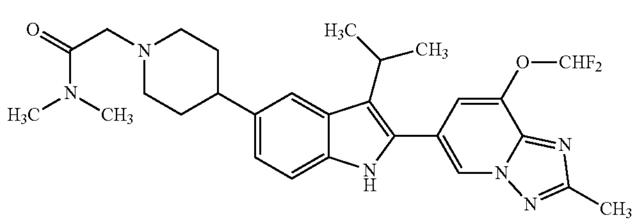 | 525.3 | 1.93 | E |

TABLE 12-continued
| Ex. No. | Template Starting Material | Structure | LCMS MH+ | R_t (min) | HPLC Method |
|---|---|---|---|---|---|
| 275 | EX-134 | 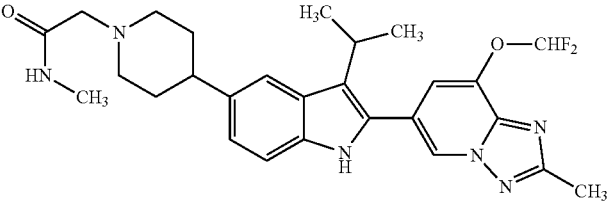 [SMILES: CNC(=O)CN1CCC(c2ccc3[nH]c(-c4cc(OC(F)F)c5nc(C)nn5c4)c(C(C)C)c3c2)CC1] | 511.3 | 1.98 | E |
| 276 | EX-135 | 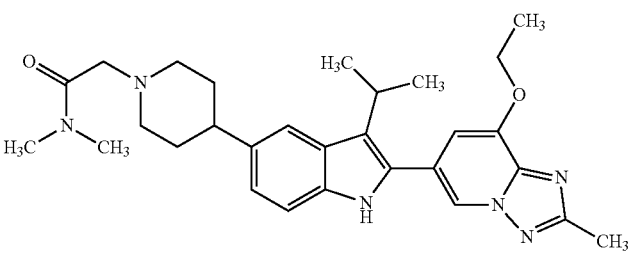 [SMILES: CCOc1cc(-c2[nH]c3ccc(C4CCN(CC(=O)N(C)C)CC4)cc3c2C(C)C)cn2nc(C)nc12] | 503.3 | 1.84 | E |
| 277 | EX-135 | 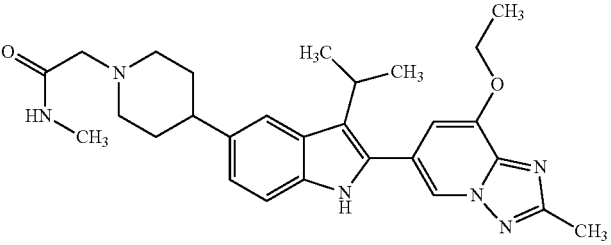 [SMILES: CCOc1cc(-c2[nH]c3ccc(C4CCN(CC(=O)NC)CC4)cc3c2C(C)C)cn2nc(C)nc12] | 489.3 | 2.09 | E |
| 278 | EX-136 | 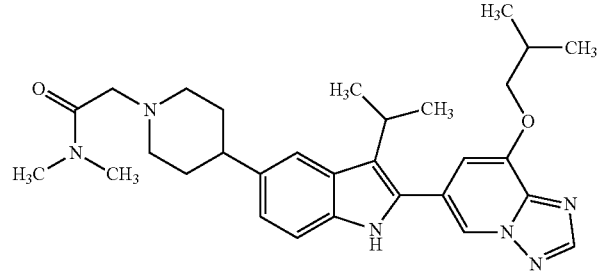 [SMILES: CC(C)COc1cc(-c2[nH]c3ccc(C4CCN(CC(=O)N(C)C)CC4)cc3c2C(C)C)cn2ncnc12] | 517.2 | 2.02 | E |
| 279 | EX-136 | 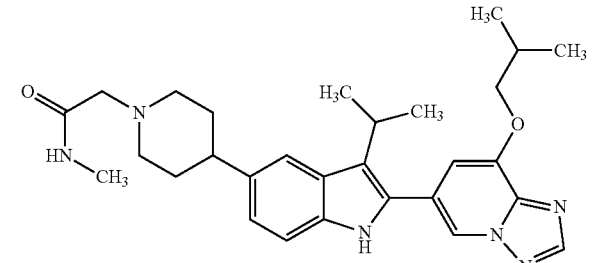 | 503.4 | 1.93 | E |
| 280 | EX-118 | 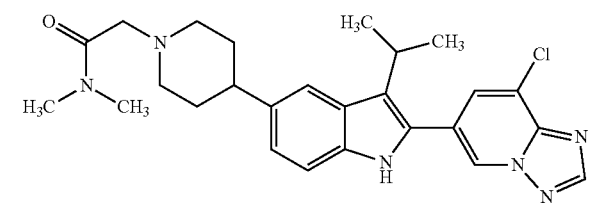 [SMILES: CC(C)c1c(-c2cc(Cl)c3ncnn3c2)[nH]c2ccc(C3CCN(CC(=O)N(C)C)CC3)cc12] | 479 | 1.68 | E |

TABLE 12-continued

| Ex. No. | Template Starting Material | Structure | LCMS MH+ | R_t (min) | HPLC Method |
|---|---|---|---|---|---|
| 281 | EX-118 | 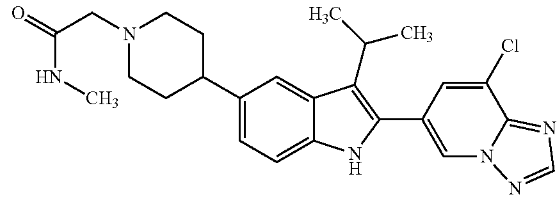 [SMILES: CNC(=O)CN1CCC(c2ccc3[nH]c(-c4cc(Cl)c5ncnn5c4)c(C(C)C)c3c2)CC1] | 465 | 1.85 | E |
| 282 | EX-118 | 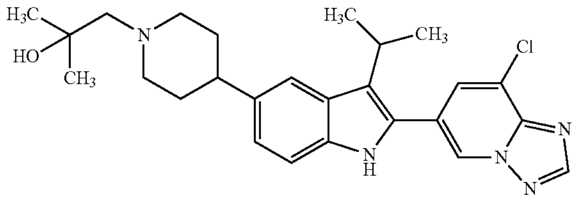 [SMILES: CC(C)c1c(-c2cc(Cl)c3ncnn3c2)[nH]c2ccc(C3CCN(CC(C)(C)O)CC3)cc12] | 466 | 1.74 | E |
| 283 | EX-137 | 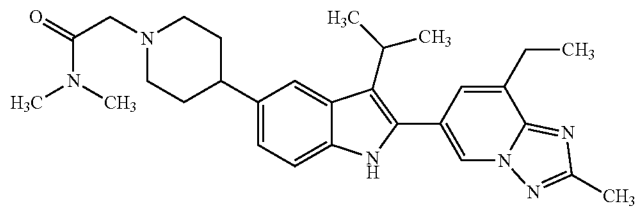 | 487.2 | 1.81 | E |
| 284 | EX-137 | 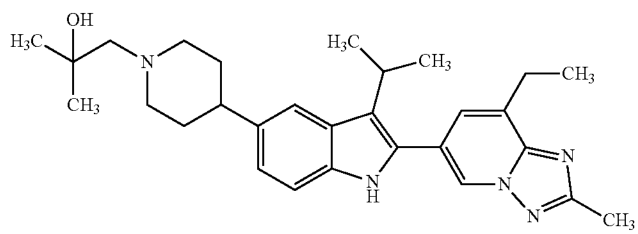 [SMILES: CCc1cc(-c2[nH]c3ccc(C4CCN(CC(C)(C)O)CC4)cc3c2C(C)C)cn2nc(C)nc12] | 474.1 | 1.95 | E |
| 285 | EX-137 | 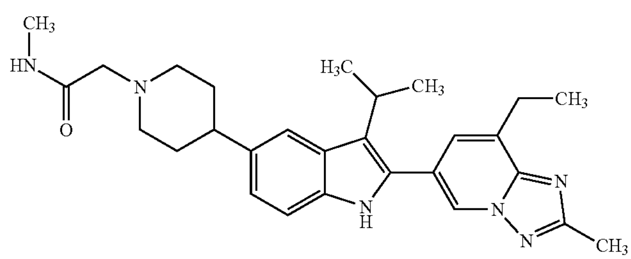 [SMILES: CCc1cc(-c2[nH]c3ccc(C4CCN(CC(=O)NC)CC4)cc3c2C(C)C)cn2nc(C)nc12] | 473.2 | 1.98 | E |
| 286 | EX-119 | 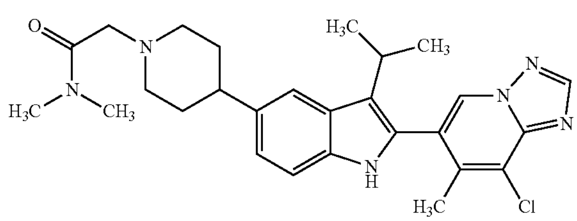 [SMILES: Cc1c(-c2[nH]c3ccc(C4CCN(CC(=O)N(C)C)CC4)cc3c2C(C)C)cn2ncnc2c1Cl] | 493.1 | 1.75 | E |
| 287 | EX-119 | 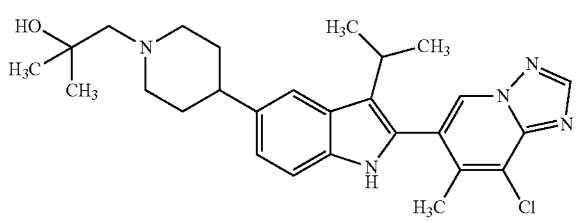 [SMILES: Cc1c(-c2[nH]c3ccc(C4CCN(CC(C)(C)O)CC4)cc3c2C(C)C)cn2ncnc2c1Cl] | 480.1 | 1.47 | E |

TABLE 12-continued

| Ex. No. | Template Starting Material | Structure | LCMS MH+ | R$_t$ (min) | HPLC Method |
|---|---|---|---|---|---|
| 288 | EX-119 | 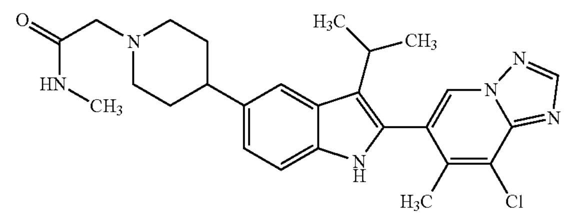 | 479.1 | 1.91 | E |
| 289 | EX-119 | 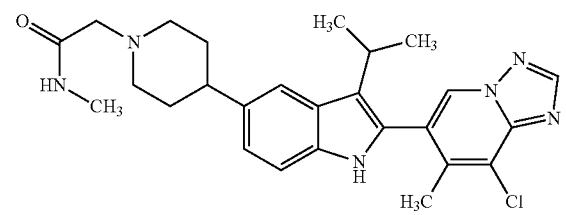 [SMILES: CNC(=O)CN1CCC(c2ccc3[nH]c(-c4cn5ncnc5c(Cl)c4C)c(C(C)C)c3c2)CC1] | 479.2 | 1.91 | E |
| 290 | EX-119 | 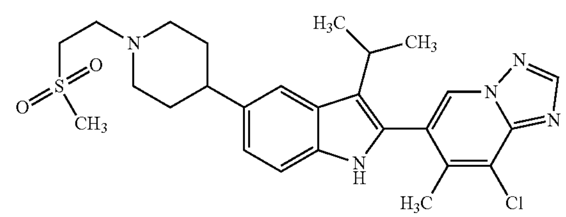 [SMILES: Cc1c(-c2[nH]c3ccc(C4CCN(CCS(C)(=O)=O)CC4)cc3c2C(C)C)cn2ncnc2c1Cl] | 514.2 | 1.97 | E |
| 291 | EX-143 | 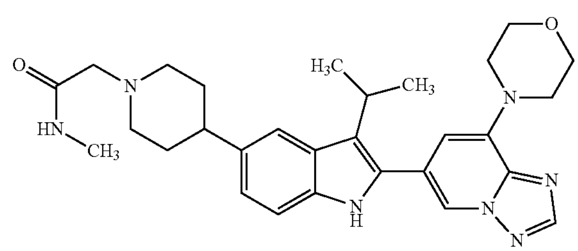 [SMILES: CNC(=O)CN1CCC(c2ccc3[nH]c(-c4cc(N5CCOCC5)c5ncnn5c4)c(C(C)C)c3c2)CC1] | 516.3 | 1.88 | E |
| 292 | EX-143 | 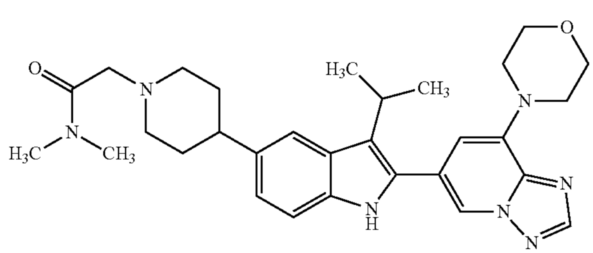 [SMILES: CC(C)c1c(-c2cc(N3CCOCC3)c3ncnn3c2)[nH]c2ccc(C3CCN(CC(=O)N(C)C)CC3)cc12] | 530.3 | 1.69 | E |
| 293 | EX-94 | 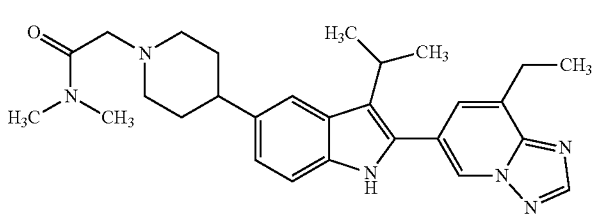 [SMILES: CCc1cc(-c2[nH]c3ccc(C4CCN(CC(=O)N(C)C)CC4)cc3c2C(C)C)cn2ncnc12] | 473.3 | 1.75 | E |

TABLE 12-continued

| Ex. No. | Template Starting Material | Structure | LCMS MH+ | R$_t$ (min) | HPLC Method |
|---|---|---|---|---|---|
| 294 | EX-94 | 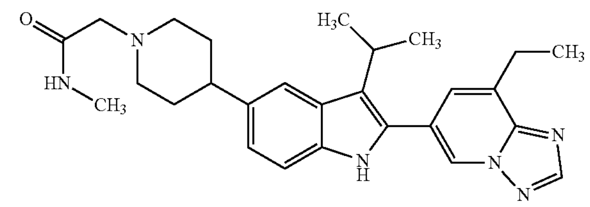 [SMILES: CCc1cc(-c2[nH]c3ccc(C4CCN(CC(=O)NC)CC4)cc3c2C(C)C)cn2ncnc12] | 459.2 | 1.95 | E |
| 295 | EX-95 | 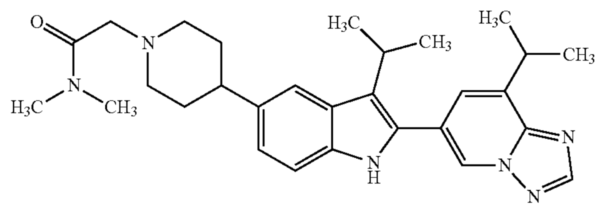 [SMILES: CC(C)c1c(-c2cc(C(C)C)c3ncnn3c2)[nH]c2ccc(C3CCN(CC(=O)N(C)C)CC3)cc12] | 487.3 | 1.91 | E |
| 296 | EX-95 | 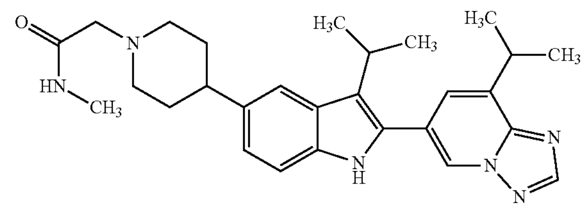 [SMILES: CNC(=O)CN1CCC(c2ccc3[nH]c(-c4cc(C(C)C)c5ncnn5c4)c(C(C)C)c3c2)CC1] | 473.3 | 2.1 | E |
| 297 | EX-144 | 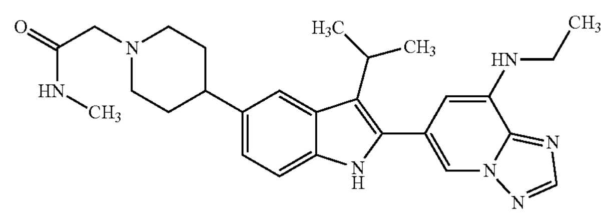 [SMILES: CCNc1cc(-c2[nH]c3ccc(C4CCN(CC(=O)NC)CC4)cc3c2C(C)C)cn2ncnc12] | 474.3 | 1.97 | E |
| 298 | EX-145 | 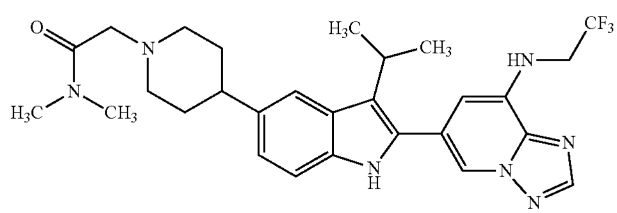 [SMILES: CC(C)c1c(-c2cc(NCC(F)(F)F)c3ncnn3c2)[nH]c2ccc(C3CCN(CC(=O)N(C)C)CC3)cc12] | 542.3 | 1.83 | E |
| 299 | EX-145 | 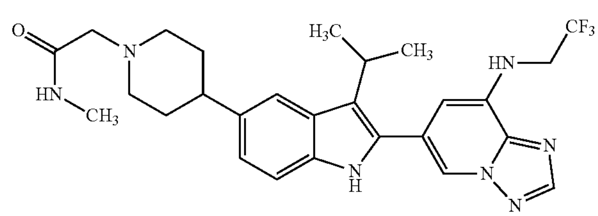 [SMILES: CNC(=O)CN1CCC(c2ccc3[nH]c(-c4cc(NCC(F)(F)F)c5ncnn5c4)c(C(C)C)c3c2)CC1] | 528.3 | 2.01 | E |
| 300 | EX-146 | 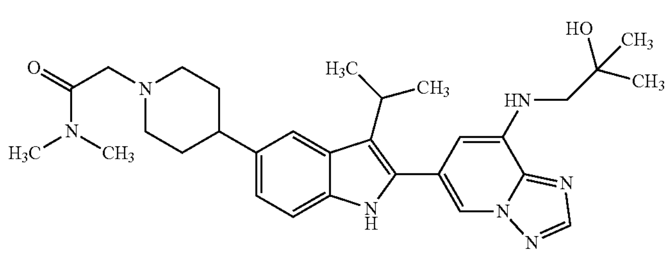 [SMILES: CC(C)c1c(-c2cc(NCC(C)(C)O)c3ncnn3c2)[nH]c2ccc(C3CCN(CC(=O)N(C)C)CC3)cc12] | 532.3 | 1.62 | E |

TABLE 12-continued
| Ex. No. | Template Starting Material | Structure | LCMS MH$^+$ | R$_t$ (min) | HPLC Method |
|---|---|---|---|---|---|
| 301 | EX-146 | 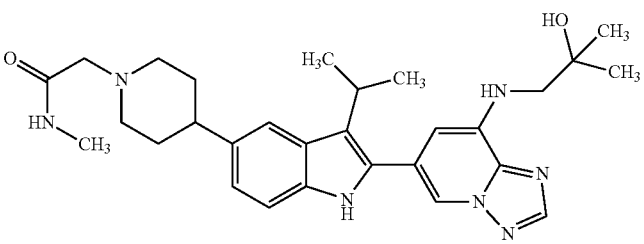 [SMILES: CNC(=O)CN1CCC(c2ccc3[nH]c(-c4cc(NCC(C)(C)O)c5ncnn5c4)c(C(C)C)c3c2)CC1] | 518.3 | 1.79 | E |
| 302 | EX-98 | 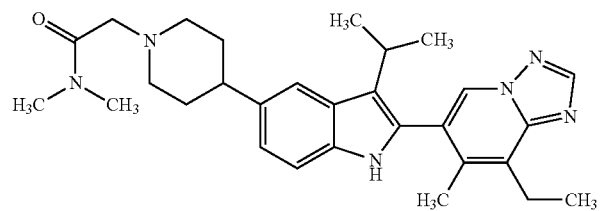 | 487.3 | 1.76 | E |
| 303 | EX-140 | 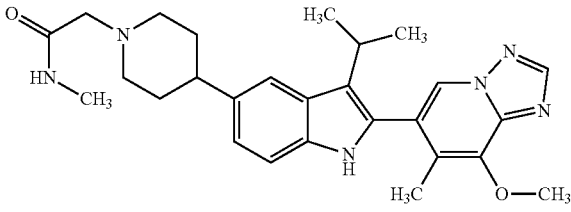 [SMILES: CNC(=O)CN1CCC(c2ccc3[nH]c(-c4cn5ncnc5c(OC)c4C)c(C(C)C)c3c2)CC1] | 475.3 | 1.9 | E |
| 304 | EX-140 | 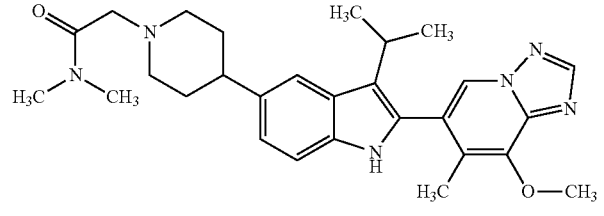 [SMILES: COc1c(C)c(-c2[nH]c3ccc(C4CCN(CC(=O)N(C)C)CC4)cc3c2C(C)C)cn2ncnc12] | 489.3 | 1.69 | E |
| 305 | EX-140 | 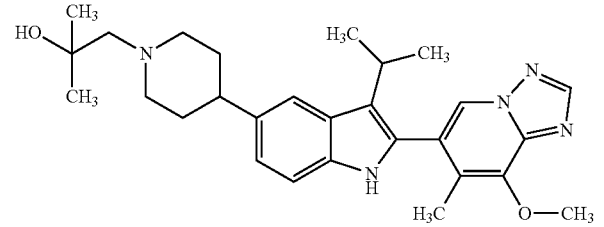 [SMILES: COc1c(C)c(-c2[nH]c3ccc(C4CCN(CC(C)(C)O)CC4)cc3c2C(C)C)cn2ncnc12] | 476.3 | 1.72 | E |
| 306 | EX-140 | 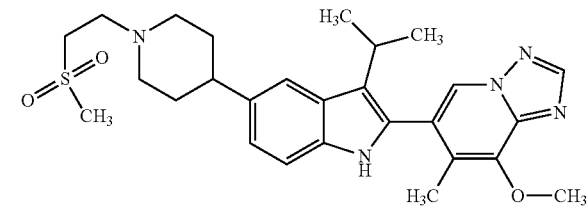 [SMILES: COc1c(C)c(-c2[nH]c3ccc(C4CCN(CCS(C)(=O)=O)CC4)cc3c2C(C)C)cn2ncnc12] | 510.3 | 1.72 | E |

TABLE 12-continued

| Ex. No. | Template Starting Material | Structure | LCMS MH+ | R$_t$ (min) | HPLC Method |
|---|---|---|---|---|---|
| 307 | EX-147 | 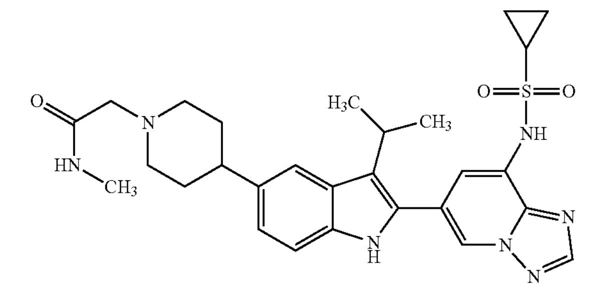 [SMILES: CNC(=O)CN1CCC(c2ccc3[nH]c(-c4cc(NS(=O)(=O)C5CC5)c5ncnn5c4)c(C(C)C)c3c2)CC1] | 550.3 | 1.32 | F |
| 308 | EX-148 | 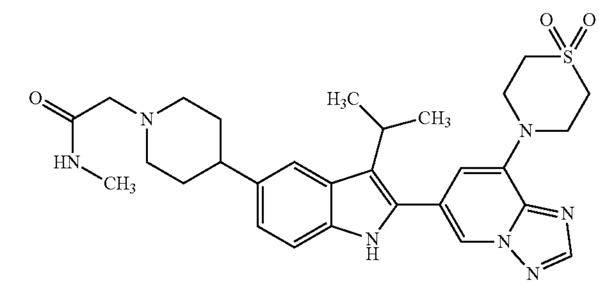 [SMILES: CNC(=O)CN1CCC(c2ccc3[nH]c(-c4cc(N5CCS(=O)(=O)CC5)c5ncnn5c4)c(C(C)C)c3c2)CC1] | 564.3 | 1.73 | E |
| 309 | EX-148 | 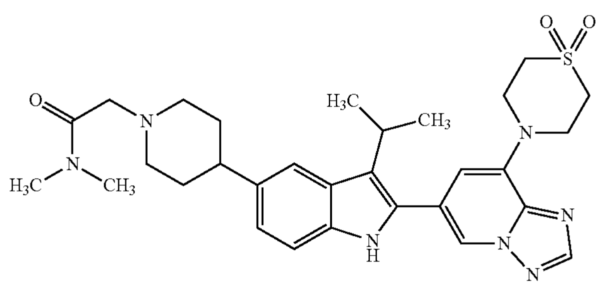 [SMILES: CC(C)c1c(-c2cc(N3CCS(=O)(=O)CC3)c3ncnn3c2)[nH]c2ccc(C3CCN(CC(=O)N(C)C)CC3)cc12] | 578.3 | 1.56 | E |
| 310 | EX-149 | 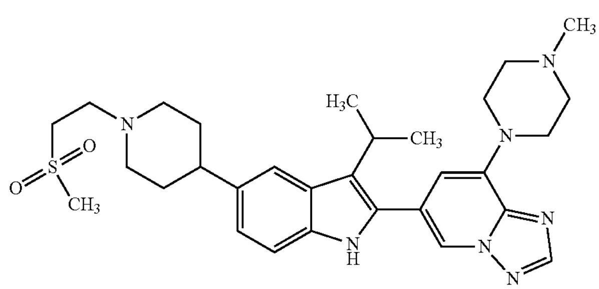 [SMILES: CC(C)c1c(-c2cc(N3CCN(C)CC3)c3ncnn3c2)[nH]c2ccc(C3CCN(CCS(C)(=O)=O)CC3)cc12] | 564.3 | 1.71 | E |
| 311 | EX-149 | 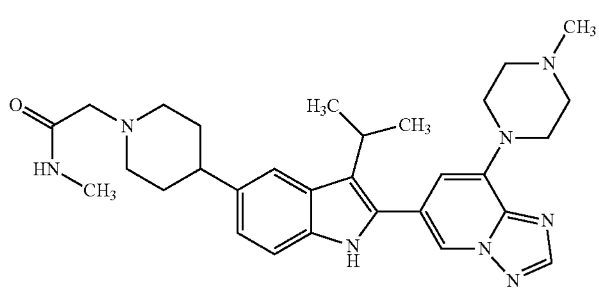 [SMILES: CNC(=O)CN1CCC(c2ccc3[nH]c(-c4cc(N5CCN(C)CC5)c5ncnn5c4)c(C(C)C)c3c2)CC1] | 529.3 | 1.64 | E |

TABLE 12-continued

| Ex. No. | Template Starting Material | Structure | LCMS MH+ | R$_t$ (min) | HPLC Method |
|---|---|---|---|---|---|
| 312 | EX-120 | 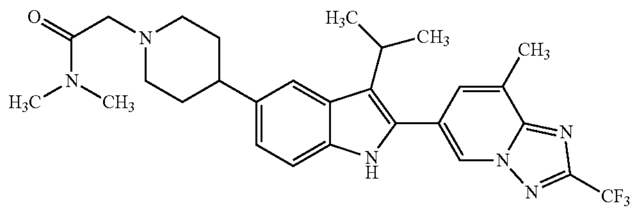 [SMILES: Cc1cc(-c2[nH]c3ccc(C4CCN(CC(=O)N(C)C)CC4)cc3c2C(C)C)cn2nc(C(F)(F)F)nc12] | 527.3 | 2.17 | E |
| 313 | EX-120 | 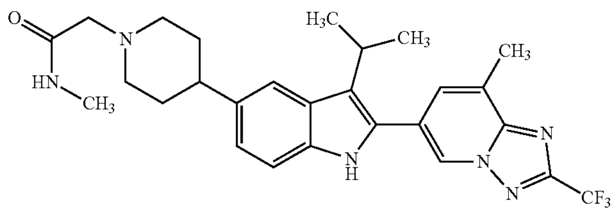 [SMILES: CNC(=O)CN1CCC(c2ccc3[nH]c(-c4cc(C)c5nc(C(F)(F)F)nn5c4)c(C(C)C)c3c2)CC1] | 513.2 | 2.38 | E |
| 314 | EX-120 | 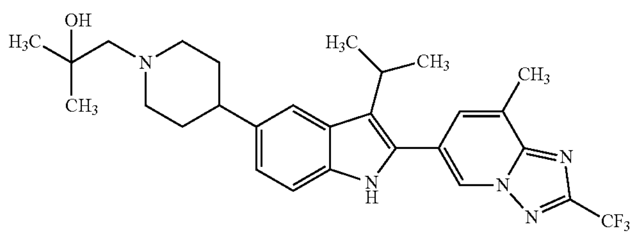 [SMILES: Cc1cc(-c2[nH]c3ccc(C4CCN(CC(C)(C)O)CC4)cc3c2C(C)C)cn2nc(C(F)(F)F)nc12] | 514.2 | 2.26 | E |
| 315 | EX-150 | 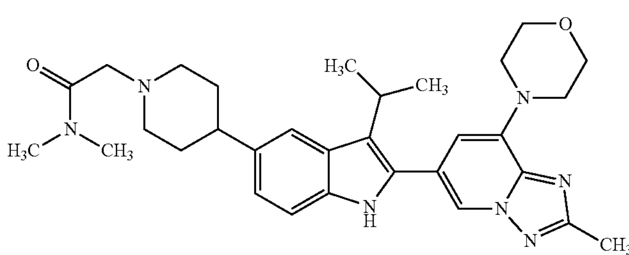 [SMILES: Cc1nc2c(N3CCOCC3)cc(-c3[nH]c4ccc(C5CCN(CC(=O)N(C)C)CC5)cc4c3C(C)C)cn2n1] | 544.3 | 1.72 | E |
| 316 | EX-150 | 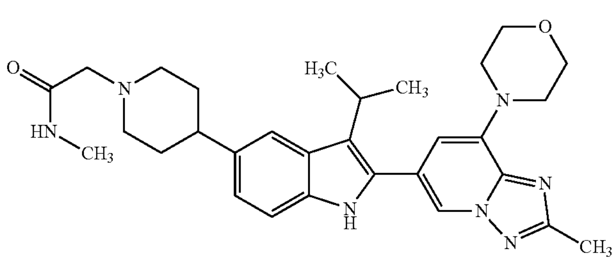 [SMILES: CNC(=O)CN1CCC(c2ccc3[nH]c(-c4cc(N5CCOCC5)c5nc(C)nn5c4)c(C(C)C)c3c2)CC1] | 530.3 | 1.91 | E |
| 317 | EX-154 | 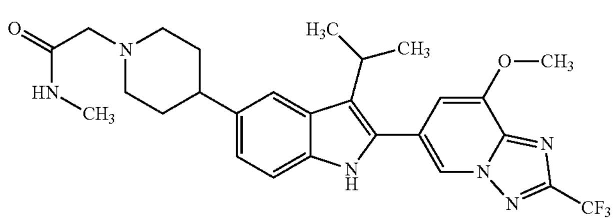 [SMILES: CNC(=O)CN1CCC(c2ccc3[nH]c(-c4cc(OC)c5nc(C(F)(F)F)nn5c4)c(C(C)C)c3c2)CC1] | 529.2 | 2.25 | E |

TABLE 12-continued

| Ex. No. | Template Starting Material | Structure | LCMS MH+ | R_t (min) | HPLC Method |
|---|---|---|---|---|---|
| 318 | EX-154 | 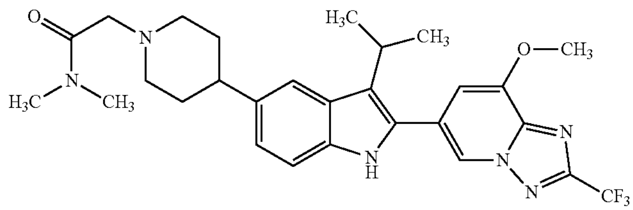 [SMILES: COc1cc(-c2[nH]c3ccc(C4CCN(CC(=O)N(C)C)CC4)cc3c2C(C)C)cn2nc(C(F)(F)F)nc12] | 543.2 | 2.08 | E |
| 319 | EX-151 | 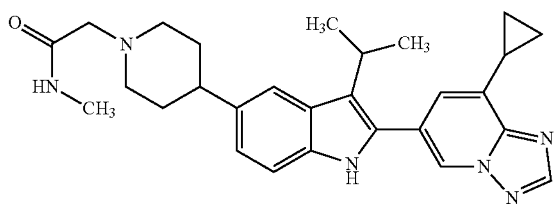 [SMILES: CNC(=O)CN1CCC(c2ccc3[nH]c(-c4cc(C5CC5)c5ncnn5c4)c(C(C)C)c3c2)CC1] | 471.3 | 1.75 | E |
| 320 | EX-151 | 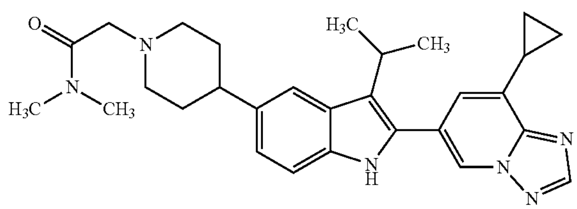 [SMILES: CC(C)c1c(-c2cc(C3CC3)c3ncnn3c2)[nH]c2ccc(C3CCN(CC(=O)N(C)C)CC3)cc12] | 485.3 | 1.27 | F |
| 321 | EX-151 | 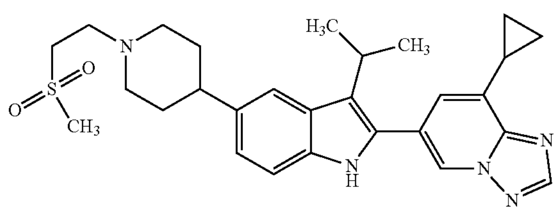 [SMILES: CC(C)c1c(-c2cc(C3CC3)c3ncnn3c2)[nH]c2ccc(C3CCN(CCS(C)(=O)=O)CC3)cc12] | 506.1 | 2.03 | E |
| 322 | EX-151 | 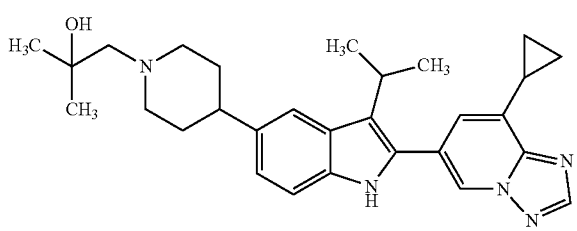 [SMILES: CC(C)c1c(-c2cc(C3CC3)c3ncnn3c2)[nH]c2ccc(C3CCN(CC(C)(C)O)CC3)cc12] | 472.2 | 1.86 | E |
| 323 | EX-141 | 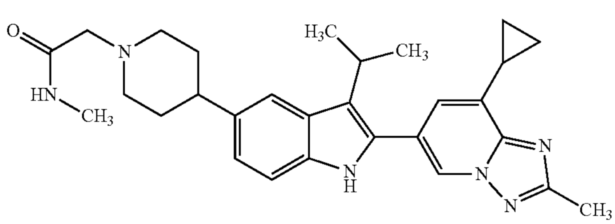 [SMILES: CNC(=O)CN1CCC(c2ccc3[nH]c(-c4cc(C5CC5)c5nc(C)nn5c4)c(C(C)C)c3c2)CC1] | 485.2 | 2.02 | E |
| 324 | EX-141 | 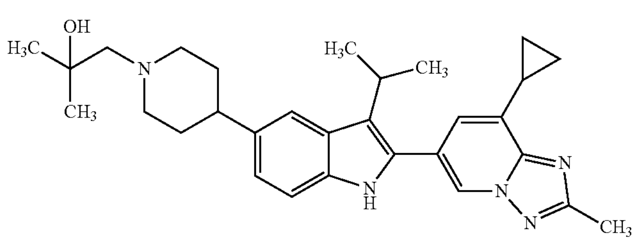 [SMILES: Cc1nc2c(C3CC3)cc(-c3[nH]c4ccc(C5CCN(CC(C)(C)O)CC5)cc4c3C(C)C)cn2n1] | 486.2 | 1.89 | E |

TABLE 12-continued

| Ex. No. | Template Starting Material | Structure | LCMS MH+ | R$_t$ (min) | HPLC Method |
|---|---|---|---|---|---|
| 325 | EX-141 | 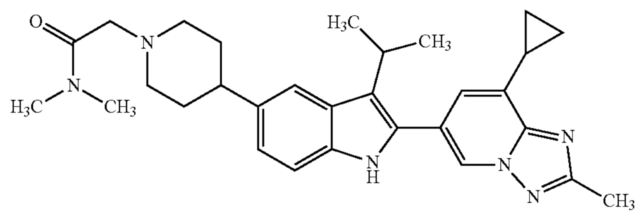 [SMILES: Cc1nc2c(C3CC3)cc(-c3[nH]c4ccc(C5CCN(CC(=O)N(C)C)CC5)cc4c3C(C)C)cn2n1] | 499.2 | 1.81 | E |
| 326 | EX-152 | 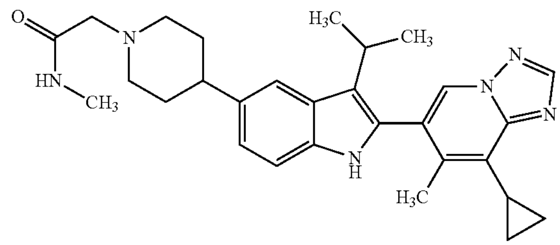 [SMILES: CNC(=O)CN1CCC(c2ccc3[nH]c(-c4cn5ncnc5c(C5CC5)c4C)c(C(C)C)c3c2)CC1] | 485.1 | 2.05 | E |
| 327 | EX-152 | 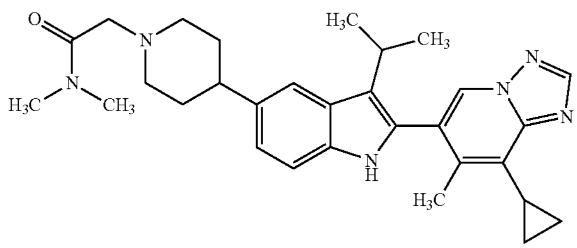 [SMILES: Cc1c(-c2[nH]c3ccc(C4CCN(CC(=O)N(C)C)CC4)cc3c2C(C)C)cn2ncnc2c1C1CC1] | 499.2 | 1.86 | E |
| 328 | EX-152 | 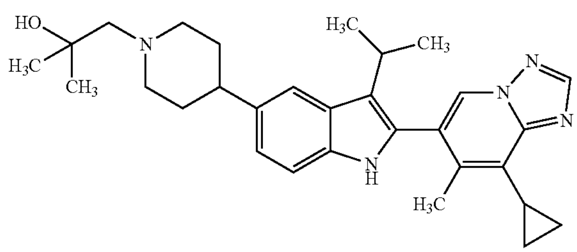 [SMILES: Cc1c(-c2[nH]c3ccc(C4CCN(CC(C)(C)O)CC4)cc3c2C(C)C)cn2ncnc2c1C1CC1] | 486.2 | 1.92 | E |
| 329 | EX-156 | 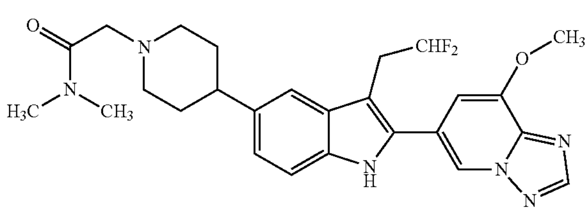 | 497.3 | 1.4 | E |
| 330 | EX-156 | 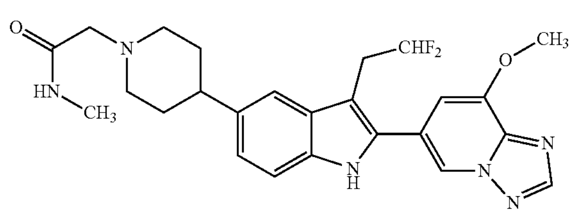 [SMILES: CNC(=O)CN1CCC(c2ccc3[nH]c(-c4cc(OC)c5ncnn5c4)c(CC(F)F)c3c2)CC1] | 483.2 | 1.55 | E |

TABLE 12-continued

| Ex. No. | Template Starting Material | Structure | LCMS MH+ | R$_t$ (min) | HPLC Method |
|---|---|---|---|---|---|
| 331 | EX-157 | 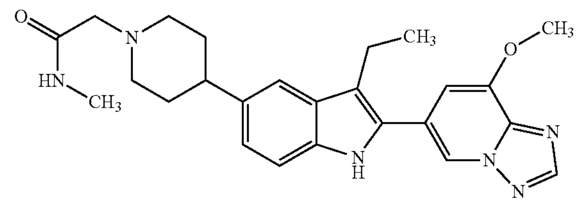 [SMILES: CCc1c(-c2cc(OC)c3ncnn3c2)[nH]c2ccc(C3CCN(CC(=O)NC)CC3)cc12] | 447.3 | 1.38 | E |
| 332 | EX-157 | 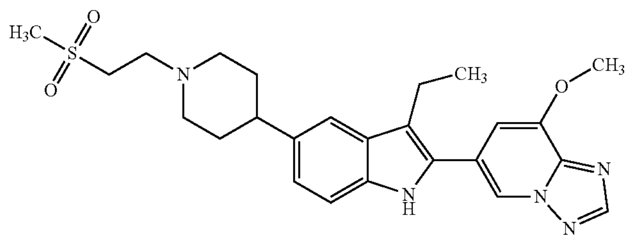 [SMILES: CCc1c(-c2cc(OC)c3ncnn3c2)[nH]c2ccc(C3CCN(CCS(C)(=O)=O)CC3)cc12] | 482.3 | 1.44 | E |
| 333 | EX-157 | 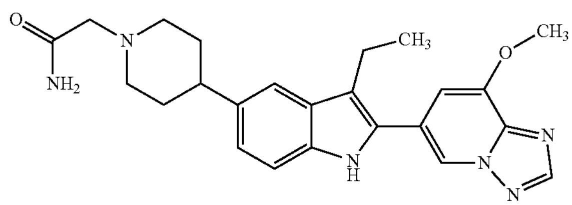 [SMILES: CCc1c(-c2cc(OC)c3ncnn3c2)[nH]c2ccc(C3CCN(CC(N)=O)CC3)cc12] | 433.3 | 1.28 | E |
| 334 | EX-157 | 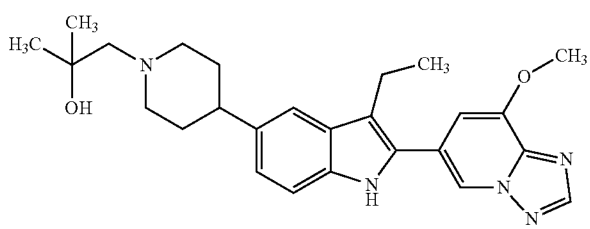 [SMILES: CCc1c(-c2cc(OC)c3ncnn3c2)[nH]c2ccc(C3CCN(CC(C)(C)O)CC3)cc12] | 448.3 | 1.26 | E |
| 335 | EX-157 | 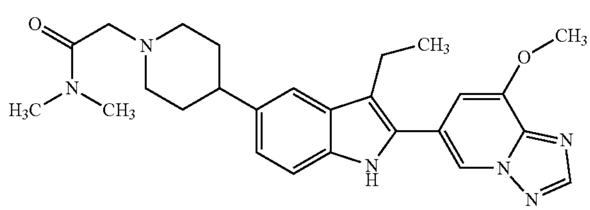 [SMILES: CCc1c(-c2cc(OC)c3ncnn3c2)[nH]c2ccc(C3CCN(CC(=O)N(C)C)CC3)cc12] | 461.3 | 1.24 | E |
| 336 | EX-157 | 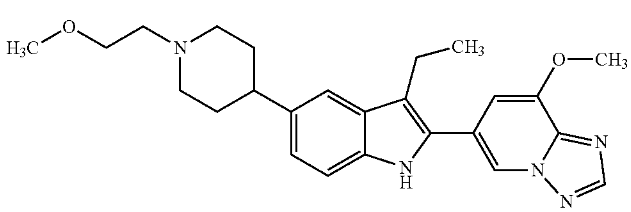 [SMILES: CCc1c(-c2cc(OC)c3ncnn3c2)[nH]c2ccc(C3CCN(CCOC)CC3)cc12] | 434.3 | 1.22 | E |
| 337 | EX-158 | 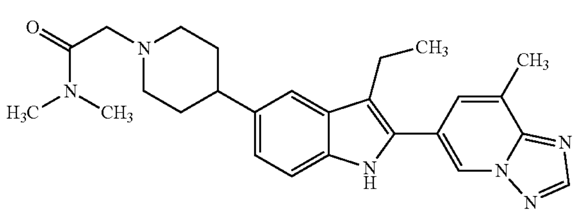 | 445.3 | 1.04 | F |

TABLE 12-continued

| Ex. No. | Template Starting Material | Structure | LCMS MH+ | R$_t$ (min) | HPLC Method |
|---|---|---|---|---|---|
| 338 | EX-158 | 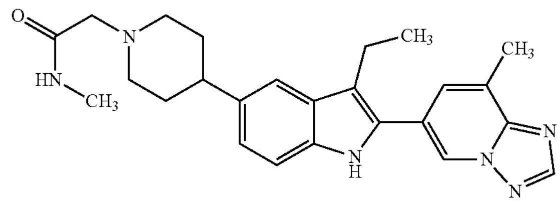 [SMILES: CCc1c(-c2cc(C)c3ncnn3c2)[nH]c2ccc(C3CCN(CC(=O)NC)CC3)cc12] | 431.3 | 1.44 | E |
| 339 | EX-158 | 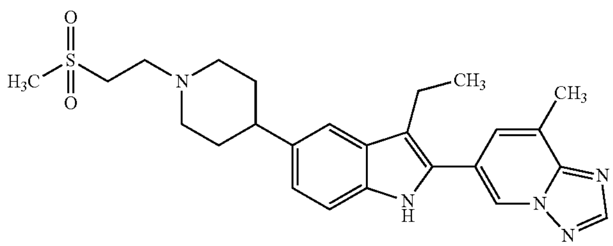 [SMILES: CCc1c(-c2cc(C)c3ncnn3c2)[nH]c2ccc(C3CCN(CCS(C)(=O)=O)CC3)cc12] | 466.3 | 1.5 | E |
| 340 | EX-158 | 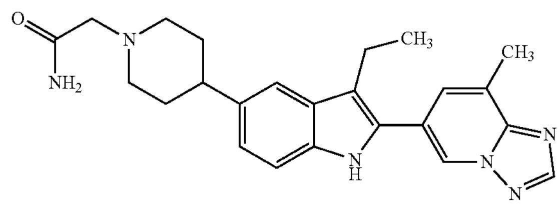 [SMILES: CCc1c(-c2cc(C)c3ncnn3c2)[nH]c2ccc(C3CCN(CC(N)=O)CC3)cc12] | 417.3 | 1.33 | E |
| 341 | EX-158 | 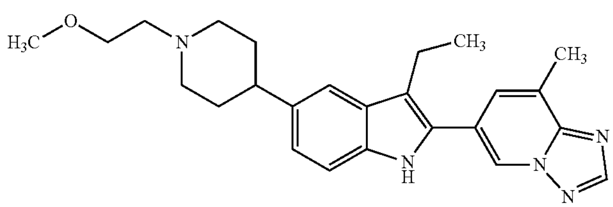 [SMILES: CCc1c(-c2cc(C)c3ncnn3c2)[nH]c2ccc(C3CCN(CCOC)CC3)cc12] | 418.3 | 1.26 | E |
| 342 | EX-158 | 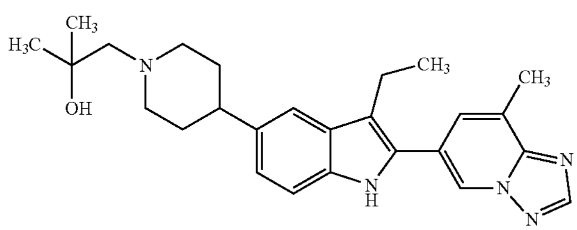 [SMILES: CCc1c(-c2cc(C)c3ncnn3c2)[nH]c2ccc(C3CCN(CC(C)(C)O)CC3)cc12] | 432.3 | 1.31 | E |
| 343 | EX-161 | 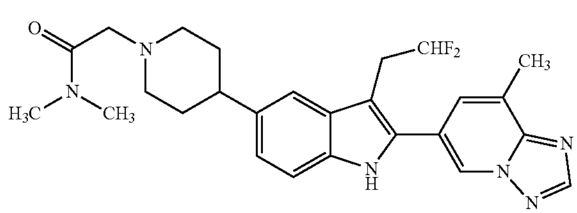 | 481.3 | 1.45 | E |
| 344 | EX-161 | 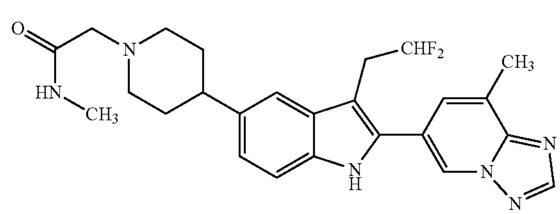 [SMILES: CNC(=O)CN1CCC(c2ccc3[nH]c(-c4cc(C)c5ncnn5c4)c(CC(F)F)c3c2)CC1] | 467.2 | 1.58 | E |

TABLE 12-continued
| Ex. No. | Template Starting Material | Structure | LCMS MH+ | $R_t$ (min) | HPLC Method |
|---|---|---|---|---|---|
| 345 | EX-162 | 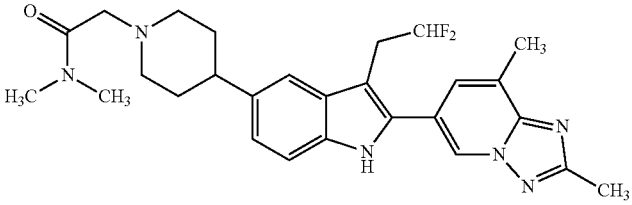 [SMILES: Cc1nc2c(C)cc(-c3[nH]c4ccc(C5CCN(CC(=O)N(C)C)CC5)cc4c3CC(F)F)cn2n1] | 495.2 | 1.53 | E |
| 346 | EX-162 | 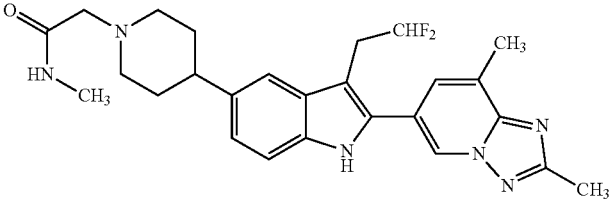 [SMILES: CNC(=O)CN1CCC(c2ccc3[nH]c(-c4cc(C)c5nc(C)nn5c4)c(CC(F)F)c3c2)CC1] | 481.2 | 1.68 | E |
| 347 | EX-160 | 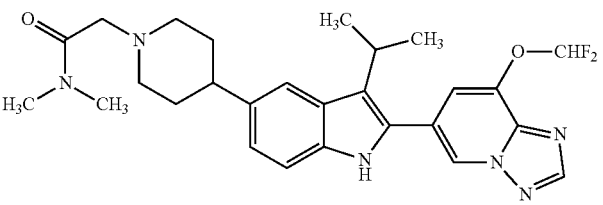 [SMILES: CC(C)c1c(-c2cc(OC(F)F)c3ncnn3c2)[nH]c2ccc(C3CCN(CC(=O)N(C)C)CC3)cc12] | 511.3 | 1.17 | E |
| 348 | EX-159 | 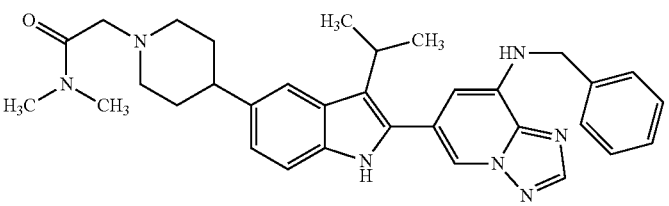 [SMILES: CC(C)c1c(-c2cc(NCc3ccccc3)c3ncnn3c2)[nH]c2ccc(C3CCN(CC(=O)N(C)C)CC3)cc12] | 550.3 | 1.97 | E |
| 349 | EX-156 | 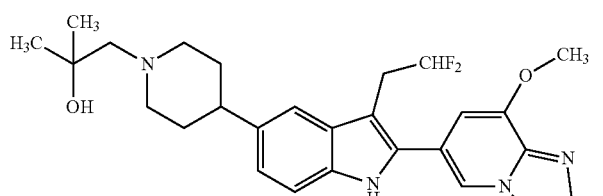 | 484.2 | 1.42 | E |
The following examples were prepared according to the general procedure of Example 26.
TABLE 13
| Ex. No. | Template Starting Material | Structure | LCMS MH+ | $R_t$ (min) | HPLC Method |
|---|---|---|---|---|---|
| 350 | EX-1 | 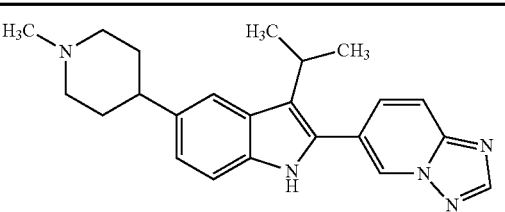 | 374.0 | 1.05 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 351 | EX-1 | 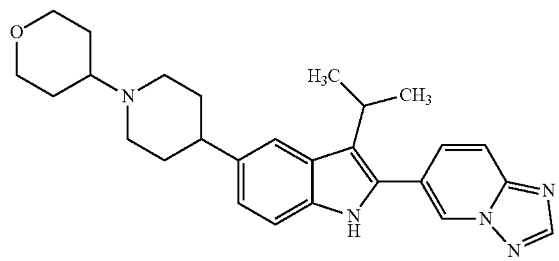 [SMILES: CC(C)c1c(-c2ccc3ncnn3c2)[nH]c2ccc(C3CCN(C4CCOCC4)CC3)cc12] | 444.4 | 1.53 | QC-ACN-AA-XB |
| 352 | EX-1 | 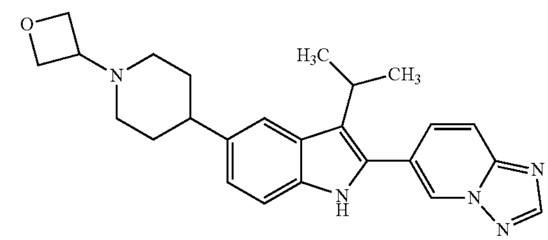 [SMILES: CC(C)c1c(-c2ccc3ncnn3c2)[nH]c2ccc(C3CCN(C4COC4)CC3)cc12] | 416.4 | 1.02 | QC-ACN-TFA-XB |
| 353 | EX-1 | 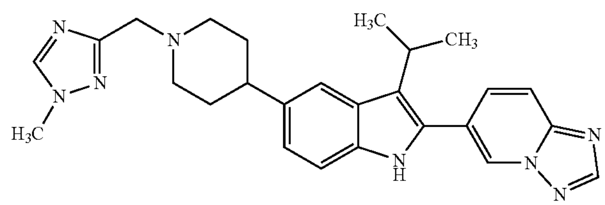 | 455.2 | 1.06 | QC-ACN-TFA-XB |
| 354 | EX-1 | 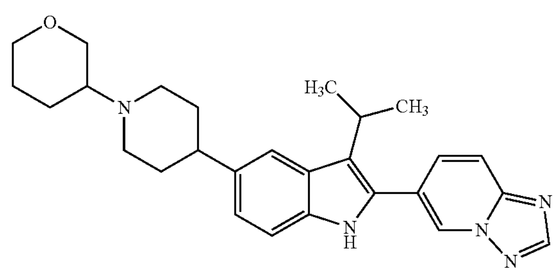 [SMILES: CC(C)c1c(-c2ccc3ncnn3c2)[nH]c2ccc(C3CCN(C4CCCOC4)CC3)cc12] | 444.4 | 1.17 | QC-ACN-TFA-XB |
| 355 | EX-1 | 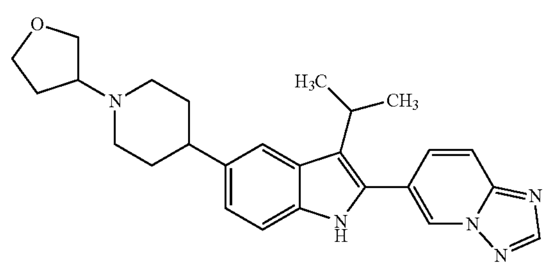 [SMILES: CC(C)c1c(-c2ccc3ncnn3c2)[nH]c2ccc(C3CCN(C4CCOC4)CC3)cc12] | 430.4 | 1.24 | QC-ACN-AA-XB |
| 356 | EX-1 | 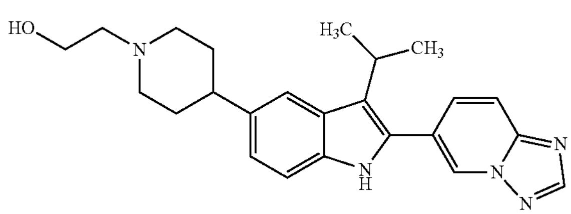 [SMILES: CC(C)c1c(-c2ccc3ncnn3c2)[nH]c2ccc(C3CCN(CCO)CC3)cc12] | 404.4 | 1.09 | QC-ACN-AA-XB |

TABLE 13-continued

| Ex. No. | Template Starting Material | Structure | LCMS MH+ | R_t (min) | HPLC Method |
|---|---|---|---|---|---|
| 357 | EX-117 | 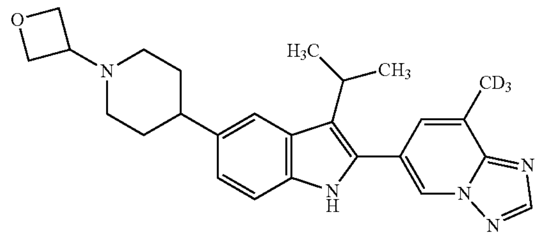 [SMILES: [2H]C([2H])([2H])c1cc(-c2[nH]c3ccc(C4CCN(C5COC5)CC4)cc3c2C(C)C)cn2ncnc12] | 433.2 | 0.66 | TS1 |
| 358 | EX-1 | 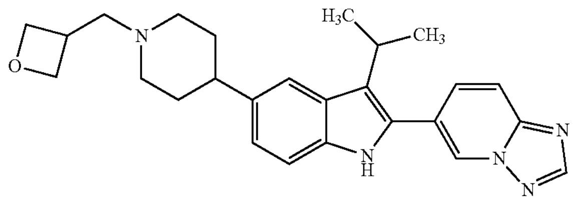 [SMILES: CC(C)c1c(-c2ccc3ncnn3c2)[nH]c2ccc(C3CCN(CC4COC4)CC3)cc12] | 430.4 | 1.13 | QC-ACN-TFA-XB |
| 359 | EX-1 | 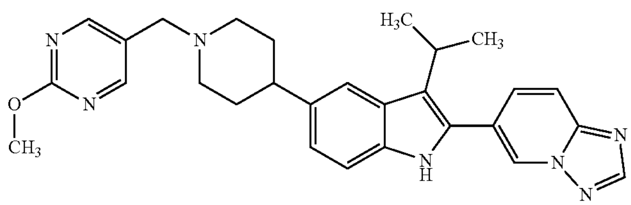 [SMILES: COc1ncc(CN2CCC(c3ccc4[nH]c(-c5ccc6ncnn6c5)c(C(C)C)c4c3)CC2)cn1] | 481.9 | 1.79 | QC-ACN-AA-XB |
| 360 | EX-1 | 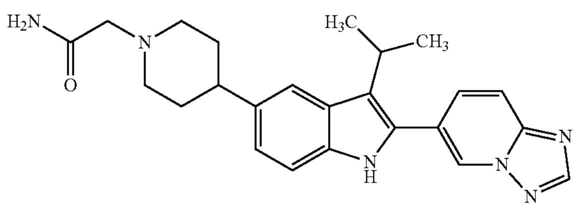 [SMILES: CC(C)c1c(-c2ccc3ncnn3c2)[nH]c2ccc(C3CCN(CC(N)=O)CC3)cc12] | 417.04, 416.86 | 0.92 | QC-ACN-TFA-XB |
| 361 | EX-1 | 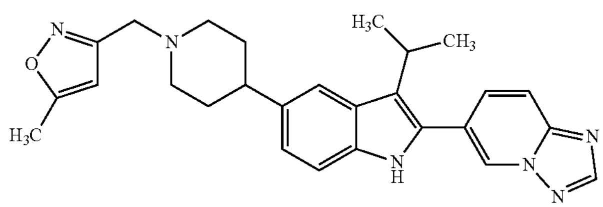 [SMILES: Cc1cc(CN2CCC(c3ccc4[nH]c(-c5ccc6ncnn6c5)c(C(C)C)c4c3)CC2)no1] | 455.2 | 1.89 | QC-ACN-AA-XB |
| 362 | EX-1 | 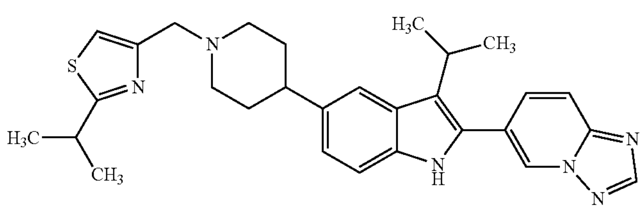 [SMILES: CC(C)c1nc(CN2CCC(c3ccc4[nH]c(-c5ccc6ncnn6c5)c(C(C)C)c4c3)CC2)cs1] | 499.2 | 1.96 | QC-ACN-AA-XB |
| 363 | EX-1 | 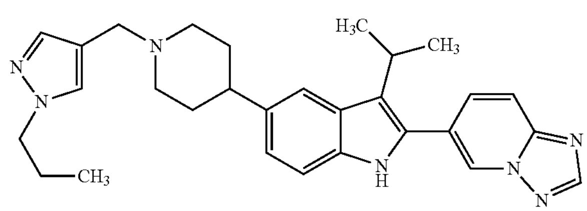 [SMILES: CCCn1cc(CN2CCC(c3ccc4[nH]c(-c5ccc6ncnn6c5)c(C(C)C)c4c3)CC2)cn1] | 482.4 | 1.44 | QC-ACN-AA-XB |

TABLE 13-continued

| Ex. No. | Template Starting Material | Structure | LCMS MH+ | R$_t$ (min) | HPLC Method |
|---|---|---|---|---|---|
| 364 | EX-1 | 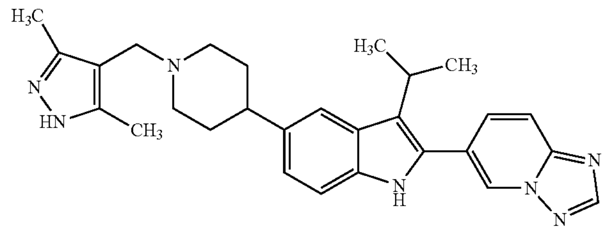 [SMILES: Cc1n[nH]c(C)c1CN1CCC(c2ccc3[nH]c(-c4ccc5ncnn5c4)c(C(C)C)c3c2)CC1] | 468.4 | 1.15 | QC-ACN-TFA-XB |
| 365 | EX-1 | 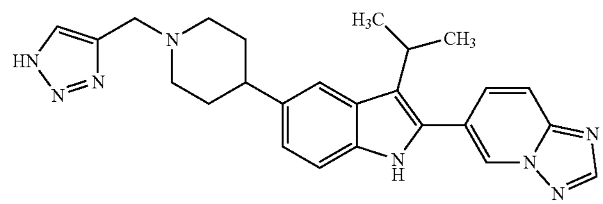 [SMILES: CC(C)c1c(-c2ccc3ncnn3c2)[nH]c2ccc(C3CCN(Cc4c[nH]nn4)CC3)cc12] | 441.3 | 1.09 | QC-ACN-TFA-XB |
| 366 | EX-1 | 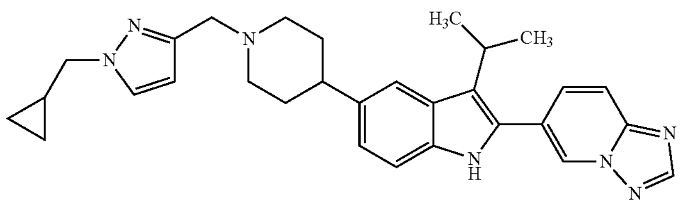 [SMILES: CC(C)c1c(-c2ccc3ncnn3c2)[nH]c2ccc(C3CCN(Cc4ccn(CC5CC5)n4)CC3)cc12] | 494.2 | 1.45 | QC-ACN-TFA-XB |
| 367 | EX-1 | 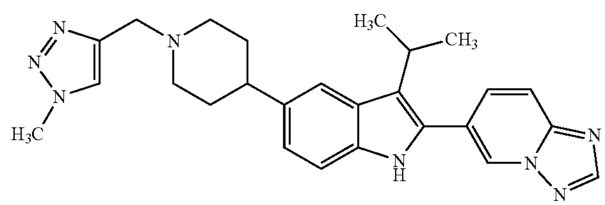 | 455.0 | 1.31 | QC-ACN-AA-XB |
| 368 | EX-1 | 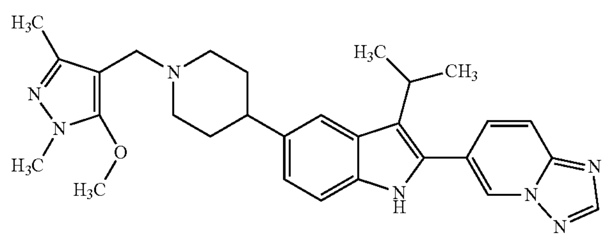 [SMILES: COc1c(CN2CCC(c3ccc4[nH]c(-c5ccc6ncnn6c5)c(C(C)C)c4c3)CC2)c(C)nn1C] | 498.4 | 1.41 | QC-ACN-AA-XB |
| 369 | EX-1 | 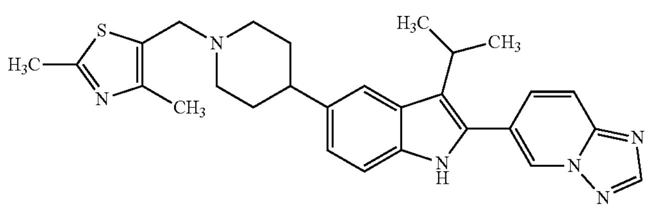 [SMILES: Cc1nc(C)c(CN2CCC(c3ccc4[nH]c(-c5ccc6ncnn6c5)c(C(C)C)c4c3)CC2)s1] | 485.2 | 1.96 | QC-ACN-AA-XB |
| 370 | EX-1 | 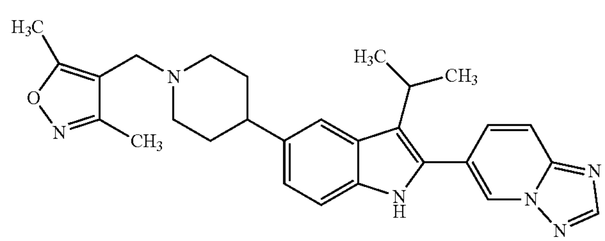 [SMILES: Cc1noc(C)c1CN1CCC(c2ccc3[nH]c(-c4ccc5ncnn5c4)c(C(C)C)c3c2)CC1] | 469.3 | 1.85 | QC-ACN-AA-XB |

TABLE 13-continued

| Ex. No. | Template Starting Material | Structure | LCMS MH+ | R$_t$ (min) | HPLC Method |
|---|---|---|---|---|---|
| 371 | EX-1 | 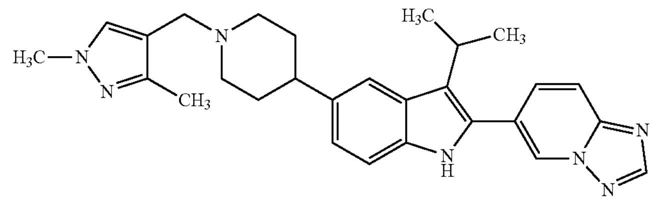 [SMILES: Cc1nn(C)cc1CN1CCC(c2ccc3[nH]c(-c4ccc5ncnn5c4)c(C(C)C)c3c2)CC1] | 468.4 | 1.21 | QC-ACN-TFA-XB |
| 372 | EX-1 | 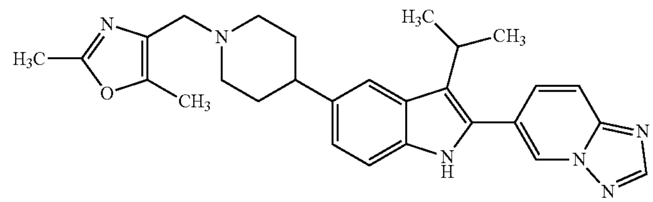 [SMILES: Cc1nc(CN2CCC(c3ccc4[nH]c(-c5ccc6ncnn6c5)c(C(C)C)c4c3)CC2)c(C)o1] | 469.0 | 1.54 | QC-ACN-AA-XB |
| 373 | EX-1 | 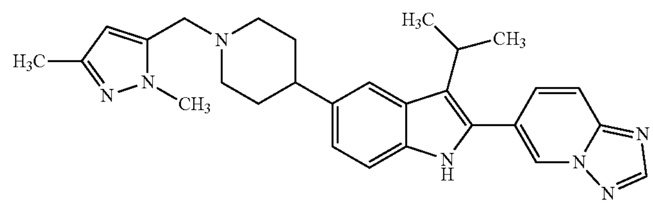 [SMILES: Cc1cc(CN2CCC(c3ccc4[nH]c(-c5ccc6ncnn6c5)c(C(C)C)c4c3)CC2)n(C)n1] | 468.0 | 1.87 | QC-ACN-AA-XB |
| 374 | EX-1 | 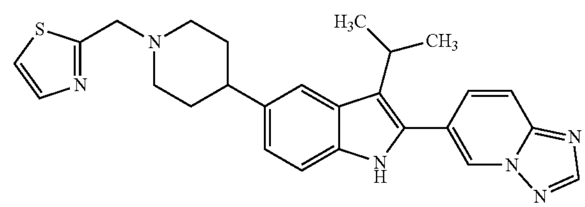 [SMILES: CC(C)c1c(-c2ccc3ncnn3c2)[nH]c2ccc(C3CCN(Cc4nccs4)CC3)cc12] | 456.9 | 1.96 | QC-ACN-AA-XB |
| 375 | EX-1 | 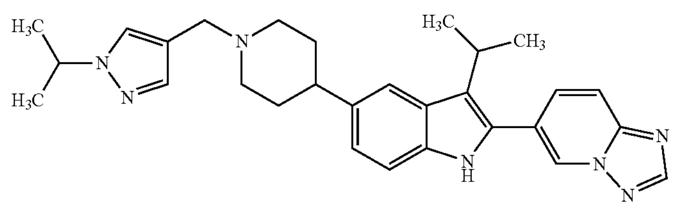 [SMILES: CC(C)c1c(-c2ccc3ncnn3c2)[nH]c2ccc(C3CCN(Cc4cnn(C(C)C)c4)CC3)cc12] | 482.4 | 1.42 | QC-ACN-AA-XB |
| 376 | EX-1 | 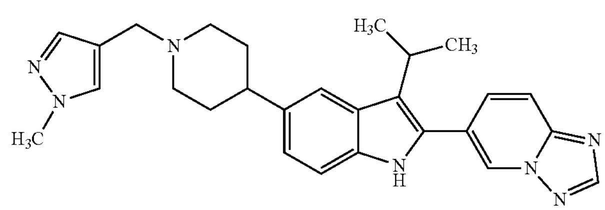 [SMILES: CC(C)c1c(-c2ccc3ncnn3c2)[nH]c2ccc(C3CCN(Cc4cnn(C)c4)CC3)cc12] | 454.0 | 1.25 | QC-ACN-AA-XB |
| 377 | EX-1 | 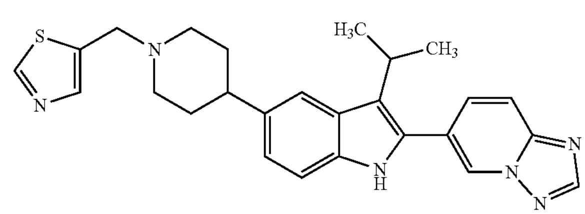 [SMILES: CC(C)c1c(-c2ccc3ncnn3c2)[nH]c2ccc(C3CCN(Cc4cncs4)CC3)cc12] | 457.2 | 1.16 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 378 | EX-1 | 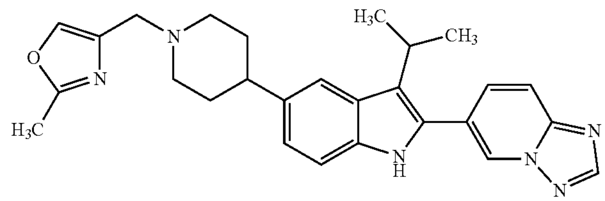 [SMILES: Cc1nc(CN2CCC(c3ccc4[nH]c(-c5ccc6ncnn6c5)c(C(C)C)c4c3)CC2)co1] | 455.4 | 1.25 | QC-ACN-TFA-XB |
| 379 | EX-1 | 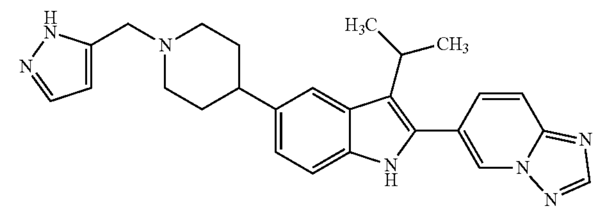 [SMILES: CC(C)c1c(-c2ccc3ncnn3c2)[nH]c2ccc(C3CCN(Cc4ccn[nH]4)CC3)cc12] | 440.2 | 1.14 | QC-ACN-TFA-XB |
| 380 | EX-1 | 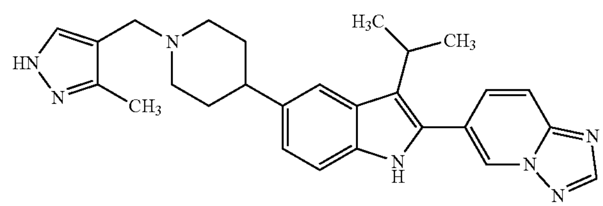 [SMILES: Cc1n[nH]cc1CN1CCC(c2ccc3[nH]c(-c4ccc5ncnn5c4)c(C(C)C)c3c2)CC1] | 454.3 | 1.19 | QC-ACN-AA-XB |
| 381 | EX-1 | 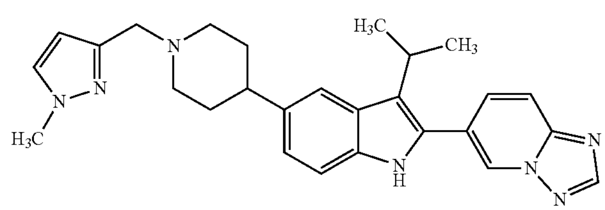 [SMILES: CC(C)c1c(-c2ccc3ncnn3c2)[nH]c2ccc(C3CCN(Cc4ccn(C)n4)CC3)cc12] | 454.4 | 1.32 | QC-ACN-AA-XB |
| 382 | EX-1 | 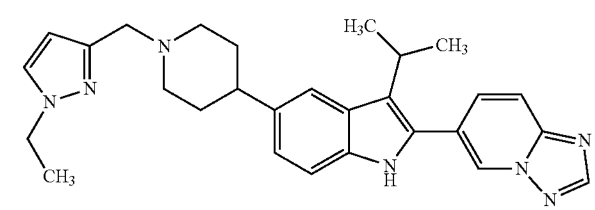 [SMILES: CCn1ccc(CN2CCC(c3ccc4[nH]c(-c5ccc6ncnn6c5)c(C(C)C)c4c3)CC2)n1] | 468.4 | 1.33 | QC-ACN-AA-XB |
| 383 | EX-1 | 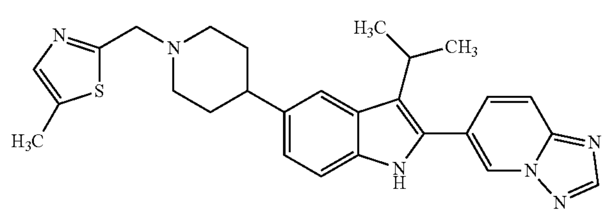 [SMILES: Cc1cnc(CN2CCC(c3ccc4[nH]c(-c5ccc6ncnn6c5)c(C(C)C)c4c3)CC2)s1] | 471.3 | 2.04 | QC-ACN-AA-XB |
| 384 | EX-1 | 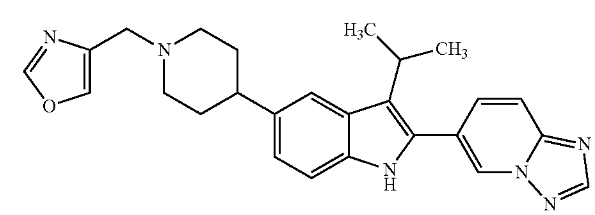 [SMILES: CC(C)c1c(-c2ccc3ncnn3c2)[nH]c2ccc(C3CCN(Cc4cocn4)CC3)cc12] | 221.2 | 1.45 | QC-ACN-AA-XB |

TABLE 13-continued

| Ex. No. | Template Starting Material | Structure | LCMS MH+ | R$_t$ (min) | HPLC Method |
|---|---|---|---|---|---|
| 385 | EX-2 | 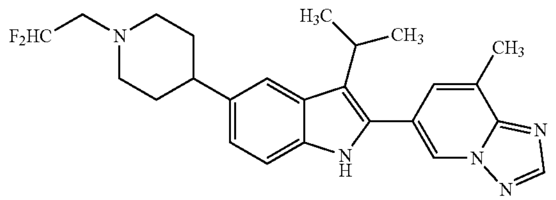 [SMILES: Cc1cc(-c2[nH]c3ccc(C4CCN(CC(F)F)CC4)cc3c2C(C)C)cn2ncnc12] | 438.2 | 1.21 | QC-ACN-TFA-XB |
| 386 | EX-2 | 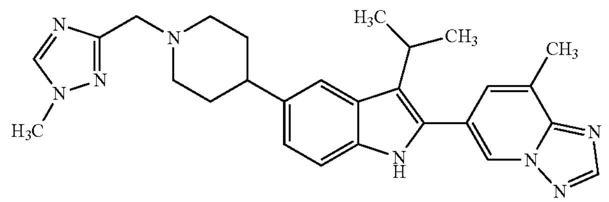 [SMILES: Cc1cc(-c2[nH]c3ccc(C4CCN(Cc5ncn(C)n5)CC4)cc3c2C(C)C)cn2ncnc12] | 469.4 | 1.2 | QC-ACN-TFA-XB |
| 387 | EX-2 | 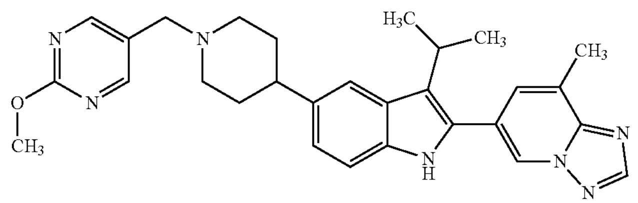 [SMILES: COc1ncc(CN2CCC(c3ccc4[nH]c(-c5cc(C)c6ncnn6c5)c(C(C)C)c4c3)CC2)cn1] | 496.1 | 1.79 | QC-ACN-AA-XB |
| 388 | EX-2 | 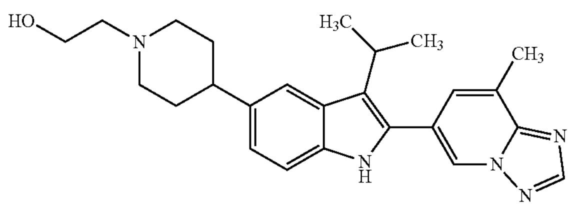 [SMILES: Cc1cc(-c2[nH]c3ccc(C4CCN(CCO)CC4)cc3c2C(C)C)cn2ncnc12] | 418.0 | 1.16 | QC-ACN-AA-XB |
| 389 | EX-2 | 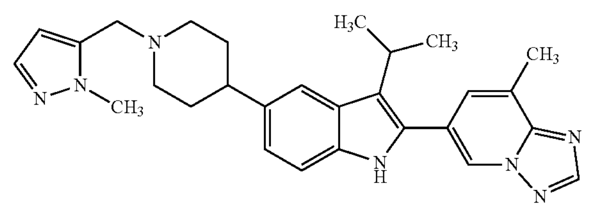 [SMILES: Cc1cc(-c2[nH]c3ccc(C4CCN(Cc5ccnn5C)CC4)cc3c2C(C)C)cn2ncnc12] | 468.2 | 1.9 | QC-ACN-AA-XB |
| 390 | EX-2 | 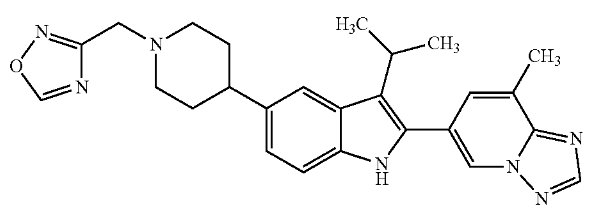 [SMILES: Cc1cc(-c2[nH]c3ccc(C4CCN(Cc5ncon5)CC4)cc3c2C(C)C)cn2ncnc12] | 456.4 | 1.86 | QC-ACN-AA-XB |
| 391 | EX-2 | 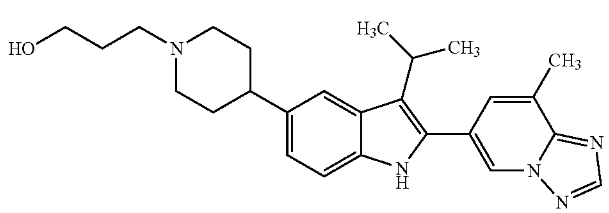 [SMILES: Cc1cc(-c2[nH]c3ccc(C4CCN(CCCO)CC4)cc3c2C(C)C)cn2ncnc12] | 432.4 | 1.19 | QC-ACN-AA-XB |

TABLE 13-continued

| Ex. No. | Template Starting Material | Structure | LCMS MH+ | R$_t$ (min) | HPLC Method |
|---|---|---|---|---|---|
| 392 | EX-2 | 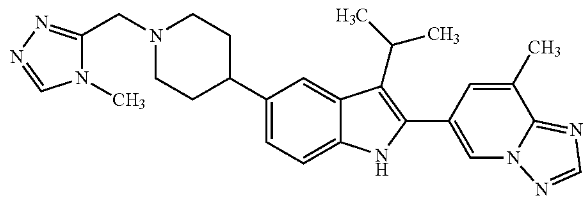 [SMILES: Cc1cc(-c2[nH]c3ccc(C4CCN(Cc5nncn5C)CC4)cc3c2C(C)C)cn2ncnc12] | 469.2 | 1.52 | QC-ACN-AA-XB |
| 393 | EX-2 | 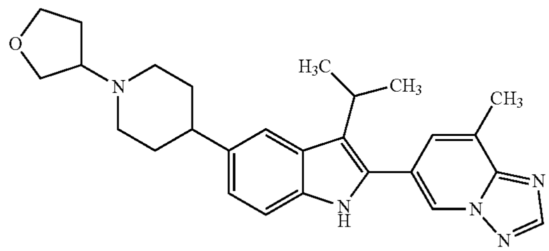 [SMILES: Cc1cc(-c2[nH]c3ccc(C4CCN(C5CCOC5)CC4)cc3c2C(C)C)cn2ncnc12] | 444.0 | 1.58 | QC-ACN-AA-XB |
| 394 | EX-2 | 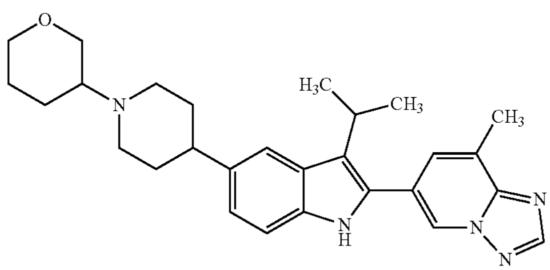 [SMILES: Cc1cc(-c2[nH]c3ccc(C4CCN(C5CCCOC5)CC4)cc3c2C(C)C)cn2ncnc12] | 458.0 | 1.58 | QC-ACN-AA-XB |
| 395 | EX-2 | 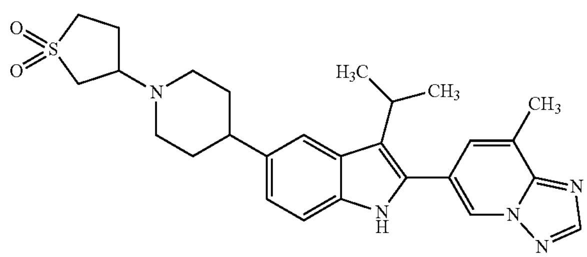 [SMILES: Cc1cc(-c2[nH]c3ccc(C4CCN(C5CCS(=O)(=O)C5)CC4)cc3c2C(C)C)cn2ncnc12] | 492.1 | 1.63 | QC-ACN-AA-XB |
| 396 | EX-2 | 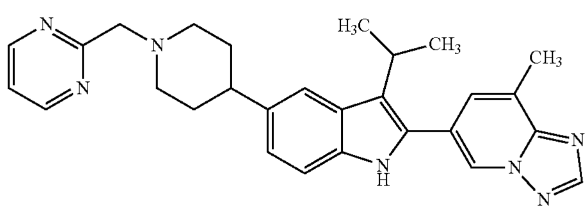 [SMILES: Cc1cc(-c2[nH]c3ccc(C4CCN(Cc5ncccn5)CC4)cc3c2C(C)C)cn2ncnc12] | 466.0 | 1.5 | QC-ACN-AA-XB |
| 397 | EX-2 | 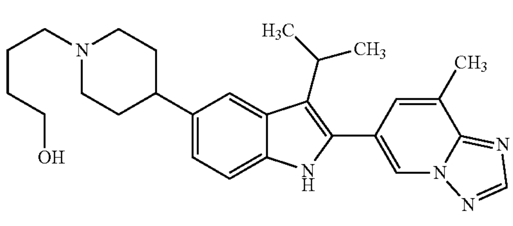 [SMILES: Cc1cc(-c2[nH]c3ccc(C4CCN(CCCCO)CC4)cc3c2C(C)C)cn2ncnc12] | 446.0 | 1.1 | QC-ACN-TFA-XB |

TABLE 13-continued
| Ex. No. | Template Starting Material | Structure | LCMS MH+ | R$_t$ (min) | HPLC Method |
|---|---|---|---|---|---|
| 398 | EX-2 | 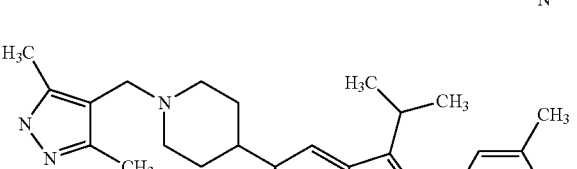 | 500.0 | 2.37 | QC-ACN-AA-XB |
| 399 | EX-2 | 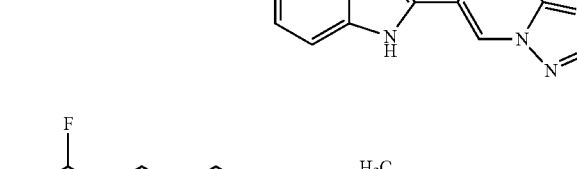 | 482.0 | 1.31 | QC-ACN-AA-XB |
| 400 | EX-2 | 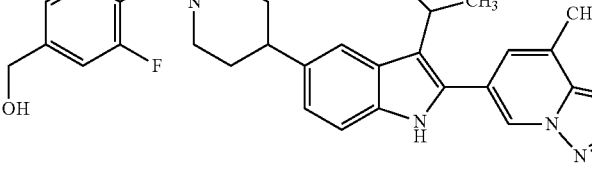 | 530.0 | 1.92 | QC-ACN-AA-XB |
| 401 | EX-2 | 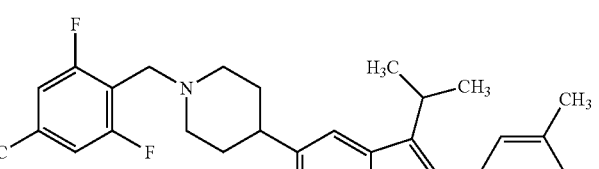 | 525.1 | 2.35 | QC-ACN-AA-XB |
| 402 | EX-2 | 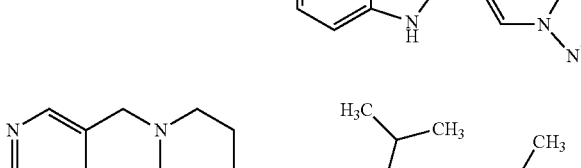 | 466.4 | 1.72 | QC-ACN-AA-XB |
| 403 | EX-2 | 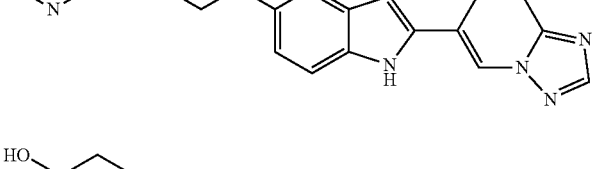 | 472.4 | 1.24 | QC-ACN-AA-XB |

US 11,672,780 B2

TABLE 13-continued

| Ex. No. | Template Starting Material | Structure | LCMS MH+ | R_t (min) | HPLC Method |
|---|---|---|---|---|---|
| 404 | EX-2 | 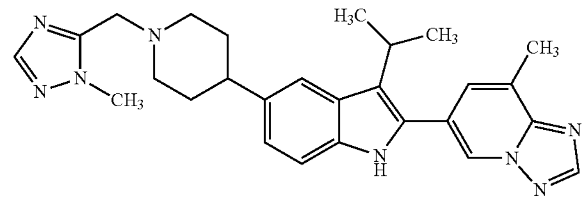 [SMILES: Cc1cc(-c2[nH]c3ccc(C4CCN(Cc5ncnn5C)CC4)cc3c2C(C)C)cn2ncnc12] | 469.0 | 1.77 | QC-ACN-AA-XB |
| 405 | EX-2 | 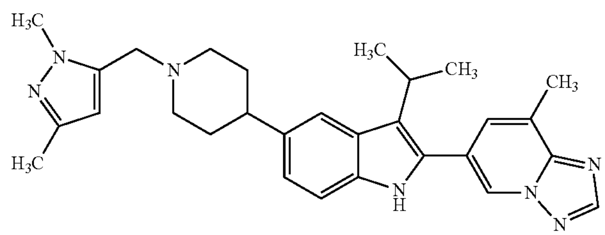 [SMILES: Cc1cc(CN2CCC(c3ccc4[nH]c(-c5cc(C)c6ncnn6c5)c(C(C)C)c4c3)CC2)n(C)n1] | 482.0 | 1.96 | QC-ACN-AA-XB |
| 406 | EX-2 | 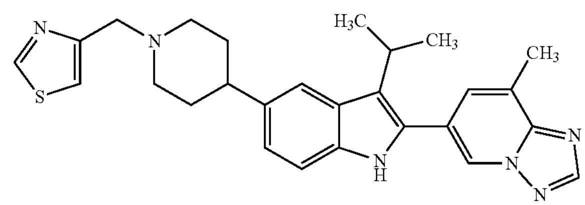 [SMILES: Cc1cc(-c2[nH]c3ccc(C4CCN(Cc5cscn5)CC4)cc3c2C(C)C)cn2ncnc12] | 471.0 | 1.6 | QC-ACN-AA-XB |
| 407 | EX-2 | 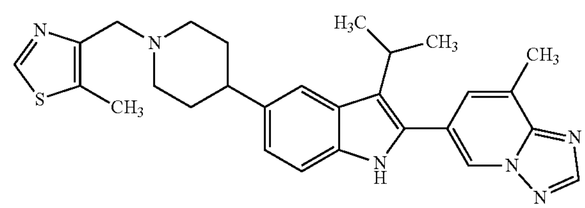 [SMILES: Cc1scnc1CN1CCC(c2ccc3[nH]c(-c4cc(C)c5ncnn5c4)c(C(C)C)c3c2)CC1] | 485.3 | 1.99 | QC-ACN-AA-XB |
| 408 | EX-2 | 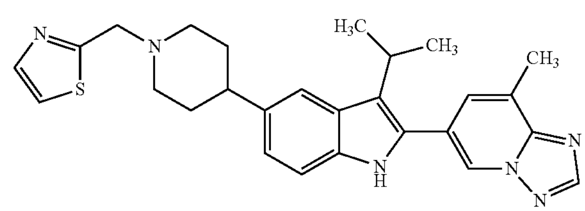 [SMILES: Cc1cc(-c2[nH]c3ccc(C4CCN(Cc5nccs5)CC4)cc3c2C(C)C)cn2ncnc12] | 471.0 | 2.18 | QC-ACN-AA-XB |
| 409 | EX-2 | 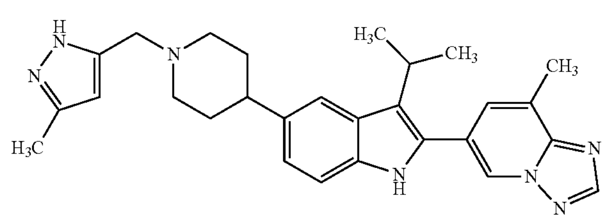 [SMILES: Cc1cc(CN2CCC(c3ccc4[nH]c(-c5cc(C)c6ncnn6c5)c(C(C)C)c4c3)CC2)[nH]n1] | 468.0 | 1.4 | QC-ACN-AA-XB |
| 410 | EX-2 | 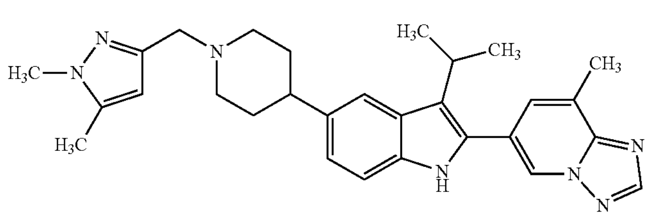 [SMILES: Cc1cc(-c2[nH]c3ccc(C4CCN(Cc5cc(C)n(C)n5)CC4)cc3c2C(C)C)cn2ncnc12] | 482.2 | 1.52 | QC-ACN-AA-XB |

TABLE 13-continued

| Ex. No. | Template Starting Material | Structure | LCMS MH+ | R$_t$ (min) | HPLC Method |
|---|---|---|---|---|---|
| 411 | EX-2 | 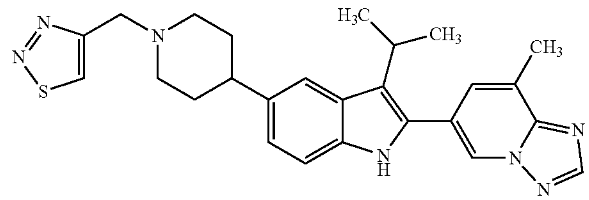 [SMILES: Cc1cc(-c2[nH]c3ccc(C4CCN(Cc5csnn5)CC4)cc3c2C(C)C)cn2ncnc12] | 472.1 | 1.36 | QC-ACN-TFA-XB |
| 412 | EX-2 | 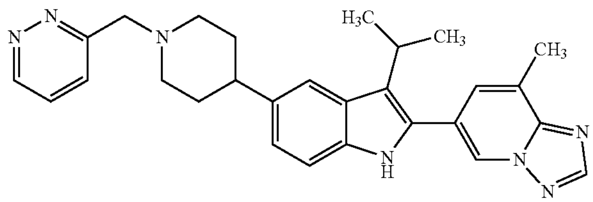 [SMILES: Cc1cc(-c2[nH]c3ccc(C4CCN(Cc5cccnn5)CC4)cc3c2C(C)C)cn2ncnc12] | 466.4 | 1.28 | QC-ACN-TFA-XB |
| 413 | EX-2 | 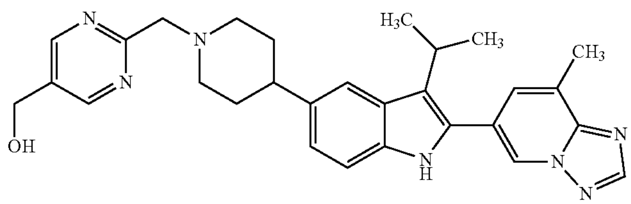 [SMILES: Cc1cc(-c2[nH]c3ccc(C4CCN(Cc5ncc(CO)cn5)CC4)cc3c2C(C)C)cn2ncnc12] | 496.4 | 1.38 | QC-ACN-AA-XB |
| 414 | EX-2 | 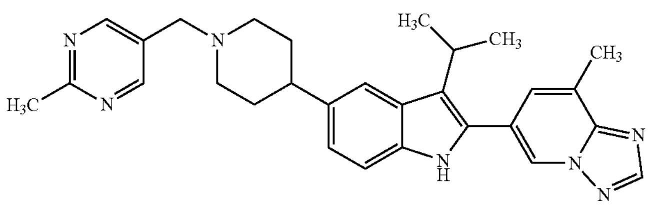 [SMILES: Cc1ncc(CN2CCC(c3ccc4[nH]c(-c5cc(C)c6ncnn6c5)c(C(C)C)c4c3)CC2)cn1] | 480.0 | 1.76 | QC-ACN-AA-XB |
| 415 | EX-2 | 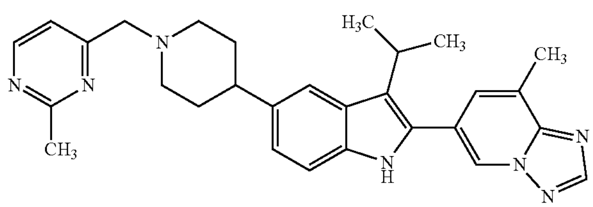 [SMILES: Cc1nccc(CN2CCC(c3ccc4[nH]c(-c5cc(C)c6ncnn6c5)c(C(C)C)c4c3)CC2)n1] | 480.2 | 1.77 | QC-ACN-AA-XB |
| 416 | EX-2 | 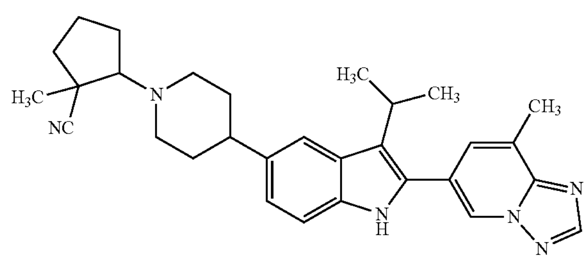 [SMILES: Cc1cc(-c2[nH]c3ccc(C4CCN(C5CCCC5(C)C#N)CC4)cc3c2C(C)C)cn2ncnc12] | 481.0 | 1.32 | QC-ACN-TFA-XB |
| 417 | EX-2 | 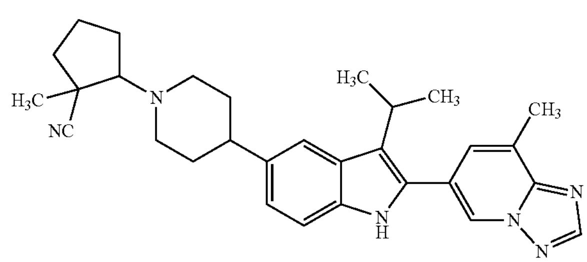 [SMILES: Cc1cc(-c2[nH]c3ccc(C4CCN(C5CCCC5(C)C#N)CC4)cc3c2C(C)C)cn2ncnc12] | 481.0 | 1.32 | QC-ACN-TFA-XB |

TABLE 13-continued
| Ex. No. | Template Starting Material | Structure | LCMS MH+ | R$_t$ (min) | HPLC Method |
|---|---|---|---|---|---|
| 418 | EX-2 | 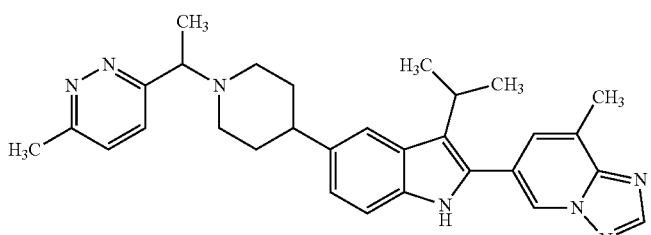 | 493.9 | 1.69 | QC-ACN-AA-XB |
| 419 | EX-2 | 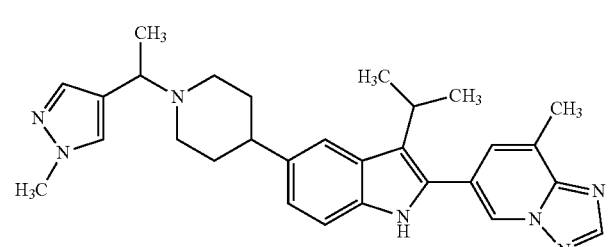 | 482.4 | 1.26 | QC-ACN-AA-XB |
| 420 | EX-2 | 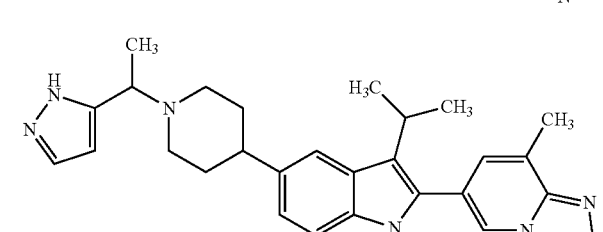 | 468.2 | 1.22 | QC-ACN-TFA-XB |
| 421 | EX-2 | 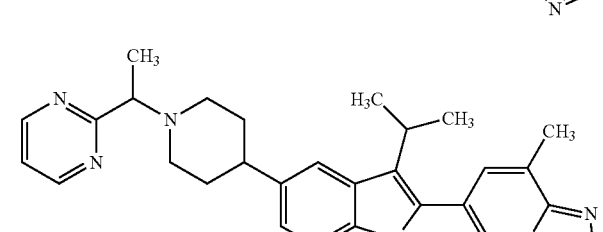 | 480.5 | 1.47 | QC-ACN-AA-XB |
| 422 | EX-2 | 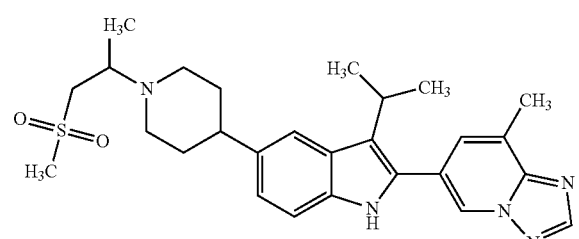 | 494.1 | 1.87 | QC-ACN-AA-XB |
| 423 | EX-2 | 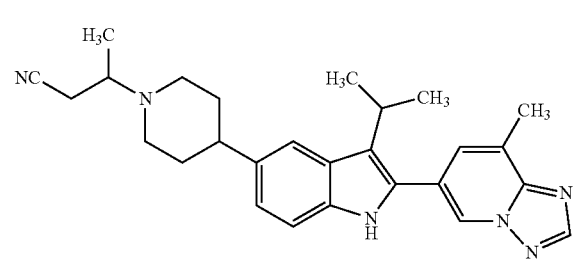 [SMILES: Cc1cc(-c2[nH]c3ccc(C4CCN(C(C)CC#N)CC4)cc3c2C(C)C)cn2ncnc12] | 441.0 | 1.36 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 424 | EX-2 | 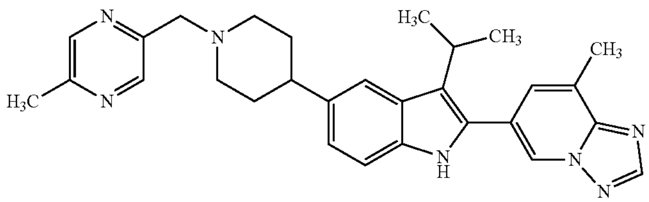 [SMILES: Cc1cnc(CN2CCC(c3ccc4[nH]c(-c5cc(C)c6ncnn6c5)c(C(C)C)c4c3)CC2)cn1] | 480.0 | 1.83 | QC-ACN-AA-XB |
| 425 | EX-2 | 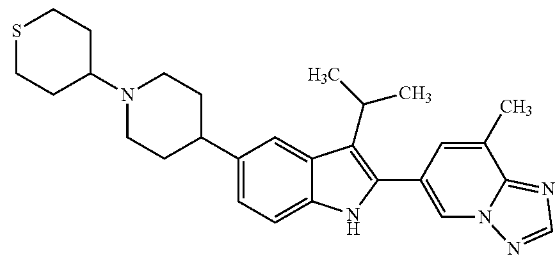 [SMILES: Cc1cc(-c2[nH]c3ccc(C4CCN(C5CCSCC5)CC4)cc3c2C(C)C)cn2ncnc12] | 474.1 | 1.67 | QC-ACN-AA-XB |
| 426 | EX-2 | 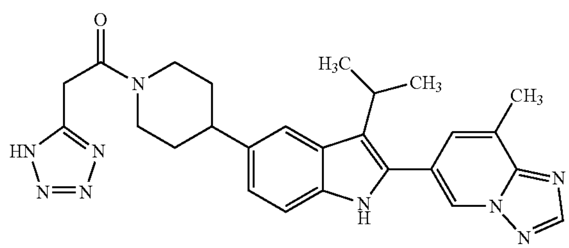 [SMILES: Cc1cc(-c2[nH]c3ccc(C4CCN(C(=O)Cc5nnn[nH]5)CC4)cc3c2C(C)C)cn2ncnc12] | 484.1 | 1.15 | QC-ACN-AA-XB |
| 427 | EX-2 | 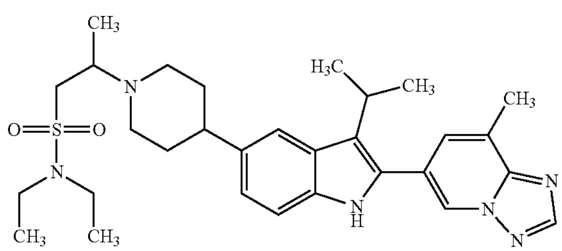 [SMILES: CCN(CC)S(=O)(=O)CC(C)N1CCC(c2ccc3[nH]c(-c4cc(C)c5ncnn5c4)c(C(C)C)c3c2)CC1] | 551.1 | 2.25 | QC-ACN-AA-XB |
| 428 | EX-2 | 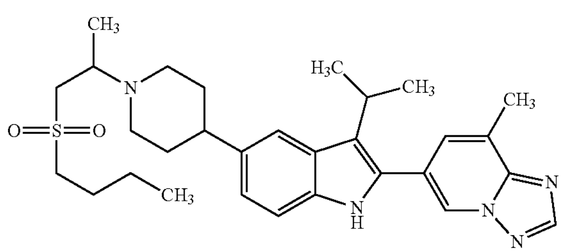 [SMILES: CCCCS(=O)(=O)CC(C)N1CCC(c2ccc3[nH]c(-c4cc(C)c5ncnn5c4)c(C(C)C)c3c2)CC1] | 536.5 | 1.53 | QC-ACN-TFA-XB |
| 429 | EX-2 | 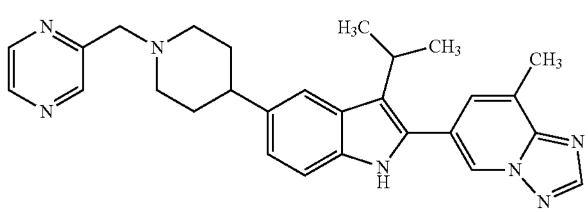 | 466.3 | 1.25 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 430 | EX-2 | 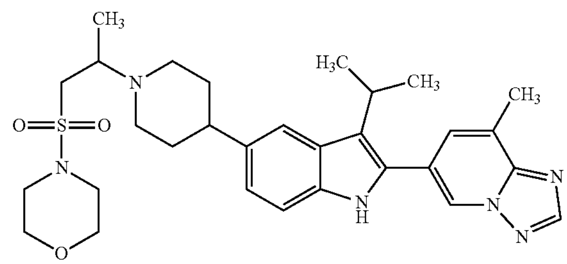 [SMILES: Cc1cc(-c2[nH]c3ccc(C4CCN(C(C)CS(=O)(=O)N5CCOCC5)CC4)cc3c2C(C)C)cn2ncnc12] | 565.4 | 1.89 | QC-ACN-AA-XB |
| 431 | EX-2 | 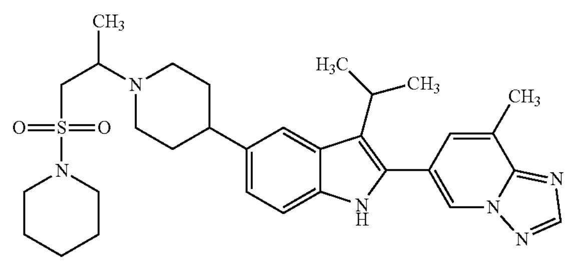 [SMILES: Cc1cc(-c2[nH]c3ccc(C4CCN(C(C)CS(=O)(=O)N5CCCCC5)CC4)cc3c2C(C)C)cn2ncnc12] | 563.4 | 2.17 | QC-ACN-AA-XB |
| 432 | EX-2 | 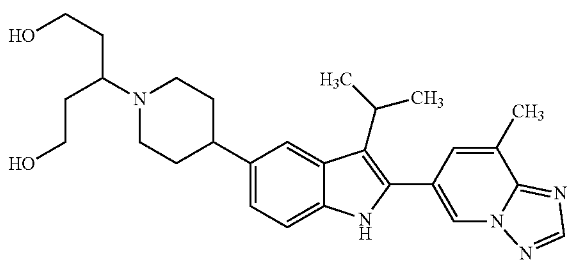 [SMILES: Cc1cc(-c2[nH]c3ccc(C4CCN(C(CCO)CCO)CC4)cc3c2C(C)C)cn2ncnc12] | 476.3 | 1.25 | QC-ACN-AA-XB |
| 433 | EX-2 | 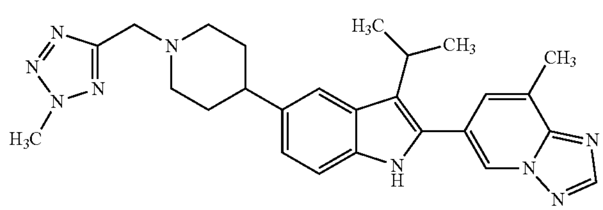 | 470.3 | 1.92 | QC-ACN-AA-XB |
| 434 | EX-2 | 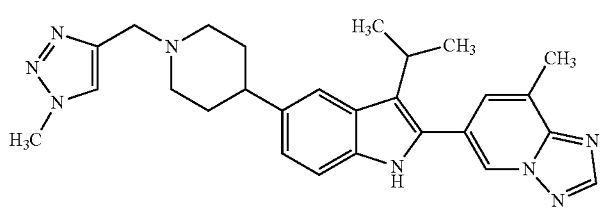 [SMILES: Cc1cc(-c2[nH]c3ccc(C4CCN(Cc5cn(C)nn5)CC4)cc3c2C(C)C)cn2ncnc12] | 469.2 | 1.27 | QC-ACN-TFA-XB |
| 435 | EX-2 | 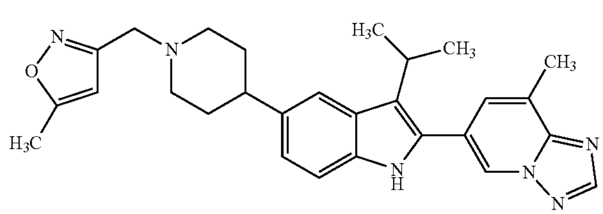 [SMILES: Cc1cc(CN2CCC(c3ccc4[nH]c(-c5cc(C)c6ncnn6c5)c(C(C)C)c4c3)CC2)no1] | 469.2 | 1.9 | QC-ACN-AA-XB |

TABLE 13-continued

| Ex. No. | Template Starting Material | Structure | LCMS MH+ | R$_t$ (min) | HPLC Method |
|---|---|---|---|---|---|
| 436 | EX-2 | 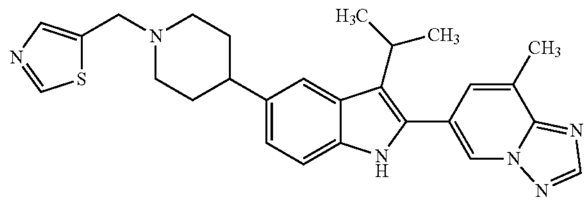 [SMILES: Cc1cc(-c2[nH]c3ccc(C4CCN(Cc5cncs5)CC4)cc3c2C(C)C)cn2ncnc12] | 471.1 | 1.93 | QC-ACN-AA-XB |
| 437 | EX-2 | 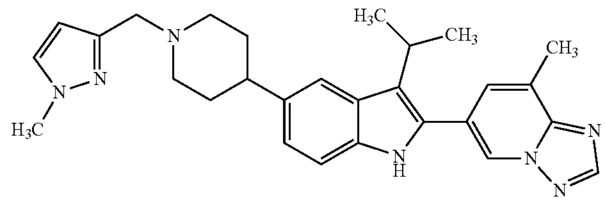 [SMILES: Cc1cc(-c2[nH]c3ccc(C4CCN(Cc5ccn(C)n5)CC4)cc3c2C(C)C)cn2ncnc12] | 468.2 | 1.49 | QC-ACN-AA-XB |
| 438 | EX-2 | 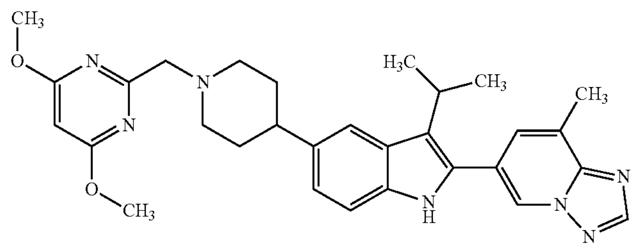 [SMILES: COc1cc(OC)nc(CN2CCC(c3ccc4[nH]c(-c5cc(C)c6ncnn6c5)c(C(C)C)c4c3)CC2)n1] | 526.2 | 1.54 | QC-ACN-TFA-XB |
| 439 | EX-2 | 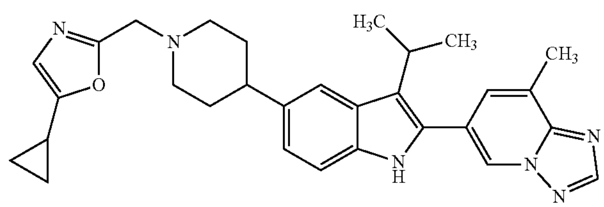 [SMILES: Cc1cc(-c2[nH]c3ccc(C4CCN(Cc5ncc(C6CC6)o5)CC4)cc3c2C(C)C)cn2ncnc12] | 496.2 | 1.34 | QC-ACN-TFA-XB |
| 440 | EX-2 | 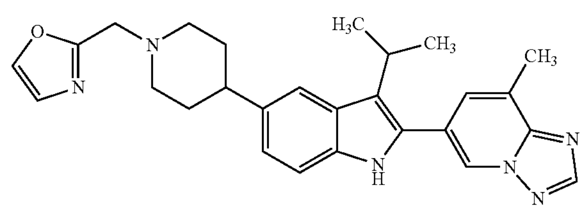 [SMILES: Cc1cc(-c2[nH]c3ccc(C4CCN(Cc5ncco5)CC4)cc3c2C(C)C)cn2ncnc12] | 455.2 | 1.28 | QC-ACN-TFA-XB |
| 441 | EX-3 | 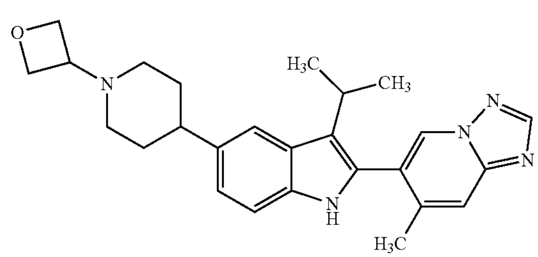 | 430.4 | 1.66 | QC-ACN-AA-XB |
| 442 | EX-3 | 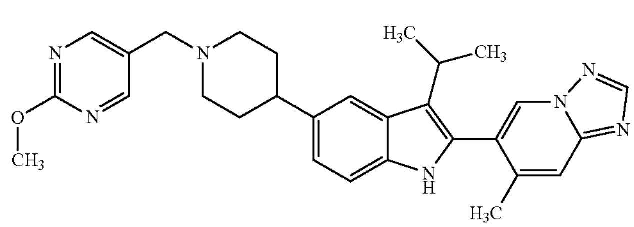 [SMILES: COc1ncc(CN2CCC(c3ccc4[nH]c(-c5cn6ncnc6cc5C)c(C(C)C)c4c3)CC2)cn1] | 496.2 | 1.08 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 443 | EX-3 | 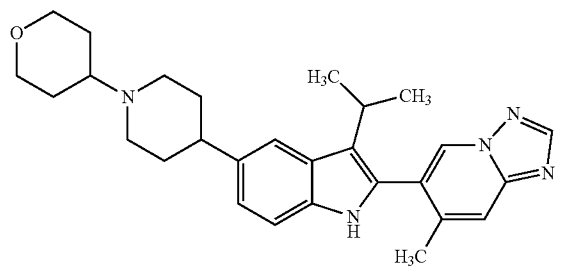 [SMILES: Cc1cc2ncnn2cc1-c1[nH]c2ccc(C3CCN(C4CCOCC4)CC3)cc2c1C(C)C] | 458.2 | 1.05 | QC-ACN-TFA-XB |
| 444 | EX-3 | 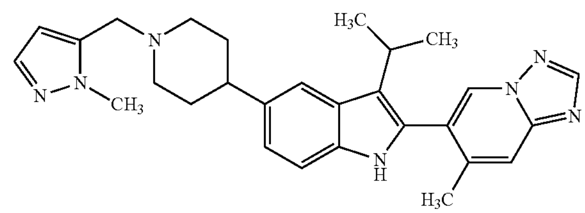 [SMILES: Cc1cc2ncnn2cc1-c1[nH]c2ccc(C3CCN(Cc4ccnn4C)CC3)cc2c1C(C)C] | 468.4 | 1.81 | QC-ACN-AA-XB |
| 445 | EX-3 | 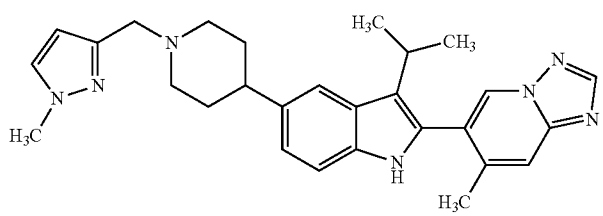 [SMILES: Cc1cc2ncnn2cc1-c1[nH]c2ccc(C3CCN(Cc4ccn(C)n4)CC3)cc2c1C(C)C] | 468.3 | 1.1 | QC-ACN-TFA-XB |
| 446 | EX-3 | 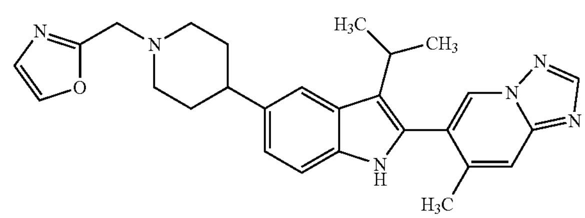 [SMILES: Cc1cc2ncnn2cc1-c1[nH]c2ccc(C3CCN(Cc4ncco4)CC3)cc2c1C(C)C] | 455.4 | 1.78 | QC-ACN-AA-XB |
| 447 | EX-3 | 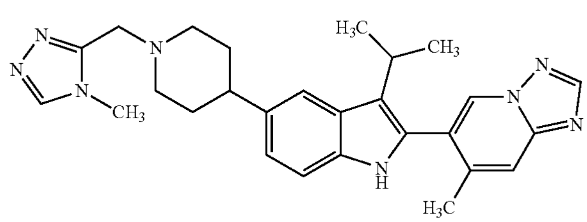 [SMILES: Cc1cc2ncnn2cc1-c1[nH]c2ccc(C3CCN(Cc4nncn4C)CC3)cc2c1C(C)C] | 469.3 | 0.98 | QC-ACN-TFA-XB |
| 448 | EX-3 | 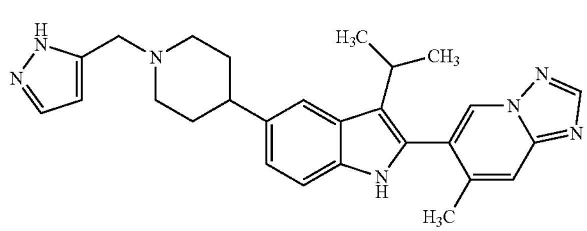 [SMILES: Cc1cc2ncnn2cc1-c1[nH]c2ccc(C3CCN(Cc4ccn[nH]4)CC3)cc2c1C(C)C] | 454.0 | 1.3 | QC-ACN-AA-XB |

TABLE 13-continued
| Ex. No. | Template Starting Material | Structure | LCMS MH+ | R$_t$ (min) | HPLC Method |
|---|---|---|---|---|---|
| 449 | EX-3 | 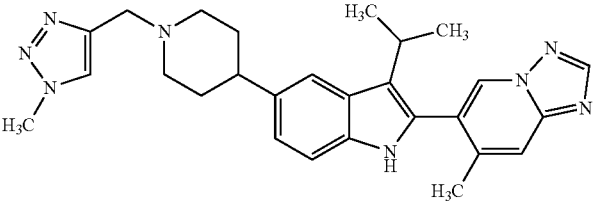 [SMILES: Cc1cc2ncnn2cc1-c1[nH]c2ccc(C3CCN(Cc4cn(C)nn4)CC3)cc2c1C(C)C] | 469.4 | 1.33 | QC-ACN-AA-XB |
| 450 | EX-3 | 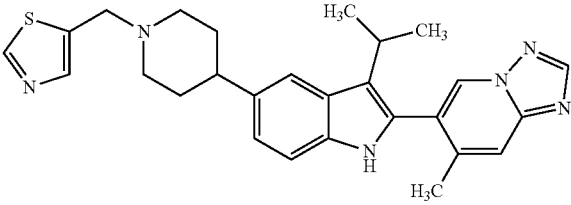 [SMILES: Cc1cc2ncnn2cc1-c1[nH]c2ccc(C3CCN(Cc4cncs4)CC3)cc2c1C(C)C] | 471.0 | 1.79 | QC-ACN-AA-XB |
| 451 | EX-3 | 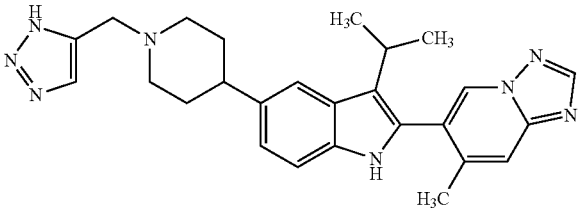 | 455.0 | 1.5 | QC-ACN-AA-XB |
| 452 | EX-3 | 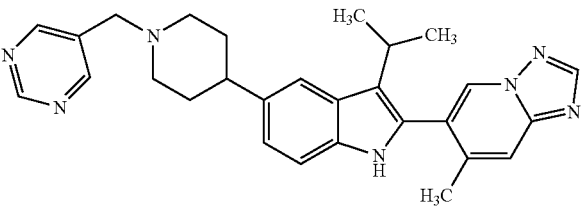 [SMILES: Cc1cc2ncnn2cc1-c1[nH]c2ccc(C3CCN(Cc4cncnc4)CC3)cc2c1C(C)C] | 465.9 | 1.69 | QC-ACN-AA-XB |
| 453 | EX-3 | 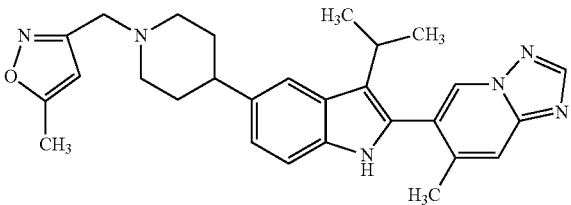 [SMILES: Cc1cc(CN2CCC(c3ccc4[nH]c(-c5cn6ncnc6cc5C)c(C(C)C)c4c3)CC2)no1] | 469.0 | 1.95 | QC-ACN-AA-XB |
| 454 | EX-3 | 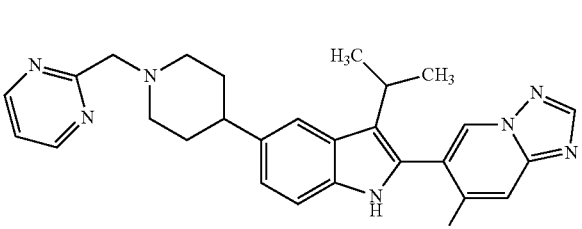 | 466.2 | 1.46 | QC-ACN-AA-XB |

TABLE 13-continued
| Ex. No. | Template Starting Material | Structure | LCMS MH+ | R_t (min) | HPLC Method |
|---|---|---|---|---|---|
| 455 | EX-3 | 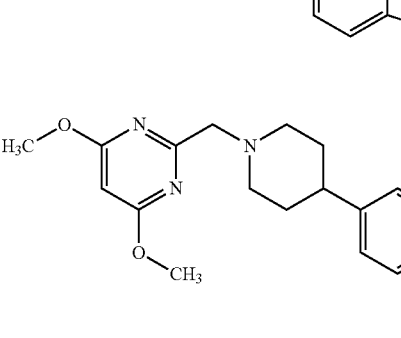 | 506.0 | 1.69 | QC-ACN-AA-XB |
| 456 | EX-3 | 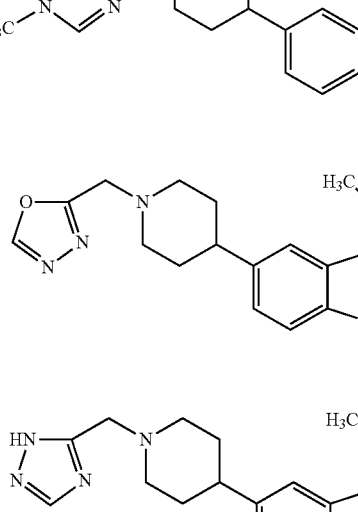 | 526.0 | 2.05 | QC-ACN-AA-XB |
| 457 | EX-3 | 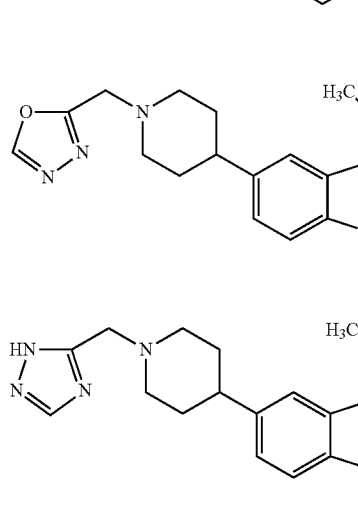 | 469.1 | 1.42 | QC-ACN-AA-XB |
| 458 | EX-3 | 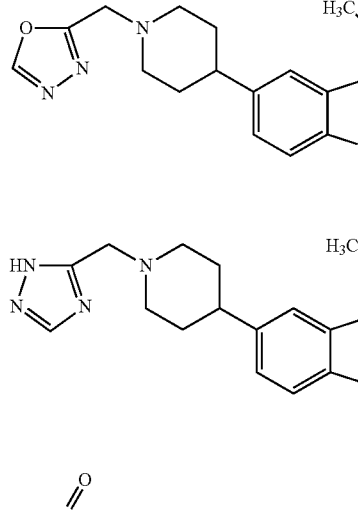 | 456.2 | 1.77 | QC-ACN-AA-XB |
| 459 | EX-3 | 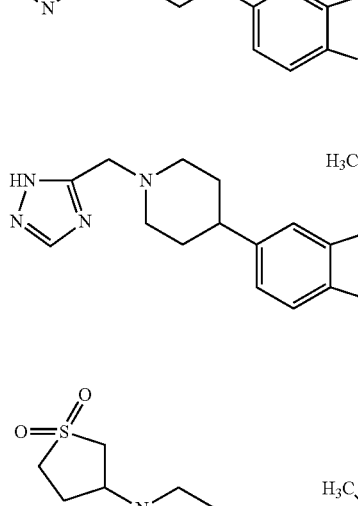 | 455.4 | 1.05 | QC-ACN-TFA-XB |
| 460 | EX-3 | 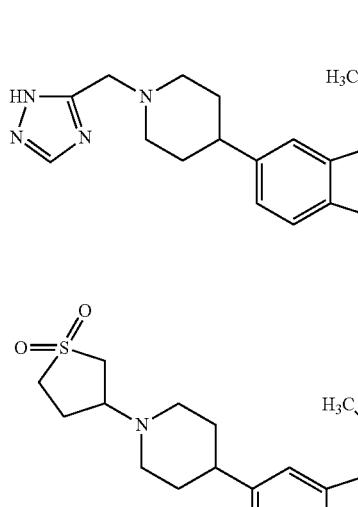 | 492.4 | 1.21 | QC-ACN-TFA-XB |

TABLE 13-continued
| Ex. No. | Template Starting Material | Structure | LCMS MH+ | R$_t$ (min) | HPLC Method |
|---|---|---|---|---|---|
| 461 | EX-3 | 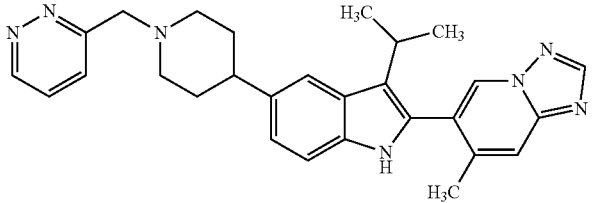 [SMILES: Cc1cc2ncnn2cc1-c1[nH]c2ccc(C3CCN(Cc4cccnn4)CC3)cc2c1C(C)C] | 466.1 | 1 | QC-ACN-TFA-XB |
| 462 | EX-3 | 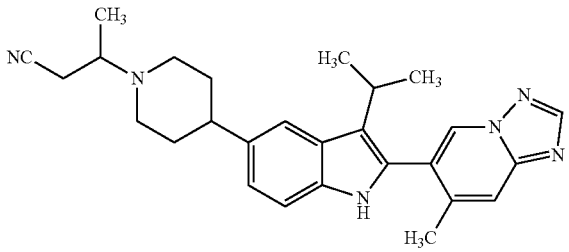 [SMILES: Cc1cc2ncnn2cc1-c1[nH]c2ccc(C3CCN(C(C)CC#N)CC3)cc2c1C(C)C] | 441.0 | 1.84 | QC-ACN-AA-XB |
| 463 | EX-3 | 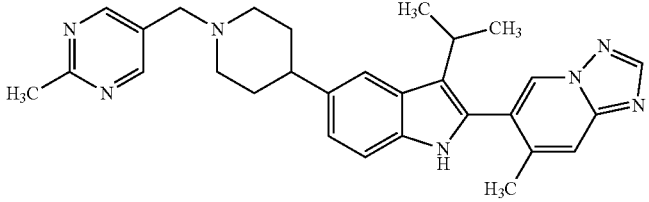 | 480.1 | 1.05 | QC-ACN-TFA-XB |
| 464 | EX-3 | 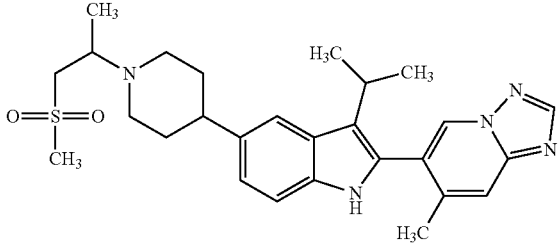 [SMILES: Cc1cc2ncnn2cc1-c1[nH]c2ccc(C3CCN(C(C)CS(C)(=O)=O)CC3)cc2c1C(C)C] | 494.1 | 1.73 | QC-ACN-AA-XB |
| 465 | EX-3 | 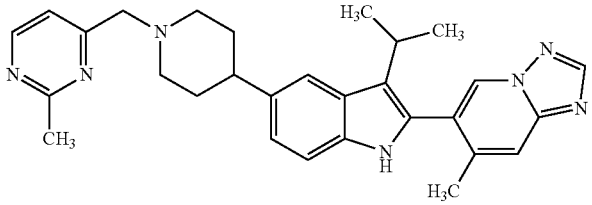 [SMILES: Cc1nccc(CN2CCC(c3ccc4[nH]c(-c5cn6ncnc6cc5C)c(C(C)C)c4c3)CC2)n1] | 480.4 | 1.71 | QC-ACN-AA-XB |
| 466 | EX-3 | 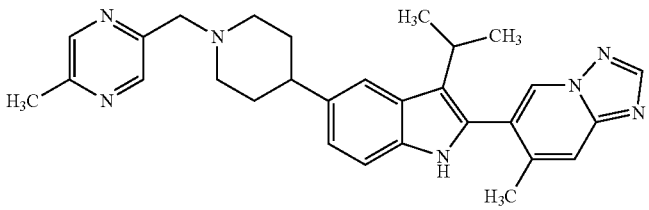 [SMILES: Cc1cnc(CN2CCC(c3ccc4[nH]c(-c5cn6ncnc6cc5C)c(C(C)C)c4c3)CC2)cn1] | 480.0 | 1.33 | QC-ACN-TFA-XB |

TABLE 13-continued
| Ex. No. | Template Starting Material | Structure | LCMS MH+ | R_t (min) | HPLC Method |
|---|---|---|---|---|---|
| 467 | EX-3 | 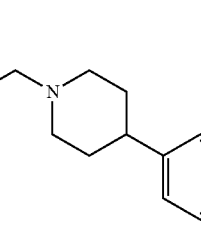 | 466.0 | 1.85 | QC-ACN-AA-XB |
| 468 | EX-112 | 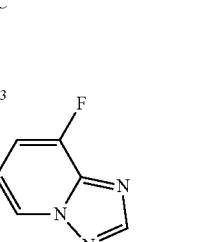 | 473.0 | 1.31 | QC-ACN-TFA-XB- |
| 469 | EX-112 | 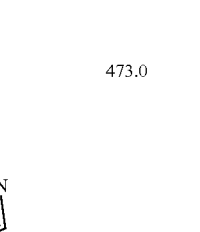 | 434.1 | 1.18 | QC-ACN-TFA-XB |
| 470 | EX-6 | 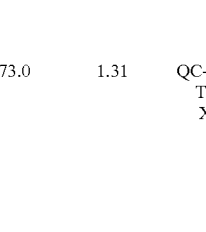 | 499.1 | 1.37 | QC-ACN-AA-XB |
| 471 | EX-6 | 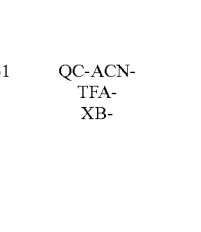 | 510.1 | 1.75 | QC-ACN-AA-XB |
| 472 | EX-6 | 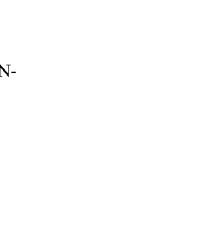 | 488.1 | 1.74 | QC-ACN-AA-XB |

TABLE 13-continued

| Ex. No. | Template Starting Material | Structure | LCMS MH+ | R$_t$ (min) | HPLC Method |
|---|---|---|---|---|---|
| 473 | EX-6 | 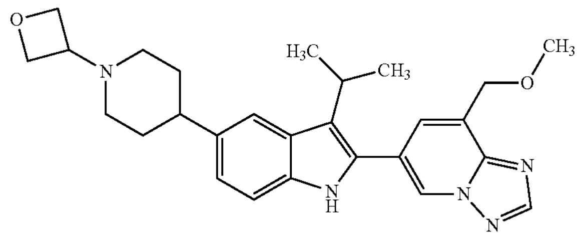 [SMILES: COCc1cc(-c2[nH]c3ccc(C4CCN(C5COC5)CC4)cc3c2C(C)C)cn2ncnc12] | 460.1 | 1.65 | QC-ACN-AA-XB |
| 474 | EX-6 | 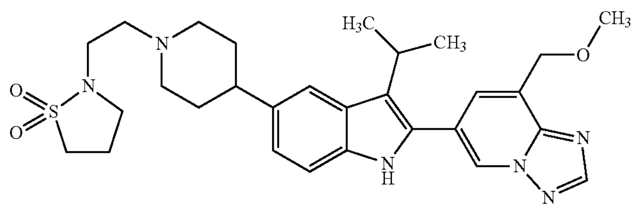 [SMILES: COCc1cc(-c2[nH]c3ccc(C4CCN(CCN5CCCS5(=O)=O)CC4)cc3c2C(C)C)cn2ncnc12] | 551.0 | 1.69 | QC-ACN-AA-XB |
| 475 | EX-4 | 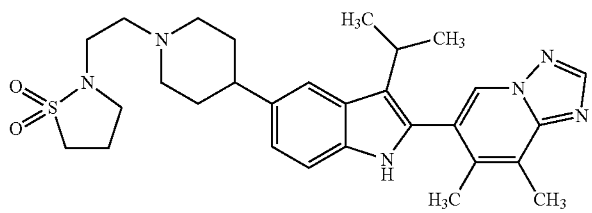 [SMILES: Cc1c(-c2[nH]c3ccc(C4CCN(CCN5CCCS5(=O)=O)CC4)cc3c2C(C)C)cn2ncnc2c1C] | 535.4 | 1.43 | QC-ACN-AA-XB |
| 476 | EX-4 | 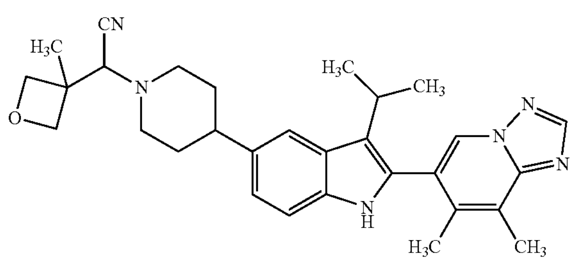 [SMILES: Cc1c(-c2[nH]c3ccc(C4CCN(C(C#N)C5(C)COC5)CC4)cc3c2C(C)C)cn2ncnc2c1C] | 497.4 | 1.94 | QC-ACN-TFA-XB |
| 477 | EX-4 | 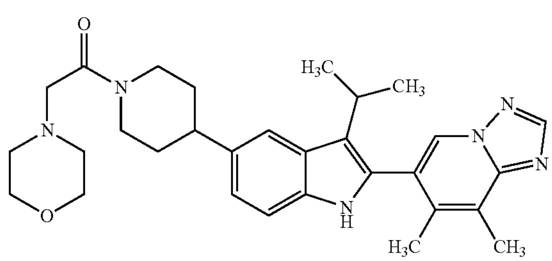 [SMILES: Cc1c(-c2[nH]c3ccc(C4CCN(C(=O)CN5CCOCC5)CC4)cc3c2C(C)C)cn2ncnc2c1C] | 515.0 | 1.29 | QC-ACN-TFA-XB |
| 478 | EX-4 | 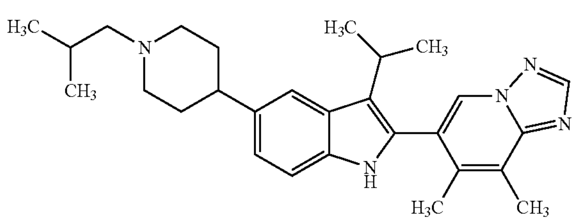 [SMILES: Cc1c(-c2[nH]c3ccc(C4CCN(CC(C)C)CC4)cc3c2C(C)C)cn2ncnc2c1C] | 444.1 | 1.74 | QC-ACN-AA-XB |

TABLE 13-continued

| Ex. No. | Template Starting Material | Structure | LCMS MH+ | R$_t$ (min) | HPLC Method |
|---|---|---|---|---|---|
| 479 | EX-4 | 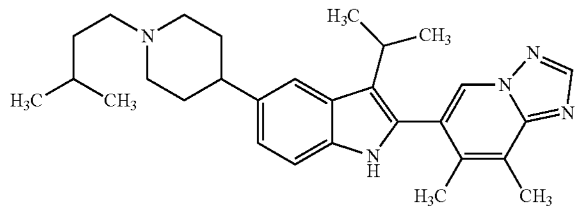 [SMILES: Cc1c(-c2[nH]c3ccc(C4CCN(CCC(C)C)CC4)cc3c2C(C)C)cn2ncnc2c1C] | 458.4 | 1.58 | QC-ACN-TFA-XB |
| 480 | EX-4 | 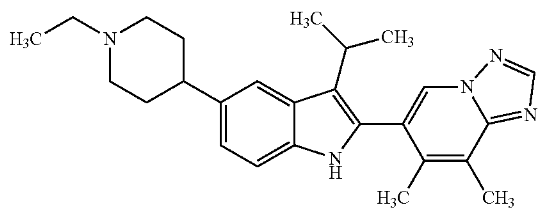 [SMILES: CCN1CCC(c2ccc3[nH]c(-c4cn5ncnc5c(C)c4C)c(C(C)C)c3c2)CC1] | 416.1 | 1.32 | QC-ACN-AA-XB |
| 481 | EX-4 | 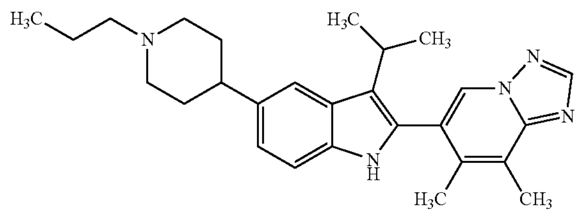 [SMILES: CCCN1CCC(c2ccc3[nH]c(-c4cn5ncnc5c(C)c4C)c(C(C)C)c3c2)CC1] | 430.0 | 1.62 | QC-ACN-AA-XB |
| 482 | EX-4 | 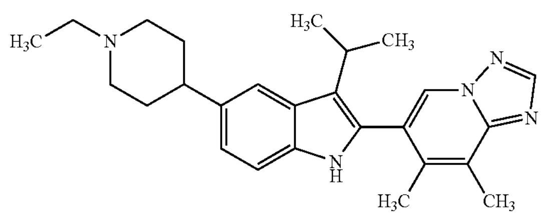 [SMILES: CCN1CCC(c2ccc3[nH]c(-c4cn5ncnc5c(C)c4C)c(C(C)C)c3c2)CC1] | 416.1 | 1.54 | QC-ACN-TFA-XB |
| 483 | EX-4 | 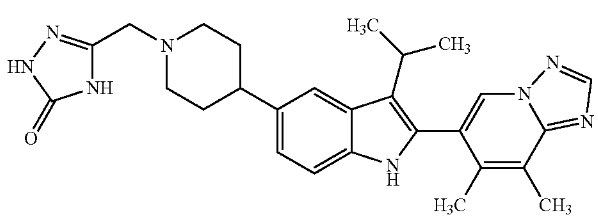 [SMILES: Cc1c(-c2[nH]c3ccc(C4CCN(Cc5n[nH]c(=O)[nH]5)CC4)cc3c2C(C)C)cn2ncnc2c1C] | 485.2 | 1.44 | QC-ACN-AA-XB |
| 484 | EX-4 | 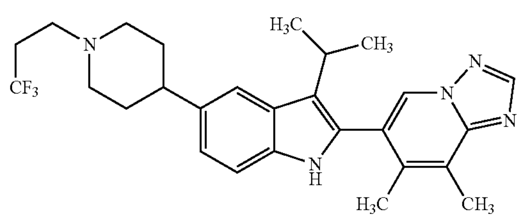 [SMILES: Cc1c(-c2[nH]c3ccc(C4CCN(CCC(F)(F)F)CC4)cc3c2C(C)C)cn2ncnc2c1C] | 484.3 | 2.29 | QC-ACN-AA-XB |
| 485 | EX-4 | 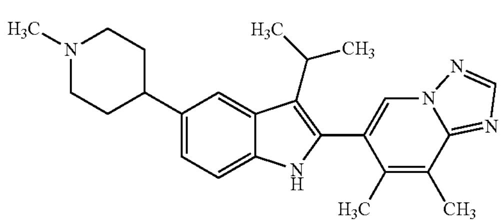 [SMILES: Cc1c(-c2[nH]c3ccc(C4CCN(C)CC4)cc3c2C(C)C)cn2ncnc2c1C] | 402.2 | 1.29 | QC-ACN-AA-XB |

TABLE 13-continued

| Ex. No. | Template Starting Material | Structure | LCMS MH+ | $R_t$ (min) | HPLC Method |
|---|---|---|---|---|---|
| 486 | EX-4 | 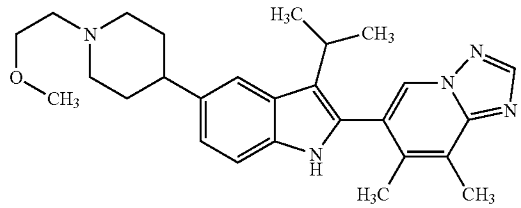 [SMILES: COCCN1CCC(c2ccc3[nH]c(-c4cn5ncnc5c(C)c4C)c(C(C)C)c3c2)CC1] | 446.2 | 1.38 | QC-ACN-AA-XB |
| 487 | EX-110 | 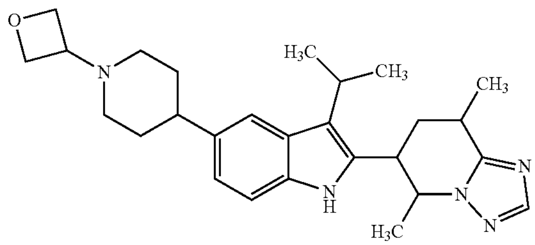 [SMILES: CC(C)c1c(C2CC(C)c3ncnn3C2C)[nH]c2ccc(C3CCN(C4COC4)CC3)cc12] | 444.3 | 1.77 | QC-ACN-AA-XB |
| 488 | EX-110 | 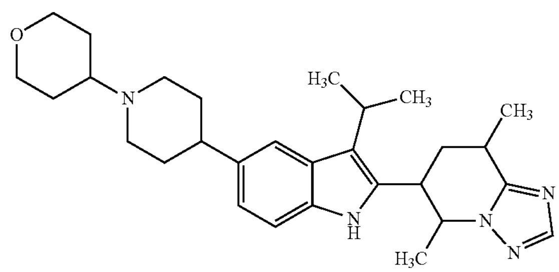 [SMILES: CC(C)c1c(C2CC(C)c3ncnn3C2C)[nH]c2ccc(C3CCN(C4CCOCC4)CC3)cc12] | 471.9 | 1.28 | QC-ACN-AA-XB |
| 489 | EX-110 | 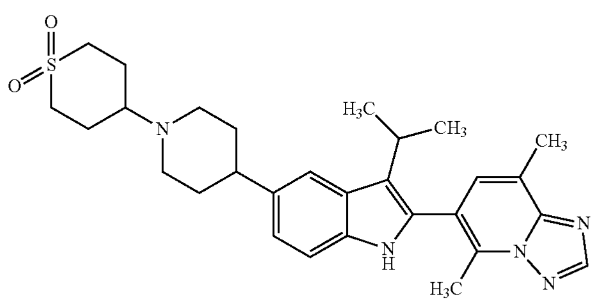 [SMILES: Cc1cc(-c2[nH]c3ccc(C4CCN(C5CCS(=O)(=O)CC5)CC4)cc3c2C(C)C)c(C)n2ncnc12] | 520.4 | 1.23 | QC-ACN-TFA-XB |
| 490 | EX-100 | 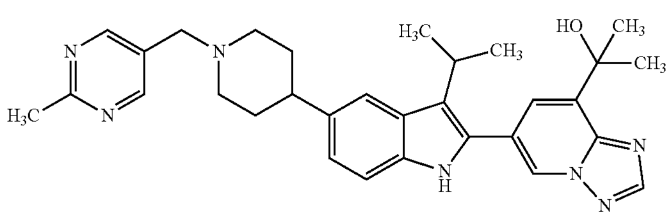 [SMILES: Cc1ncc(CN2CCC(c3ccc4[nH]c(-c5cc(C(C)(C)O)c6ncnn6c5)c(C(C)C)c4c3)CC2)cn1] | 524.2 | 1.8 | QC-ACN-AA-XB |
| 491 | EX-100 | 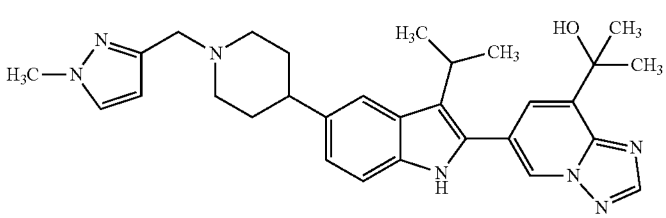 [SMILES: CC(C)c1c(-c2cc(C(C)(C)O)c3ncnn3c2)[nH]c2ccc(C3CCN(Cc4ccn(C)n4)CC3)cc12] | 512.2 | 1.53 | QC-ACN-AA-XB |

TABLE 13-continued
| Ex. No. | Template Starting Material | Structure | LCMS MH+ | $R_t$ (min) | HPLC Method |
|---|---|---|---|---|---|
| 492 | EX-100 | 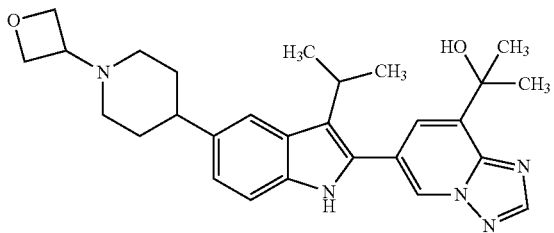 [SMILES: CC(C)c1c(-c2cc(C(C)(C)O)c3ncnn3c2)[nH]c2ccc(C3CCN(C4COC4)CC3)cc12] | 474.4 | 1.15 | QC-ACN-TFA-XB |
| 493 | EX-100 | 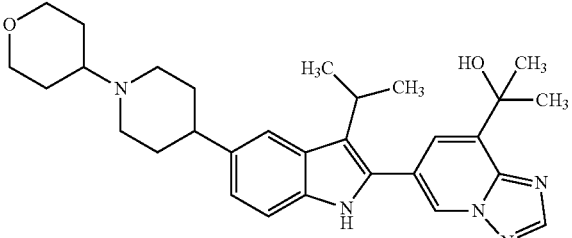 | 502.1 | 1.35 | QC-ACN-AA-XB |
| 494 | EX-100 | 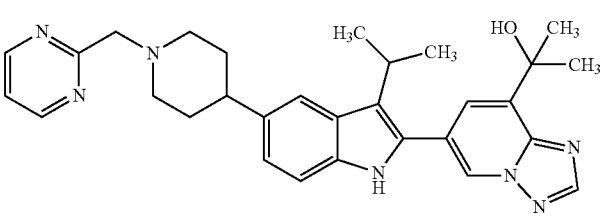 [SMILES: CC(C)c1c(-c2cc(C(C)(C)O)c3ncnn3c2)[nH]c2ccc(C3CCN(Cc4ncccn4)CC3)cc12] | 510.4 | 1.22 | QC-ACN-TFA-XB |
| 495 | EX-100 | 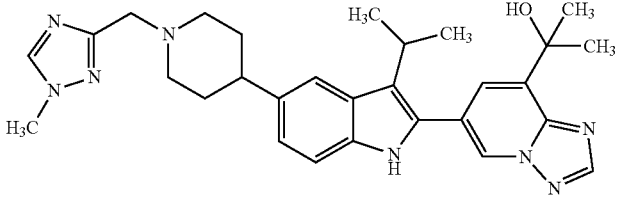 [SMILES: CC(C)c1c(-c2cc(C(C)(C)O)c3ncnn3c2)[nH]c2ccc(C3CCN(Cc4ncn(C)n4)CC3)cc12] | 513.4 | 1.15 | QC-ACN-TFA-XB |
| 496 | EX-100 | 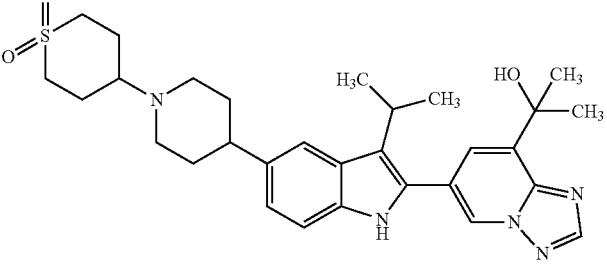 | 550.1 | 1.46 | QC-ACN-AA-XB |
| 497 | EX-100 | 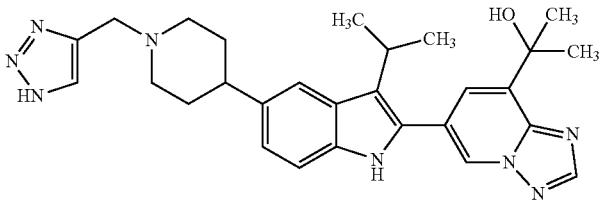 [SMILES: CC(C)c1c(-c2cc(C(C)(C)O)c3ncnn3c2)[nH]c2ccc(C3CCN(Cc4c[nH]nn4)CC3)cc12] | 499.1 | 1.38 | QC-ACN-AA-XB |

TABLE 13-continued

| Ex. No. | Template Starting Material | Structure | LCMS MH+ | R$_t$ (min) | HPLC Method |
|---|---|---|---|---|---|
| 498 | EX-100 | 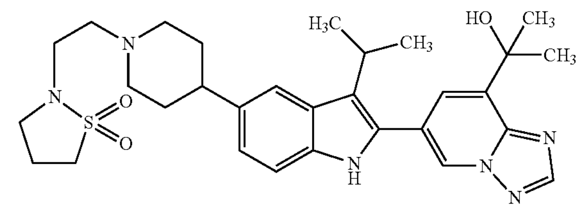 [SMILES: CC(C)c1c(-c2cc(C(C)(C)O)c3ncnn3c2)[nH]c2ccc(C3CCN(CCN4CCCS4(=O)=O)CC3)cc12] | 565.3 | 1.38 | QC-ACN-AA-XB |
| 499 | EX-101 | 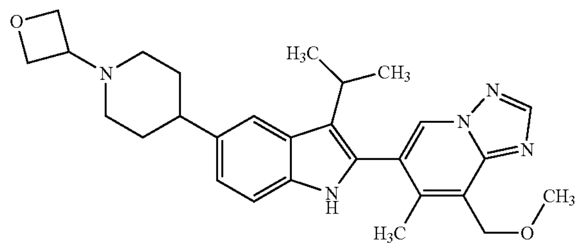 [SMILES: COCc1c(C)c(-c2[nH]c3ccc(C4CCN(C5COC5)CC4)cc3c2C(C)C)cn2ncnc12] | 474.1 | 1.09 | QC-ACN-TFA-XB |
| 500 | EX-111 | 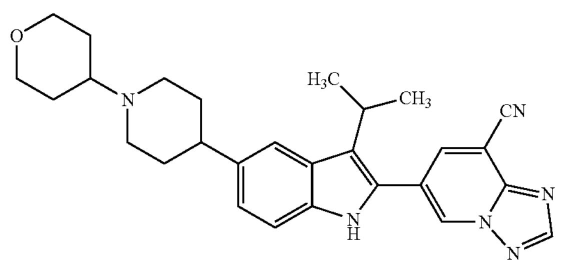 [SMILES: CC(C)c1c(-c2cc(C#N)c3ncnn3c2)[nH]c2ccc(C3CCN(C4CCOCC4)CC3)cc12] | 469.2 | 1.42 | QC-ACN-AA-XB |
| 501 | EX-111 | 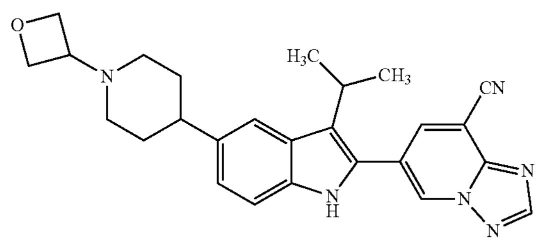 [SMILES: CC(C)c1c(-c2cc(C#N)c3ncnn3c2)[nH]c2ccc(C3CCN(C4COC4)CC3)cc12] | 441.2 | 1.18 | QC-ACN-TFA-XB |
| 502 | EX-102 | 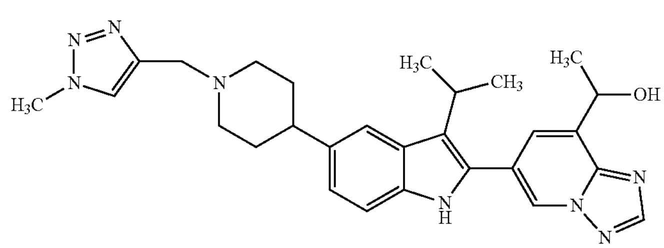 [SMILES: CC(C)c1c(-c2cc(C(C)O)c3ncnn3c2)[nH]c2ccc(C3CCN(Cc4cn(C)nn4)CC3)cc12] | 499.3 | 1.08 | QC-ACN-TFA-XB |
| 503 | EX-102 | 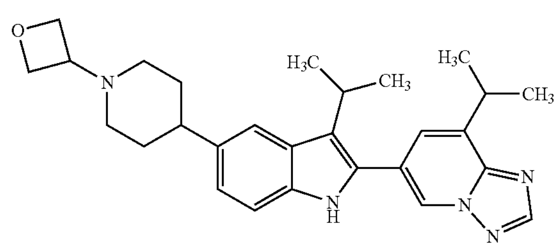 [SMILES: CC(C)c1c(-c2cc(C(C)C)c3ncnn3c2)[nH]c2ccc(C3CCN(C4COC4)CC3)cc12] | 460.3 | 1.06 | QC-ACN-TFA-XB |

TABLE 13-continued

| Ex. No. | Template Starting Material | Structure | LCMS MH+ | R$_t$ (min) | HPLC Method |
|---|---|---|---|---|---|
| 504 | EX-104 | 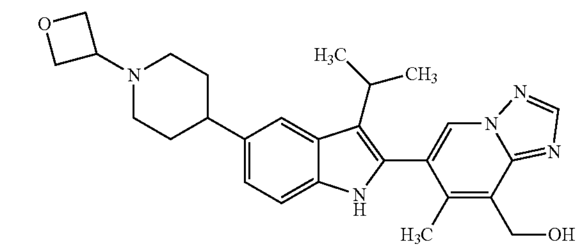 [SMILES: Cc1c(-c2[nH]c3ccc(C4CCN(C5COC5)CC4)cc3c2C(C)C)cn2ncnc2c1CO] | 460.2 | 1.49 | QC-ACN-AA-XB |
| 505 | EX-104 | 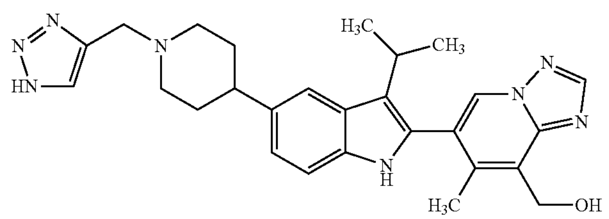 [SMILES: Cc1c(-c2[nH]c3ccc(C4CCN(Cc5c[nH]nn5)CC4)cc3c2C(C)C)cn2ncnc2c1CO] | 485.3 | 0.97 | QC-ACN-TFA-XB |
| 506 | EX-105 | 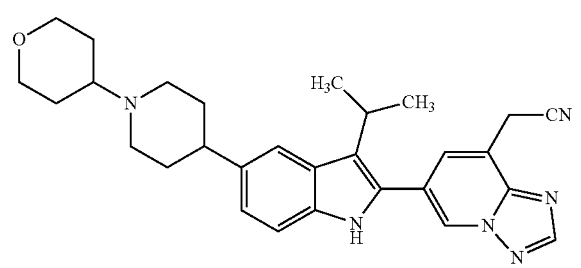 [SMILES: CC(C)c1c(-c2cc(CC#N)c3ncnn3c2)[nH]c2ccc(C3CCN(C4CCOCC4)CC3)cc12] | 483.2 | 1.26 | QC-ACN-TFA-XB |
| 507 | EX-107 | 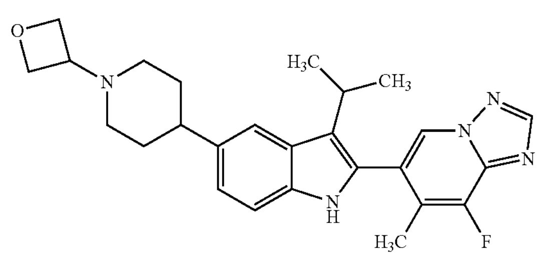 [SMILES: Cc1c(-c2[nH]c3ccc(C4CCN(C5COC5)CC4)cc3c2C(C)C)cn2ncnc2c1F] | 447.9 | 1.35 | QC-ACN-AA-XB |
| 508 | EX-108 | 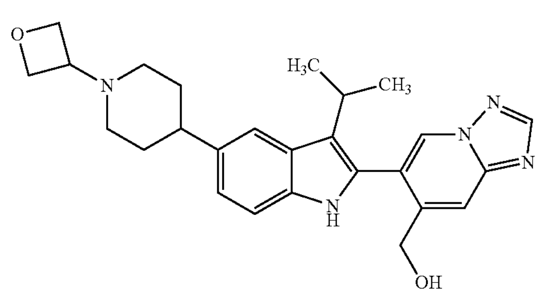 [SMILES: CC(C)c1c(-c2cn3ncnc3cc2CO)[nH]c2ccc(C3CCN(C4COC4)CC3)cc12] | 446.3 | 1.53 | QC-ACN-AA-XB |
| 509 | EX-108 | 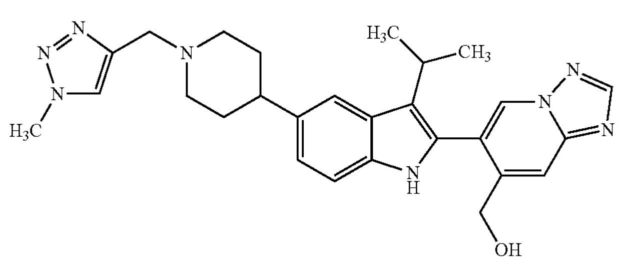 [SMILES: CC(C)c1c(-c2cn3ncnc3cc2CO)[nH]c2ccc(C3CCN(Cc4cn(C)nn4)CC3)cc12] | 485.1 | 0.92 | QC-ACN-TFA-XB |

TABLE 13-continued
| Ex. No. | Template Starting Material | Structure | LCMS MH+ | R$_t$ (min) | HPLC Method |
|---|---|---|---|---|---|
| 510 | EX-113 | 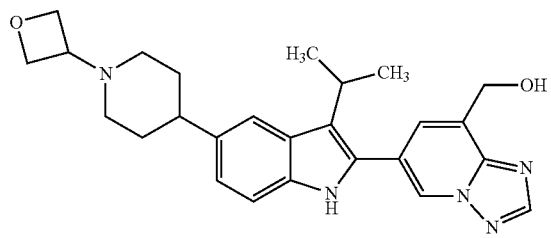 [SMILES: CC(C)c1c(-c2cc(CO)c3ncnn3c2)[nH]c2ccc(C3CCN(C4COC4)CC3)cc12] | 446.0 | 1.39 | QC-ACN-AA-XB |
| 511 | EX-113 | 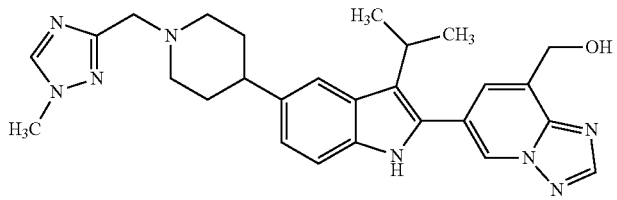 [SMILES: CC(C)c1c(-c2cc(CO)c3ncnn3c2)[nH]c2ccc(C3CCN(Cc4ncn(C)n4)CC3)cc12] | 485.3 | 1.16 | QC-ACN-AA-XB |
| 512 | EX-113 | 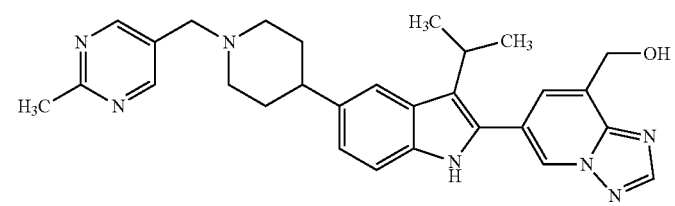 [SMILES: Cc1ncc(CN2CCC(c3ccc4[nH]c(-c5cc(CO)c6ncnn6c5)c(C(C)C)c4c3)CC2)cn1] | 496.4 | 1.04 | QC-ACN-TFA-XB |
| 513 | EX-113 | 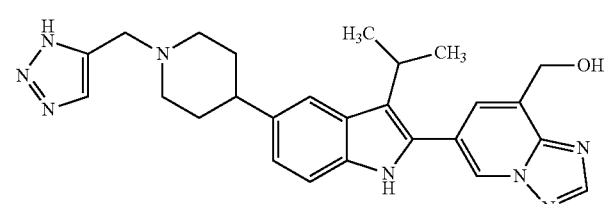 | 471.1 | 1 | QC-ACN-TFA-XB |
| 514 | EX-113 | 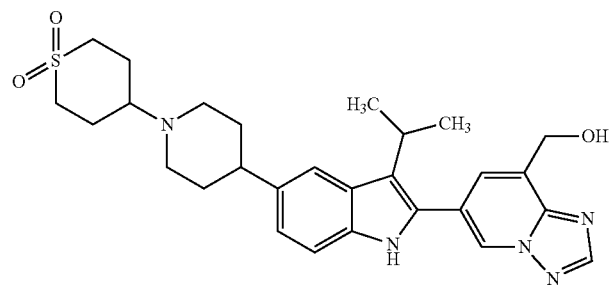 [SMILES: CC(C)c1c(-c2cc(CO)c3ncnn3c2)[nH]c2ccc(C3CCN(C4CCS(=O)(=O)CC4)CC3)cc12] | 522.4 | 1.34 | QC-ACN-AA-XB |
| 515 | EX-113 | 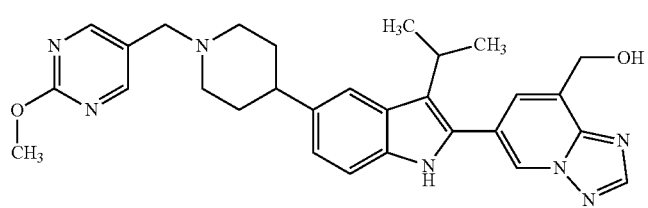 [SMILES: COc1ncc(CN2CCC(c3ccc4[nH]c(-c5cc(CO)c6ncnn6c5)c(C(C)C)c4c3)CC2)cn1] | 512.4 | 1.56 | QC-ACN-AA-XB |

TABLE 13-continued

| Ex. No. | Template Starting Material | Structure | LCMS MH+ | R$_t$ (min) | HPLC Method |
|---|---|---|---|---|---|
| 516 | EX-113 | 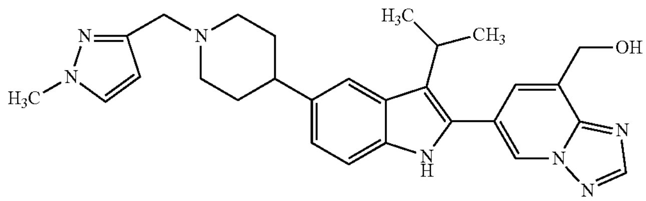 [SMILES: CC(C)c1c(-c2cc(CO)c3ncnn3c2)[nH]c2ccc(C3CCN(Cc4ccn(C)n4)CC3)cc12] | 484.1 | 1.27 | QC-ACN-AA-XB |
| 517 | EX-113 | 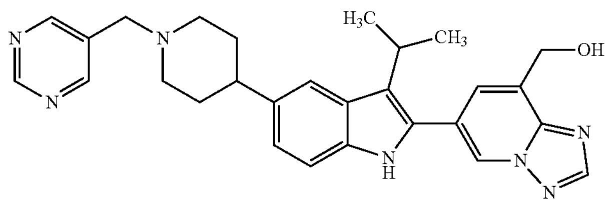 [SMILES: CC(C)c1c(-c2cc(CO)c3ncnn3c2)[nH]c2ccc(C3CCN(Cc4cncnc4)CC3)cc12] | 482.1 | 1.45 | QC-ACN-AA-XB |
| 518 | EX-113 | 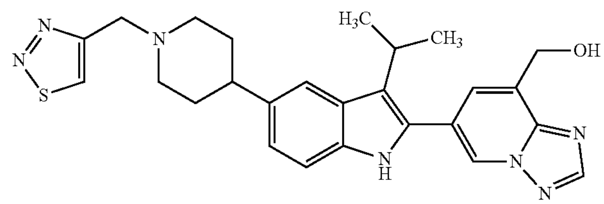 [SMILES: CC(C)c1c(-c2cc(CO)c3ncnn3c2)[nH]c2ccc(C3CCN(Cc4csnn4)CC3)cc12] | 488.0 | 1.26 | QC-ACN-TFA-XB |
| 519 | EX-113 | 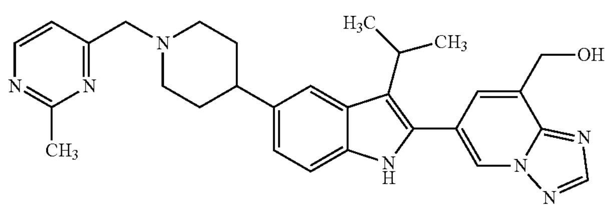 [SMILES: Cc1nccc(CN2CCC(c3ccc4[nH]c(-c5cc(CO)c6ncnn6c5)c(C(C)C)c4c3)CC2)n1] | 496.4 | 1.55 | QC-ACN-AA-XB |
| 520 | EX-113 | 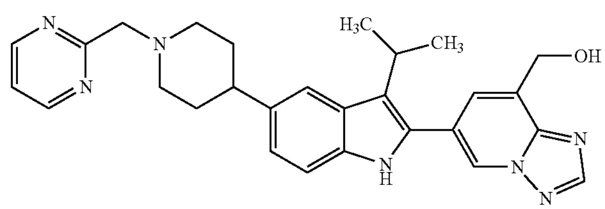 [SMILES: CC(C)c1c(-c2cc(CO)c3ncnn3c2)[nH]c2ccc(C3CCN(Cc4ncccn4)CC3)cc12] | 482.1 | 1.31 | QC-ACN-AA-XB |
| 521 | EX-113 | 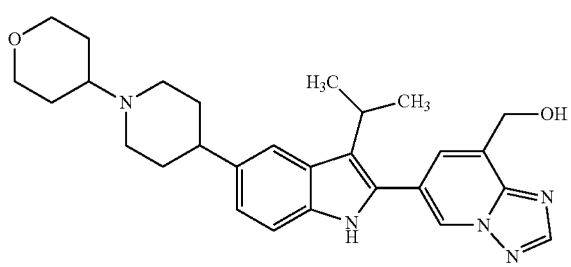 | 474.3 | 1.03 | QC-ACN-TFA-XB |
| 522 | EX-113 | 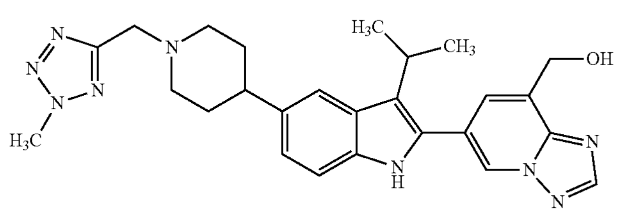 | 486.1 | 1.46 | QC-ACN-AA-XB |

TABLE 13-continued

| Ex. No. | Template Starting Material | Structure | LCMS MH+ | R_t (min) | HPLC Method |
|---|---|---|---|---|---|
| 523 | EX-113 | 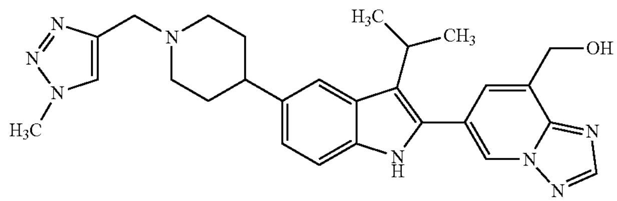 [SMILES: CC(C)c1c(-c2cc(CO)c3ncnn3c2)[nH]c2ccc(C3CCN(Cc4nnn(C)n4)CC3)cc12] | 485.2 | 1.01 | QC-ACN-TFA-XB |
| 524 | EX-113 | 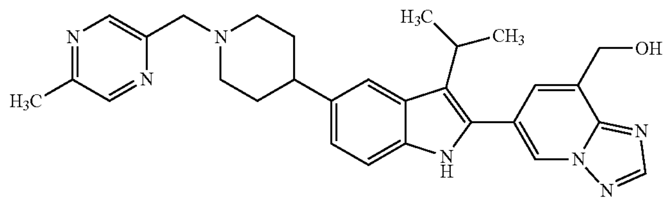 [SMILES: Cc1cnc(CN2CCC(c3ccc4[nH]c(-c5cc(CO)c6ncnn6c5)c(C(C)C)c4c3)CC2)cn1] | 496.0 | 1.39 | QC-ACN-AA-XB |
| 525 | EX-114 | 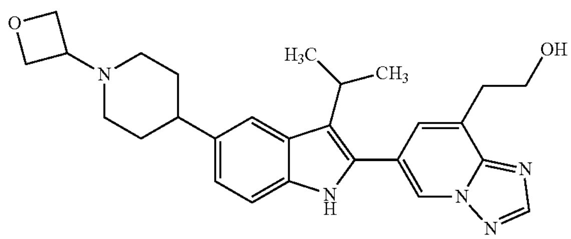 [SMILES: CC(C)c1c(-c2cc(CCO)c3ncnn3c2)[nH]c2ccc(C3CCN(C4COC4)CC3)cc12] | 460.3 | 1.44 | QC-ACN-AA-XB |
| 526 | EX-114 | 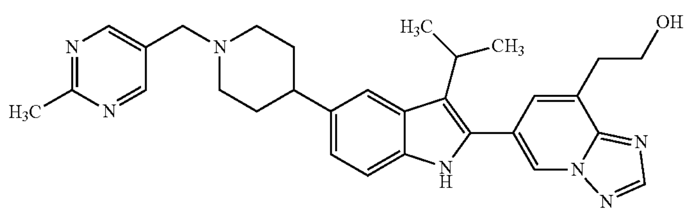 [SMILES: Cc1ncc(CN2CCC(c3ccc4[nH]c(-c5cc(CCO)c6ncnn6c5)c(C(C)C)c4c3)CC2)cn1] | 510.0 | 1.48 | QC-ACN-AA-XB |
| 527 | EX-114 | 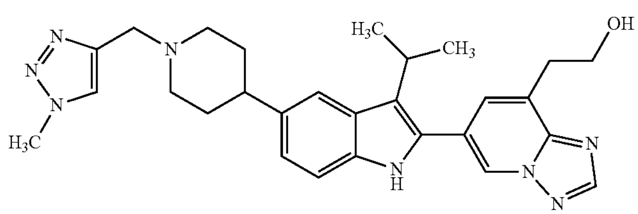 [SMILES: CC(C)c1c(-c2cc(CCO)c3ncnn3c2)[nH]c2ccc(C3CCN(Cc4cn(C)nn4)CC3)cc12] | 499.3 | 1.02 | QC-ACN-TFA-XB |
| 528 | EX-116 | 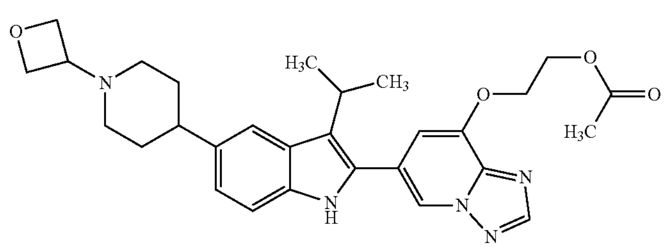 [SMILES: CC(=O)OCCOc1cc(-c2[nH]c3ccc(C4CCN(C5COC5)CC4)cc3c2C(C)C)cn2ncnc12] | 518.0 | 1.71 | QC-ACN-AA-XB |
| 529 | EX-116 | 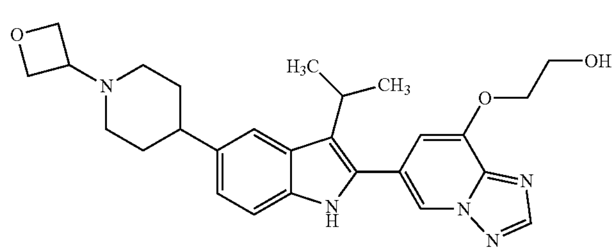 [SMILES: CC(C)c1c(-c2cc(OCCO)c3ncnn3c2)[nH]c2ccc(C3CCN(C4COC4)CC3)cc12] | 475.9 | 1.11 | QC-ACN-TFA-XB |

TABLE 13-continued
| Ex. No. | Template Starting Material | Structure | LCMS MH+ | R$_t$ (min) | HPLC Method |
|---|---|---|---|---|---|
| 530 | EX-116 | 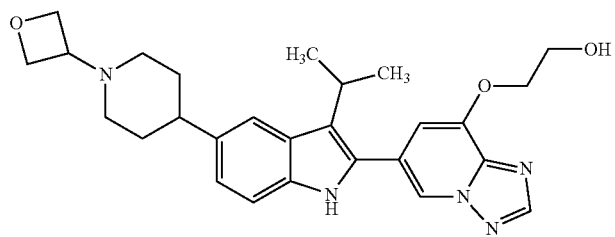 [SMILES: CC(C)c1c(-c2cc(OCCO)c3ncnn3c2)[nH]c2ccc(C3CCN(C4COC4)CC3)cc12] | 476.0 | 1.3 | QC-ACN-AA-XB |
TABLE 14
| Ex. No. | Fragment Starting Material | Structure | LCMS MH+ | R$_t$ (min) | HPLC Method |
|---|---|---|---|---|---|
| 531 | EX-122 | 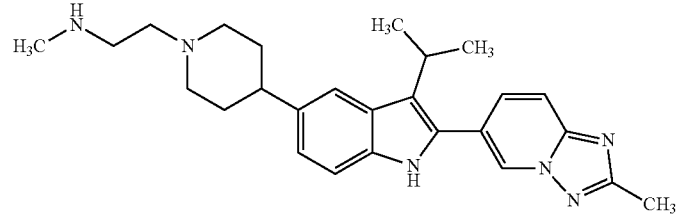 | 431.3 | 0.93 | E |
| 532 | EX-122 | 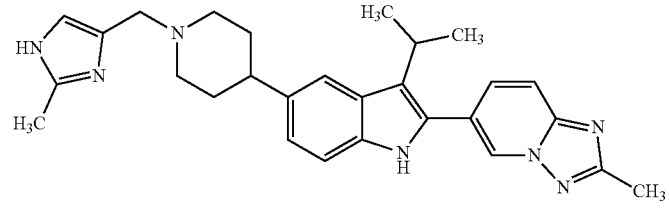 [SMILES: Cc1nc2ccc(-c3[nH]c4ccc(C5CCN(Cc6c[nH]c(C)n6)CC5)cc4c3C(C)C)cn2n1] | 467.3 | 1.56 | E |
| 533 | EX-122 | 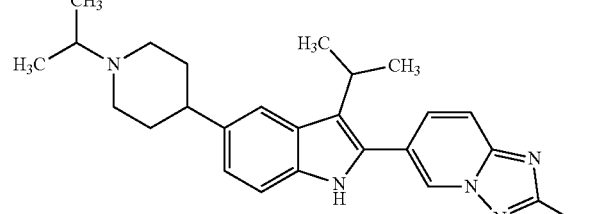 | 416.3 | 1.48 | E |
| 534 | EX-122 | 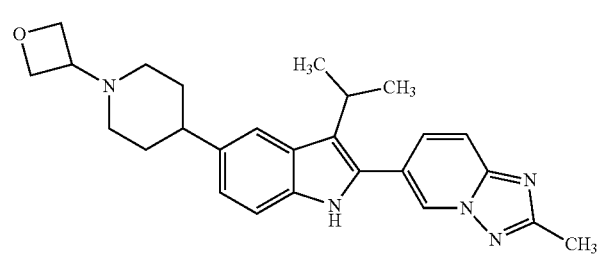 [SMILES: Cc1nc2ccc(-c3[nH]c4ccc(C5CCN(C6COC6)CC5)cc4c3C(C)C)cn2n1] | 430.3 | 1.8 | E |

TABLE 14-continued
| Ex. No. | Fragment Starting Material | Structure | LCMS MH+ | R$_t$ (min) | HPLC Method |
|---|---|---|---|---|---|
| 535 | EX-122 | 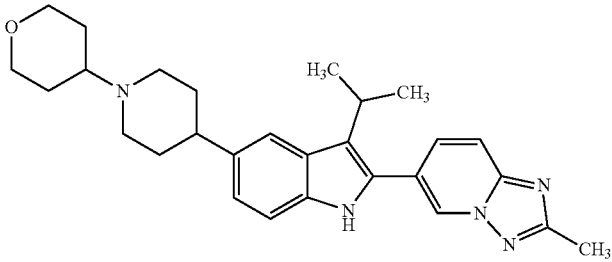 [SMILES: Cc1nc2ccc(-c3[nH]c4ccc(C5CCN(C6CCOCC6)CC5)cc4c3C(C)C)cn2n1] | 458.3 | 1.45 | E |
| 536 | EX-1 | 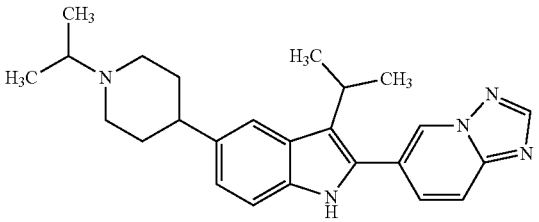 [SMILES: CC(C)c1c(-c2ccc3ncnn3c2)[nH]c2ccc(C3CCN(C(C)C)CC3)cc12] | 402.3 | 1.47 | E |
| 537 | EX-2 | 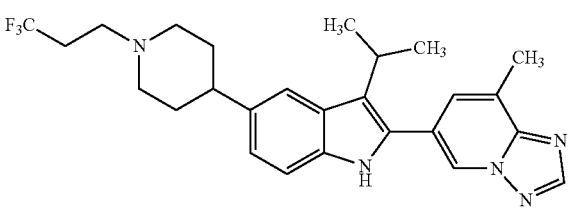 [SMILES: Cc1cc(-c2[nH]c3ccc(C4CCN(CCC(F)(F)F)CC4)cc3c2C(C)C)cn2ncnc12] | 470.2 | 2.5 | E |
| 538 | EX-2 | 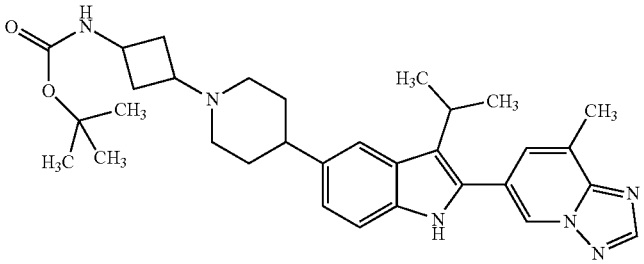 [SMILES: Cc1cc(-c2[nH]c3ccc(C4CCN(C5CC(NC(=O)OC(C)(C)C)C5)CC4)cc3c2C(C)C)cn2ncnc12] | 543 | 2.12 | E |
| 539 | EX-2 | 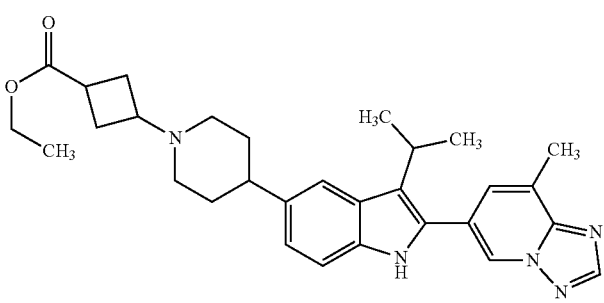 [SMILES: CCOC(=O)C1CC(N2CCC(c3ccc4[nH]c(-c5cc(C)c6ncnn6c5)c(C(C)C)c4c3)CC2)C1] | 500 | 2.11 | E |
| 540 | EX-2 | 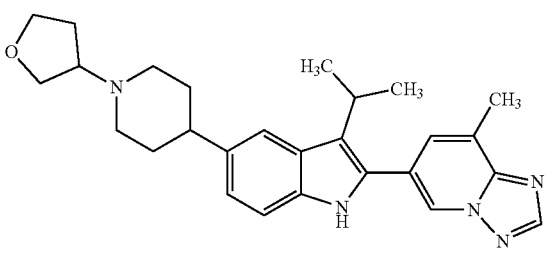 | 444.2 | 1.71 | E |

TABLE 14-continued

| Ex. No. | Fragment Starting Material | Structure | LCMS MH+ | R$_t$ (min) | HPLC Method |
|---|---|---|---|---|---|
| 541 | EX-2 | 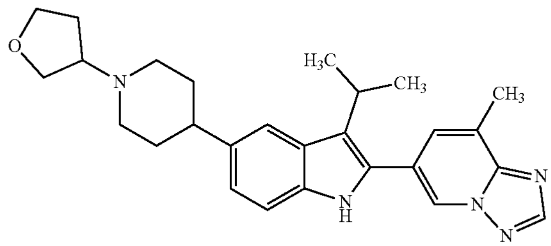 [SMILES: Cc1cc(-c2[nH]c3ccc(C4CCN(C5CCOC5)CC4)cc3c2C(C)C)cn2ncnc12] | 444.2 | 1.72 | E |
| 542 | EX-124 | 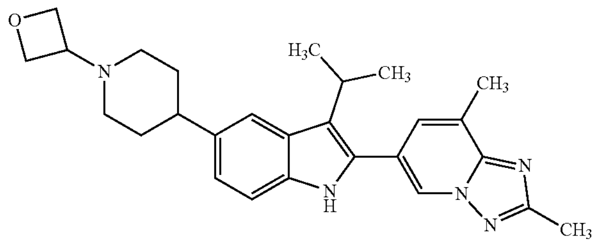 [SMILES: Cc1nc2c(C)cc(-c3[nH]c4ccc(C5CCN(C6COC6)CC5)cc4c3C(C)C)cn2n1] | 444.3 | 1.74 | E |
| 543 | EX-124 | 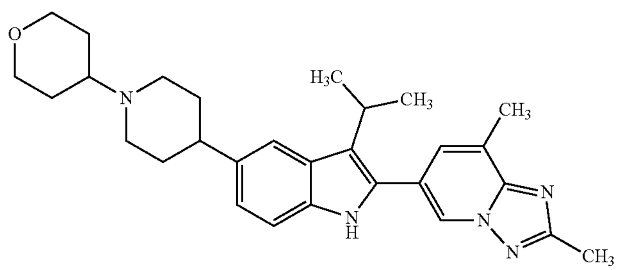 [SMILES: Cc1nc2c(C)cc(-c3[nH]c4ccc(C5CCN(C6CCOCC6)CC5)cc4c3C(C)C)cn2n1] | 473.3 | 1.71 | E |
| 544 | EX-124 | 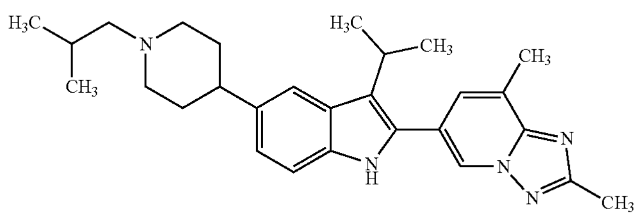 [SMILES: Cc1nc2c(C)cc(-c3[nH]c4ccc(C5CCN(CC(C)C)CC5)cc4c3C(C)C)cn2n1] | 444 | 1.82 | E |
| 545 | EX-124 | 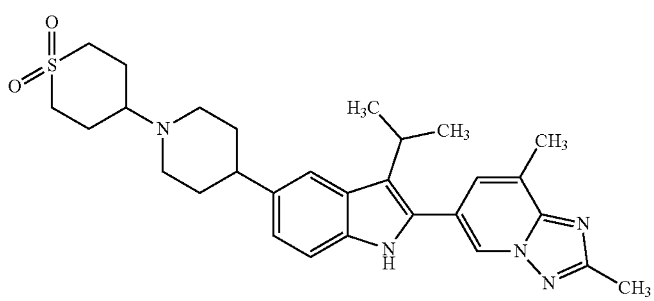 [SMILES: Cc1nc2c(C)cc(-c3[nH]c4ccc(C5CCN(C6CCS(=O)(=O)CC6)CC5)cc4c3C(C)C)cn2n1] | 520.3 | 1.93 | E |
| 546 | EX-125 | 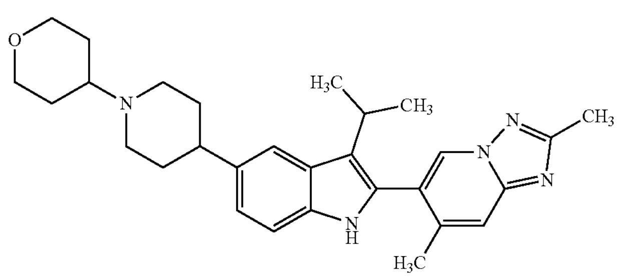 [SMILES: Cc1nc2cc(C)c(-c3[nH]c4ccc(C5CCN(C6CCOCC6)CC5)cc4c3C(C)C)cn2n1] | 472.3 | 1.56 | E |

TABLE 14-continued
| Ex. No. | Fragment Starting Material | Structure | LCMS MH+ | R$_t$ (min) | HPLC Method |
|---|---|---|---|---|---|
| 547 | EX-125 | 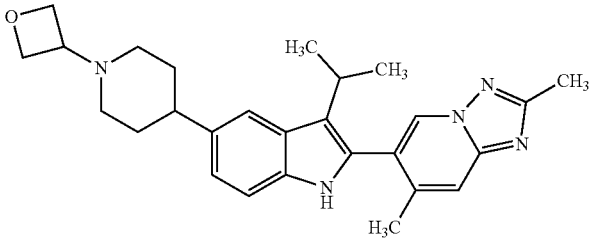 [SMILES: Cc1nc2cc(C)c(-c3[nH]c4ccc(C5CCN(C6COC6)CC5)cc4c3C(C)C)cn2n1] | 444.4 | 1.69 | E |
| 548 | EX-125 | 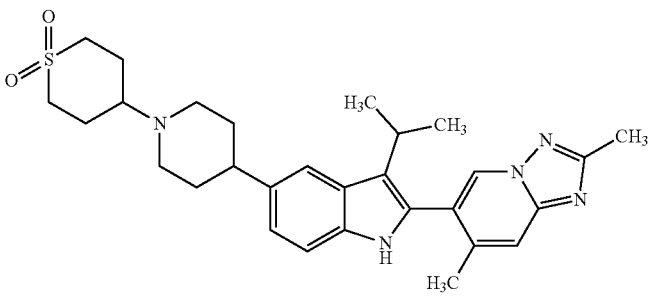 [SMILES: Cc1nc2cc(C)c(-c3[nH]c4ccc(C5CCN(C6CCS(=O)(=O)CC6)CC5)cc4c3C(C)C)cn2n1] | 520 | 1.58 | E |
| 549 | EX-128 | 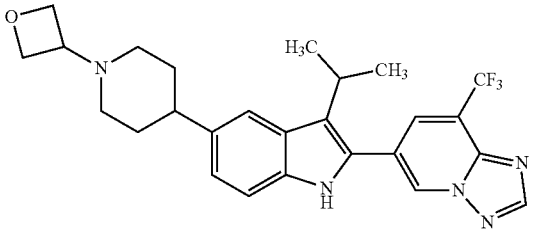 [SMILES: CC(C)c1c(-c2cc(C(F)(F)F)c3ncnn3c2)[nH]c2ccc(C3CCN(C4COC4)CC3)cc12] | 484 | 2.03 | E |
| 550 | EX-128 | 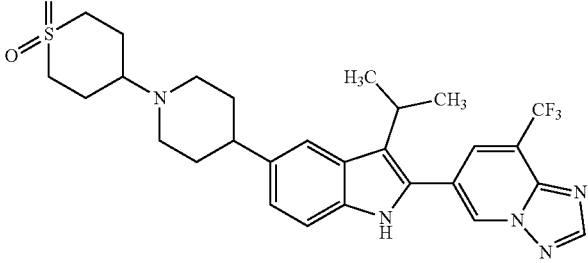 | 560 | 1.88 | E |
| 551 | EX-128 | 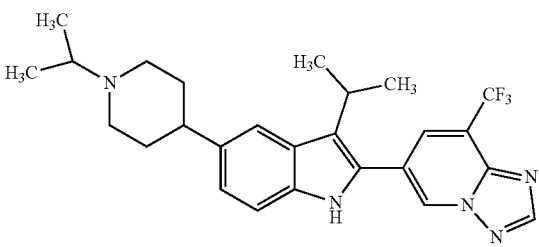 [SMILES: CC(C)c1c(-c2cc(C(F)(F)F)c3ncnn3c2)[nH]c2ccc(C3CCN(C(C)C)CC3)cc12] | 470 | 1.56 | E |

TABLE 14-continued

| Ex. No. | Fragment Starting Material | Structure | LCMS MH+ | R_t (min) | HPLC Method |
|---|---|---|---|---|---|
| 552 | EX-128 | 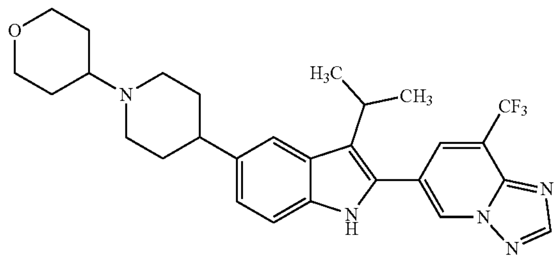 | 512 | 2.5 | D |
| 553 | EX-128 | 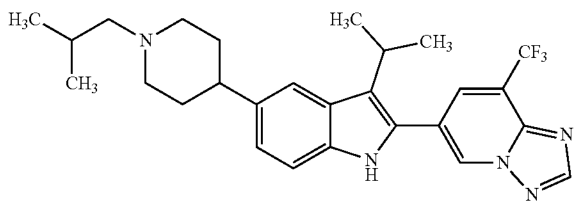 | 484.2 | 2.24 | E |
| 554 | EX-128 | 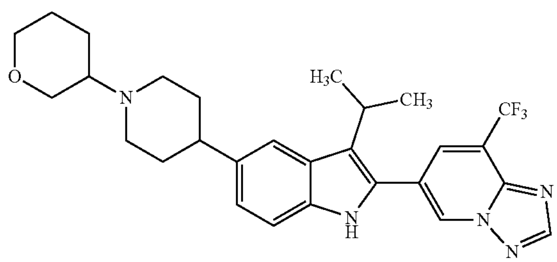 | 512.1 | 2.13 | E |
| 555 | EX-128 | 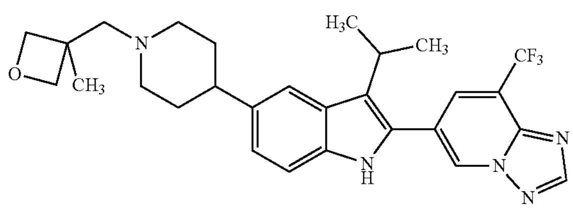 [SMILES: CC(C)c1c(-c2cc(C(F)(F)F)c3ncnn3c2)[nH]c2ccc(C3CCN(CC4(C)COC4)CC3)cc12] | 512.3 | 2.15 | E |
| 556 | EX-128 | 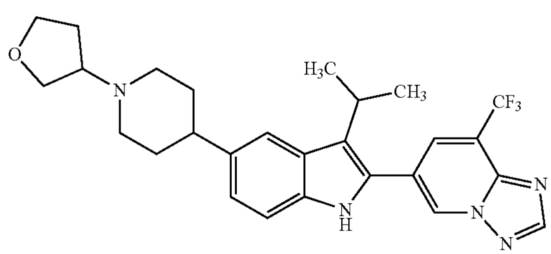 | 498.2 | 1.51 | F |
| 557 | EX-128 | 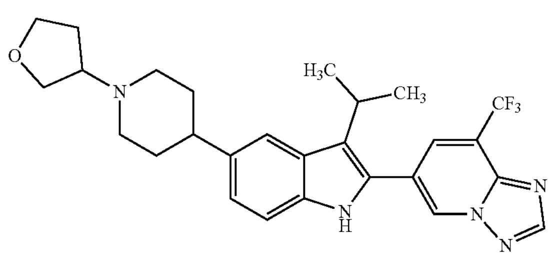 [SMILES: CC(C)c1c(-c2cc(C(F)(F)F)c3ncnn3c2)[nH]c2ccc(C3CCN(C4CCOC4)CC3)cc12] | 498.2 | 2.03 | E |

TABLE 14-continued

| Ex. No. | Fragment Starting Material | Structure | LCMS MH+ | R$_t$ (min) | HPLC Method |
|---|---|---|---|---|---|
| 558 | EX-155 | 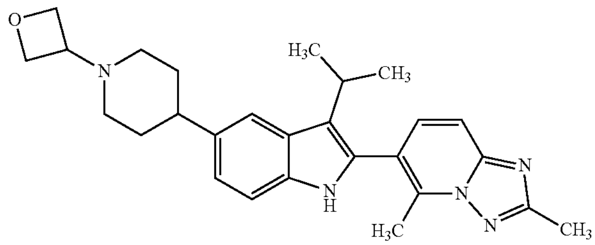 [SMILES: Cc1nc2ccc(-c3[nH]c4ccc(C5CCN(C6COC6)CC5)cc4c3C(C)C)c(C)n2n1] | 444.3 | 1.65 | E |
| 559 | EX-155 | 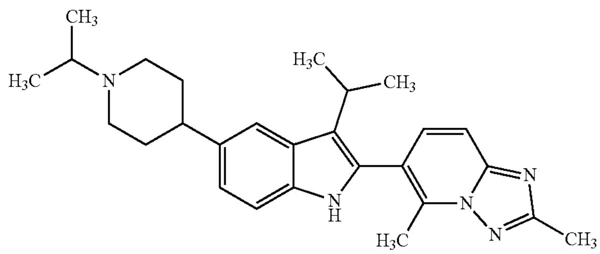 | 430.3 | 1.53 | E |
| 560 | EX-155 | 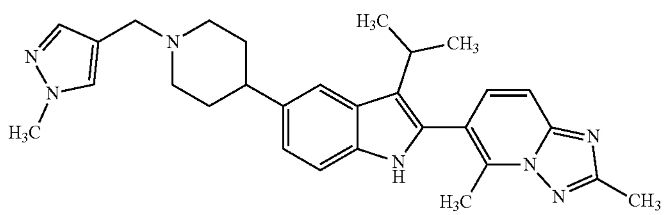 [SMILES: Cc1nc2ccc(-c3[nH]c4ccc(C5CCN(Cc6cnn(C)c6)CC5)cc4c3C(C)C)c(C)n2n1] | 482.3 | 1.5 | E |
| 561 | EX-5 | 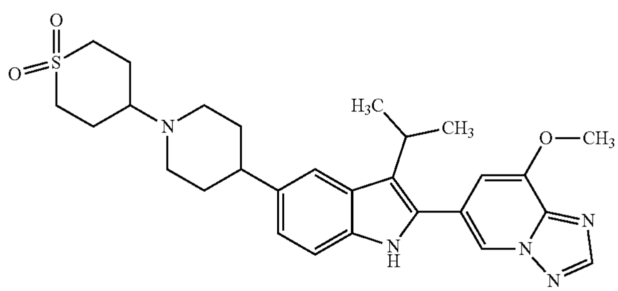 [SMILES: COc1cc(-c2[nH]c3ccc(C4CCN(C5CCS(=O)(=O)CC5)CC4)cc3c2C(C)C)cn2ncnc12] | 522.4 | 1.51 | E |
| 562 | EX-5 | 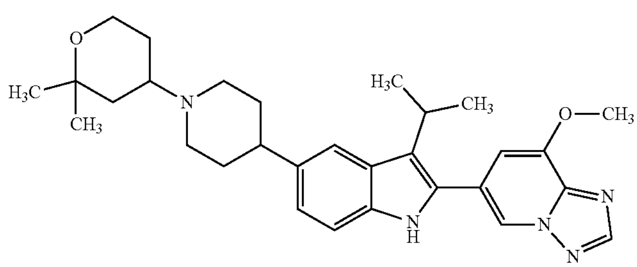 [SMILES: COc1cc(-c2[nH]c3ccc(C4CCN(C5CCOC(C)(C)C5)CC4)cc3c2C(C)C)cn2ncnc12] | 502.3 | 1.71 | E |
| 563 | EX-5 | 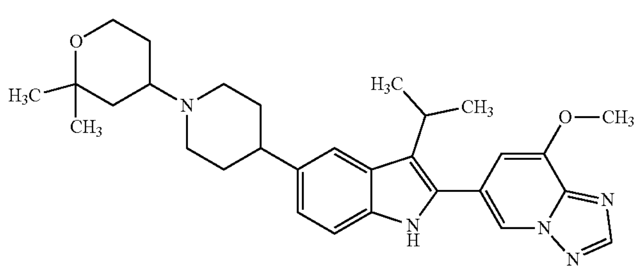 [SMILES: COc1cc(-c2[nH]c3ccc(C4CCN(C5CCOC(C)(C)C5)CC4)cc3c2C(C)C)cn2ncnc12] | 502.2 | 6.03 | I |

TABLE 14-continued
| Ex. No. | Fragment Starting Material | Structure | LCMS MH+ | R$_t$ (min) | HPLC Method |
|---|---|---|---|---|---|
| 564 | EX-5 | 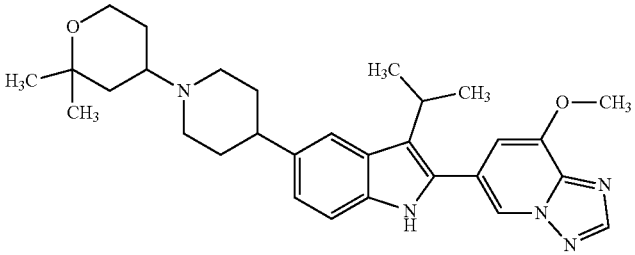 [SMILES: COc1cc(-c2[nH]c3ccc(C4CCN(C5CCOC(C)(C)C5)CC4)cc3c2C(C)C)cn2ncnc12] | 502.4 | 6.06 | I |
| 565 | EX-5 | 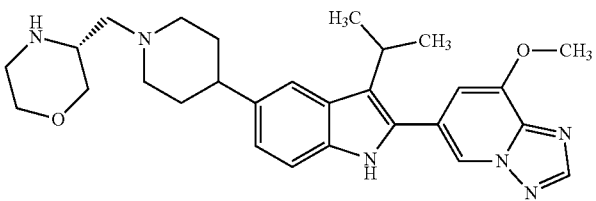 [SMILES: COc1cc(-c2[nH]c3ccc(C4CCN(C[C@@H]5COCCN5)CC4)cc3c2C(C)C)cn2ncnc12] | 489.3 | 1.55 | E |
| 566 | EX-5 | 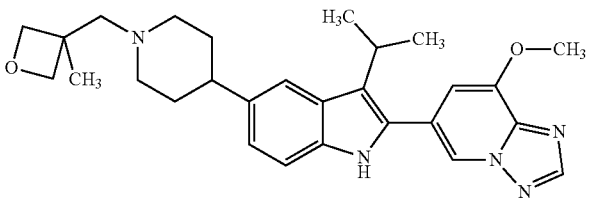 [SMILES: COc1cc(-c2[nH]c3ccc(C4CCN(CC5(C)COC5)CC4)cc3c2C(C)C)cn2ncnc12] | 474.3 | 1.86 | E |
| 567 | EX-5 | 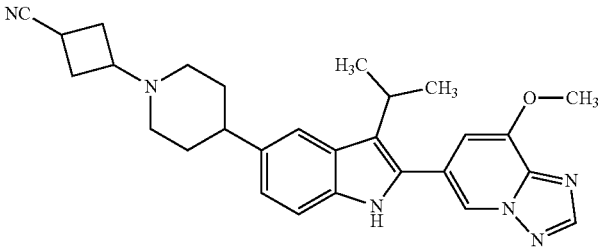 [SMILES: COc1cc(-c2[nH]c3ccc(C4CCN(C5CC(C#N)C5)CC4)cc3c2C(C)C)cn2ncnc12] | 469.2 | 1.89 | E |
| 568 | EX-5 | 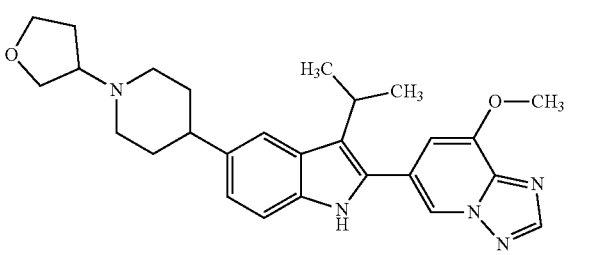 [SMILES: COc1cc(-c2[nH]c3ccc(C4CCN(C5CCOC5)CC4)cc3c2C(C)C)cn2ncnc12] | 460.2 | 1.87 | D |
| 569 | EX-5 | 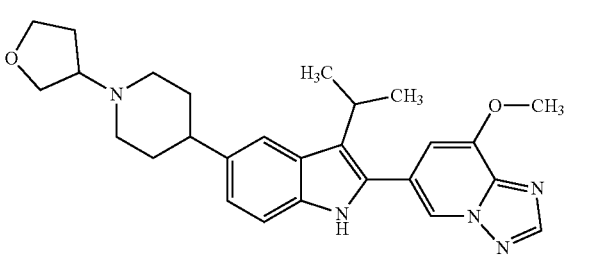 [SMILES: COc1cc(-c2[nH]c3ccc(C4CCN(C5CCOC5)CC4)cc3c2C(C)C)cn2ncnc12] | 460.1 | 1.73 | E |

TABLE 14-continued
| Ex. No. | Fragment Starting Material | Structure | LCMS MH+ | $R_t$ (min) | HPLC Method |
|---|---|---|---|---|---|
| 570 | EX-5 | 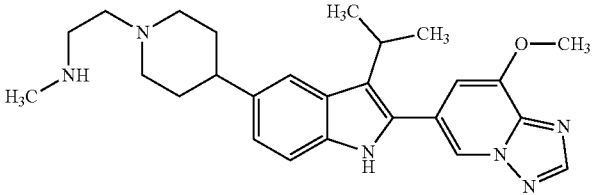 [SMILES: CNCCN1CCC(c2ccc3[nH]c(-c4cc(OC)c5ncnn5c4)c(C(C)C)c3c2)CC1] | 447.1 | 1.44 | E |
| 571 | EX-132 | 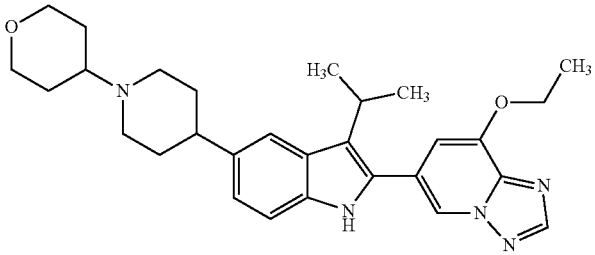 [SMILES: CCOc1cc(-c2[nH]c3ccc(C4CCN(C5CCOCC5)CC4)cc3c2C(C)C)cn2ncnc12] | 488 | 1.66 | E |
| 572 | EX-132 | 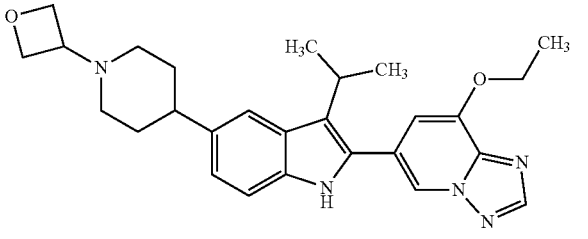 [SMILES: CCOc1cc(-c2[nH]c3ccc(C4CCN(C5COC5)CC4)cc3c2C(C)C)cn2ncnc12] | 460.1 | 1.34 | F |
| 573 | EX-132 | 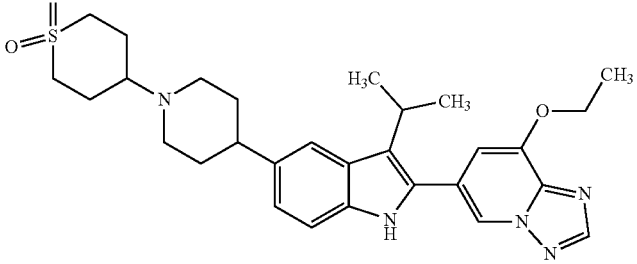 | 536 | 1.9 | E |
| 574 | EX-133 | 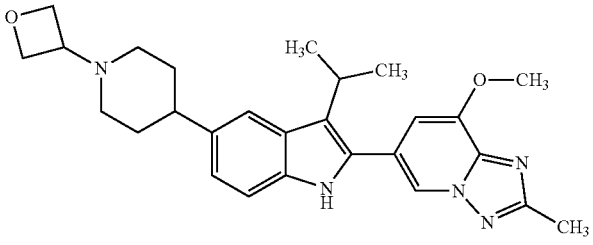 [SMILES: COc1cc(-c2[nH]c3ccc(C4CCN(C5COC5)CC4)cc3c2C(C)C)cn2nc(C)nc12] | 460.2 | 1.94 | E |
| 575 | EX-133 | 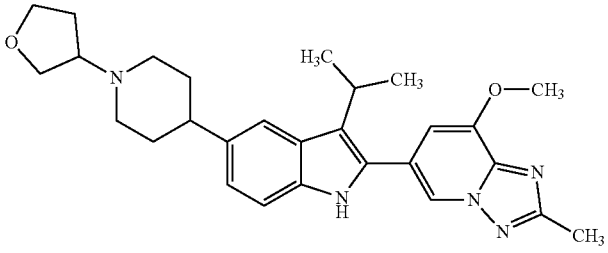 [SMILES: COc1cc(-c2[nH]c3ccc(C4CCN(C5CCOC5)CC4)cc3c2C(C)C)cn2nc(C)nc12] | 474.2 | 1.92 | D |

TABLE 14-continued
| Ex. No. | Fragment Starting Material | Structure | LCMS MH+ | $R_t$ (min) | HPLC Method |
|---|---|---|---|---|---|
| 576 | EX-133 | 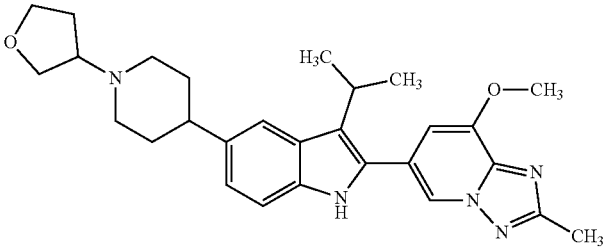 [SMILES: COc1cc(-c2[nH]c3ccc(C4CCN(C5CCOC5)CC4)cc3c2C(C)C)cn2nc(C)nc12] | 474.2 | 1.94 | D |
| 577 | EX-137 | 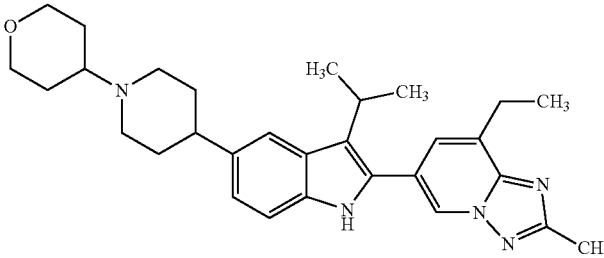 | 486.2 | 1.8 | E |
| 578 | EX-137 | 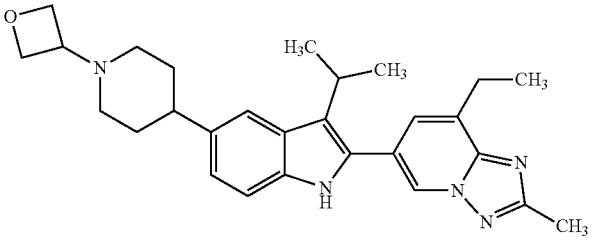 [SMILES: CCc1cc(-c2[nH]c3ccc(C4CCN(C5COC5)CC4)cc3c2C(C)C)cn2nc(C)nc12] | 458.3 | 1.96 | E |
| 579 | EX-119 | 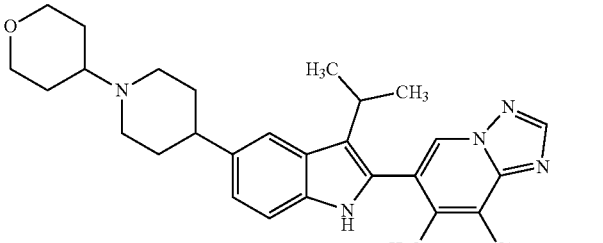 | 492.2 | 1.7 | E |
| 580 | EX-119 | 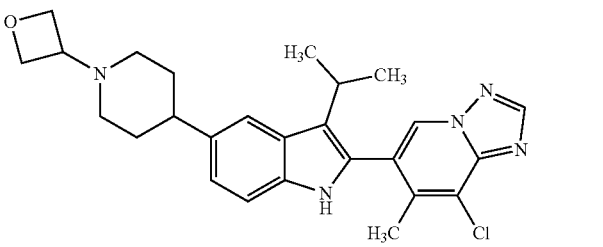 [SMILES: Cc1c(-c2[nH]c3ccc(C4CCN(C5COC5)CC4)cc3c2C(C)C)cn2ncnc2c1Cl] | 464.2 | 2.1 | E |
| 581 | EX-143 | 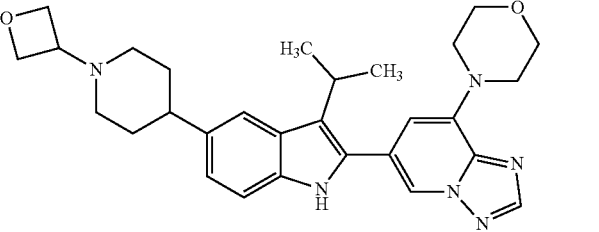 [SMILES: CC(C)c1c(-c2cc(N3CCOCC3)c3ncnn3c2)[nH]c2ccc(C3CCN(C4COC4)CC3)cc12] | 501.3 | 2.01 | E |

TABLE 14-continued
| Ex. No. | Fragment Starting Material | Structure | LCMS MH+ | R_t (min) | HPLC Method |
|---|---|---|---|---|---|
| 582 | EX-94 | 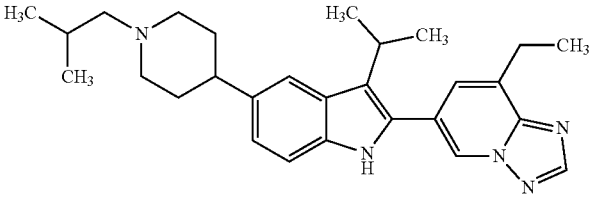 | 444.3 | 2.07 | E |
| 583 | EX-94 | 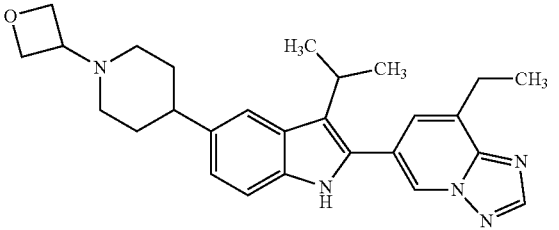 | 444.3 | 2.08 | E |
| 584 | EX-95 | 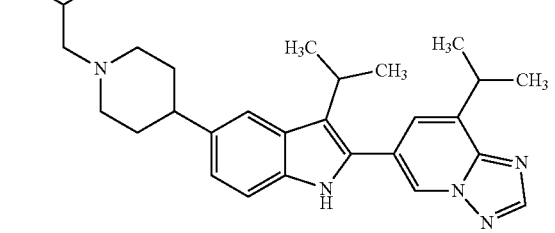 | 458.3 | 2.25 | E |
| 585 | EX-95 | 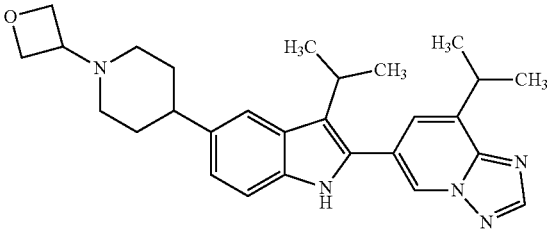 [SMILES: CC(C)c1c(-c2cc(C(C)C)c3ncnn3c2)[nH]c2ccc(C3CCN(C4COC4)CC3)cc12] | 458.2 | 2.24 | E |
| 586 | EX-145 | 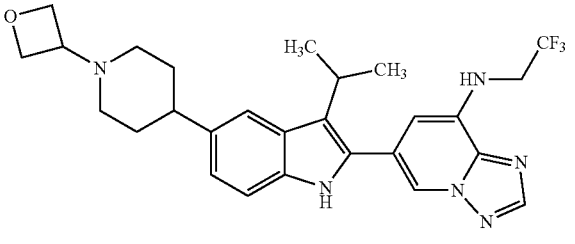 [SMILES: CC(C)c1c(-c2cc(NCC(F)(F)F)c3ncnn3c2)[nH]c2ccc(C3CCN(C4COC4)CC3)cc12] | 513.2 | 2.15 | E |
| 587 | EX-98 | 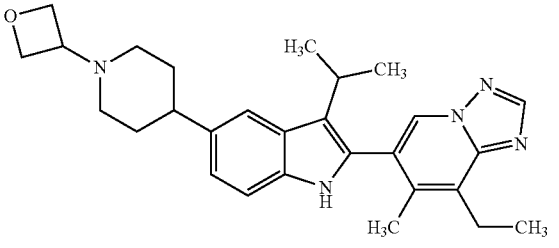 [SMILES: CCc1c(C)c(-c2[nH]c3ccc(C4CCN(C5COC5)CC4)cc3c2C(C)C)cn2ncnc12] | 458.3 | 2.11 | E |

TABLE 14-continued

| Ex. No. | Fragment Starting Material | Structure | LCMS MH+ | R$_t$ (min) | HPLC Method |
|---|---|---|---|---|---|
| 588 | EX-140 | 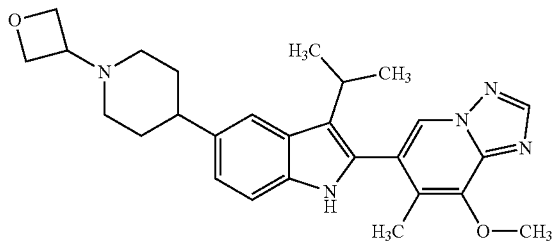 [SMILES: COc1c(C)c(-c2[nH]c3ccc(C4CCN(C5COC5)CC4)cc3c2C(C)C)cn2ncnc12] | 460.2 | 2.04 | E |
| 589 | EX-140 | 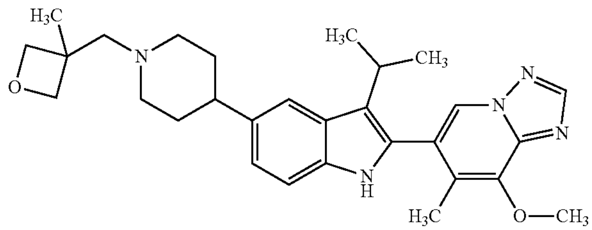 [SMILES: COc1c(C)c(-c2[nH]c3ccc(C4CCN(CC5(C)COC5)CC4)cc3c2C(C)C)cn2ncnc12] | 488.3 | 2.05 | E |
| 590 | EX-147 | 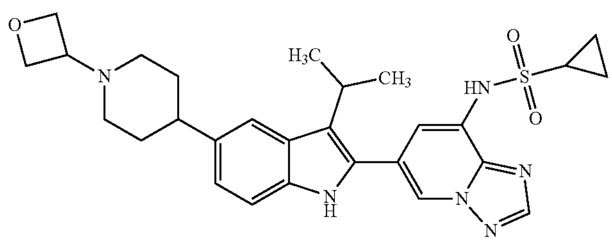 [SMILES: CC(C)c1c(-c2cc(NS(=O)(=O)C3CC3)c3ncnn3c2)[nH]c2ccc(C3CCN(C4COC4)CC3)cc12] | 535.2 | 1.32 | F |
| 591 | EX-148 | 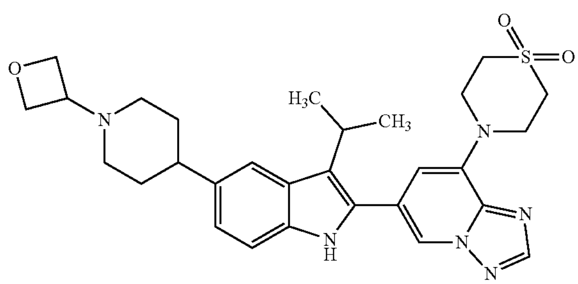 [SMILES: CC(C)c1c(-c2cc(N3CCS(=O)(=O)CC3)c3ncnn3c2)[nH]c2ccc(C3CCN(C4COC4)CC3)cc12] | 549.2 | 1.87 | E |
| 592 | EX-149 | 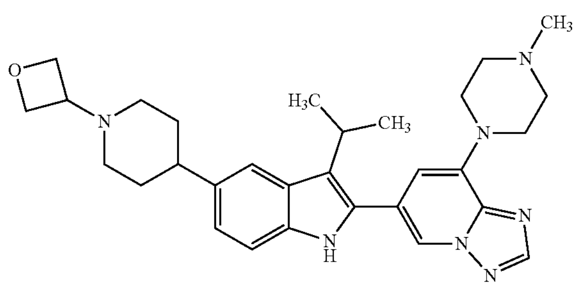 [SMILES: CC(C)c1c(-c2cc(N3CCN(C)CC3)c3ncnn3c2)[nH]c2ccc(C3CCN(C4COC4)CC3)cc12] | 514.3 | 1.76 | E |
| 593 | EX-151 | 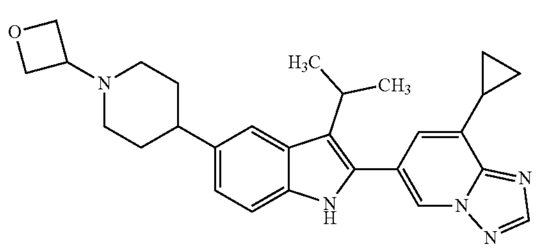 [SMILES: CC(C)c1c(-c2cc(C3CC3)c3ncnn3c2)[nH]c2ccc(C3CCN(C4COC4)CC3)cc12] | 456.3 | 1.88 | E |

TABLE 14-continued
| Ex. No. | Fragment Starting Material | Structure | LCMS MH+ | $R_t$ (min) | HPLC Method |
|---|---|---|---|---|---|
| 594 | EX-141 | 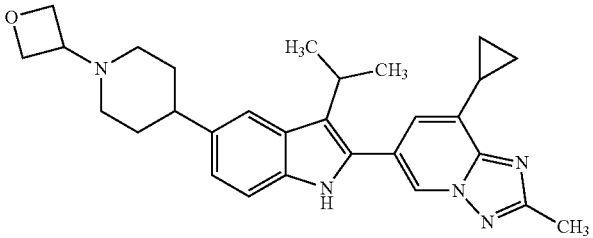 [SMILES: Cc1nc2c(C3CC3)cc(-c3[nH]c4ccc(C5CCN(C6COC6)CC5)cc4c3C(C)C)cn2n1] | 470.3 | 1.92 | E |
| 595 | EX-152 | 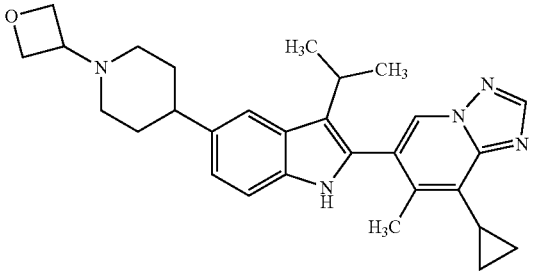 [SMILES: Cc1c(-c2[nH]c3ccc(C4CCN(C5COC5)CC4)cc3c2C(C)C)cn2ncnc2c1C1CC1] | 470.1 | 2.21 | E |
| 596 | EX-158 | 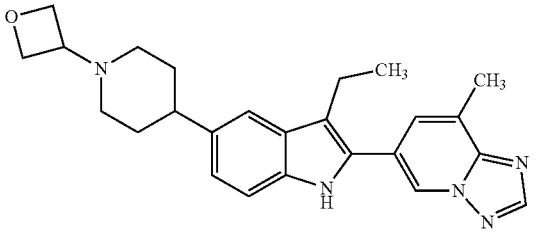 [SMILES: CCc1c(-c2cc(C)c3ncnn3c2)[nH]c2ccc(C3CCN(C4COC4)CC3)cc12] | 416.3 | 1.54 | E |
| 597 | EX-161 | 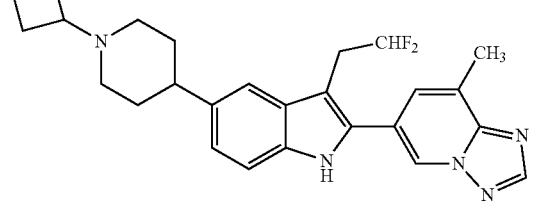 | 452.2 | 1.67 | E |
| 598 | EX-156 | 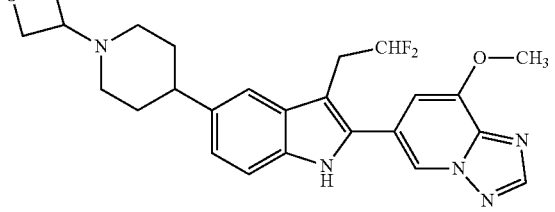 | 468.2 | 1.67 | E |
| 599 | EX-124 | 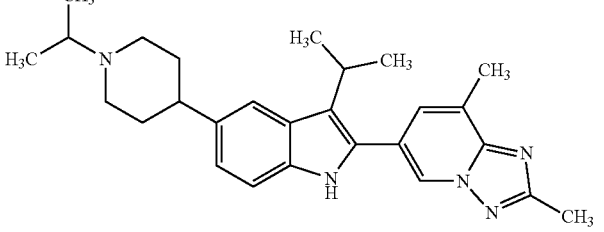 | 430.3 | 1.49 | E |

TABLE 14-continued

| Ex. No. | Fragment Starting Material | Structure | LCMS MH+ | R$_t$ (min) | HPLC Method |
|---|---|---|---|---|---|
| 600 | EX-157 | 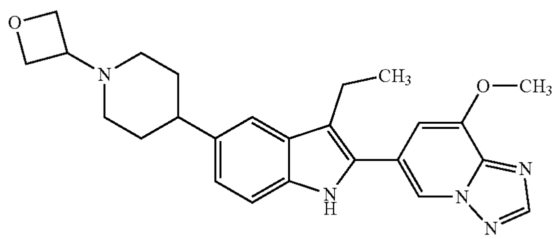 [SMILES: CCc1c(-c2cc(OC)c3ncnn3c2)[nH]c2ccc(C3CCN(C4COC4)CC3)cc12] | 432.3 | 1.49 | E |

The following examples were prepared according to the general methods disclosed in Examples 46 and 47.

TABLE 15

| Ex. No. | Template Starting Material | Structure | LCMS MH+ | R$_t$ (min) | HPLC Method |
|---|---|---|---|---|---|
| 601 | EX-1 | 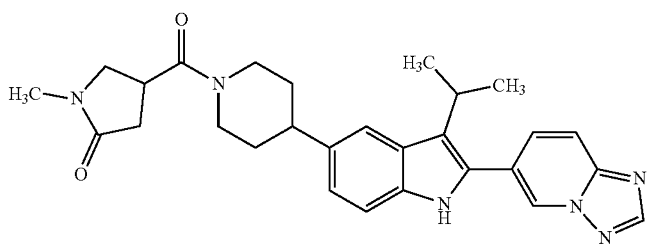 [SMILES: CC(C)c1c(-c2ccc3ncnn3c2)[nH]c2ccc(C3CCN(C(=O)C4CC(=O)N(C)C4)CC3)cc12] | 484.9 | 1.43 | QC-ACN-AA-XB |
| 602 | EX-2 | 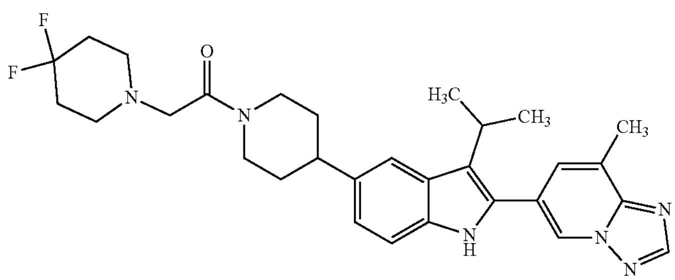 [SMILES: Cc1cc(-c2[nH]c3ccc(C4CCN(C(=O)CN5CCC(F)(F)CC5)CC4)cc3c2C(C)C)cn2ncnc12] | 535.2 | 1.95 | QC-ACN-AA-XB |
| 603 | EX-2 | 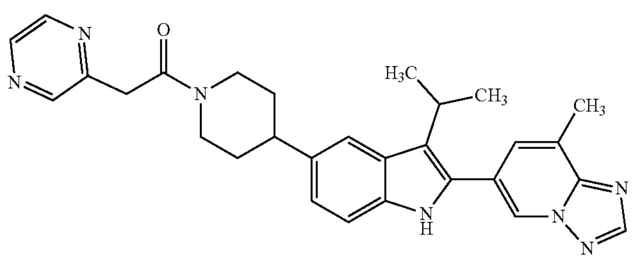 [SMILES: Cc1cc(-c2[nH]c3ccc(C4CCN(C(=O)Cc5cnccn5)CC4)cc3c2C(C)C)cn2ncnc12] | 494.2 | 1.65 | QC-ACN-AA-XB |
| 604 | EX-2 | 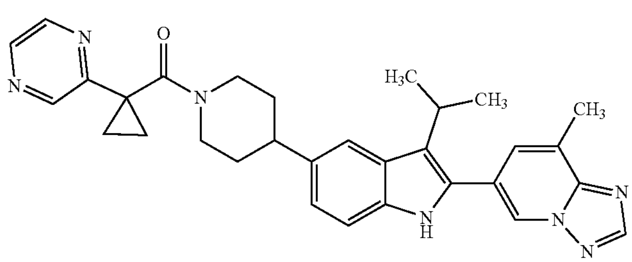 [SMILES: Cc1cc(-c2[nH]c3ccc(C4CCN(C(=O)C5(c6cnccn6)CC5)CC4)cc3c2C(C)C)cn2ncnc12] | 520.3 | 1.78 | QC-ACN-TFA-XB |

TABLE 15-continued

| Ex. No. | Template Starting Material | Structure | LCMS MH+ | R$_t$ (min) | HPLC Method |
|---|---|---|---|---|---|
| 605 | EX-2 | 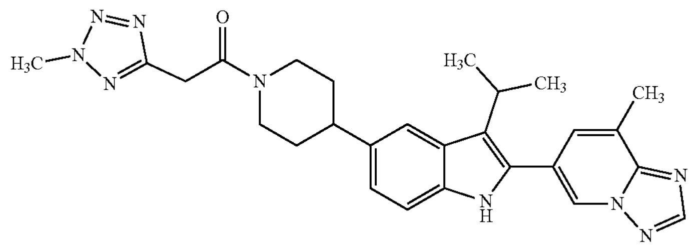 [SMILES: Cc1cc(-c2[nH]c3ccc(C4CCN(C(=O)Cc5nnn(C)n5)CC4)cc3c2C(C)C)cn2ncnc12] | 498.0 | 1.63 | QC-ACN-TFA-XB |
| 606 | EX-2 | 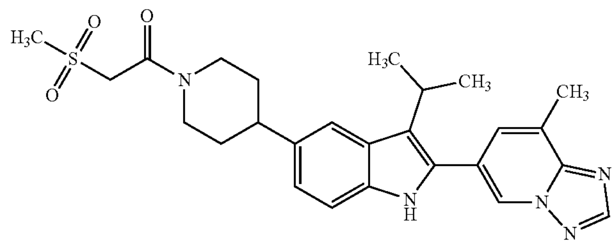 [SMILES: Cc1cc(-c2[nH]c3ccc(C4CCN(C(=O)CS(C)(=O)=O)CC4)cc3c2C(C)C)cn2ncnc12] | 494.2 | 1.68 | QC-ACN-AA-XB |
| 607 | EX-2 | 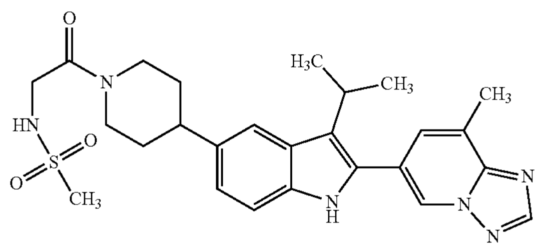 [SMILES: Cc1cc(-c2[nH]c3ccc(C4CCN(C(=O)CNS(C)(=O)=O)CC4)cc3c2C(C)C)cn2ncnc12] | 509.4 | 1.66 | QC-ACN-AA-XB |
| 608 | EX-2 | 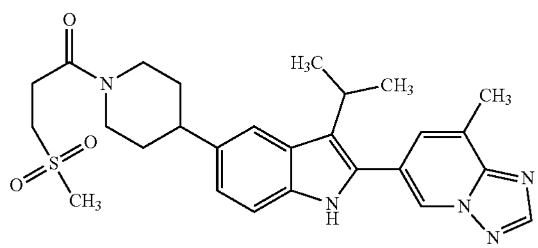 [SMILES: Cc1cc(-c2[nH]c3ccc(C4CCN(C(=O)CCS(C)(=O)=O)CC4)cc3c2C(C)C)cn2ncnc12] | 508.2 | 1.64 | QC-ACN-AA-XB |
| 609 | EX-4 | 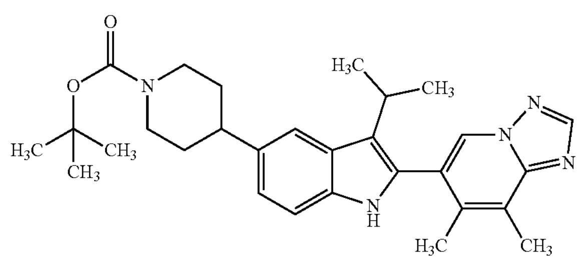 [SMILES: Cc1c(-c2[nH]c3ccc(C4CCN(C(=O)OC(C)(C)C)CC4)cc3c2C(C)C)cn2ncnc2c1C] | 488.0 | 2.39 | QC-ACN-AA-XB |
| 610 | EX-4 | 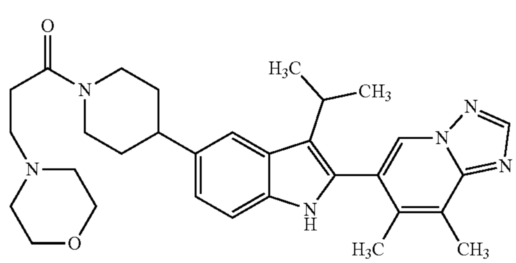 [SMILES: Cc1c(-c2[nH]c3ccc(C4CCN(C(=O)CCN5CCOCC5)CC4)cc3c2C(C)C)cn2ncnc2c1C] | 529.4 | 1.63 | QC-ACN-AA-XB |

TABLE 15-continued
| Ex. No. | Template Starting Material | Structure | LCMS MH+ | R$_t$ (min) | HPLC Method |
|---|---|---|---|---|---|
| 611 | EX-110 | 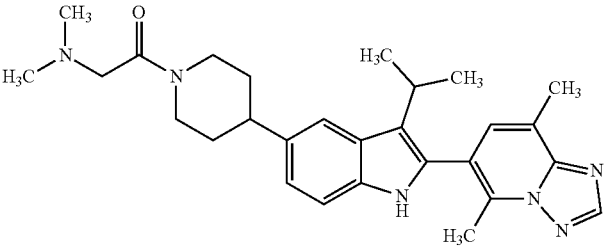 [SMILES: Cc1cc(-c2[nH]c3ccc(C4CCN(C(=O)CN(C)C)CC4)cc3c2C(C)C)c(C)n2ncnc12] | 473.4 | 1.37 | QC-ACN-AA-XB |
TABLE 16
| Ex. No. | Template Starting Material | Structure | LCMS MH+ | R$_t$ (min) | HPLC Method |
|---|---|---|---|---|---|
| 612 | EX-122 | 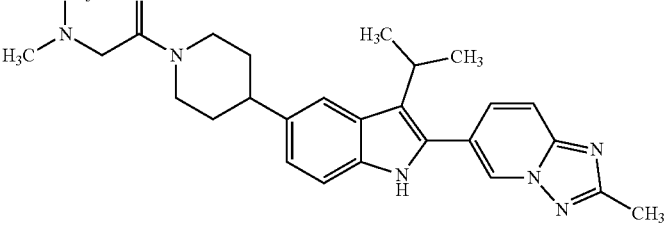 | 459.3 | 2.76 | D |
| 613 | EX-122 | 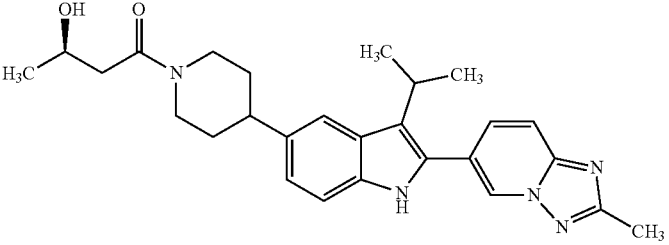 [SMILES: Cc1nc2ccc(-c3[nH]c4ccc(C5CCN(C(=O)C[C@@H](C)O)CC5)cc4c3C(C)C)cn2n1] | 460.3 | 1.64 | E |
| 614 | EX-122 | 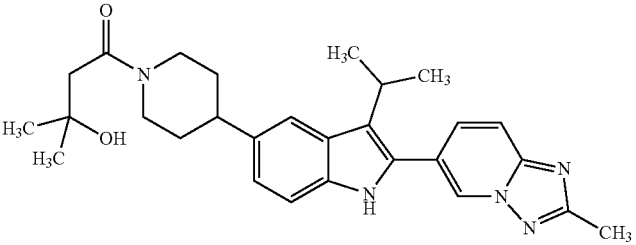 [SMILES: Cc1nc2ccc(-c3[nH]c4ccc(C5CCN(C(=O)CC(C)(C)O)CC5)cc4c3C(C)C)cn2n1] | 474.3 | 1.83 | E |
| 615 | EX-122 | 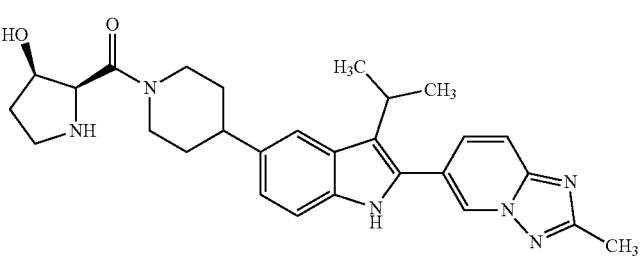 [SMILES: Cc1nc2ccc(-c3[nH]c4ccc(C5CCN(C(=O)[C@H]6NCC[C@H]6O)CC5)cc4c3C(C)C)cn2n1] | 487.3 | 1.36 | E |

TABLE 16-continued

| Ex. No. | Template Starting Material | Structure | LCMS MH+ | R$_t$ (min) | HPLC Method |
|---|---|---|---|---|---|
| 616 | EX-122 | 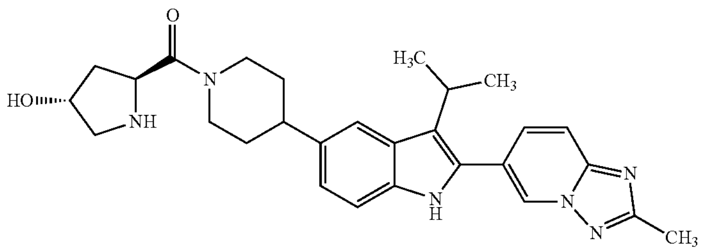 [SMILES: Cc1nc2ccc(-c3[nH]c4ccc(C5CCN(C(=O)[C@@H]6C[C@@H](O)CN6)CC5)cc4c3C(C)C)cn2n1] | 487.3 | 1.3 | E |
| 617 | EX-122 | 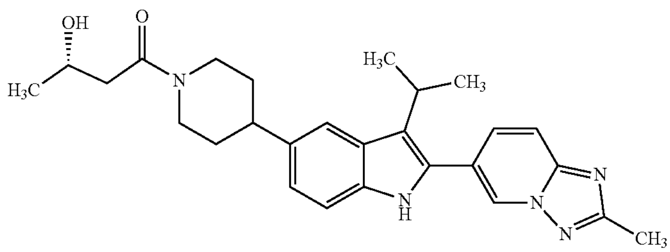 [SMILES: Cc1nc2ccc(-c3[nH]c4ccc(C5CCN(C(=O)C[C@H](C)O)CC5)cc4c3C(C)C)cn2n1] | 460.3 | 1.67 | E |
| 618 | EX-122 | 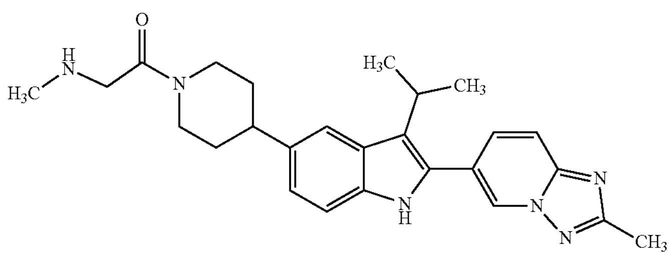 | 445.2 | 1.38 | E |
| 619 | EX-1 | 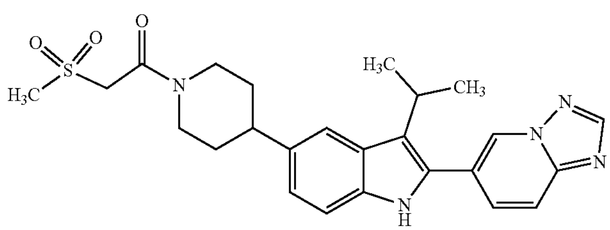 [SMILES: CC(C)c1c(-c2ccc3ncnn3c2)[nH]c2ccc(C3CCN(C(=O)CS(C)(=O)=O)CC3)cc12] | 480.2 | 1.67 | E |
| 620 | EX-2 | 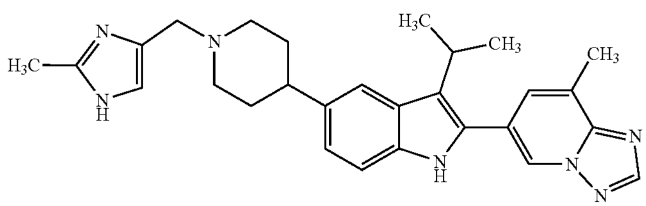 [SMILES: Cc1nc(CN2CCC(c3ccc4[nH]c(-c5cc(C)c6ncnn6c5)c(C(C)C)c4c3)CC2)c[nH]1] | 468.3 | 1.23 | F |
| 621 | EX-2 | 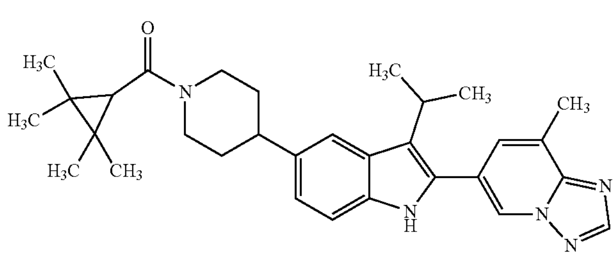 [SMILES: Cc1cc(-c2[nH]c3ccc(C4CCN(C(=O)C5C(C)(C)C5(C)C)CC4)cc3c2C(C)C)cn2ncnc12] | 498.5 | 2.29 | E |

TABLE 16-continued

| Ex. No. | Template Starting Material | Structure | LCMS MH+ | R_t (min) | HPLC Method |
|---|---|---|---|---|---|
| 622 | EX-2 | 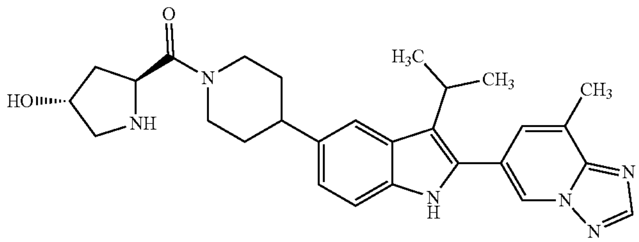 [SMILES: Cc1cc(-c2[nH]c3ccc(C4CCN(C(=O)[C@@H]5C[C@@H](O)CN5)CC4)cc3c2C(C)C)cn2ncnc12] | 487.3 | 1.42 | F |
| 623 | EX-2 | 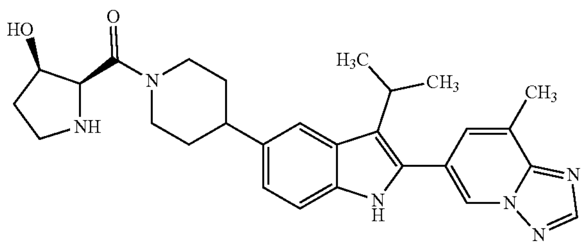 [SMILES: Cc1cc(-c2[nH]c3ccc(C4CCN(C(=O)[C@H]5NCC[C@H]5O)CC4)cc3c2C(C)C)cn2ncnc12] | 487.3 | 1.4 | E |
| 624 | EX-2 | 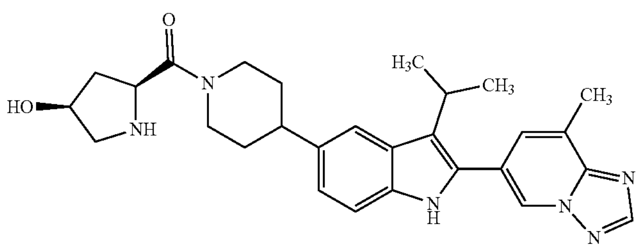 [SMILES: Cc1cc(-c2[nH]c3ccc(C4CCN(C(=O)[C@@H]5C[C@H](O)CN5)CC4)cc3c2C(C)C)cn2ncnc12] | 487.3 | 1.3 | F |
| 625 | EX-2 | 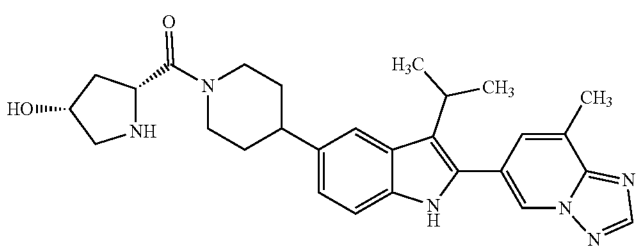 [SMILES: Cc1cc(-c2[nH]c3ccc(C4CCN(C(=O)[C@H]5C[C@@H](O)CN5)CC4)cc3c2C(C)C)cn2ncnc12] | 487 | 1.4 | E |
| 626 | EX-2 | 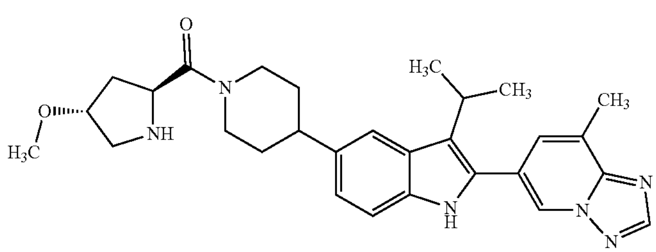 [SMILES: CO[C@H]1CN[C@H](C(=O)N2CCC(c3ccc4[nH]c(-c5cc(C)c6ncnn6c5)c(C(C)C)c4c3)CC2)C1] | 501.2 | 1.46 | F |
| 627 | EX-2 | 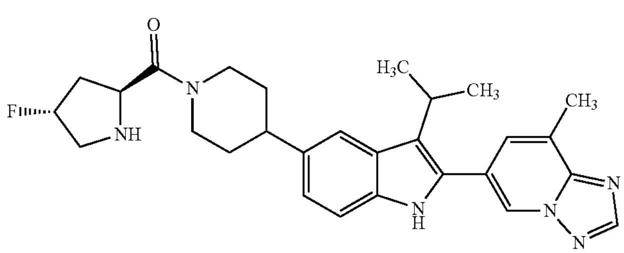 [SMILES: Cc1cc(-c2[nH]c3ccc(C4CCN(C(=O)[C@@H]5C[C@@H](F)CN5)CC4)cc3c2C(C)C)cn2ncnc12] | 489.1 | 1.74 | E |

TABLE 16-continued

| Ex. No. | Template Starting Material | Structure | LCMS MH+ | R$_t$ (min) | HPLC Method |
|---|---|---|---|---|---|
| 628 | EX-2 | 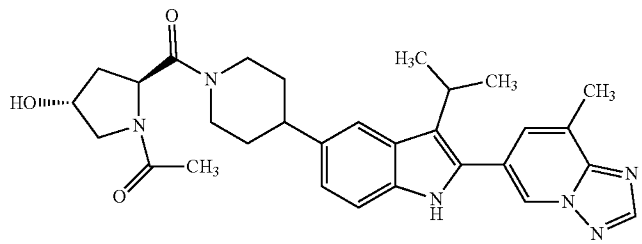 [SMILES: CC(=O)N1C[C@H](O)C[C@H]1C(=O)N1CCC(c2ccc3[nH]c(-c4cc(C)c5ncnn5c4)c(C(C)C)c3c2)CC1] | 529.3 | 1.5 | E |
| 629 | EX-124 | 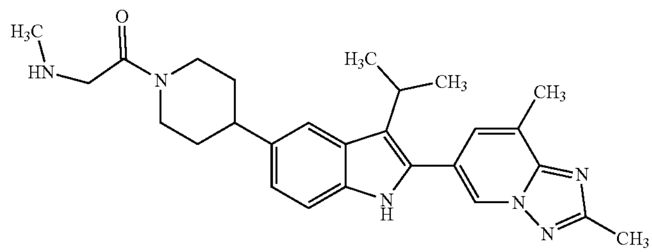 | 459.3 | 1.95 | D |
| 630 | EX-124 | 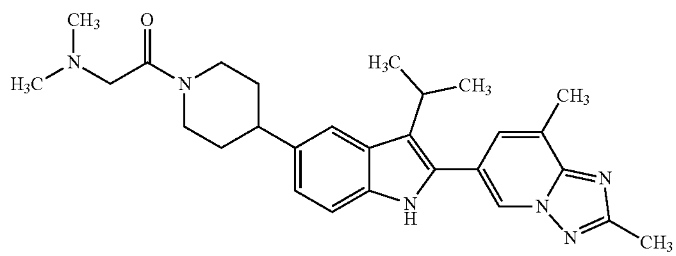 | 473.3 | 2.35 | D |
| 631 | EX-124 | 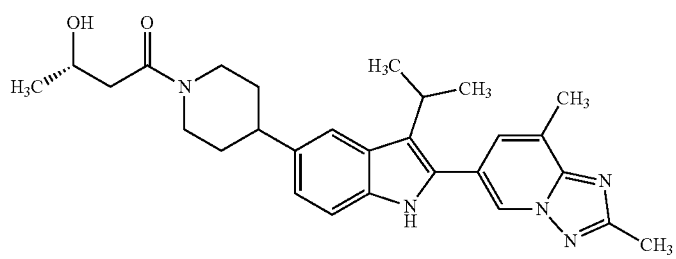 | 474.3 | 1.85 | E |
| 632 | EX-124 | 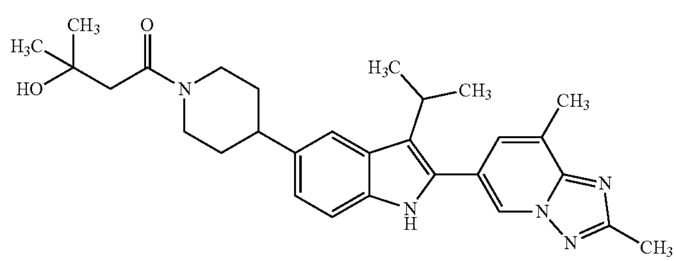 [SMILES: Cc1nc2c(C)cc(-c3[nH]c4ccc(C5CCN(C(=O)CC(C)(C)O)CC5)cc4c3C(C)C)cn2n1] | 488.3 | 1.96 | E |
| 633 | EX-124 | 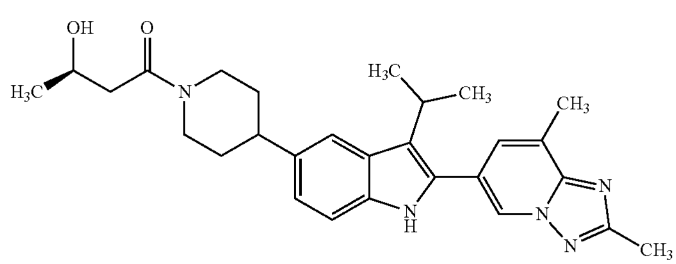 [SMILES: Cc1nc2c(C)cc(-c3[nH]c4ccc(C5CCN(C(=O)C[C@@H](C)O)CC5)cc4c3C(C)C)cn2n1] | 474.3 | 1.82 | E |

TABLE 16-continued

| Ex. No. | Template Starting Material | Structure | LCMS MH+ | R_t (min) | HPLC Method |
|---|---|---|---|---|---|
| 634 | EX-124 | 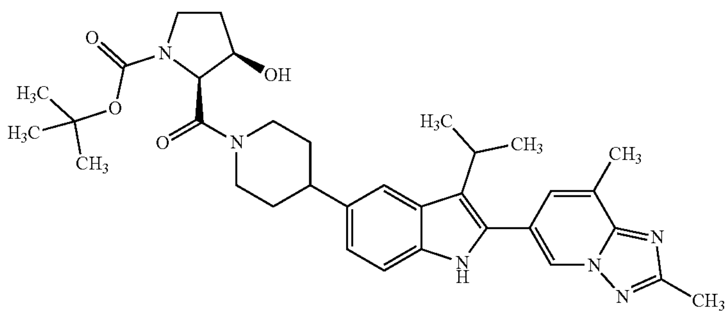 [SMILES: Cc1nc2c(C)cc(-c3[nH]c4ccc(C5CCN(C(=O)[C@@H]6[C@H](O)CCN6C(=O)OC(C)(C)C)CC5)cc4c3C(C)C)cn2n1] | 601 | 1.92 | E |
| 635 | EX-124 | 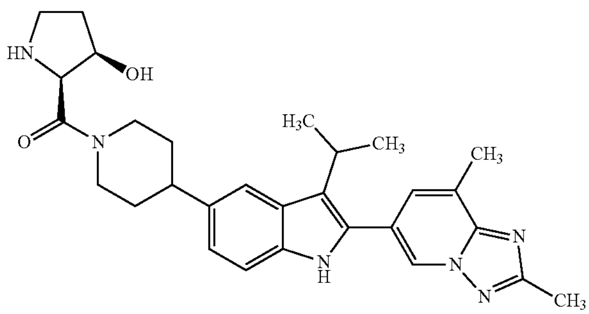 [SMILES: Cc1nc2c(C)cc(-c3[nH]c4ccc(C5CCN(C(=O)[C@H]6NCC[C@H]6O)CC5)cc4c3C(C)C)cn2n1] | 501.3 | 1.36 | E |
| 636 | EX-124 | 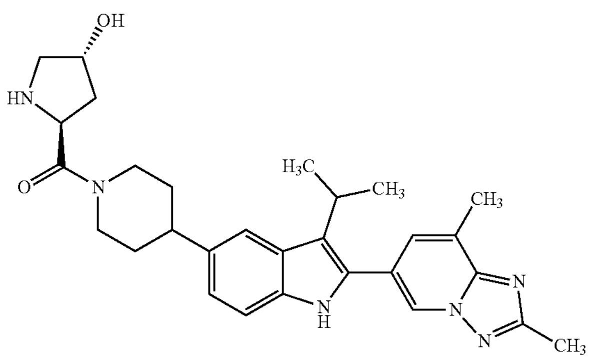 [SMILES: Cc1nc2c(C)cc(-c3[nH]c4ccc(C5CCN(C(=O)[C@@H]6C[C@@H](O)CN6)CC5)cc4c3C(C)C)cn2n1] | 501.3 | 1.88 | D |
| 637 | EX-125 | 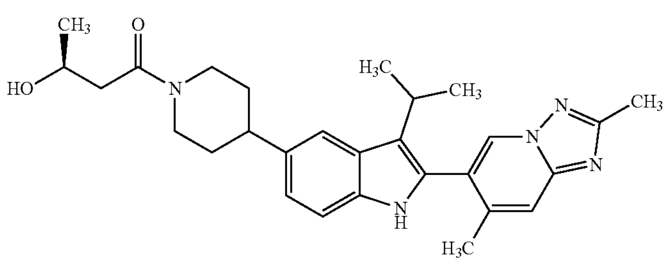 [SMILES: Cc1nc2cc(C)c(-c3[nH]c4ccc(C5CCN(C(=O)C[C@H](C)O)CC5)cc4c3C(C)C)cn2n1] | 474.3 | 1.71 | E |
| 638 | EX-125 | 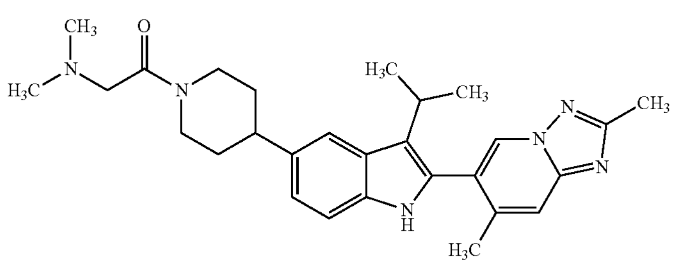 | 473 | 1.54 | E |

TABLE 16-continued

| Ex. No. | Template Starting Material | Structure | LCMS MH+ | R$_t$ (min) | HPLC Method |
|---|---|---|---|---|---|
| 639 | EX-125 | 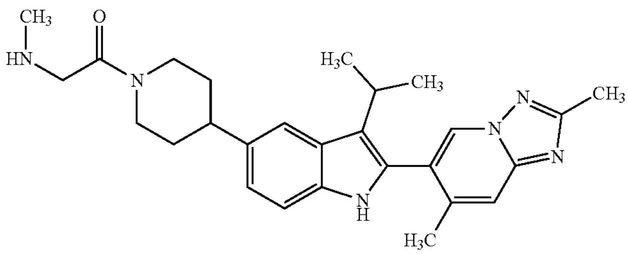 [SMILES: CNCC(=O)N1CCC(c2ccc3[nH]c(-c4cn5nc(C)nc5cc4C)c(C(C)C)c3c2)CC1] | 459 | 1.21 | E |
| 640 | EX-112 | 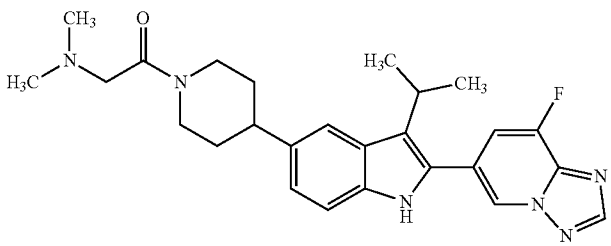 [SMILES: CC(C)c1c(-c2cc(F)c3ncnn3c2)[nH]c2ccc(C3CCN(C(=O)CN(C)C)CC3)cc12] | 463.4 | 1.06 | F |
| 641 | EX-128 | 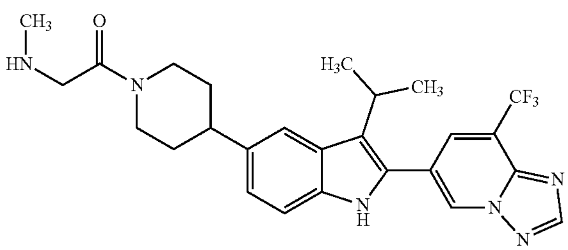 [SMILES: CNCC(=O)N1CCC(c2ccc3[nH]c(-c4cc(C(F)(F)F)c5ncnn5c4)c(C(C)C)c3c2)CC1] | 499.3 | 1.59 | E |
| 642 | EX-128 | 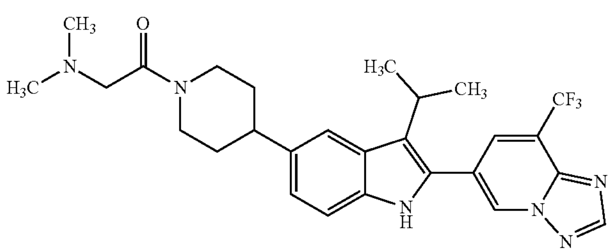 | 513.3 | 1.75 | E |
| 643 | EX-128 | 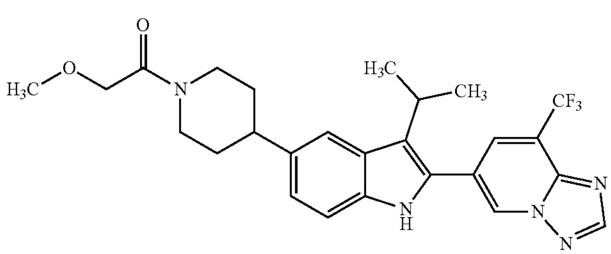 [SMILES: COCC(=O)N1CCC(c2ccc3[nH]c(-c4cc(C(F)(F)F)c5ncnn5c4)c(C(C)C)c3c2)CC1] | 500.3 | 1.83 | E |
| 644 | EX-128 | 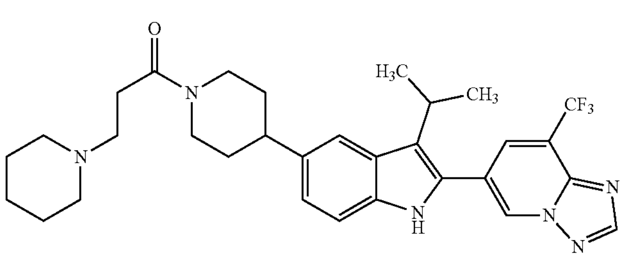 [SMILES: CC(C)c1c(-c2cc(C(F)(F)F)c3ncnn3c2)[nH]c2ccc(C3CCN(C(=O)CCN4CCCCC4)CC3)cc12] | 567.4 | 1.7 | E |

TABLE 16-continued
| Ex. No. | Template Starting Material | Structure | LCMS MH+ | R_t (min) | HPLC Method |
|---|---|---|---|---|---|
| 645 | EX-128 | 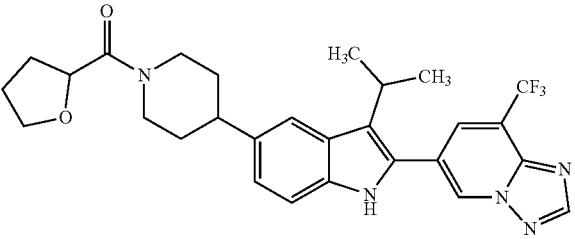 [SMILES: CC(C)c1c(-c2cc(C(F)(F)F)c3ncnn3c2)[nH]c2ccc(C3CCN(C(=O)C4CCCO4)CC3)cc12] | 526.4 | 1.9 | E |
| 646 | EX-128 | 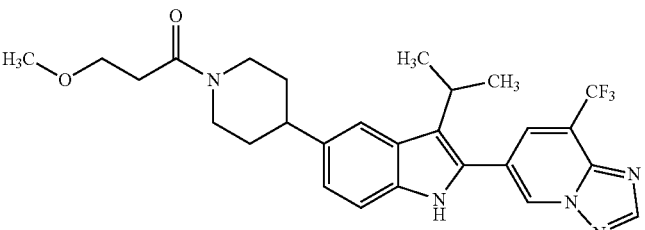 | 514.4 | 1.88 | E |
| 647 | EX-128 | 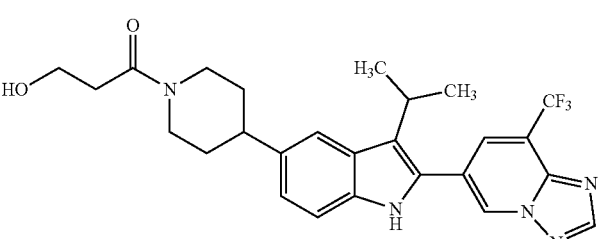 | 500.3 | 1.64 | E |
| 648 | EX-128 | 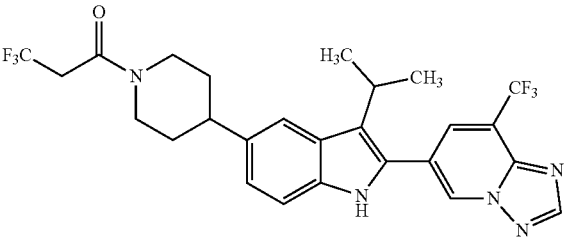 [SMILES: CC(C)c1c(-c2cc(C(F)(F)F)c3ncnn3c2)[nH]c2ccc(C3CCN(C(=O)CC(F)(F)F)CC3)cc12] | 538.3 | 2.07 | E |
| 649 | EX-128 | 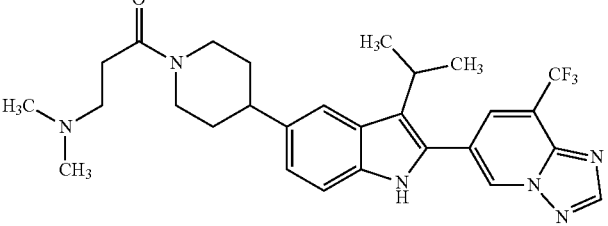 | 527.4 | 1.48 | E |
| 650 | EX-128 | 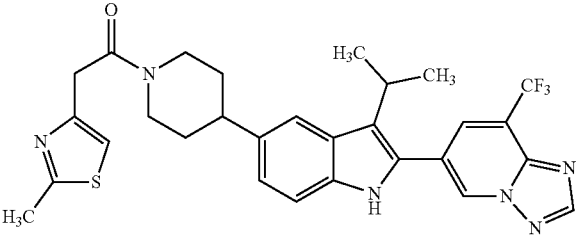 [SMILES: Cc1nc(CC(=O)N2CCC(c3ccc4[nH]c(-c5cc(C(F)(F)F)c6ncnn6c5)c(C(C)C)c4c3)CC2)cs1] | 567.3 | 1.95 | E |

TABLE 16-continued

| Ex. No. | Template Starting Material | Structure | LCMS MH+ | R_t (min) | HPLC Method |
|---|---|---|---|---|---|
| 651 | EX-128 | 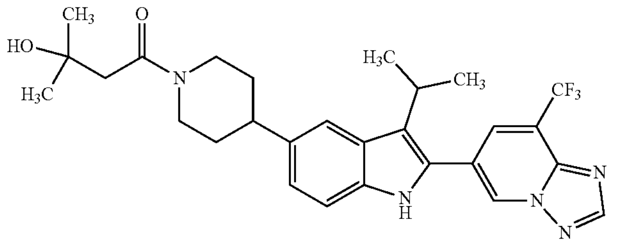 [SMILES: CC(C)c1c(-c2cc(C(F)(F)F)c3ncnn3c2)[nH]c2ccc(C3CCN(C(=O)CC(C)(C)O)CC3)cc12] | 528.2 | 1.92 | E |
| 652 | EX-128 | 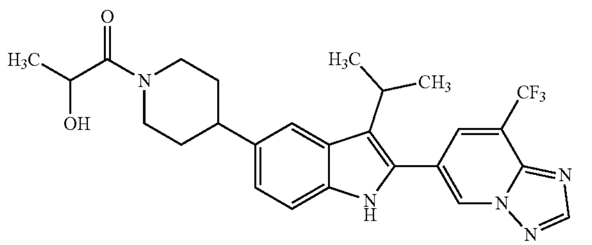 [SMILES: CC(O)C(=O)N1CCC(c2ccc3[nH]c(-c4cc(C(F)(F)F)c5ncnn5c4)c(C(C)C)c3c2)CC1] | 500.2 | 1.77 | E |
| 653 | EX-128 | 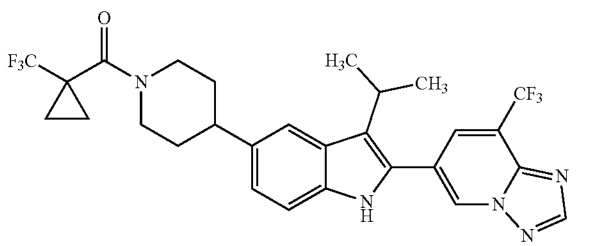 [SMILES: CC(C)c1c(-c2cc(C(F)(F)F)c3ncnn3c2)[nH]c2ccc(C3CCN(C(=O)C4(C(F)(F)F)CC4)CC3)cc12] | 564.3 | 2.22 | E |
| 654 | EX-128 | 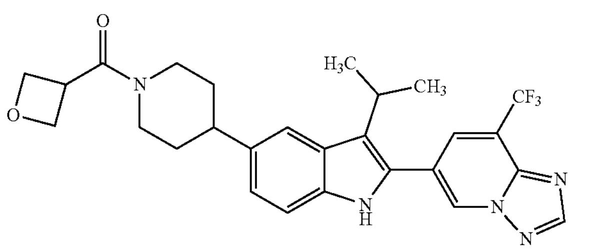 [SMILES: CC(C)c1c(-c2cc(C(F)(F)F)c3ncnn3c2)[nH]c2ccc(C3CCN(C(=O)C4COC4)CC3)cc12] | 512.3 | 1.68 | E |
| 655 | EX-128 | 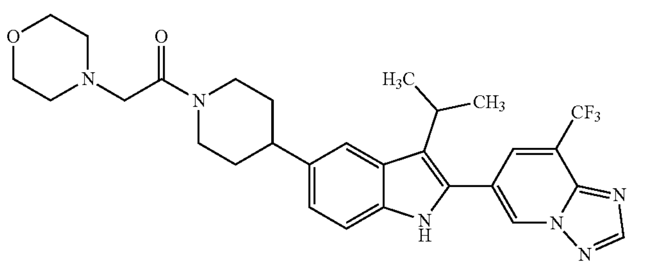 [SMILES: CC(C)c1c(-c2cc(C(F)(F)F)c3ncnn3c2)[nH]c2ccc(C3CCN(C(=O)CN4CCOCC4)CC3)cc12] | 555.4 | 1.82 | E |
| 656 | EX-142 | 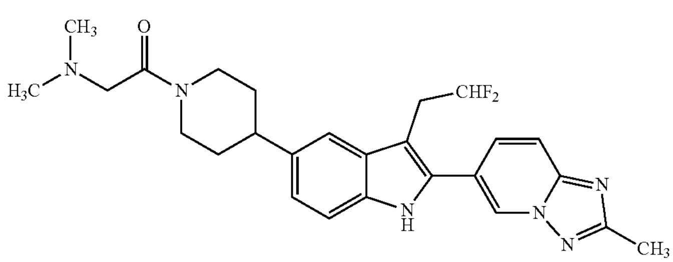 | 481.3 | 1.49 | E |

TABLE 16-continued

| Ex. No. | Template Starting Material | Structure | LCMS MH+ | R_t (min) | HPLC Method |
|---|---|---|---|---|---|
| 657 | EX-142 | 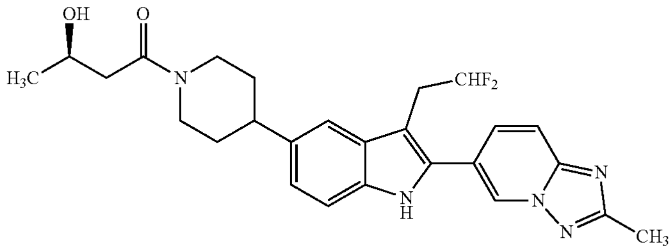 [SMILES: Cc1nc2ccc(-c3[nH]c4ccc(C5CCN(C(=O)C[C@@H](C)O)CC5)cc4c3CC(F)F)cn2n1] | 482.2 | 1.7 | E |
| 658 | EX-142 | 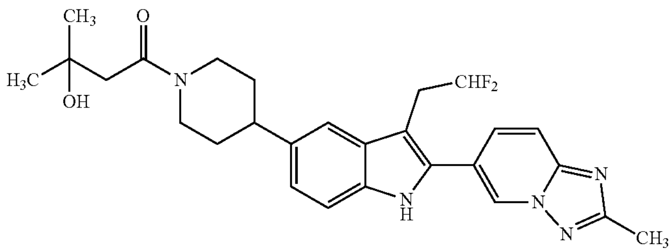 [SMILES: Cc1nc2ccc(-c3[nH]c4ccc(C5CCN(C(=O)CC(C)(C)O)CC5)cc4c3CC(F)F)cn2n1] | 496.2 | 1.72 | E |
| 659 | EX-142 | 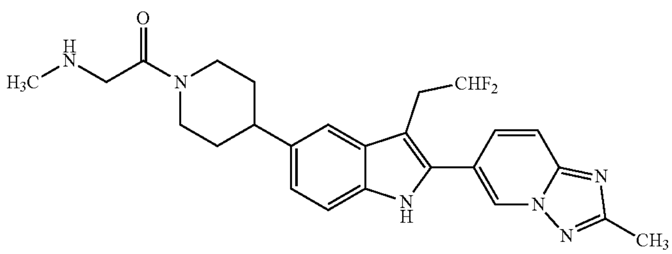 | 467.3 | 1.4 | E |
| 660 | EX-155 | 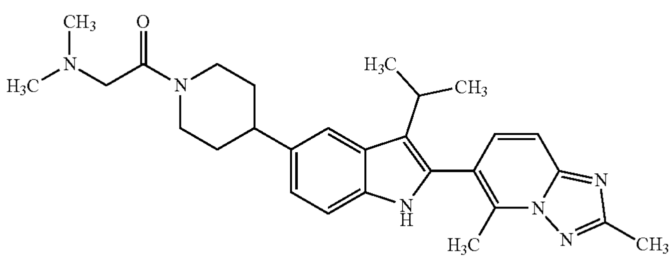 | 473 | 1.6 | E |
| 661 | EX-155 | 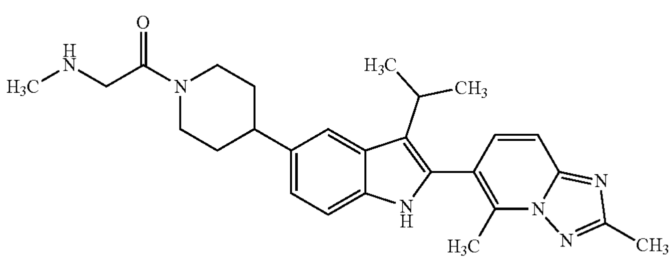 | 459 | 1.49 | E |
| 662 | EX-96 | 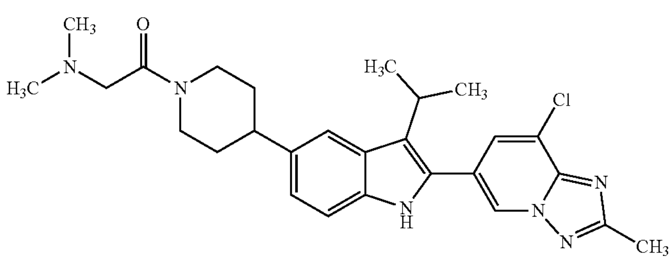 | 493.3 | 1.46 | E |

TABLE 16-continued

| Ex. No. | Template Starting Material | Structure | LCMS MH+ | R$_t$ (min) | HPLC Method |
|---|---|---|---|---|---|
| 663 | EX-5 | 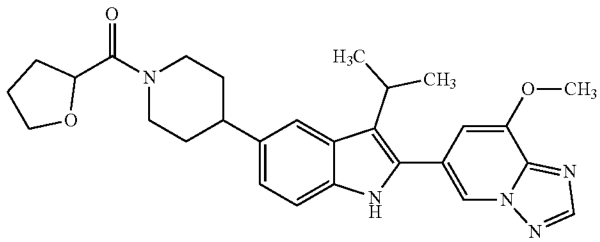 [SMILES: COc1cc(-c2[nH]c3ccc(C4CCN(C(=O)C5CCCO5)CC4)cc3c2C(C)C)cn2ncnc12] | 488.4 | 1.62 | E |
| 664 | EX-5 | 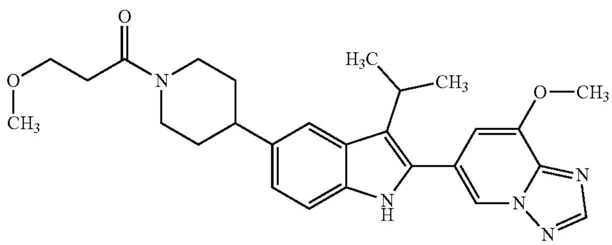 [SMILES: COCCC(=O)N1CCC(c2ccc3[nH]c(-c4cc(OC)c5ncnn5c4)c(C(C)C)c3c2)CC1] | 476.4 | 1.59 | E |
| 665 | EX-5 | 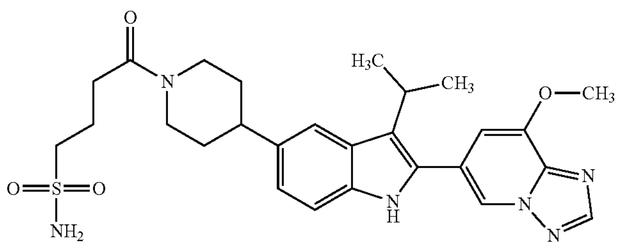 [SMILES: COc1cc(-c2[nH]c3ccc(C4CCN(C(=O)CCCS(N)(=O)=O)CC4)cc3c2C(C)C)cn2ncnc12] | 539.4 | 1.38 | E |
| 666 | EX-5 | 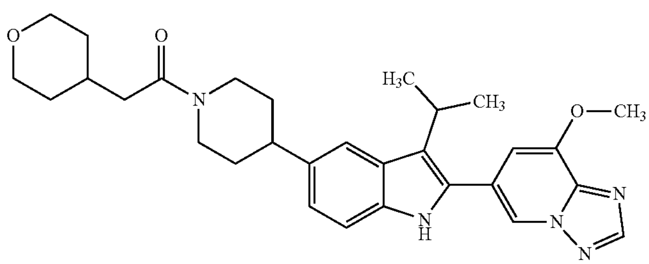 [SMILES: COc1cc(-c2[nH]c3ccc(C4CCN(C(=O)CC5CCOCC5)CC4)cc3c2C(C)C)cn2ncnc12] | 516.4 | 1.69 | E |
| 667 | EX-5 | 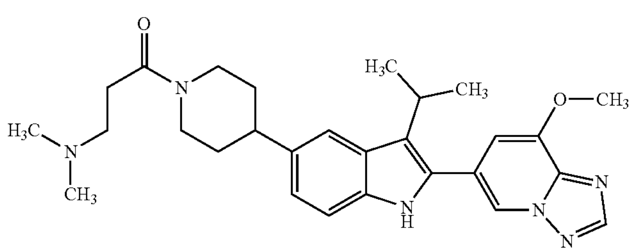 [SMILES: COc1cc(-c2[nH]c3ccc(C4CCN(C(=O)CCN(C)C)CC4)cc3c2C(C)C)cn2ncnc12] | 489.4 | 1.32 | E |
| 668 | EX-5 | 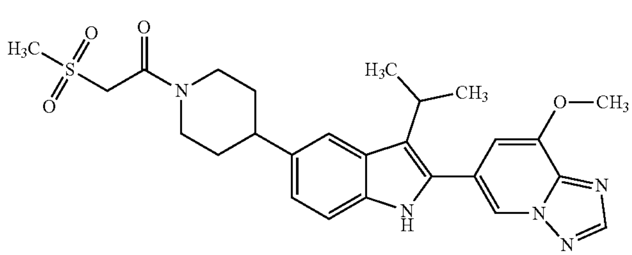 [SMILES: COc1cc(-c2[nH]c3ccc(C4CCN(C(=O)CS(C)(=O)=O)CC4)cc3c2C(C)C)cn2ncnc12] | 510.3 | 1.43 | E |

TABLE 16-continued

| Ex. No. | Template Starting Material | Structure | LCMS MH+ | R_t (min) | HPLC Method |
|---|---|---|---|---|---|
| 669 | EX-5 | 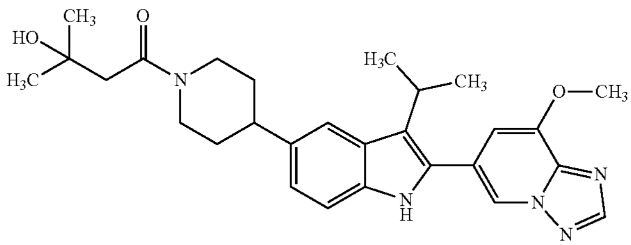 [SMILES: COc1cc(-c2[nH]c3ccc(C4CCN(C(=O)CC(C)(C)O)CC4)cc3c2C(C)C)cn2ncnc12] | 490.4 | 1.64 | E |
| 670 | EX-5 | 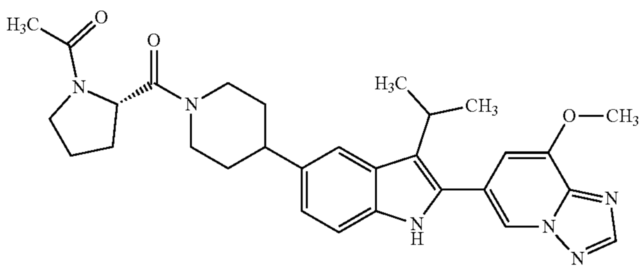 [SMILES: COc1cc(-c2[nH]c3ccc(C4CCN(C(=O)[C@@H]5CCCN5C(C)=O)CC4)cc3c2C(C)C)cn2ncnc12] | 529.4 | 1.46 | E |
| 671 | EX-5 | 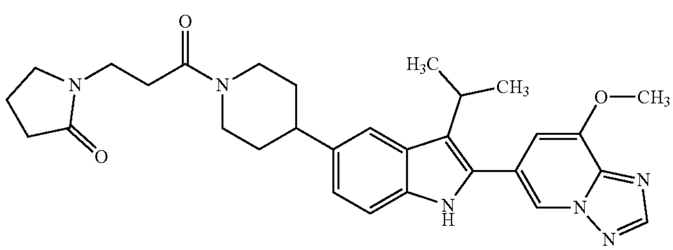 [SMILES: COc1cc(-c2[nH]c3ccc(C4CCN(C(=O)CCN5CCCC5=O)CC4)cc3c2C(C)C)cn2ncnc12] | 529.3 | 1.46 | E |
| 672 | EX-5 | 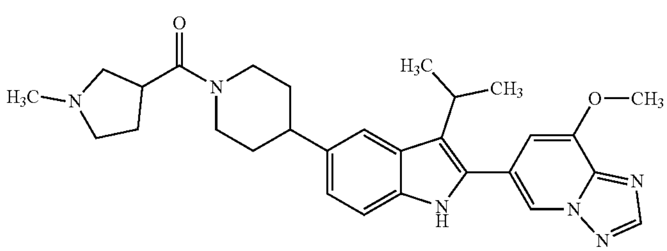 [SMILES: COc1cc(-c2[nH]c3ccc(C4CCN(C(=O)C5CCN(C)C5)CC4)cc3c2C(C)C)cn2ncnc12] | 501.1 | 1.16 | E |
| 673 | EX-5 | 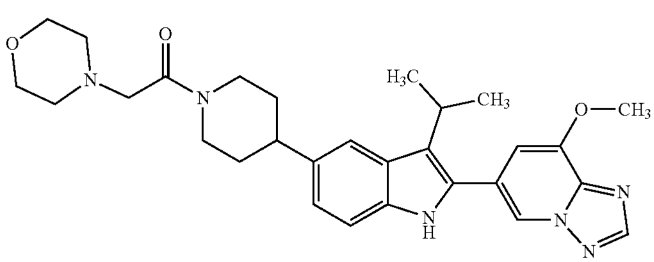 [SMILES: COc1cc(-c2[nH]c3ccc(C4CCN(C(=O)CN5CCOCC5)CC4)cc3c2C(C)C)cn2ncnc12] | 517.4 | 1.55 | E |
| 674 | EX-5 | 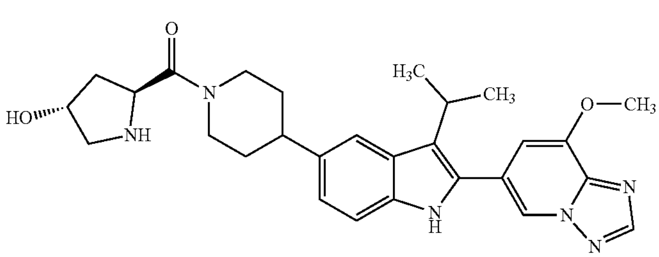 [SMILES: COc1cc(-c2[nH]c3ccc(C4CCN(C(=O)[C@@H]5C[C@@H](O)CN5)CC4)cc3c2C(C)C)cn2ncnc12] | 503.1 | 1.37 | E |

TABLE 16-continued
| Ex. No. | Template Starting Material | Structure | LCMS MH+ | R$_t$ (min) | HPLC Method |
|---|---|---|---|---|---|
| 675 | EX-5 | 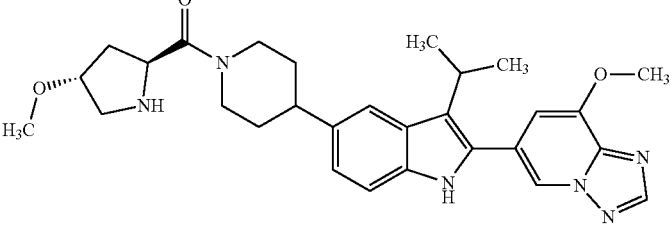 | 517.3 | 1.56 | E |
| 676 | EX-5 | 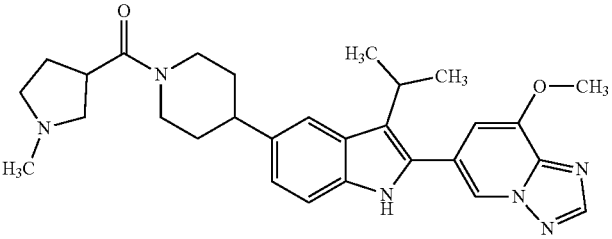 [SMILES: COc1cc(-c2[nH]c3ccc(C4CCN(C(=O)C5CCN(C)C5)CC4)cc3c2C(C)C)cn2ncnc12] | 501.3 | 1.43 | E |
| 677 | EX-5 | 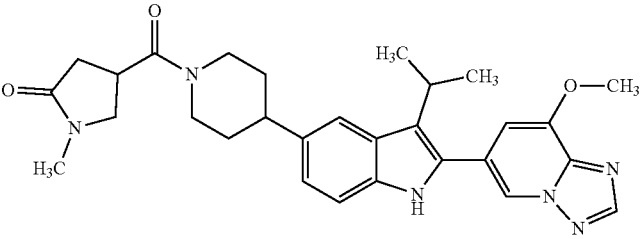 [SMILES: COc1cc(-c2[nH]c3ccc(C4CCN(C(=O)C5CC(=O)N(C)C5)CC4)cc3c2C(C)C)cn2ncnc12] | 515.2 | 7.94 | I |
| 678 | EX-5 | 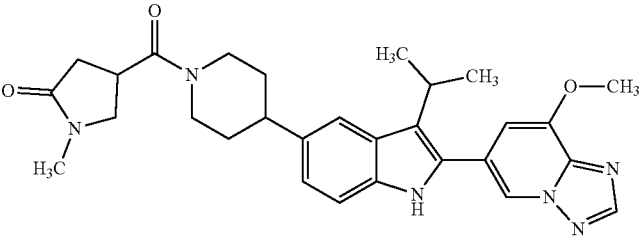 [SMILES: COc1cc(-c2[nH]c3ccc(C4CCN(C(=O)C5CC(=O)N(C)C5)CC4)cc3c2C(C)C)cn2ncnc12] | 515.2 | 7.95 | I |
| 679 | EX-5 | 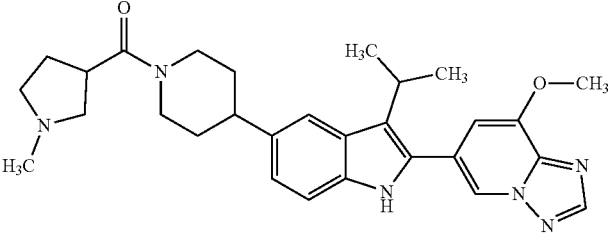 [SMILES: COc1cc(-c2[nH]c3ccc(C4CCN(C(=O)C5CCN(C)C5)CC4)cc3c2C(C)C)cn2ncnc12] | 501.3 | 1.43 | E |
| 680 | EX-132 | 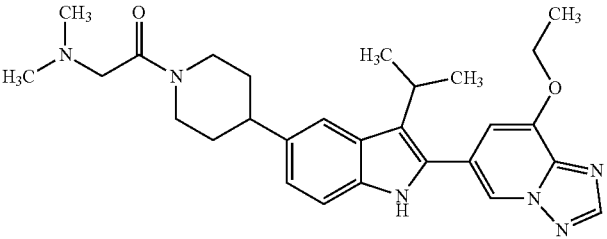 [SMILES: CCOc1cc(-c2[nH]c3ccc(C4CCN(C(=O)CN(C)C)CC4)cc3c2C(C)C)cn2ncnc12] | 489.1 | 1.62 | E |

TABLE 16-continued

| Ex. No. | Template Starting Material | Structure | LCMS MH+ | R_t (min) | HPLC Method |
|---|---|---|---|---|---|
| 681 | EX-132 | 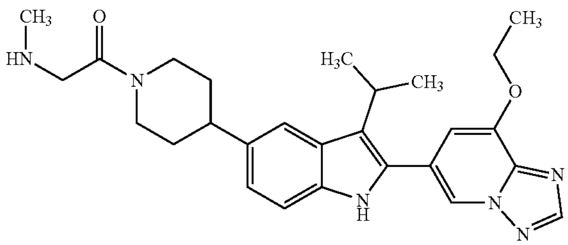 [SMILES: CCOc1cc(-c2[nH]c3ccc(C4CCN(C(=O)CNC)CC4)cc3c2C(C)C)cn2ncnc12] | 475.1 | 1.48 | E |
| 682 | EX-133 | 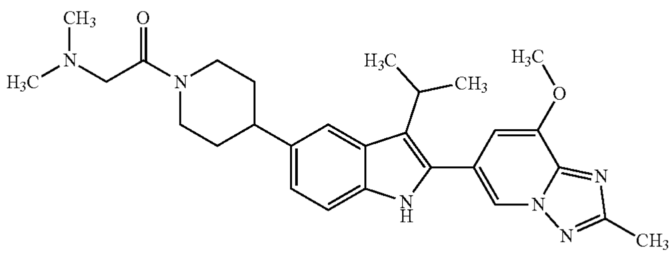 | 489.3 | 1.6 | E |
| 683 | EX-133 | 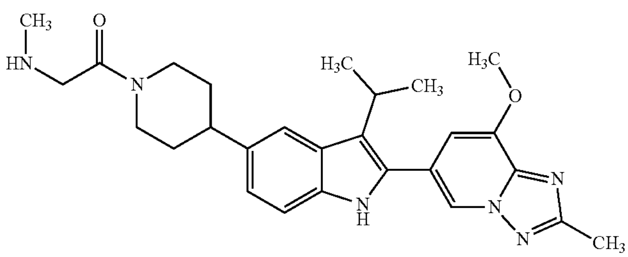 [SMILES: CNCC(=O)N1CCC(c2ccc3[nH]c(-c4cc(OC)c5nc(C)nn5c4)c(C(C)C)c3c2)CC1] | 475.3 | 1.42 | E |
| 684 | EX-136 | 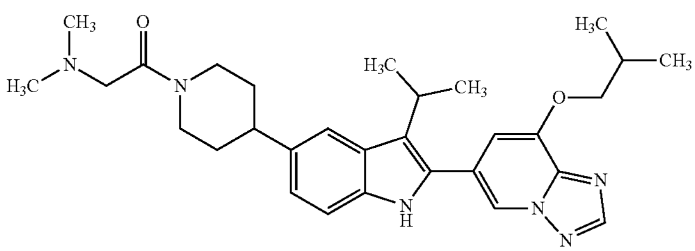 [SMILES: CC(C)COc1cc(-c2[nH]c3ccc(C4CCN(C(=O)CN(C)C)CC4)cc3c2C(C)C)cn2ncnc12] | 517.4 | 1.65 | E |
| 685 | EX-118 | 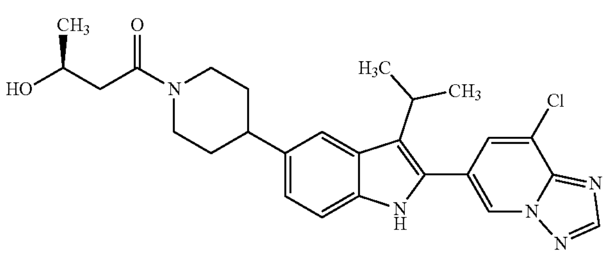 | 480.2 | 1.02 | E |
| 686 | EX-118 | 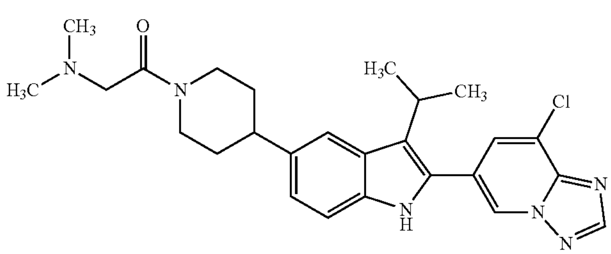 [SMILES: CC(C)c1c(-c2cc(Cl)c3ncnn3c2)[nH]c2ccc(C3CCN(C(=O)CN(C)C)CC3)cc12] | 479.2 | 1.6 | E |

TABLE 16-continued
| Ex. No. | Template Starting Material | Structure | LCMS MH+ | R_t (min) | HPLC Method |
|---|---|---|---|---|---|
| 687 | EX-137 | 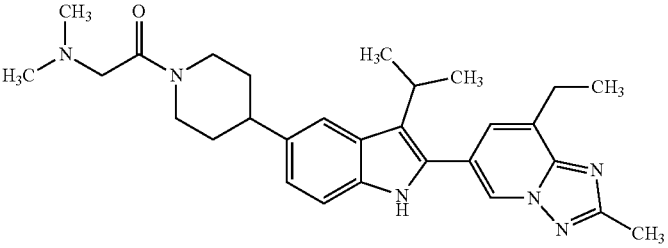 | 487.4 | 1.64 | E |
| 688 | EX-137 | 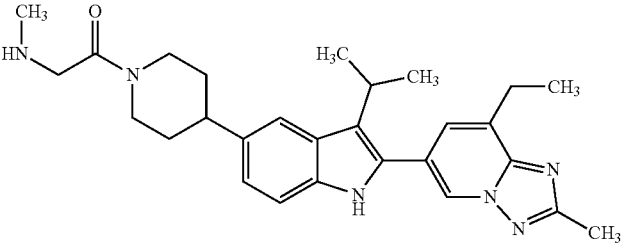 [SMILES: CCc1cc(-c2[nH]c3ccc(C4CCN(C(=O)CNC)CC4)cc3c2C(C)C)cn2nc(C)nc12] | 473.3 | 1.59 | E |
| 689 | EX-119 | 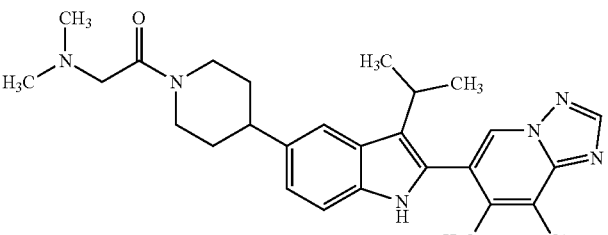 | 493.1 | 1.68 | E |
| 690 | EX-143 | 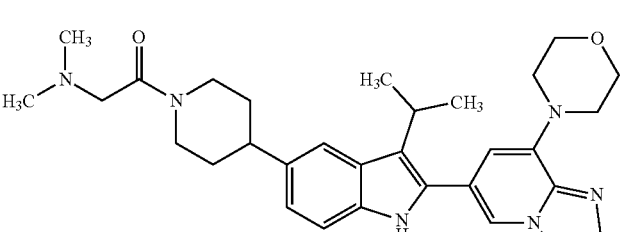 | 530.4 | 1.4 | E |
| 691 | EX-148 | 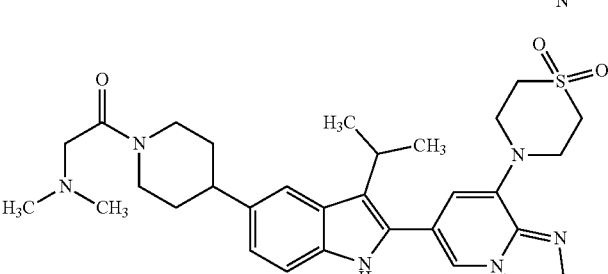 | 578.3 | 1.52 | E |
| 692 | EX-120 | 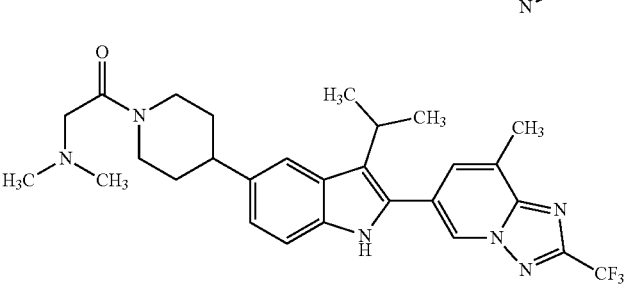 | 527.3 | 2.08 | E |

TABLE 16-continued
| Ex. No. | Template Starting Material | Structure | LCMS MH+ | R$_t$ (min) | HPLC Method |
|---|---|---|---|---|---|
| 693 | EX-120 | 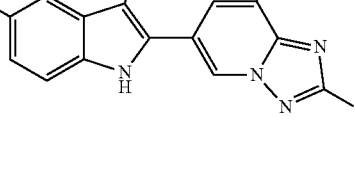 | 513.3 | 1.93 | E |
| 694 | EX-120 | 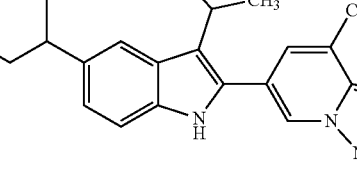 | 567.3 | 1.97 | E |
| 695 | EX-154 | 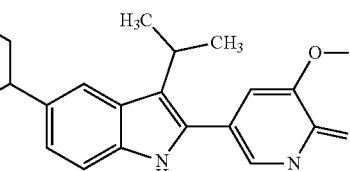 | 543.2 | 1.98 | E |
| 696 | EX-151 | 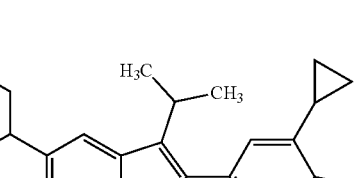 | 485.3 | 1.5 | E |
| 697 | EX-151 | 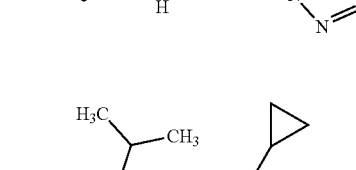 | 471.2 | 1.56 | E |
| 698 | EX-141 | 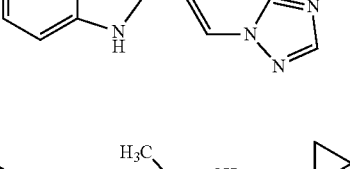 | 499.2 | 1.75 | E |

TABLE 16-continued

| Ex. No. | Template Starting Material | Structure | LCMS MH+ | R$_t$ (min) | HPLC Method |
|---|---|---|---|---|---|
| 699 | EX-152 | 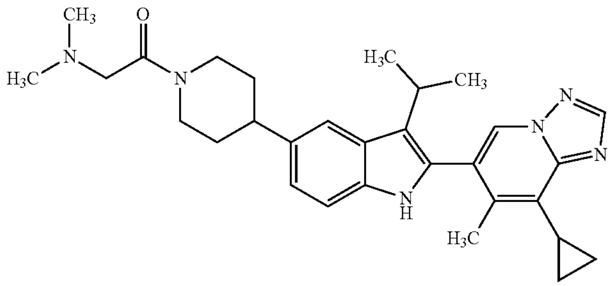 [SMILES: Cc1c(-c2[nH]c3ccc(C4CCN(C(=O)CN(C)C)CC4)cc3c2C(C)C)cn2ncnc2c1C1CC1] | 499.2 | 1.77 | E |
| 700 | EX-152 | 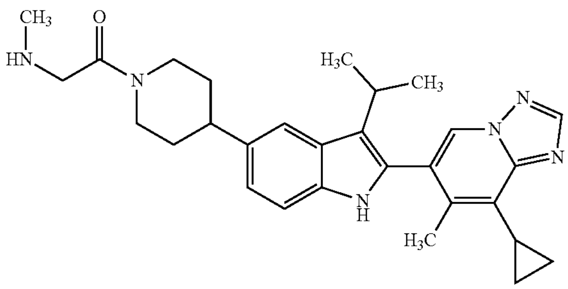 [SMILES: CNCC(=O)N1CCC(c2ccc3[nH]c(-c4cn5ncnc5c(C5CC5)c4C)c(C(C)C)c3c2)CC1] | 485.2 | 1.62 | E |
| 701 | EX-157 | 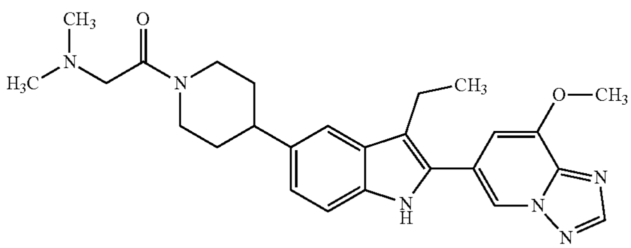 [SMILES: CCc1c(-c2cc(OC)c3ncnn3c2)[nH]c2ccc(C3CCN(C(=O)CN(C)C)CC3)cc12] | 461.3 | 1.19 | E |
| 702 | EX-157 | 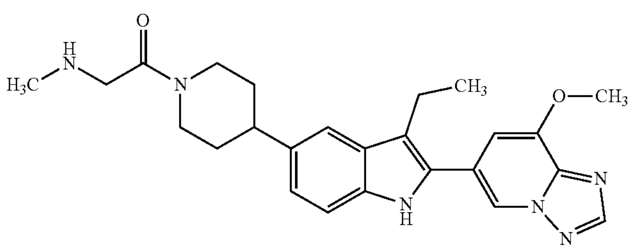 [SMILES: CCc1c(-c2cc(OC)c3ncnn3c2)[nH]c2ccc(C3CCN(C(=O)CNC)CC3)cc12] | 447.3 | 1.08 | E |
| 703 | EX-158 | 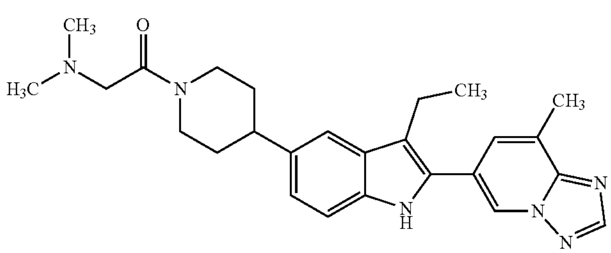 [SMILES: CCc1c(-c2cc(C)c3ncnn3c2)[nH]c2ccc(C3CCN(C(=O)CN(C)C)CC3)cc12] | 445.3 | 1.24 | E |
| 704 | EX-158 | 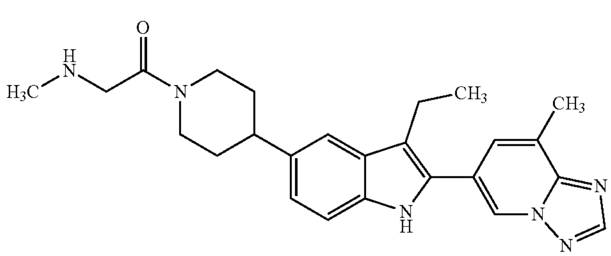 [SMILES: CCc1c(-c2cc(C)c3ncnn3c2)[nH]c2ccc(C3CCN(C(=O)CNC)CC3)cc12] | 431.3 | 1.12 | E |

TABLE 16-continued

| Ex. No. | Template Starting Material | Structure | LCMS MH+ | R_t (min) | HPLC Method |
|---|---|---|---|---|---|
| 705 | EX-161 | 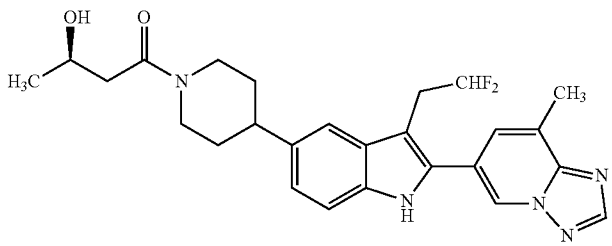 [SMILES: Cc1cc(-c2[nH]c3ccc(C4CCN(C(=O)C[C@@H](C)O)CC4)cc3c2CC(F)F)cn2ncnc12] | 482.2 | 1.57 | E |
| 706 | EX-161 | 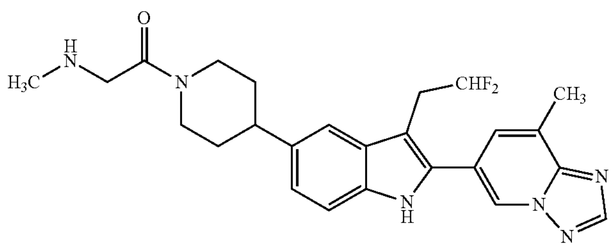 | 467.2 | 1.27 | E |
| 707 | EX-161 | 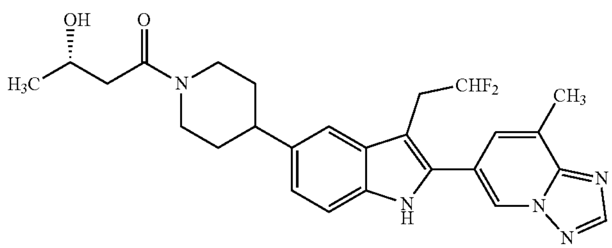 [SMILES: Cc1cc(-c2[nH]c3ccc(C4CCN(C(=O)C[C@H](C)O)CC4)cc3c2CC(F)F)cn2ncnc12] | 482.2 | 1.58 | E |
| 708 | EX-161 | 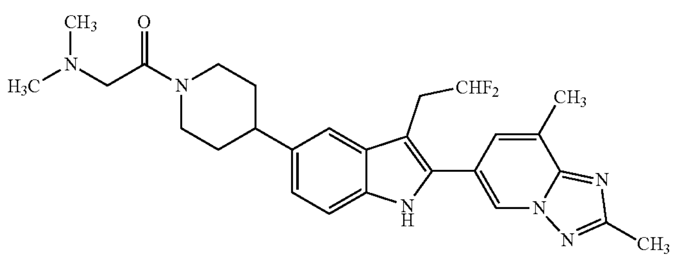 | 495.2 | 1.48 | E |
| 709 | EX-161 | 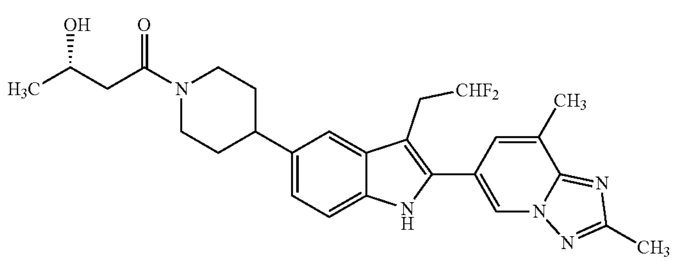 [SMILES: Cc1nc2c(C)cc(-c3[nH]c4ccc(C5CCN(C(=O)C[C@H](C)O)CC5)cc4c3CC(F)F)cn2n1] | 496.2 | 1.68 | E |
| 710 | EX-161 | 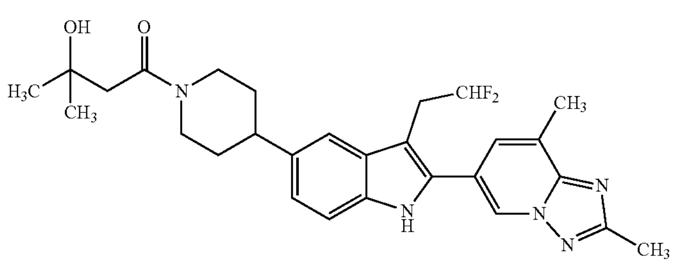 [SMILES: Cc1nc2c(C)cc(-c3[nH]c4ccc(C5CCN(C(=O)CC(C)(C)O)CC5)cc4c3CC(F)F)cn2n1] | 510.3 | 1.82 | E |

TABLE 16-continued

| Ex. No. | Template Starting Material | Structure | LCMS MH+ | R$_t$ (min) | HPLC Method |
|---|---|---|---|---|---|
| 711 | EX-161 | 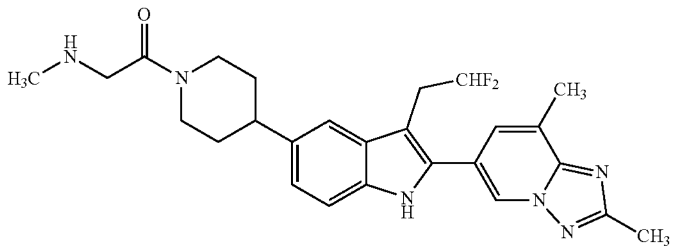 | 481.3 | 1.37 | E |
| 712 | EX-161 | 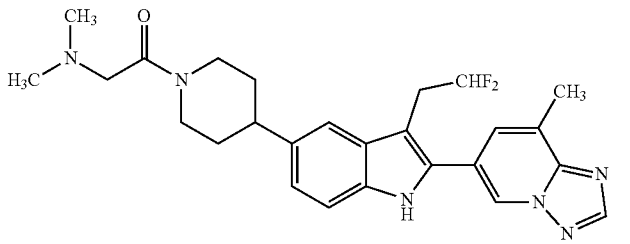 | 481.2 | 1.41 | E |

The following examples were prepared according to the general process disclosed in Example 68.

TABLE 17

| Ex. No. | Template Starting Material | Structure | LCMS MH+ | R$_t$ (min) | HPLC Method |
|---|---|---|---|---|---|
| 713 | EX-1 | 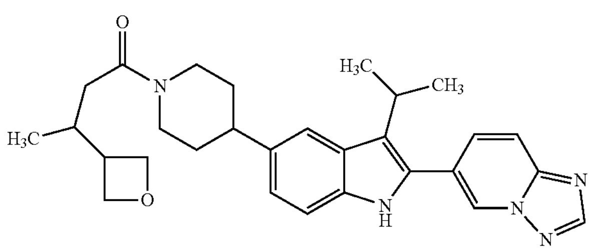 [SMILES: CC(C)c1c(-c2ccc3ncnn3c2)[nH]c2ccc(C3CCN(C(=O)CC(C)C4COC4)CC3)cc12] | 487.2 | 1.17 | QC-ACN-TFA-XB |
| 714 | EX-2 | 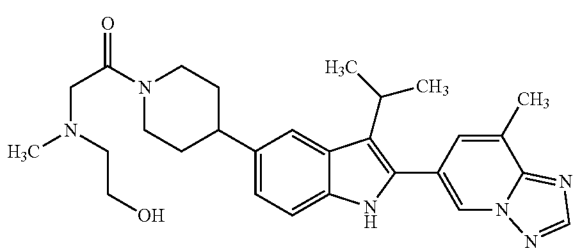 [SMILES: Cc1cc(-c2[nH]c3ccc(C4CCN(C(=O)CN(C)CCO)CC4)cc3c2C(C)C)cn2ncnc12] | 489.1 | 1.26 | QC-ACN-TFA-XB |
| 715 | EX-2 | 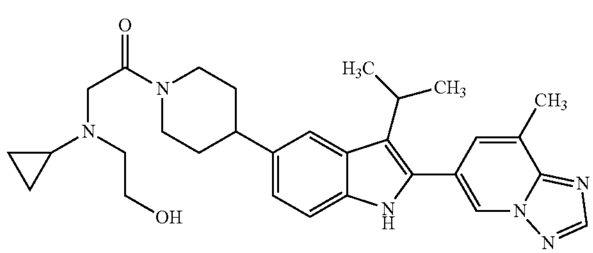 [SMILES: Cc1cc(-c2[nH]c3ccc(C4CCN(C(=O)CN(CCO)C5CC5)CC4)cc3c2C(C)C)cn2ncnc12] | 515.2 | 2.36 | QC-ACN-AA-XB |

TABLE 17-continued

| Ex. No. | Template Starting Material | Structure | LCMS MH+ | R$_t$ (min) | HPLC Method |
|---|---|---|---|---|---|
| 716 | Ex-2 | 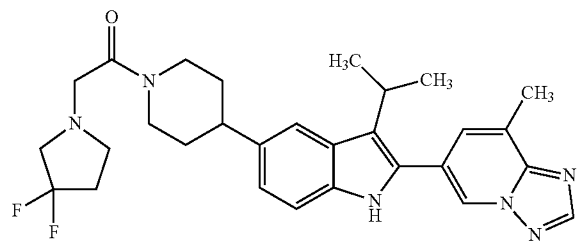 [SMILES: Cc1cc(-c2[nH]c3ccc(C4CCN(C(=O)CN5CCC(F)(F)C5)CC4)cc3c2C(C)C)cn2ncnc12] | 520.9 | 2.55 | QC-ACN-AA-XB |
| 717 | EX-2 | 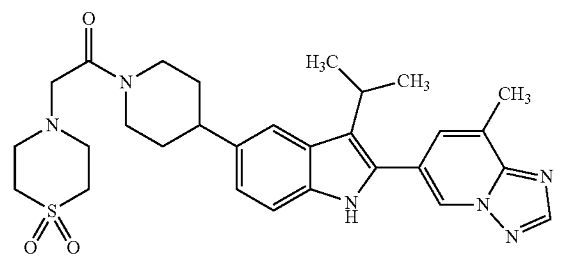 [SMILES: Cc1cc(-c2[nH]c3ccc(C4CCN(C(=O)CN5CCS(=O)(=O)CC5)CC4)cc3c2C(C)C)cn2ncnc12] | 549.1 | 2.08 | QC-ACN-AA-XB |
| 718 | EX-4 | 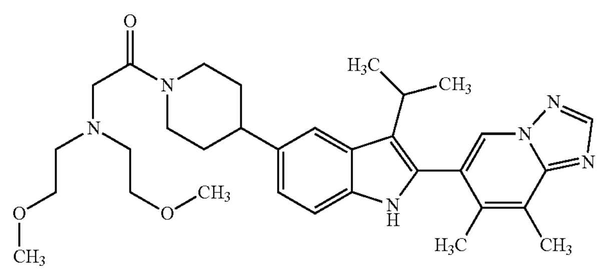 [SMILES: COCCN(CCOC)CC(=O)N1CCC(c2ccc3[nH]c(-c4cn5ncnc5c(C)c4C)c(C(C)C)c3c2)CC1] | 561.4 | 1.46 | QC-ACN-TFA-XB |
| 719 | EX-4 | 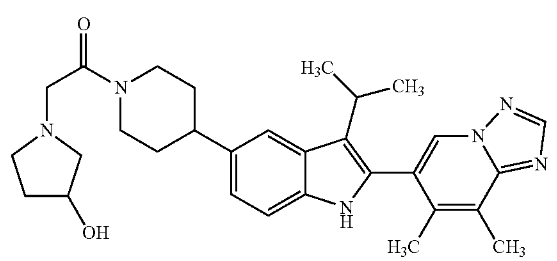 [SMILES: Cc1c(-c2[nH]c3ccc(C4CCN(C(=O)CN5CCC(O)C5)CC4)cc3c2C(C)C)cn2ncnc2c1C] | 258.1 | 1.22 | QC-ACN-TFA-XB |
| 720 | EX-4 | 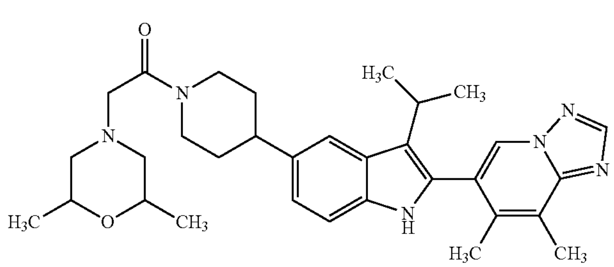 [SMILES: Cc1c(-c2[nH]c3ccc(C4CCN(C(=O)CN5CC(C)OC(C)C5)CC4)cc3c2C(C)C)cn2ncnc2c1C] | 543.1 | 1.97 | QC-ACN-AA-XB |

TABLE 17-continued
| Ex. No. | Template Starting Material | Structure | LCMS MH+ | R$_t$ (min) | HPLC Method |
|---|---|---|---|---|---|
| 721 | EX-4 | 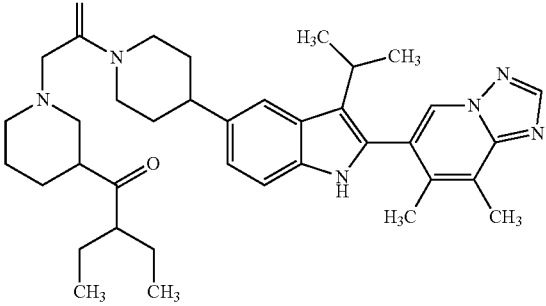 | 612.2 | 1.83 | QC-ACN-AA-XB |
| 722 | EX-4 | 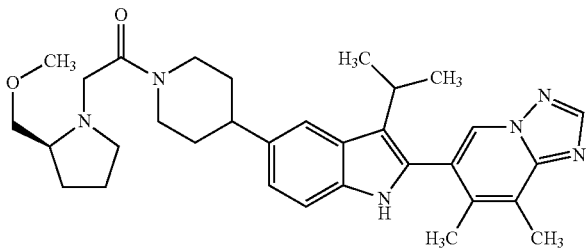 [SMILES: COC[C@@H]1CCCN1CC(=O)N1CCC(c2ccc3[nH]c(-c4cn5ncnc5c(C)c4C)c(C(C)C)c3c2)CC1] | 543.3 | 1.78 | QC-ACN-AA-XB |
| 723 | EX-4 | 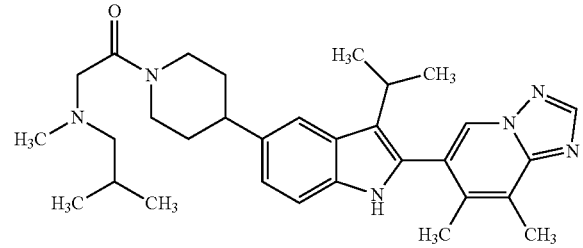 [SMILES: Cc1c(-c2[nH]c3ccc(C4CCN(C(=O)CN(C)CC(C)C)CC4)cc3c2C(C)C)cn2ncnc2c1C] | 258.4 | 1.44 | QC-ACN-TFA-XB |
| 724 | EX-4 | 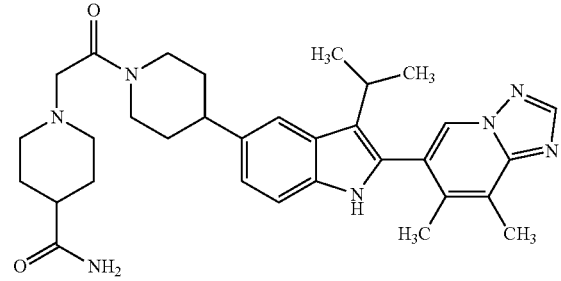 [SMILES: Cc1c(-c2[nH]c3ccc(C4CCN(C(=O)CN5CCC(C(N)=O)CC5)CC4)cc3c2C(C)C)cn2ncnc2c1C] | 556.3 | 1.2 | QC-ACN-TFA-XB |
| 725 | EX-4 | 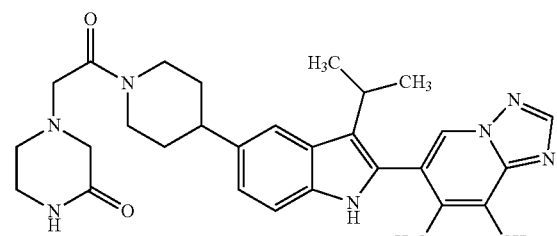 | 528.2 | 1.68 | QC-ACN-AA-XB |

TABLE 17-continued

| Ex. No. | Template Starting Material | Structure | LCMS MH+ | R$_t$ (min) | HPLC Method |
|---|---|---|---|---|---|
| 726 | EX-4 | 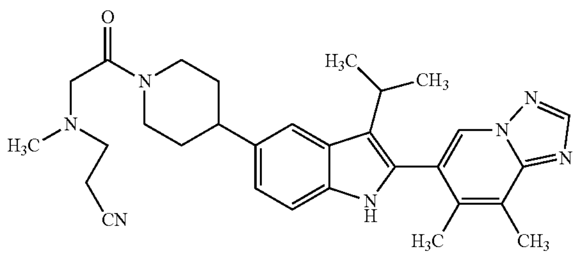 [SMILES: Cc1c(-c2[nH]c3ccc(C4CCN(C(=O)CN(C)CCC#N)CC4)cc3c2C(C)C)cn2ncnc2c1C] | 512.1 | 1.87 | QC-ACN-AA-XB |
| 727 | EX-4 | 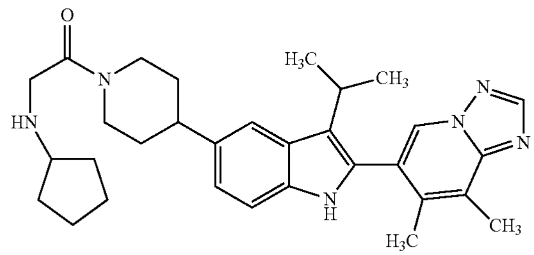 [SMILES: Cc1c(-c2[nH]c3ccc(C4CCN(C(=O)CNC5CCCC5)CC4)cc3c2C(C)C)cn2ncnc2c1C] | 513.2 | 1.53 | QC-ACN-TFA-XB |
| 728 | EX-4 | 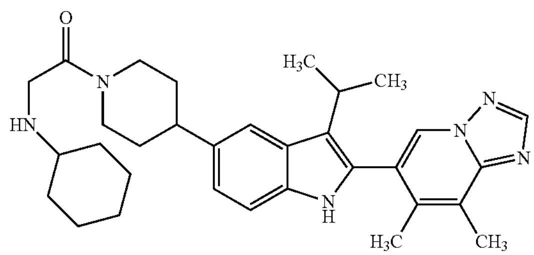 [SMILES: Cc1c(-c2[nH]c3ccc(C4CCN(C(=O)CNC5CCCCC5)CC4)cc3c2C(C)C)cn2ncnc2c1C] | 527.2 | 1.77 | QC-ACN-AA-XB |
| 729 | EX-4 | 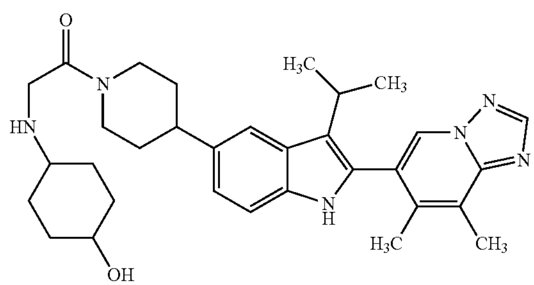 [SMILES: Cc1c(-c2[nH]c3ccc(C4CCN(C(=O)CNC5CCC(O)CC5)CC4)cc3c2C(C)C)cn2ncnc2c1C] | 543.3 | 1.39 | QC-ACN-AA-XB |
| 730 | EX-4 | 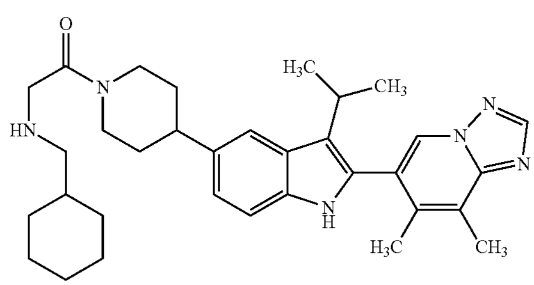 [SMILES: Cc1c(-c2[nH]c3ccc(C4CCN(C(=O)CNCC5CCCCC5)CC4)cc3c2C(C)C)cn2ncnc2c1C] | 271.4 | 1.59 | QC-ACN-TFA-XB |

TABLE 17-continued
| Ex. No. | Template Starting Material | Structure | LCMS MH+ | R$_t$ (min) | HPLC Method |
|---|---|---|---|---|---|
| 731 | EX-4 | 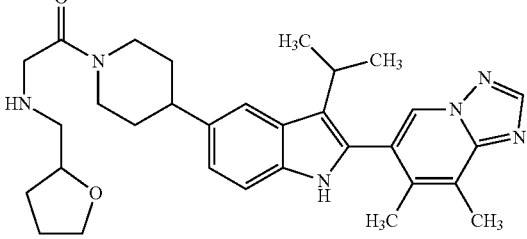 | 529.3 | 1.6 | QC-ACN-AA-XB |
| 732 | EX-4 | 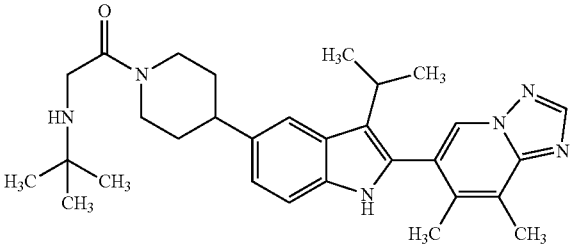 [SMILES: Cc1c(-c2[nH]c3ccc(C4CCN(C(=O)CNC(C)(C)C)CC4)cc3c2C(C)C)cn2ncnc2c1C] | 501.2 | 1.49 | QC-ACN-AA-XB |
| 733 | EX-4 | 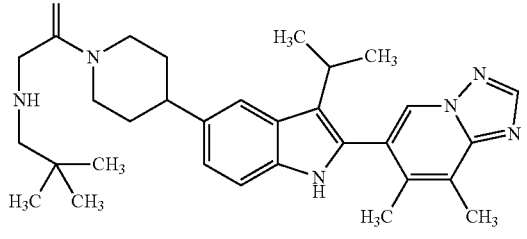 | 515.3 | 1.84 | QC-ACN-AA-XB |
| 734 | EX-4 | 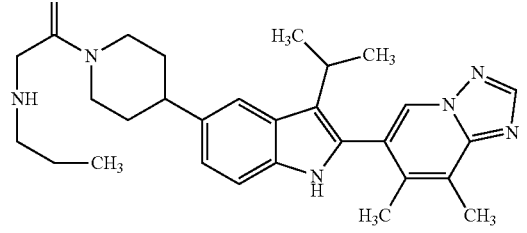 | 244.2 | 1.33 | QC-ACN-TFA-XB |
| 735 | EX-4 | 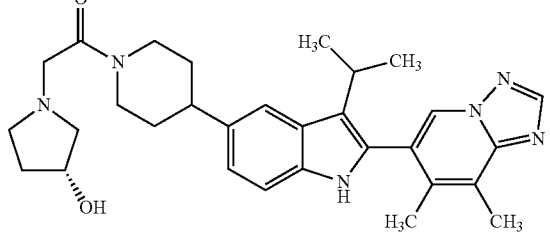 | 515.1 | 1.41 | QC-ACN-TFA-XB |
| 736 | EX-4 | 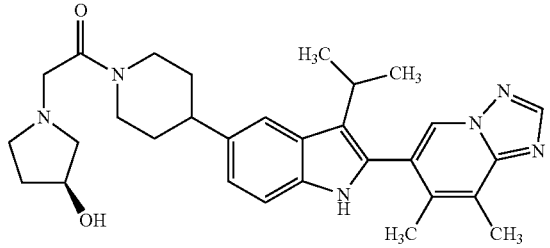 [SMILES: Cc1c(-c2[nH]c3ccc(C4CCN(C(=O)CN5CC[C@H](O)C5)CC4)cc3c2C(C)C)cn2ncnc2c1C] | 515.1 | 1.54 | QC-ACN-AA-XB |

TABLE 17-continued
| Ex. No. | Template Starting Material | Structure | LCMS MH+ | R$_t$ (min) | HPLC Method |
|---|---|---|---|---|---|
| 737 | EX-4 | 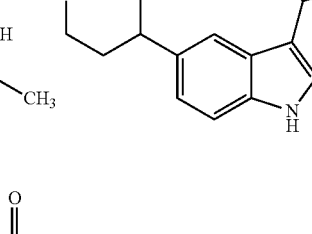 | 487.1 | 1.54 | QC-ACN-AA-XB |
| 738 | EX-4 | 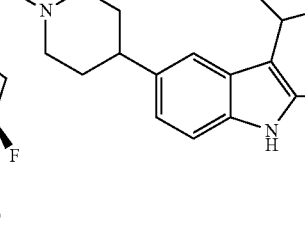 | 259.4 | 1.29 | QC-ACN-TFA-XB |
| 739 | EX-4 | 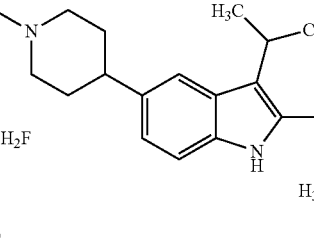 | 246.4 | 1.24 | QC-ACN-TFA-XB |
| 740 | EX-4 | 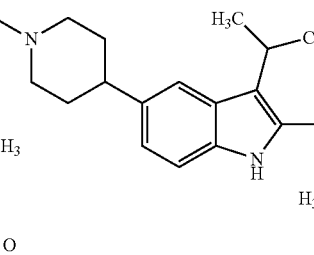 | 473.2 | 1.37 | QC-ACN-AA-XB |
| 741 | EX-4 | 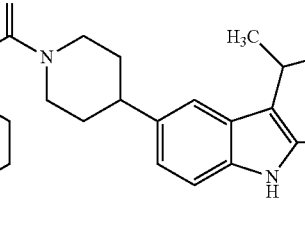 | 549.0 | 2.01 | QC-ACN-AA-XB |
| 742 | EX-4 | 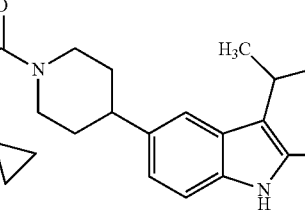 | 485.1 | 1.76 | QC-ACN-AA-XB |

TABLE 17-continued

| Ex. No. | Template Starting Material | Structure | LCMS MH+ | R$_t$ (min) | HPLC Method |
|---|---|---|---|---|---|
| 743 | EX-4 | 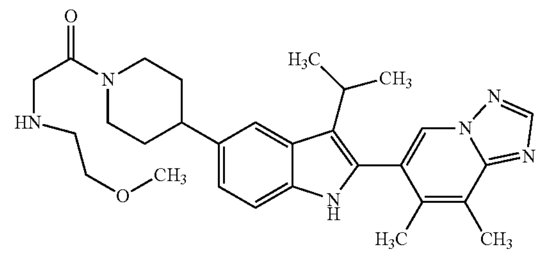 [SMILES: COCCNCC(=O)N1CCC(c2ccc3[nH]c(-c4cn5ncnc5c(C)c4C)c(C(C)C)c3c2)CC1] | 503.0 | 1.57 | QC-ACN-AA-XB |
| 744 | EX-4 | 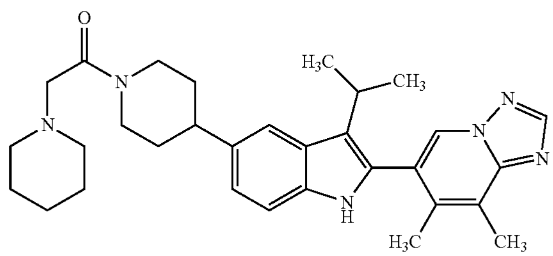 | 513.4 | 1.73 | QC-ACN-AA-XB |
| 745 | EX-4 | 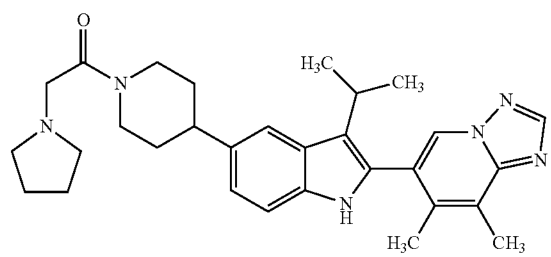 [SMILES: Cc1c(-c2[nH]c3ccc(C4CCN(C(=O)CN5CCCC5)CC4)cc3c2C(C)C)cn2ncnc2c1C] | 250.3 | 1.3 | QC-ACN-TFA-XB |
| 746 | EX-4 | 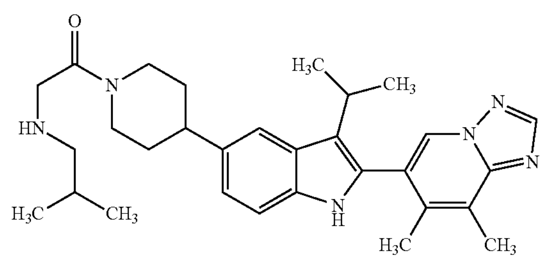 [SMILES: Cc1c(-c2[nH]c3ccc(C4CCN(C(=O)CNCC(C)C)CC4)cc3c2C(C)C)cn2ncnc2c1C] | 501.4 | 1.41 | QC-ACN-TFA-XB |
| 747 | EX-4 | 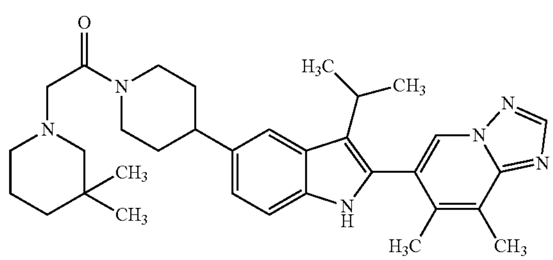 [SMILES: Cc1c(-c2[nH]c3ccc(C4CCN(C(=O)CN5CCCC(C)(C)C5)CC4)cc3c2C(C)C)cn2ncnc2c1C] | 541.1 | 2.28 | QC-ACN-AA-XB |
| 748 | EX-4 | 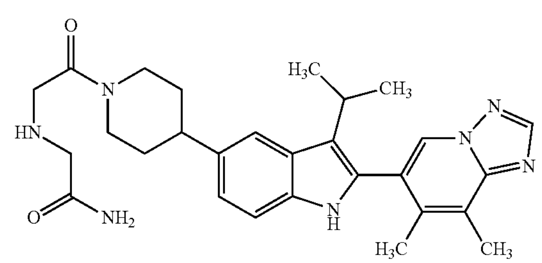 [SMILES: Cc1c(-c2[nH]c3ccc(C4CCN(C(=O)CNCC(N)=O)CC4)cc3c2C(C)C)cn2ncnc2c1C] | 502.4 | 1.37 | QC-ACN-TFA-XB |

TABLE 17-continued

| Ex. No. | Template Starting Material | Structure | LCMS MH+ | R$_t$ (min) | HPLC Method |
|---|---|---|---|---|---|
| 749 | EX-4 | 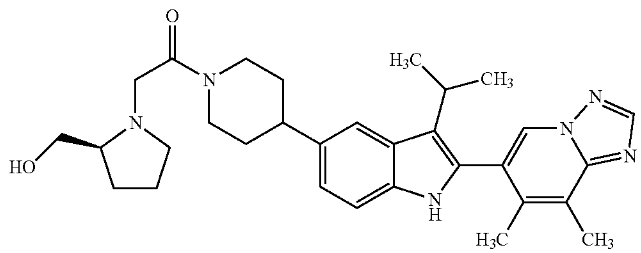 [SMILES: Cc1c(-c2[nH]c3ccc(C4CCN(C(=O)CN5CCC[C@H]5CO)CC4)cc3c2C(C)C)cn2ncnc2c1C] | 529.0 | 1.34 | QC-ACN-TFA-XB |
| 750 | EX-4 | 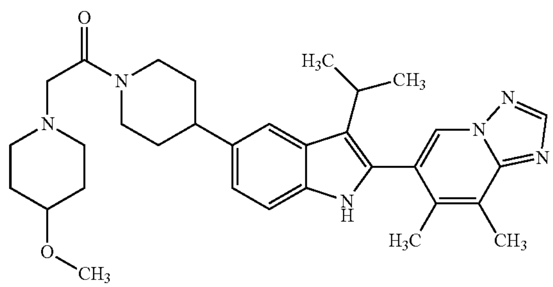 [SMILES: COC1CCN(CC(=O)N2CCC(c3ccc4[nH]c(-c5cn6ncnc6c(C)c5C)c(C(C)C)c4c3)CC2)CC1] | 543.1 | 1.76 | QC-ACN-AA-XB |
| 751 | EX-4 | 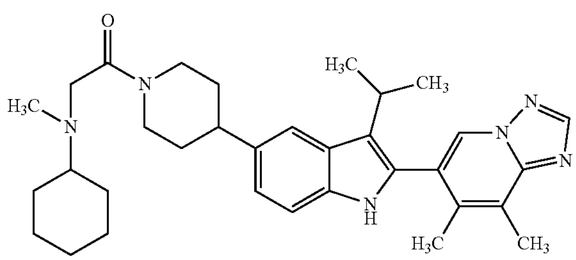 [SMILES: Cc1c(-c2[nH]c3ccc(C4CCN(C(=O)CN(C)C5CCCCC5)CC4)cc3c2C(C)C)cn2ncnc2c1C] | 541.14 541.14 | | QC-ACN-TFA-XB |
| 752 | EX-4 | 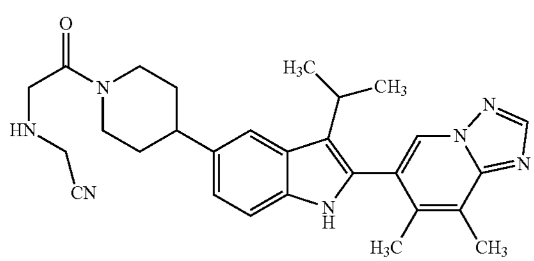 [SMILES: Cc1c(-c2[nH]c3ccc(C4CCN(C(=O)CNCC#N)CC4)cc3c2C(C)C)cn2ncnc2c1C] | 484.4 | 1.47 | QC-ACN-TFA-XB |
| 753 | EX-4 | 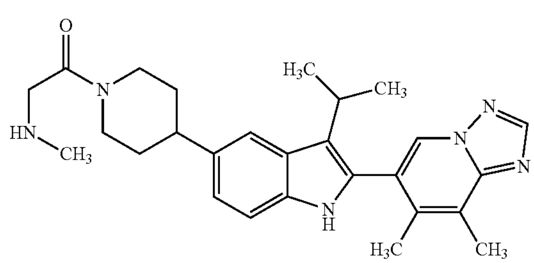 [SMILES: CNCC(=O)N1CCC(c2ccc3[nH]c(-c4cn5ncnc5c(C)c4C)c(C(C)C)c3c2)CC1] | 459.0 | 1.4 | QC-ACN-AA-XB |

TABLE 17-continued

| Ex. No. | Template Starting Material | Structure | LCMS MH+ | R$_t$ (min) | HPLC Method |
|---|---|---|---|---|---|
| 754 | EX-4 | 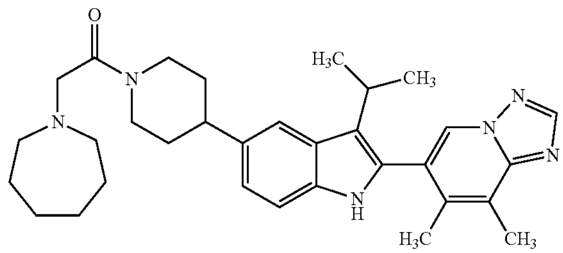 [SMILES: Cc1c(-c2[nH]c3ccc(C4CCN(C(=O)CN5CCCCCC5)CC4)cc3c2C(C)C)cn2ncnc2c1C] | 264.4 | 1.41 | QC-ACN-TFA-XB |
| 755 | EX-4 | 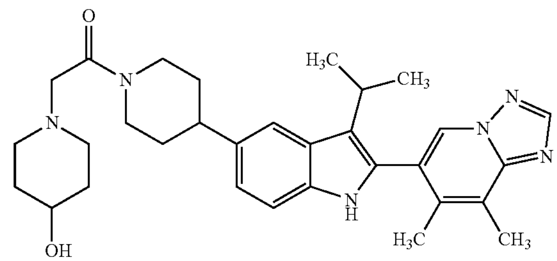 [SMILES: Cc1c(-c2[nH]c3ccc(C4CCN(C(=O)CN5CCC(O)CC5)CC4)cc3c2C(C)C)cn2ncnc2c1C] | 529.3 | 1.46 | QC-ACN-AA-XB |
| 756 | EX-4 | 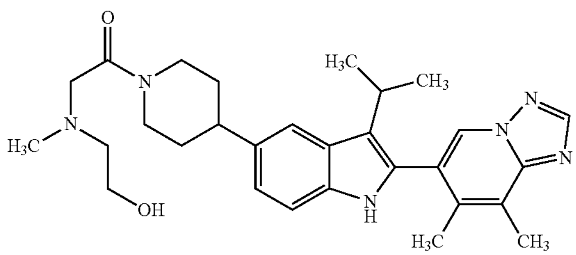 [SMILES: Cc1c(-c2[nH]c3ccc(C4CCN(C(=O)CN(C)CCO)CC4)cc3c2C(C)C)cn2ncnc2c1C] | 252.3 | 1.22 | QC-ACN-TFA-XB |
| 757 | EX-4 | 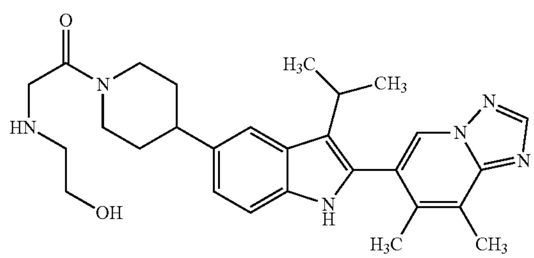 [SMILES: Cc1c(-c2[nH]c3ccc(C4CCN(C(=O)CNCCO)CC4)cc3c2C(C)C)cn2ncnc2c1C] | 489.2 | 1.28 | QC-ACN-AA-XB |
| 758 | EX-4 | 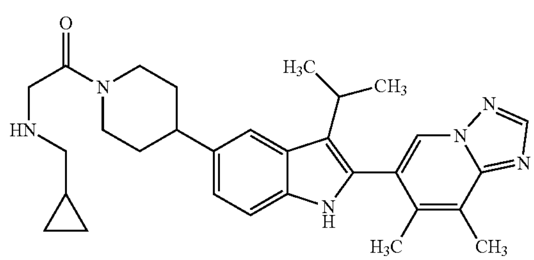 [SMILES: Cc1c(-c2[nH]c3ccc(C4CCN(C(=O)CNCC5CC5)CC4)cc3c2C(C)C)cn2ncnc2c1C] | 250.3 | 1.35 | QC-ACN-TFA-XB |
| 759 | EX-4 | 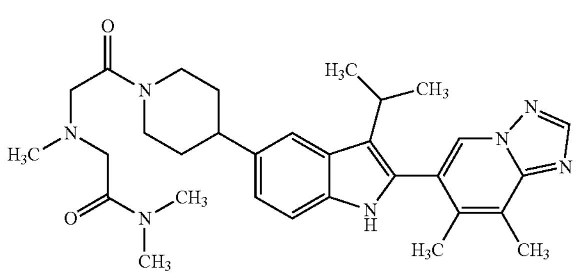 [SMILES: Cc1c(-c2[nH]c3ccc(C4CCN(C(=O)CN(C)CC(=O)N(C)C)CC4)cc3c2C(C)C)cn2ncnc2c1C] | 544.1 | 1.64 | QC-ACN-AA-XB |

TABLE 17-continued

| Ex. No. | Template Starting Material | Structure | LCMS MH+ | R$_t$ (min) | HPLC Method |
|---|---|---|---|---|---|
| 760 | EX-4 | 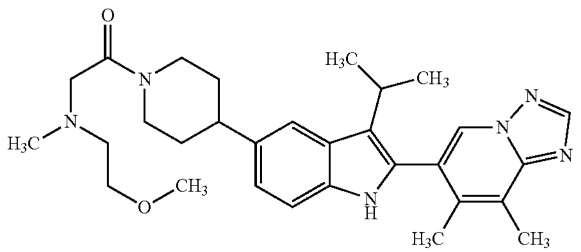 [SMILES: COCCN(C)CC(=O)N1CCC(c2ccc3[nH]c(-c4cn5ncnc5c(C)c4C)c(C(C)C)c3c2)CC1] | 517.5 | 1.32 | QC-ACN-TFA-XB |
| 761 | EX-4 | 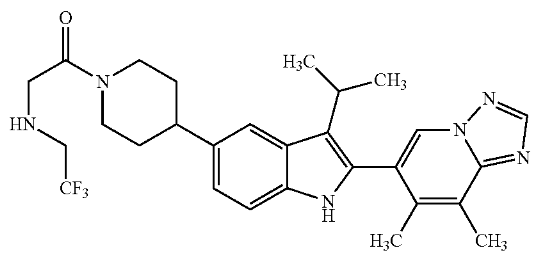 [SMILES: Cc1c(-c2[nH]c3ccc(C4CCN(C(=O)CNCC(F)(F)F)CC4)cc3c2C(C)C)cn2ncnc2c1C] | 527.2 | 1.86 | QC-ACN-AA-XB |
| 762 | EX-4 | 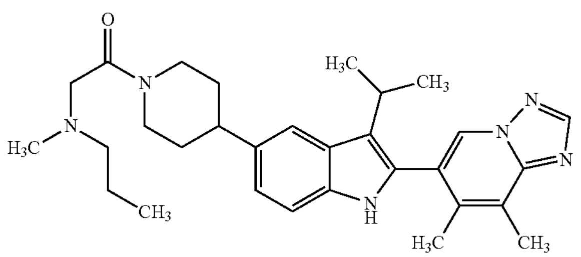 [SMILES: CCCN(C)CC(=O)N1CCC(c2ccc3[nH]c(-c4cn5ncnc5c(C)c4C)c(C(C)C)c3c2)CC1] | 501.1 | 1.74 | QC-ACN-AA-XB |
| 763 | EX-4 | 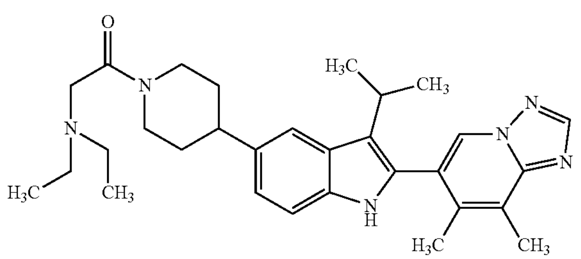 [SMILES: CCN(CC)CC(=O)N1CCC(c2ccc3[nH]c(-c4cn5ncnc5c(C)c4C)c(C(C)C)c3c2)CC1] | 501.2 | 1.58 | QC-ACN-AA-XB |
| 764 | EX-4 | 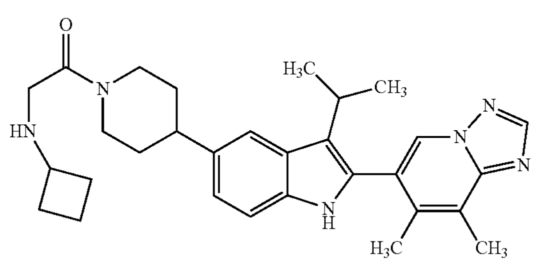 [SMILES: Cc1c(-c2[nH]c3ccc(C4CCN(C(=O)CNC5CCC5)CC4)cc3c2C(C)C)cn2ncnc2c1C] | 499.5 | 1.37 | QC-ACN-TFA-XB |
| 765 | EX-4 | 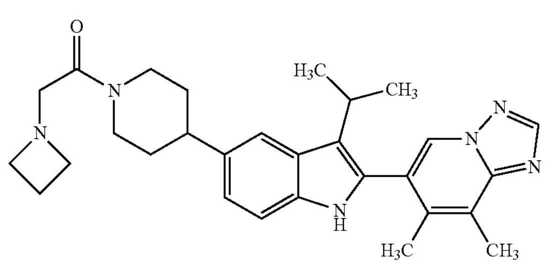 [SMILES: Cc1c(-c2[nH]c3ccc(C4CCN(C(=O)CN5CCC5)CC4)cc3c2C(C)C)cn2ncnc2c1C] | 485.4 | 1.35 | QC-ACN-AA-XB |

TABLE 17-continued

| Ex. No. | Template Starting Material | Structure | LCMS MH+ | R$_t$ (min) | HPLC Method |
|---|---|---|---|---|---|
| 766 | EX-4 | 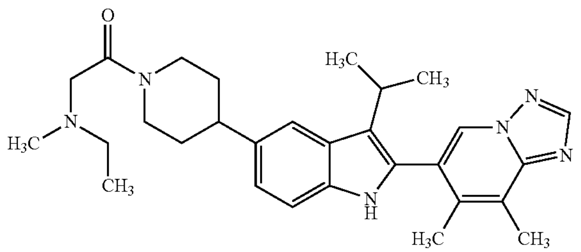 [SMILES: CCN(C)CC(=O)N1CCC(c2ccc3[nH]c(-c4cn5ncnc5c(C)c4C)c(C(C)C)c3c2)CC1] | 487.5 | 1.32 | QC-ACN-TFA-XB |
| 767 | EX-4 | 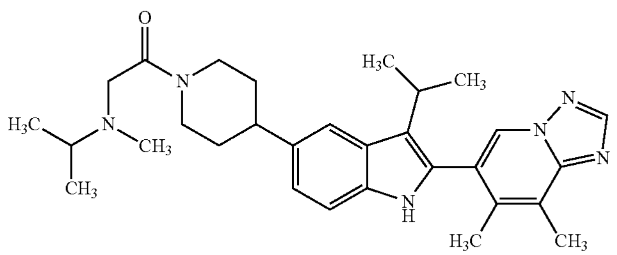 [SMILES: Cc1c(-c2[nH]c3ccc(C4CCN(C(=O)CN(C)C(C)C)CC4)cc3c2C(C)C)cn2ncnc2c1C] | 501.4 | 1.37 | QC-ACN-TFA-XB |

TABLE 18

| Ex. No. | Template Starting Material | Structure | LCMS MH+ | R$_t$ (min) | HPLC Method |
|---|---|---|---|---|---|
| 768 | EX-2 | 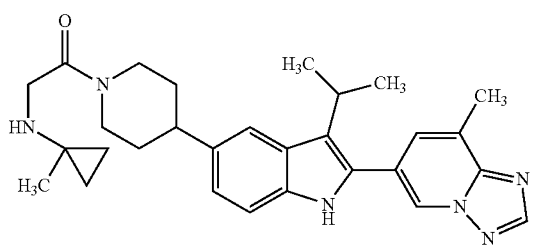 [SMILES: Cc1cc(-c2[nH]c3ccc(C4CCN(C(=O)CNC5(C)CC5)CC4)cc3c2C(C)C)cn2ncnc12] | 485.4 | 1.72 | E |
| 769 | EX-2 | 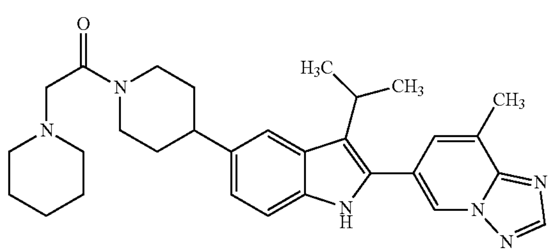 [SMILES: Cc1cc(-c2[nH]c3ccc(C4CCN(C(=O)CN5CCCCC5)CC4)cc3c2C(C)C)cn2ncnc12] | 499.4 | 1.62 | E |
| 770 | EX-2 | 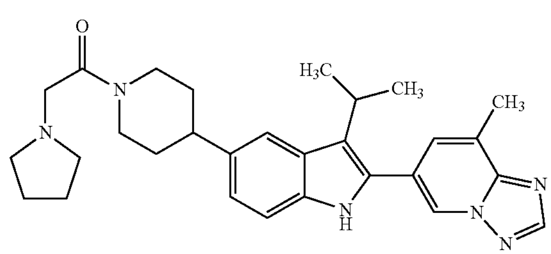 [SMILES: Cc1cc(-c2[nH]c3ccc(C4CCN(C(=O)CN5CCCC5)CC4)cc3c2C(C)C)cn2ncnc12] | 485.4 | 1.35 | E |

TABLE 18-continued
| Ex. No. | Template Starting Material | Structure | LCMS MH+ | R$_t$ (min) | HPLC Method |
|---|---|---|---|---|---|
| 771 | EX-2 | 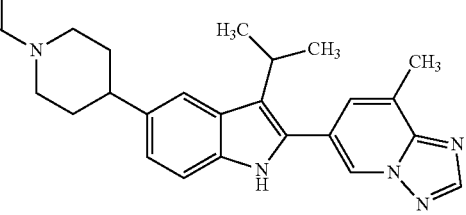 | 513.4 | 1.37 | E |
| 772 | EX-2 | 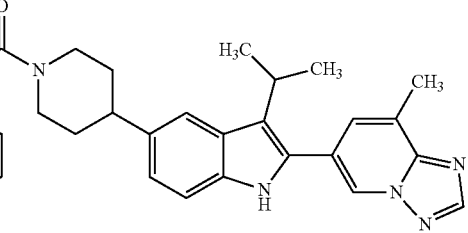 | 558.5 | 1.53 | E |
| 773 | EX-2 | 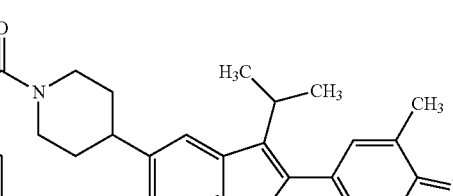 | 529.4 | 1.65 | E |
| 774 | EX-2 | 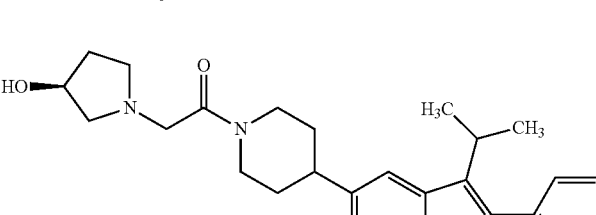 | 501.4 | 1.29 | E |
| 775 | EX-2 | 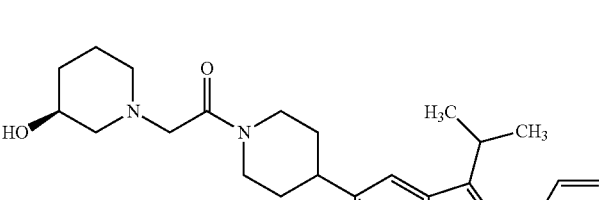 | 515.4 | 1.47 | E |

TABLE 18-continued

| Ex. No. | Template Starting Material | Structure | LCMS MH+ | R_t (min) | HPLC Method |
|---|---|---|---|---|---|
| 776 | EX-2 | 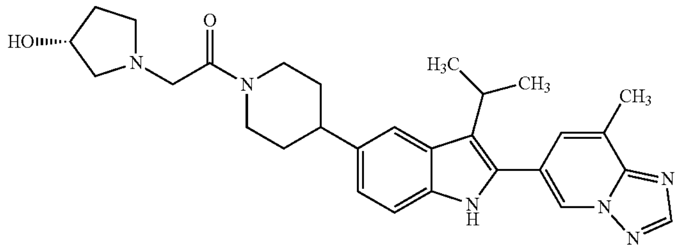 [SMILES: Cc1cc(-c2[nH]c3ccc(C4CCN(C(=O)CN5CC[C@@H](O)C5)CC4)cc3c2C(C)C)cn2ncnc12] | 501.4 | 1.29 | E |
| 777 | EX-128 | 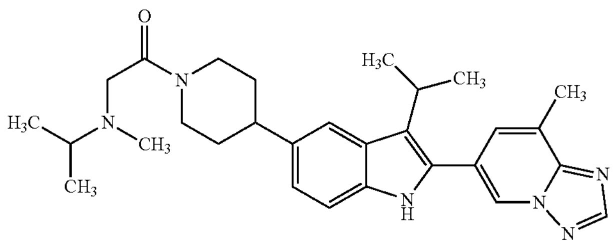 [SMILES: Cc1cc(-c2[nH]c3ccc(C4CCN(C(=O)CN(C)C(C)C)CC4)cc3c2C(C)C)cn2ncnc12] | 541.4 | 1.51 | F |
| 778 | EX-128 | 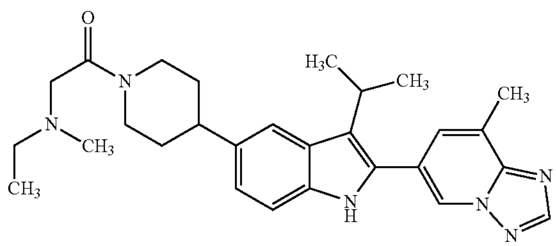 [SMILES: CCN(C)CC(=O)N1CCC(c2ccc3[nH]c(-c4cc(C)c5ncnn5c4)c(C(C)C)c3c2)CC1] | 527.4 | 1.44 | F |
| 779 | EX-128 | 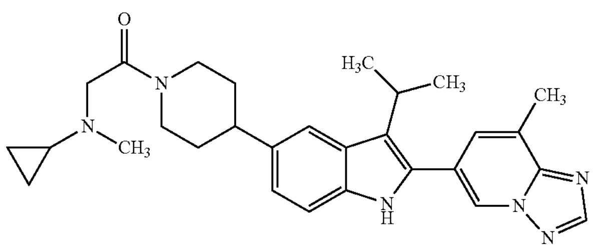 [SMILES: Cc1cc(-c2[nH]c3ccc(C4CCN(C(=O)CN(C)C5CC5)CC4)cc3c2C(C)C)cn2ncnc12] | 539.4 | 2.14 | E |
| 780 | EX-5 | 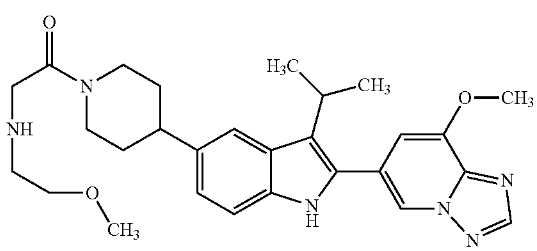 [SMILES: COCCNCC(=O)N1CCC(c2ccc3[nH]c(-c4cc(OC)c5ncnn5c4)c(C(C)C)c3c2)CC1] | 505.3 | 1.55 | E |
| 781 | EX-5 | 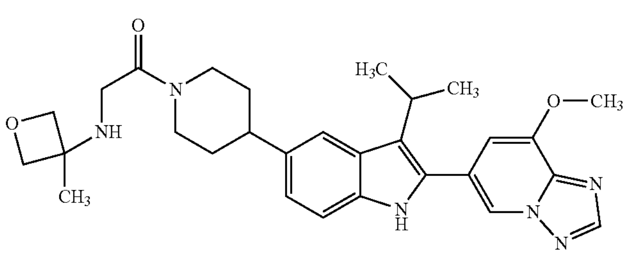 [SMILES: COc1cc(-c2[nH]c3ccc(C4CCN(C(=O)CNC5(C)COC5)CC4)cc3c2C(C)C)cn2ncnc12] | 517.3 | 1.69 | E |

The following examples were prepared according to the general process described in Example 74.
TABLE 19
| Ex. No. | Template Starting Material | Structure | LCMS MH+ | R_t (min) | HPLC Method |
|---|---|---|---|---|---|
| 782 | EX-2 | 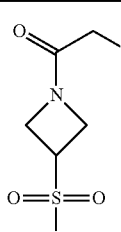 | 549.2 | 1.29 | QC-ACN-TFA-XB |
| 783 | EX-2 | 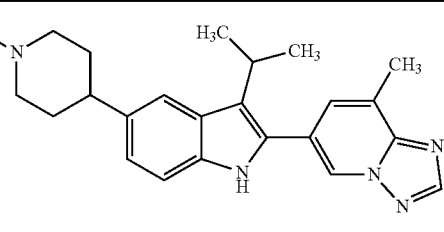 | 535.4 | 1.31 | QC-ACN-TFA-XB |
| 784 | EX-2 | 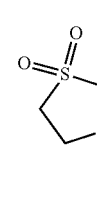 | 535.32 | 1.64 | QC-ACN-AA-XB |
| 785 | EX-2 | 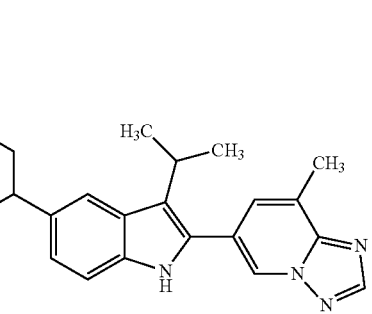 | 505.1 | 1.77 | QC-ACN-AA-XB |
| 786 | EX-2 | 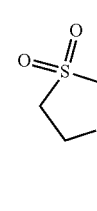 | 545.2 | 1.55 | QC-ACN-AA-XB |

TABLE 19-continued
| Ex. No. | Template Starting Material | Structure | LCMS MH+ | R$_t$ (min) | HPLC Method |
|---|---|---|---|---|---|
| 787 | EX-2 | 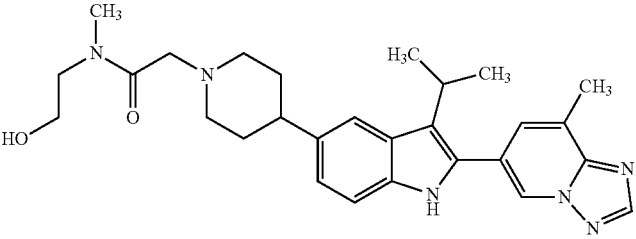 [SMILES: Cc1cc(-c2[nH]c3ccc(C4CCN(CC(=O)N(C)CCO)CC4)cc3c2C(C)C)cn2ncnc12] | 511.1 | 1.21 | QC-ACN-TFA-XB |
| 788 | EX-2 | 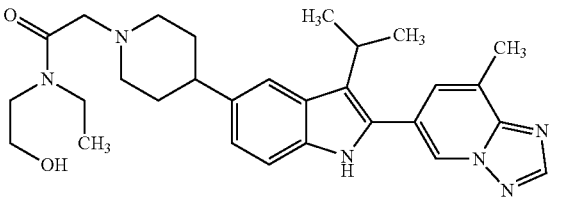 [SMILES: CCN(CCO)C(=O)CN1CCC(c2ccc3[nH]c(-c4cc(C)c5ncnn5c4)c(C(C)C)c3c2)CC1] | 503.2 | 1.26 | QC-ACN-TFA-XB |
| 789 | EX-2 | 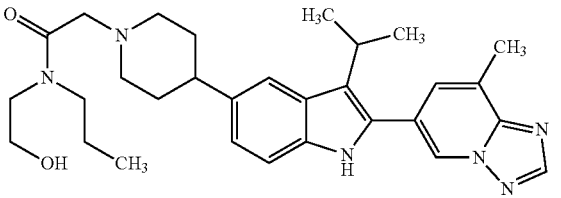 [SMILES: CCCN(CCO)C(=O)CN1CCC(c2ccc3[nH]c(-c4cc(C)c5ncnn5c4)c(C(C)C)c3c2)CC1] | 517.4 | 1.35 | QC-ACN-TFA-XB |
| 790 | EX-2 | 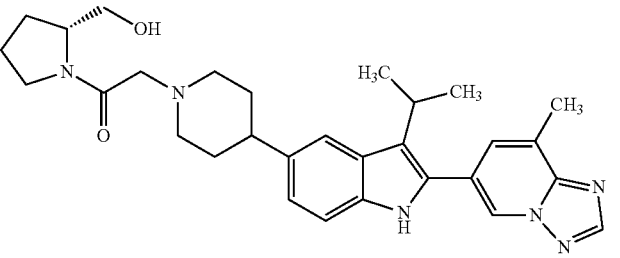 [SMILES: Cc1cc(-c2[nH]c3ccc(C4CCN(CC(=O)N5CCC[C@@H]5CO)CC4)cc3c2C(C)C)cn2ncnc12] | 515.2 | 1.54 | QC-ACN-AA-XB |
| 791 | EX-2 | 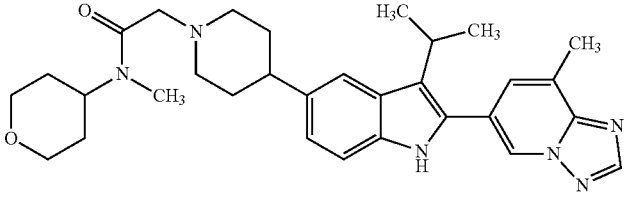 [SMILES: Cc1cc(-c2[nH]c3ccc(C4CCN(CC(=O)N(C)C5CCOCC5)CC4)cc3c2C(C)C)cn2ncnc12] | 529.4 | 1.58 | QC-ACN-AA-XB |
| 792 | EX-2 | 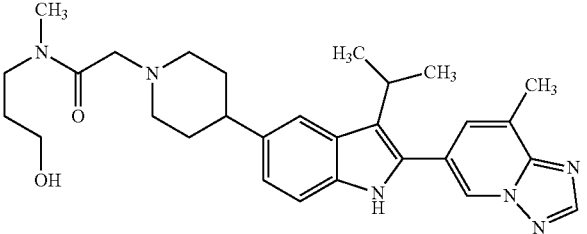 [SMILES: Cc1cc(-c2[nH]c3ccc(C4CCN(CC(=O)N(C)CCCO)CC4)cc3c2C(C)C)cn2ncnc12] | 503.2 | 1.49 | QC-ACN-AA-XB |

TABLE 19-continued

| Ex. No. | Template Starting Material | Structure | LCMS MH+ | R_t (min) | HPLC Method |
|---|---|---|---|---|---|
| 793 | EX-2 | 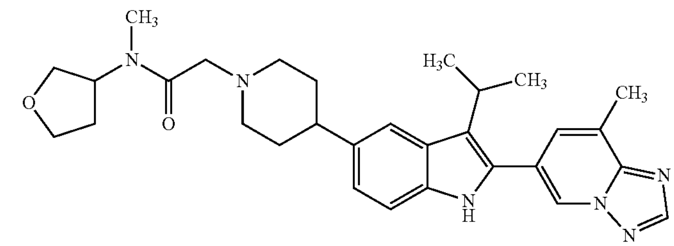 [SMILES: Cc1cc(-c2[nH]c3ccc(C4CCN(CC(=O)N(C)C5CCOC5)CC4)cc3c2C(C)C)cn2ncnc12] | 515.2 | 1.33 | QC-ACN-TFA-XB |
| 794 | EX-2 | 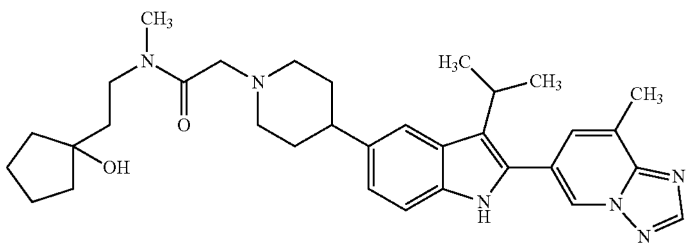 [SMILES: Cc1cc(-c2[nH]c3ccc(C4CCN(CC(=O)N(C)CCC5(O)CCCC5)CC4)cc3c2C(C)C)cn2ncnc12] | 579.2 | 1.44 | QC-ACN-TFA-XB |
| 795 | EX-2 | 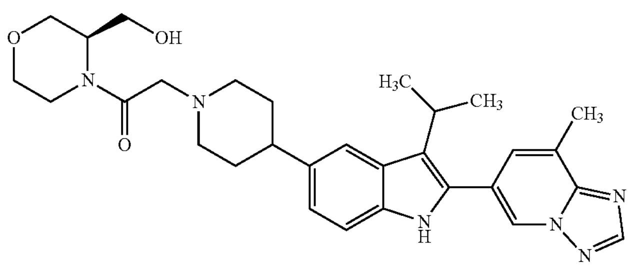 [SMILES: Cc1cc(-c2[nH]c3ccc(C4CCN(CC(=O)N5CCOC[C@H]5CO)CC4)cc3c2C(C)C)cn2ncnc12] | 531.2 | 1.22 | QC-ACN-TFA-XB |
| 796 | EX-2 | 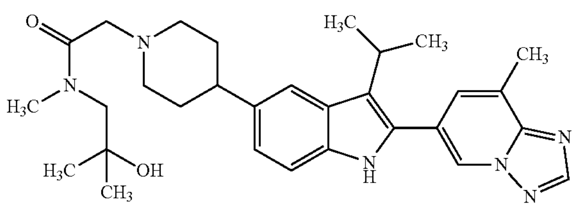 [SMILES: Cc1cc(-c2[nH]c3ccc(C4CCN(CC(=O)N(C)CC(C)(C)O)CC4)cc3c2C(C)C)cn2ncnc12] | 517.2 | 1.6 | QC-ACN-AA-XB |
| 797 | EX-2 | 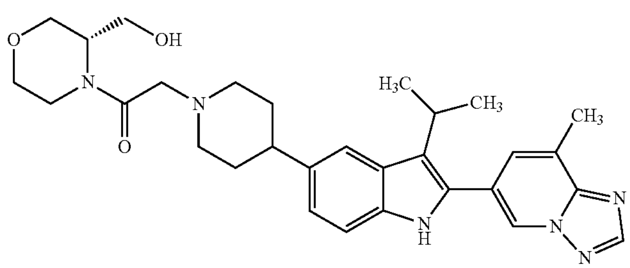 [SMILES: Cc1cc(-c2[nH]c3ccc(C4CCN(CC(=O)N5CCOC[C@@H]5CO)CC4)cc3c2C(C)C)cn2ncnc12] | 531.2 | 1.25 | QC-ACN-TFA-XB |
| 798 | EX-2 | 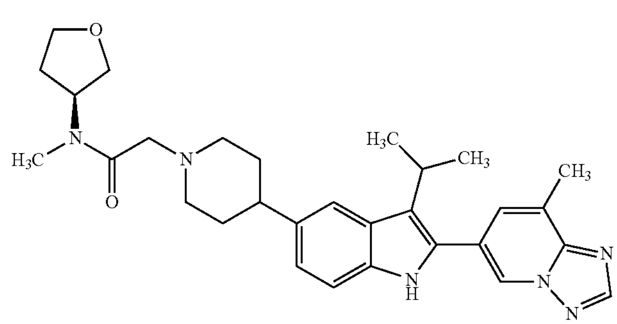 [SMILES: Cc1cc(-c2[nH]c3ccc(C4CCN(CC(=O)N(C)[C@H]5CCOC5)CC4)cc3c2C(C)C)cn2ncnc12] | 515.2 | 1.63 | QC-ACN-AA-XB |

TABLE 19-continued

| Ex. No. | Template Starting Material | Structure | LCMS MH+ | R$_t$ (min) | HPLC Method |
|---|---|---|---|---|---|
| 799 | EX-2 | 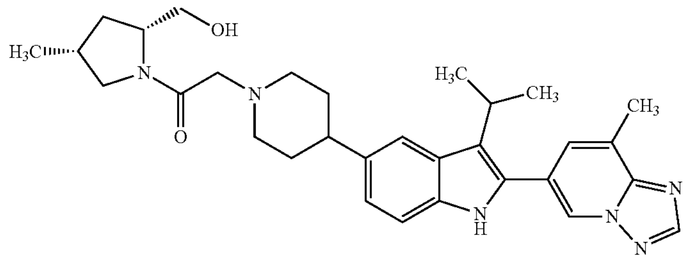 [SMILES: Cc1cc(-c2[nH]c3ccc(C4CCN(CC(=O)N5C[C@H](C)C[C@@H]5CO)CC4)cc3c2C(C)C)cn2ncnc12] | 529.3 | 1.7 | QC-ACN-AA-XB |
| 800 | EX-2 | 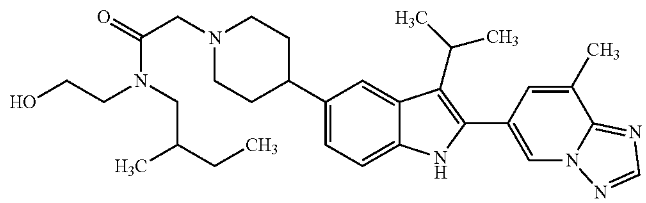 [SMILES: CCC(C)CN(CCO)C(=O)CN1CCC(c2ccc3[nH]c(-c4cc(C)c5ncnn5c4)c(C(C)C)c3c2)CC1] | 545.2 | 1.56 | QC-ACN-TFA-XB |
| 801 | EX-2 | 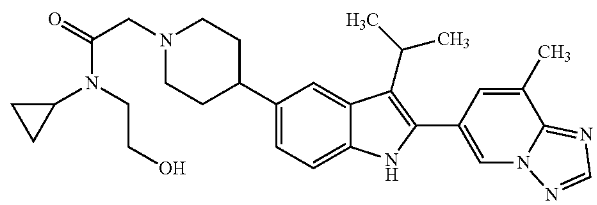 [SMILES: Cc1cc(-c2[nH]c3ccc(C4CCN(CC(=O)N(CCO)C5CC5)CC4)cc3c2C(C)C)cn2ncnc12] | 515.4 | 1.24 | QC-ACN-TFA-XB |
| 802 | EX-3 | 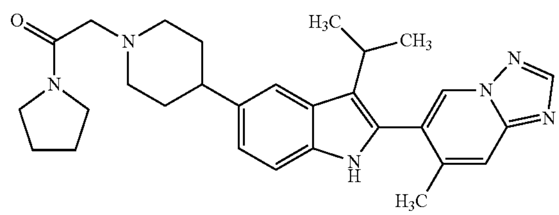 [SMILES: Cc1cc2ncnn2cc1-c1[nH]c2ccc(C3CCN(CC(=O)N4CCCC4)CC3)cc2c1C(C)C] | 485.0 | 1.33 | QC-ACN-TFA-XB |
| 803 | EX-3 | 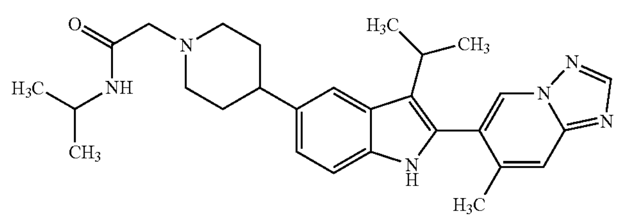 [SMILES: Cc1cc2ncnn2cc1-c1[nH]c2ccc(C3CCN(CC(=O)NC(C)C)CC3)cc2c1C(C)C] | 473.1 | 1.76 | QC-ACN-AA-XB |
| 804 | EX-3 | 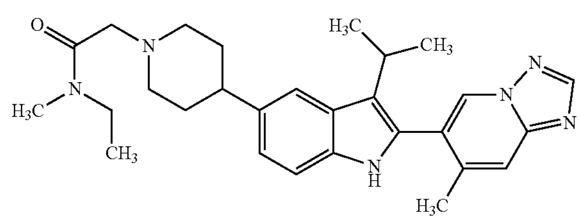 [SMILES: CCN(C)C(=O)CN1CCC(c2ccc3[nH]c(-c4cn5ncnc5cc4C)c(C(C)C)c3c2)CC1] | 473.0 | 1.63 | QC-ACN-AA-XB |
| 805 | EX-3 | 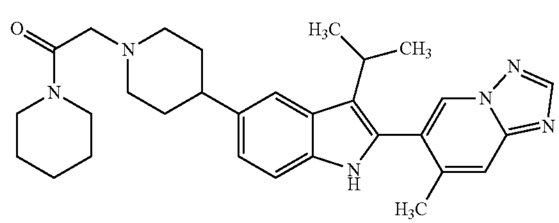 [SMILES: Cc1cc2ncnn2cc1-c1[nH]c2ccc(C3CCN(CC(=O)N4CCCCC4)CC3)cc2c1C(C)C] | 499.2 | 1.42 | QC-ACN-TFA-XB |

TABLE 19-continued

| Ex. No. | Template Starting Material | Structure | LCMS MH+ | R$_t$ (min) | HPLC Method |
|---|---|---|---|---|---|
| 806 | EX-3 | 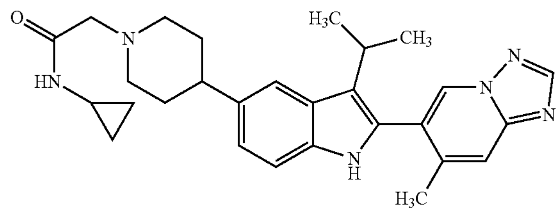 [SMILES: Cc1cc2ncnn2cc1-c1[nH]c2ccc(C3CCN(CC(=O)NC4CC4)CC3)cc2c1C(C)C] | 471.4 | 1.59 | QC-ACN-AA-XB |
| 807 | EX-3 | 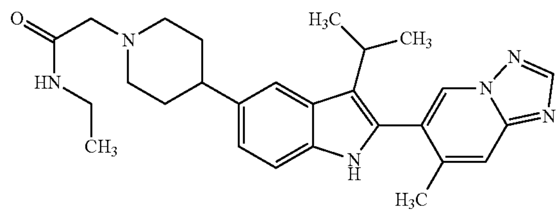 [SMILES: CCNC(=O)CN1CCC(c2ccc3[nH]c(-c4cn5ncnc5cc4C)c(C(C)C)c3c2)CC1] | 459.1 | 1.25 | QC-ACN-TFA-XB |
| 808 | EX-3 | 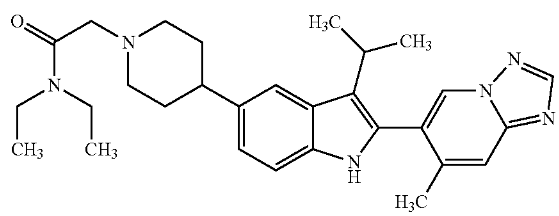 [SMILES: CCN(CC)C(=O)CN1CCC(c2ccc3[nH]c(-c4cn5ncnc5cc4C)c(C(C)C)c3c2)CC1] | 487.4 | 1.35 | QC-ACN-TFA-XB |
| 809 | EX-3 | 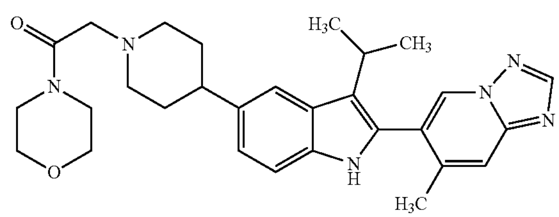 [SMILES: Cc1cc2ncnn2cc1-c1[nH]c2ccc(C3CCN(CC(=O)N4CCOCC4)CC3)cc2c1C(C)C] | 501.3 | 1.5 | QC-ACN-AA-XB |
| 810 | EX-3 | 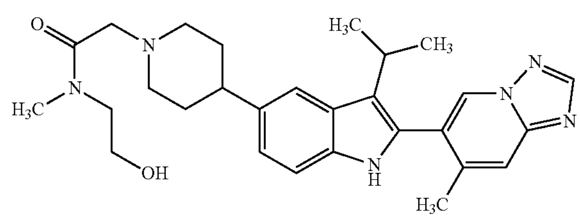 [SMILES: Cc1cc2ncnn2cc1-c1[nH]c2ccc(C3CCN(CC(=O)N(C)CCO)CC3)cc2c1C(C)C] | 489.3 | 1.23 | QC-ACN-TFA-XB |
| 811 | EX-6 | 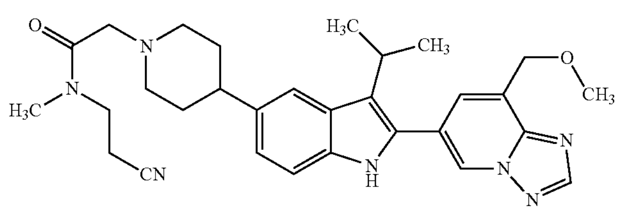 [SMILES: COCc1cc(-c2[nH]c3ccc(C4CCN(CC(=O)N(C)CCC#N)CC4)cc3c2C(C)C)cn2ncnc12] | 528.0 | 1.46 | QC-ACN-AA-XB |
| 812 | EX-6 | 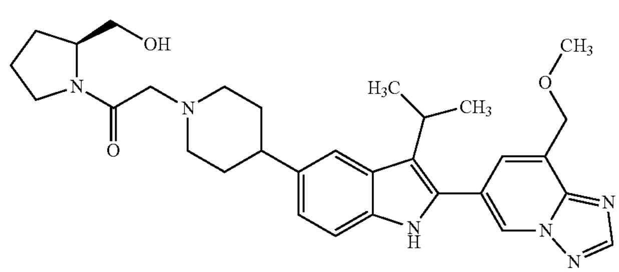 [SMILES: COCc1cc(-c2[nH]c3ccc(C4CCN(CC(=O)N5CCC[C@H]5CO)CC4)cc3c2C(C)C)cn2ncnc12] | 545.0 | 1.31 | QC-ACN-TFA-XB |

TABLE 19-continued

| Ex. No. | Template Starting Material | Structure | LCMS MH+ | R$_t$ (min) | HPLC Method |
|---|---|---|---|---|---|
| 813 | EX-6 | 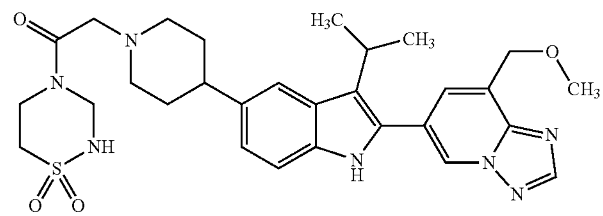 [SMILES: COCc1cc(-c2[nH]c3ccc(C4CCN(CC(=O)N5CCS(=O)(=O)NC5)CC4)cc3c2C(C)C)cn2ncnc12] | 580.1 | 1.58 | QC-ACN-AA-XB |
| 814 | EX-6 | 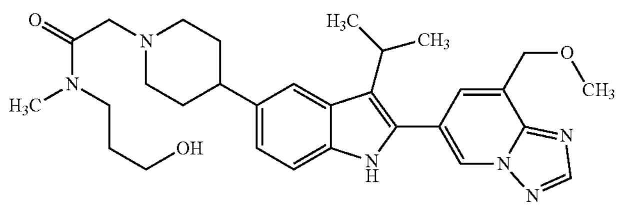 [SMILES: COCc1cc(-c2[nH]c3ccc(C4CCN(CC(=O)N(C)CCCO)CC4)cc3c2C(C)C)cn2ncnc12] | 533.2 | 1.48 | QC-ACN-AA-XB |
| 815 | EX-6 | 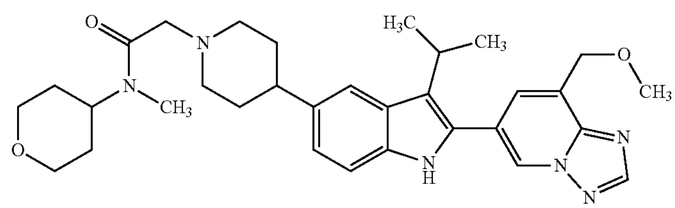 [SMILES: COCc1cc(-c2[nH]c3ccc(C4CCN(CC(=O)N(C)C5CCOCC5)CC4)cc3c2C(C)C)cn2ncnc12] | 558.9 | 1.53 | QC-ACN-AA-XB |
| 816 | EX-6 | 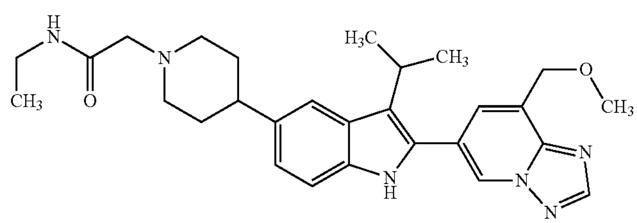 [SMILES: CCNC(=O)CN1CCC(c2ccc3[nH]c(-c4cc(COC)c5ncnn5c4)c(C(C)C)c3c2)CC1] | 489.0 | 1.63 | QC-ACN-AA-XB |
| 817 | EX-6 | 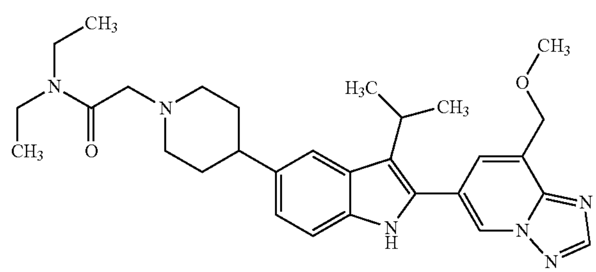 [SMILES: CCN(CC)C(=O)CN1CCC(c2ccc3[nH]c(-c4cc(COC)c5ncnn5c4)c(C(C)C)c3c2)CC1] | 517.0 | 1.58 | QC-ACN-AA-XB |
| 818 | EX-6 | 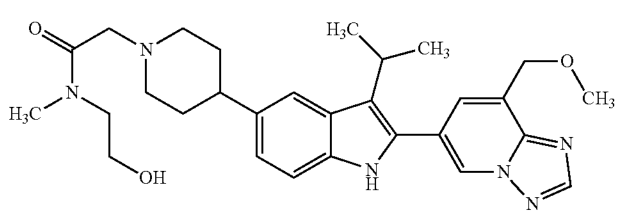 [SMILES: COCc1cc(-c2[nH]c3ccc(C4CCN(CC(=O)N(C)CCO)CC4)cc3c2C(C)C)cn2ncnc12] | 519.0 | 1.28 | QC-ACN-AA-XB |
| 819 | EX-6 | 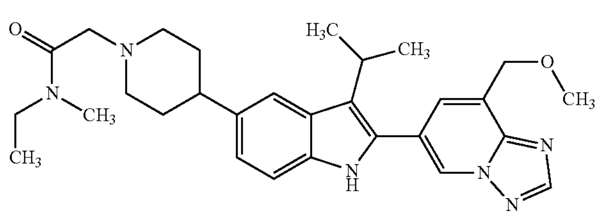 [SMILES: CCN(C)C(=O)CN1CCC(c2ccc3[nH]c(-c4cc(COC)c5ncnn5c4)c(C(C)C)c3c2)CC1] | 503.0 | 1.44 | QC-ACN-TFA-XB |

TABLE 19-continued

| Ex. No. | Template Starting Material | Structure | LCMS MH+ | R$_t$ (min) | HPLC Method |
|---|---|---|---|---|---|
| 820 | EX-6 | 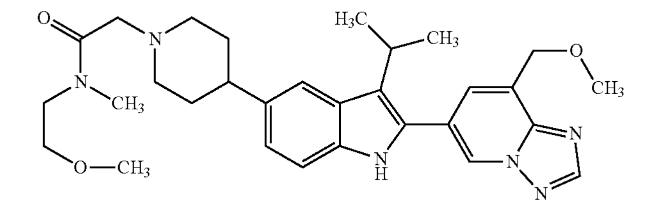 [SMILES: COCCN(C)C(=O)CN1CCC(c2ccc3[nH]c(-c4cc(COC)c5ncnn5c4)c(C(C)C)c3c2)CC1] | 532.9 | 1.37 | QC-ACN-TFA-XB |
| 821 | EX-6 | 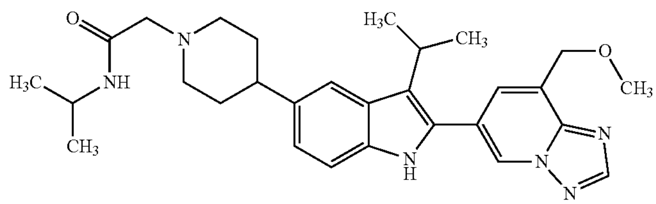 [SMILES: COCc1cc(-c2[nH]c3ccc(C4CCN(CC(=O)NC(C)C)CC4)cc3c2C(C)C)cn2ncnc12] | 503.0 | 1.3 | QC-ACN-TFA-XB |
| 822 | EX-6 | 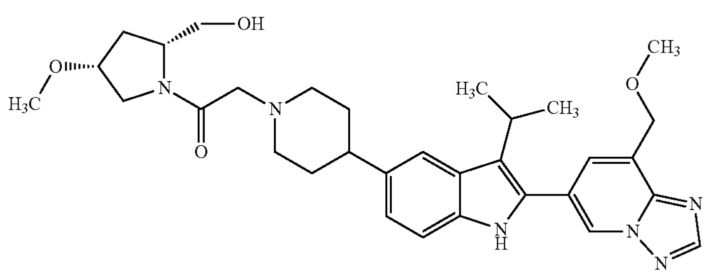 [SMILES: COCc1cc(-c2[nH]c3ccc(C4CCN(CC(=O)N5C[C@H](OC)C[C@@H]5CO)CC4)cc3c2C(C)C)cn2ncnc12] | 575.0 | 1.39 | QC-ACN-AA-XB |
| 823 | EX-6 | 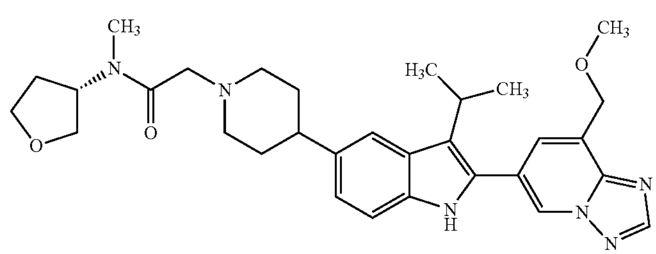 [SMILES: COCc1cc(-c2[nH]c3ccc(C4CCN(CC(=O)N(C)[C@H]5CCOC5)CC4)cc3c2C(C)C)cn2ncnc12] | 545.0 | 1.43 | QC-ACN-AA-XB |
| 824 | EX-6 | 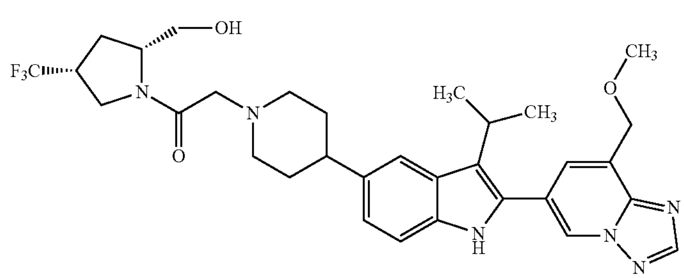 [SMILES: COCc1cc(-c2[nH]c3ccc(C4CCN(CC(=O)N5C[C@H](C(F)(F)F)C[C@@H]5CO)CC4)cc3c2C(C)C)cn2ncnc12] | 613.3 | 1.62 | QC-ACN-AA-XB |
| 825 | EX-6 | 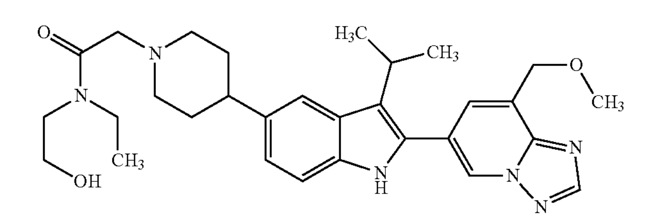 [SMILES: CCN(CCO)C(=O)CN1CCC(c2ccc3[nH]c(-c4cc(COC)c5ncnn5c4)c(C(C)C)c3c2)CC1] | 533.0 | 1.4 | QC-ACN-AA-XB |

TABLE 19-continued

| Ex. No. | Template Starting Material | Structure | LCMS MH+ | R$_t$ (min) | HPLC Method |
|---|---|---|---|---|---|
| 826 | EX-6 | 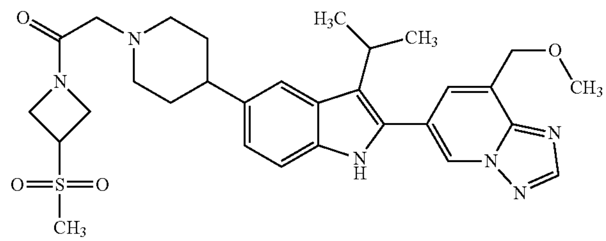 [SMILES: COCc1cc(-c2[nH]c3ccc(C4CCN(CC(=O)N5CC(S(C)(=O)=O)C5)CC4)cc3c2C(C)C)cn2ncnc12] | 578.9 | 1.46 | QC-ACN-AA-XB |
| 827 | EX-6 | 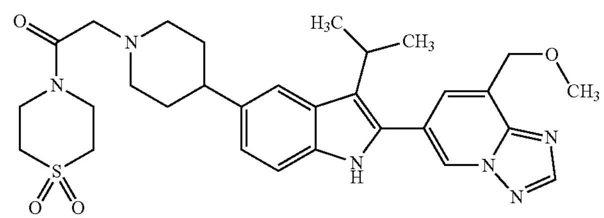 [SMILES: COCc1cc(-c2[nH]c3ccc(C4CCN(CC(=O)N5CCS(=O)(=O)CC5)CC4)cc3c2C(C)C)cn2ncnc12] | 579.0 | 1.45 | QC-ACN-AA-XB |
| 828 | EX-6 | 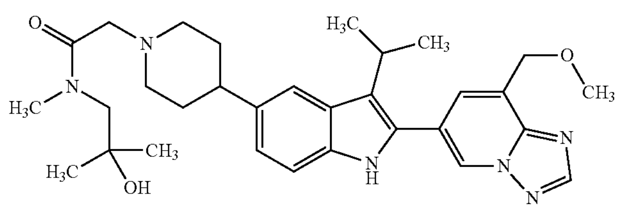 [SMILES: COCc1cc(-c2[nH]c3ccc(C4CCN(CC(=O)N(C)CC(C)(C)O)CC4)cc3c2C(C)C)cn2ncnc12] | 547.0 | 1.34 | QC-ACN-TFA-XB |
| 829 | EX-6 | 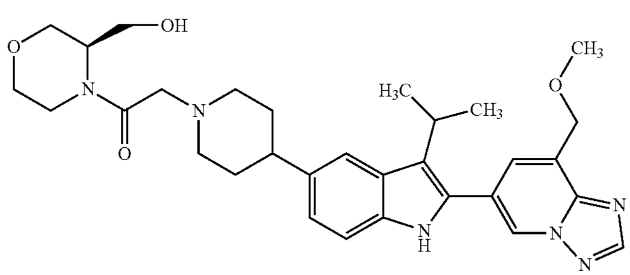 [SMILES: COCc1cc(-c2[nH]c3ccc(C4CCN(CC(=O)N5CCOC[C@H]5CO)CC4)cc3c2C(C)C)cn2ncnc12] | 561.0 | 1.27 | QC-ACN-TFA-XB |
| 830 | EX-6 | 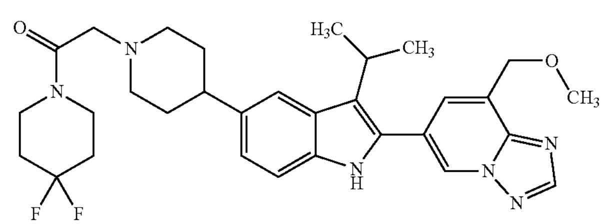 [SMILES: COCc1cc(-c2[nH]c3ccc(C4CCN(CC(=O)N5CCC(F)(F)CC5)CC4)cc3c2C(C)C)cn2ncnc12] | 565.1 | 1.66 | QC-ACN-AA-XB |
| 831 | EX-6 | 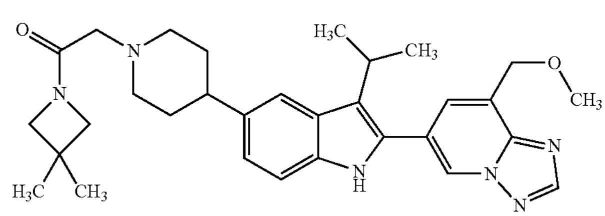 [SMILES: COCc1cc(-c2[nH]c3ccc(C4CCN(CC(=O)N5CC(C)(C)C5)CC4)cc3c2C(C)C)cn2ncnc12] | 529.3 | 1.69 | QC-ACN-AA-XB |

TABLE 19-continued
| Ex. No. | Template Starting Material | Structure | LCMS MH+ | R$_t$ (min) | HPLC Method |
|---|---|---|---|---|---|
| 832 | EX-6 | 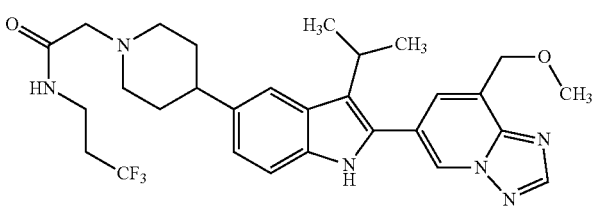 [SMILES: COCc1cc(-c2[nH]c3ccc(C4CCN(CC(=O)NCCC(F)(F)F)CC4)cc3c2C(C)C)cn2ncnc12] | 557.0 | 1.85 | QC-ACN-AA-XB |
| 833 | EX-6 | 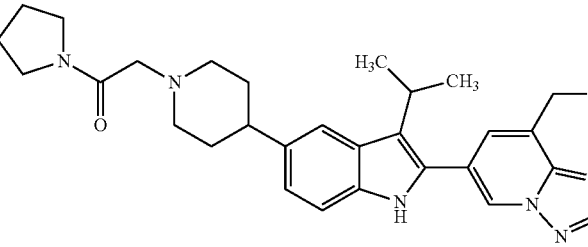 | 551.0 | 1.63 | QC-ACN-AA-XB |
| 834 | EX-6 | 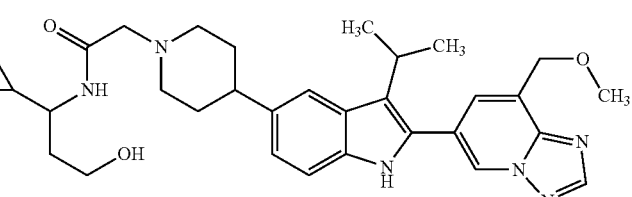 | 559.1 | 1.63 | QC-ACN-AA-XB |
| 835 | EX-6 | 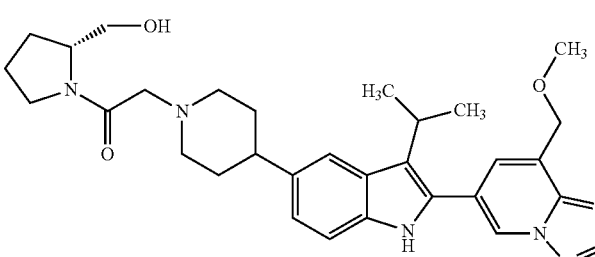 | 545.0 | 1.31 | QC-ACN-TFA-XB |
| 836 | EX-6 | 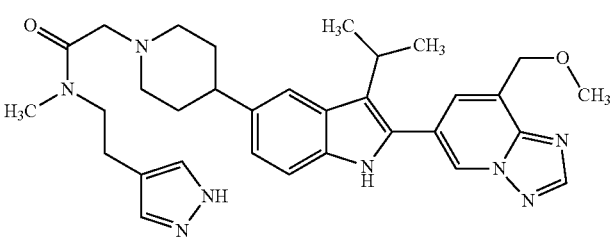 [SMILES: COCc1cc(-c2[nH]c3ccc(C4CCN(CC(=O)N(C)CCc5cn[nH]c5)CC4)cc3c2C(C)C)cn2ncnc12] | 569.1 | 1.3 | QC-ACN-AA-XB |
| 837 | EX-6 | 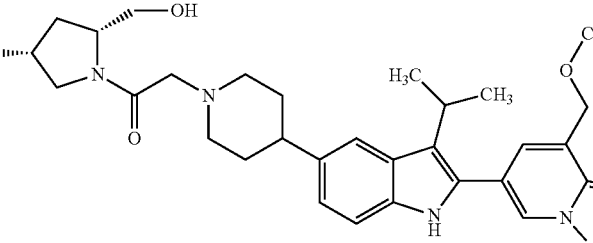 | 559.1 | 1.31 | QC-ACN-TFA-XB |

TABLE 19-continued
| Ex. No. | Template Starting Material | Structure | LCMS MH+ | R$_t$ (min) | HPLC Method |
|---|---|---|---|---|---|
| 838 | EX-6 | 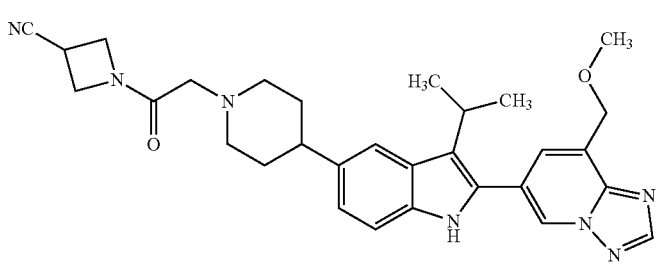 [SMILES: COCc1cc(-c2[nH]c3ccc(C4CCN(CC(=O)N5CC(C#N)C5)CC4)cc3c2C(C)C)cn2ncnc12] | 52.0 | 1.8 | QC-ACN-AA-XB |
| 839 | EX-6 | 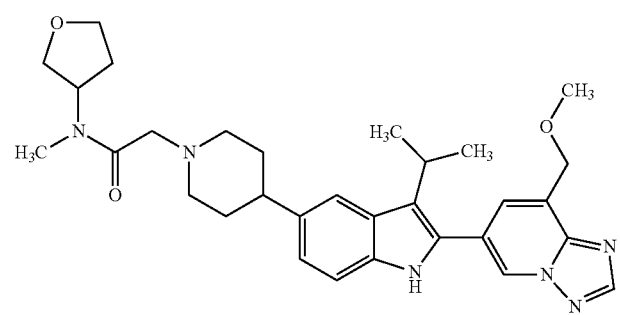 [SMILES: COCc1cc(-c2[nH]c3ccc(C4CCN(CC(=O)N(C)C5CCOC5)CC4)cc3c2C(C)C)cn2ncnc12] | 545.0 | 1.59 | QC-ACN-AA-XB |
| 840 | EX-6 | 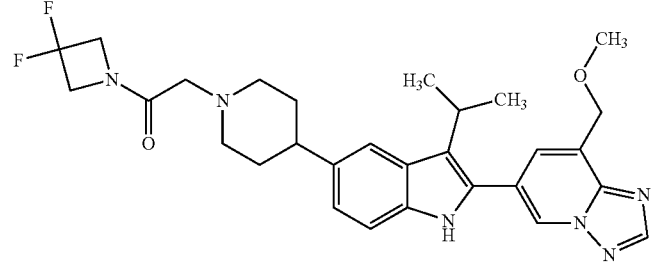 [SMILES: COCc1cc(-c2[nH]c3ccc(C4CCN(CC(=O)N5CC(F)(F)C5)CC4)cc3c2C(C)C)cn2ncnc12] | 537.1 | 1.74 | QC-ACN-AA-XB |
| 841 | EX-6 | 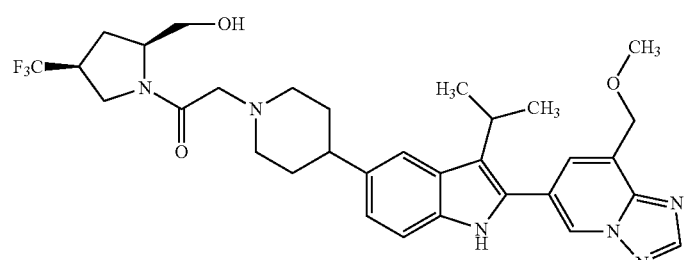 | 613.0 | 1.79 | QC-ACN-AA-XB |
| 842 | EX-6 | 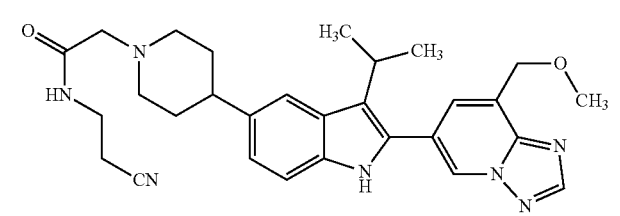 [SMILES: COCc1cc(-c2[nH]c3ccc(C4CCN(CC(=O)NCCC#N)CC4)cc3c2C(C)C)cn2ncnc12] | 514.2 | 1.57 | QC-ACN-AA-XB |

TABLE 19-continued
| Ex. No. | Template Starting Material | Structure | LCMS MH+ | $R_t$ (min) | HPLC Method |
|---|---|---|---|---|---|
| 843 | EX-4 | 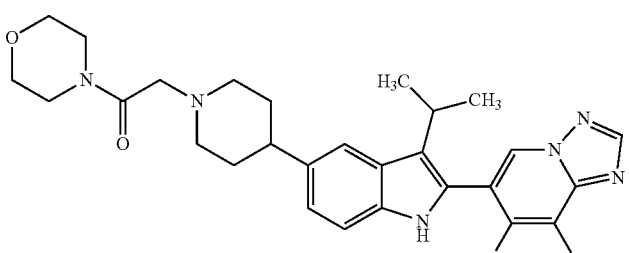 | 515.2 | 1.32 | QC-ACN-TFA-XB |
| 844 | EX-4 | 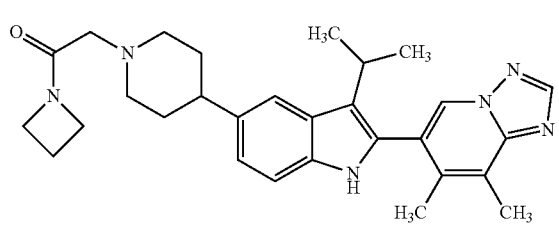 [SMILES: Cc1c(-c2[nH]c3ccc(C4CCN(CC(=O)N5CCC5)CC4)cc3c2C(C)C)cn2ncnc2c1C] | 485.4 | 1.74 | QC-ACN-AA-XB |
| 845 | EX-4 | 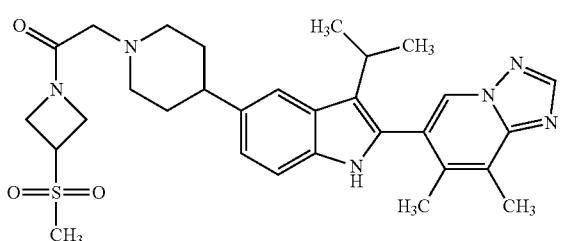 | 563.3 | 1.56 | QC-ACN-AA-XB |
| 846 | EX-4 | 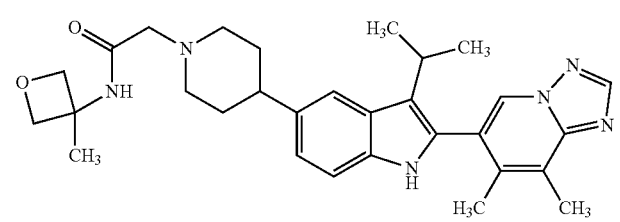 [SMILES: Cc1c(-c2[nH]c3ccc(C4CCN(CC(=O)NC5(C)COC5)CC4)cc3c2C(C)C)cn2ncnc2c1C] | 515.1 | 1.32 | QC-ACN-TFA-XB |
| 847 | EX-4 | 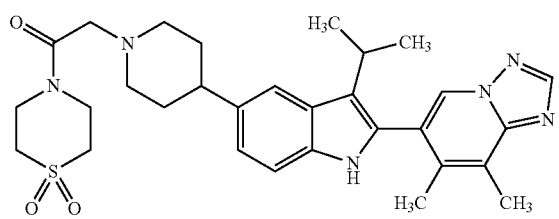 [SMILES: Cc1c(-c2[nH]c3ccc(C4CCN(CC(=O)N5CCS(=O)(=O)CC5)CC4)cc3c2C(C)C)cn2ncnc2c1C] | 563.1 | 1.45 | QC-ACN-AA-XB |
| 848 | EX-4 | 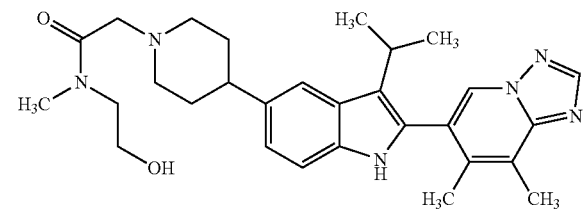 [SMILES: Cc1c(-c2[nH]c3ccc(C4CCN(CC(=O)N(C)CCO)CC4)cc3c2C(C)C)cn2ncnc2c1C] | 503.2 | 1.29 | QC-ACN-TFA-XB |

TABLE 19-continued

| Ex. No. | Template Starting Material | Structure | LCMS MH+ | R$_t$ (min) | HPLC Method |
|---|---|---|---|---|---|
| 849 | EX-4 | 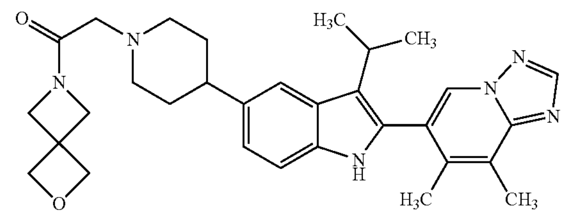 [SMILES: Cc1c(-c2[nH]c3ccc(C4CCN(CC(=O)N5CC6(COC6)C5)CC4)cc3c2C(C)C)cn2ncnc2c1C] | 527.2 | 1.67 | QC-ACN-AA-XB |
| 850 | EX-100 | 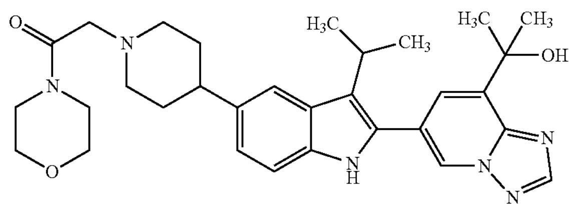 [SMILES: CC(C)c1c(-c2cc(C(C)(C)O)c3ncnn3c2)[nH]c2ccc(C3CCN(CC(=O)N4CCOCC4)CC3)cc12] | 545.0 | 1.3 | QC-ACN-TFA-XB |

TABLE 20

| Ex. No. | Fragment Starting Material | Structure | LCMS MH+ | R$_t$ (min) | HPLC Method |
|---|---|---|---|---|---|
| 851 | EX-124 | 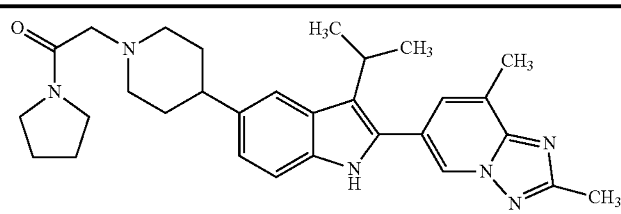 | 499 | 1.83 | E |
| 852 | EX-124 | 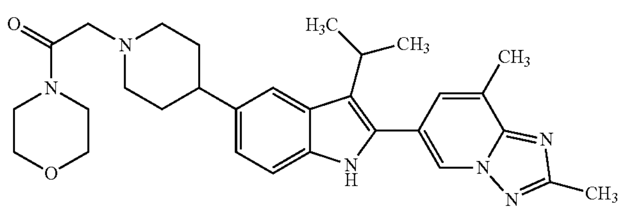 [SMILES: Cc1nc2c(C)cc(-c3[nH]c4ccc(C5CCN(CC(=O)N6CCOCC6)CC5)cc4c3C(C)C)cn2n1] | 515 | 1.75 | E |
| 853 | EX-124 | 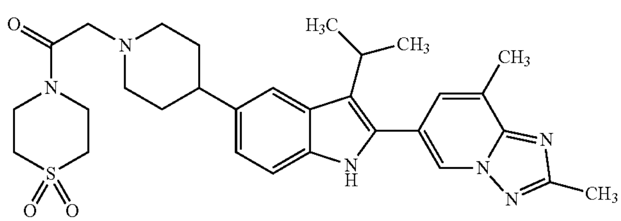 [SMILES: Cc1nc2c(C)cc(-c3[nH]c4ccc(C5CCN(CC(=O)N6CCS(=O)(=O)CC6)CC5)cc4c3C(C)C)cn2n1] | 563.3 | 1.76 | E |
| 854 | EX-5 | 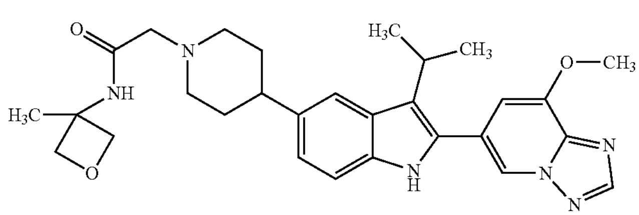 [SMILES: COc1cc(-c2[nH]c3ccc(C4CCN(CC(=O)NC5(C)COC5)CC4)cc3c2C(C)C)cn2ncnc12] | 517.2 | 1.86 | E |

TABLE 20-continued
| Ex. No. | Fragment Starting Material | Structure | LCMS MH+ | $R_t$ (min) | HPLC Method |
|---|---|---|---|---|---|
| 855 | EX-5 | 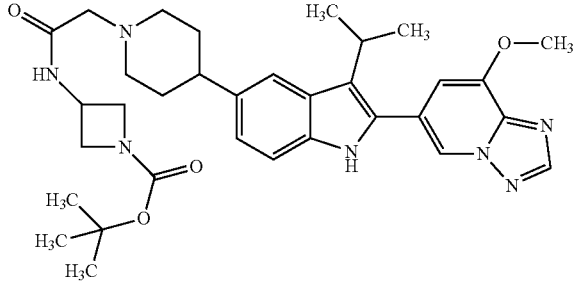 [SMILES: COc1cc(-c2[nH]c3ccc(C4CCN(CC(=O)NC5CN(C(=O)OC(C)(C)C)C5)CC4)cc3c2C(C)C)cn2ncnc12] | 602.4 | 1.89 | E |
| 856 | EX-5 | 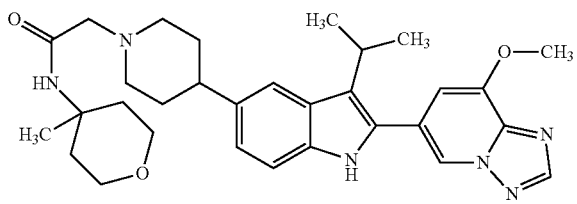 [SMILES: COc1cc(-c2[nH]c3ccc(C4CCN(CC(=O)NC5(C)CCOCC5)CC4)cc3c2C(C)C)cn2ncnc12] | 545.4 | 1.72 | E |
| 857 | EX-5 | 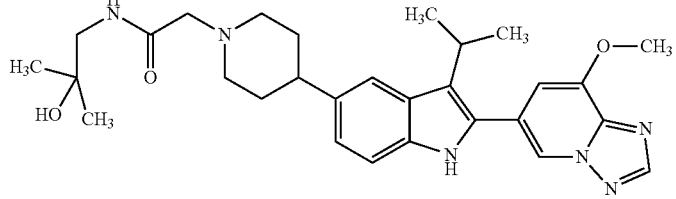 | 519.3 | 1.49 | E |
| 858 | EX-5 | 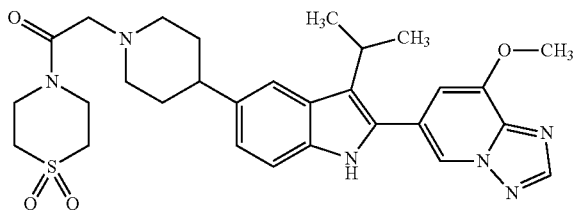 [SMILES: COc1cc(-c2[nH]c3ccc(C4CCN(CC(=O)N5CCS(=O)(=O)CC5)CC4)cc3c2C(C)C)cn2ncnc12] | 565.3 | 1.44 | E |
| 859 | EX-5 | 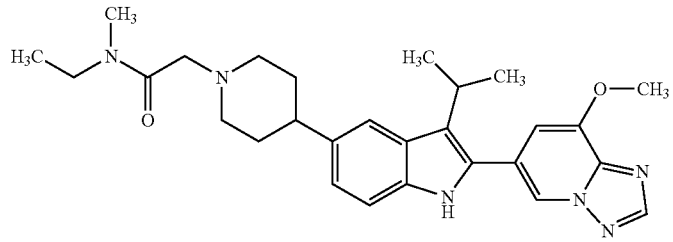 [SMILES: CCN(C)C(=O)CN1CCC(c2ccc3[nH]c(-c4cc(OC)c5ncnn5c4)c(C(C)C)c3c2)CC1] | 489.3 | 1.46 | E |
| 860 | EX-5 | 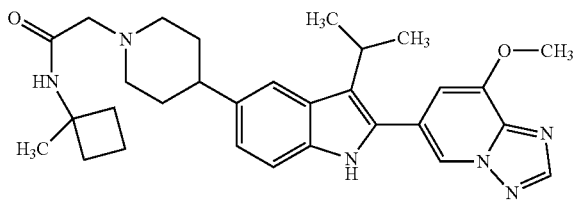 [SMILES: COc1cc(-c2[nH]c3ccc(C4CCN(CC(=O)NC5(C)CCC5)CC4)cc3c2C(C)C)cn2ncnc12] | 515.3 | 1.92 | E |

TABLE 20-continued

| Ex. No. | Fragment Starting Material | Structure | LCMS MH+ | R$_t$ (min) | HPLC Method |
|---|---|---|---|---|---|
| 861 | EX-5 | 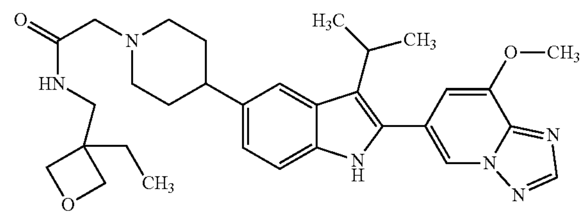 [SMILES: CCC1(CNC(=O)CN2CCC(c3ccc4[nH]c(-c5cc(OC)c6ncnn6c5)c(C(C)C)c4c3)CC2)COC1] | 545.3 | 1.9 | E |
| 862 | EX-5 | 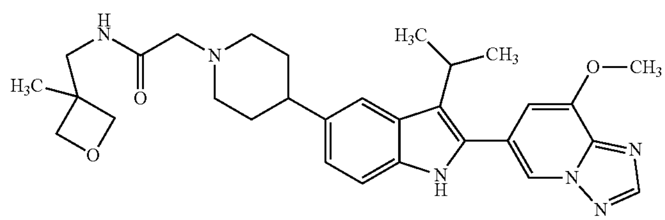 [SMILES: COc1cc(-c2[nH]c3ccc(C4CCN(CC(=O)NCC5(C)COC5)CC4)cc3c2C(C)C)cn2ncnc12] | 531.3 | 1.79 | E |
| 863 | EX-5 | 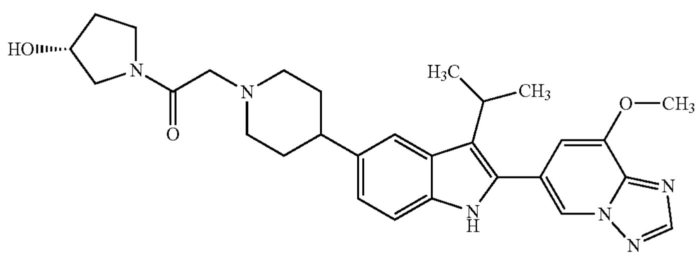 [SMILES: COc1cc(-c2[nH]c3ccc(C4CCN(CC(=O)N5CC[C@@H](O)C5)CC4)cc3c2C(C)C)cn2ncnc12] | 517.3 | 1.21 | E |
| 864 | EX-5 | 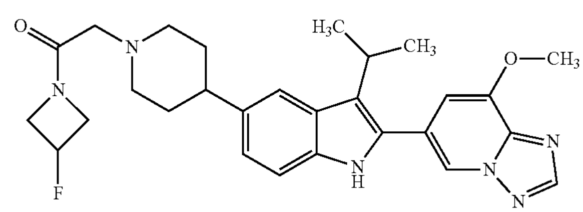 [SMILES: COc1cc(-c2[nH]c3ccc(C4CCN(CC(=O)N5CC(F)C5)CC4)cc3c2C(C)C)cn2ncnc12] | 505.3 | 1.56 | E |
| 865 | EX-5 | 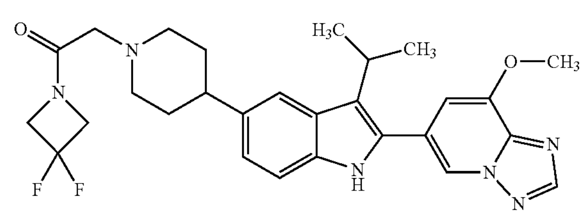 [SMILES: COc1cc(-c2[nH]c3ccc(C4CCN(CC(=O)N5CC(F)(F)C5)CC4)cc3c2C(C)C)cn2ncnc12] | 523.3 | 1.18 | F |
| 866 | EX-5 | 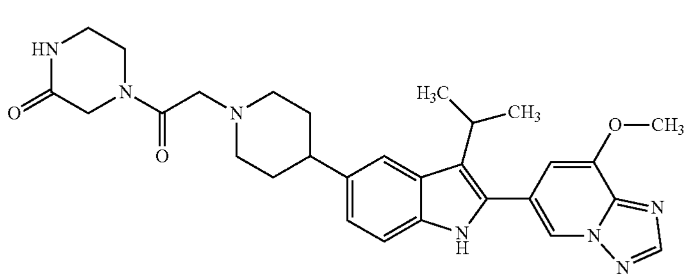 [SMILES: COc1cc(-c2[nH]c3ccc(C4CCN(CC(=O)N5CCNC(=O)C5)CC4)cc3c2C(C)C)cn2ncnc12] | 530.3 | 1.23 | E |

TABLE 20-continued

| Ex. No. | Fragment Starting Material | Structure | LCMS MH+ | R_t (min) | HPLC Method |
|---|---|---|---|---|---|
| 867 | EX-5 | (structure) | 503.3 | 1.26 | E |
| 868 | EX-5 | (structure) | 519.3 | 1.15 | F |
| 869 | EX-5 | (structure) | 545.4 | 1.69 | E |
| 870 | EX-5 | (structure) | 487.3 | 1.5 | E |
| 871 | EX-5 | (structure) | 531.3 | 1.16 | F |
| 872 | EX-5 | (structure) | 537.3 | 1.71 | E |

TABLE 20-continued

| Ex. No. | Fragment Starting Material | Structure | LCMS MH+ | R$_t$ (min) | HPLC Method |
|---|---|---|---|---|---|
| 873 | EX-5 | 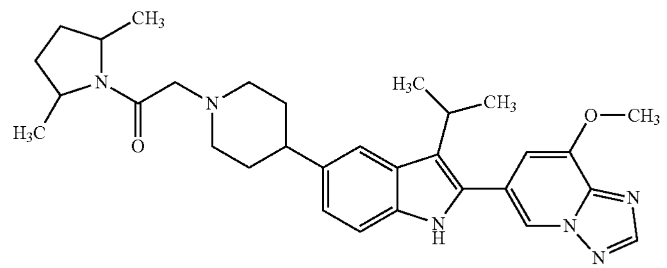 [SMILES: COc1cc(-c2[nH]c3ccc(C4CCN(CC(=O)N5C(C)CCC5C)CC4)cc3c2C(C)C)cn2ncnc12] | 529.4 | 1.77 | E |
| 874 | EX-5 | 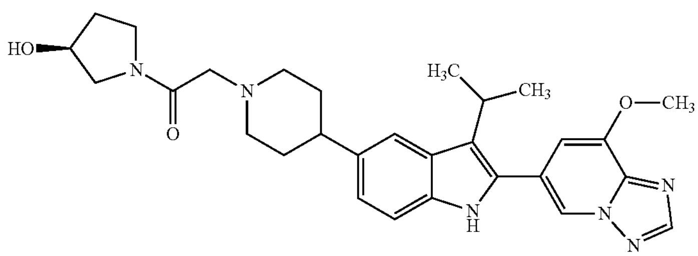 [SMILES: COc1cc(-c2[nH]c3ccc(C4CCN(CC(=O)N5CC[C@H](O)C5)CC4)cc3c2C(C)C)cn2ncnc12] | 517.3 | 1.02 | F |
| 875 | EX-5 | 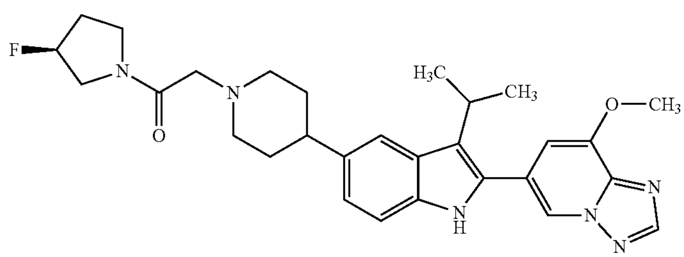 [SMILES: COc1cc(-c2[nH]c3ccc(C4CCN(CC(=O)N5CC[C@H](F)C5)CC4)cc3c2C(C)C)cn2ncnc12] | 519.3 | 1.51 | E |
| 876 | EX-140 | 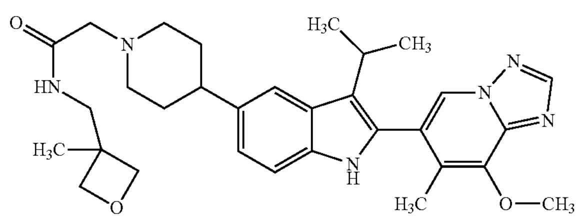 [SMILES: COc1c(C)c(-c2[nH]c3ccc(C4CCN(CC(=O)NCC5(C)COC5)CC4)cc3c2C(C)C)cn2ncnc12] | 545.3 | 1.73 | E |
| 877 | EX-140 | 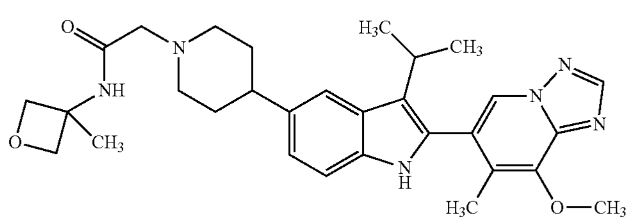 [SMILES: COc1c(C)c(-c2[nH]c3ccc(C4CCN(CC(=O)NC5(C)COC5)CC4)cc3c2C(C)C)cn2ncnc12] | 531.3 | 1.73 | E |
| 878 | EX-140 | 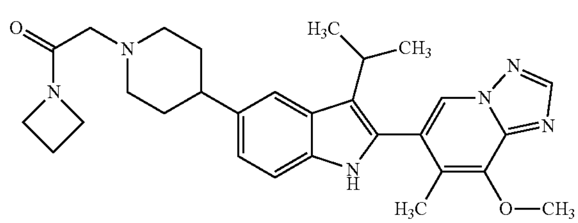 [SMILES: COc1c(C)c(-c2[nH]c3ccc(C4CCN(CC(=O)N5CCC5)CC4)cc3c2C(C)C)cn2ncnc12] | 501.4 | 1.21 | F |

TABLE 20-continued

| Ex. No. | Fragment Starting Material | Structure | LCMS MH+ | $R_t$ (min) | HPLC Method |
|---|---|---|---|---|---|
| 879 | EX-140 | 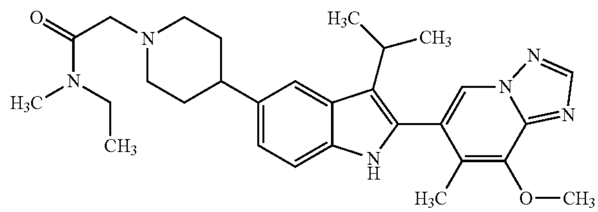 [SMILES: CCN(C)C(=O)CN1CCC(c2ccc3[nH]c(-c4cn5ncnc5c(OC)c4C)c(C(C)C)c3c2)CC1] | 503.4 | 1.29 | F |
| 880 | EX-140 | 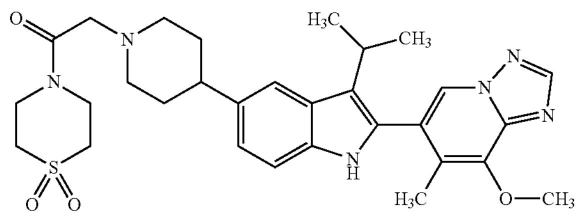 [SMILES: COc1c(C)c(-c2[nH]c3ccc(C4CCN(CC(=O)N5CCS(=O)(=O)CC5)CC4)cc3c2C(C)C)cn2ncnc12] | 579.3 | 1.6 | E |
| 881 | EX-140 | 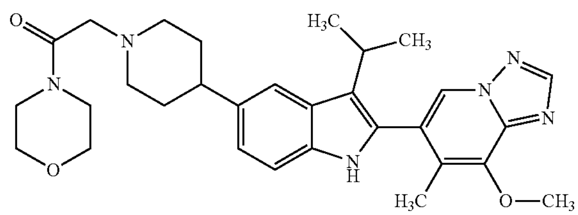 [SMILES: COc1c(C)c(-c2[nH]c3ccc(C4CCN(CC(=O)N5CCOCC5)CC4)cc3c2C(C)C)cn2ncnc12] | 531.3 | 1.56 | E |

Example 882

1-(4-(3-isopropyl-2-(8-methyl-[1,2,4]triazolo[1,5-a]pyridin-6-yl)-1H-indol-5-yl)piperidin-1-yl)-3-morpholinopropan-1-one

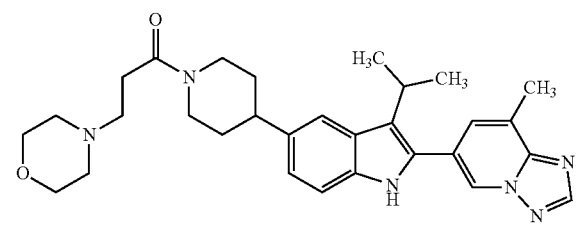

(882)

To a two dram vial were added the TFA salt of 6-(3-isopropyl-5-(piperidin-4-yl)-1H-indol-2-yl)-7-methyl-[1,2,4]triazolo[1,5-a]pyridine (0.025 g, 0.053 mmol), CH₃CN, HATU (1.0 equiv.), TEA (3.0 equiv.), and 3-morpholinopropanoic acid (0.250 g, 1.570 mmol). The reaction vial was capped and stirred overnight at room temperature. The mixture was diluted with solvent (90:10:0.1 CH₃CN:Water:TFA) and filtered. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 19 minutes, then a 3-minute hold at 100% B; Flow: 20 mL/min. Fractions containing the product were combined and dried via centrifugal evaporation to afford 1-(4-(3-isopropyl-2-(8-methyl-[1,2,4]triazolo[1,5-a]pyridin-6-yl)-1H-indol-5-yl)piperidin-1-yl)-3-morpholinopropan-1-one (21.2 mg, 0.041 mmol, 78% yield). LCMS MH+: 515.2 HPLC Ret. Time 1.52 min. Method QC-ACN-AA-XB. ¹H NMR (500 MHz, DMSO-d₆) δ 8.85-8.72 (m, 1H), 8.55-8.48 (m, 1H), 7.63-7.50 (m, 2H), 7.36-7.22 (m, 1H), 7.06-6.94 (m, 1H), 4.63-4.51 (m, 1H), 4.06-3.98 (m, 1H), 3.63-3.56 (m, 5H), 3.30-3.20 (m, 1H), 2.70-2.53 (m, 11H), 2.46-2.39 (m, 3H), 1.89-1.79 (m, 2H), 1.70-1.59 (m, 1H), 1.53-1.46 (m, 1H), 1.45-1.39 (m, 6H).

The following examples were prepared according to the general process described in Example 882.

TABLE 21

| Ex. No. | Template Starting Material | Structure | LCMS MH+ | R_t (min) | HPLC Method |
|---|---|---|---|---|---|
| 883 | EX-2 | 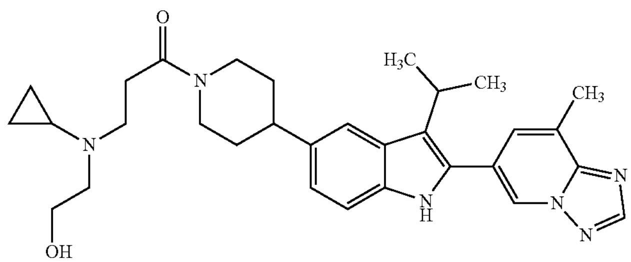 [SMILES: Cc1cc(-c2[nH]c3ccc(C4CCN(C(=O)CCN(CCO)C5CC5)CC4)cc3c2C(C)C)cn2ncnc12] | 529.0 | 1.63 | QC-ACN-AA-XB |
| 884 | EX-2 | 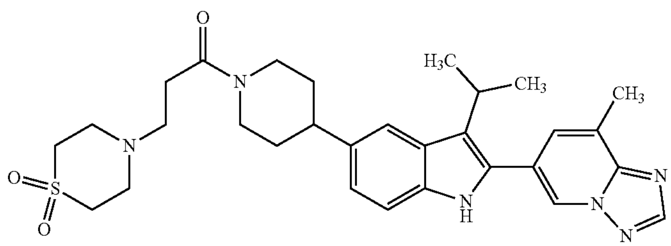 [SMILES: Cc1cc(-c2[nH]c3ccc(C4CCN(C(=O)CCN5CCS(=O)(=O)CC5)CC4)cc3c2C(C)C)cn2ncnc12] | 563.2 | 1.29 | QC-ACN-TFA-XB |
| 885 | EX-3 | 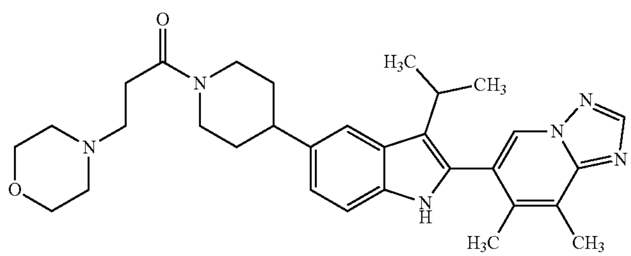 [SMILES: Cc1c(-c2[nH]c3ccc(C4CCN(C(=O)CCN5CCOCC5)CC4)cc3c2C(C)C)cn2ncnc2c1C] | 515.5 | 1.56 | QC-ACN-AA-XB |
| 886 | EX-4 | 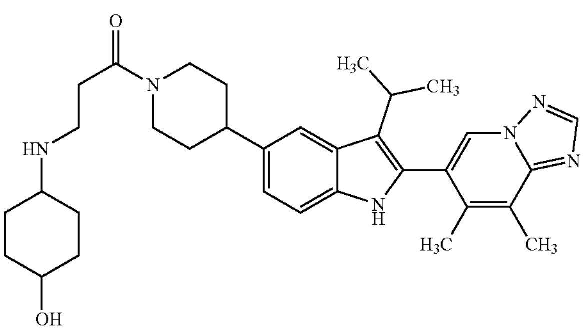 [SMILES: Cc1c(-c2[nH]c3ccc(C4CCN(C(=O)CCNC5CCC(O)CC5)CC4)cc3c2C(C)C)cn2ncnc2c1C] | 557.2 | 1.28 | QC-ACN-TFA-XB |
| 887 | EX-4 | 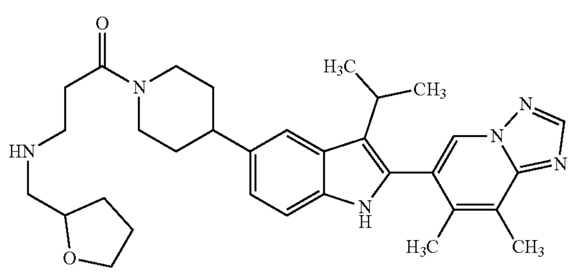 [SMILES: Cc1c(-c2[nH]c3ccc(C4CCN(C(=O)CCNCC5CCCO5)CC4)cc3c2C(C)C)cn2ncnc2c1C] | 543.2 | 1.44 | QC-ACN-AA-XB |

TABLE 21-continued

| Ex. No. | Template Starting Material | Structure | LCMS MH+ | R$_t$ (min) | HPLC Method |
|---|---|---|---|---|---|
| 888 | EX-4 | 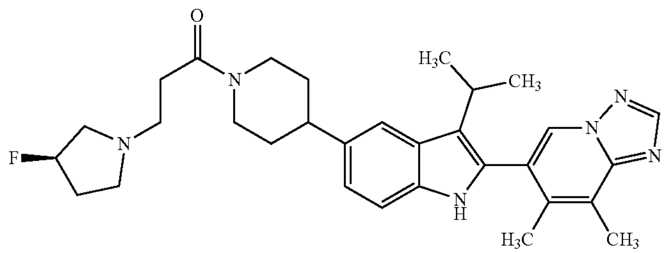 [SMILES: Cc1c(-c2[nH]c3ccc(C4CCN(C(=O)CCN5CC[C@@H](F)C5)CC4)cc3c2C(C)C)cn2ncnc2c1C] | 531.2 | 1.32 | QC-ACN-TFA-XB |
| 889 | EX-4 | 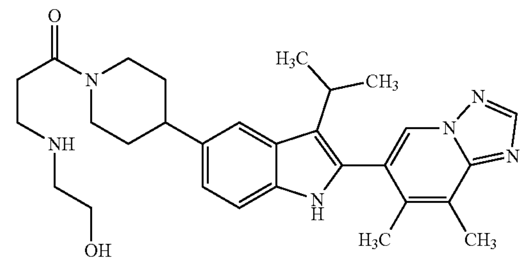 [SMILES: Cc1c(-c2[nH]c3ccc(C4CCN(C(=O)CCNCCO)CC4)cc3c2C(C)C)cn2ncnc2c1C] | 503.1 | 1.3 | QC-ACN-AA-XB |
| 890 | EX-4 | 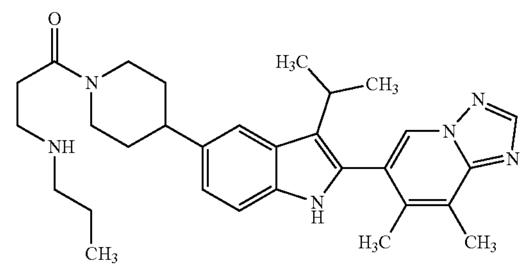 [SMILES: CCCNCCC(=O)N1CCC(c2ccc3[nH]c(-c4cn5ncnc5c(C)c4C)c(C(C)C)c3c2)CC1] | 501.2 | 1.42 | QC-ACN-AA-XB |
| 891 | EX-4 | 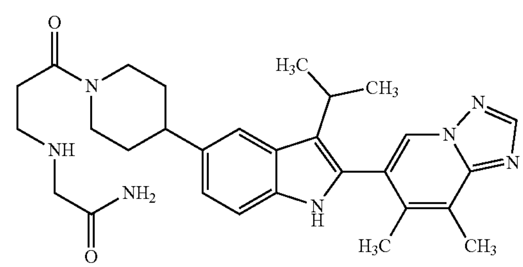 [SMILES: Cc1c(-c2[nH]c3ccc(C4CCN(C(=O)CCNCC(N)=O)CC4)cc3c2C(C)C)cn2ncnc2c1C] | 516.1 | 1.33 | QC-ACN-AA-XB |
| 892 | EX-4 | 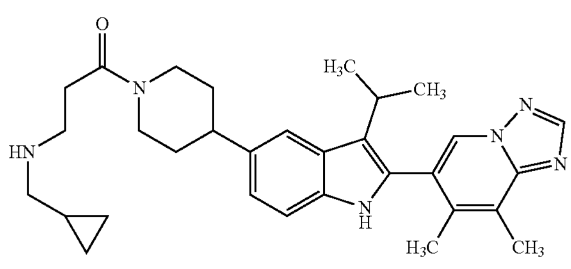 [SMILES: Cc1c(-c2[nH]c3ccc(C4CCN(C(=O)CCNCC5CC5)CC4)cc3c2C(C)C)cn2ncnc2c1C] | 513.1 | 1.44 | QC-ACN-AA-XB |
| 893 | EX-4 | 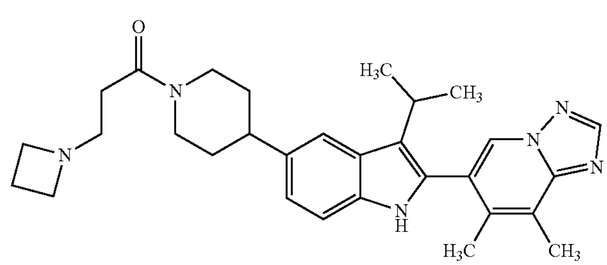 [SMILES: Cc1c(-c2[nH]c3ccc(C4CCN(C(=O)CCN5CCC5)CC4)cc3c2C(C)C)cn2ncnc2c1C] | 499.2 | 1.28 | QC-ACN-TFA-XB |

TABLE 21-continued
| Ex. No. | Template Starting Material | Structure | LCMS MH+ | R$_t$ (min) | HPLC Method |
|---|---|---|---|---|---|
| 894 | EX-4 | 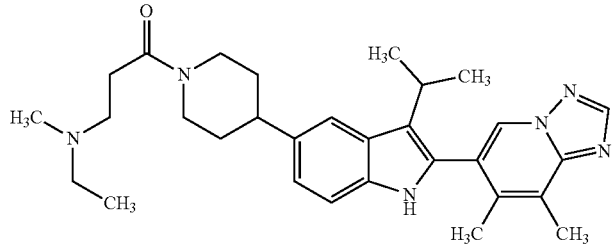 [SMILES: CCN(C)CCC(=O)N1CCC(c2ccc3[nH]c(-c4cn5ncnc5c(C)c4C)c(C(C)C)c3c2)CC1] | 501.2 | 1.31 | QC-ACN-TFA-XB |
| 895 | EX-4 | 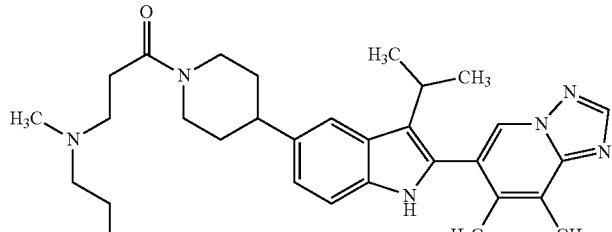 | 515.2 | 1.45 | QC-ACN-AA-XB |
| 896 | EX-4 | 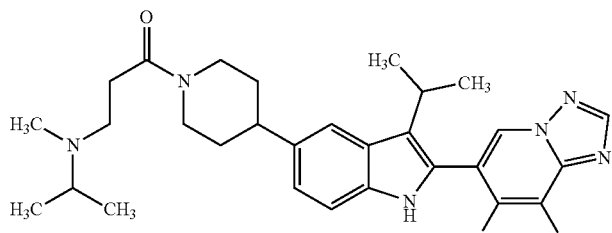 | 515.2 | 1.35 | QC-ACN-TFA-XB |
| 897 | EX-4 | 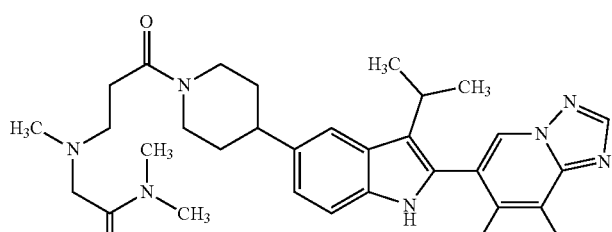 | 558.2 | 1.42 | QC-ACN-AA-XB |
| 898 | EX-4 | 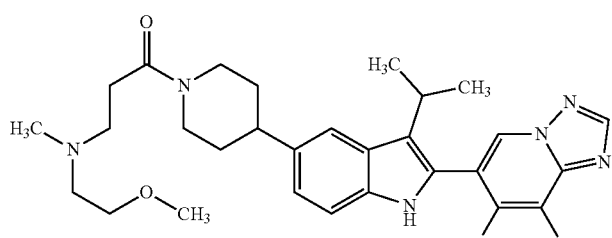 | 531.2 | 1.35 | QC-ACN-TFA-XB |

TABLE 21-continued

| Ex. No. | Template Starting Material | Structure | LCMS MH+ | R$_t$ (min) | HPLC Method |
|---|---|---|---|---|---|
| 899 | EX-4 | 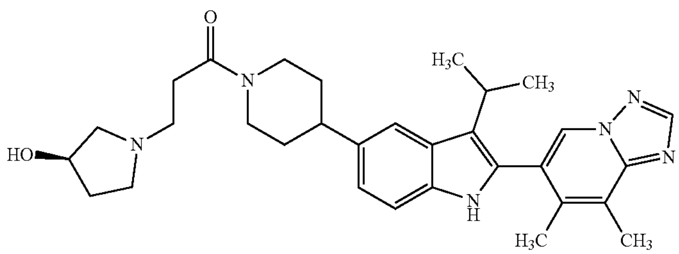 [SMILES: Cc1c(-c2[nH]c3ccc(C4CCN(C(=O)CCN5CC[C@@H](O)C5)CC4)cc3c2C(C)C)cn2ncnc2c1C] | 529.2 | 1.32 | QC-ACN-AA-XB |
| 900 | EX-4 | 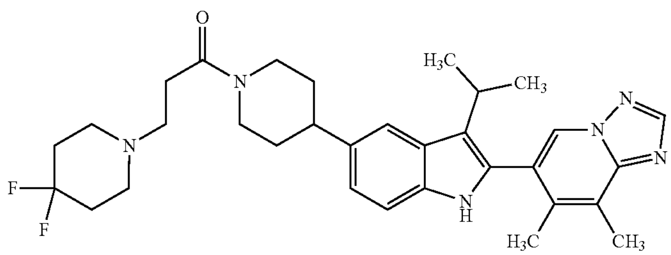 [SMILES: Cc1c(-c2[nH]c3ccc(C4CCN(C(=O)CCN5CCC(F)(F)CC5)CC4)cc3c2C(C)C)cn2ncnc2c1C] | 563.2 | 1.37 | QC-ACN-TFA-XB |
| 901 | EX-4 | 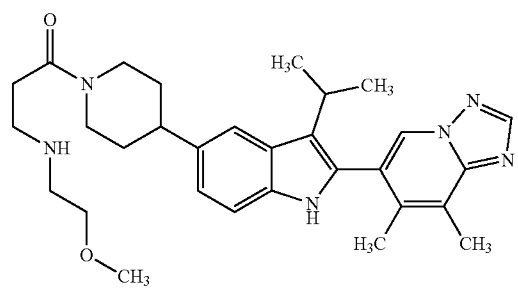 [SMILES: COCCNCCC(=O)N1CCC(c2ccc3[nH]c(-c4cn5ncnc5c(C)c4C)c(C(C)C)c3c2)CC1] | 517.2 | 1.32 | QC-ACN-TFA-XB |
| 902 | EX-4 | 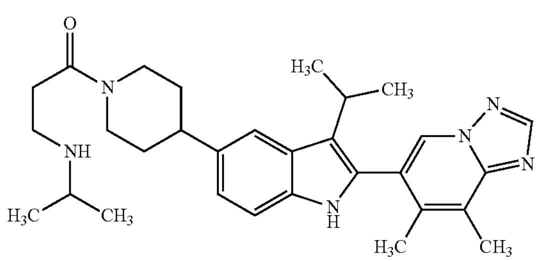 [SMILES: Cc1c(-c2[nH]c3ccc(C4CCN(C(=O)CCNC(C)C)CC4)cc3c2C(C)C)cn2ncnc2c1C] | 501.2 | 1.33 | QC-ACN-TFA-XB |
| 903 | EX-4 | 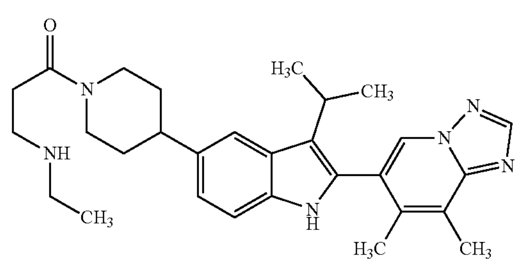 [SMILES: CCNCCC(=O)N1CCC(c2ccc3[nH]c(-c4cn5ncnc5c(C)c4C)c(C(C)C)c3c2)CC1] | 487.1 | 1.29 | QC-ACN-TFA-XB |

TABLE 21-continued

| Ex. No. | Template Starting Material | Structure | LCMS MH+ | R$_t$ (min) | HPLC Method |
|---|---|---|---|---|---|
| 904 | EX-4 | 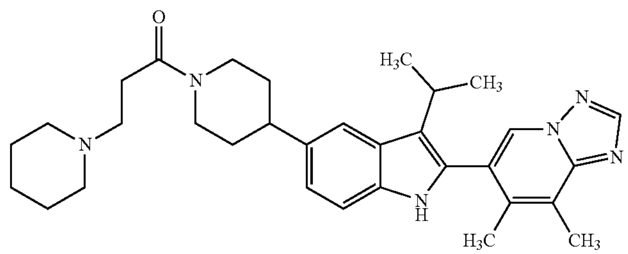 [SMILES: Cc1c(-c2[nH]c3ccc(C4CCN(C(=O)CCN5CCCCC5)CC4)cc3c2C(C)C)cn2ncnc2c1C] | 527.0 | 1.35 | QC-ACN-TFA-XB |
| 905 | EX-4 | 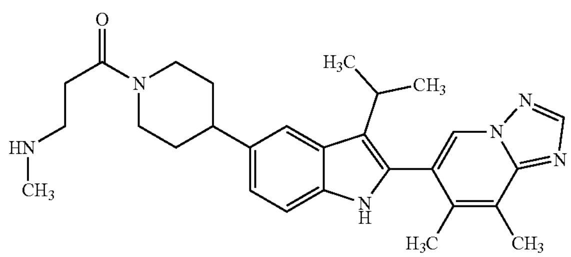 [SMILES: CNCCC(=O)N1CCC(c2ccc3[nH]c(-c4cn5ncnc5c(C)c4C)c(C(C)C)c3c2)CC1] | 473.1 | 1.31 | QC-ACN-AA-XB |
| 906 | EX-4 | 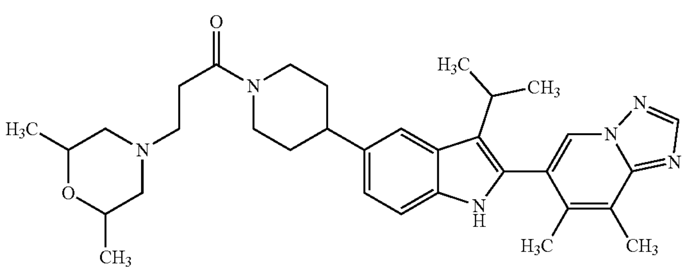 [SMILES: Cc1c(-c2[nH]c3ccc(C4CCN(C(=O)CCN5CC(C)OC(C)C5)CC4)cc3c2C(C)C)cn2ncnc2c1C] | 557.2 | 1.65 | QC-ACN-AA-XB |
| 907 | EX-4 | 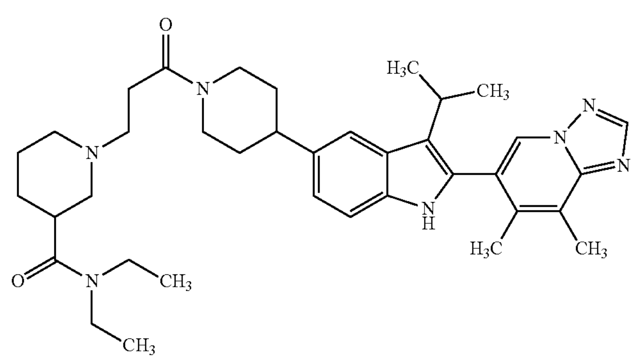 [SMILES: CCN(CC)C(=O)C1CCCN(CCC(=O)N2CCC(c3ccc4[nH]c(-c5cn6ncnc6c(C)c5C)c(C(C)C)c4c3)CC2)C1] | 626.2 | 1.56 | QC-ACN-AA-XB |
| 908 | EX-4 | 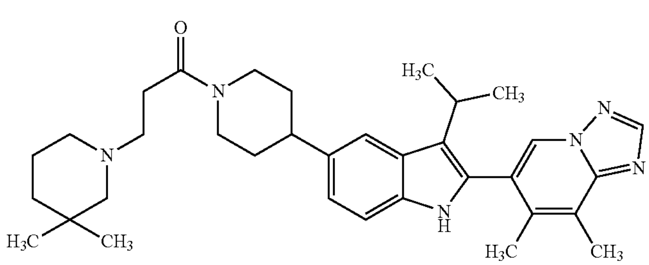 [SMILES: Cc1c(-c2[nH]c3ccc(C4CCN(C(=O)CCN5CCCC(C)(C)C5)CC4)cc3c2C(C)C)cn2ncnc2c1C] | 555.2 | 1.62 | QC-ACN-AA-XB |

TABLE 21-continued

| Ex. No. | Template Starting Material | Structure | LCMS MH+ | R_t (min) | HPLC Method |
|---|---|---|---|---|---|
| 909 | EX-4 | 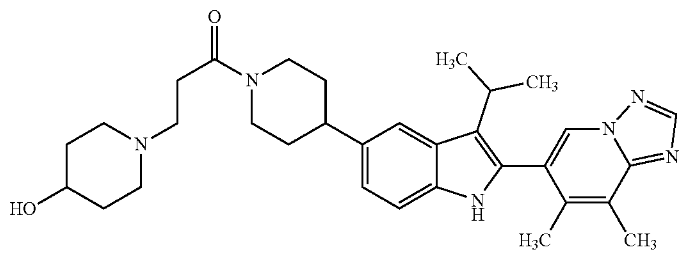 [SMILES: Cc1c(-c2[nH]c3ccc(C4CCN(C(=O)CCN5CCC(O)CC5)CC4)cc3c2C(C)C)cn2ncnc2c1C] | 543.2 | 1.32 | QC-ACN-AA-XB |
| 910 | EX-4 | 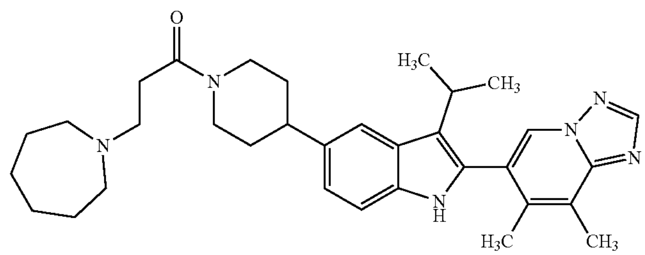 [SMILES: Cc1c(-c2[nH]c3ccc(C4CCN(C(=O)CCN5CCCCCC5)CC4)cc3c2C(C)C)cn2ncnc2c1C] | 541.2 | 1.5 | QC-ACN-AA-XB |
| 911 | EX-4 | 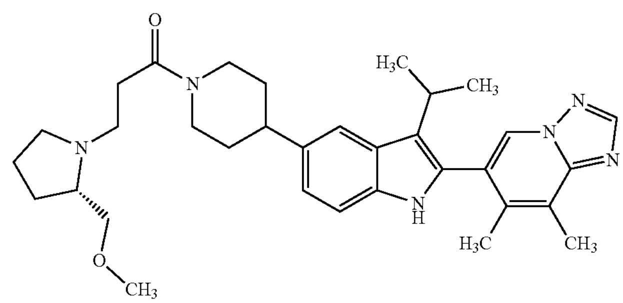 [SMILES: COC[C@@H]1CCCN1CCC(=O)N1CCC(c2ccc3[nH]c(-c4cn5ncnc5c(C)c4C)c(C(C)C)c3c2)CC1] | 557.2 | 1.48 | QC-ACN-AA-XB |
| 912 | EX-4 | 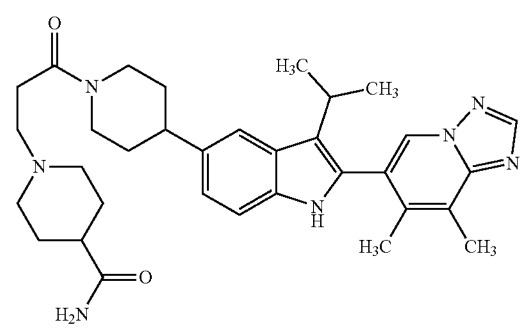 [SMILES: Cc1c(-c2[nH]c3ccc(C4CCN(C(=O)CCN5CCC(C(N)=O)CC5)CC4)cc3c2C(C)C)cn2ncnc2c1C] | 570.2 | 1.31 | QC-ACN-AA-XB |
| 913 | EX-4 | 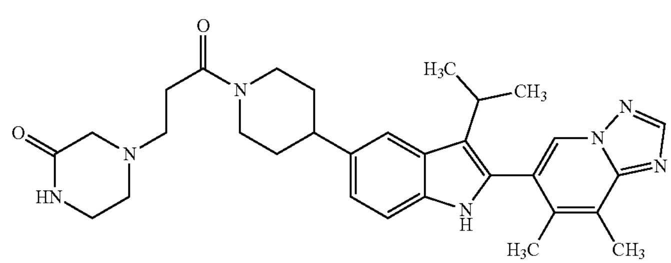 [SMILES: Cc1c(-c2[nH]c3ccc(C4CCN(C(=O)CCN5CCNC(=O)C5)CC4)cc3c2C(C)C)cn2ncnc2c1C] | 542.2 | 1.44 | QC-ACN-AA-XB |

TABLE 21-continued

| Ex. No. | Template Starting Material | Structure | LCMS MH+ | R$_t$ (min) | HPLC Method |
|---|---|---|---|---|---|
| 914 | EX-4 | 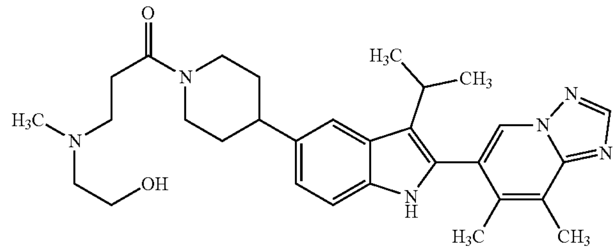 [SMILES: Cc1c(-c2[nH]c3ccc(C4CCN(C(=O)CCN(C)CCO)CC4)cc3c2C(C)C)cn2ncnc2c1C] | 517.2 | 1.32 | QC-ACN-AA-XB |
| 915 | EX-4 | 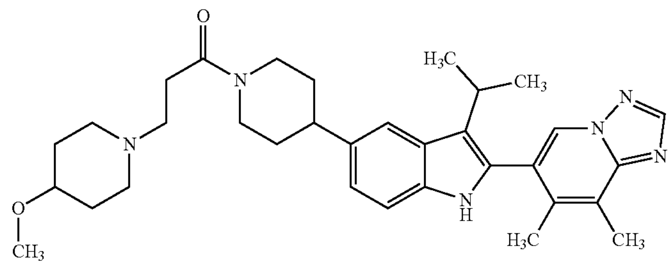 [SMILES: COC1CCN(CCC(=O)N2CCC(c3ccc4[nH]c(-c5cn6ncnc6c(C)c5C)c(C(C)C)c4c3)CC2)CC1] | 557.2 | 1.43 | QC-ACN-AA-XB |
| 916 | EX-4 | 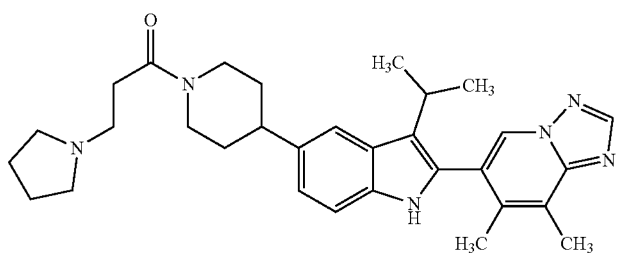 [SMILES: Cc1c(-c2[nH]c3ccc(C4CCN(C(=O)CCN5CCCC5)CC4)cc3c2C(C)C)cn2ncnc2c1C] | 513.1 | 1.38 | QC-ACN-AA-XB |
| 917 | EX-4 | 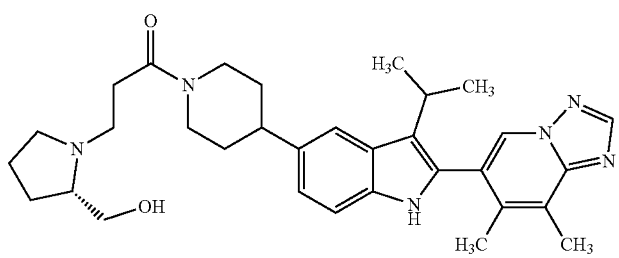 [SMILES: Cc1c(-c2[nH]c3ccc(C4CCN(C(=O)CCN5CCC[C@H]5CO)CC4)cc3c2C(C)C)cn2ncnc2c1C] | 543.2 | 1.35 | QC-ACN-AA-XB |
| 918 | EX-4 | 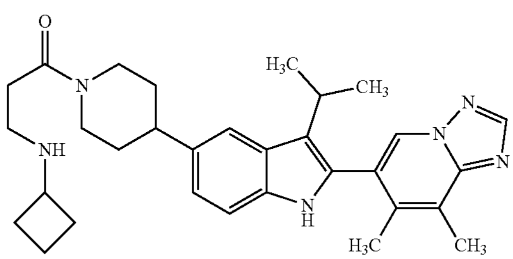 [SMILES: Cc1c(-c2[nH]c3ccc(C4CCN(C(=O)CCNC5CCC5)CC4)cc3c2C(C)C)cn2ncnc2c1C] | 513.2 | 1.39 | QC-ACN-TFA-XB |
| 919 | EX-4 | 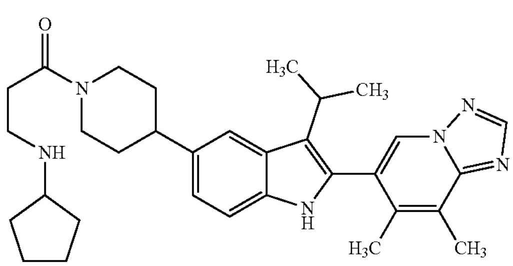 [SMILES: Cc1c(-c2[nH]c3ccc(C4CCN(C(=O)CCNC5CCCC5)CC4)cc3c2C(C)C)cn2ncnc2c1C] | 527.2 | 1.42 | QC-ACN-TFA-XB |

TABLE 21-continued

| Ex. No. | Template Starting Material | Structure | LCMS MH+ | $R_t$ (min) | HPLC Method |
|---|---|---|---|---|---|
| 920 | EX-4 | 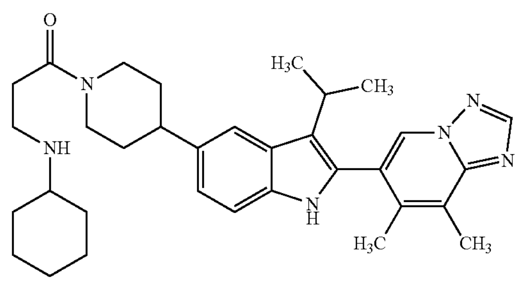 [SMILES: Cc1c(-c2[nH]c3ccc(C4CCN(C(=O)CCNC5CCCCC5)CC4)cc3c2C(C)C)cn2ncnc2c1C] | 541.2 | 1.49 | QC-ACN-TFA-XB |
| 921 | EX-4 | 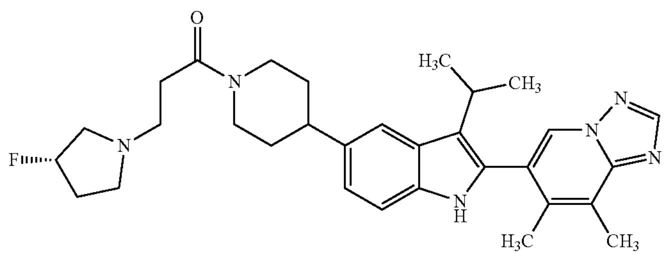 [SMILES: Cc1c(-c2[nH]c3ccc(C4CCN(C(=O)CCN5CC[C@H](F)C5)CC4)cc3c2C(C)C)cn2ncnc2c1C] | 531.2 | 1.49 | QC-ACN-AA-XB |
| 922 | EX-4 | 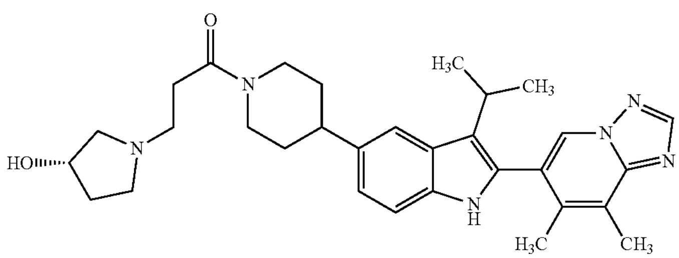 [SMILES: Cc1c(-c2[nH]c3ccc(C4CCN(C(=O)CCN5CC[C@H](O)C5)CC4)cc3c2C(C)C)cn2ncnc2c1C] | 529.2 | 1.32 | QC-ACN-AA-XB |
| 923 | EX-4 | 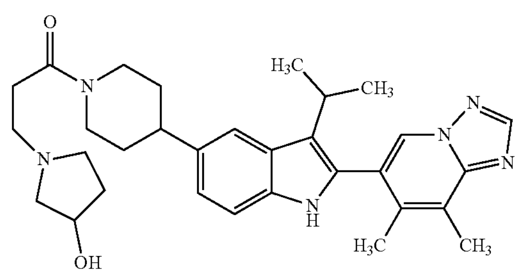 [SMILES: Cc1c(-c2[nH]c3ccc(C4CCN(C(=O)CCN5CCC(O)C5)CC4)cc3c2C(C)C)cn2ncnc2c1C] | 529.2 | 1.32 | QC-ACN-AA-XB |
| 924 | EX-4 | 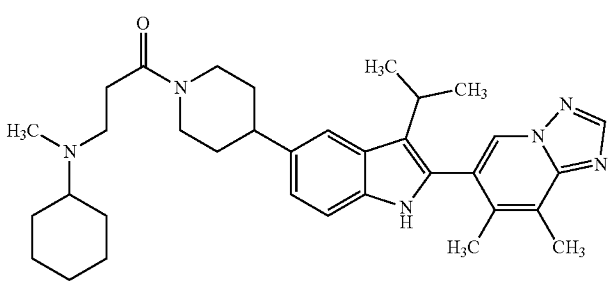 [SMILES: Cc1c(-c2[nH]c3ccc(C4CCN(C(=O)CCN(C)C5CCCCC5)CC4)cc3c2C(C)C)cn2ncnc2c1C] | 555.2 | 1.52 | QC-ACN-TFA-XB |

TABLE 21-continued

| Ex. No. | Template Starting Material | Structure | LCMS MH+ | $R_t$ (min) | HPLC Method |
|---|---|---|---|---|---|
| 925 | EX-4 | 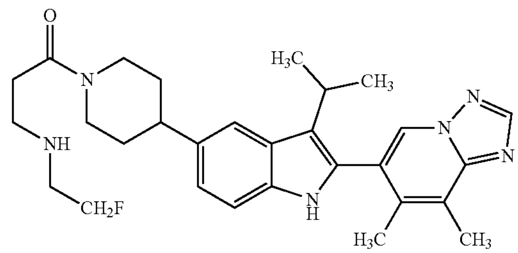 | 505.2 | 1.31 | QC-ACN-TFA-XB |
| 926 | EX-4 | 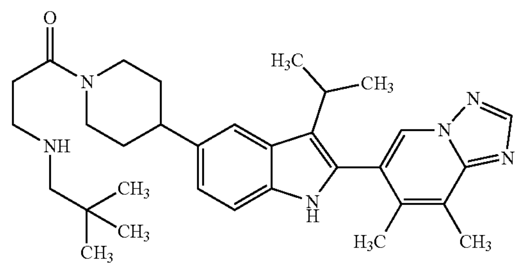 [SMILES: Cc1c(-c2[nH]c3ccc(C4CCN(C(=O)CCNCC(C)(C)C)CC4)cc3c2C(C)C)cn2ncnc2c1C] | 529.3 | 1.54 | QC-ACN-TFA-XB |

Example 927

Azetidin-3-yl 4-(2-(7,8-dimethyl-[1,2,4]triazolo[1,5-a]pyridin-6-yl)-3-isopropyl-1H-indol-5-yl)piperidine-1-carboxylate (927)

1-(tert-butoxycarbonyl)azetidin-3-yl 4-(2-(7,8-dimethyl-[1,2,4]triazolo[1,5-a]pyridin-6-yl)-3-isopropyl-1H-indol-5-yl)piperidine-1-carboxylate (15 mg, 0.026 mmol) and 2:1 trifluoroacetic acid:dichloromethane (1.2 mL, 0.026 mmol) were combined in a 1-dram vial containing a stir bar. The resulting clear, yellow solution was stirred at room temperature for 30 min. After completion of the reaction, toluene (150 μL) was added to the reaction mixture. The reaction mixture was stirred briefly and excess solvent was evaporated. The residue was taken up in DMF (1.5 mL) and purified by semi-preparative HPLC on a C-18 column on the Shimadzu instrument, eluting with water/acetonitrile/TFA. Excess solvent was evaporated from product-containing fractions to afford azetidin-3-yl 4-(2-(7,8-dimethyl-[1,2,4]triazolo[1,5-a]pyridin-6-yl)-3-isopropyl-1H-indol-5-yl)piperidine-1-carboxylate, TFA (14.9 mg, 0.025 mmol, 96% yield) as a white solid. LCMS MH+: 487.3. HPLC Ret. Time 1.40 min. Method QC-ACN-TFA-XB. $^1$H NMR (400 MHz, METHANOL-$d_4$) δ 8.68 (s, 1H), 8.58 (s, 1H), 7.60 (s, 1H), 7.33 (d, J=8.3 Hz, 1H), 7.08 (dd, J=8.4, 1.5 Hz, 1H), 5.33-5.24 (m, 1H), 4.45 (dd, J=12.7, 7.0 Hz, 2H), 4.38-4.25 (m, 2H), 4.21 (br. s., 2H), 3.17-3.06 (m, 1H), 2.98 (dq, J=13.6, 6.8 Hz, 4H), 2.88 (tt, J=12.0, 3.3 Hz, 1H), 2.67 (s, 3H), 2.30 (s, 3H), 1.96 (d, J=12.0 Hz, 2H), 1.75 (br. s., 2H), 1.40 (d, J=7.1 Hz, 6H).

The following examples were prepared according to the general process described in Example 929.

TABLE 22

| Ex. No. | Structure | LCMS MH+ | $R_t$ (min) | HPLC Method |
|---|---|---|---|---|
| 928 | 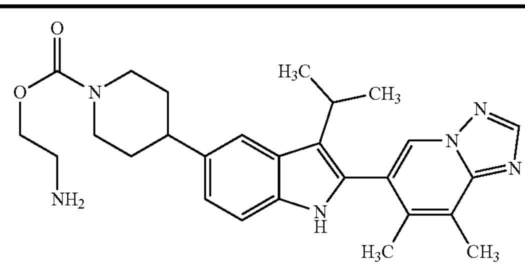 | 475.1 | 1.45 | QC-ACN-TFA-XB |

TABLE 22-continued

| Ex. No. | Structure | LCMS MH+ | R$_t$ (min) | HPLC Method |
|---|---|---|---|---|
| 929 | 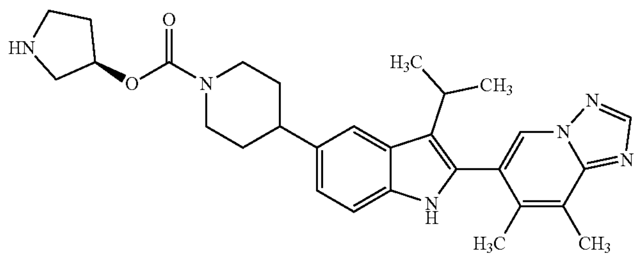 [SMILES: Cc1c(-c2[nH]c3ccc(C4CCN(C(=O)O[C@@H]5CCNC5)CC4)cc3c2C(C)C)cn2ncnc2c1C] | 501.4 | 1.48 | QC-ACN-TFA-XB |
| 930 | 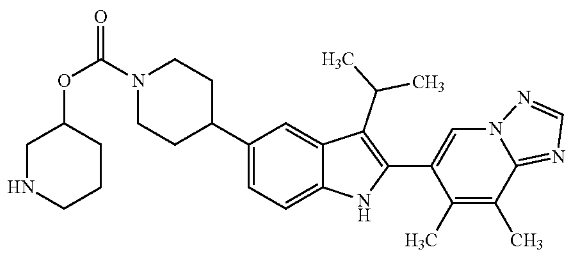 [SMILES: Cc1c(-c2[nH]c3ccc(C4CCN(C(=O)OC5CCCNC5)CC4)cc3c2C(C)C)cn2ncnc2c1C] | 515.4 | 1.42 | QC-ACN-TFA-XB |
| 931 | 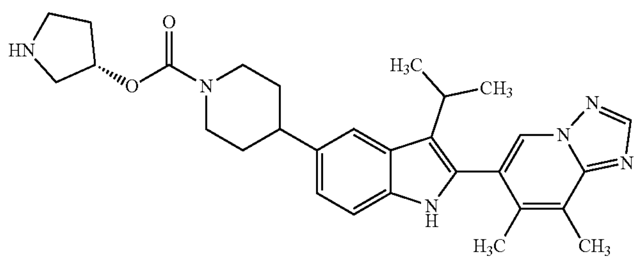 [SMILES: Cc1c(-c2[nH]c3ccc(C4CCN(C(=O)O[C@H]5CCNC5)CC4)cc3c2C(C)C)cn2ncnc2c1C] | 501.4 | 1.37 | QC-ACN-TFA-XB |
| 932 | 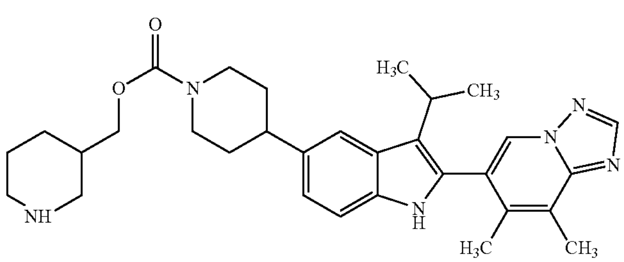 [SMILES: Cc1c(-c2[nH]c3ccc(C4CCN(C(=O)OCC5CCCNC5)CC4)cc3c2C(C)C)cn2ncnc2c1C] | 529.3 | 1.54 | QC-ACN-AA-XB |
| 933 | 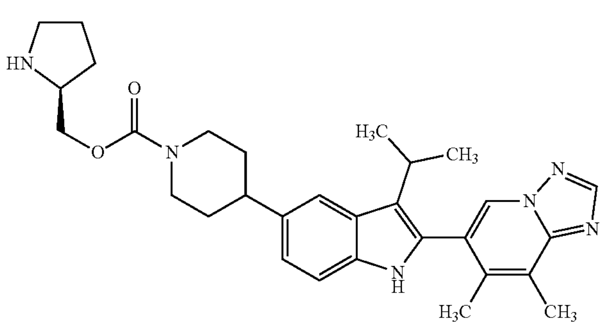 [SMILES: Cc1c(-c2[nH]c3ccc(C4CCN(C(=O)OC[C@@H]5CCCN5)CC4)cc3c2C(C)C)cn2ncnc2c1C] | 515.4 | 1.4 | QC-ACN-TFA-XB |

TABLE 22-continued

| Ex. No. | Structure | LCMS MH+ | R_t (min) | HPLC Method |
|---|---|---|---|---|
| 934 | 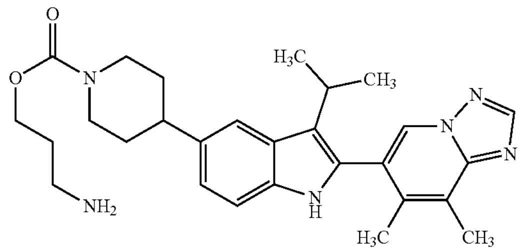 [SMILES: Cc1c(-c2[nH]c3ccc(C4CCN(C(=O)OCCCN)CC4)cc3c2C(C)C)cn2ncnc2c1C] | 489.4 | 1.36 | QC-ACN-TFA-XB |
| 935 | 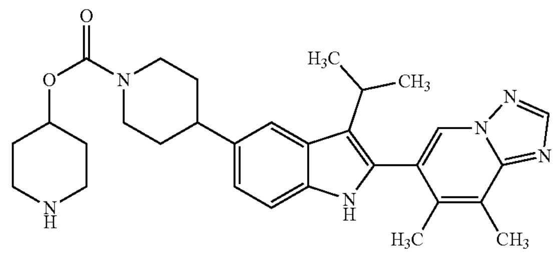 [SMILES: Cc1c(-c2[nH]c3ccc(C4CCN(C(=O)OC5CCNCC5)CC4)cc3c2C(C)C)cn2ncnc2c1C] | 515.4 | 1.4 | QC-ACN-TFA-XB |
| 936 | 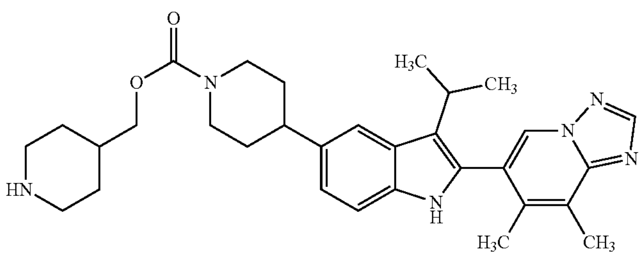 [SMILES: Cc1c(-c2[nH]c3ccc(C4CCN(C(=O)OCC5CCNCC5)CC4)cc3c2C(C)C)cn2ncnc2c1C] | 529.4 | 1.52 | QC-ACN-AA-XB |
| 937 | 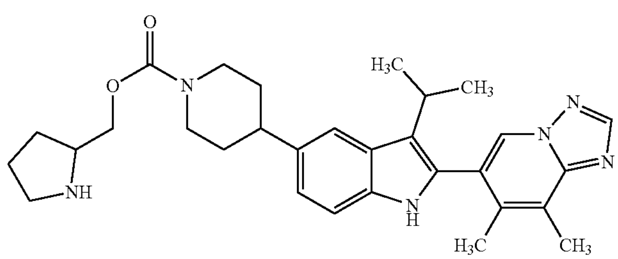 [SMILES: Cc1c(-c2[nH]c3ccc(C4CCN(C(=O)OCC5CCCN5)CC4)cc3c2C(C)C)cn2ncnc2c1C] | 515.0 | 1.52 | QC-ACN-TFA-XB |
| 938 | 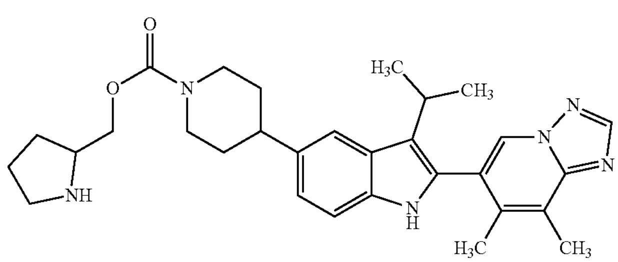 [SMILES: Cc1c(-c2[nH]c3ccc(C4CCN(C(=O)OCC5CCCN5)CC4)cc3c2C(C)C)cn2ncnc2c1C] | 515.0 | 1.58 | QC-ACN-AA-XB |

TABLE 22-continued

| Ex. No. | Structure | LCMS MH+ | R<sub>t</sub> (min) | HPLC Method |
|---|---|---|---|---|
| 939 | 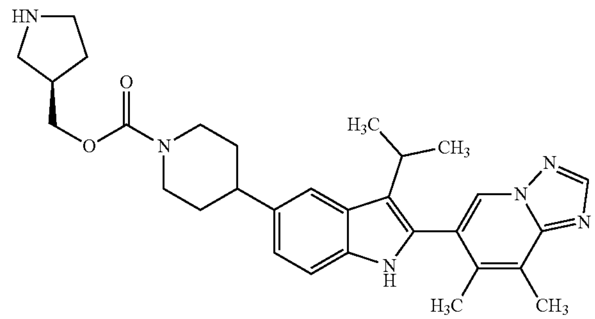 [SMILES: Cc1c(-c2[nH]c3ccc(C4CCN(C(=O)OC[C@@H]5CCNC5)CC4)cc3c2C(C)C)cn2ncnc2c1C] | 515.1 | 1.52 | QC-ACN-TFA-XB |
| 940 | 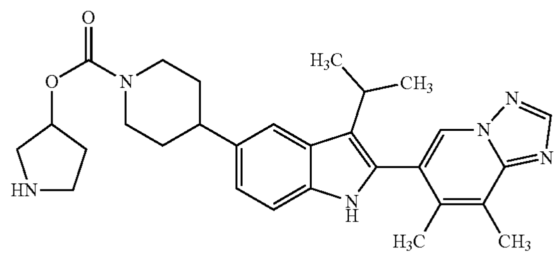 [SMILES: Cc1c(-c2[nH]c3ccc(C4CCN(C(=O)OC5CCNC5)CC4)cc3c2C(C)C)cn2ncnc2c1C] | 501.1 | 1.55 | QC-ACN-AA-XB |
| 941 | 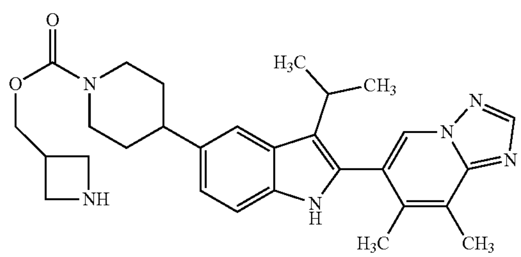 [SMILES: Cc1c(-c2[nH]c3ccc(C4CCN(C(=O)OCC5CNC5)CC4)cc3c2C(C)C)cn2ncnc2c1C] | 501.4 | 1.37 | QC-ACN-TFA-XB |
| 942 | 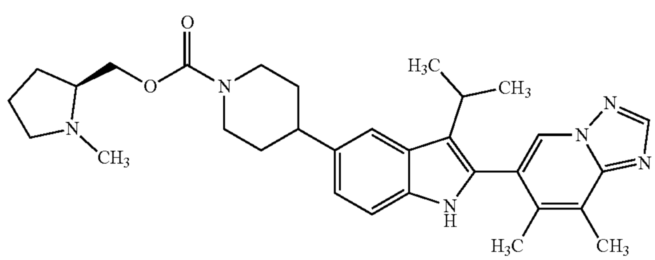 [SMILES: Cc1c(-c2[nH]c3ccc(C4CCN(C(=O)OC[C@@H]5CCCN5C)CC4)cc3c2C(C)C)cn2ncnc2c1C] | 528.9 | 1.64 | QC-ACN-AA-XB |
| 943 | 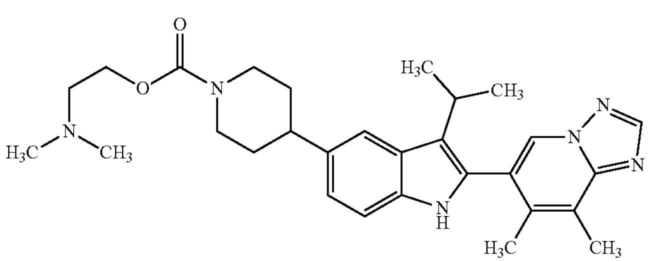 [SMILES: Cc1c(-c2[nH]c3ccc(C4CCN(C(=O)OCCN(C)C)CC4)cc3c2C(C)C)cn2ncnc2c1C] | 503.4 | 1.35 | QC-ACN-TFA-XB |

TABLE 22-continued

| Ex. No. | Structure | LCMS MH+ | R$_t$ (min) | HPLC Method |
|---|---|---|---|---|
| 944 | 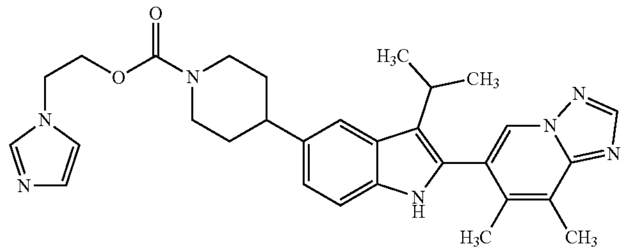 [SMILES: Cc1c(-c2[nH]c3ccc(C4CCN(C(=O)OCCn5ccnc5)CC4)cc3c2C(C)C)cn2ncnc2c1C] | 526.3 | 1.37 | QC-ACN-TFA-XB |
| 945 | 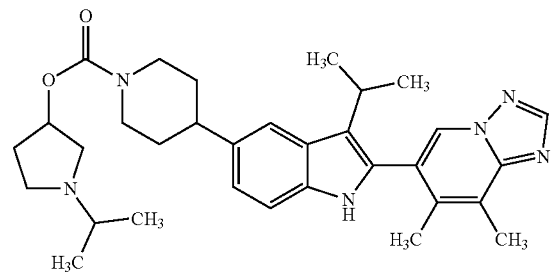 [SMILES: Cc1c(-c2[nH]c3ccc(C4CCN(C(=O)OC5CCN(C(C)C)C5)CC4)cc3c2C(C)C)cn2ncnc2c1C] | 543.5 | 1.45 | QC-ACN-TFA-XB |
| 946 | 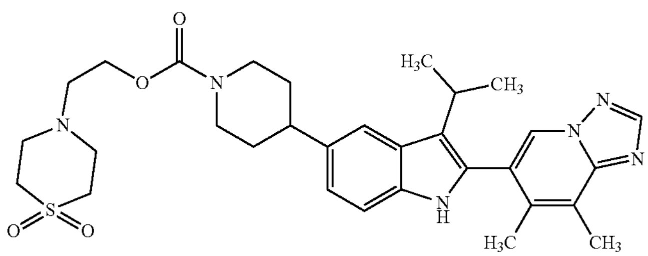 [SMILES: Cc1c(-c2[nH]c3ccc(C4CCN(C(=O)OCCN5CCS(=O)(=O)CC5)CC4)cc3c2C(C)C)cn2ncnc2c1C] | 593.4 | 1.45 | QC-ACN-TFA-XB |
| 947 | 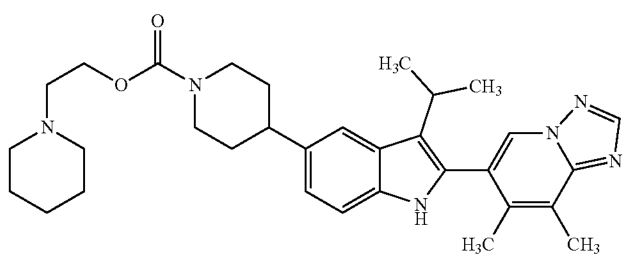 [SMILES: Cc1c(-c2[nH]c3ccc(C4CCN(C(=O)OCCN5CCCCC5)CC4)cc3c2C(C)C)cn2ncnc2c1C] | 543.5 | 1.45 | QC-ACN-TFA-XB |
| 948 | 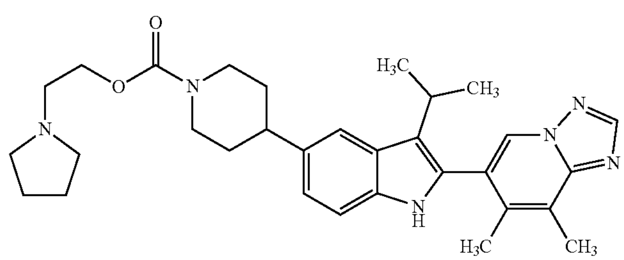 [SMILES: Cc1c(-c2[nH]c3ccc(C4CCN(C(=O)OCCN5CCCC5)CC4)cc3c2C(C)C)cn2ncnc2c1C] | 529.5 | 1.41 | QC-ACN-TFA-XB |
| 949 | 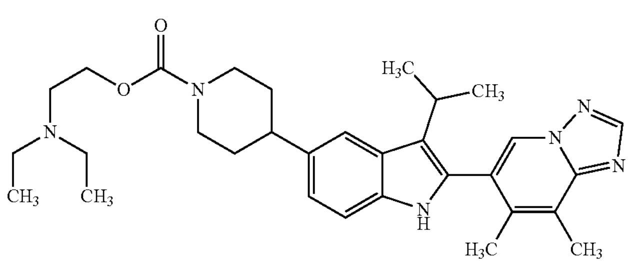 [SMILES: CCN(CC)CCOC(=O)N1CCC(c2ccc3[nH]c(-c4cn5ncnc5c(C)c4C)c(C(C)C)c3c2)CC1] | 531.3 | 1.47 | QC-ACN-TFA-XB |

TABLE 22-continued

| Ex. No. | Structure | LCMS MH+ | R$_t$ (min) | HPLC Method |
|---|---|---|---|---|
| 950 | 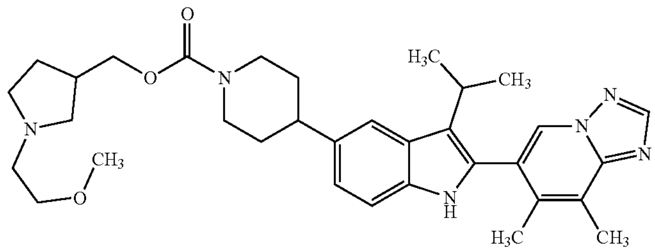 [SMILES: COCCN1CCC(COC(=O)N2CCC(c3ccc4[nH]c(-c5cn6ncnc6c(C)c5C)c(C(C)C)c4c3)CC2)C1] | 573.1 | 1.55 | QC-ACN-AA-XB |
| 951 | 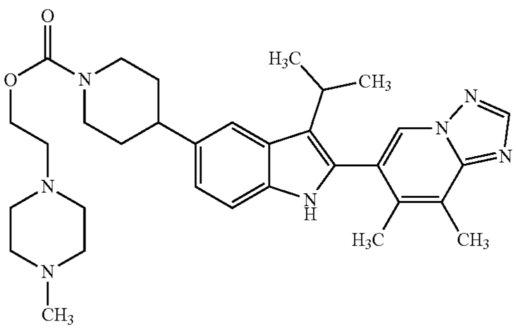 [SMILES: Cc1c(-c2[nH]c3ccc(C4CCN(C(=O)OCCN5CCN(C)CC5)CC4)cc3c2C(C)C)cn2ncnc2c1C] | 558.1 | 1.48 | QC-ACN-AA-XB |
| 952 | 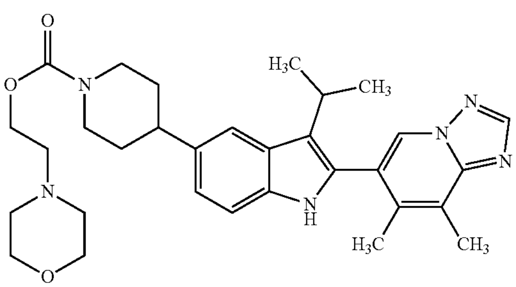 [SMILES: Cc1c(-c2[nH]c3ccc(C4CCN(C(=O)OCCN5CCOCC5)CC4)cc3c2C(C)C)cn2ncnc2c1C] | 545.0 | 1.8 | QC-ACN-AA-XB |
| 953 | 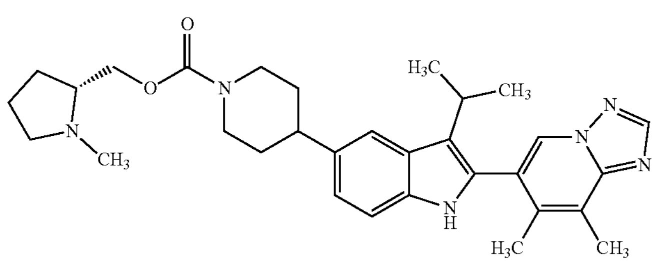 [SMILES: Cc1c(-c2[nH]c3ccc(C4CCN(C(=O)OC[C@H]5CCCN5C)CC4)cc3c2C(C)C)cn2ncnc2c1C] | 265.2 | 1.52 | QC-ACN-TFA-XB |
| 954 | 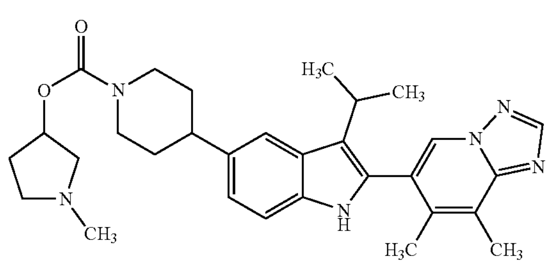 [SMILES: Cc1c(-c2[nH]c3ccc(C4CCN(C(=O)OC5CCN(C)C5)CC4)cc3c2C(C)C)cn2ncnc2c1C] | 515.1 | 1.67 | QC-ACN-AA-XB |

TABLE 22-continued

| Ex. No. | Structure | LCMS MH+ | R$_t$ (min) | HPLC Method |
|---|---|---|---|---|
| 955 | 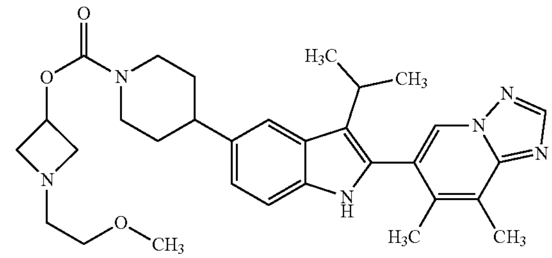 [SMILES: COCCN1CC(OC(=O)N2CCC(c3ccc4[nH]c(-c5cn6ncnc6c(C)c5C)c(C(C)C)c4c3)CC2)C1] | 545.1 | 1.76 | QC-ACN-AA-XB |
| 956 | 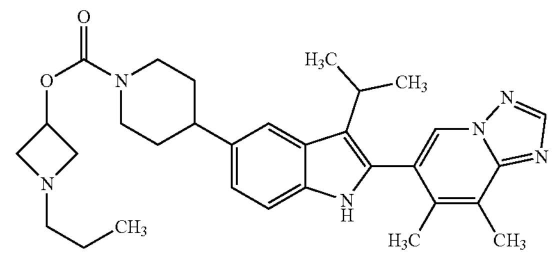 [SMILES: CCCN1CC(OC(=O)N2CCC(c3ccc4[nH]c(-c5cn6ncnc6c(C)c5C)c(C(C)C)c4c3)CC2)C1] | 529.1 | 1.59 | QC-ACN-TFA-XB |

Example 957

(4-(2-(7,8-dimethyl-[1,2,4]triazolo[1,5-a]pyridin-6-yl)-3-isopropyl-1H-indol-5-yl)piperid in-1-yl)(4-methylpiperazin-1-yl)methanone (957)

6-(3-isopropyl-5-(piperidin-4-yl)-1H-indol-2-yl)-7,8-dimethyl-[1,2,4]triazolo[1,5-a]pyridine (10 mg, 0.026 mmol) was dissolved in THF (0.25 mL). Phenyl carbonochloridate (6.06 mg, 0.039 mmol) was added to the solution. The reaction mixture was stirred overnight at room temperature. The reaction mixture was blown down on a ZYmark Turbovap at 45° C. for 1 h. The residue was dissolved in NMP (0.25 mL). Next, 1-methylpiperazine (7.75 mg, 0.077 mmol) and DIPEA (6.76 μl, 0.039 mmol) were added to the NMP solution of the intermediate. The reaction mixture was stirred at 100° C. overnight. Crude samples with final volume of 1.8 mL in DMF/NMP in a stubby tube were purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the product were combined and dried via centrifugal evaporation to afford (4-(2-(7,8-dimethyl-[1,2,4]triazolo[1,5-a]pyridin-6-yl)-3-isopropyl-1H-indol-5-yl) piperid in-1-yl)(4-methylpiperazin-1-yl) methanone (4 mg, 7.63 μmol, 29.6% yield). LCMS MH+: 514.4. HPLC Ret. Time 1.29 min. Method QC-ACN-TFA-XB.

The following examples were prepared according to the general process described in Example 957.

TABLE 23

| Ex. No. | Starting Material | Structure | LCMS MH+ | R$_t$ (min) | HPLC Method |
|---|---|---|---|---|---|
| 958 | EX-4 | 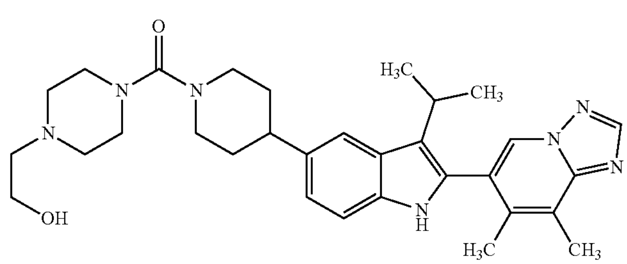 [SMILES: Cc1c(-c2[nH]c3ccc(C4CCN(C(=O)N5CCN(CCO)CC5)CC4)cc3c2C(C)C)cn2ncnc2c1C] | 565.9 | 1.57 | QC-ACN-AA-XB |

TABLE 23-continued

| Ex. No. | Starting Material | Structure | LCMS MH+ | R$_t$ (min) | HPLC Method |
|---|---|---|---|---|---|
| 959 | EX-4 | 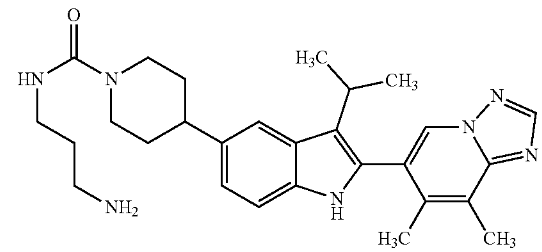 [SMILES: Cc1c(-c2[nH]c3ccc(C4CCN(C(=O)NCCCN)CC4)cc3c2C(C)C)cn2ncnc2c1C] | 488.3 | 1.27 | QC-ACN-TFA-XB |
| 960 | EX-4 | 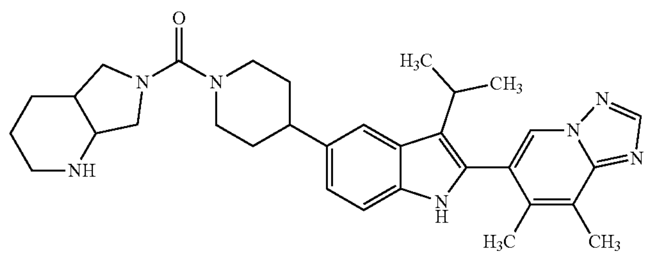 [SMILES: Cc1c(-c2[nH]c3ccc(C4CCN(C(=O)N5CC6CCCNC6C5)CC4)cc3c2C(C)C)cn2ncnc2c1C] | 540.5 | 1.46 | QC-ACN-TFA-XB |
| 961 | EX-4 | 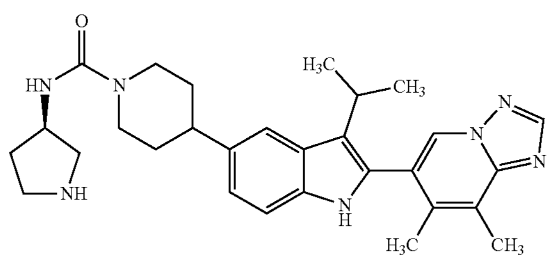 [SMILES: Cc1c(-c2[nH]c3ccc(C4CCN(C(=O)N[C@@H]5CCNC5)CC4)cc3c2C(C)C)cn2ncnc2c1C] | 500.0 | 1.31 | QC-ACN-AA-XB |
| 962 | EX-4 | 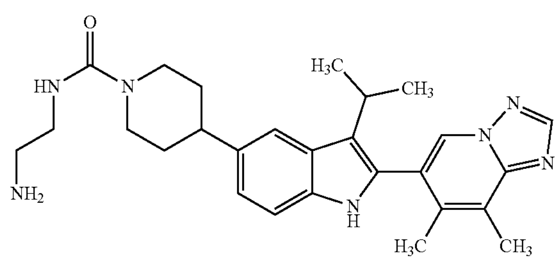 [SMILES: Cc1c(-c2[nH]c3ccc(C4CCN(C(=O)NCCN)CC4)cc3c2C(C)C)cn2ncnc2c1C] | 474.4 | 1.27 | QC-ACN-AA-XB |
| 963 | EX-4 | 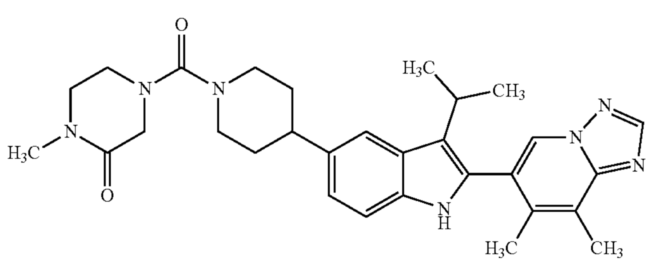 [SMILES: Cc1c(-c2[nH]c3ccc(C4CCN(C(=O)N5CCN(C)C(=O)C5)CC4)cc3c2C(C)C)cn2ncnc2c1C] | 528.5 | 1.56 | QC-ACN-AA-XB |
| 964 | EX-4 | 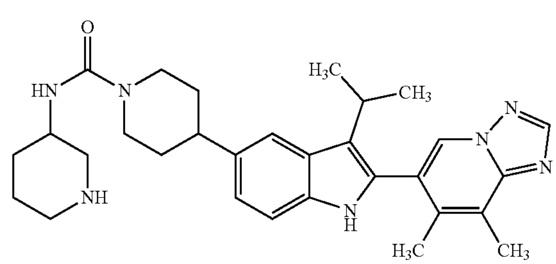 [SMILES: Cc1c(-c2[nH]c3ccc(C4CCN(C(=O)NC5CCCNC5)CC4)cc3c2C(C)C)cn2ncnc2c1C] | 514.2 | 1.36 | QC-ACN-AA-XB |

TABLE 23-continued

| Ex. No. | Starting Material | Structure | LCMS MH+ | R_t (min) | HPLC Method |
|---|---|---|---|---|---|
| 965 | EX-4 | 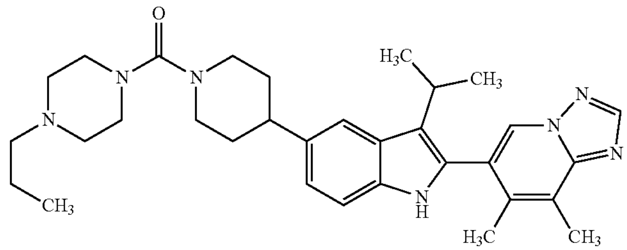 | 542.6 | 1.83 | QC-ACN-AA-XB |
| 966 | EX-4 | 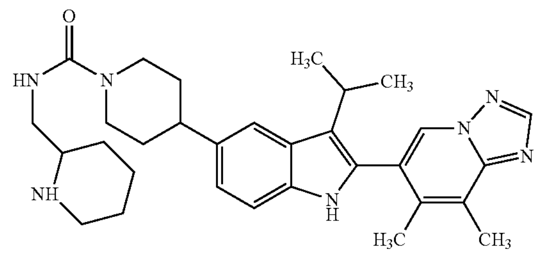 [SMILES: Cc1c(-c2[nH]c3ccc(C4CCN(C(=O)NCC5CCCCN5)CC4)cc3c2C(C)C)cn2ncnc2c1C] | 528.5 | 1.39 | QC-ACN-TFA-XB |
| 967 | EX-4 | 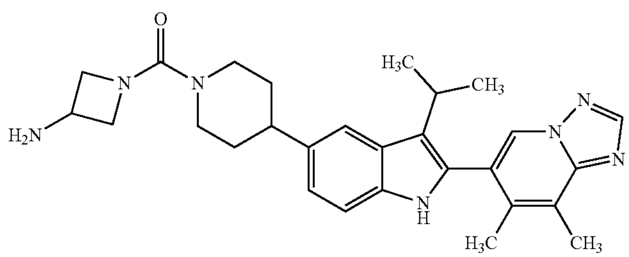 [SMILES: Cc1c(-c2[nH]c3ccc(C4CCN(C(=O)N5CC(N)C5)CC4)cc3c2C(C)C)cn2ncnc2c1C] | 486.0 | 1.55 | QC-ACN-AA-XB |
| 968 | EX-4 | 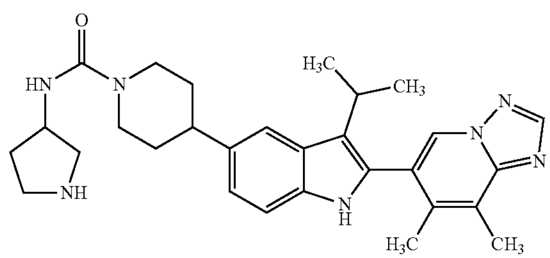 [SMILES: Cc1c(-c2[nH]c3ccc(C4CCN(C(=O)NC5CCNC5)CC4)cc3c2C(C)C)cn2ncnc2c1C] | 500.5 | 1.31 | QC-ACN-AA-XB |
| 969 | EX-4 | 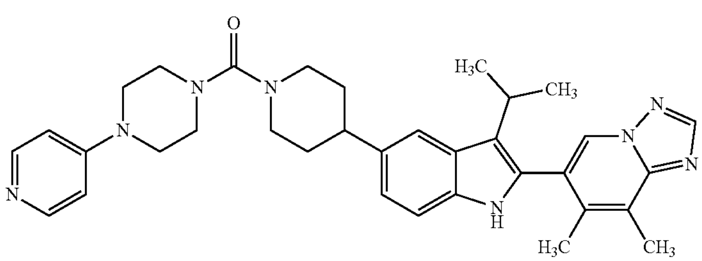 [SMILES: Cc1c(-c2[nH]c3ccc(C4CCN(C(=O)N5CCN(c6ccncc6)CC5)CC4)cc3c2C(C)C)cn2ncnc2c1C] | 577.6 | 1.45 | QC-ACN-TFA-XB |
| 970 | EX-4 | 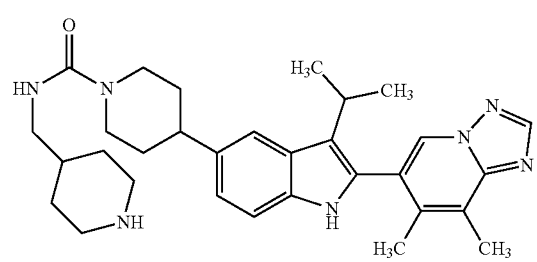 [SMILES: Cc1c(-c2[nH]c3ccc(C4CCN(C(=O)NCC5CCNCC5)CC4)cc3c2C(C)C)cn2ncnc2c1C] | 528.5 | 1.33 | QC-ACN-TFA-XB |

TABLE 23-continued

| Ex. No. | Starting Material | Structure | LCMS MH+ | R$_t$ (min) | HPLC Method |
|---|---|---|---|---|---|
| 971 | EX-4 | 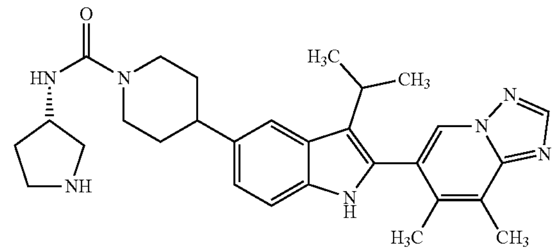 | 500.3 | 1.3 | QC-ACN-TFA-XB |
| 972 | EX-4 | 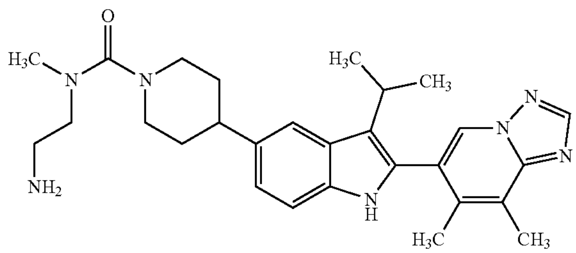 [SMILES: Cc1c(-c2[nH]c3ccc(C4CCN(C(=O)N(C)CCN)CC4)cc3c2C(C)C)cn2ncnc2c1C] | 488.0 | 1.43 | QC-ACN-TFA-XB |
| 973 | EX-4 | 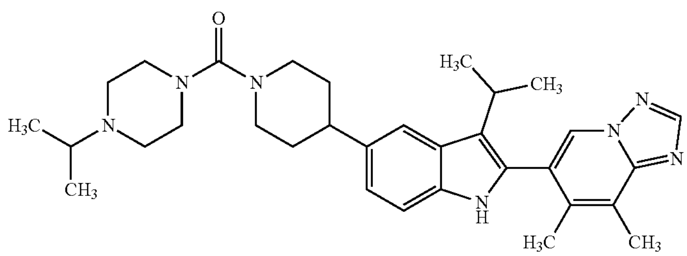 [SMILES: Cc1c(-c2[nH]c3ccc(C4CCN(C(=O)N5CCN(C(C)C)CC5)CC4)cc3c2C(C)C)cn2ncnc2c1C] | 542.0 | 1.68 | QC-ACN-AA-XB |
| 974 | EX-4 | 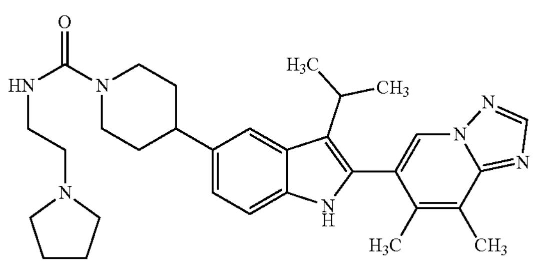 [SMILES: Cc1c(-c2[nH]c3ccc(C4CCN(C(=O)NCCN5CCCC5)CC4)cc3c2C(C)C)cn2ncnc2c1C] | 528.4 | 1.32 | QC-ACN-TFA-XB |
| 975 | EX-4 | 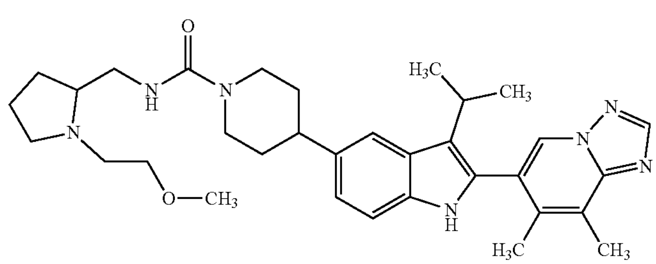 [SMILES: COCCN1CCCC1CNC(=O)N1CCC(c2ccc3[nH]c(-c4cn5ncnc5c(C)c4C)c(C(C)C)c3c2)CC1] | 572.5 | 1.45 | QC-ACN-TFA-XB |

TABLE 23-continued

| Ex. No. | Starting Material | Structure | LCMS MH+ | R_t (min) | HPLC Method |
|---|---|---|---|---|---|
| 976 | EX-4 | 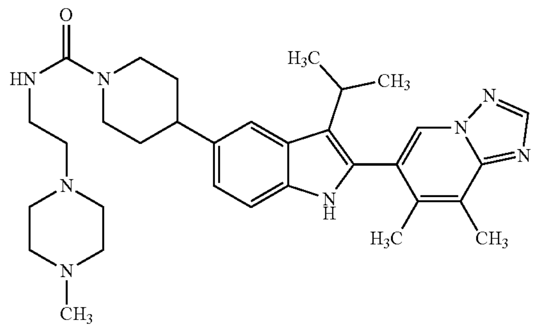 [SMILES: Cc1c(-c2[nH]c3ccc(C4CCN(C(=O)NCCN5CCN(C)CC5)CC4)cc3c2C(C)C)cn2ncnc2c1C] | 557.3 | 1.3 | QC-ACN-AA-XB |
| 977 | EX-4 | 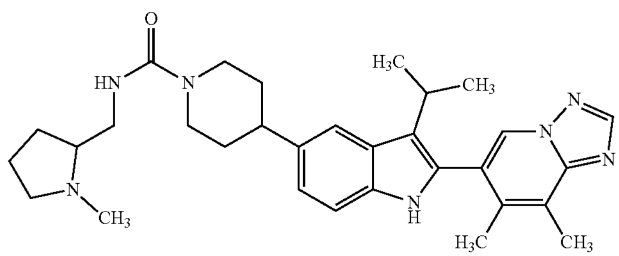 [SMILES: Cc1c(-c2[nH]c3ccc(C4CCN(C(=O)NCC5CCCN5C)CC4)cc3c2C(C)C)cn2ncnc2c1C] | 528.4 | 1.36 | QC-ACN-TFA-XB |
| 978 | EX-4 | 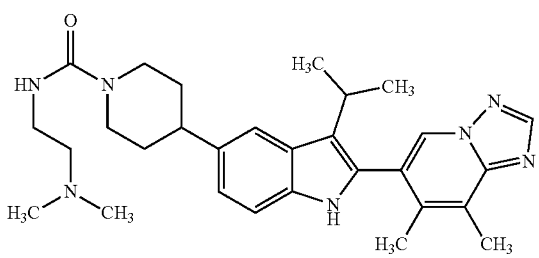 [SMILES: Cc1c(-c2[nH]c3ccc(C4CCN(C(=O)NCCN(C)C)CC4)cc3c2C(C)C)cn2ncnc2c1C] | 502.4 | 1.33 | QC-ACN-AA-XB |
| 979 | EX-4 | 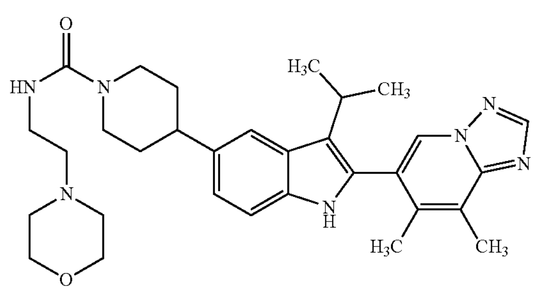 [SMILES: Cc1c(-c2[nH]c3ccc(C4CCN(C(=O)NCCN5CCOCC5)CC4)cc3c2C(C)C)cn2ncnc2c1C] | 544.5 | 1.3 | QC-ACN-TFA-XB |
| 980 | EX-4 | 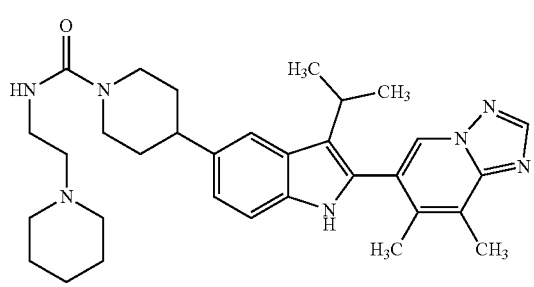 [SMILES: Cc1c(-c2[nH]c3ccc(C4CCN(C(=O)NCCN5CCCCC5)CC4)cc3c2C(C)C)cn2ncnc2c1C] | 542.6 | 1.41 | QC-ACN-TFA-XB |

Example 981

2-(3-(2-(7,8-dimethyl-[1,2,4]triazolo[1,5-a]pyridin-6-yl)-3-isopropyl-1H-indol-5-yl)-8-azabicyclo[3.2.1]octan-8-yl)acetonitrile

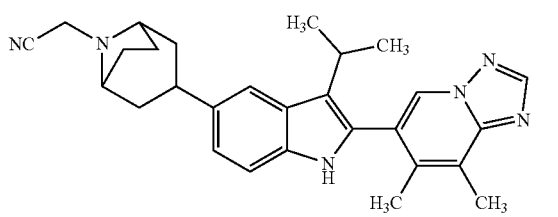
(981)

Intermediate 981A: 3-isopropyl-1H-indole

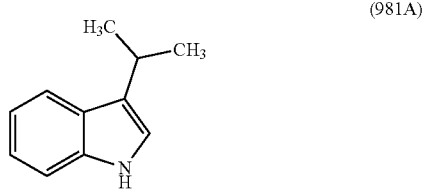
(981A)

To a 500 mL round bottom flask were added 2,2,2-trichloroacetic acid (23.60 g, 144 mmol), toluene (150 mL), and triethylsilane (46.1 mL, 289 mmol). With stirring, the solution was heated to 70° C. and a solution of 1H-indole (11.28 g, 96 mmol) and acetone (8.48 mL, 116 mmol) in 75 mL of toluene was added drop-wise via an addition funnel. The reaction mixture was heated to 90° C. for 2.5 hours. The reaction mixture was cooled to room temperature, then to 5° C. To this were added 1.5 M dibasic potassium phosphate solution and diethyl ether. The layers were separated and the organic layer was washed with brine, dried over $Na_2SO_4$, filtered and concentrated. The residue was purified on silica gel using ethyl acetate/hexane as the eluent to afford 3-isopropyl-1H-indole (12 g, 78%) as a white solid. LC retention time=1.04 min [A1]. MS ($E^+$) m/z: 160.2 (M+H). $^1$H NMR (400 MHz, CHLOROFORM-d) δ 7.72-7.65 (m, 1H), 7.41-7.36 (m, 1H), 7.21 (d, J=0.9 Hz, 1H), 7.14 (s, 1H), 6.99 (dd, J=2.2, 0.7 Hz, 1H), 3.31-3.17 (m, 1H), 1.40 (d, J=6.8 Hz, 6H).

Intermediate 981B: 6-(3-isopropyl-1H-indol-2-yl)-7,8-dimethyl-[1,2,4]triazolo[1,5-a]pyridine

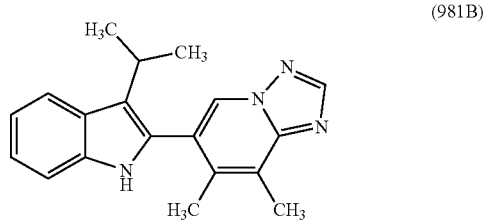 [SMILES: Cc1c(-c2[nH]c3ccccc3c2C(C)C)cn2ncnc2c1C]
(981B)

To a 100 mL bottom flask were added 3H-ol indole (1.000 g, 6.28 mmol) and DCE (10 mL). NBS (1.062 g, 5.97 mmol) was dissolved in 10 mL of DCE and added to the reaction mixture drop-wise via an addition funnel over 15 minutes. The reaction was quenched with 5 mL of a 10% sodium sulfite solution. The volatiles were removed. Next, THF (10 mL), 7,8-dimethyl-6-(4,4,5,5-tetramethyl-1,3,2-dioxaborolan-2-yl)-[1,2,4]triazolo[1,5-a]pyridine (1.54 g, 5.56 mmol), $PdCl_2$(dppf)-$CH_2Cl_2$ adduct (0.25 g, 0.314 μmol), and 3 M tribasic potassium phosphate solution (6.3 mL, 18.8 mmol) were added. The reaction vessel was capped and pump/purged with nitrogen gas three times. The reaction mixture was set to heat at 70° C. for 1 hour. The mixture was cooled to room temperature and concentrated. The crude residue was taken up in DCM (3 mL), filtered and purified on silica gel using ethyl acetate/hexane to afford 6-(3-isopropyl-1H-indol-2-yl)-7,8-dimethyl-[1,2,4]triazolo[1,5-a]pyridine (0.8 g, 41.8%) as a white foam. LC retention time=2.04 min [D1]. MS ($E^+$) m/z: 305.0 (M+H). $^1$H NMR (400 MHz, METHANOL-$d_4$) δ 8.54-8.44 (m, 1H), 8.38-8.28 (m, 1H), 7.56 (d, J=1.1 Hz, 1H), 7.45 (d, J=8.4 Hz, 1H), 7.13-7.01 (m, 2H), 3.28-3.16 (m, 1H), 2.66 (s, 3H), 2.32 (s, 3H), 1.38 (d, J=6.8 Hz, 6H).

Intermediate 981C: Tert-butyl 5-bromo-2-(7,8-dimethyl-[1,2,4]triazolo[1,5-a]pyridin-6-yl)-3-isopropyl-1H-indole-1-carboxylate

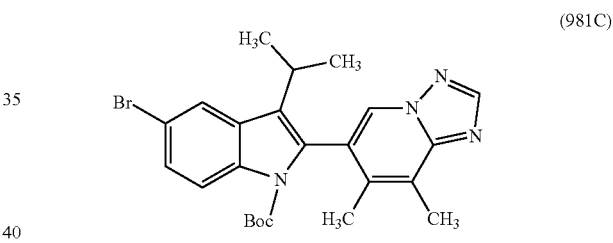
(981C)

To a 40 mL reaction vial were added 6-(3-isopropyl-1H-indol-2-yl)-7,8-dimethyl-[1,2,4]triazolo[1,5-a]pyridine (0.450 g, 1.478 mmol), AcOH (4 mL), water (0.5 mL), and NBS (0.263 g, 1.478 mmol). The vial was sealed and stirred at 80° C. for 30 minutes. The reaction mixture was cooled to room temperature and 1 mL of a 10% sodium sulfite was added. This mixture was concentrated, dissolved in DCM/MeOH, filtered, and purified on silica gel using ethyl acetate/hexane to afford 5-bromo-2-(7,8-dimethyl-[1,2,4]triazolo[1,5-a]pyridin-6-yl)-3-isopropyl-1H-indole as a tan solid. LC retention time=1.01 min [A1]. MS ($E^+$) m/z: 83/385 (M+H). $^1$H NMR (400 MHz, DMSO-$d_6$) δ 11.26 (s, 1H), 8.82 (s, 1H), 8.48 (s, 1H), 7.70 (d, J=8.4 Hz, 1H), 7.52 (d, J=1.5 Hz, 1H), 7.16 (dd, J=8.6, 1.8 Hz, 1H), 2.88 (br d, J=14.1 Hz, 1H), 2.60 (s, 3H), 2.15 (s, 3H), 1.43-1.15 (m, 5H), 1.18-1.09 (m, 1H).

To this material were added DMAP (0.010 g, 0.0148 mmol), THF (10 mL), and BOC-anhydride (0.59 g, 2.95 mmol). The reaction mixture was stirred for 2 hours at room temperature, concentrated to a viscous oil, diluted with DCM, and washed with dilute 1N HCl. The organic was washed with water and then brine. The solution was dried over $Na_2SO_4$, filtered, and concentrated. The residue was purified on silica gel using ethyl acetate/hexane to afford tert-butyl 5-bromo-2-(7,8-dimethyl-[1,2,4]triazolo[1,5-a]pyridin-6-yl)-3-isopropyl-1H-indole-1-carboxylate (0.45 g, 63%) as a yellowish solid. LC retention time=1.15 min [A1]. MS (E+) m/z: 483/485 (M+H).

Intermediate 981D: Tert-butyl 5-(8-(tert-butoxycarbonyl)-8-azabicyclo[3.2.1]oct-2-en-3-yl)-2-(7,8-dimethyl-[1,2,4]triazolo[1,5-a]pyridin-6-yl)-3-isopropyl-1H-indole-1-carboxylate

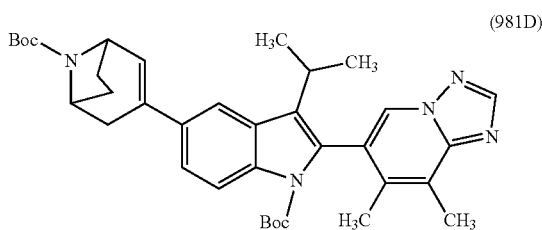 [SMILES: Cc1c(-c2c(C(C)C)c3cc(C4=CC5CCC(C4)N5C(=O)OC(C)(C)C)ccc3n2C(=O)OC(C)(C)C)cn2ncnc2c1C]
(981D)

To a Mixture of Tert-Butyl 5-bromo-2-(7,8-dimethyl-[1,2,4]triazolo[1,5-a]pyridin-6-yl)-3-isopropyl-1H-indole-1-carboxylate (0.130 g, 0.269 mmol), PdCl$_2$(dppf)-CH$_2$Cl$_2$ adduct (10.98 mg, 0.013 mmol), and (8-(tert-butoxycarbonyl)-8-azabicyclo[3.2.1]oct-3-en-3-yl) boronic acid (0.071 g, 0.282 mmol) in a screw cap vial was added THF (2 mL) followed by 3 M aqueous solution of tripotassium phosphate (0.269 mL, 0.807 mmol). The vial was fitted with a Teflon lined septum cap. The system was evacuated under vacuum and backfilled with nitrogen gas. The procedure was repeated three times. The vial was sealed and heated at 75° C. for 18 hours. The reaction mixture was diluted with EtOAc (100 mL) and poured into a separatory funnel. The organic layer was washed with water (2×50 mL), saturated aqueous NaCl solution (50 mL), dried (Na$_2$SO$_4$), filtered and concentrated in vacuo to afford crude product. The crude product was purified on silica gel using 0-100% ethyl acetate/hexane. Following concentration of the fractions, the product was collected as a tan oil (0.11 g, 65%). LC retention time=1.19 min [A1]. MS (E+) m/z: 612.2 (M+H).

Intermediate 981E: Tert-butyl 5-(8-(tert-butoxycarbonyl)-8-azabicyclo[3.2.1]octan-3-yl)-2-(7,8-dimethyl-[1,2,4]triazolo[1,5-a]pyridin-6-yl)-3-isopropyl-1H-indole-1-carboxylate

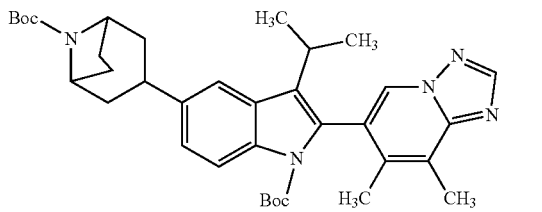
(981E)

In a Parr bottle, tert-butyl 5-(8-(tert-butoxycarbonyl)-8-azabicyclo[3.2.1]oct-2-en-3-yl)-2-(7,8-dimethyl-[1,2,4]triazolo[1,5-a]pyridin-6-yl)-3-isopropyl-1H-indole-1-carboxylate (0.11 g, 0.18 mmol) was suspended in ethyl acetate (3 mL) and treated with 10 mol % of 5% Pd/C (0.057 g, 0.027 mmol). Following degassing, the reaction mixture was placed under a hydrogen gas atmosphere (50 psi) and shaken for 16 hours at room temperature. Following the removal of the hydrogen atmosphere and back-filling with nitrogen gas, the reaction mixture was diluted with MeOH, filtered through celite, and concentrated to afford tert-butyl 5-(8-(tert-butoxycarbonyl)-8-azabicyclo[3.2.1]octan-3-yl)-2-(7,8-dimethyl-[1,2,4]triazolo [1,5-a]pyridin-6-yl)-3-isopropyl-1H-indole-1-carboxylate (0.11 g, 100%) as a mixture of isomers. LC retention time=1.20 min [A1]. MS (E+) m/z: 614.4 (M+H).

Intermediate 981F 6-(5-(8-azabicyclo[3.2.1]octan-3-yl)-3-isopropyl-1H-indol-2-yl)-7,8-dimethyl-[1,2,4]triazolo[1,5-a]pyridine TFA Salt

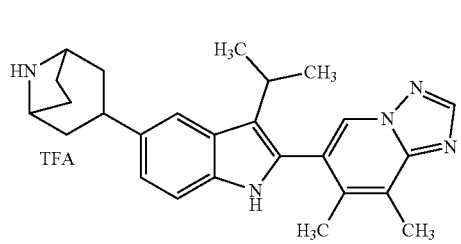
(981F)

To a Solution of Tert-Butyl 5-(8-(tert-butoxycarbonyl)-8-azabicyclo[3.2.1]octan-3-yl)-2-(7,8-dimethyl-[1,2,4]triazolo[1,5-a]pyridin-6-yl)-3-isopropyl-1H-indole-1-carboxylate (0.025 g, 0.041 mmol) was added DCM (0.5 mL) in a 2 dram reaction vial. To this was added TFA (1 mL) and the reaction vial was capped. The reaction mixture was stirred for 2 hours at room temperature. The volatiles were removed under a stream of nitrogen gas. The yield was considered quantitative. This material was used as is for final derivatization to prepare the compounds shown in Table 24. One example is described below for Example 981.

Example 981

In a 2 dram reaction vial were added 6-(5-(8-azabicyclo [3.2.1]octan-3-yl)-3-isopropyl-1H-indol-2-yl)-7,8-dimethyl-[1,2,4]triazolo[1,5-a]pyridine, TFA salt (0.021 g, 0.041 mmol), NMP, DBU (0.025 mL, 0.164 mmol), and drop-wise, bromoacetonitrile (0.017 g, 0.15 mmol). The reaction mixture was stirred for 1 hour at room temperature, then diluted with water, and filtered through a 0.45 micron syringe filter. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 25 minutes, then a 5-minute hold at 100% B; Flow: 20 mL/min. Fractions containing the product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min. Fractions containing the product were combined and dried via centrifugal evaporation.

2-(3-(2-(7,8-dimethyl-[1,2,4]triazolo[1,5-a]pyridin-6-yl)-3-isopropyl-1H-indol-5-yl)-8-azabicyclo[3.2.1]octan-8-yl)acetonitrile (0.0021 g, 6.4% yield) was collected as a mixture of isomers. Two analytical LC/MS injections were used to determine the final purity. LC retention time 2.18 min [C1]. MS (E$^+$) m/z: 453.0 (M+H). $^1$H NMR (500 MHz, DMSO-d$_6$) δ 10.95 (br d, J=18.2 Hz, 1H), 8.73-8.64 (m, 1H), 8.69 (br s, 1H), 8.52-8.39 (m, 1H), 8.46 (s, 1H), 7.62 (s, 1H), 7.62 (br d, J=18.2 Hz, 1H), 7.19 (s, 1H), 7.23 (br s, 1H), 7.01-6.88 (m, 1H), 7.05-6.84 (m, 1H), 3.34 (br s, 1H), 3.17 (s, 1H), 3.13-3.01 (m, 1H), 2.99-2.93 (m, 1H), 2.88-2.76 (m, 1H), 2.57 (s, 2H), 2.15 (s, 2H), 2.02-1.94 (m, 1H), 1.90 (br d, J=8.2 Hz, 1H), 1.75 (br s, 4H), 1.68-1.57 (m, 1H), 1.29 (br s, 5H).

The following examples were prepared according to the general procedures disclosed in Example 981.

Example 986

6-(3-isopropyl-5-(1-(pyridin-2-yl)piperidin-4-yl)-1H-indol-2-yl)-7,8-dimethyl-[1,2,4]triazolo[1,5-a]pyridine (986)

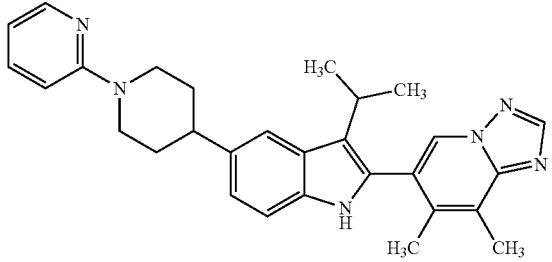

TABLE 24

| Ex. No. | Structure | LCMS MH$^+$ | R$_t$ (min) | HPLC Method |
|---|---|---|---|---|
| 982 | Isomer 1 | 499.1 | 1.57 | C1 |
| 983 | Isomer 2 | 499.1 | 1.50 | C1 |
| 984 | Isomer 1 | 520.0 | 1.58 | C1 |
| 985 | Isomer 2 | 520.1 | 1.53 | C1 |

6-(3-isopropyl-5-(piperidin-4-yl)-1H-indol-2-yl)-7,8-dimethyl-[1,2,4]triazolo[1,5-a]pyridine (19.4 mg, 0.050 mmol), 2-chloropyridine (6.2 mg, 0.055 mmol), 4,5-bis(diphenylphosphino)-9,9-dimethylxanthene (5.8 mg, 10.00 μmol), Pd$_2$(dba)$_3$ (4.6 mg, 5.00 μmol) and Cs$_2$CO$_3$ (48.9 mg, 0.150 mmol) were suspended in dioxane (0.5 mL). The mixture was degassed with nitrogen gas for 5 minutes. The reaction vessel was sealed and heated to 90° C. for 2 hours. Upon completion, the reaction mixture was filtered, concentrated, dissolved in DMF, and purified via preparative LCMS using the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 19 minutes, then a 5-minute hold at 100% B; Flow: 20 mL/min. Fractions containing the product were combined and dried via centrifugal evaporation to afford 6-(3-isopropyl-5-(1-(pyridin-2-yl)piperidin-4-yl)-1H-indol-2-yl)-7,8-dimethyl-[1,2,4]triazolo[1,5-a]pyridine, TFA (10.1 mg, 0.017 mmol, 35% yield). LCMS retention time 1.25 [QC-ACN-TFA-XB]. MS (ES$^+$) m/z: 465.4 (M+H). $^1$H NMR (500 MHz, DMSO-d$_6$) δ 8.81 (s, 1H), 8.63 (br d, J=7.9 Hz, 1H), 8.44-8.38 (m, 2H), 8.36 (br d, J=9.5 Hz, 1H), 7.82-7.73 (m, 1H), 7.67 (s, 1H), 7.48 (d, J=8.5 Hz, 1H), 7.28-7.24 (m, 1H), 7.22 (d, J=7.9 Hz, 1H), 7.12 (br d, J=8.5 Hz, 1H), 3.41 (br d, J=11.3 Hz, 2H), 3.11-2.93 (m, 3H), 2.85 (dt, J=14.0, 7.0 Hz, 1H), 2.42 (s, 3H), 2.06-1.96 (m, 2H), 1.96-1.82 (m, 5H), 1.35 (dd, J=16.5, 7.0 Hz, 6H).

The following examples were prepared in a manner similar to Example 986.

Example 989

6-(3-isopropyl-5-(1-(pyrimidin-2-yl)piperidin-4-yl)-1H-indol-2-yl)-7,8-dimethyl-[1,2,4]triazolo[1,5-a]pyridine

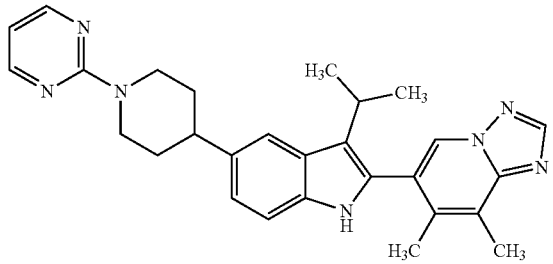

(989)

6-(3-isopropyl-5-(piperidin-4-yl)-1H-indol-2-yl)-7,8-dimethyl-[1,2,4]triazolo[1,5-a]pyridine (19.4 mg, 0.050 mmol) and Et$_3$N (0.021 mL, 0.150 mmol) were mixed in DMSO (1 mL). Next, 2-chloropyrimidine (6.9 mg, 0.060 mmol) was added. The reaction vial was sealed and heated to 90° C. for 2 hours. Upon completion, the reaction mixture was cooled to room temperature, diluted with water (0.05 mL) and 1 mL of DMSO, and purified on preparative LCMS via the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-100% B over 20 minutes, then a 10-minute hold at 100% B; Flow: 20 mL/min. Fractions containing the

TABLE 25

| Ex. No. | Structure | LCMS MH$^+$ | R$_t$ (min) | HPLC Method |
|---|---|---|---|---|
| 987 | 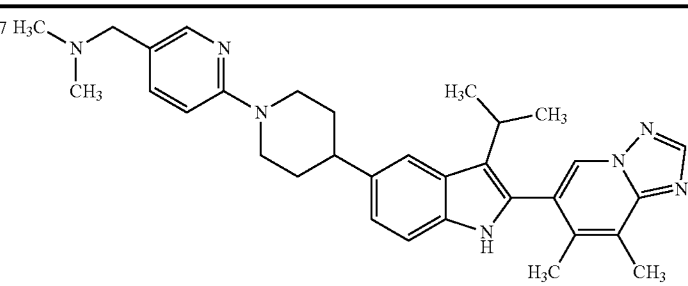 | 522.5 | 0.96 | QC-ACN-TFA-XB |
| 988 | | 522.5 | 0.95 | QC-ACN-TFA-XB | product were combined and dried via centrifugal evaporation to provide 6-(3-isopropyl-5-(1-(pyrimidin-2-yl)piperidin-4-yl)-1H-indol-2-yl)-7,8-dimethyl-[1,2,4]triazolo[1,5-a]pyridine (5.0 mg, 10.2 µmol, 20.4% yield). LCMS retention time 1.71 [QC-ACN-TFA-XB]. MS (ES+) m/z: 466.3 (M+H).

Example 990

2-(4-(2-(8-amino-[1,2,4]triazolo[1,5-a]pyridin-6-yl)-3-isopropyl-1H-indol-5-yl)piperidin-1-yl)-N,N-dimethylacetamide

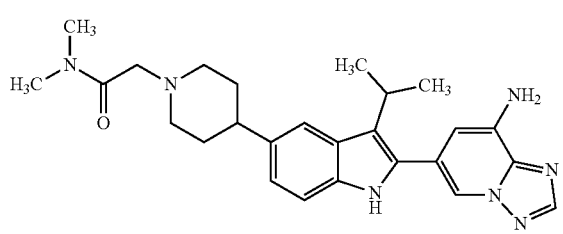

(990)

To a solution of 2-(4-(2-(8-(benzylamino)-[1,2,4]triazolo[1,5-a]pyridin-6-yl)-3-isopropyl-1H-indol-5-yl) piperidin-1-yl)-N,N-dimethylacetamide (0.040 g, 0.073 mmol) in methanol (10.0 mL) was added Pd/C (0.023 g, 0.218 mmol). The reaction mixture was stirred at room temperature for 6 h under hydrogen. The reaction mixture was diluted with ethyl acetate:methanol (1:1) filtered and washed with excess ethyl acetate. The combined organic layers were evaporated to afford crude compound. The crude material was purified via preparative LC/MS with the following conditions: Column: Waters XBridge C18, 19×150 mm, 5-µm particles; Mobile Phase A: 0.05% TFA; Mobile Phase B: acetonitrile; Gradient: 15-50% B over 20 minutes, then a 5-minute hold at 100% B; Flow: 15 mL/min. Fractions containing the product were combined and dried via centrifugal evaporation to afford 2-(4-(2-(8-amino-[1,2,4]triazolo[1,5-a]pyridin-6-yl)-3-isopropyl-1H-indol-5-yl) piperidin-1-yl)-N,N-dimethylacetamide (7.3 mg). LCMS retention time 1.44 min [E]. MS (E−) m/z: 460.3 (M−H). ¹H NMR (400 MHz, METHANOL-d₄) δ ppm 8.31-8.39 (m, 1H) 8.16 (d, J=1.47 Hz, 1H) 7.66 (s, 1H) 7.36 (d, J=8.31 Hz, 1H) 7.08 (d, J=8.80 Hz, 1H) 6.84-6.97 (m, 1H) 4.26 (s, 2H) 3.76 (d, J=13.21 Hz, 2H) 3.33-3.43 (m, 2H) 3.25 (br. s., 2H) 2.94-3.12 (m, 8H) 2.19 (br. s., 4H) 1.50 (d, J=7.09 Hz, 7H) 1.28 (br. s., 1H).

Example 991

2-(4-(4-fluoro-3-isopropyl-2-(8-methoxy-[1,2,4]triazolo[1,5-a]pyridin-6-yl)-1H-indol-5-yl)piperidin-1-yl)-N,N-dimethylacetamide

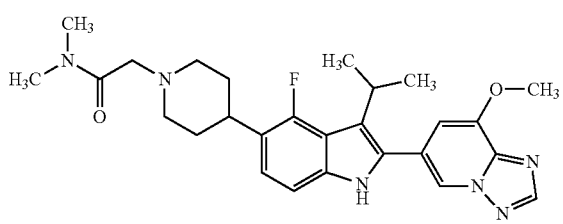

(991)

Intermediate 991A: 4-fluoro-3-isopropyl-1H-indole

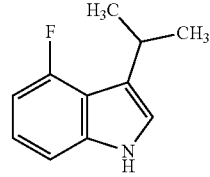

(991A)

To a 40 mL vial with a red pressure-release cap were added 2,2,2-trichloroacetic acid (0.907 g, 5.55 mmol), toluene (7.40 mL) and triethylsilane (1.773 mL, 11.10 mmol). With stirring, the solution was heated to 70° C. and a solution of 4-fluoro-H-indole (0.500 g, 3.70 mmol) and acetone (0.326 mL, 4.44 mmol) in 1 mL of toluene was added drop-wise via a syringe. The reaction mixture was stirred and heated to 90° C. for 3 h, venting with a nitrogen line. The reaction mixture was allowed to cool to 5° C., and to the reaction mixture were added 1 M aqueous K₃PO₄ solution (~4 mL) and ethyl acetate (4 mL). The layers were separated and the aqueous phase was extracted with EtOAc (2×5 mL). The combined organic extracts were dried over sodium sulfate and filtered, and excess solvent was evaporated off. The resulting red oil was taken up in DCM (~2 mL) and purified by flash chromatography to afford 4-fluoro-3-isopropyl-1H-indole as a yellow liquid (483.2 mg, 2.67 mmol, 72.2% yield). ¹H NMR (400 MHz, CHLOROFORM-d) δ 7.97 (br s, 1H), 7.16-7.07 (m, 2H), 6.95 (d, J=2.2 Hz, 1H), 6.77 (ddd, J=11.3, 7.4, 1.1 Hz, 1H), 3.38 (dt, J=13.7, 6.8 Hz, 1H), 1.38 (dd, J=6.8, 0.6 Hz, 6H). HPLC Ret. Time 0.99 min. Method G.

Intermediate 991B: 4-fluoro-3-isopropyl-1-(triisopropylsilyl)-1H-indole

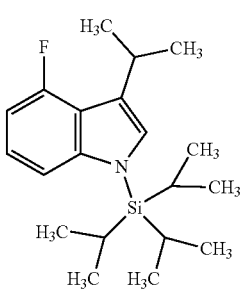

(991B)

4-fluoro-3-isopropyl-1H-indole (0.475 g, 2.68 mmol) was dissolved in THF (10.72 mL) in a 40 mL vial. The solution was cooled to 0° C. under a nitrogen atmosphere with an ice bath, and sodium hydride (0.214 g, 5.36 mmol) was added to the reaction mixture. The reaction mixture was allowed to warm to room temperature, then triisopropylsilyl chloride (0.860 mL, 4.02 mmol) was added dropwise via syringe. The reaction mixture was then stirred at 50° C. for 1 h. The reaction completed. The reaction mixture was cooled to 0° C. and quenched by addition of 1 M KHSO₄ (~4 mL) and water (4 mL). Ethyl acetate (4 mL) was added, and the phases were separated. The aqueous phase was extracted with ethyl acetate (2×3 mL). The combined organic phases were extracted with brine (1×4 mL), and excess solvent was evaporated off. The resulting yellow oil was taken up in DCM (3.5 mL total volume) and purified by flash chromatography on a 24 g silica column, eluting with ethyl acetate and hexanes. The product 4-fluoro-3-isopropyl-1-(triisopropylsilyl)-1H-indole was obtained as a clear, colorless liquid (0.92 g, 2.48 mmol, 92% yield). $^1$H NMR (400 MHz, CHLOROFORM-d) δ 7.24 (d, J=8.3 Hz, 1H), 7.03 (td, J=8.1, 5.4 Hz, 1H), 6.94 (s, 1H), 6.76 (dd, J=11.0, 7.8 Hz, 1H), 3.36 (spt, J=6.8 Hz, 1H), 1.36 (d, J=6.8 Hz, 6H), 1.16 (d, J=7.6 Hz, 18H). LCMS MH$^+$: 334.3. HPLC Ret. Time 1.43 min. Method G.

Intermediate 991C: 5-bromo-4-fluoro-3-isopropyl-1-(triisopropylsilyl)-1H-indole

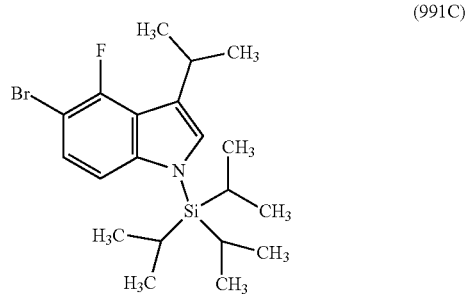 [SMILES: CC(C)c1cn([Si](C(C)C)(C(C)C)C(C)C)c2ccc(Br)c(F)c12]

(991C)

Sec-butyllithium (2.144 mL, 3.00 mmol, 90% purity) was added to a −75° C. (dry ice/methanol bath) solution of 4-fluoro-3-isopropyl-1-(triisopropylsilyl)-1H-indole (0.910 g, 2.73 mmol) and 1,1,4,7,7-pentamethyldiethylenetriamine (0.572 mL, 2.73 mmol) in THF (13.64 mL) in an oven-dried 50 mL recovery flask under a nitrogen atmosphere. The solution was stirred for 6.5 h at −75° C. for 6 h. Next, 1,2-dibromotetrafluoroethane (0.325 mL, 2.73 mmol) was added to the reaction mixture. The solution was stirred for 10 min at −75° C., then allowed to warm to room temperature. The reaction progressed 50%. Excess solvent was evaporated from the reaction mixture. The resulting orange oil was taken up in DCM (total volume 4 mL) and purified by flash chromatography on a 24 g silica column, eluting with hexanes. The product and remaining starting indole co-eluted. Fractions were pooled and excess solvent was evaporated off to yield 5-bromo-4-fluoro-3-isopropyl-1-(triisopropylsilyl)-1H-indole (1.07 g, 1.68 mmol, 65% yield) and 4-fluoro-3-isopropyl-1-(triisopropylsilyl)-1H-indole as a mixture in a clear, colorless liquid. The mixed products were taken forward directly. LCMS MH$^+$: 412.08. HPLC Ret. Time 1.50 min. Method G.

Intermediate 991D: Tert-butyl 4-(4-fluoro-3-isopropyl-1-(triisopropylsilyl)-1H-indol-5-yl)-3,6-dihydropyridine-1(2H)-carboxylate

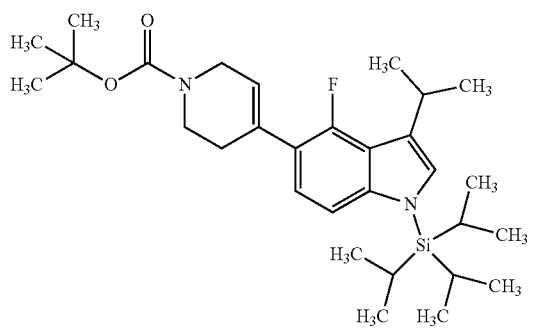

(991D)

5-bromo-4-fluoro-3-isopropyl-1-(triisopropylsilyl)-1H-indole (650 mg, 1.576 mmol) was dissolved in THF (7880 μl) in a 40 mL scintillation vial with a red pressure-release cap and containing a Teflon-covered stir bar. Tert-butyl 4-(4,4,5,5-tetramethyl-1,3,2-dioxaborolan-2-yl)-5,6-dihydropyridine-1(2H)-carboxylate (585 mg, 1.891 mmol) was added to the vial, followed by tripotassium phosphate (2364 μl, 4.73 mmol). The reaction mixture was degassed by bubbling nitrogen through the solution for 5 min, then 2nd generation XPhos precatalyst (31.0 mg, 0.039 mmol) was added to the reaction mixture. The clear, yellow reaction mixture was placed under a nitrogen atmosphere and heated to 60° C. with stirring for 6 h. The reaction mixture was allowed to cool to room temperature. The aqueous phase was removed, and excess TH was evaporated from the reaction. The resulting oil residue was taken up in DCM (~4 mL total volume) and purified by flash chromatography eluting with ethyl acetate and hexanes. The product fractions was concentrated and vacuumed to afford tert-butyl 4-(4-fluoro-3-isopropyl-1-(triisopropylsilyl)-1H-indol-5-yl)-5,6-dihydropyridine-1(2H)-carboxylate as a pale yellow sticky solid (0.65 g, 1.14 mmol, 72.6% yield). $^1$H NMR (400 MHz, CHLOROFORM-d) δ 7.18 (d, J=8.6 Hz, 1H), 6.99-6.94 (m, 1H), 6.92 (s, 1H), 5.90 (br s, 1H), 4.10 (br s, 2H), 3.66 (br t, J=5.2 Hz, 2H), 3.36 (spt, J=6.8 Hz, 1H), 2.61 (br s, 2H), 1.53 (s, 9H), 1.35 (d, J=6.7 Hz, 6H), 1.16 (d, J=7.6 Hz, 18H). LCMS MH$^+$: 515.5. HPLC Ret. Time 1.53 min. Method G.

Intermediate 991E: tert-butyl 4-(4-fluoro-3-isopropyl-1-(triisopropylsilyl)-1H-indol-5-yl) piperidine-1-carboxylate

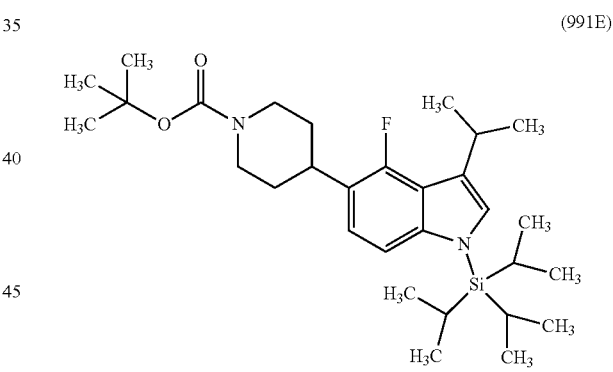

(991E)

5% Pd on Carbon (100 mg, 1.271 mmol) was weighed into a 20 mL scintillation vial containing a Teflon-coated stir bar with a red pressure-release cap. Tert-butyl 4-(4-fluoro-3-isopropyl-1-(triisopropylsilyl)-1H-indol-5-yl)-5,6-dihydropyridine-1(2H)-carboxylate (654.4 mg, 1.271 mmol) was dissolved in MeOH (12.71 mL) and transferred into the vial containing the Pd on C while under a nitrogen atmosphere. Ammonium formate (401 mg, 6.36 mmol) was added to the reaction mixture, and the vial was capped. The reaction mixture was stirred at 50° C. for 4 h. Additional ammonium formate (401 mg, 6.36 mmol) was added to the reaction mixture, and the reaction mixture was stirred at 60° C. for 3 h but did not reach completion. The reaction mixture was stirred at 50° C. overnight. The reaction mixture was filtered through celite to remove Pd/C. Excess methanol was evaporated from the reaction mixture to afford tert-butyl 4-(4-fluoro-3-isopropyl-1-(triisopropylsilyl)-1H-indol-5-yl) piperidine-1-carboxylate (654 mg, 1.271 mmol, 100% yield, 30% purity) a clear, pale yellow oil. Product was checked by ¹H NMR and was approximately 30% reduced and 70% starting material alkene. LCMS MH⁺: 517.5. HPLC Ret. Time 1.53 min. Method G.

Intermediate 991F: Tert-butyl 4-(4-fluoro-3-isopropyl-1H-indol-5-yl)-3,6-dihydropyridine-1(2H)-carboxylate

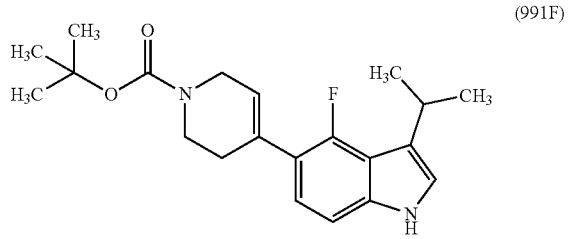 [SMILES: CC(C)c1c[nH]c2ccc(C3=CCN(C(=O)OC(C)(C)C)CC3)c(F)c12]

(991F)

Tert-butyl 4-(4-fluoro-3-isopropyl-1-(triisopropylsilyl)-1H-indol-5-yl)-3,6-dihydropyridine-1(2H)-carboxylate (0.650 g, 1.263 mmol) (7:3 mix of piperidine alkene and piperidine alkane) and tetra-n-butylammonium fluoride (0.660 g, 2.53 mmol) were dissolved in THF (6.31 mL) in a 20 mL scintillation vial. The reaction mixture was stirred for 10 min at room temperature. The reaction was complete with 2 peaks corresponding to the product alkene (1.15 min, M+H⁺=359.3) and alkane (1.16 min, M+H⁺=359.3, 361.3). The reaction mixture was partitioned between brine and ethyl acetate (1:1, total volume 16 mL). The phases were separated, and the aqueous phase was extracted with ethyl acetate (2×4 mL). The combined organic phases were washed with brine (2×5 mL), dried over sodium sulfate, and filtered. Excess solvent was evaporated from the organic phase to afford tert-butyl 4-(4-fluoro-3-isopropyl-1H-indol-5-yl)-3,6-dihydropyridine-1(2H)-carboxylate (0.476 g, 1.263 mmol) as a pale yellow oil. LCMS MH⁺: 359.3. HPLC Ret. Time 1.15 min. Method G.

Intermediate 991G: Tert-butyl 4-(4-fluoro-3-isopropyl-1H-indol-5-yl)-3,6-dihydropyridine-1(2H)-carboxylate

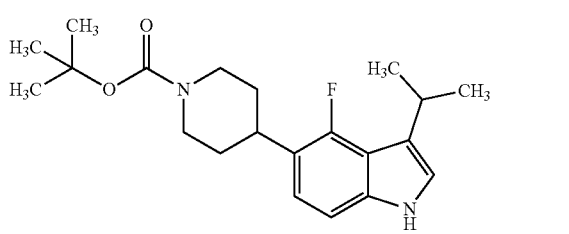

(991G)

5% Pd on Carbon (150 mg, 1.264 mmol) was weighed into a 20 mL scintillation vial containing a Teflon-coated stir bar with a red pressure-release cap. Tert-butyl 4-(4-fluoro-3-isopropyl-1H-indol-5-yl)-5,6-dihydropyridine-1(2H)-carboxylate (453 mg, 1.264 mmol) was dissolved in MeOH (6.32 mL) and transferred into the vial containing the Pd on C while under a nitrogen atmosphere. Ammonium formate (797 mg, 12.64 mmol) was added to the reaction mixture, and the vial was capped. The reaction mixture was stirred at 60° C. for 30 min. The reaction completed. The reaction mixture was filtered through celite to remove Pd/C. Excess methanol was evaporated from the reaction mixture. The resulting yellow oil was taken up in DCM (3 mL) and purified by flash chromatography on a 24 g silica column, eluting with ethyl acetate and hexanes to afford tert-butyl 4-(4-fluoro-3-isopropyl-1H-indol-5-yl)piperidine-1-carboxylate as a white crystalline solid (370.3 mg, 1.017 mmol, 80% yield). ¹H NMR (400 MHz, CHLOROFORM-d) δ 7.96 (br s, 1H), 7.10 (d, J=8.4 Hz, 1H), 7.02-6.97 (m, 1H), 6.93 (d, J=2.1 Hz, 1H), 4.28 (br s, 2H), 3.37 (spt, J=6.8 Hz, 1H), 3.17 (tt, J=12.0, 3.6 Hz, 1H), 2.88 (br t, J=11.3 Hz, 2H), 1.89-1.81 (m, 2H), 1.81-1.68 (m, 2H), 1.52 (s, 9H), 1.36 (d, J=6.8 Hz, 6H). LCMS MH⁺: 361.3. HPLC Ret. Time 1.16 min. Method G.

Intermediate 991H: Tert-butyl 5-(1-(tert-butoxycarbonyl)piperidin-4-yl)-4-fluoro-3-isopropyl-1H-indole-1-carboxylate

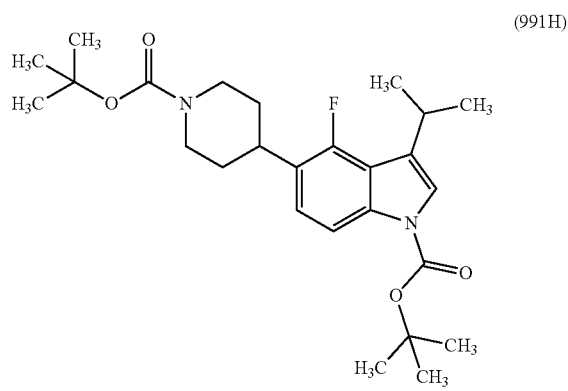 [SMILES: CC(C)c1cn(C(=O)OC(C)(C)C)c2ccc(C3CCN(C(=O)OC(C)(C)C)CC3)c(F)c12]

(991H)

Tert-butyl 4-(4-fluoro-3-isopropyl-1H-indol-5-yl)piperidine-1-carboxylate (370 mg, 1.026 mmol) and di-tert-butyl dicarbonate (540 μl, 2.258 mmol) were dissolved in THF (5132 μl) in a 20 mL vial containing a Teflon-covered stir bar. Next, 4-dimethylaminopyridine (12.54 mg, 0.103 mmol) was added. The vial was capped and the clear, pale yellow solution was stirred at room temperature for 2 h. The reaction finished. Excess solvent was evaporated from the reaction mixture. The residue was taken up in DCM (~2 mL) and purified by flash chromatography on a 24 g silica column, eluting with ethyl acetate and hexanes to afford tert-butyl 5-(1-(tert-butoxycarbonyl)piperidin-4-yl)-4-fluoro-3-isopropyl-1H-indole-1-carboxylate as a white foam (4.57 g, 0.98 mmol, 99% yield). ¹H NMR (400 MHz, CHLOROFORM-d) δ 7.85 (br s, 1H), 7.28 (br s, 1H), 7.12 (dd, J=8.4, 7.2 Hz, 1H), 3.29 (spt, J=6.8 Hz, 1H), 3.14 (tt, J=12.0, 3.5 Hz, 1H), 2.87 (br t, J=11.4 Hz, 2H), 1.88-1.79 (m, 2H), 1.51 (s, 9H), 1.34 (d, J=6.8 Hz, 6H). LCMS MH⁺: 461.4. HPLC Ret. Time 1.36 min. Method G.

Intermediate 991I: Tert-butyl 5-(1-(tert-butoxycarbonyl)piperidin-4-yl)-4-fluoro-3-isopropyl-2-(4,4,5,5-tetramethyl-1,3,2-dioxaborolan-2-yl)-1H-indole-1-carboxylate

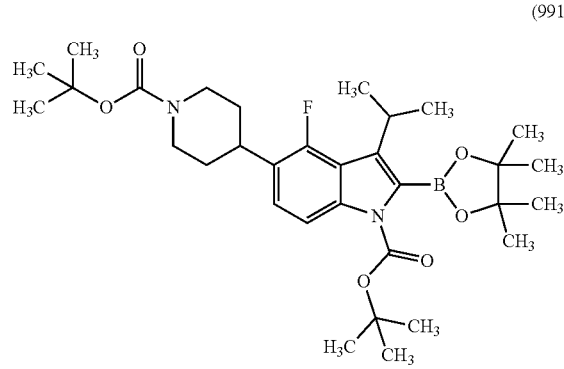

(991I)

Tert-butyl 5-(1-(tert-butoxycarbonyl)piperidin-4-yl)-4-fluoro-3-isopropyl-1H-indole-1-carboxylate (456.7 mg, 0.992 mmol) and 2-isopropoxy-4,4,5,5-tetramethyl-1,3,2-dioxaborolane (324 µl, 1.587 mmol) were dissolved in THF (7933 µl) in a 20 mL vial containing a Teflon-covered stir bar. The vial was cooled to −20° C. (dry ice/NMP bath) under a nitrogen atmosphere. Lithium diisopropylamide (992 µl, 1.983 mmol) was added dropwise to the vial (via a syringe through the septum cap) over 5 min. The reaction mixture was stirred at −20° C. for 1 h, then allowed to slowly warm to 0° C. Most starting material (75%) converted to product. The reaction mixture was allowed to warm to 10° C., then quenched by addition of 1 M KHSO$_4$ (5 mL). The resulting mixture was extracted with EtOAc (2×3 mL). The combined organic extracts were washed with brine (2×3 mL), and excess solvent was evaporated off. The residue was taken up in DCM (2 mL) and purified by flash chromatography on a 24 g silica column, eluting with ethyl acetate and hexane to afford tert-butyl 5-(1-(tert-butoxycarbonyl)piperidin-4-yl)-4-fluoro-3-isopropyl-2-(4,4,5,5-tetramethyl-1,3,2-dioxaborolan-2-yl)-1H-indole-1-carboxylate as a white solid (468.9 mg, 0.72 mmol, 72.6% yield, 90% purity). $^1$H NMR (400 MHz, CHLOROFORM-d) δ 7.61 (d, J=8.6 Hz, 1H), 7.06 (dd, J=8.4, 7.1 Hz, 1H), 4.28 (br s, 2H), 3.35-3.26 (m, 1H), 3.14 (br s, 1H), 2.87 (br t, J=11.9 Hz, 2H), 1.88-1.81 (m, 2H), 1.71 (br s, 1H), 1.67 (s, 9H), 1.44 (s, 12H). LCMS MH$^+$−56: 531.4. HPLC Ret. Time 1.39 min. Method G.

Intermediate 991J: Tert-butyl 5-(1-(tert-butoxycarbonyl)piperidin-4-yl)-2-(8-ethyl-[1,2,4]triazolo[1,5-a]pyridin-6-yl)-4-fluoro-3-isopropyl-1H-indole-1-carboxylate

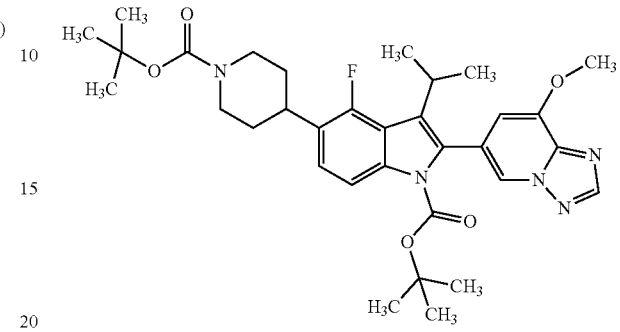

(991J)

Tert-butyl 5-(1-(tert-butoxycarbonyl)piperidin-4-yl)-4-fluoro-3-isopropyl-2-(4,4,5,5-tetramethyl-1,3,2-dioxaborolan-2-yl)-1H-indole-1-carboxylate (100 mg, 0.170 mmol) and 6-bromo-8-methoxy-[1,2,4]triazolo[1,5-a]pyridine (42.8 mg, 0.188 mmol) were weighed into a 1-dram vial with a red pressure-release cap and containing a Teflon-coated stir bar. THF (852 µl) and tripotassium phosphate (170 µl, 0.511 mmol) were added to the vial, and the reaction mixture was degassed by bubbling nitrogen through the reaction mixture for 3 min. 2ND generation XPhos precatalyst (4.02 mg, 5.11 µmol) was added to the vial, and the reaction mixture was placed under a nitrogen atmosphere and stirred at 60° C. overnight. The reaction was completed. The aqueous phase was removed, and excess solvent was evaporated from the organic phase. The resulting orange residue was taken up in DCM (~3 mL) and purified by flash chromatography on a 12 g silica column, eluting with ethyl acetate and hexanes to afford tert-butyl 5-(1-(tert-butoxycarbonyl)piperidin-4-yl)-4-fluoro-3-isopropyl-2-(8-methoxy-[1,2,4]triazolo[1,5-a]pyridin-6-yl)-1H-indole-1-carboxylate as a cloudy colorless glass (100.7 mg, 0.124 mmol, 72.9% yield, 75% purity). $^1$H NMR (400 MHz, CHLOROFORM-d) δ 8.36 (s, 1H), 8.22 (d, J=1.1 Hz, 1H), 8.04 (d, J=8.7 Hz, 1H), 7.28 (s, 1H), 7.23 (dd, J=8.6, 7.2 Hz, 1H), 6.72 (d, J=1.0 Hz, 1H), 4.39-4.22 (m, 2H), 4.04 (s, 3H), 3.19 (tt, J=12.0, 3.3 Hz, 1H), 2.99 (dtd, J=14.1, 7.0, 3.0 Hz, 1H), 2.88 (br t, J=11.2 Hz, 2H), 1.91-1.82 (m, 2H), 1.74 (br dd, J=12.5, 3.8 Hz, 2H), 1.50 (s, 9H), 1.24 (d, J=2.0 Hz, 15H). LCMS MH$^+$: 608.6. HPLC Ret. Time 1.22 min. Method G.

Example 991

Tert-butyl 5-(1-(tert-butoxycarbonyl)piperidin-4-yl)-4-fluoro-3-isopropyl-2-(8-methoxy-[1,2,4]triazolo[1,5-a]pyridin-6-yl)-1H-indole-1-carboxylate (25 mg, 0.041 mmol) was Boc-deprotected by reacting with 2:1 trifluoroacetic acid/dichloromethane (1.2 mL, 0.041 mmol) in a 1-dram vial for 30 min. Toluene (~0.15 mL) was added, and excess solvent was then evaporated from the reaction mixture. The resulting residue was stirred with 2-chloro-N,N-dimethylacetamide (10.00 mg, 0.082 mmol) and potassium carbonate (28.4 mg, 0.206 mmol) in NMP (0.411 mL) at 22° C. for 1.5 h. The reaction did not finish. The reaction mixture was stirred at 22° C. over the weekend. The reaction was completed. The reaction mixture was partitioned between water and ethyl acetate (3 mL total volume), and the aqueous phase was extracted with ethyl acetate (2×1 mL). Excess solvent was evaporated from the combined organic extracts. DMF (~1.5 mL) was added to the resulting residue. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 4-minute hold at 100% B; Flow: 20 mL/min. Fractions containing the product were combined and dried via centrifugal evaporation to afford 2-(4-(4-fluoro-3-isopropyl-2-(8-methoxy-[1,2,4]triazolo[1,5-a]pyridin-6-yl)-1H-indol-5-yl)piperidin-1-yl)-N,N-dimethylacetamide (8.5 mg, 0.017 mmol, 42.1% yield). $^1$H NMR (500 MHz, DMSO-$d_6$) δ 11.44 (br s, 1H), 8.58 (s, 1H), 8.54-8.47 (m, 1H), 7.18 (br d, J=8.5 Hz, 1H), 7.13 (s, 1H), 7.09 (t, J=7.0 Hz, 1H), 4.06 (s, 3H), 3.30 (br s, 1H), 3.17 (s, 2H), 3.07 (s, 3H), 3.01-2.88 (m, 3H), 2.88-2.78 (m, 3H), 2.20 (br t, J=10.5 Hz, 3H), 1.83-1.75 (m, 3H), 1.73 (br s, 4H), 1.36 (br d, J=6.4 Hz, 6H). LCMS MH$^+$: 493. HPLC Ret. Time 1.30 min. Method QC-ACN-AA-XB.

The following examples were prepared in a manner similar to that described in Example 991.

6-(3-isopropyl-5-(piperidin-4-yl)-1H-indol-2-yl)-8-methyl-[1,2,4]triazolo[1,5-a]pyridine (15.77 mg, 0.042 mmol) was stirred with 1H-pyrazole-1-carboximidamide (5.81 mg, 0.053 mmol) and DIPEA (0.037 mL, 0.211 mmol) in DMF (0.422 mL) at 75° C. for 8 h. DMF (1 mL) was added to the reaction mixture and the reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 5-minute hold at 100% B; Flow: 20 mL/min. Fractions containing the product were combined and dried via centrifugal evaporation to afford 4-(3-isopropyl-2-(8-methyl-[1,2,4]triazolo[1,5-a]pyridin-6-yl)-1H-indol-5-yl)piperidine-1-carboximidamide (8.4 mg, 0.019 mmol, 45.0% yield). LCMS MH$^+$: 416.2 HPLC Ret. Time 1.23 min. Method QC-ACN-AA-XB. $^1$H NMR (500 MHz, DMSO-$d_6$) δ 9.29 (s, 1H), 8.39 (s, 1H), 7.99 (s, 1H), 7.33-7.33 (m, 1H), 7.31 (d, J=7.9 Hz, 1H), 7.15 (s, 1H), 7.11

TABLE 26

| Ex. No. | Structure | LCMS MH$^+$ | R$_t$ (min) | HPLC Method |
|---|---|---|---|---|
| 992 | [structure] | 464.5 | 1.5 | QC-ACN-AA-XB |
| 993 | [structure] | 522 | 1.7 | QC-ACN-AA-XB |

Example 994

4-(3-isopropyl-2-(8-methyl-[1,2,4]triazolo[1,5-a]pyridin-6-yl)-1H-indol-5-yl)piperidine-1-carboximidamide

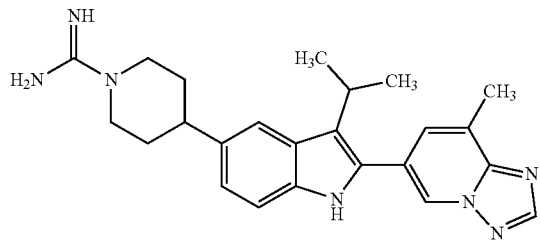

(994)

(br d, J=8.1 Hz, 1H), 2.99-2.88 (m, 3H), 2.79 (s, 2H), 2.77-2.70 (m, 1H), 2.16-2.06 (m, 1H), 1.74-1.64 (m, 2H), 1.51 (s, 4H), 1.50-1.40 (m, 2H), 1.08-0.98 (m, 6H).

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 27

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 1 | 34.5 | 69 | 3177 |
| 2 | 3.7 | 5.1 | 9015 |
| 3 | 3.9 | 2.2 | 1912 |
| 4 | 0.3 | 0.7 | 1589 |
| 5 | 0.5 | 2.7 | 818 |
| 6 | 1.1 | 9.8 | 1193 |
| 7 | 0.7 | 4.7 | 6636 |
| 8 | 0.3 | 2.2 | 1172 |
| 9 | — | 0.5 | 21167 |
| 10 | 0.5 | 1.7 | 479 |
| 11 | 0.3 | 2.4 | 5385 |
| 12 | 0.8 | 1.9 | 3063 |
| 13 | 1 | 2.5 | 4778 |
| 14 | 2.4 | 1.5 | 23273 |
| 15 | 1.4 | 1.4 | 5113 |
| 16 | 1 | 1.6 | 6321 |
| 17 | 1.9 | 0.5 | 2501 |
| 18 | 1.5 | 1.5 | 15008 |
| 19 | 1 | 0.9 | 4802 |
| 20 | 2.1 | 0.8 | 2694 |
| 21 | 0.7 | 7.6 | — |
| 22 | — | 2 | 1845 |
| 23 | 0.4 | 3.3 | 4811 |
| 24 | 0.4 | 0.8 | 2865 |
| 25 | 0.3 | 3 | 2425 |
| 26 | 0.9 | 6.8 | 11110 |
| 27 | 0.8 | 3.4 | 1767 |
| 28 | 0.9 | 3.7 | 3052 |
| 29 | 0.3 | 1.8 | 1159 |
| 30 | 0.8 | 1.2 | 1534 |
| 31 | 0.7 | 1.5 | 1998 |
| 32 | 0.5 | 1.8 | 2399 |
| 33 | 8.5 | 22.9 | 13118 |
| 34 | 18.6 | 136.1 | 50000 |
| 35 | 0.5 | 2.2 | 1426 |
| 36 | 0.6 | 3.9 | 3545 |
| 37 | 0.6 | 1.2 | 1907 |
| 38 | 1.8 | 3.3 | 29477 |
| 39 | 1.1 | 0.8 | 4245 |
| 40 | 0.7 | 0.5 | 2462 |
| 41 | 0.5 | 1.2 | 4334 |
| 42 | 1.6 | 0.7 | 3114 |
| 43 | 2.3 | 1.1 | 7816 |
| 44 | 0.8 | 7 | 11301 |
| 45 | 0.3 | 1.1 | 1757 |
| 46 | 0.5 | 5.5 | 3032 |
| 47 | 4.8 | 45.5 | 10643 |
| 48 | 2.1 | 83.7 | 9585 |
| 49 | 14.2 | 56.8 | 50000 |
| 50 | 0.8 | 6.2 | 3409 |
| 51 | 12.2 | 61.4 | 4680 |
| 52 | 1.8 | 50.4 | 44293 |
| 53 | 32.2 | 210.6 | 50000 |
| 54 | 0.6 | 34.6 | 30085 |
| 55 | 3.1 | 86.3 | 6521 |
| 56 | 1.5 | 23.9 | 1602 |
| 57 | 4.7 | 7.4 | 3749 |
| 58 | 2.7 | 41.6 | 2939 |
| 59 | 4.3 | 65.9 | 3116 |
| 60 | 1.2 | 42.5 | 40436 |
| 61 | 1.6 | 78.8 | 42221 |
| 62 | 0.7 | 4.5 | 644 |
| 63 | 1.8 | 46.5 | 37047 |
| 64 | 1.4 | 61.6 | — |
| 65 | 10.1 | 175.6 | 11138 |
| 66 | 0.7 | 3.7 | 2659 |
| 67 | 1.1 | 9.2 | 5849 |
| 68 | 1.4 | 29 | 42823 |
| 69 | 2.1 | 13.1 | 3833 |
| 70 | 82.4 | 558.7 | 50000 |
| 71 | 1.1 | 10.7 | 2476 |
| 72 | 0.4 | 7.5 | 1383 |
| 73 | 0.9 | 6 | 1270 |
| 74 | 2.9 | 3.3 | 6631 |
| 75 | 1 | 3.9 | 7158 |
| 76 | 0.8 | 3.7 | 2587 |
| 77 | 0.6 | 2.5 | 1579 |
| 78 | 0.7 | 5.8 | 7303 |
| 79 | 1.4 | 3.5 | 6255 |
| 80 | 1 | 6.1 | 2209 |
| 81 | 0.8 | 7 | 29110 |
| 82 | 0.5 | 4.7 | 1654 |
| 83 | 0.9 | 4 | 1958 |
| 84 | 0.6 | 3.8 | 974 |
| 85 | 0.6 | 2.9 | 481 |
| 86 | 1 | 2.5 | 2326 |
| 87 | 1 | 5.7 | 36053 |
| 88 | 1.2 | 3.7 | 2005 |
| 89 | 0.9 | 6.1 | 1594 |
| 90 | 0.2 | 3.4 | 1388 |
| 91 | 1 | 1.3 | 2784 |
| 92 | 1.2 | 3.3 | 6613 |
| 93 | 1 | 5.6 | 2645 |
| 94 | 0.3 | 5.7 | 3200 |
| 95 | 0.4 | 18.9 | 1964 |
| 96 | 0.6 | 19.7 | 1281 |
| 97 | 3.5 | 5.2 | 1549 |
| 98 | 0.8 | 2.0 | 1756 |
| 99 | 29.3 | 33.5 | 4652 |
| 100 | 8.6 | 169.4 | 1721 |
| 101 | 10.9 | 16.8 | 11330 |
| 102 | 116.8 | 3125.0 | 13829 |
| 103 | 5.3 | 174.1 | 2192 |
| 104 | 7.0 | 10.0 | 1722 |
| 105 | 0.8 | 27.1 | 813 |
| 106 | 126.2 | 3125.0 | 12485 |
| 107 | 2.1 | 5.3 | 2330 |
| 108 | 79.7 | 29.0 | 4236 |
| 109 | 153.0 | 699.9 | 427 |
| 110 | 1.5 | 4.5 | 1516 |
| 111 | 1.0 | | 1129 |
| 112 | 1.1 | 16.6 | 1974 |
| 118 | 0.8 | 3.3 | 2382 |
| 119 | 0.2 | 0.6 | 2487 |
| 120 | 3.4 | 47.5 | 2015 |
| 121 | 20.1 | 15.5 | 519 |
| 122 | 9.6 | 89.5 | 663 |
| 123 | 28.9 | 32.0 | 2091 |
| 124 | 4.6 | 33.7 | 5036 |
| 125 | 5.0 | 67.2 | 1695 |
| 126 | 18.7 | 312.9 | 605 |
| 127 | 81.5 | 21.6 | 1339 |
| 128 | 0.4 | 12.1 | 2648 |
| 131 | 109.2 | 16.6 | 1605 |
| 132 | 2.6 | 8.2 | 844 |
| 133 | 1.1 | 9.5 | 1436 |
| 134 | 1.0 | 10.3 | 1076 |
| 135 | 3.2 | 30.0 | 291 |
| 136 | 42.1 | 189.3 | 2708 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 138 | 0.3 | 19.6 | 760 |
| 140 | 0.7 | 7.2 | 2512 |
| 141 | 0.9 | 13.2 | 1331 |
| 142 | 58.4 | 1543.0 | 343 |
| 143 | 5.7 | — | 424 |
| 144 | 2.0 | 7.8 | 779 |
| 145 | 9.9 | 92.0 | 2127 |
| 146 | 27.1 | 178.6 | 1487 |
| 147 | 92.1 | 730.8 | 19901 |
| 148 | 12.8 | 4.2 | 602 |
| 149 | 47.3 | 709.4 | 214 |
| 150 | 142.1 | 338.2 | 692 |
| 151 | 0.3 | 5.0 | 1567 |
| 152 | 0.8 | 3.7 | 1148 |
| 153 | 6.4 | 144.5 | 3429 |
| 154 | 10.4 | 35.4 | 1064 |
| 155 | 599.7 | 191.0 | 862 |
| 156 | 2.8 | 17.2 | 2267 |
| 157 | 0.8 | 3.0 | 1149 |
| 158 | 0.7 | 2.9 | 1927 |
| 159 | 7.0 | 63.2 | 8794 |
| 160 | 0.7 | 5.4 | 4991 |
| 161 | 1.8 | 13.4 | 1402 |
| 162 | 3.2 | 45.3 | 1711 |
| 163 | 86.4 | 73.6 | 4947 |
| 164 | 9.0 | 15.0 | 3664 |
| 165 | 2.1 | 7.4 | 1816 |
| 166 | 2.7 | 17.8 | 3220 |
| 167 | 0.8 | 4.3 | 2471 |
| 168 | 0.4 | 1.9 | 3414 |
| 169 | 1.2 | 12.5 | 7752 |
| 170 | 1.2 | 4.4 | 8087 |
| 171 | 1.3 | 3.7 | 11528 |
| 172 | 0.4 | 4.1 | 5243 |
| 173 | 2.3 | 14.6 | 2860 |
| 174 | 0.5 | 2.1 | 3681 |
| 175 | 0.8 | 5.8 | 23314 |
| 176 | 0.5 | 1.9 | 1708 |
| 177 | 1.0 | 2.3 | 10674 |
| 178 | 0.8 | 3.5 | 1802 |
| 179 | 1.3 | 3.9 | 2038 |
| 180 | 33.6 | 5.9 | 12825 |
| 181 | 1.9 | 2.6 | 1770 |
| 182 | 12.6 | 0.8 | 4939 |
| 183 | 8.4 | 2.0 | 5208 |
| 184 | 3.3 | 2.0 | 5470 |
| 185 | 7.7 | 3.3 | 6266 |
| 186 | 5.2 | 8.3 | 14248 |
| 187 | 12.0 | 3.0 | 14559 |
| 188 | 6.5 | 1.9 | 17971 |
| 189 | 6.5 | 1.7 | 2760 |
| 190 | 2.3 | 11.0 | 12310 |
| 191 | 14.8 | 6.8 | 6359 |
| 192 | 8.7 | 3.3 | 9593 |
| 193 | 5.7 | 44.0 | 4975 |
| 194 | 5.0 | 22.3 | 15692 |
| 195 | 1.6 | 35.9 | 3957 |
| 196 | 1.3 | 25.1 | 8048 |
| 197 | 2.9 | 79.6 | 15694 |
| 198 | 2.7 | 9.8 | 4107 |
| 199 | 1.8 | 12.8 | 8321 |
| 200 | 8.0 | 17.1 | 34036 |
| 201 | 1.8 | 9.6 | 1952 |
| 202 | 1.4 | 16.7 | 15339 |
| 203 | 2.3 | 6.9 | 6028 |
| 204 | 0.7 | 0.7 | 2020 |
| 205 | 0.6 | 0.9 | 2764 |
| 206 | 0.9 | 1.5 | 5737 |
| 207 | 10.8 | 8.8 | 4618 |
| 208 | 14.2 | 4.0 | 5041 |
| 209 | 3.9 | 5.9 | 8219 |
| 210 | 3.4 | 6.2 | 4283 |
| 211 | 14.8 | 211.6 | 14365 |
| 212 | 10.6 | 347.6 | 2855 |
| 213 | 5.0 | 103.3 | 7241 |
| 214 | 5.2 | 111.2 | 16506 |
| 215 | 15.5 | 142.8 | 7579 |
| 216 | 3.2 | 243.5 | 19247 |
| 217 | 8.2 | 238.7 | 8148 |
| 218 | 5.2 | 103.9 | 11257 |
| 219 | 34.0 | 18.3 | 10959 |
| 220 | 0.7 | 3.2 | 672 |
| 221 | 0.4 | 1.3 | 5315 |
| 222 | 1.0 | 6.2 | 18169 |
| 223 | 0.8 | 12.0 | 1074 |
| 224 | 1.5 | 9.5 | 6973 |
| 225 | 9.9 | 249.7 | 12206 |
| 226 | 8.9 | 8.9 | 18002 |
| 227 | 11.6 | 20.8 | 5074 |
| 228 | 78.3 | 962.0 | 38220 |
| 229 | 2.0 | 43.5 | 1047 |
| 230 | 68.1 | 51.4 | 7285 |
| 231 | 2.4 | 6.0 | 6641 |
| 232 | 2.3 | 7.0 | 1099 |
| 233 | 1.0 | 1.5 | 15605 |
| 234 | 0.6 | 6.2 | 7219 |
| 235 | 1.7 | 10.4 | 3087 |
| 236 | 19.6 | 9.1 | 1180 |
| 237 | 10.8 | 588.3 | 5935 |
| 238 | 8.9 | 347.5 | 2625 |
| 239 | 22.5 | 96.7 | — |
| 240 | 6.6 | 22.9 | 6003 |
| 241 | 18.9 | 4.9 | 2988 |
| 242 | 2.9 | 5.6 | 3600 |
| 243 | 2.8 | 33.5 | 44062 |
| 244 | 1.0 | 10.0 | 6270 |
| 245 | 1.2 | 10.5 | 2648 |
| 246 | 0.2 | 2.3 | 2259 |
| 247 | 7.4 | 48.5 | 4394 |
| 248 | 4.2 | 65.7 | 4582 |
| 249 | 11.5 | 20.1 | 1823 |
| 250 | 0.7 | 8.6 | 3422 |
| 251 | 0.5 | 7.8 | 6316 |
| 252 | 0.5 | 2.0 | 2551 |
| 253 | 0.2 | 13.6 | 1001 |
| 254 | 0.6 | 6.1 | 16008 |
| 255 | 95.0 | 1125.6 | 3771 |
| 256 | 178.6 | 1881.8 | 2121 |
| 257 | 1703.8 | 435.7 | 995 |
| 258 | 1235.5 | 404.7 | 5885 |
| 259 | 12.2 | 137.1 | 1355 |
| 260 | 0.4 | 13.9 | 2603 |
| 261 | 2.1 | 28.3 | 8114 |
| 262 | 0.6 | 5.3 | 1895 |
| 263 | 1.1 | 2.8 | 5301 |
| 264 | 0.5 | 2.3 | 3949 |
| 265 | 0.7 | 9.3 | 7028 |
| 266 | 560.4 | 448.9 | 7984 |
| 267 | 102.9 | 30.8 | 7300 |
| 268 | 2.8 | 15.7 | 1894 |
| 269 | 4.2 | 37.1 | 12314 |
| 270 | 5.2 | 4.6 | 1573 |
| 271 | 0.6 | 12.8 | 1346 |
| 272 | 0.6 | 11.7 | 2416 |
| 273 | 2.1 | 4.7 | 973 |
| 274 | 1.1 | 19.0 | 3731 |
| 275 | 3.1 | 25.5 | 10188 |
| 276 | 5.4 | 52.0 | 1824 |
| 277 | 10.4 | 61.2 | 2442 |
| 278 | 100.6 | 70.6 | 2134 |
| 279 | 61.7 | 58.7 | 3164 |
| 280 | 0.6 | 12.4 | 4300 |
| 281 | 0.7 | 15.0 | 6153 |
| 282 | 1.7 | 5.9 | 10082 |
| 283 | 4.9 | 6.3 | 2430 |
| 284 | 3.3 | 8.0 | 1900 |
| 285 | 1.5 | 15.1 | 6012 |
| 286 | 0.5 | 0.8 | 3147 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 287 | 1.0 | 0.5 | 3056 |
| 288 | 0.6 | 1.4 | 14105 |
| 289 | 1.0 | 25.9 | 6126 |
| 290 | 1.8 | 35.6 | 6254 |
| 291 | 8.2 | 2.1 | 1568 |
| 292 | 18.3 | 1.4 | 1303 |
| 293 | 0.5 | 15.8 | 5709 |
| 294 | 0.8 | 21.1 | 19539 |
| 295 | 1.9 | 45.6 | 2449 |
| 296 | 3.1 | 47.4 | 10442 |
| 297 | 5.0 | 26.3 | 2153 |
| 298 | 10.8 | 45.7 | 625 |
| 299 | 26.3 | 139.7 | 3432 |
| 300 | 29.0 | 113.1 | 2658 |
| 301 | 54.5 | 252.5 | 6442 |
| 302 | 4.3 | 6.1 | 2971 |
| 303 | 1.6 | 7.0 | 17114 |
| 304 | 0.9 | 3.3 | 4541 |
| 305 | 2.7 | 1.8 | 7034 |
| 306 | 1.2 | 2.7 | 16966 |
| 307 | 48.2 | 103.0 | 5320 |
| 308 | 40.0 | 2.1 | 1533 |
| 309 | 43.1 | 2.0 | 709 |
| 310 | 181.4 | 307.2 | 112 |
| 311 | 90.5 | 352.3 | 155 |
| 312 | 5.7 | 55.6 | 4305 |
| 313 | 5.4 | 80.6 | 3132 |
| 314 | 11.9 | 18.3 | 1640 |
| 315 | 268.6 | 557.9 | 1931 |
| 316 | 318.9 | 491.7 | 3692 |
| 317 | 19.8 | 71.8 | 8575 |
| 318 | 6.8 | 25.5 | 2227 |
| 319 | 0.2 | 7.9 | 10520 |
| 320 | 0.3 | 14.2 | 3024 |
| 321 | 0.7 | 4.6 | 6178 |
| 322 | 2.0 | 7.7 | 2086 |
| 323 | 2.6 | 35.3 | 5189 |
| 324 | 1.6 | 2.9 | 1001 |
| 325 | 1.4 | 12.4 | 1114 |
| 326 | 1.2 | 6.7 | 2187 |
| 327 | 0.9 | 4.1 | 1453 |
| 328 | 4.3 | 4.3 | 1901 |
| 329 | 3.2 | 18.5 | 1051 |
| 330 | 1.0 | 14.4 | 1121 |
| 331 | 2.5 | 6.4 | 5294 |
| 332 | 3.6 | 4.1 | 3165 |
| 333 | 3.3 | 5.3 | 3183 |
| 334 | 2.9 | 1.9 | 2092 |
| 335 | 1.1 | 6.3 | 1501 |
| 336 | 4.9 | 4.7 | 2835 |
| 337 | 2.0 | 5.2 | 2106 |
| 338 | 1.6 | 5.8 | 8874 |
| 339 | 4.1 | 5.6 | 14877 |
| 340 | 1.5 | 6.5 | 5866 |
| 341 | 1.9 | 4.2 | 2860 |
| 342 | 3.7 | 3.0 | 1785 |
| 343 | 3.6 | 19.0 | 330 |
| 344 | 1.5 | 13.4 | 5474 |
| 345 | 5.1 | 37.6 | 1412 |
| 346 | 4.2 | 66.6 | 4614 |
| 347 | 1511.5 | 2255.2 | 8618 |
| 348 | 5.5 | — | 1145 |
| 349 | 1.5 | 3.9 | 1787 |
| 350 | 5.6 | 12.5 | 4809 |
| 351 | 39.9 | 18.4 | 5322 |
| 352 | 29.5 | 56.5 | 11409 |
| 353 | 38.5 | 44.2 | 24690 |
| 354 | 18.2 | 12.5 | 2258 |
| 355 | 8.3 | 107.0 | 6231 |
| 358 | 13.6 | 29.7 | 6035 |
| 359 | 6.8 | 8.9 | 1819 |
| 360 | 3.5 | 22.3 | 3619 |
| 361 | 14.4 | 9.9 | 9225 |
| 362 | 325.0 | 149.2 | 15799 |
| 363 | 19.4 | 10.1 | 822 |
| 364 | 9.2 | 7.0 | 1523 |
| 365 | 5.6 | 10.6 | 3587 |
| 366 | 29.0 | 8.7 | 1917 |
| 367 | 16.3 | 3.8 | 4404 |
| 368 | 57.0 | 19.1 | 2067 |
| 369 | 19.2 | 4.7 | 1839 |
| 370 | 23.4 | 15.8 | 2260 |
| 371 | 17.0 | 6.1 | 1927 |
| 372 | 37.1 | 21.1 | 3472 |
| 373 | 21.4 | 6.5 | 2329 |
| 374 | 32.2 | 17.2 | 10078 |
| 375 | 11.6 | 10.3 | 2104 |
| 376 | 9.5 | 5.2 | 1996 |
| 377 | 9.0 | 3.0 | — |
| 378 | 11.1 | 8.6 | 5732 |
| 379 | 2.7 | 1.2 | 990 |
| 380 | 6.7 | 12.1 | 1195 |
| 381 | 7.8 | 2.4 | 764 |
| 382 | 19.9 | 3.8 | 1894 |
| 383 | 79.8 | 59.6 | 18177 |
| 384 | 5.9 | 7.0 | 2266 |
| 385 | 7.8 | 62.9 | 31598 |
| 386 | 0.9 | 9.3 | 5157 |
| 387 | 1.4 | 6.1 | 3362 |
| 388 | 1.6 | 7.1 | 6145 |
| 389 | 2.8 | 2.1 | 7128 |
| 390 | 33.2 | 151.4 | 50000 |
| 391 | 0.2 | 0.9 | 1904 |
| 392 | 1.7 | 6.0 | 50000 |
| 393 | 2.7 | 1.5 | 1484 |
| 394 | 1.2 | 2.7 | 1379 |
| 395 | 2.3 | 10.4 | 44660 |
| 396 | 2.6 | 8.9 | 5113 |
| 397 | 0.6 | 2.9 | 2183 |
| 398 | 6.3 | 41.9 | 12558 |
| 399 | 1.1 | 3.8 | 857 |
| 400 | 2.5 | 13.5 | 2003 |
| 401 | 5.9 | 98.5 | 21445 |
| 402 | 2.5 | 8.6 | 6271 |
| 403 | 5.5 | 12.9 | 1662 |
| 404 | 1.3 | 7.2 | 50000 |
| 405 | 2.1 | 1.9 | 2379 |
| 406 | 0.6 | 1.8 | 747 |
| 407 | 1.5 | 1.9 | 2290 |
| 408 | 2.0 | 4.9 | 9828 |
| 409 | 0.5 | 1.1 | 658 |
| 410 | 1.5 | 1.0 | 1150 |
| 411 | 1.7 | 7.8 | 45491 |
| 412 | 0.5 | 1.8 | 2865 |
| 413 | 1.2 | 33.5 | 632 |
| 414 | 1.4 | 4.9 | 3627 |
| 415 | 2.7 | 4.9 | 2503 |
| 416 | 5.4 | 16.4 | 22305 |
| 417 | 10.1 | 46.9 | 26022 |
| 418 | 5.4 | 11.8 | 7590 |
| 419 | 1.1 | 2.6 | 279 |
| 420 | 1.0 | 1.5 | 725 |
| 421 | 2.2 | 5.2 | 3405 |
| 422 | 0.6 | 3.3 | 7855 |
| 423 | 0.9 | 3.3 | 8387 |
| 424 | 1.0 | 4.3 | 3152 |
| 425 | 3.7 | 5.1 | 1149 |
| 426 | 9.8 | 877.3 | 50000 |
| 427 | 1.6 | 5.9 | 3650 |
| 428 | 1.3 | 9.1 | 9034 |
| 429 | 1.6 | 5.3 | 2074 |
| 430 | 0.7 | 3.1 | 3572 |
| 431 | 2.6 | 9.0 | 5462 |
| 432 | 0.1 | 1.8 | 1552 |
| 433 | 6.3 | 6.6 | 32563 |
| 434 | 1.4 | 3.7 | 5273 |
| 435 | 7.7 | 11.8 | 24316 |
| 436 | 3.0 | 3.3 | 6254 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 437 | 0.8 | 0.7 | 1186 |
| 438 | 2.7 | 5.7 | 2205 |
| 439 | 7.7 | 17.3 | 23290 |
| 440 | 3.4 | 5.7 | 24466 |
| 441 | 8.5 | 10.0 | 41305 |
| 442 | 9.1 | 3.9 | 2823 |
| 443 | 19.7 | 3.4 | 5143 |
| 444 | 42.1 | 5.4 | 16934 |
| 445 | 13.6 | 1.6 | 3324 |
| 446 | 41.5 | 6.3 | 43852 |
| 447 | 55.8 | 10.8 | 50000 |
| 448 | 7.8 | 0.5 | 2338 |
| 449 | 13.6 | 4.4 | 7125 |
| 450 | 15.8 | 2.0 | 11508 |
| 451 | 14.5 | 2.5 | 5148 |
| 452 | 11.0 | 2.8 | 996 |
| 453 | 20.9 | 3.4 | 18886 |
| 454 | 38.9 | 3.1 | 10042 |
| 455 | 7.3 | 1.4 | 2198 |
| 456 | 98.6 | 27.6 | 15101 |
| 457 | 16.4 | 1.6 | 6631 |
| 458 | 7.8 | 8.1 | 30283 |
| 459 | 14.4 | 6.4 | 13406 |
| 460 | 7.3 | 6.0 | 50000 |
| 461 | 4.3 | 1.1 | — |
| 462 | 3.0 | 2.2 | — |
| 463 | 41.4 | 3.6 | 6221 |
| 464 | 3.1 | 3.8 | 13473 |
| 465 | 18.5 | 1.8 | 4038 |
| 466 | 21.7 | 3.1 | 8713 |
| 467 | 14.1 | 2.2 | 4589 |
| 468 | 3.7 | 11.4 | 2776 |
| 469 | 4.5 | 37.1 | 10275 |
| 470 | 8.2 | 10.0 | 3881 |
| 471 | 8.5 | 14.7 | 5311 |
| 472 | 5.3 | 2.6 | 2659 |
| 473 | 6.0 | 16.9 | 25227 |
| 474 | — | 13.6 | 2095 |
| 475 | 0.5 | 1.8 | 4172 |
| 476 | 0.4 | 0.8 | 1355 |
| 477 | 6.1 | 49.1 | 50000 |
| 478 | 1.7 | 0.7 | 2435 |
| 479 | 2.9 | 3.7 | 3906 |
| 480 | 0.6 | 1.0 | 4213 |
| 481 | 0.7 | 0.8 | 2203 |
| 482 | 2.1 | 11.8 | 4192 |
| 483 | 5.2 | 1.6 | 28163 |
| 484 | 6.5 | 6.3 | 50000 |
| 485 | 0.8 | 1.4 | 3415 |
| 486 | 1.3 | 1.0 | 3158 |
| 487 | 7.1 | 11.2 | 17398 |
| 488 | 3.6 | 2.1 | 4172 |
| 489 | — | 2.7 | 4570 |
| 490 | 10.3 | 156.9 | 9234 |
| 491 | 11.5 | 49.9 | 2983 |
| 492 | 5.6 | 173.4 | 16217 |
| 493 | 7.1 | 76.4 | 3973 |
| 494 | 5.5 | 82.8 | 6106 |
| 495 | 14.4 | 186.5 | 10106 |
| 496 | 6.4 | 104.3 | 8003 |
| 497 | 2.2 | 97.2 | 4370 |
| 498 | 6.5 | 154.2 | 9516 |
| 499 | 55.0 | 31.2 | 50000 |
| 500 | 0.7 | 6.8 | 1348 |
| 501 | 1.5 | 11.4 | 8063 |
| 502 | 11.9 | 47.9 | 3449 |
| 503 | — | 143.5 | 50000 |
| 504 | 12.4 | 7.1 | 47457 |
| 505 | 4.4 | 2.5 | 3098 |
| 506 | 4.0 | 28.4 | 6661 |
| 507 | 645.6 | 3125.0 | 25265 |
| 508 | 51.0 | 14.0 | 48633 |
| 509 | 59.8 | 5.9 | 2801 |
| 510 | 1.4 | 4.6 | 15300 |
| 511 | 5.2 | 6.2 | 5624 |
| 512 | 2.8 | 1.2 | 2568 |
| 513 | 2.6 | 2.6 | 4138 |
| 514 | 3.1 | 1.9 | 3749 |
| 515 | 1.5 | 1.2 | 1675 |
| 516 | 3.3 | 1.4 | 3510 |
| 517 | 5.7 | 1.5 | 6413 |
| 518 | 1.9 | 2.5 | 11591 |
| 519 | 3.0 | 2.4 | 3723 |
| 520 | 2.8 | 3.2 | 6885 |
| 521 | 2.6 | 3.9 | 4828 |
| 522 | 4.5 | 6.2 | 25614 |
| 523 | 2.5 | 3.6 | 3660 |
| 524 | 1.4 | 4.3 | 6234 |
| 525 | 8.3 | 4.3 | 13427 |
| 526 | 4.4 | 1.8 | 2474 |
| 527 | 4.4 | 1.5 | 569 |
| 528 | 30.8 | 16.5 | 9591 |
| 529 | 33.7 | 17.0 | 10201 |
| 530 | 10.5 | 7.0 | 653 |
| 532 | 33.3 | 435.3 | 55 |
| 533 | 8.0 | 281.1 | 1227 |
| 534 | 27.4 | 677.0 | 7557 |
| 535 | 29.9 | 209.0 | 1443 |
| 536 | 8.4 | 15.9 | 3538 |
| 537 | 2.2 | 3.3 | 6503 |
| 538 | 0.5 | 12.5 | 1459 |
| 539 | 1.2 | 15.1 | 3234 |
| 540 | 0.4 | 1.5 | 1836 |
| 541 | 0.3 | 1.8 | 1637 |
| 542 | 2.3 | 56.7 | 50000 |
| 543 | 1.7 | 11.0 | 1632 |
| 544 | 1.8 | 6.5 | 5008 |
| 545 | 1.5 | 4.9 | 1301 |
| 546 | 71.6 | 85.3 | 7699 |
| 547 | 42.4 | 135.0 | 6042 |
| 548 | 5.5 | 30.0 | 4303 |
| 549 | 1.5 | 20.7 | — |
| 550 | 1.3 | 7.7 | 6413 |
| 551 | 0.8 | 6.1 | 2317 |
| 552 | 0.6 | 3.5 | 995 |
| 553 | 5.3 | 29.0 | 3486 |
| 554 | 1.8 | 10.9 | 6093 |
| 555 | 0.3 | 2.1 | 2160 |
| 556 | 0.4 | 5.5 | 3924 |
| 557 | 0.4 | 6.5 | 2730 |
| 558 | 3125.0 | 3125.0 | 16753 |
| 559 | 634.2 | 288.6 | 483 |
| 560 | 1308.6 | 149.4 | 1897 |
| 561 | 1.5 | 5.8 | 1327 |
| 562 | 2.2 | 6.2 | 6348 |
| 563 | 0.8 | 2.6 | 1133 |
| 564 | 0.4 | 1.8 | 1234 |
| 565 | 0.4 | 1.2 | 549 |
| 566 | 0.3 | 1.2 | 1469 |
| 567 | 0.4 | 3.0 | 2235 |
| 568 | 0.7 | 1.8 | 1451 |
| 569 | 0.4 | 1.3 | 1565 |
| 570 | 0.4 | 0.7 | 535 |
| 571 | 5.1 | 1.9 | 1238 |
| 572 | 20.3 | 30.5 | 24538 |
| 573 | 2.6 | 3.6 | 1571 |
| 574 | — | 20.5 | 6570 |
| 575 | 1.1 | 8.0 | 1859 |
| 576 | 0.9 | 6.5 | 1914 |
| 577 | 2.0 | 9.7 | 2237 |
| 578 | 5.4 | 23.2 | 7859 |
| 579 | 2.1 | 18.7 | 1799 |
| 580 | 4.1 | 84.8 | 5087 |
| 581 | 31.5 | 1.9 | 2472 |
| 582 | 0.6 | 3.6 | 2556 |
| 583 | 1.0 | 12.2 | 13615 |
| 584 | 2.1 | 12.1 | 3296 |
| 585 | 6.4 | 95.3 | 25590 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 586 | 34.6 | 84.5 | 2111 |
| 587 | 4.4 | 7.9 | 7380 |
| 588 | 2.4 | 10.6 | 50000 |
| 589 | 2.6 | 0.7 | 4122 |
| 590 | 172.6 | 132.0 | 6275 |
| 591 | 180.4 | 2.0 | 5677 |
| 592 | 384.6 | 353.6 | 81 |
| 593 | 0.7 | 16.1 | 1785 |
| 594 | 10.8 | 85.1 | 3928 |
| 595 | 4.1 | 15.9 | 14361 |
| 596 | 4.3 | 12.2 | 16277 |
| 597 | 8.8 | 44.3 | 10928 |
| 598 | 5.2 | 49.6 | 6302 |
| 599 | 2.9 | 10.9 | 1738 |
| 600 | 6.5 | 14.1 | 2652 |
| 601 | 28.7 | 147.9 | 50000 |
| 602 | 2.8 | 41.8 | — |
| 603 | 2.1 | 50.0 | 42404 |
| 604 | 4.5 | 132.1 | 37270 |
| 605 | 0.8 | 25.8 | 40711 |
| 606 | 0.7 | 36.1 | 43596 |
| 607 | 0.9 | 42.6 | 44356 |
| 608 | 1.8 | 55.6 | 50000 |
| 609 | 69.6 | 243.3 | 50000 |
| 610 | 1.7 | 13.7 | 5711 |
| 611 | 3.2 | 6.1 | 3382 |
| 612 | 5.6 | 174.9 | 2353 |
| 613 | 48.8 | 3125.0 | 50000 |
| 614 | 56.3 | 3125.0 | 47110 |
| 615 | 12.8 | 470.8 | 1595 |
| 616 | 12.5 | 607.4 | 901 |
| 617 | 32.7 | 3125.0 | 50000 |
| 618 | 9.1 | 634.9 | 2547 |
| 619 | 19.3 | 310.2 | 50000 |
| 620 | 0.7 | 1.3 | 58 |
| 621 | 16.3 | 258.0 | 6809 |
| 622 | 1.3 | 21.6 | 1590 |
| 623 | 2.7 | 9.1 | 1106 |
| 624 | 1.6 | 12.1 | 1490 |
| 625 | 0.9 | 11.2 | 554 |
| 626 | 0.5 | 6.7 | 3181 |
| 627 | 0.4 | 11.3 | 5872 |
| 628 | — | 231.9 | 50000 |
| 629 | 0.7 | 7.4 | 3171 |
| 630 | 1.1 | 8.7 | 1988 |
| 631 | 3.5 | 66.9 | 45473 |
| 632 | 2.4 | 56.5 | 37917 |
| 633 | 568.1 | 3125.0 | 50000 |
| 634 | 8.7 | 31.5 | 35483 |
| 635 | 3.1 | 17.0 | 1515 |
| 636 | 2.4 | 16.3 | 2448 |
| 637 | 34.0 | 1077.5 | 42907 |
| 638 | 5.8 | 152.6 | 3221 |
| 639 | 5.0 | 140.1 | 3028 |
| 640 | 1838.5 | 3125.0 | 3723 |
| 641 | 0.3 | 14.9 | 1067 |
| 642 | 0.2 | 14.0 | 2517 |
| 643 | 0.6 | 197.5 | 22162 |
| 644 | 4.8 | 34.7 | 5784 |
| 645 | 2.8 | 240.1 | 50000 |
| 646 | 5.7 | 538.0 | 50000 |
| 647 | 1.3 | 202.1 | 50000 |
| 648 | 14.7 | 1700.8 | 50000 |
| 649 | 1.6 | 10.1 | 7355 |
| 650 | 16.3 | 931.3 | 50000 |
| 651 | 3.2 | 260.9 | 12737 |
| 652 | 1.5 | 157.2 | 36400 |
| 653 | 24.0 | 3125.0 | 50000 |
| 654 | 7.9 | 603.3 | 50000 |
| 655 | 1.4 | 115.5 | 9585 |
| 656 | 131.7 | 2533.8 | 707 |
| 657 | 416.4 | 3125.0 | 50000 |
| 658 | 385.2 | 3125.0 | 50000 |
| 659 | 809.7 | 3125.0 | 3750 |
| 660 | 1717.8 | 268.1 | 1001 |
| 661 | 868.3 | 85.9 | 544 |
| 662 | 1.0 | 14.0 | 1349 |
| 663 | 1.6 | 43.5 | 50000 |
| 664 | 2.2 | 56.9 | 5998 |
| 665 | 4.1 | 77.9 | 11847 |
| 666 | 5.8 | 55.4 | 12108 |
| 667 | 3.0 | 8.6 | 4501 |
| 668 | 1.2 | 36.9 | 34156 |
| 669 | 311.0 | 3125.0 | 50000 |
| 670 | 8.3 | 59.6 | 50000 |
| 671 | 2.1 | 30.3 | 18365 |
| 672 | 1.0 | 8.4 | 2519 |
| 673 | 1.9 | 29.2 | 42411 |
| 674 | 1.2 | 14.4 | 663 |
| 675 | 0.8 | 14.5 | 3586 |
| 676 | 7.8 | 64.6 | 1693 |
| 677 | 1.9 | 43.8 | 33978 |
| 678 | 3.0 | 39.3 | 42260 |
| 679 | 0.4 | 5.2 | 1181 |
| 680 | 2.7 | 25.9 | 956 |
| 681 | 5.5 | 47.7 | 1195 |
| 682 | 1261.1 | 8.2 | 778 |
| 683 | — | 1.7 | 124 |
| 684 | 57.2 | 338.4 | 1468 |
| 685 | 12.4 | 590.1 | 50000 |
| 686 | 0.6 | 13.9 | 2172 |
| 687 | 1.0 | 15.1 | 1738 |
| 688 | — | 18.6 | 4136 |
| 689 | 0.5 | 3.3 | 2779 |
| 690 | 9.4 | 4.9 | 901 |
| 691 | 50.6 | 6.2 | 408 |
| 692 | 10.8 | 81.2 | 2415 |
| 693 | 6.6 | 46.7 | 893 |
| 694 | 5.8 | 70.3 | 1288 |
| 695 | 6.2 | 23.5 | 1082 |
| 696 | 0.2 | 13.4 | 1547 |
| 697 | 0.2 | 9.3 | 1093 |
| 698 | 2.6 | 41.4 | 1434 |
| 699 | 1.1 | 18.1 | 1215 |
| 700 | 1.8 | 25.6 | 1844 |
| 701 | 2.4 | 8.0 | 2048 |
| 702 | 2.9 | 9.9 | 658 |
| 703 | 2.9 | 10.7 | 4601 |
| 704 | 1.1 | 5.6 | 2013 |
| 705 | 6.6 | 217.7 | 32501 |
| 706 | 2.3 | 30.3 | 473 |
| 707 | 5.2 | 156.8 | 27366 |
| 708 | 6.0 | 55.2 | 2110 |
| 709 | 6.3 | 357.5 | 8846 |
| 710 | 16.2 | 290.8 | 16893 |
| 711 | 3.6 | 35.1 | 989 |
| 712 | 1.6 | 49.1 | 3058 |
| 713 | 24.4 | 177.5 | 6626 |
| 714 | 0.8 | 3.7 | 2537 |
| 715 | 0.2 | 3.6 | 3257 |
| 716 | 0.6 | 117.2 | 43816 |
| 717 | 5.5 | 46.3 | 46627 |
| 718 | 3.4 | 36.7 | 44471 |
| 719 | 0.5 | 3.1 | 616 |
| 720 | 5.2 | 35.4 | 5037 |
| 721 | 3.9 | 9.9 | 190 |
| 722 | 3.3 | 17.5 | 2973 |
| 723 | 2.9 | 21.0 | 7713 |
| 724 | 1.4 | 4.4 | 782 |
| 725 | 11.6 | 55.4 | 50000 |
| 726 | 10.7 | 35.8 | 50000 |
| 727 | 1.7 | 9.8 | 4497 |
| 728 | 3.0 | 15.4 | 3903 |
| 729 | 2.2 | 5.4 | 462 |
| 730 | 27.4 | 152.8 | 13740 |
| 731 | 1.7 | 8.6 | 3025 |
| 732 | 2.3 | 7.6 | 3127 |
| 733 | 10.1 | 78.2 | 23792 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 734 | 1.4 | 6.6 | 2862 |
| 735 | 1.2 | 7.7 | 1963 |
| 736 | 1.2 | 5.9 | 812 |
| 737 | 1.1 | 5.9 | 4342 |
| 738 | 0.4 | 5.5 | 4312 |
| 739 | 2.0 | 11.2 | 15195 |
| 740 | 1.0 | 4.7 | 2044 |
| 741 | 12.2 | 93.6 | 50000 |
| 742 | 1.0 | 9.2 | 5878 |
| 743 | 0.9 | 5.1 | 2418 |
| 744 | 3.7 | 13.4 | 1387 |
| 745 | 0.7 | 5.1 | 1440 |
| 746 | 4.5 | 12.9 | 4678 |
| 747 | 3.5 | 20.0 | 6211 |
| 748 | 1.8 | 14.3 | 3623 |
| 749 | 0.8 | 3.5 | 1354 |
| 750 | 1.3 | 5.4 | 1632 |
| 751 | 2.7 | 11.6 | 2560 |
| 752 | 33.7 | 144.7 | 50000 |
| 753 | 0.9 | 4.3 | 1923 |
| 754 | 1.4 | 9.5 | 3789 |
| 755 | 2.1 | 7.8 | 1019 |
| 756 | 0.9 | 2.7 | 1275 |
| 757 | 1.8 | 5.9 | 782 |
| 758 | 1.0 | 8.1 | 2893 |
| 759 | 0.7 | 12.5 | 3997 |
| 760 | 1.2 | 8.0 | 2950 |
| 761 | 8.9 | 71.5 | 50000 |
| 762 | 0.9 | 8.1 | 5102 |
| 763 | 2.5 | 8.1 | 4756 |
| 764 | 1.4 | 10.9 | 4042 |
| 765 | 0.9 | 3.4 | 1182 |
| 766 | 1.3 | 11.4 | 4842 |
| 767 | 0.2 | 2.7 | 2496 |
| 768 | 2.3 | 12.5 | 6751 |
| 769 | 1.0 | 7.3 | 1769 |
| 770 | 0.7 | 7.4 | 1794 |
| 771 | 1.5 | 12.3 | 2281 |
| 772 | 1.7 | 30.2 | 4855 |
| 773 | 1.0 | 11.9 | 3304 |
| 774 | 0.5 | 5.9 | 1009 |
| 775 | 0.7 | 5.6 | 1735 |
| 776 | 0.4 | 5.8 | 1398 |
| 777 | 0.4 | 22.6 | 4974 |
| 778 | 0.3 | 17.0 | 2934 |
| 779 | 1.1 | 64.8 | 7100 |
| 780 | 0.4 | 8.0 | 6227 |
| 781 | — | 4.3 | 368 |
| 782 | 1.6 | 6.2 | 5308 |
| 783 | 0.5 | 4.1 | 3026 |
| 784 | 2.3 | 6.3 | 6602 |
| 785 | 1.0 | 5.8 | — |
| 786 | 2.0 | 8.9 | 5342 |
| 787 | 0.8 | 4.1 | 3246 |
| 788 | 2.6 | 7.5 | 4575 |
| 789 | 4.2 | 15.5 | 4153 |
| 790 | 1.8 | 6.7 | 5742 |
| 791 | 1.7 | 9.7 | 5028 |
| 792 | 1.3 | 6.4 | 3377 |
| 793 | 1.5 | 5.9 | 4963 |
| 794 | 2.9 | 13.9 | 5588 |
| 795 | 2.2 | 8.6 | 3548 |
| 796 | 1.7 | 7.2 | 5141 |
| 797 | 1.4 | 5.4 | 4075 |
| 798 | 2.1 | 7.9 | 3146 |
| 799 | 8.3 | 18.1 | 6791 |
| 800 | 8.5 | 37.4 | 16645 |
| 801 | 1.8 | 10.5 | 2874 |
| 802 | 3.3 | 5.8 | 5686 |
| 803 | 7.6 | 10.0 | 41531 |
| 804 | 5.1 | 5.2 | 5283 |
| 805 | 2.4 | 6.3 | 2830 |
| 806 | 1.6 | 4.3 | 22288 |
| 807 | 11.5 | 7.1 | 16216 |
| 808 | 8.5 | 5.8 | 5987 |
| 809 | 17.3 | 10.3 | 6047 |
| 810 | 6.6 | 4.3 | 3609 |
| 811 | 1.1 | 13.8 | 4068 |
| 812 | 1.3 | 14.4 | 3769 |
| 813 | 7.8 | 14.5 | 5006 |
| 814 | 1.7 | 19.8 | 5168 |
| 815 | 9.2 | 46.0 | 7886 |
| 816 | 4.8 | 38.1 | 20361 |
| 817 | 5.3 | 55.5 | 5416 |
| 818 | 4.7 | 18.0 | 3734 |
| 819 | 6.3 | 39.7 | 8031 |
| 820 | 3.8 | 23.5 | 6111 |
| 821 | 8.2 | 61.0 | 22760 |
| 822 | 9.8 | 44.2 | 4011 |
| 823 | 6.7 | 26.9 | 3040 |
| 824 | 16.3 | 76.4 | 16936 |
| 825 | 11.5 | 34.3 | 5468 |
| 826 | 13.4 | 30.3 | 6312 |
| 827 | 15.5 | 23.7 | 7064 |
| 828 | 16.3 | 73.1 | 12747 |
| 829 | 4.8 | 32.1 | 1999 |
| 830 | 6.7 | 37.8 | 9523 |
| 831 | 9.5 | 68.3 | 23615 |
| 832 | 11.3 | 61.7 | 50000 |
| 833 | 13.0 | 43.9 | 10940 |
| 834 | 20.0 | 91.8 | 17529 |
| 835 | 9.9 | 33.3 | 3968 |
| 836 | 10.6 | 33.4 | 3228 |
| 837 | 10.4 | 35.7 | 5202 |
| 838 | 622.3 | 2352.4 | 28501 |
| 839 | 6.0 | 21.0 | 5577 |
| 840 | 17.0 | 82.8 | 50000 |
| 841 | 16.9 | 112.1 | 31037 |
| 842 | 58.2 | 342.0 | 50000 |
| 843 | 1.3 | 1.7 | 3654 |
| 844 | 6.0 | 9.0 | 23608 |
| 845 | 1.4 | 1.1 | 9868 |
| 846 | 1.1 | 1.3 | 14078 |
| 847 | 1.6 | 1.1 | 4430 |
| 848 | 0.7 | 2.1 | 4492 |
| 849 | 0.9 | 1.4 | 5017 |
| 850 | 5.8 | 206.0 | 5624 |
| 851 | 1.0 | 14.3 | — |
| 852 | 3.5 | 34.6 | 10807 |
| 853 | 0.5 | 3.2 | 2064 |
| 854 | 0.4 | 4.9 | 13602 |
| 855 | 2.4 | 7.6 | 7042 |
| 856 | 2.0 | 16.5 | 8337 |
| 857 | 1.3 | 13.3 | 16943 |
| 858 | 0.8 | 2.4 | 3330 |
| 859 | 0.7 | 6.8 | 3367 |
| 860 | 1.7 | 24.5 | 35290 |
| 861 | 0.8 | 6.0 | 13098 |
| 862 | 0.3 | 2.9 | 1324 |
| 863 | 0.4 | 2.0 | 182 |
| 864 | 0.4 | 3.5 | 3008 |
| 865 | 0.2 | 3.4 | 4108 |
| 866 | 1.1 | 2.8 | 312 |
| 867 | 1.1 | 4.6 | 1371 |
| 868 | 0.5 | 5.6 | 2088 |
| 869 | 2.0 | 11.8 | 2042 |
| 870 | 0.5 | 4.7 | 3106 |
| 871 | 0.7 | 6.9 | 2472 |
| 872 | 0.5 | 7.2 | 2838 |
| 873 | 0.8 | 8.6 | 3913 |
| 874 | 1.7 | 10.9 | 766 |
| 875 | 0.4 | 6.5 | 2240 |
| 876 | 4.5 | 3.9 | 10992 |
| 877 | 5.3 | 1.9 | 16225 |
| 878 | 1.8 | 2.0 | 5697 |
| 879 | 2.2 | 4.9 | 5146 |
| 880 | 2.0 | 1.3 | 6187 |
| 881 | 2.9 | 5.0 | 6005 |

TABLE 27-continued

TLR7/8/9 Reporter Assay Data

| Ex. No. | TLR7 IC$_{50}$ (nM) | TLR8 IC$_{50}$ (nM) | TLR9 IC$_{50}$ (nM) |
| --- | --- | --- | --- |
| 882 | 4.7 | 31.3 | 37052 |
| 883 | 2.7 | 21.3 | 12076 |
| 884 | 12.1 | 71.7 | 50000 |
| 885 | 20.7 | 18.5 | 15041 |
| 886 | 3.4 | 11.6 | 467 |
| 887 | 2.5 | 11.6 | 1836 |
| 888 | 1.0 | 4.8 | 1776 |
| 889 | 2.0 | 7.6 | 421 |
| 890 | 4.9 | 24.0 | 4315 |
| 891 | 0.2 | 5.2 | 534 |
| 892 | 1.6 | 7.5 | 1379 |
| 893 | 1.3 | 5.0 | 1100 |
| 894 | 2.3 | 1.8 | 3303 |
| 895 | 1.1 | 3.3 | 1000 |
| 896 | 2.4 | 9.4 | 2732 |
| 897 | 1.2 | 2.2 | 2357 |
| 898 | 2.2 | 12.0 | 3608 |
| 899 | 3.8 | 21.2 | 2298 |
| 900 | 4.1 | 19.7 | 16642 |
| 901 | 2.5 | 8.7 | 1286 |
| 902 | 1.4 | 7.0 | 707 |
| 903 | 1.6 | 6.4 | 724 |
| 904 | 1.1 | 4.9 | 1239 |
| 905 | 1.1 | 4.4 | 567 |
| 906 | 6.2 | 22.8 | 8854 |
| 907 | 1.1 | 3.9 | 1053 |
| 908 | 3.8 | 17.8 | 2192 |
| 909 | 1.4 | 4.0 | 460 |
| 910 | 1.6 | 7.2 | 789 |
| 911 | 1.0 | 5.6 | 1386 |
| 912 | 3.2 | 7.4 | 439 |
| 913 | 9.2 | 40.7 | 50000 |
| 914 | 0.9 | 4.2 | 1410 |
| 915 | 1.1 | 4.5 | 1361 |
| 916 | 1.6 | 5.5 | 1958 |
| 917 | 1.1 | 4.3 | 1539 |
| 918 | 1.9 | 11.2 | 3508 |
| 919 | 3.8 | 21.0 | 3197 |
| 920 | 3.9 | 15.2 | 1524 |
| 921 | 1.4 | 10.0 | 2943 |
| 922 | 3.0 | 12.4 | 3234 |
| 923 | 1.6 | 6.6 | 652 |
| 924 | 3.0 | 11.9 | 1986 |
| 925 | 1.0 | 7.9 | 2357 |
| 926 | 5.3 | 35.2 | 2859 |
| 927 | 0.9 | 6.0 | 3676 |
| 928 | 1.3 | 10.6 | 12118 |
| 929 | 0.8 | 3.1 | 1289 |
| 930 | 1.1 | 3.7 | 2277 |
| 931 | 1.0 | 3.9 | 1317 |
| 932 | 1.7 | 10.7 | 2686 |
| 933 | 1.5 | 3.9 | 1814 |
| 934 | 0.5 | 1.3 | 1715 |
| 935 | 0.4 | 3.9 | 875 |
| 936 | 6.2 | 13.8 | 1601 |
| 937 | 1.4 | 3.1 | 1532 |
| 938 | 1.2 | 5.6 | 1698 |
| 939 | 2.1 | 7.0 | 1962 |
| 940 | 0.7 | 2.6 | 1912 |
| 941 | 0.4 | 1.5 | 1520 |
| 942 | 2.5 | 14.7 | 7172 |
| 943 | 1.0 | 6.2 | 9610 |
| 944 | 2.0 | 17.2 | 7735 |
| 945 | 1.3 | 6.9 | 1954 |
| 946 | 9.5 | 38.9 | 30228 |
| 947 | 2.6 | 12.4 | 2448 |
| 948 | 24.3 | 125.9 | 18223 |
| 949 | 18.6 | 128.9 | 18701 |
| 950 | 2.3 | 40.7 | 5688 |
| 951 | 0.9 | 10.1 | 3767 |
| 952 | 3.4 | 35.9 | 27912 |
| 953 | 2.3 | 13.4 | 5808 |
| 954 | 1.2 | 4.0 | 2148 |
| 955 | 1.8 | 10.0 | 13172 |
| 956 | 1.3 | 8.5 | 1629 |
| 957 | 1.1 | 21.0 | 50000 |
| 958 | 1.3 | 9.4 | 4557 |
| 959 | 69.8 | 186.9 | 24350 |
| 960 | 2.5 | 12.3 | 5034 |
| 961 | 16.3 | 37.7 | 5021 |
| 962 | 6.0 | 12.7 | 2523 |
| 963 | 4.2 | 30.9 | 50000 |
| 964 | 3.7 | 7.7 | 1522 |
| 965 | 1.6 | 11.5 | 5622 |
| 966 | 14.8 | 31.8 | 3080 |
| 967 | 0.8 | 5.8 | 3780 |
| 968 | 12.1 | 24.4 | 3588 |
| 969 | 0.7 | 2.4 | 542 |
| 970 | 11.4 | 28.9 | 3387 |
| 971 | 20.9 | 22.3 | 2635 |
| 972 | 3.9 | 15.5 | 2311 |
| 973 | 32.8 | 134.2 | 50000 |
| 974 | 2.6 | 4.9 | 2241 |
| 975 | 2.9 | 5.2 | 2223 |
| 976 | 1.5 | 6.8 | 6155 |
| 977 | 1.0 | 1.6 | 604 |
| 978 | 2.0 | 3.4 | 3040 |
| 979 | 8.1 | 12.4 | 11509 |
| 980 | 1.9 | 3.6 | 868 |
| 981 | 16.9 | 249.7 | 7530 |
| 982 | 1.4 | — | 3106 |
| 983 | 69.2 | 258.9 | 6108 |
| 984 | 0.9 | 8.4 | 4750 |
| 985 | 2.4 | 59.6 | 4832 |
| 986 | 50.5 | 335.8 | 1256 |
| 987 | 196.7 | 384.6 | 160 |
| 988 | 1835.0 | 3125.0 | 413 |
| 989 | 74.2 | 302.1 | 50000 |
| 990 | 1.9 | 12.1 | 2592 |
| 991 | 0.5 | 1.8 | 5591 |
| 992 | 2.2 | 1.7 | 1461 |
| 993 | 2.0 | 5.4 | 6521 |
| 994 | 9.1 | 85.4 | 13067 |

Inhibition Data

In Vivo Mouse TLR7 PD Model:

Adult male C57BL/6 mice were used for the experiments. Mice (7 to 10 per group) were randomized into different treatment groups based on body weight. Mice from the respective treatment groups were administered orally with vehicle or test compound. Thirty min after the oral administration of vehicle or test compound, mice were challenged with intraperitoneal injection of gardiquimod for TLR7 PD model. Ninety minutes after gardiquimod injection, mice were bled under isoflurane anaesthesia and plasma IL-6 and IFN-alpha levels were estimated by using commercially available ELISA kit (BD Biosciences, PBL Life Sciences). At the end of experiment, mean cytokine data was plotted and one way ANOVA with Dunnett's test was performed to calculate the significance of test compound treated group vs. vehicle control group. Percent inhibition of cytokine induction was calculated for test compound treated group vs vehicle control group. Data from multiple studies with different test compounds is shown in Table 28.

TABLE 28

Percent inhibition of IL-6 and IFN-alpha in mouse TLR7 PD model

| Ex. No. | Dose (mg/kg) | % inhibition of IL6 | % inhibition of IFN-alpha |
|---|---|---|---|
| 6 | 0.0000375 | 10 | 9 |
|   | 0.0001875 | 30 | 31 |
|   | 0.00075 | 56 | 55 |
|   | 0.003 | 64 | 66 |
|   | 0.015 | 86 | 96 |
| 15 | 0.000625 | 18 | 11 |
|   | 0.0025 | 49 | 27 |
|   | 0.01 | 65 | 62 |
|   | 0.04 | 84 | 88 |
|   | 0.16 | 91 | 99 |
| 18 | 0.00055 | 9 | 7 |
|   | 0.0022 | 22 | 10 |
|   | 0.0088 | 50 | 44 |
|   | 0.0352 | 60 | 66 |
|   | 0.1408 | 80 | 99 |
| 25 | 0.00096 | 22 | 2 |
|   | 0.00385 | 39 | 44 |
|   | 0.01540 | 62 | 62 |
|   | 0.06160 | 89 | 98 |
|   | 0.24640 | 95 | 100 |
| 26 | 0.000655 | 20 | 1 |
|   | 0.003276 | 40 | 33 |
|   | 0.01638 | 56 | 68 |
|   | 0.0819 | 91 | 99 |
|   | 0.4095 | 98 | 100 |

NZB/W Model of Systemic Lupus Erythematosus (SLE):

Female NZB/W mice of were screened and randomized based on the titers of anti-dsDNA antibodies and urinary NGAL (Neutrophil Gelatinase Associated Lipocalin). Mice were treated orally, once daily for 24 weeks with vehicle or test compound. The effect of test compound on disease severity was assessed by measuring end points including proteinuria, urinary-NGAL, urinary TIMP1, blood urea nitrogen (BUN), anti-dsDNA Ab titer, anti-smRNP Ab titer, and plasma levels of IL10 and IL12p40. In case of BUN the absolute increase was measured by subtracting the BUN values estimated before the initiation of treatment, from BUN values estimated after the completion of treatment. At the end of experiment, all mice were euthanized by $CO_2$ asphyxiation and kidney samples were subjected for histology. To calculate the significance of test compound treated group vs. vehicle control group, one way ANOVA with Dunnett's test was performed. Percent reduction in disease severity was calculated for each parameter, for test compound treated group vs vehicle control group. A cumulative disease score and the percent reduction in cumulative disease score was calculated by considering the average inhibition in proteinuria, urinary-NGAL, anti-dsDNA Ab titer and anti-sm Ab titer to reflect the impact on the overall severity of disease progression. Data from multiple studies with different test compounds is shown in Table 30.

TABLE 30

Inhibition of Disease Development by TLR7/8 Inhibitors in NZB/W Model of Lupus

| | | % inhibition | | | | | | | | |
|---|---|---|---|---|---|---|---|---|---|---|
| Ex No | Dose (mg/kg) | Proteinuria | Urinary NGAL | Urinary TIMP1 | BUN | Anti-SmRNP Ab titer | Anti-dsDNA Ab titer | IL-12p40 | IL-10 | Cumulative score |
| 15 | 0.06 | 96 | 79 | 66 | 100 | 28 | 20 | 68 | 98 | 56 |
|    | 0.25 | 96 | 84 | 73 | 100 | 48 | 34 | 78 | 93 | 66 |
|    | 0.75 | 98 | 86 | 72 | 100 | 51 | 45 | 81 | 93 | 70 |
|    | 2.5 | 97 | 93 | 80 | 100 | 55 | 55 | 83 | 97 | 75 |
| 18 | 0.1 | 98 | 78 | 94 | 100 | 40 | 23 | 75 | 100 | 60 |
|    | 0.5 | 98 | 93 | 94 | 100 | 52 | 33 | 88 | 98 | 69 |
|    | 1.5 | 99 | 93 | 95 | 100 | 61 | 43 | 87 | 100 | 74 |
|    | 5 | 98 | 93 | 92 | 100 | 66 | 57 | 89 | 100 | 79 |
| 25 | 0.5 | 99 | 77 | 71 | 97 | 41 | 4 | 91 | 97 | 65 |
|    | 3 | 99 | 80 | 73 | 100 | 51 | 51 | 93 | 98 | 70 |
|    | 9 | 99 | 83 | 81 | 98 | 65 | 54 | 92 | 100 | 75 |
|    | 30 | 98 | 84 | 82 | 100 | 68 | 62 | 93 | 97 | 78 |

The invention claimed is:

1. A compound of Formula (I)

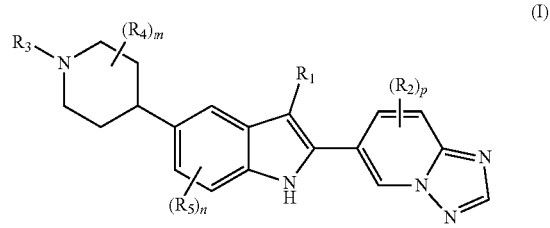

(I)

or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

each $R_2$ is independently halo, —CN, —OH, —$NO_2^+$, $C_{1-3}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O(C_{1-4}$ alkyl), $C_{1-3}$ fluoroalkoxy, —$(CH_2)_{1-4}O(C_{1-3}$ alkyl), —$O(CH_2)_{1-2}OC(O)(C_{1-3}$ alkyl), —$O(CH_2)_{1-2}NR_xR_x$, —C(O)O($C_{1-3}$ alkyl), —C(O)$NR_yR_y$, —$NR_yR_y$, —$NR_y(C_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$(CH$_2$-cyclopropyl), C$_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl);

R$_3$ is -L$_1$-A;

L$_1$ is —C(O)CH$_2$— or —C(O)(CH$_2$)$_2$—;

A is 2-oxa-6-azaspiro[3,3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, C$_{3-6}$ cycloalkyl, diazepanyl, dihydroinonyl, dihydropyrimidinonyl, dioxanyl, dioxidothiadiazinanyl, dioxidothiazolidinyl, dioxidothiomorpholinyl, dioxoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, octahydropyrrolo[3,4-b]pyridinyl, oxazolidinonyl, oxadiazolyl, oxazolyl, oxetanyl, phenyl, piperidinyl, piperidinonyl, piperazinyl, piperazinonyl, pyrazinyl, pyrazolyl, pyridazinyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrahydrothiopyranyl, tetrazolyl, thiadiazolyl, thiazolyl, triazolonyl, or triazolyl, each substituted with -L$_2$-R$_a$ and zero to 4 R$_b$;

L$_2$ is a bond or —CR$_x$R$_x$—;

R$_a$ is:
(a) H, F, Cl, —CN, —OH, C$_{1-6}$ alkyl, C$_{1-3}$ fluoroalkyl, C$_{1-5}$ hydroxyalkyl, —(CH$_2$)$_{0-4}$O(C$_{1-3}$ alkyl), —(CR$_x$R$_x$)$_{1-3}$S(C$_{1-3}$ alkyl), —NHC(O)OC(CH$_3$)$_3$, —(CR$_x$R$_x$)$_{1-3}$NHC(O)O(C$_{1-4}$ alkyl), —(CR$_x$R$_x$)$_{1-3}$NR$_y$R$_y$, —(CR$_x$R$_x$)$_{1-3}$C(O)NR$_y$R$_y$, —O(C$_{1-3}$ fluoroalkyl), —S(O)$_2$NR$_x$R$_x$, —O(CR$_x$R$_x$)$_{1-3}$NR$_x$R$_x$, —NHS(O)$_2$(C$_{1-3}$ alkyl), —NR$_x$R$_x$, —NR$_x$(C$_{1-4}$ alkyl), —NR$_x$C(O)(C$_{1-4}$ alkyl), —(CR$_x$R$_x$)$_{0-3}$C(O)OH, —C(O)(C$_{1-5}$ alkyl), —C(O)(C$_{1-3}$ fluoroalkyl), —C(O)O(C$_{1-4}$ alkyl), —C(O)NH(C$_{1-3}$ cyanoalkyl), —C(O)NR$_y$R$_y$, —C(O)NR$_x$CH$_2$C(O)NR$_x$R$_x$, or —C(O)NR$_x$CH$_2$CH$_2$NHC(O)(C$_{1-3}$ alkyl);
(b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or
(c) A$_1$, —CH$_2$A$_1$, —C(O)A$_1$, —NR$_x$A$_1$, or —C(O)NR$_x$A$_1$, wherein A$_1$ is furanyl, imidazolyl, indolyl, isoxazolyl, morpholinyl, octahydropyrrolo[3,4-c]pyrrolyl, oxazolyl, oxetanyl, phenyl, piperazinonyl, piperazinyl, piperidinyl, pyrazinyl, pyrazolyl, pyridinyl, pyrimidinyl, pyrrolidinonyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl);

each R$_b$ is independently F, —OH, —CH$_3$, —CF$_3$, or —OCH$_3$;

each R$_x$ is independently H or —CH$_3$;

each R$_y$ is independently H or C$_{1-6}$ alkyl;

R$_z$ is H, C$_{1-2}$ alkyl, or C$_{1-2}$ fluoroalkyl;

each R$_4$ is independently F, —OH, C$_{1-2}$ alkyl, or —OCH$_3$; or two R$_4$ attached to the same carbon atom form ═O; or wherein when m is at least 2, two R$_4$, each attached to a different carbon atom adjacent to the nitrogen atom in the piperidinyl ring, can form a —CH$_2$CH$_2$— bridge;

each R$_5$ is independently F, Cl, —CN, C$_{1-2}$ alkyl, C$_{1-2}$ fluoroalkyl, or —OCH$_3$;

m is zero, 1, 2, 3, or 4;

n is zero, 1, or 2; and p is zero, 1, 2, 3, or 4.

2. The compound according to claim 1 or salt thereof, wherein:

R$_1$ is H, Cl, —CN, C$_{1-4}$ alkyl, or C$_{1-2}$ fluoroalkyl;

each R$_2$ is independently F, Cl, —CN, —OH, C$_{1-3}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —O(C$_{1-4}$ alkyl), C$_{1-2}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_y$R$_x$, —C(O)O (C$_{1-3}$ alkyl), —C(O)NR$_y$R$_y$, —NR$_y$R$_y$, —NR$_y$ (C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$(CH$_2$-cyclopropyl), C$_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl);

A is azepanyl, azetidinyl, C$_{3-6}$ cycloalkyl, dioxotetrahydrothiopyranyl, dioxidothiadiazinanyl, dioxidothiomorpholinyl, furanyl, imidazolyl, isoquinolinyl, morpholinyl, oxazolyl, 2-oxa-6-azaspiro[3.3]heptanyl, octahydropyrrolo[3,4-b]pyridinyl, oxetanyl, phenyl, piperazinonyl, piperazinyl, piperidinyl, pyrazinyl, pyrazolyl, pyridinyl, pyrimidinyl, pyrrolidinonyl, pyrrolidinyl, pyrrolyl, quinolinyl, tetrahydrofuranyl, tetrahydropyranyl, tetrazolyl, thiadiazolyl, thiazolyl, or triazolyl, each substituted with -L$_2$-R$_a$ and zero to 4 R$_b$;

R$_a$ is:
(a) H, F, —CN, —OH, C$_{1-3}$ alkyl, C$_{1-2}$ fluoroalkyl, C$_{1-3}$ hydroxyalkyl, —(CH$_2$)$_{0-2}$O(C$_{1-3}$ alkyl), —NHC(O)OC(CH$_3$)$_3$, —(CR$_x$R$_x$)$_{1-3}$NHC(O)O(C$_{1-4}$ alkyl), —(CR$_x$R$_x$)$_{1-3}$NH$_2$, —(CR$_x$R$_x$)$_{1-3}$NR$_x$(C$_{1-4}$ alkyl), —O(C$_{1-2}$ fluoroalkyl), —S(O)$_2$NR$_x$R$_x$, —NHS(O)$_2$(C$_{1-3}$ alkyl), —NR$_x$R$_x$, —NR$_x$(C$_{1-4}$ alkyl), —(CR$_x$R$_x$)$_{1-2}$C(O)OH, —C(O)OH, —C(O)(C$_{1-3}$ alkyl), —C(O)O(C$_{1-4}$ alkyl), —C(O)NH$_2$, —C(O)NR$_x$(C$_{1-3}$ alkyl), —C(O)N(C$_{1-3}$ alkyl)$_2$, —C(O)NR$_x$CH$_2$C(O)NR$_x$R$_x$, or —C(O)NR$_x$CH$_2$CH$_2$NHC(O)(C$_{1-3}$ alkyl);
(b) C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); or
(c) A$_1$, —CH$_2$A$_1$, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethylphenyl, —CH$_2$(bromophenyl), and —CH$_2$CH$_2$(pyrrolidinyl);

each R$_4$ is independently F, —OH, C$_{1-2}$ alkyl, or —OCH$_3$; or two R$_4$ attached to the same carbon atom form ═O;

513

$R_5$ is F, Cl, —CN, —CH$_3$, —CF$_3$, or —OCH$_3$;
each $R_b$ is independently F, —OH, —CH$_3$, or —CF$_3$;
each $R_x$ is independently H or —CH$_3$;
each $R_y$ is independently H or C$_{1-5}$ alkyl;
m is zero, 1, or 2;
n is zero or 1; and
p is zero, 1, or 2.

3. The compound according to claim 1 or salt thereof, wherein:
$R_1$ is —CH(CH$_3$)$_2$;
each $R_2$ is independently —CH$_3$, —CF$_3$, or —OCH$_3$;
A is azepanyl, azetidinyl, dioxothiomorpholinyl, morpholinyl, oxa-6-azaspiro[3.3]heptanyl, oxetanyl, piperazinonyl, piperidinyl, pyrimidinyl, pyrrolidinonyl, pyrrolidinyl, tetrahydropyranyl, tetrazolyl, or thiazolyl; each substituted with -L$_2$-R$_a$ and zero to 4 R$_b$;
L$_2$ is a bond;
$R_a$ is F, —OH, —CH$_3$, —CH$_2$OH, —OCH$_3$, —CH$_2$OCH$_3$, —CH$_2$CH$_2$OCH$_3$, —C(O)NH$_2$, —C(O)CH(CH$_2$CH$_3$)$_2$, or —C(O)N(CH$_2$CH$_3$)$_2$;
$R_b$ is F or —CH$_3$;
m is zero;
n is zero; and
p is zero, 1 or 2.

4. The compound according to claim 1 or salt thereof, wherein:
L$_1$ is —C(O)CH$_2$—.

5. The compound according to claim 1 or salt thereof, wherein:
L$_1$ is —C(O)(CH$_2$)$_2$—.

6. The compound according to claim 1 or a salt thereof, wherein said compound is:
1-(4-(3-isopropyl-2-(8-methyl-[1,2,4]triazolo[1,5-a]pyridin-6-yl)-1H-indol-5-yl) piperidin-1-yl)-2-morpholinoethan-1-one (68);
1-(4-(3-isopropyl-2-(8-methyl-[1,2,4]triazolo[1,5-a]pyridin-6-yl)-1H-indol-5-yl)piperidin-1-yl)-2-(1H-tetrazol-5-yl)ethan-1-one (426);
2-(4,4-difluoropiperidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (602);
1-(4-(3-isopropyl-2-(8-methyl-[1,2,4]triazolo[1,5-a]pyridin-6-yl)-1H-indol-5-yl)piperidin-1-yl)-2-(pyrazin-2-yl)ethan-1-one (603);
1-(4-(3-isopropyl-2-(8-methyl-[1,2,4]triazolo[1,5-a]pyridin-6-yl)-1H-indol-5-yl)piperidin-1-yl)-2-(2-methyl-2H-tetrazol-5-yl)ethan-1-one (605);
1-(4-(2-(7,8-dimethyl-[1,2,4]triazolo[1,5-a]pyridin-6-yl)-3-isopropyl-1H-indol-5-yl)piperidin-1-yl)-3-morpholinopropan-1-one (610);
1-(4-(3-isopropyl-2-(8-(trifluoromethyl)-[1,2,4]triazolo[1,5-a]pyridin-6-yl)-1H-indol-5-yl)piperidin-1-yl)-3-(piperidin-1-yl)propan-1-one (644);
1-(4-(3-isopropyl-2-(8-(trifluoromethyl)-[1,2,4]triazolo[1,5-a]pyridin-6-yl)-1H-indol-5-yl)piperidin-1-yl)-2-(2-methylthiazol-4-yl)ethan-1-one (650);
1-(4-(3-isopropyl-2-(8-(trifluoromethyl)-[1,2,4]triazolo[1,5-a]pyridin-6-yl)-1H-indol-5-yl)piperidin-1-yl)-2-morpholinoethan-1-one (655);
1-(4-(3-isopropyl-2-(8-methoxy-[1,2,4]triazolo[1,5-a]pyridin-6-yl)-1H-indol-5-yl)piperidin-1-yl)-2-(tetrahydro-2H-pyran-4-yl)ethan-1-one (666);
1-(3-(4-(3-isopropyl-2-(8-methoxy-[1,2,4]triazolo[1,5-a]pyridin-6-yl)-1H-indol-5-yl)piperidin-1-yl)-3-oxopropyl)pyrrolidin-2-one (671);

514

1-(4-(3-isopropyl-2-(8-methoxy-[1,2,4]triazolo[1,5-a]pyridin-6-yl)-1H-indol-5-yl)piperidin-1-yl)-2-morpholinoethan-1-one (673);
1-(4-(2-([1,2,4]triazolo[1,5-a]pyridin-6-yl)-3-isopropyl-1H-indol-5-yl)piperidin-1-yl)-3-(oxetan-3-yl)butan-1-one (713);
2-(3,3-difluoropyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (716);
2-(1,1-dioxidothiomorpholino)-1-(4-(3-isopropyl-2-(8-methyl-[1,2,4]triazolo[1,5-a]pyridin-6-yl)-1H-indol-5-yl)piperidin-1-yl)ethan-1-one (717);
1-(4-(2-(7,8-dimethyl-[1,2,4]triazolo[1,5-a]pyridin-6-yl)-3-isopropyl-1H-indol-5-yl)piperidin-1-yl)-2-(3-hydroxypyrrolidin-1-yl)ethan-1-one (719);
1-(4-(2-(7,8-dimethyl-[1,2,4]triazolo[1,5-a]pyridin-6-yl)-3-isopropyl-1H-indol-5-yl)piperidin-1-yl)-2-(2,6-dimethylmorpholino)ethan-1-one (720);
1-(1-(2-(4-(2-(7,8-dimethyl-[1,2,4]triazolo[1,5-a]pyridin-6-yl)-3-isopropyl-1H-indol-5-yl)piperidin-1-yl)-2-oxoethyl)piperidin-3-yl)-2-ethylbutan-1-one (721);
(S)-1-(4-(2-(7,8-dimethyl-[1,2,4]triazolo[1,5-a]pyridin-6-yl)-3-isopropyl-1H-indol-5-yl)piperidin-1-yl)-2-(2-(methoxymethyl)pyrrolidin-1-yl)ethan-1-one (722);
1-(2-(4-(2-(7,8-dimethyl-[1,2,4]triazolo[1,5-a]pyridin-6-yl)-3-isopropyl-1H-indol-5-yl)piperidin-1-yl)-2-oxoethyl)piperidine-4-carboxamide (724);
4-(2-(4-(2-(7,8-dimethyl-[1,2,4]triazolo[1,5-a]pyridin-6-yl)-3-isopropyl-1H-indol-5-yl)piperidin-1-yl)-2-oxoethyl)piperazin-2-one (725);
(R)-1-(4-(2-(7,8-dimethyl-[1,2,4]triazolo[1,5-a]pyridin-6-yl)-3-isopropyl-1H-indol-5-yl)piperidin-1-yl)-2-(3-hydroxypyrrolidin-1-yl)ethan-1-one (735);
(S)-1-(4-(2-(7,8-dimethyl-[1,2,4]triazolo[1,5-a]pyridin-6-yl)-3-isopropyl-1H-indol-5-yl)piperidin-1-yl)-2-(3-hydroxypyrrolidin-1-yl)ethan-1-one (736);
(S)-1-(4-(2-(7,8-dimethyl-[1,2,4]triazolo[1,5-a]pyridin-6-yl)-3-isopropyl-1H-indol-5-yl)piperidin-1-yl)-2-(3-fluoropyrrolidin-1-yl)ethan-1-one (738);
2-(4,4-difluoropiperidin-1-yl)-1-(4-(2-(7,8-dimethyl-[1,2,4]triazolo[1,5-a]pyridin-6-yl)-3-isopropyl-1H-indol-5-yl)piperidin-1-yl)ethan-1-one (741);
1-(4-(2-(7,8-dimethyl-[1,2,4]triazolo[1,5-a]pyridin-6-yl)-3-isopropyl-1H-indol-5-yl)piperidin-1-yl)-2-(piperidin-1-yl)ethan-1-one (744);
1-(4-(2-(7,8-dimethyl-[1,2,4]triazolo[1,5-a]pyridin-6-yl)-3-isopropyl-1H-indol-5-yl)piperidin-1-yl)-2-(pyrrolidin-1-yl)ethan-1-one (745);
1-(4-(2-(7,8-dimethyl-[1,2,4]triazolo[1,5-a]pyridin-6-yl)-3-isopropyl-1H-indol-5-yl)piperidin-1-yl)-2-(3,3-dimethylpiperidin-1-yl)ethan-1-one (747);
(S)-1-(4-(2-(7,8-dimethyl-[1,2,4]triazolo[1,5-a]pyridin-6-yl)-3-isopropyl-1H-indol-5-yl)piperidin-1-yl)-2-(2-(hydroxymethyl)pyrrolidin-1-yl)ethan-1-one (749);
1-(4-(2-(7,8-dimethyl-[1,2,4]triazolo[1,5-a]pyridin-6-yl)-3-isopropyl-1H-indol-5-yl)piperidin-1-yl)-2-(4-methoxypiperidin-1-yl)ethan-1-one (750);
2-(azepan-1-yl)-1-(4-(2-(7,8-dimethyl-[1,2,4]triazolo[1,5-a]pyridin-6-yl)-3-isopropyl-1H-indol-5-yl)piperidin-1-yl)ethan-1-one (754);
1-(4-(2-(7,8-dimethyl-[1,2,4]triazolo[1,5-a]pyridin-6-yl)-3-isopropyl-1H-indol-5-yl)piperidin-1-yl)-2-(4-hydroxypiperidin-1-yl)ethan-1-one (755);
2-(azetidin-1-yl)-1-(4-(2-(7,8-dimethyl-[1,2,4]triazolo[1,5-a]pyridin-6-yl)-3-isopropyl-1H-indol-5-yl)piperidin-1-yl)ethan-1-one (765);

1-(4-(3-isopropyl-2-(8-methyl-[1,2,4]triazolo[1,5-a]pyridin-6-yl)-1H-indol-5-yl)piperidin-1-yl)-2-(piperidin-1-yl)ethan-1-one (769);

1-(4-(3-isopropyl-2-(8-methyl-[1,2,4]triazolo[1,5-a]pyridin-6-yl)-1H-indol-5-yl)piperidin-1-yl)-2-(pyrrolidin-1-yl)ethan-1-one (770);

1-(4-(3-isopropyl-2-(8-methyl-[1,2,4]triazolo[1,5-a]pyridin-6-yl)-1H-indol-5-yl)piperidin-1-yl)-2-(2-oxa-6-azaspiro[3.3]heptan-6-yl)ethan-1-one (771);

1-(4-(3-isopropyl-2-(8-methyl-[1,2,4]triazolo[1,5-a]pyridin-6-yl)-1H-indol-5-yl)piperidin-1-yl)-2-(4-(2-methoxyethyl)piperazin-1-yl)ethan-1-one (772);

1-(4-(3-isopropyl-2-(8-methyl-[1,2,4]triazolo[1,5-a]pyridin-6-yl)-1H-indol-5-yl)piperidin-1-yl)-2-(4-methoxypiperidin-1-yl)ethan-1-one (773);

(S)-2-(3-hydroxypyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (774);

(S)-2-(3-hydroxypiperidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (775);

(R)-2-(3-hydroxypyrrolidin-1-yl)-1-(4-(3-isopropyl-2-(8-methyl-[1,2,4]triazolo[1,5-a]pyridin-6-yl)-1H-indol-5-yl)piperidin-1-yl)ethan-1-one (776);

1-(4-(3-isopropyl-2-(8-methyl-[1,2,4]triazolo[1,5-a]pyridin-6-yl)-1H-indol-5-yl)piperidin-1-yl)-3-morpholinopropan-1-one (882);

3-(1,1-dioxidothiomorpholino)-1-(4-(3-isopropyl-2-(8-methyl-[1,2,4]triazolo[1,5-a]pyridin-6-yl)-1H-indol-5-yl)piperidin-1-yl)propan-1-one (884);

1-(4-(3-isopropyl-2-(7-methyl-[1,2,4]triazolo[1,5-a]pyridin-6-yl)-1H-indol-5-yl)piperidin-1-yl)-3-morpholinopropan-1-one (885);

(R)-1-(4-(2-(7,8-dimethyl-[1,2,4]triazolo[1,5-a]pyridin-6-yl)-3-isopropyl-1H-indol-5-yl)piperidin-1-yl)-3-(3-fluoropyrrolidin-1-yl)propan-1-one (888);

3-(azetidin-1-yl)-1-(4-(2-(7,8-dimethyl-[1,2,4]triazolo[1,5-a]pyridin-6-yl)-3-isopropyl-1H-indol-5-yl)piperidin-1-yl)propan-1-one (893);

(R)-1-(4-(2-(7,8-dimethyl-[1,2,4]triazolo[1,5-a]pyridin-6-yl)-3-isopropyl-1H-indol-5-yl)piperidin-1-yl)-3-(3-hydroxypyrrolidin-1-yl)propan-1-one (899);

3-(4,4-difluoropiperidin-1-yl)-1-(4-(2-(7,8-dimethyl-[1,2,4]triazolo[1,5-a]pyridin-6-yl)-3-isopropyl-1H-indol-5-yl)piperidin-1-yl)propan-1-one (900);

1-(4-(2-(7,8-dimethyl-[1,2,4]triazolo[1,5-a]pyridin-6-yl)-3-isopropyl-1H-indol-5-yl)piperidin-1-yl)-3-(piperidin-1-yl)propan-1-one (904);

1-(4-(2-(7,8-dimethyl-[1,2,4]triazolo[1,5-a]pyridin-6-yl)-3-isopropyl-1H-indol-5-yl)piperidin-1-yl)-3-(2,6-dimethylmorpholino)propan-1-one (906);

1-(3-(4-(2-(7,8-dimethyl-[1,2,4]triazolo[1,5-a]pyridin-6-yl)-3-isopropyl-1H-indol-5-yl)piperidin-1-yl)-3-oxopropyl)-N,N-diethylpiperidine-3-carboxamide (907);

1-(4-(2-(7,8-dimethyl-[1,2,4]triazolo[1,5-a]pyridin-6-yl)-3-isopropyl-1H-indol-5-yl)piperidin-1-yl)-3-(3,3-dimethylpiperidin-1-yl)propan-1-one (908);

1-(4-(2-(7,8-dimethyl-[1,2,4]triazolo[1,5-a]pyridin-6-yl)-3-isopropyl-1H-indol-5-yl)piperidin-1-yl)-3-(4-hydroxypiperidin-1-yl)propan-1-one (909);

3-(azepan-1-yl)-1-(4-(2-(7,8-dimethyl-[1,2,4]triazolo[1,5-a]pyridin-6-yl)-3-isopropyl-1H-indol-5-yl)piperidin-1-yl)propan-1-one (910);

(S)-1-(4-(2-(7,8-dimethyl-[1,2,4]triazolo[1,5-a]pyridin-6-yl)-3-isopropyl-1H-indol-5-yl)piperidin-1-yl)-3-(2-(methoxymethyl)pyrrolidin-1-yl)propan-1-one (911);

1-(3-(4-(2-(7,8-dimethyl-[1,2,4]triazolo[1,5-a]pyridin-6-yl)-3-isopropyl-1H-indol-5-yl)piperidin-1-yl)-3-oxopropyl)piperidine-4-carboxamide (912);

4-(3-(4-(2-(7,8-dimethyl-[1,2,4]triazolo[1,5-a]pyridin-6-yl)-3-isopropyl-1H-indol-5-yl)piperidin-1-yl)-3-oxopropyl)piperazin-2-one (913);

1-(4-(2-(7,8-dimethyl-[1,2,4]triazolo[1,5-a]pyridin-6-yl)-3-isopropyl-1H-indol-5-yl)piperidin-1-yl)-3-(4-methoxypiperidin-1-yl)propan-1-one (915);

1-(4-(2-(7,8-dimethyl-[1,2,4]triazolo[1,5-a]pyridin-6-yl)-3-isopropyl-1H-indol-5-yl)piperidin-1-yl)-3-(pyrrolidin-1-yl)propan-1-one (916);

(S)-1-(4-(2-(7,8-dimethyl-[1,2,4]triazolo[1,5-a]pyridin-6-yl)-3-isopropyl-1H-indol-5-yl) piperidin-1-yl)-3-(2-(hydroxymethyl)pyrrolidin-1-yl)propan-1-one (917);

3-(cyclohexylamino)-1-(4-(2-(7,8-dimethyl-[1,2,4]triazolo[1,5-a]pyridin-6-yl)-3-isopropyl-1H-indol-5-yl) piperidin-1-yl)propan-1-one (920);

(S)-1-(4-(2-(7,8-dimethyl-[1,2,4]triazolo[1,5-a]pyridin-6-yl)-3-isopropyl-1H-indol-5-yl) piperidin-1-yl)-3-(3-fluoropyrrolidin-1-yl)propan-1-one (921); or (S)-1-(4-(2-(7,8-dimethyl-[1,2,4]triazolo[1,5-a]pyridin-6-yl)-3-isopropyl-1H-indol-5-yl) piperidin-1-yl)-3-(3-hydroxypyrrolidin-1-yl)propan-1-one (922).

7. The compound according to claim 1 or a salt thereof, wherein said compound is:

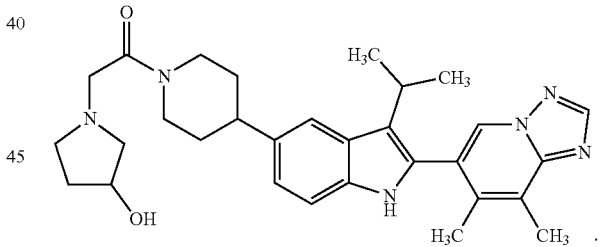

8. The compound according to claim 1 or a salt thereof, wherein said compound is:

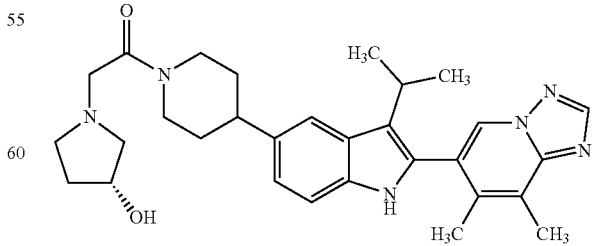

9. The compound according to claim 1 or a salt thereof, wherein said compound is:

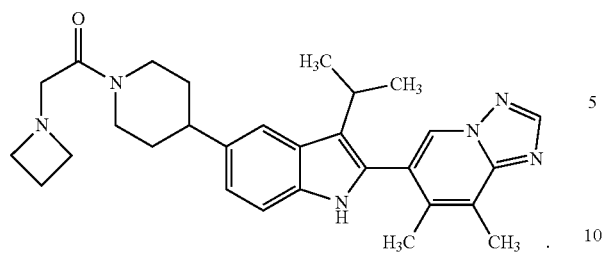

10. A pharmaceutical composition comprising a compound according to claim 1 or a pharmaceutically-acceptable salt thereof; and a pharmaceutically acceptable carrier.

11. A pharmaceutical composition comprising a compound according to claim 7 or a pharmaceutically-acceptable salt thereof; and a pharmaceutically acceptable carrier.

12. A pharmaceutical composition comprising a compound according to claim 8 or a pharmaceutically-acceptable salt thereof; and a pharmaceutically acceptable carrier.

13. A pharmaceutical composition comprising a compound according to claim 9 or a pharmaceutically-acceptable salt thereof; and a pharmaceutically acceptable carrier.

* * * * *